United States Patent
Wang et al.

(10) Patent No.: US 12,187,713 B2
(45) Date of Patent: Jan. 7, 2025

(54) IMMUNOMODULATORS, COMPOSITIONS AND METHODS THEREOF

(71) Applicant: Betta Pharmaceuticals Co., Ltd, Zhejiang (CN)

(72) Inventors: Yiqian Wang, Beijing (CN); Yao Zhang, Beijing (CN); Bang Fu, Beijing (CN); Jiabing Wang, Beijing (CN); Lieming Ding, Zhejiang (CN)

(73) Assignee: Betta Pharmaceuticals Co., Ltd, Zhejiang (CN)

( * ) Notice: Subject to any disclaimer, the term of this patent is extended or adjusted under 35 U.S.C. 154(b) by 701 days.

(21) Appl. No.: 17/427,112

(22) PCT Filed: Jan. 20, 2020

(86) PCT No.: PCT/CN2020/073222
§ 371 (c)(1),
(2) Date: Jul. 30, 2021

(87) PCT Pub. No.: WO2020/156323
PCT Pub. Date: Aug. 6, 2020

(65) Prior Publication Data
US 2022/0098183 A1    Mar. 31, 2022

(30) Foreign Application Priority Data

Jan. 31, 2019  (WO) ................ PCT/CN2019/074217
Jul. 4, 2019   (WO) ................ PCT/CN2019/094726

(51) Int. Cl.
| | |
|---|---|
| *C07D 413/14* | (2006.01) |
| *C07D 451/02* | (2006.01) |
| *C07D 471/10* | (2006.01) |
| *C07D 487/04* | (2006.01) |
| *C07D 487/08* | (2006.01) |
| *C07D 491/107* | (2006.01) |
| *C07D 495/10* | (2006.01) |
| *C07D 498/04* | (2006.01) |

(52) U.S. Cl.
CPC ......... *C07D 413/14* (2013.01); *C07D 451/02* (2013.01); *C07D 471/10* (2013.01); *C07D 487/04* (2013.01); *C07D 487/08* (2013.01); *C07D 491/107* (2013.01); *C07D 495/10* (2013.01); *C07D 498/04* (2013.01)

(58) Field of Classification Search
None
See application file for complete search history.

(56) References Cited

FOREIGN PATENT DOCUMENTS

| | | |
|---|---|---|
| TW | 201835073 A | 10/2018 |
| WO | 2017087777 A1 | 5/2017 |
| WO | 2018026971 A1 | 2/2018 |
| WO | 2018119224 A1 | 6/2018 |
| WO | 2018119266 A1 | 6/2018 |
| WO | 2019175897 A1 | 9/2019 |

OTHER PUBLICATIONS

Corresponding TW application search report issued on Sep. 8, 2023.
The first office action of family IN application No. 202117035418 issue on Jan. 3, 2023.

*Primary Examiner* — Bong-Sook Baek
(74) *Attorney, Agent, or Firm* — Samson G. Yu

(57) ABSTRACT

Provided herein are compounds of Formula (I), methods of using the compounds as immunomodulators, and pharmaceutical compositions comprising such compounds. The compounds are useful in treating, preventing or ameliorating diseases or disorders such as cancer or infections.

(I)

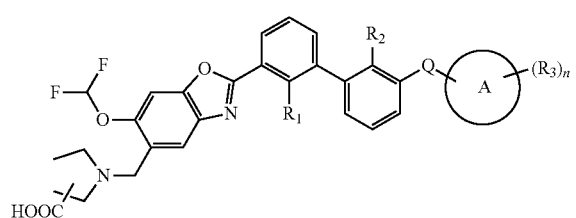

20 Claims, No Drawings

IMMUNOMODULATORS, COMPOSITIONS AND METHODS THEREOF

FIELD OF THE INVENTION

The present invention relates to compounds that are inhibitors of PD-1/PD-L1 protein/protein interaction. The present invention also relates to pharmaceutical compositions comprising such compounds and methods of using such compounds in the treatment of cancer, pre-cancerous syndromes and other diseases associated with inhibition of PD-1/PD-L1 protein/protein interaction.

BACKGROUND OF THE INVENTION

Cancer immunotherapy has been increasingly utilized to treat advanced malignancies. The signaling network of immune checkpoints has attracted considerable attention. Several cancers are highly refractory to conventional chemotherapy. The survival of tumors in several cases is assisted by checkpoint immunomodulation to maintain the imbalance between immune surveillance and cancer cell proliferation. Immune checkpoint inhibitors are revolutionizing the treatment options and expectations for patients with cancer.

Programmed cell death-1 (PD-1), also known as CD279, is a cell surface receptor expressed on activated T cells, natural killer T cells, B cells, and macrophages. It functions as an intrinsic negative feedback system to prevent the activation of T-cells, which in turn reduces autoimmunity and promotes self-tolerance. In addition, PD-1 is also known to play a critical role in the suppression of antigen-specific T cell response in diseases like cancer and viral infection. The interaction between PD-1 and PD-L1 results in a decrease in tumor infiltrating lymphocytes, a decrease in T-cell receptor mediated proliferation, and immune evasion by the cancerous cells. Immune suppression can be reversed by inhibiting the local interaction of PD-1 with PD-L1, and the effect is additive when the interaction of PD-1 with PD-L2 is blocked as well.

The development of a therapeutic approach to block the PD-1 mediated inhibitory signaling cascade in order to augment or "rescue" T cell response. Most of the currently approved medicines in immunotherapy are monoclonal antibodies. These monoclonal antibodies have shown impressive clinical results in treatment of several types of tumors. Therapeutic antibodies however exhibit several disadvantages such as limited tissue and tumor penetration, very long half life time, lacking oral bioavailability, immunogenicity, and difficult and expensive production.

Recently, small molecules have been described to binding to PD-L1 in WO2015033299, WO2015033301, WO2015034820, WO2018183171, WO2018119224, WO2018119266, etc. Moreover, small molecule inhibitors that directly target PD-1 or PD-L1 are still not approved.

Accordingly, there is still great demand for more potent, and more easily administered therapeutics against PD-1/PD-L1 protein/protein interactions. In this invention, applicant discovered potent small molecules that can have activity as inhibitors of the interaction of PD-L1 with PD-1, and thus may be useful for therapeutic administration to enhance immunity against cancer and/or infectious diseases. These small molecules are expected to be useful as pharmaceuticals with desirable stability, solubility, bioavailability, therapeutic index and toxicity values that are crucial to become efficient medicines to promote human health.

SUMMARY OF INVENTION

The present invention relates to compounds that are used as inhibitors of the functional interaction between PD-L1 and PD-1. Inhibitors of the interaction between PD-L1 and PD-1 are useful in the treatment of cancers and infectious diseases.

The compounds of the invention have the general structures as Formula (I).

A compound of Formula (I), or a stereoisomer, tautomer, pharmaceutically acceptable salt, prodrug, chelate, non-covalent complex, or solvate thereof, Formula (I)

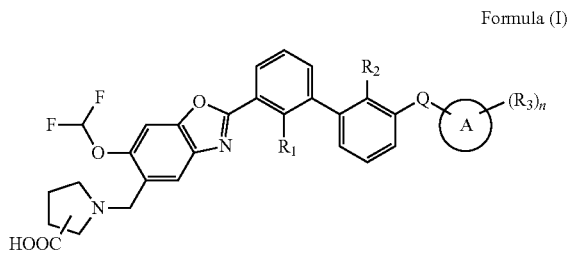

wherein, $R_1$ and $R_2$ are each independently selected from halogen, CN, $C_{1-6}$ alkyl, or $C_{1-4}$haloalkyl;

Q is a bond, —NH—, or —$(CH_2)_m$—O—;

Ring A is $C_{5-6}$ aryl, $C_{5-6}$ heteroaryl, $C_{4-6}$ cycloalkyl or $C_{4-6}$ heterocycloalkyl, wherein the $C_{5-6}$ heteroaryl and $C_{4-6}$ heterocycloalkyl optionally comprising 1, 2 or 3 hetero atoms independently selected from N, S, or O; or Ring A is $C_{8-10}$ fused bicyclic ring;

$R_3$ is H, halogen, —$(CH_2)_s$—$NR_4R_5$, $C_{1-4}$ alkyl, $C_{1-4}$alkoxyl, hydroxyl, oxo, CN, $(CH_2)_q$—$CONR_4R_5$, —$COR_4$, —$NR_4R_5$, —$NR_4C(=O)NR_4R_5$, —$NR_4C(=NR_4)NR_4R_5$, —$S(O)_2R_4$, —$S(O)_2NR_4R_5$, —$S(O)R_4$, —$S(O)NR_4R_5$, $C_{2-6}$ alkenyl, $C_{2-6}$ alknyl, $C_{1-6}$ haloalkyl, $C_{5-6}$ aryl, $C_{5-6}$ heteroaryl, $C_{3-6}$ cycloalkyl or $C_{3-6}$ heterocycloalkyl, wherein the $C_{5-6}$ heteroaryl and $C_{3-6}$ heterocycloalkyl optionally comprising 1, 2 or 3 hetero atoms independently selected from N, S, or O; the $C_{1-4}$ alkyl, $C_{1-4}$ alkoxyl, $C_{2-6}$ alkenyl, $C_{2-6}$ alknyl, $C_{1-6}$ haloalkyl, $C_{5-6}$ aryl, $C_{5-6}$ heteroaryl, $C_{3-6}$ cycloalkyl and $C_{3-6}$ heterocycloalkyl optionally substituted with one or more substitutents independently selected $R_6$ substituents;

$R_4$ and $R_5$ are each independently selected from H, $C_{1-4}$ alkyl, or $C_{3-6}$ cycloalkyl, $C_{3-6}$ heterocyclyl, the $C_{1-4}$ alkyl, $C_{3-6}$ cycloalkyl, or $C_{3-6}$ heterocyclyl optionally substituted with one or more substitutents independently selected $R_6$ substituents; or $R_4$ and $R_5$ together with the atoms to which they are attached form a 4-10-member heterocyclic ring optionally substituted with one or more substituents independently selected $R_6$ substituents;

$R_6$ is H, halogen, hydroxyl, oxo, CN, —$(CH_2)_k$—$NR_7R_8$, —$COR_7$, —$NR_7R_8$, —$NR_7C(=O)NR_7R_8$, —$NR_7C(=NR_7)NR_7R_8$, —$S(O)_2R_7$, —$S(O)_2NR_7R_8$, —$S(O)R_7$, —$S(O)NR_7R_8$, or $R_6$ is selected from substituted or unsubstituted $C_{1-4}$ alkyl, $C_{1-4}$ alkoxyl, $C_{2-6}$ alkenyl, $C_{2-6}$ alknyl, $C_{1-6}$ haloalkyl, $C_{5-6}$ aryl, $C_{5-6}$ heteroaryl, $C_{3-10}$ heterocyclic ring, wherein the $C_{5-6}$ heteroaryl and $C_{3-10}$ heterocyclic ring optionally comprising 1, 2 or 3 hetero atoms independently selected from N, S, or O;

$R_7$ and $R_8$ are each independently selected from H, halogen, hydroxyl, oxo, CN, —$S(O)_2$— $C_{1-4}$ alkyl, —$NH_2$, —NH—$C_{1-4}$ alkyl, —$(CH_2)$—$N(C_{1-4}$ alkyl$)_2$, or $R_7$ and $R_8$ are each independently selected from substituted or unsubstituted $C_{1-4}$ alkyl, $C_{1-4}$ alkoxyl, $C_{2-6}$ alkenyl, $C_{2-6}$ alknyl, $C_{1-6}$ haloalkyl, $C_{5-6}$ aryl, $C_{5-6}$ heteroaryl, $C_{3-6}$ cycloalkyl, $C_{3-6}$ heterocycloalkyl; wherein the $C_{5-6}$ heteroaryl and $C_{3-6}$ heterocycloalkyl optionally comprising 1, 2 or 3 hetero atoms independently selected from N, S, or O;

m, n, q, k and s are each independently selected from 0, 1, 2, 3 or 4.

In some embodiments of Formula (I), wherein, $R_3$ is H, halogen, —$(CH_2)_s$—$NR_4R_5$, $C_{1-4}$ alkyl, CM alkoxyl, hydroxyl, oxo, CN, $(CH_2)_q$—$CONR_4R_5$, —$NR_4R_5$, —$NR_4C(=NR_4)NR_4R_5$, —$S(O)_2R_4$, $C_{2-6}$ alkenyl, $C_{2-6}$ alknyl, $C_{1-6}$ haloalkyl or $C_{3-6}$ heterocycloalkyl, wherein the $C_{3-6}$ heterocycloalkyl optionally comprising 1, 2 or 3 hetero atoms independently selected from N, S, or O; the $C_{1-4}$ alkyl, $C_{1-4}$ alkoxyl, $C_{2-6}$ alkenyl, $C_{2-6}$ alknyl, $C_{1-6}$ haloalkyl, and $C_{3-6}$ heterocycloalkyl optionally substituted with one or more substituents independently selected $R_6$ substituents.

In some embodiments of Formula (I), wherein, $R_3$ is H, halogen, —$(CH_2)_s$—$NR_4R_5$, —CN, —$S(O)_2R_4$, $C_{1-4}$ alkyl, $C_{1-4}$ alkoxyl, the —$(CH_2)_s$—$NR_4R_5$, $C_{1-4}$ alkyl, $C_{1-4}$ alkoxyl optionally substituted with one or more substituents independently selected $R_6$ substituents.

In some embodiments of Formula (I), wherein, $R_6$ is H, halogen, hydroxyl, oxo, CN, —$(CH_2)_k$—$NR_7R_8$, —$COR_7$, —$NR_7R_8$, —$NR_7C(=O)NR_7R_8$, —$S(O)_2R_7$ or $R_6$ is selected from substituted or unsubstituted $C_{1-4}$ alkyl, $C_{1-4}$ alkoxyl, $C_{2-6}$ alkenyl, $C_{2-6}$ alknyl, $C_{1-6}$ haloalkyl, $C_{5-6}$ aryl, $C_{5-6}$ heteroaryl, $C_{3-10}$ heterocyclic ring, wherein the $C_{5-6}$ heteroaryl and $C_{3-10}$ heterocyclic ring optionally comprising 1, 2 or 3 hetero atoms independently selected from N, S, or O.

In some embodiments of Formula (I), wherein, $R_6$ is H, halogen, hydroxyl, oxo, CN, —$(CH_2)$—N—$(C_{1-4}$ alkyl$)_2$, —$(CH_2)$—$NH_2$, —N—$(C_{1-4}$ alkyl$)_2$, —$NH_2$, —CO—N—$(C_{1-4}$ alkyl$)_2$, —CO—$NH_2$, —$S(O)_2$—$C_{1-4}$ alkyl, $C_{1-4}$alkyl-OH, $C_{1-4}$ alkyl, $C_{1-4}$ alkoxyl, $C_{2-6}$ alkenyl, $C_{2-6}$ alknyl, $C_{1-6}$ haloalkyl, $C_{5-6}$ aryl, $C_{5-6}$ heteroaryl, $C_{3-10}$ heterocyclic ring, wherein the $C_{5-6}$ heteroaryl and $C_{3-10}$ heterocyclic ring optionally comprising 1, 2 or 3 hetero atoms independently selected from N, S, or O.

In some embodiments of Formula (I), $R_6$ is halogen, oxo, —OH, —$NH_2$, —$N(CH_3)_2$, —$C_{1-4}$ alkyl-OH, —$C_{1-4}$ alkyl-NH—$CH_3$, —NH—$C_{1-4}$ alkyl, $C_{1-4}$ alkyl, $C_{1-4}$ haloalkyl, $C_{1-4}$ alkoxyl, $C_{5-6}$ aryl, $C_{5-6}$ heteroaryl, $C_{3-6}$ heterocyclyl, guanidine, or sulfone.

In some embodiments of Formula (I), wherein, $R_1$ and $R_2$ are each independently selected from halogen, CN, —$C_{1-6}$alkyl, or —$C_{1-4}$ haloalkyl;

Q is a bond, —NH—, or —$(CH_2)_m$—O—;

ring A is $C_{5-6}$ aryl or $C_{5-6}$ heteroaryl ring, wherein the $C_{5-6}$ heteroaryl ring optionally comprising 1, 2 or 3 hetero atoms independently selected from N, S, or O; or ring A is $C_{8-10}$ fused bicyclic ring;

$R_3$ is H, halogen, —$(CH_2)_s$—$NR_4R_5$, —$C_{1-4}$ alkyl, —$C_{1-4}$ alkoxyl, the —$(CH_2)_s$—$NR_4R_5$, —$C_{1-4}$ alkyl, —$C_{1-4}$ alkoxyl optionally substituted with one or more substitutents independently selected from halogen, —$C_{1-4}$ alkyl, —$C_{1-4}$ haloalkyl, —$C_{1-4}$ alkoxyl, $C_{5-6}$ heteroaryl, $C_{5-6}$ aryl, carboxyl, amino, hydroxyl, guanidine, or sulfone;

$R_4$ and $R_5$ are each independently selected from H, —$C_{1-4}$ alkyl, or $C_{3-6}$ cycloalkyl, $C_{3-6}$ heterocyclyl, the —$C_{1-4}$ alkyl, or $C_{3-6}$ cycloalkyl, $C_{3-6}$ heterocyclyl optionally substituted with halogen, —OH, $N(CH_3)_2$, —$C_{1-4}$ alkyl, —$C_{1-4}$ haloalkyl, —$C_{3-6}$ heterocyclyl, —NH—$C_{1-4}$ alkyl, or sulfone; or $R_4$ and $R_5$ together with the atoms to which they are attached form a 4- to 6-member heterocyclic ring optionally substituted with one or more substituents independently selected from —OH, —$N(CH_3)_2$, —$NH_2$, oxo, halogen, —$C_{1-4}$ alkyl, —$C_{1-4}$ alkoxyl, —$C_{1-4}$ alkyl-OH, —$C_{1-4}$alkyl-NH—$CH_3$, or sulfone;

m, n and s are each independently selected from 0, 1, 2, 3 or 4.

In some embodiments of Formula (I), wherein, wherein Q is selected from bond, —NH— or —$CH_2$—O—.

In some embodiments of Formula (I), wherein ring A is selected from

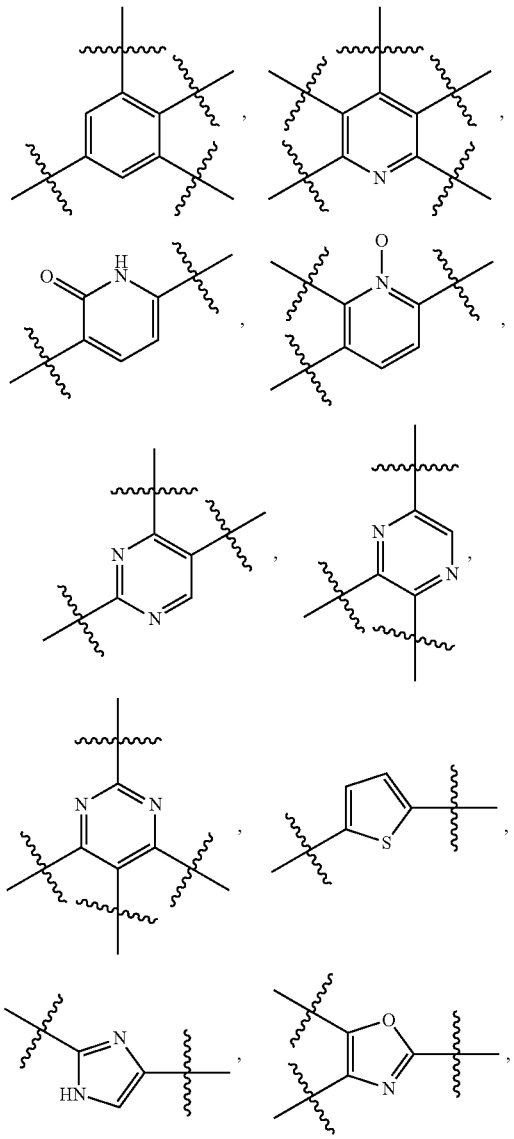

In some embodiments of Formula (I), wherein ring A is selected from

-continued

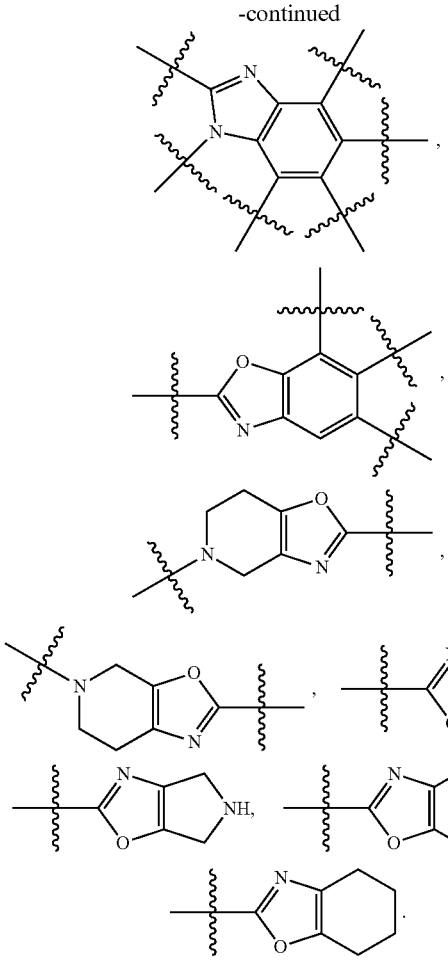

In some embodiments of Formula (I), wherein ring A is selected from

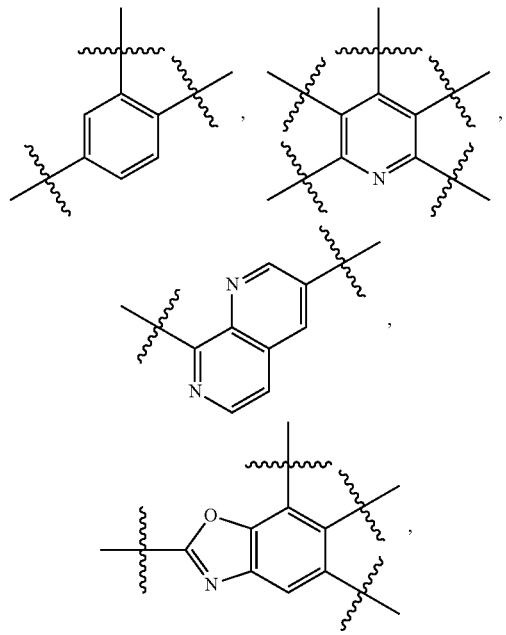

-continued

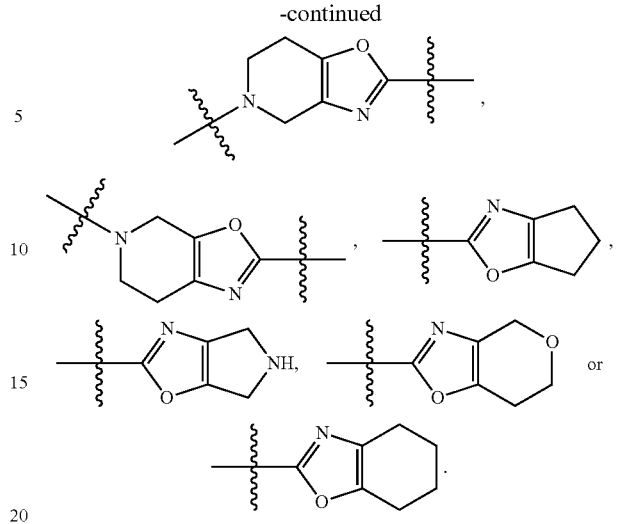

In some embodiments, the compound is of Formula (II):

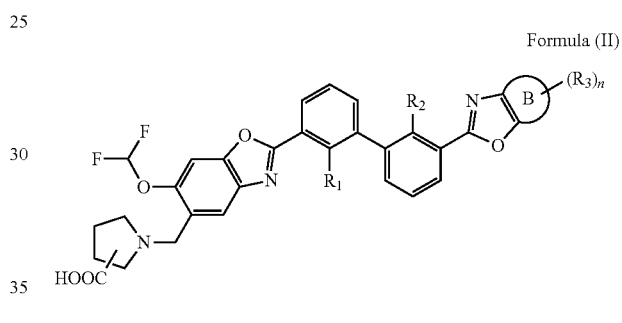

Formula (II)

or a stereoisomer, tautomer, pharmaceutically acceptable salt, prodrug, chelate, non-covalent complex, or solvate thereof, wherein, ring B is $C_{5-6}$ cycloalkyl or $C_{5-6}$ heterocycloalkyl;

$R_1$, $R_2$, $R_3$ and the subscript n are as defined in any embodiments of Formula (I).

In some embodiments, the compound is of Formula (III):

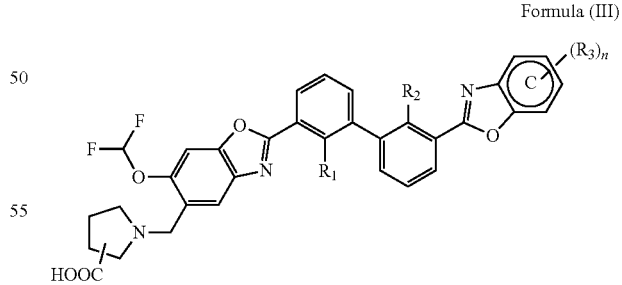

Formula (III)

or a stereoisomer, tautomer, pharmaceutically acceptable salt, prodrug, chelate, non-covalent complex, or solvate thereof, wherein, ring C is phenyl or heteroaryl, and the heteroaryl comprising 1, 2 or 3 N;

$R_1$, $R_2$, $R_3$ and the subscript n are as defined in any embodiments of Formula (I).

In some embodiments, the compound is of Formula (IV):

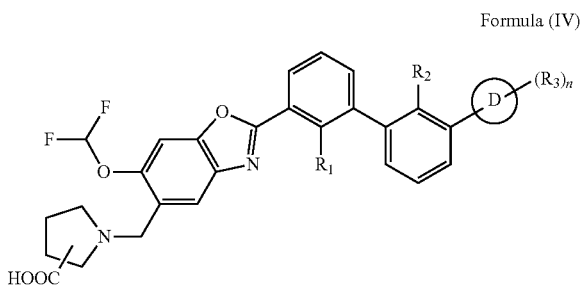

Formula (IV)

or a stereoisomer, tautomer, pharmaceutically acceptable salt, prodrug, chelate, non-covalent complex, or solvate thereof, wherein,
ring D is $C_{5-6}$ aryl, $C_{5-6}$ heteroaryl, or $C_{5-6}$ heterocycloalkyl, and the $C_{5-6}$ heteroaryl and $C_{5-6}$ heterocycloalkyl optionally comprising 1, 2 or 3 hetero atoms independently selected from N, S, or O;
$R_1$, $R_2$, $R_3$ and the subscript n are as defined in any embodiments of Formula (I).

In some embodiments, the compound is of Formula (V):

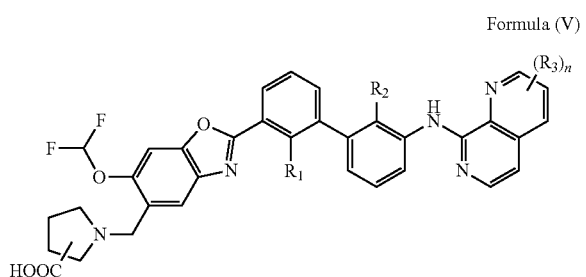

Formula (V)

or a stereoisomer, tautomer, pharmaceutically acceptable salt, prodrug, chelate, non-covalent complex, or solvate thereof, wherein,
$R_1$, $R_2$, $R_3$ and the subscript n are as defined in any embodiments of Formula (I).

In some embodiments, the compound is of Formula (VI):

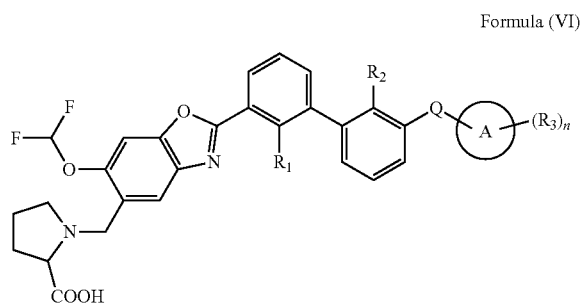

Formula (VI)

or a stereoisomer, tautomer, pharmaceutically acceptable salt, prodrug, chelate, non-covalent complex, or solvate thereof, wherein,
ring A, Q, $R_1$, $R_2$, $R_3$ and the subscript n are as defined in any embodiments of Formula (I).

In some embodiments, wherein, $R_1$ is selected from selected from F, Cl, —$CH_3$, —CN or —O—$CH_3$.

In some embodiments, wherein, $R_1$ is selected from selected from —$CH_3$, F, or —O—$CH_3$.

In some embodiments, wherein, $R_2$ is selected from —$CH_3$, F, Cl, or Br.

In some embodiments, wherein, $R_2$ is —$CH_3$.

In some embodiments, wherein, $R_3$ is selected from H, F, Cl, —$CH_3$, —$CF_3$, —O—$CF_3$, —O—$CHF_2$, —O—$CH_3$, —CN, —$NH_2$,

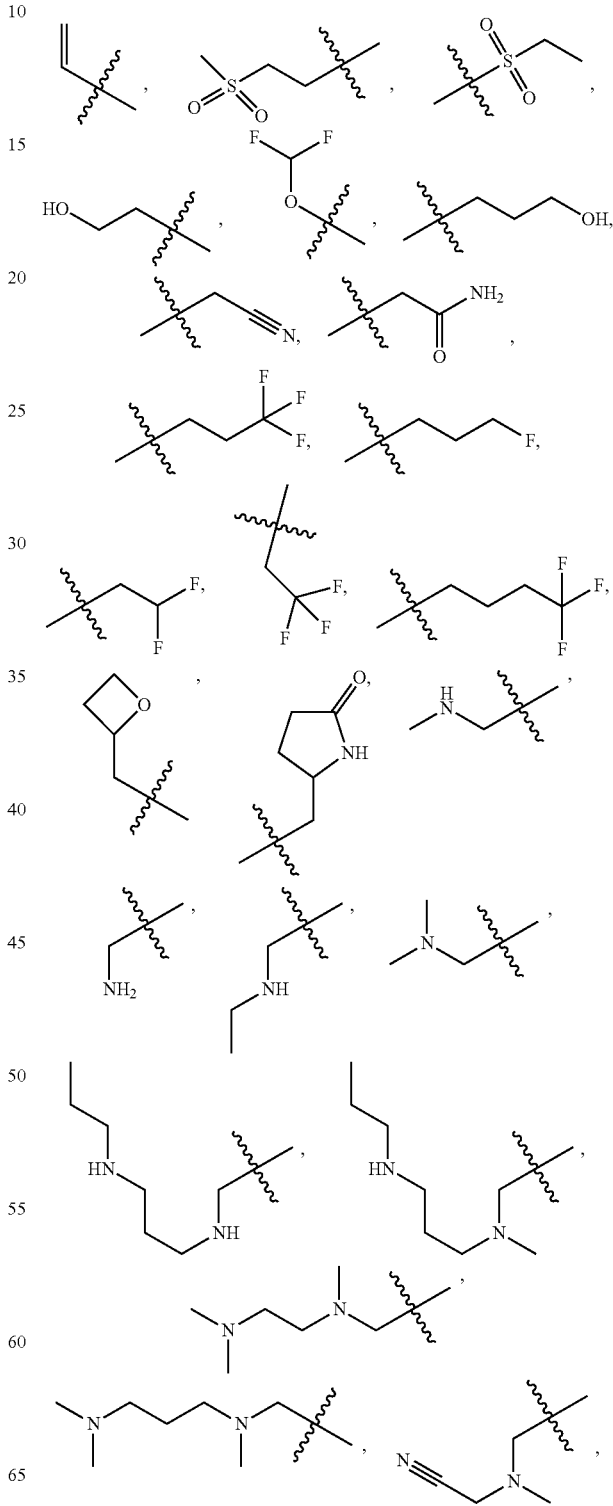

-continued
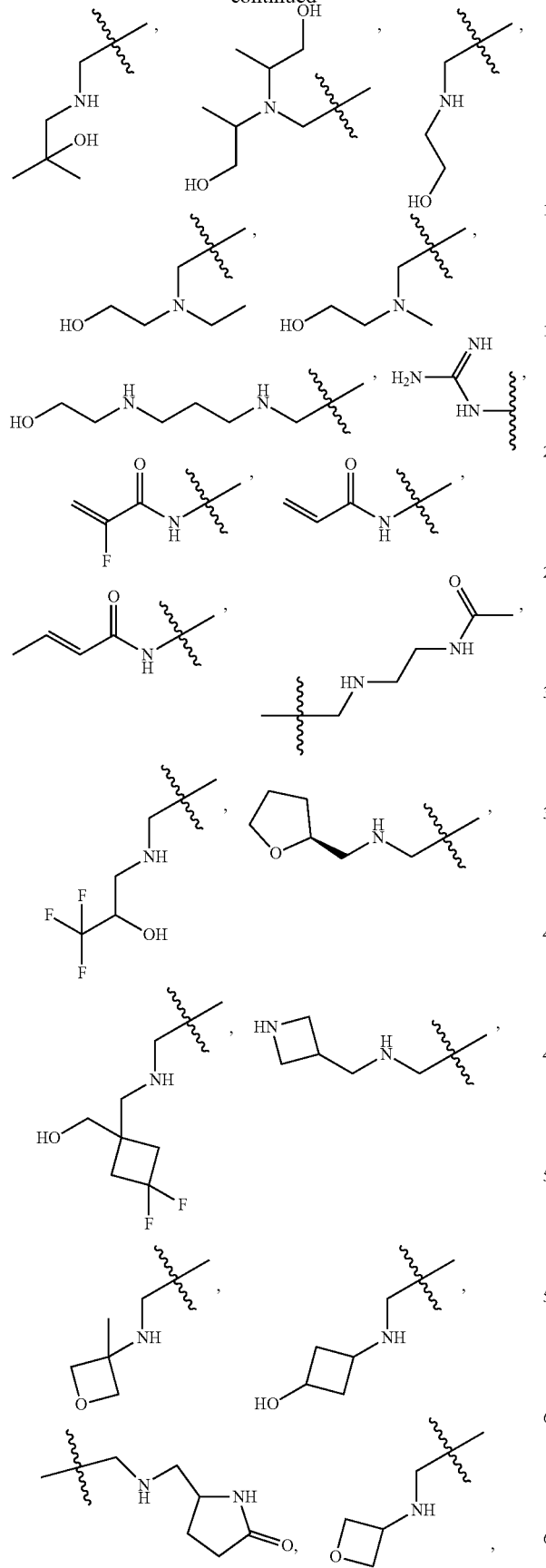
-continued
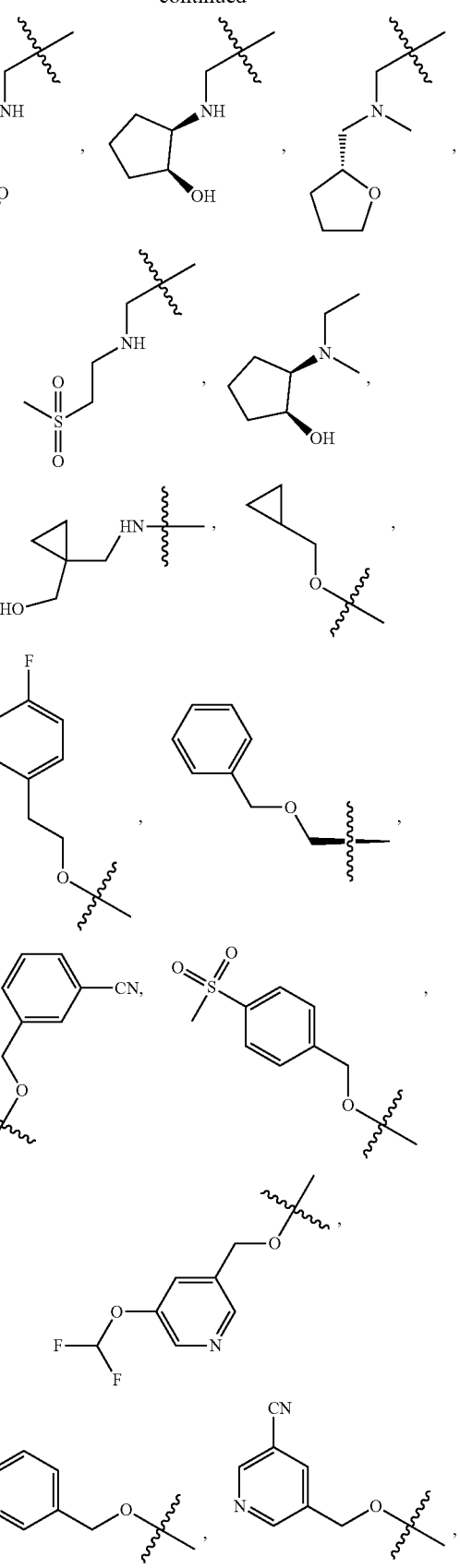

-continued
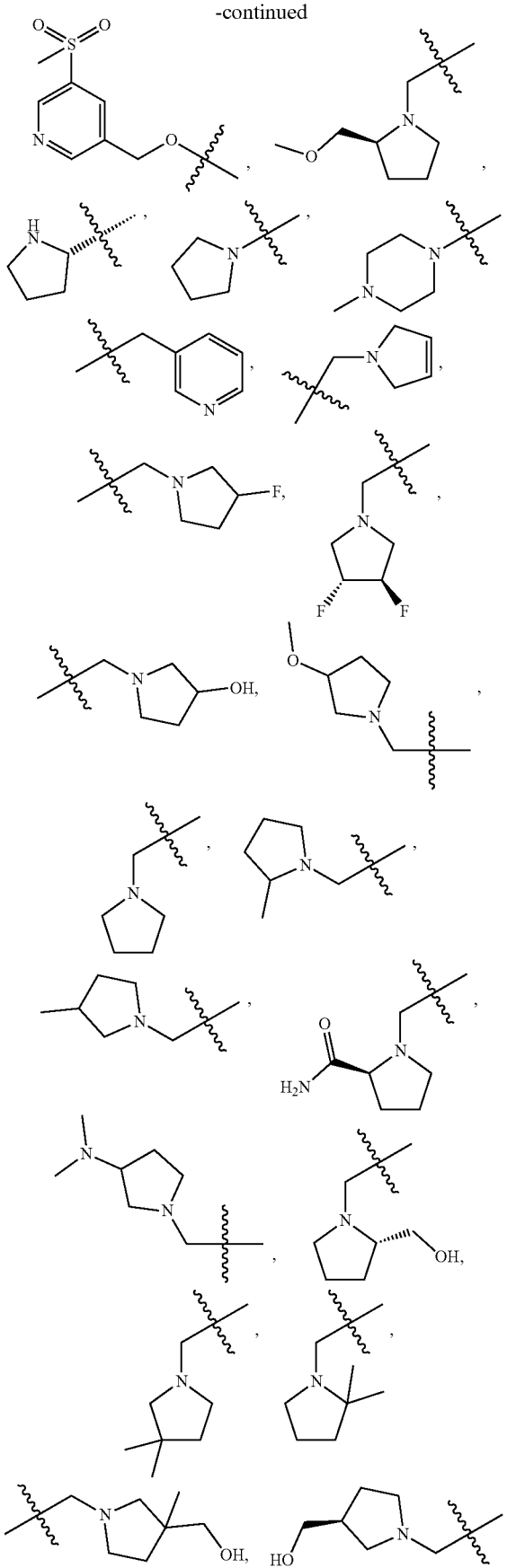
-continued
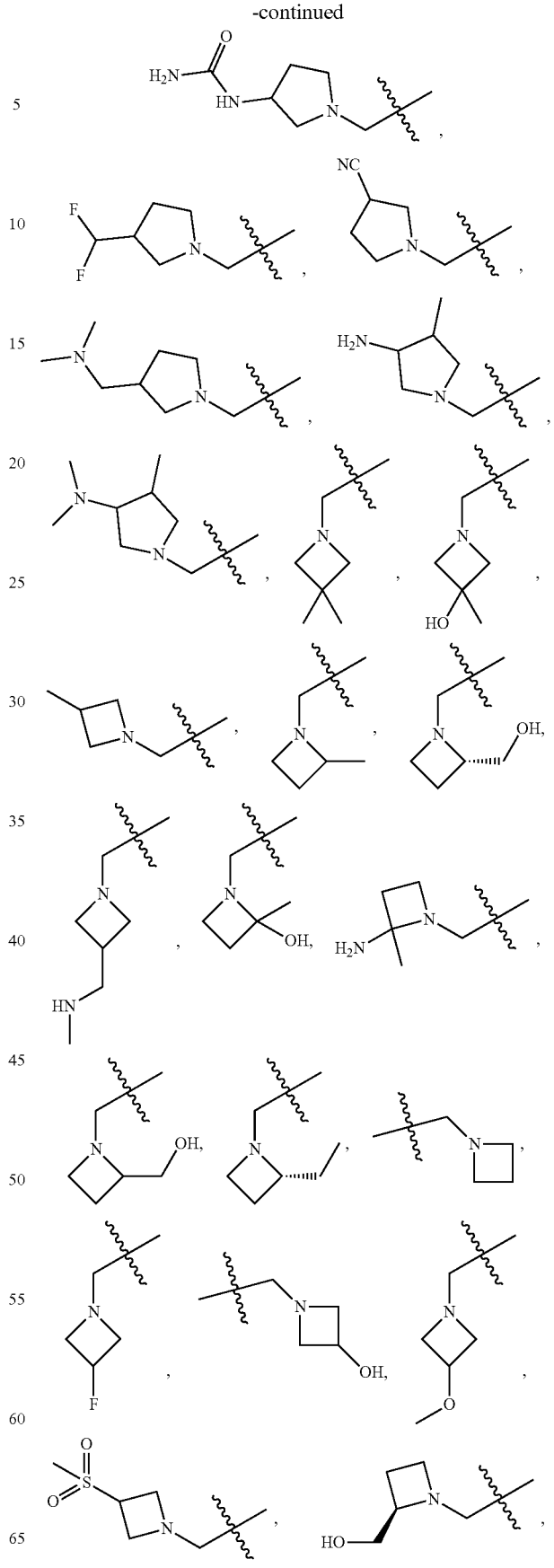

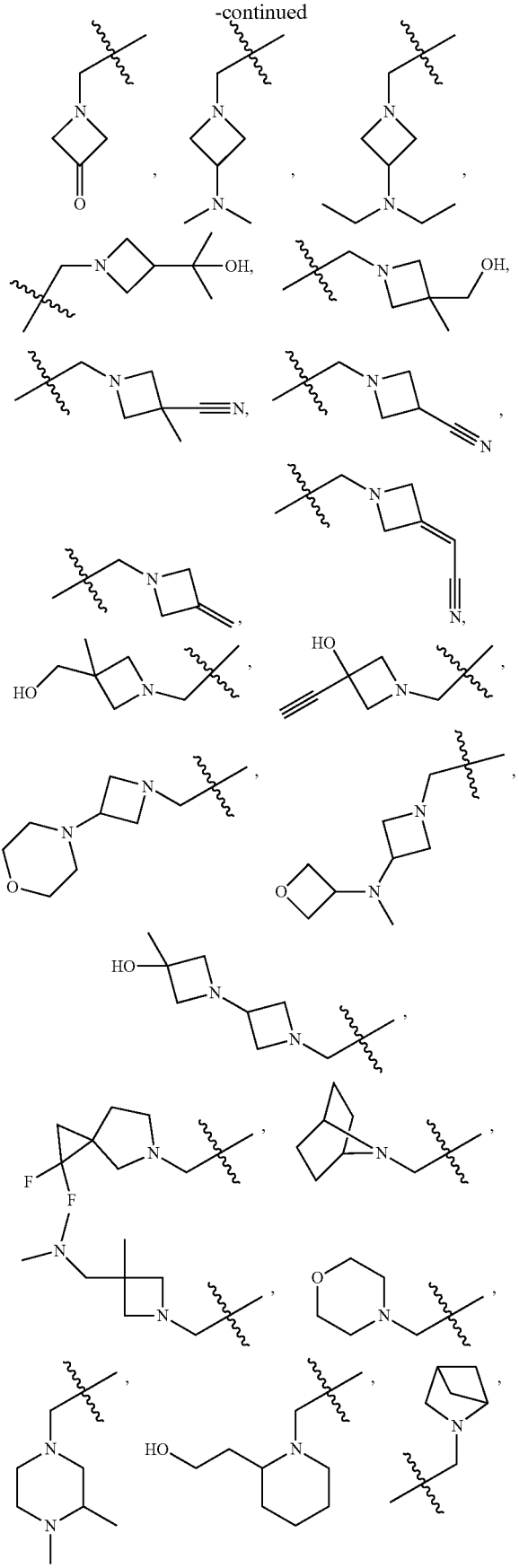
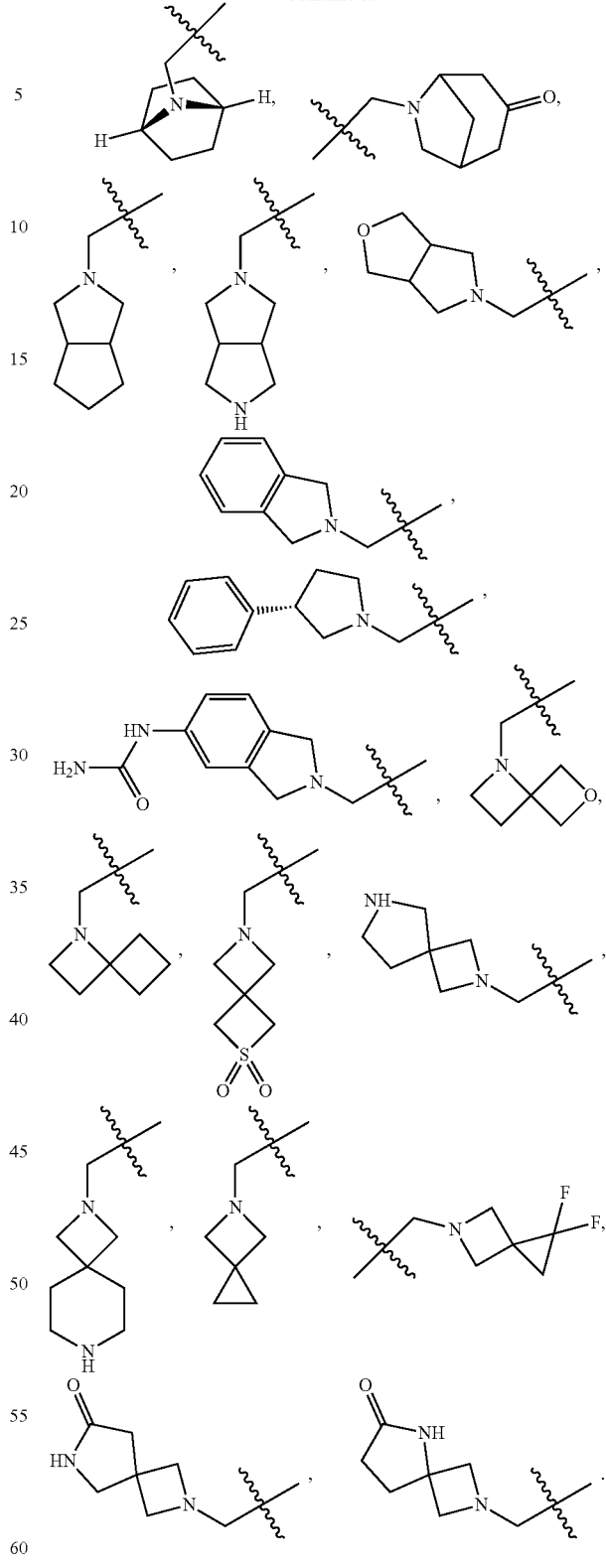
In some embodiments, wherein n is 1, 2 or 3.
In some embodiments, wherein m is 1.
In some embodiments, wherein s is 1.
In some embodiments, wherein q is 1.
In some embodiments, wherein k is 1.

In some embodiments of Formula I, wherein the compound is:
1) ((6-(difluoromethoxy)-2-(3'-(6-(difluoromethoxy)-5-(((((1R,2S)-2-hydroxycyclopentyl)(methyl)amino) methyl)benzo[d]oxazol-2-yl)-2,2'-dimethyl-[1,1'-biphenyl]-3-yl)benzo[d]oxazol-5-yl)methyl)-L-proline;
2) (2'S)-(((2,2'-dimethyl-[1,1'-biphenyl]-3,3'-diyl)bis(6-(difluoromethoxy)benzo[d]oxazole-2,5-diyl))bis(methylene))di-L-proline;
3) ((6-(difluoromethoxy)-2-(3'-(6-(difluoromethoxy)-5-(((S)-2-(methoxycarbonyl)pyrrolidin-1-yl)methyl)benzo[d]oxazol-2-yl)-2,2'-dimethyl-[1,1'-biphenyl]-3-yl)benzo[d]oxazol-5-yl)methyl)-L-proline;
4) ((2-(2'-cyano-3'-(6-(difluoromethoxy)-5-((3,3-dimethylazetidin-1-yl)methyl)benzo[d]oxazol-2-yl)-2-methyl-[1,1'-biphenyl]-3-yl)-6-(difluoromethoxy)benzo[d]oxazol-5-yl)methyl)-L-proline;
5) ((6-(difluoromethoxy)-2-(3'-(6-(difluoromethoxy)-5-(pyrrolidin-1-ylmethyl)benzo[d]oxazol-2-yl)-2,2'-dimethyl-[1,1'-biphenyl]-3-yl)benzo[d]oxazol-5-yl)methyl)-L-proline;
6) ((6-(difluoromethoxy)-2-(3'-(6-(difluoromethoxy)-5-(pyrrolidin-1-ylmethyl)benzo[d]oxazol-2-yl)-2'-fluoro-2-methyl-[1,1'-biphenyl]-3-yl)benzo[d]oxazol-5-yl)methyl)-L-proline;
7) ((6-(difluoromethoxy)-2-(3'-(6-(difluoromethoxy)-5-(((2-hydroxyethyl)amino)methyl)benzo[d]oxazol-2-yl)-2,2'-dimethyl-[1,1'-biphenyl]-3-yl)benzo[d]oxazol-5-yl)methyl)-L-proline;
8) ((2-(3'-(5-(azetidin-1-ylmethyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline;
9) ((6-(difluoromethoxy)-2-(3'-(6-(difluoromethoxy)-5-((3-fluoroazetidin-1-yl)methyl)benzo[d]oxazol-2-yl)-2,2'-dimethyl-[1,1'-biphenyl]-3-yl)benzo[d]oxazol-5-yl)methyl)-L-proline;
10) ((6-(difluoromethoxy)-2-(3'-(6-(difluoromethoxy)-5-((3-fluoropyrrolidin-1-yl)methyl)benzo[d]oxazol-2-yl)-2,2'-dimethyl-[1,1'-biphenyl]-3-yl)benzo[d]oxazol-5-yl)methyl)-L-proline;
11) ((2-(3'-(5-(((S)-2-carbamoylpyrrolidin-1-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline;
12) ((6-(difluoromethoxy)-2-(3'-(6-(difluoromethoxy)-5-(((S)-2-(hydroxymethyl)pyrrolidin-1-yl)methyl)benzo[d]oxazol-2-yl)-2,2'-dimethyl-[1,1'-biphenyl]-3-yl)benzo[d]oxazol-5-yl)methyl)-L-proline;
13) ((6-(difluoromethoxy)-2-(3'-(6-(difluoromethoxy)-5-(morpholinomethyl)benzo[d]oxazol-2-yl)-2,2'-dimethyl-[1,1'-biphenyl]-3-yl)benzo[d]oxazol-5-yl)methyl)-L-proline;
14) ((6-(difluoromethoxy)-2-(3'-(6-(difluoromethoxy)-5-((3-hydroxypyrrolidin-1-yl)methyl)benzo[d]oxazol-2-yl)-2,2'-dimethyl-[1,1'-biphenyl]-3-yl)benzo[d]oxazol-5-yl)methyl)-L-proline;
15) ((6-(difluoromethoxy)-2-(3'-(6-(difluoromethoxy)-5-((methylamino)methyl)benzo[d]oxazol-2-yl)-2,2'-dimethyl-[1,1'-biphenyl]-3-yl)benzo[d]oxazol-5-yl)methyl)-L-proline;
16) ((6-(difluoromethoxy)-2-(3'-(6-(difluoromethoxy)-5-((dimethylamino)methyl)benzo[d]oxazol-2-yl)-2,2'-dimethyl-[1,1'-biphenyl]-3-yl)benzo[d]oxazol-5-yl)methyl)-L-proline;
17) ((6-(difluoromethoxy)-2-(3'-(6-(difluoromethoxy)-5-(((2-hydroxyethyl)(methyl)amino)methyl)benzo[d]oxazol-2-yl)-2,2'-dimethyl-[1,1'-biphenyl]-3-yl)benzo[d]oxazol-5-yl)methyl)-L-proline;
18) ((6-(difluoromethoxy)-2-(3'-(6-(difluoromethoxy)-5-(((3R,4R)-3,4-difluoropyrrolidin-1-yl)methyl)benzo[d]oxazol-2-yl)-2,2'-dimethyl-[1,1'-biphenyl]-3-yl)benzo[d]oxazol-5-yl)methyl)-L-proline;
19) ((6-(difluoromethoxy)-2-(3'-(6-(difluoromethoxy)-5-(((((S)-5-oxopyrrolidin-2-yl)methyl)amino)methyl)benzo[d]oxazol-2-yl)-2,2'-dimethyl-[1,1'-biphenyl]-3-yl)benzo[d]oxazol-5-yl)methyl)-L-proline;
20) ((6-(difluoromethoxy)-2-(3'-(6-(difluoromethoxy)-5-((3-hydroxyazetidin-1-yl)methyl)benzo[d]oxazol-2-yl)-2,2'-dimethyl-[1,1'-biphenyl]-3-yl)benzo[d]oxazol-5-yl)methyl)-L-proline;
21) ((6-(difluoromethoxy)-2-(3'-(6-(difluoromethoxy)-5-((ethylamino)methyl)benzo[d]oxazol-2-yl)-2,2'-dimethyl-[1,1'-biphenyl]-3-yl)benzo[d]oxazol-5-yl)methyl)-L-proline;
22) ((6-(difluoromethoxy)-2-(3'-(6-(difluoromethoxy)-5-(((3,3,3-trifluoro-2-hydroxypropyl)amino)methyl)benzo[d]oxazol-2-yl)-2,2'-dimethyl-[1,1'-biphenyl]-3-yl)benzo[d]oxazol-5-yl)methyl)-L-proline;
23) ((6-(difluoromethoxy)-2-(3'-(6-(difluoromethoxy)-5-((3,4-dimethylpiperazin-1-yl)methyl)benzo[d]oxazol-2-yl)-2,2'-dimethyl-[1,1'-biphenyl]-3-yl)benzo[d]oxazol-5-yl)methyl)-L-proline;
24) ((2-(3'-(5-(aminomethyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline;
25) ((6-(difluoromethoxy)-2-(3'-(6-(difluoromethoxy)-5-(((((1R,2S)-2-hydroxycyclopentyl)amino)methyl)benzo[d]oxazol-2-yl)-2,2'-dimethyl-[1,1'-biphenyl]-3-yl)benzo[d]oxazol-5-yl)methyl)-L-proline;
26) ((6-(difluoromethoxy)-2-(3'-(6-(difluoromethoxy)-5-(((((1R,2S)-2-hydroxycyclopentyl)(methyl)amino) methyl)benzo[d]oxazol-2-yl)-2,2'-dimethyl-[1,1'-biphenyl]-3-yl)benzo[d]oxazol-5-yl)methyl)-D-proline;
27) ((6-(difluoromethoxy)-2-(3'-(6-(difluoromethoxy)-5-(((((1S,2R)-2-hydroxycyclopentyl)amino)methyl)benzo[d]oxazol-2-yl)-2,2'-dimethyl-[1,1'-biphenyl]-3-yl)benzo[d]oxazol-5-yl)methyl)-L-proline;
28) ((6-(difluoromethoxy)-2-(3'-(6-(difluoromethoxy)-5-((oxetan-3-ylamino)methyl)benzo[d]oxazol-2-yl)-2,2'-dimethyl-[1,1'-biphenyl]-3-yl)benzo[d]oxazol-5-yl)methyl)-L-proline;
29) ((6-(difluoromethoxy)-2-(3'-(6-(difluoromethoxy)-5-(((((R)-tetrahydrofuran-2-yl)methyl)amino)methyl)benzo[d]oxazol-2-yl)-2,2'-dimethyl-[1,1'-biphenyl]-3-yl)benzo[d]oxazol-5-yl)methyl)-L-proline;
30) ((6-(difluoromethoxy)-2-(3'-(6-(difluoromethoxy)-5-((methyl(((R)-tetrahydrofuran-2-yl)methyl)amino) methyl)benzo[d]oxazol-2-yl)-2,2'-dimethyl-[1,1'-biphenyl]-3-yl)benzo[d]oxazol-5-yl)methyl)-L-proline;
31) ((6-(difluoromethoxy)-2-(3'-(6-(difluoromethoxy)-5-(((S)-2-(hydroxymethyl)azetidin-1-yl)methyl)benzo[d]oxazol-2-yl)-2,2'-dimethyl-[1,1'-biphenyl]-3-yl)benzo[d]oxazol-5-yl)methyl)-L-proline;
32) ((6-(difluoromethoxy)-2-(3'-(6-(difluoromethoxy)-5-(((2-(methylsulfonyl)ethyl)amino)methyl)benzo[d]oxazol-2-yl)-2,2'-dimethyl-[1,1'-biphenyl]-3-yl)benzo[d]oxazol-5-yl)methyl)-L-proline;
33) ((6-(difluoromethoxy)-2-(3'-(6-(difluoromethoxy)-5-((3-(dimethylamino)azetidin-1-yl)methyl)benzo[d]oxazol-2-yl)-2,2'-dimethyl-[1,1'-biphenyl]-3-yl)benzo[d]oxazol-5-yl)methyl)-L-proline;

34) ((6-(difluoromethoxy)-2-(3'-(6-(difluoromethoxy)-5-((3,3-dimethylazetidin-1-yl)methyl)benzo[d]oxazol-2-yl)-2,2'-dimethyl-[1,1'-biphenyl]-3-yl)benzo[d]oxazol-5-yl)methyl)-L-proline;
35) ((6-(difluoromethoxy)-2-(3'-(6-(difluoromethoxy)-5-(((R)-2-(hydroxymethyl)azetidin-1-yl)methyl)benzo[d]oxazol-2-yl)-2,2'-dimethyl-[1,1'-biphenyl]-3-yl)benzo[d]oxazol-5-yl)methyl)-L-proline;
36) ((6-(difluoromethoxy)-2-(3'-(6-(difluoromethoxy)-5-((2-methylazetidin-1-yl)methyl)benzo[d]oxazol-2-yl)-2,2'-dimethyl-[1,1'-biphenyl]-3-yl)benzo[d]oxazol-5-yl)methyl)-L-proline;
37) ((6-(difluoromethoxy)-2-(3'-(6-(difluoromethoxy)-5-((2-hydroxy-2-methylazetidin-1-yl)methyl)benzo[d]oxazol-2-yl)-2,2'-dimethyl-[1,1'-biphenyl]-3-yl)benzo[d]oxazol-5-yl)methyl)-L-proline;
38) ((6-(difluoromethoxy)-2-(3'-(6-(difluoromethoxy)-5-((2-methylpyrrolidin-1-yl)methyl)benzo[d]oxazol-2-yl)-2,2'-dimethyl-[1,1'-biphenyl]-3-yl)benzo[d]oxazol-5-yl)methyl)-L-proline;
39) ((2-(3'-(5-((6-oxa-1-azaspiro[3.3]heptan-1-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline;
40) ((2-(3'-(5-((2-amino-2-methylazetidin-1-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline;
41) ((6-(difluoromethoxy)-2-(3'-(6-(difluoromethoxy)-5-((3-(methylsulfonyl)azetidin-1-yl)methyl)benzo[d]oxazol-2-yl)-2,2'-dimethyl-[1,1'-biphenyl]-3-yl)benzo[d]oxazol-5-yl)methyl)-L-proline;
42) ((6-(difluoromethoxy)-2-(3'-(6-(difluoromethoxy)-5-(((R)-2-ethylazetidin-1-yl)methyl)benzo[d]oxazol-2-yl)-2,2'-dimethyl-[1,1'-biphenyl]-3-yl)benzo[d]oxazol-5-yl)methyl)-L-proline;
43) ((6-(difluoromethoxy)-2-(3'-(6-(difluoromethoxy)-5-((3-methoxyazetidin-1-yl)methyl)benzo[d]oxazol-2-yl)-2,2'-dimethyl-[1,1'-biphenyl]-3-yl)benzo[d]oxazol-5-yl)methyl)-L-proline;
44) ((6-(difluoromethoxy)-2-(3'-(6-(difluoromethoxy)-5-((3-hydroxy-3-methylazetidin-1-yl)methyl)benzo[d]oxazol-2-yl)-2,2'-dimethyl-[1,1'-biphenyl]-3-yl)benzo[d]oxazol-5-yl)methyl)-L-proline;
45) ((6-(difluoromethoxy)-2-(3'-(6-(difluoromethoxy)-5-((3-((methylamino)methyl)azetidin-1-yl)methyl)benzo[d]oxazol-2-yl)-2,2'-dimethyl-[1,1'-biphenyl]-3-yl)benzo[d]oxazol-5-yl)methyl)-L-proline;
46) ((6-(difluoromethoxy)-2-(3'-(6-(difluoromethoxy)-5-((3-oxoazetidin-1-yl)methyl)benzo[d]oxazol-2-yl)-2,2'-dimethyl-[1,1'-biphenyl]-3-yl)benzo[d]oxazol-5-yl)methyl)-L-proline;
47) ((2-(3'-(5-((2-oxa-6-azaspiro[3.3]heptan-6-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline;
48) ((2-(3'-(5-((2-azaspiro[3.3]heptan-2-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline;
49) ((6-(difluoromethoxy)-2-(3'-(6-(difluoromethoxy)-5-((hexahydrocyclopenta[c]pyrrol-2(1H)-yl)methyl)benzo[d]oxazol-2-yl)-2,2'-dimethyl-[1,1'-biphenyl]-3-yl)benzo[d]oxazol-5-yl)methyl)-L-proline;
50) ((6-(difluoromethoxy)-2-(3'-(6-(difluoromethoxy)-5-((hexahydropyrrolo[3,4-c]pyrrol-2(1H)-yl)methyl)benzo[d]oxazol-2-yl)-2,2'-dimethyl-[1,1'-biphenyl]-3-yl)benzo[d]oxazol-5-yl)methyl)-L-proline;
51) ((2-(3'-(5-((2,7-diazaspiro[3.5]nonan-2-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline;
52) ((6-(difluoromethoxy)-2-(3'-(6-(difluoromethoxy)-5-(((3-(propylamino)propyl)amino)methyl)benzo[d]oxazol-2-yl)-2,2'-dimethyl-[1,1'-biphenyl]-3-yl)benzo[d]oxazol-5-yl)methyl)-L-proline;
53) ((6-(difluoromethoxy)-2-(3'-(6-(difluoromethoxy)-5-((methyl(3-(propylamino)propyl)amino)methyl)benzo[d]oxazol-2-yl)-2,2'-dimethyl-[1,1'-biphenyl]-3-yl)benzo[d]oxazol-5-yl)methyl)-L-proline;
54) ((6-(difluoromethoxy)-2-(3'-(6-(difluoromethoxy)-5-((2,2-dioxido-2-thia-6-azaspiro[3.3]heptan-6-yl)methyl)benzo[d]oxazol-2-yl)-2,2'-dimethyl-[1,1'-biphenyl]-3-yl)benzo[d]oxazol-5-yl)methyl)-L-proline;
55) ((6-(difluoromethoxy)-2-(3'-(6-(difluoromethoxy)-5-((tetrahydro-1H-furo[3,4-c]pyrrol-5(3H)-yl)methyl)benzo[d]oxazol-2-yl)-2,2'-dimethyl-[1,1'-biphenyl]-3-yl)benzo[d]oxazol-5-yl)methyl)-L-proline;
56) ((6-(difluoromethoxy)-2-(3'-(6-(difluoromethoxy)-5-((3-methylazetidin-1-yl)methyl)benzo[d]oxazol-2-yl)-2,2'-dimethyl-[1,1'-biphenyl]-3-yl)benzo[d]oxazol-5-yl)methyl)-L-proline;
57) ((6-(difluoromethoxy)-2-(3'-(6-(difluoromethoxy)-5-(((((1R,2R)-2-hydroxycyclopentyl)(methyl)amino)methyl)benzo[d]oxazol-2-yl)-2,2'-dimethyl-[1,1'-biphenyl]-3-yl)benzo[d]oxazol-5-yl)methyl)-L-proline;
58) ((6-(difluoromethoxy)-2-(3'-(6-(difluoromethoxy)-5-(((3-((2-hydroxyethyl)amino)propyl)amino)methyl)benzo[d]oxazol-2-yl)-2,2'-dimethyl-[1,1'-biphenyl]-3-yl)benzo[d]oxazol-5-yl)methyl)-L-proline;
59) ((6-(difluoromethoxy)-2-(3'-(6-(difluoromethoxy)-5-(((2-(dimethylamino)ethyl)(methyl)amino)methyl)benzo[d]oxazol-2-yl)-2,2'-dimethyl-[1,1'-biphenyl]-3-yl)benzo[d]oxazol-5-yl)methyl)-L-proline;
60) ((6-(difluoromethoxy)-2-(3'-(6-(difluoromethoxy)-5-((2-methylazetidin-1-yl)methyl)benzo[d]oxazol-2-yl)-2,2'-dimethyl-[1,1'-biphenyl]-3-yl)benzo[d]oxazol-5-yl)methyl)-L-proline;
61) ((6-(difluoromethoxy)-2-(3'-(6-(difluoromethoxy)-5-((3-methylpyrrolidin-1-yl)methyl)benzo[d]oxazol-2-yl)-2,2'-dimethyl-[1,1'-biphenyl]-3-yl)benzo[d]oxazol-5-yl)methyl)-L-proline;
62) ((6-(difluoromethoxy)-2-(3'-(6-(difluoromethoxy)-5-((2,2-dimethylpyrrolidin-1-yl)methyl)benzo[d]oxazol-2-yl)-2,2'-dimethyl-[1,1'-biphenyl]-3-yl)benzo[d]oxazol-5-yl)methyl)-L-proline;
63) ((6-(difluoromethoxy)-2-(3'-(6-(difluoromethoxy)-5-(((S)-2-(methoxymethyl)pyrrolidin-1-yl)methyl)benzo[d]oxazol-2-yl)-2,2'-dimethyl-[1,1'-biphenyl]-3-yl)benzo[d]oxazol-5-yl)methyl)-L-proline;
64) ((6-(difluoromethoxy)-2-(3'-(6-(difluoromethoxy)-5-(((((S)-tetrahydrofuran-2-yl)methyl)amino)methyl)benzo[d]oxazol-2-yl)-2,2'-dimethyl-[1,1'-biphenyl]-3-yl)benzo[d]oxazol-5-yl)methyl)-L-proline;
65) ((2-(2'-cyano-3'-(6-(difluoromethoxy)-5-(pyrrolidin-1-ylmethyl)benzo[d]oxazol-2-yl)-2-methyl-[1,1'-biphenyl]-3-yl)-6-(difluoromethoxy)benzo[d]oxazol-5-yl)methyl)proline;
66) ((6-(difluoromethoxy)-2-(3'-(6-(difluoromethoxy)-5-(pyrrolidin-1-ylmethyl)benzo[d]oxazol-2-yl)-2,2'-dimethyl-[1,1'-biphenyl]-3-yl)benzo[d]oxazol-5-yl)methyl)-D-proline;

67) ((6-(difluoromethoxy)-2-(3'-(6-(difluoromethoxy)-5-((3,3-dimethylpyrrolidin-1-yl)methyl)benzo[d]oxazol-2-yl)-2,2'-dimethyl-[1,1'-biphenyl]-3-yl)benzo[d]oxazol-5-yl)methyl)-L-proline;

68) ((2-(3'-(5-((3-(diethylamino)azetidin-1-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline;

69) ((6-(difluoromethoxy)-2-(3'-(6-(difluoromethoxy)-5-((3-(2-hydroxypropan-2-yl)azetidin-1-yl)methyl)benzo[d]oxazol-2-yl)-2,2'-dimethyl-[1,1'-biphenyl]-3-yl)benzo[d]oxazol-5-yl)methyl)-L-proline;

70) ((6-(difluoromethoxy)-2-(3'-(6-(difluoromethoxy)-5-((2,5-dihydro-1H-pyrrol-1-yl)methyl)benzo[d]oxazol-2-yl)-2,2'-dimethyl-[1,1'-biphenyl]-3-yl)benzo[d]oxazol-5-yl)methyl)-L-proline;

71) ((2-(3'-(5-((2-azabicyclo[2.1.1]hexan-2-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline;

72) ((2-(3'-(5-(((1s,4s)-7-azabicyclo[2.2.1]heptan-7-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline;

73) ((2-(3'-(5-((((3,3-difluoro-1-(hydroxymethyl)cyclobutyl)methyl)amino)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline;

74) ((2-(3'-(5-((5-azaspiro[2.3]hexan-5-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline;

75) ((6-(difluoromethoxy)-2-(3'-(6-(difluoromethoxy)-5-((3-oxo-6-azabicyclo[3.2.1]octan-6-yl)methyl)benzo[d]oxazol-2-yl)-2,2'-dimethyl-[1,1'-biphenyl]-3-yl)benzo[d]oxazol-5-yl)methyl)-L-proline;

76) ((2-(3'-(5-((1,1-difluoro-5-azaspiro[2.3]hexan-5-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline;

77) ((6-(difluoromethoxy)-2-(3'-(6-(difluoromethoxy)-5-((3-(hydroxymethyl)-3-methylpyrrolidin-1-yl)methyl)benzo[d]oxazol-2-yl)-2,2'-dimethyl-[1,1'-biphenyl]-3-yl)benzo[d]oxazol-5-yl)methyl)-L-proline;

78) ((6-(difluoromethoxy)-2-(3'-(6-(difluoromethoxy)-5-((3-(hydroxymethyl)-3-methylazetidin-1-yl)methyl)benzo[d]oxazol-2-yl)-2,2'-dimethyl-[1,1'-biphenyl]-3-yl)benzo[d]oxazol-5-yl)methyl)-L-proline;

79) ((2-(3'-(5-((3-cyano-3-methylazetidin-1-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline;

80) ((2-(3'-(5-((3-cyanoazetidin-1-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline;

81) ((6-(difluoromethoxy)-2-(3'-(6-(difluoromethoxy)-5-((3-methyleneazetidin-1-yl)methyl)benzo[d]oxazol-2-yl)-2,2'-dimethyl-[1,1'-biphenyl]-3-yl)benzo[d]oxazol-5-yl)methyl)-L-proline;

82) ((2-(3'-(5-((3-(cyanomethylene)azetidin-1-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline;

83) ((2-(2,2'-dicyano-3'-(6-(difluoromethoxy)-5-((3,3-dimethylazetidin-1-yl)methyl)benzo[d]oxazol-2-yl)-[1,1'-biphenyl]-3-yl)-6-(difluoromethoxy)benzo[d]oxazol-5-yl)methyl)-L-proline;

84) ((6-(difluoromethoxy)-2-(3'-(5-((3,4-dimethylpyrrolidin-1-yl)methyl)-7-(trifluoromethyl)benzo[d]oxazol-2-yl)-2,2'-dimethyl-[1,1'-biphenyl]-3-yl)benzo[d]oxazol-5-yl)methyl)-L-proline;

85) (R)-1-((6-(difluoromethoxy)-2-(3'-(6-(difluoromethoxy)-5-((3,3-dimethylazetidin-1-yl)methyl)benzo[d]oxazol-2-yl)-2,2'-dimethyl-[1,1'-biphenyl]-3-yl)benzo[d]oxazol-5-yl)methyl)pyrrolidine-3-carboxylic acid;

86) (S)-1-((6-(difluoromethoxy)-2-(3'-(6-(difluoromethoxy)-5-((3,3-dimethylazetidin-1-yl)methyl)benzo[d]oxazol-2-yl)-2,2'-dimethyl-[1,1'-biphenyl]-3-yl)benzo[d]oxazol-5-yl)methyl)pyrrolidine-3-carboxylic acid;

87) ((2-(2'-cyano-3'-(6-(difluoromethoxy)-5-((3,3-dimethylazetidin-1-yl)methyl)benzo[d]oxazol-2-yl)-2-methyl-[1,1'-biphenyl]-3-yl)-6-(difluoromethoxy)benzo[d]oxazol-5-yl)methyl)-D-proline;

88) ((6-(difluoromethoxy)-2-(2,2'-dimethyl-3'-(5-((3-methylpyrrolidin-1-yl)methyl)-7-(trifluoromethyl)benzo[d]oxazol-2-yl)-[1,1'-biphenyl]-3-yl)benzo[d]oxazol-5-yl)methyl)-L-proline;

89) ((2-(3'-(5-((2-azabicyclo[2.1.1]hexan-2-yl)methyl)-7-(trifluoromethyl)benzo[d]oxazol-2-yl)-2,2'-dimethyl-[1,1'-biphenyl]-3-yl)-6-(difluoromethoxy)benzo[d]oxazol-5-yl)methyl)-L-proline;

90) ((6-(difluoromethoxy)-2-(2,2'-dimethyl-3'-(5-((3-methylpyrrolidin-1-yl)methyl)-7-(trifluoromethyl)benzo[d]oxazol-2-yl)-[1,1'-biphenyl]-3-yl)benzo[d]oxazol-5-yl)methyl)-D-proline;

91) (3R)-1-((6-(difluoromethoxy)-2-(2,2'-dimethyl-3'-(5-((3-methylpyrrolidin-1-yl)methyl)-7-(trifluoromethyl)benzo[d]oxazol-2-yl)-[1,1'-biphenyl]-3-yl)benzo[d]oxazol-5-yl)methyl)pyrrolidine-3-carboxylic acid;

92) (3S)-1-((6-(difluoromethoxy)-2-(2,2'-dimethyl-3'-(5-((3-methylpyrrolidin-1-yl)methyl)-7-(trifluoromethyl)benzo[d]oxazol-2-yl)-[1,1'-biphenyl]-3-yl)benzo[d]oxazol-5-yl)methyl)pyrrolidine-3-carboxylic acid;

93) ((6-(difluoromethoxy)-2-(3'-(5-((3,3-dimethylazetidin-1-yl)methyl)-7-(trifluoromethyl)benzo[d]oxazol-2-yl)-2,2'-dimethyl-[1,1'-biphenyl]-3-yl)benzo[d]oxazol-5-yl)methyl)-L-proline;

94) ((2-(3'-(5-(azetidin-1-ylmethyl)-7-methylbenzo[d]oxazol-2-yl)-2,2'-dimethyl-[1,1'-biphenyl]-3-yl)-6-(difluoromethoxy)benzo[d]oxazol-5-yl)methyl)-L-proline;

95) ((6-(difluoromethoxy)-2-(3'-(7-fluoro-5-(pyrrolidin-1-ylmethyl)benzo[d]oxazol-2-yl)-2,2'-dimethyl-[1,1'-biphenyl]-3-yl)benzo[d]oxazol-5-yl)methyl)-L-proline;

96) ((6-(difluoromethoxy)-2-(3'-(5-((ethylamino)methyl)-6-fluorobenzo[d]oxazol-2-yl)-2,2'-dimethyl-[1,1'-biphenyl]-3-yl)benzo[d]oxazol-5-yl)methyl)-L-proline;

97) ((2-(3'-(6-chloro-5-((ethylamino)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

98) ((6-(difluoromethoxy)-2-(2,2'-dimethyl-3'-(5-(pyrrolidin-1-ylmethyl)benzo[d]oxazol-2-yl)-[1,1'-biphenyl]-3-yl)benzo[d]oxazol-5-yl)methyl)-L-proline;

99) ((6-(difluoromethoxy)-2-(3'-(5-((((1R,2S)-2-hydroxycyclopentyl)amino)methyl)benzo[d]oxazol-2-yl)-2,2'-dimethyl-[1,1'-biphenyl]-3-yl)benzo[d]oxazol-5-yl)methyl)-L-proline;

100) ((6-(difluoromethoxy)-2-(2,2'-dimethyl-3'-(5-(pyrrolidin-1-ylmethyl)-7-(trifluoromethyl)benzo[d]oxazol-2-yl)-[1,1'-biphenyl]-3-yl)benzo[d]oxazol-5-yl)methyl)-L-proline;

101) ((6-(difluoromethoxy)-2-(2,2'-dimethyl-3'-(5-(pyrrolidin-1-ylmethyl)-6-(trifluoromethyl)benzo[d]oxazol-2-yl)-[1,1'-biphenyl]-3-yl)benzo[d]oxazol-5-yl)methyl)-L-proline;

102) ((2-(3'-(6,7-difluoro-5-(pyrrolidin-1-ylmethyl)benzo[d]oxazol-2-yl)-2,2'-dimethyl-[1,1'-biphenyl]-3-yl)-6-(difluoromethoxy)benzo[d]oxazol-5-yl)methyl)-L-proline;

103) ((2-(3'-(7-cyano-5-((3,3-dimethylazetidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

104) ((6-(difluoromethoxy)-2-(3'-(5-((2-hydroxy-2-methylazetidin-1-yl)methyl)benzo[d]oxazol-2-yl)-2,2'-dimethyl-[1,1'-biphenyl]-3-yl)benzo[d]oxazol-5-yl)methyl)-L-proline;

105) ((6-(difluoromethoxy)-2-(3'-(5-((2-(hydroxymethyl)azetidin-1-yl)methyl)benzo[d]oxazol-2-yl)-2,2'-dimethyl-[1,1'-biphenyl]-3-yl)benzo[d]oxazol-5-yl)methyl)-L-proline;

106) ((2-(3'-(5-((6-oxa-1-azaspiro[3.3]heptan-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

107) ((2-(3'-(5-((1-azaspiro[3.3]heptan-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

108) ((6-(difluoromethoxy)-2-(2,2'-dimethyl-3'-(6-(pyrrolidin-1-ylmethyl)benzo[d]oxazol-2-yl)-[1,1'-biphenyl]-3-yl)benzo[d]oxazol-5-yl)methyl)-L-proline;

109) ((6-(difluoromethoxy)-2-(3'-(6-((3,3-dimethylazetidin-1-yl)methyl)benzo[d]oxazol-2-yl)-2,2'-dimethyl-[1,1'-biphenyl]-3-yl)benzo[d]oxazol-5-yl)methyl)-L-proline;

110) ((2-(2'-chloro-3'-(6-((3,3-dimethylazetidin-1-yl)methyl)benzo[d]oxazol-2-yl)-2-methyl-[1,1'-biphenyl]-3-yl)-6-(difluoromethoxy)benzo[d]oxazol-5-yl)methyl)-L-proline;

111) ((2-(2'-chloro-3'-(6-((3,3-dimethylazetidin-1-yl)methyl)benzo[d]oxazol-2-yl)-2-methyl-[1,1'-biphenyl]-3-yl)-6-(difluoromethoxy)benzo[d]oxazol-5-yl)methyl)-D-proline;

112) ((6-(difluoromethoxy)-2-(2,2'-dimethyl-3'-(6-(pyrrolidin-1-ylmethyl)oxazolo[5,4-b]pyridin-2-yl)-[1,1'-biphenyl]-3-yl)benzo[d]oxazol-5-yl)methyl)-L-proline;

113) ((6-(difluoromethoxy)-2-(3'-(6-((3,3-dimethylazetidin-1-yl)methyl)oxazolo[5,4-b]pyridin-2-yl)-2,2'-dimethyl-[1,1'-biphenyl]-3-yl)benzo[d]oxazol-5-yl)methyl)-L-proline;

114) ((6-(difluoromethoxy)-2-(2,2'-dimethyl-3'-(6-(((R)-3-methylpyrrolidin-1-yl)methyl)oxazolo[5,4-b]pyridin-2-yl)-[1,1'-biphenyl]-3-yl)benzo[d]oxazol-5-yl)methyl)-L-proline;

115) ((6-(difluoromethoxy)-2-(2,2'-dimethyl-3'-(6-((((5-oxopyrrolidin-2-yl)methyl)amino)methyl)oxazolo[5,4-b]pyridin-2-yl)-[1,1'-biphenyl]-3-yl)benzo[d]oxazol-5-yl)methyl)-L-proline;

116) ((6-(difluoromethoxy)-2-(3'-(6-((3-(dimethylamino)azetidin-1-yl)methyl)oxazolo[5,4-b]pyridin-2-yl)-2,2'-dimethyl-[1,1'-biphenyl]-3-yl)benzo[d]oxazol-5-yl)methyl)-L-proline;

117) ((2-(3'-(6,7-difluoro-5-(pyrrolidin-1-ylmethyl)benzo[d]oxazol-2-yl)-2'-methoxy-2-methyl-[1,1'-biphenyl]-3-yl)-6-(difluoromethoxy)benzo[d]oxazol-5-yl)methyl)-L-proline;

118) ((2-(2'-cyano-3'-(6,7-difluoro-5-(pyrrolidin-1-ylmethyl)benzo[d]oxazol-2-yl)-2-methyl-[1,1'-biphenyl]-3-yl)-6-(difluoromethoxy)benzo[d]oxazol-5-yl)methyl)-L-proline;

119) ((2-(3'-(6-((6-cyanopyridin-3-yl)methoxy)-5-(((2-hydroxyethyl)amino)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

120) ((2-(3'-(6-((5-cyanopyridin-3-yl)methoxy)-5-(((2-hydroxyethyl)amino)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

121) ((6-(difluoromethoxy)-2-(3'-(5-(((2-hydroxyethyl)amino)methyl)-6-((5-(methylsulfonyl)pyridin-3-yl)methoxy)benzo[d]oxazol-2-yl)-2,2'-dimethyl-[1,1'-biphenyl]-3-yl)benzo[d]oxazol-5-yl)methyl)-L-proline;

122) ((6-(difluoromethoxy)-2-(3'-(5-((ethylamino)methyl)-6-((5-(methylsulfonyl)pyridin-3-yl)methoxy)benzo[d]oxazol-2-yl)-2,2'-dimethyl-[1,1'-biphenyl]-3-yl)benzo[d]oxazol-5-yl)methyl)-L-proline;

123) ((6-(difluoromethoxy)-2-(3'-(5-((dimethylamino)methyl)-6-((5-(methylsulfonyl)pyridin-3-yl)methoxy)benzo[d]oxazol-2-yl)-2,2'-dimethyl-[1,1'-biphenyl]-3-yl)benzo[d]oxazol-5-yl)methyl)-L-proline;

124) ((6-(difluoromethoxy)-2-(2,2'-dimethyl-3'-(5-((methylamino)methyl)-6-((3-(methylsulfonyl)benzyl)oxy)benzo[d]oxazol-2-yl)-[1,1'-biphenyl]-3-yl)benzo[d]oxazol-5-yl)methyl)-L-proline;

125) ((6-(difluoromethoxy)-2-(2,2'-dimethyl-3'-(5-((methylamino)methyl)-6-((4-(methylsulfonyl)benzyl)oxy)benzo[d]oxazol-2-yl)-[1,1'-biphenyl]-3-yl)benzo[d]oxazol-5-yl)methyl)-L-proline;

126) ((6-(difluoromethoxy)-2-(3'-(5-((dimethylamino)methyl)-6-((4-(methylsulfonyl)benzyl)oxy)benzo[d]oxazol-2-yl)-2,2'-dimethyl-[1,1'-biphenyl]-3-yl)benzo[d]oxazol-5-yl)methyl)-L-proline;

127) ((2-(3'-(7-cyano-5-(pyrrolidin-1-ylmethyl)benzo[d]oxazol-2-yl)-2,2'-dimethyl-[1,1'-biphenyl]-3-yl)-6-(difluoromethoxy)benzo[d]oxazol-5-yl)methyl)-L-proline;

128) ((2-(2-cyano-3'-(6-(difluoromethoxy)-5-((3,3-dimethylazetidin-1-yl)methyl)benzo[d]oxazol-2-yl)-2'-methyl-[1,1'-biphenyl]-3-yl)-6-(difluoromethoxy)benzo[d]oxazol-5-yl)methyl)-L-proline;

129) ((2-(3'-(7-cyano-5-((3-(hydroxymethyl)-3-methylazetidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

130) ((2-(3'-(7-cyano-5-(((S)-3-methylpyrrolidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

131) ((2-(3'-(7-cyano-5-(((R)-3-methylpyrrolidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

132) ((2-(3'-(7-cyano-5-(((R)-3-methylpyrrolidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-D-proline;

133) ((2-(3'-(7-cyano-5-(((3-methyloxetan-3-yl)amino)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

134) ((2-(3'-(7-cyano-5-((3-(dimethylamino)azetidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

135) ((2-(3'-(7-cyano-5-((2-(2-hydroxyethyl)piperidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

136) ((2-(3'-(7-cyano-5-(((cyanomethyl)(methyl)amino) methyl)benzo[d]oxazol-2-yl)-2,2'-dimethyl-[1,1'-biphenyl]-3-yl)-6-(difluoromethoxy)benzo[d]oxazol-5-yl) methyl)-L-proline;

137) ((2-(3'-(7-cyano-5-((3-(hydroxymethyl)azetidin-1-yl) methyl)benzo[d]oxazol-2-yl)-2,2'-dimethyl-[1,1'-biphenyl]-3-yl)-6-(difluoromethoxy)benzo[d]oxazol-5-yl) methyl)-L-proline;

138) ((2-(3'-(7-cyano-5-(((2-hydroxy-2-methylpropyl) amino)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

139) ((2-(3'-(7-cyano-5-((((5-oxopyrrolidin-2-yl)methyl) amino)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

140) ((2-(3'-(7-cyano-5-((3,3-dimethylazetidin-1-yl)methyl) benzo[d]oxazol-2-yl)-2,2'-dimethyl-[1,1'-biphenyl]-3-yl)-6-(difluoromethoxy)benzo[d]oxazol-5-yl)methyl)-D-proline;

141) ((2-(3'-(7-cyano-5-((ethyl(2-hydroxyethyl)amino) methyl)benzo[d]oxazol-2-yl)-2,2'-dimethyl-[1,1'-biphenyl]-3-yl)-6-(difluoromethoxy)benzo[d]oxazol-5-yl) methyl)-L-proline;

142) ((2-(3'-(7-cyano-5-((3-cyanopyrrolidin-1-yl)methyl) benzo[d]oxazol-2-yl)-2,2'-dimethyl-[1,1'-biphenyl]-3-yl)-6-(difluoromethoxy)benzo[d]oxazol-5-yl)methyl)-L-proline;

143) ((2-(3'-(7-cyano-5-((3-cyanopyrrolidin-1-yl)methyl) benzo[d]oxazol-2-yl)-2,2'-dimethyl-[1,1'-biphenyl]-3-yl)-6-(difluoromethoxy)benzo[d]oxazol-5-yl)methyl)-D-proline;

144) ((2-(3'-(7-cyano-5-((3-ethynyl-3-hydroxyazetidin-1-yl)methyl)benzo[d]oxazol-2-yl)-2,2'-dimethyl-[1,1'-biphenyl]-3-yl)-6-(difluoromethoxy)benzo[d]oxazol-5-yl) methyl)-L-proline;

145) ((2-(3'-(7-cyano-5-(pyrrolidin-1-ylmethyl)benzo[d] oxazol-2-yl)-2,2'-dimethyl-[1,1'-biphenyl]-3-yl)-6-(difluoromethoxy)benzo[d]oxazol-5-yl)methyl)-D-proline;

146) ((2-(3'-(7-cyano-5-((7-oxo-2,6-diazaspiro[3.4]octan-2-yl)methyl)benzo[d]oxazol-2-yl)-2,2'-dimethyl-[1,1'-biphenyl]-3-yl)-6-(difluoromethoxy)benzo[d]oxazol-5-yl) methyl)-L-proline;

147) ((2-(3'-(5-((bis(1-hydroxypropan-2-yl)amino)methyl)-7-cyanobenzo[d]oxazol-2-yl)-2,2'-dimethyl-[1,1'-biphenyl]-3-yl)-6-(difluoromethoxy)benzo[d]oxazol-5-yl) methyl)-L-proline;

148) ((2-(3'-(7-cyano-5-((3-morpholinoazetidin-1-yl) methyl)benzo[d]oxazol-2-yl)-2,2'-dimethyl-[1,1'-biphenyl]-3-yl)-6-(difluoromethoxy)benzo[d]oxazol-5-yl) methyl)-L-proline;

149) ((2-(3'-(7-cyano-5-((3-(methyl(oxetan-3-yl)amino)azetidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

150) ((2-(3'-(7-cyano-5-((3-hydroxy-3-methyl-[1,3'-biazetidin]-1'-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

151) ((2-(3'-(7-cyano-5-((6-oxo-2,5-diazaspiro[3.4]octan-2-yl)methyl)benzo[d]oxazol-2-yl)-2,2'-dimethyl-[1,1'-biphenyl]-3-yl)-6-(difluoromethoxy)benzo[d]oxazol-5-yl) methyl)-L-proline;

152) ((2-(3'-(7-cyano-5-((3-((dimethylamino)methyl)pyrrolidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

153) ((2-(3'-(7-cyano-5-((1,1-difluoro-5-azaspiro[2.4]heptan-5-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

154) ((2-(3'-(7-cyano-5-(((R)-3-(hydroxymethyl)pyrrolidin-1-yl)methyl)benzo[d]oxazol-2-yl)-2,2'-dimethyl-[1,1'-biphenyl]-3-yl)-6-(difluoromethoxy)benzo[d]oxazol-5-yl) methyl)-L-proline;

155) ((2-(3'-(7-cyano-5-(((3-hydroxycyclobutyl)amino) methyl)benzo[d]oxazol-2-yl)-2,2'-dimethyl-[1,1'-biphenyl]-3-yl)-6-(difluoromethoxy)benzo[d]oxazol-5-yl) methyl)-L-proline;

156) ((2-(3'-(5-((3-amino-4-methylpyrrolidin-1-yl)methyl)-7-cyanobenzo[d]oxazol-2-yl)-2,2'-dimethyl-[1,1'-biphenyl]-3-yl)-6-(difluoromethoxy)benzo[d]oxazol-5-yl) methyl)-L-proline;

157) ((2-(3'-(5-(((azetidin-3-ylmethyl)amino)methyl)-7-cyanobenzo[d]oxazol-2-yl)-2,2'-dimethyl-[1,1'-biphenyl]-3-yl)-6-(difluoromethoxy)benzo[d]oxazol-5-yl) methyl)-L-proline;

158) ((2-(3'-(7-cyano-5-((3-(dimethylamino)-4-methylpyrrolidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

159) ((2-(3'-(7-cyano-5-((3-((dimethylamino)methyl)-3-methylazetidin-1-yl)methyl)benzo[d]oxazol-2-yl)-2,2'-dimethyl-[1,1'-biphenyl]-3-yl)-6-(difluoromethoxy) benzo[d]oxazol-5-yl)methyl)-L-proline;

160) ((2-(3'-(7-cyano-5-((((1-methyl-1H-imidazol-4-yl) methyl)amino)methyl)benzo[d]oxazol-2-yl)-2,2'-dimethyl-[1,1'-biphenyl]-3-yl)-6-(difluoromethoxy)benzo[d] oxazol-5-yl)methyl)-L-proline;

161) ((2-(3'-(5-((3-(aminomethyl)-3-methylazetidin-1-yl) methyl)-7-cyanobenzo[d]oxazol-2-yl)-2,2'-dimethyl-[1,1'-biphenyl]-3-yl)-6-(difluoromethoxy)benzo[d]oxazol-5-yl)methyl)-L-proline;

162) ((2-(3'-(7-cyano-5-((3-fluoropyrrolidin-1-yl)methyl) benzo[d]oxazol-2-yl)-2,2'-dimethyl-[1,1'-biphenyl]-3-yl)-6-(difluoromethoxy)benzo[d]oxazol-5-yl)methyl)-L-proline;

163) ((2-(3'-(7-cyano-5-((3-fluoropyrrolidin-1-yl)methyl) benzo[d]oxazol-2-yl)-2,2'-dimethyl-[1,1'-biphenyl]-3-yl)-6-(difluoromethoxy)benzo[d]oxazol-5-yl)methyl)-D-proline;

164) ((2-(3'-(7-cyano-5-((3,4-difluoropyrrolidin-1-yl) methyl)benzo[d]oxazol-2-yl)-2,2'-dimethyl-[1,1'-biphenyl]-3-yl)-6-(difluoromethoxy)benzo[d]oxazol-5-yl) methyl)-L-proline;

165) ((2-(3'-(7-cyano-5-(((R)-3-cyanopyrrolidin-1-yl) methyl)benzo[d]oxazol-2-yl)-2,2'-dimethyl-[1,1'-biphenyl]-3-yl)-6-(difluoromethoxy)benzo[d]oxazol-5-yl) methyl)-L-proline;

166) ((6-(difluoromethoxy)-2-(3'-(5-((3-fluoropyrrolidin-1-yl)methyl)-7-(trifluoromethyl)benzo[d]oxazol-2-yl)-2,2'-dimethyl-[1,1'-biphenyl]-3-yl)benzo[d]oxazol-5-yl) methyl)-L-proline;

167) ((2-(3'-(7-cyano-5-((3-fluoro-3-methylpyrrolidin-1-yl) methyl)benzo[d]oxazol-2-yl)-2,2'-dimethyl-[1,1'-biphenyl]-3-yl)-6-(difluoromethoxy)benzo[d]oxazol-5-yl) methyl)-L-proline;

168) ((2-(3'-(7-cyano-5-(((R)-3-(fluoromethyl)pyrrolidin-1-yl)methyl)benzo[d]oxazol-2-yl)-2,2'-dimethyl-[1,1'-biphenyl]-3-yl)-6-(difluoromethoxy)benzo[d]oxazol-5-yl) methyl)-L-proline;

169) (R)-1-((2-(3'-(7-cyano-5-(pyrrolidin-1-ylmethyl)benzo[d]oxazol-2-yl)-2,2'-dimethyl-[1,1'-biphenyl]-3-yl)-6-(difluoromethoxy)benzo[d]oxazol-5-yl)methyl)pyrrolidine-3-carboxylic acid;

170) ((6-(difluoromethoxy)-2-(3'-(6-((3,3-dimethylazetidin-1-yl)methyl)oxazolo[5,4-b]pyridin-2-yl)-2,2'-dimethyl-[1,1'-biphenyl]-3-yl)benzo[d]oxazol-5-yl)methyl)-D-proline;

171) S)-1-((8-((3'-(5-(((S)-2-carboxypyrrolidin-1-yl)methyl)-6-(difluoromethoxy)benzo[d]oxazol-2-yl)-2,2'-dimethyl-[1,1'-biphenyl]-3-yl)amino)-1,7-naphthyridin-3-yl)methyl)-2-methylpyrrolidine-2-carboxylic acid;

172) ((2-(3'-((3-(((carboxymethyl)amino)methyl)-1,7-naphthyridin-8-yl)amino)-2,2'-dimethyl-[1,1'-biphenyl]-3-yl)-6-(difluoromethoxy)benzo[d]oxazol-5-yl)methyl)-L-proline;

173) (S)-1-((8-((3'-(5-(((S)-2-carboxypyrrolidin-1-yl)methyl)-6-(difluoromethoxy)benzo[d]oxazol-2-yl)-2,2'-dimethyl-[1,1'-biphenyl]-3-yl)amino)-1,7-naphthyridin-3-yl)methyl)piperidine-2-carboxylic acid;

174) ((6-(difluoromethoxy)-2-(3'-((3-((3-fluoropyrrolidin-1-yl)methyl)-1,7-naphthyridin-8-yl)amino)-2,2'-dimethyl-[1,1'-biphenyl]-3-yl)benzo[d]oxazol-5-yl)methyl)-L-proline;

175) ((6-(difluoromethoxy)-2-(3'-((3-((3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)-L-proline;

176) ((6-(difluoromethoxy)-2-(2,2'-dimethyl-3'-((3-(morpholinomethyl)-1,7-naphthyridin-8-yl)amino)-[1,1'-biphenyl]-3-yl)benzo[d]oxazol-5-yl)methyl)-L-proline;

177) ((2-(3'-((3-(azetidin-1-ylmethyl)-1,7-naphthyridin-8-yl)amino)-2,2'-dimethyl-[1,1'-biphenyl]-3-yl)-6-(difluoromethoxy)benzo[d]oxazol-5-yl)methyl)proline;

178) ((6-(difluoromethoxy)-2-(3'-((3-((3-hydroxyazetidin-1-yl)methyl)-1,7-naphthyridin-8-yl)amino)-2,2'-dimethyl-[1,1'-biphenyl]-3-yl)benzo[d]oxazol-5-yl)methyl)proline;

179) ((6-(difluoromethoxy)-2-(2,2'-dimethyl-3'-((3-((((5-oxopyrrolidin-2-yl)methyl)amino)methyl)-1,7-naphthyridin-8-yl)amino)-[1,1'-biphenyl]-3-yl)benzo[d]oxazol-5-yl)methyl)proline;

180) (3S)-1-((6-(difluoromethoxy)-2-(3'-((3-((3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid;

181) (3R)-1-((6-(difluoromethoxy)-2-(3'-((3-((3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid;

182) ((6-(difluoromethoxy)-2-(3'-((3-((3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)-D-proline;

183) ((5-(difluoromethoxy)-2-(2,2'-dimethyl-3'-((4-(pyrrolidin-1-ylmethyl)pyridin-2-yl)amino)-[1,1'-biphenyl]-3-yl)benzo[d]oxazol-6-yl)methyl)-L-proline;

184) ((2-(3'-(5-(carboxymethyl)-4,5,6,7-tetrahydrooxazolo[4,5-c]pyridin-2-yl)-2,2'-dimethyl-[1,1'-biphenyl]-3-yl)-6-(difluoromethoxy)benzo[d]oxazol-5-yl)methyl)-L-proline;

185) ((6-(difluoromethoxy)-2-(2,2'-dimethyl-3'-(5-(2-(methylsulfonyl)ethyl)-4,5,6,7-tetrahydrooxazolo[4,5-c]pyridin-2-yl)-[1,1'-biphenyl]-3-yl)benzo[d]oxazol-5-yl)methyl)-L-proline;

186) ((2-(3'-(5-(1-carboxyethyl)-4,5,6,7-tetrahydrooxazolo[4,5-c]pyridin-2-yl)-2,2'-dimethyl-[1,1'-biphenyl]-3-yl)-6-(difluoromethoxy)benzo[d]oxazol-5-yl)methyl)-L-proline;

187) ((2-(3'-(5-(2-carboxyethyl)-4,5,6,7-tetrahydrooxazolo[4,5-c]pyridin-2-yl)-2,2'-dimethyl-[1,1'-biphenyl]-3-yl)-6-(difluoromethoxy)benzo[d]oxazol-5-yl)methyl)-L-proline;

188) ((6-(difluoromethoxy)-2-(2,2'-dimethyl-3'-(5-methyl-4,5,6,7-tetrahydrooxazolo[5,4-c]pyridin-2-yl)-[1,1'-biphenyl]-3-yl)benzo[d]oxazol-5-yl)methyl)-L-proline;

189) ((6-(difluoromethoxy)-2-(3'-(5-(2-hydroxyethyl)-4,5,6,7-tetrahydrooxazolo[5,4-c]pyridin-2-yl)-2,2'-dimethyl-[1,1'-biphenyl]-3-yl)benzo[d]oxazol-5-yl)methyl)-L-proline;

190) ((6-(difluoromethoxy)-2-(2,2'-dimethyl-3'-(4,5,6,7-tetrahydrooxazolo[4,5-c]pyridin-2-yl)-[1,1'-biphenyl]-3-yl)benzo[d]oxazol-5-yl)methyl)-L-proline;

191) ((6-(difluoromethoxy)-2-(2,2'-dimethyl-3'-(5-(4,4,4-trifluorobutyl)-4,5,6,7-tetrahydrooxazolo[4,5-c]pyridin-2-yl)-[1,1'-biphenyl]-3-yl)benzo[d]oxazol-5-yl)methyl)proline;

192) ((6-(difluoromethoxy)-2-(2,2'-dimethyl-3'-(5-(oxetan-2-ylmethyl)-4,5,6,7-tetrahydrooxazolo[4,5-c]pyridin-2-yl)-[1,1'-biphenyl]-3-yl)benzo[d]oxazol-5-yl)methyl)proline;

193) ((6-(difluoromethoxy)-2-(2,2'-dimethyl-3'-(5-((5-oxopyrrolidin-2-yl)methyl)-4,5,6,7-tetrahydrooxazolo[4,5-c]pyridin-2-yl)-[1,1'-biphenyl]-3-yl)benzo[d]oxazol-5-yl)methyl)proline;

194) ((6-(difluoromethoxy)-2-(2,2'-dimethyl-3'-(5-(pyridin-3-ylmethyl)-4,5,6,7-tetrahydrooxazolo[4,5-c]pyridin-2-yl)-[1,1'-biphenyl]-3-yl)benzo[d]oxazol-5-yl)methyl)proline;

195) ((2-(3'-(5-(cyanomethyl)-4,5,6,7-tetrahydrooxazolo[4,5-c]pyridin-2-yl)-2,2'-dimethyl-[1,1'-biphenyl]-3-yl)-6-(difluoromethoxy)benzo[d]oxazol-5-yl)methyl)proline;

196) ((2-(3'-(5-(2-amino-2-oxoethyl)-4,5,6,7-tetrahydrooxazolo[4,5-c]pyridin-2-yl)-2,2'-dimethyl-[1,1'-biphenyl]-3-yl)-6-(difluoromethoxy)benzo[d]oxazol-5-yl)methyl)proline;

197) ((6-(difluoromethoxy)-2-(3'-(5-(ethylsulfonyl)-4,5,6,7-tetrahydrooxazolo[4,5-c]pyridin-2-yl)-2,2'-dimethyl-[1,1'-biphenyl]-3-yl)benzo[d]oxazol-5-yl)methyl)proline;

198) ((6-(difluoromethoxy)-2-(2,2'-dimethyl-3'-(5-(3,3,3-trifluoropropyl)-4,5,6,7-tetrahydrooxazolo[4,5-c]pyridin-2-yl)-[1,1'-biphenyl]-3-yl)benzo[d]oxazol-5-yl)methyl)proline;

199) ((6-(difluoromethoxy)-2-(3'-(5-(3-hydroxypropyl)-4,5,6,7-tetrahydrooxazolo[4,5-c]pyridin-2-yl)-2,2'-dimethyl-[1,1'-biphenyl]-3-yl)benzo[d]oxazol-5-yl)methyl)proline;

200) ((6-(difluoromethoxy)-2-(3'-(5-(3-fluoropropyl)-4,5,6,7-tetrahydrooxazolo[4,5-c]pyridin-2-yl)-2,2'-dimethyl-[1,1'-biphenyl]-3-yl)benzo[d]oxazol-5-yl)methyl)proline;

201) ((2-(3'-(5-(2,2-difluoroethyl)-4,5,6,7-tetrahydrooxazolo[4,5-c]pyridin-2-yl)-2,2'-dimethyl-[1,1'-biphenyl]-3-yl)-6-(difluoromethoxy)benzo[d]oxazol-5-yl)methyl)proline;

202) ((6-(difluoromethoxy)-2-(3'-(5,6-dihydro-4H-pyrrolo[3,4-d]oxazol-2-yl)-2,2'-dimethyl-[1,1'-biphenyl]-3-yl)benzo[d]oxazol-5-yl)methyl)proline;

203) ((6-(difluoromethoxy)-2-(3'-(6,7-dihydro-4H-pyrano[3,4-d]oxazol-2-yl)-2,2'-dimethyl-[1,1'-biphenyl]-3-yl)benzo[d]oxazol-5-yl)methyl)proline;

204) ((6-(difluoromethoxy)-2-(3'-(5,6-dihydro-4H-cyclopenta[d]oxazol-2-yl)-2,2'-dimethyl-[1,1'-biphenyl]-3-yl)benzo[d]oxazol-5-yl)methyl)proline;

205) ((6-(difluoromethoxy)-2-(2,2'-dimethyl-3'-(4,5,6,7-tetrahydrobenzo[d]oxazol-2-yl)-[1,1'-biphenyl]-3-yl)benzo[d]oxazol-5-yl)methyl)proline;
206) ((6-(difluoromethoxy)-2-(3'-(5-(2-hydroxyethyl)-4,5,6,7-tetrahydrooxazolo[4,5-c]pyridin-2-yl)-2,2'-dimethyl-[1,1'-biphenyl]-3-yl)benzo[d]oxazol-5-yl)methyl)-L-proline;
207) 2-((2-(2'-cyano-2-methyl-3'-(4,5,6,7-tetrahydrooxazolo[4,5-c]pyridin-2-yl)-[1,1'-biphenyl]-3-yl)-6-(difluoromethoxy)benzo[d]oxazol-5-yl)methyl)pyrrolidine-1-carboxylic acid;
208) ((2-(3'-((2-chloro-5-((5-(difluoromethoxy)pyridin-3-yl)methoxy)-4-(((R)-3-hydroxypyrrolidin-1-yl)methyl)phenoxy)methyl)-2,2'-dimethyl-[1,1'-biphenyl]-3-yl)-6-(difluoromethoxy)benzo[d]oxazol-5-yl)methyl)-L-proline;
209) ((2-(3'-((2-chloro-5-((5-(difluoromethoxy)pyridin-3-yl)methoxy)-4-((3-fluoropyrrolidin-1-yl)methyl)phenoxy)methyl)-2,2'-dimethyl-[1,1'-biphenyl]-3-yl)-6-(difluoromethoxy)benzo[d]oxazol-5-yl)methyl)-L-proline;
210) ((2-(3'-((4-(((2-acetamidoethyl)amino)methyl)-2-chloro-5-((3-cyanobenzyl)oxy)phenoxy)methyl)-2,2'-dimethyl-[1,1'-biphenyl]-3-yl)-6-(difluoromethoxy)benzo[d]oxazol-5-yl)methyl)-L-proline;
211) ((2-(3'-((4-(((S)-2-carboxypyrrolidin-1-yl)methyl)-2-chloro-5-((3-cyanobenzyl)oxy)phenoxy)methyl)-2,2'-dimethyl-[1,1'-biphenyl]-3-yl)-6-(difluoromethoxy)benzo[d]oxazol-5-yl)methyl)-L-proline;
212) ((6-(difluoromethoxy)-2-(3'-(((4,6-dimethoxy-5-(pyrrolidin-1-ylmethyl)pyrimidin-2-yl)oxy)methyl)-2,2'-dimethyl-[1,1'-biphenyl]-3-yl)benzo[d]oxazol-5-yl)methyl)-L-proline;
213) ((6-(difluoromethoxy)-2-(3'-(((5-((3,3-dimethylazetidin-1-yl)methyl)-4,6-dimethoxypyrimidin-2-yl)oxy)methyl)-2,2'-dimethyl-[1,1'-biphenyl]-3-yl)benzo[d]oxazol-5-yl)methyl)-L-proline;
214) ((6-(difluoromethoxy)-2-(2,2'-dimethyl-3'-((5-(((((S)-5-oxopyrrolidin-2-yl)methyl)amino)methyl)pyridin-2-yl)oxy)-[1,1'-biphenyl]-3-yl)benzo[d]oxazol-5-yl)methyl)-L-proline;
215) ((6-(difluoromethoxy)-2-(2'-fluoro-2-methyl-4"-(((((S)-5-oxopyrrolidin-2-yl)methyl)amino)methyl)-[1,1':3',1"-terphenyl]-3-yl)benzo[d]oxazol-5-yl)methyl)-L-proline;
216) ((6-(difluoromethoxy)-2-(3"-(difluoromethoxy)-2'-fluoro-2-methyl-4"-(((((S)-5-oxopyrrolidin-2-yl)methyl)amino)methyl)-[1,1':3',1"-terphenyl]-3-yl)benzo[d]oxazol-5-yl)methyl)-L-proline;
217) ((6-(difluoromethoxy)-2-(4"-(((2-hydroxyethyl)amino)methyl)-2,2'-dimethyl-[1,1':3',1"-terphenyl]-3-yl)benzo[d]oxazol-5-yl)methyl)-L-proline;
218) ((6-(difluoromethoxy)-2-(2,2',3"-trimethyl-4"-(pyrrolidin-1-ylmethyl)-[1,1':3',1"-terphenyl]-3-yl)benzo[d]oxazol-5-yl)methyl)proline;
219) ((2-(3"-chloro-2,2'-dimethyl-4"-(pyrrolidin-1-ylmethyl)-[1,1':3',1"-terphenyl]-3-yl)-6-(difluoromethoxy)benzo[d]oxazol-5-yl)methyl)proline;
220) ((6-(difluoromethoxy)-2-(2"-fluoro-2,2'-dimethyl-4"-(pyrrolidin-1-ylmethyl)-[1,1':3',1"-terphenyl]-3-yl)benzo[d]oxazol-5-yl)methyl)proline;
221) ((2-(2'-bromo-2"-fluoro-2-methyl-4"-(pyrrolidin-1-ylmethyl)-[1,1':3',1"-terphenyl]-3-yl)-6-(difluoromethoxy)benzo[d]oxazol-5-yl)methyl)proline;
222) ((2-(2'-chloro-2"-fluoro-2-methyl-4"-(pyrrolidin-1-ylmethyl)-[1,1':3',1"-terphenyl]-3-yl)-6-(difluoromethoxy)benzo[d]oxazol-5-yl)methyl)proline;
223) ((2-(2'-chloro-2"-fluoro-2-methyl-4"-(pyrrolidin-1-ylmethyl)-[1,1':3',1"-terphenyl]-3-yl)-6-(difluoromethoxy)benzo[d]oxazol-5-yl)methyl)-L-proline;
224) ((2-(2'-chloro-2"-fluoro-2-methyl-4"-(pyrrolidin-1-ylmethyl)-[1,1':3',1"-terphenyl]-3-yl)-6-(difluoromethoxy)benzo[d]oxazol-5-yl)methyl)-D-proline;
225) ((6-(difluoromethoxy)-2-(4"-guanidino-2,2'-dimethyl-[1,1':3',1"-terphenyl]-3-yl)benzo[d]oxazol-5-yl)methyl)-L-proline;
226) ((6-(difluoromethoxy)-2-(4"-(((3-(dimethylamino)propyl)(methyl)amino)methyl)-2,2'-dimethyl-[1,1':3',1"-terphenyl]-3-yl)benzo[d]oxazol-5-yl)methyl)-L-proline;
227) ((6-(difluoromethoxy)-2-(4"-((3-methoxypyrrolidin-1-yl)methyl)-2,2'-dimethyl-[1,1':3',1"-terphenyl]-3-yl)benzo[d]oxazol-5-yl)methyl)-L-proline;
228) ((6-(difluoromethoxy)-2-(4"-((3-(dimethylamino)pyrrolidin-1-yl)methyl)-2,2'-dimethyl-[1,1':3',1"-terphenyl]-3-yl)benzo[d]oxazol-5-yl)methyl)-L-proline;
229) ((2-(3"-chloro-2,2'-dimethyl-4"-(pyrrolidin-1-ylmethyl)-[1,1':3',1"-terphenyl]-3-yl)-6-(difluoromethoxy)benzo[d]oxazol-5-yl)methyl)-L-proline;
230) ((6-(difluoromethoxy)-2-(2,2',3"-trimethyl-4"-(pyrrolidin-1-ylmethyl)-[1,1':3',1"-terphenyl]-3-yl)benzo[d]oxazol-5-yl)methyl)-L-proline;
231) ((2-(2"-chloro-2,2'-dimethyl-4"-(pyrrolidin-1-ylmethyl)-[1,1':3',1"-terphenyl]-3-yl)-6-(difluoromethoxy)benzo[d]oxazol-5-yl)methyl)-L-proline;
232) ((6-(difluoromethoxy)-2-(2,2'-dimethyl-4"-(pyrrolidin-1-ylmethyl)-3"-(trifluoromethoxy)-[1,1':3',1"-terphenyl]-3-yl)benzo[d]oxazol-5-yl)methyl)-L-proline;
233) ((6-(difluoromethoxy)-2-(2,2'-dimethyl-4"-(pyrrolidin-1-ylmethyl)-3"-(trifluoromethyl)-[1,1':3',1"-terphenyl]-3-yl)benzo[d]oxazol-5-yl)methyl)-L-proline;
234) ((6-(difluoromethoxy)-2-(2,2',3",5"-tetramethyl-4"-(pyrrolidin-1-ylmethyl)-[1,1':3',1"-terphenyl]-3-yl)benzo[d]oxazol-5-yl)methyl)-L-proline;
235) ((6-(difluoromethoxy)-2-(3"-fluoro-5"-methoxy-2,2'-dimethyl-4"-(pyrrolidin-1-ylmethyl)-[1,1':3',1"-terphenyl]-3-yl)benzo[d]oxazol-5-yl)methyl)-L-proline;
236) ((2-(3"-carboxy-2,2'-dimethyl-4"-(pyrrolidin-1-ylmethyl)-[1,1':3',1"-terphenyl]-3-yl)-6-(difluoromethoxy)benzo[d]oxazol-5-yl)methyl)-L-proline;
237) ((6-(difluoromethoxy)-2-(4"-((3,3-dimethylazetidin-1-yl)methyl)-3"-fluoro-2,2'-dimethyl-[1,1':3',1"-terphenyl]-3-yl)benzo[d]oxazol-5-yl)methyl)-L-proline;
238) ((6-(difluoromethoxy)-2-(3"-fluoro-2,2'-dimethyl-4"-((3-methylpyrrolidin-1-yl)methyl)-[1,1':3',1"-terphenyl]-3-yl)benzo[d]oxazol-5-yl)methyl)-L-proline;
239) ((6-(difluoromethoxy)-2-(3"-fluoro-4"-(((2-hydroxyethyl)amino)methyl)-2,2'-dimethyl-[1,1':3',1"-terphenyl]-3-yl)benzo[d]oxazol-5-yl)methyl)-L-proline;
240) ((2-(3"-cyano-4"-(((S)-3-(hydroxymethyl)pyrrolidin-1-yl)methyl)-2,2'-dimethyl-[1,1':3',1"-terphenyl]-3-yl)-6-(difluoromethoxy)benzo[d]oxazol-5-yl)methyl)-L-proline;
241) ((6-(difluoromethoxy)-2-(3"-fluoro-4"-(isoindolin-2-ylmethyl)-2,2'-dimethyl-[1,1':3',1"-terphenyl]-3-yl)benzo[d]oxazol-5-yl)methyl)proline;
242) ((6-(difluoromethoxy)-2-(4"-((3-fluoropyrrolidin-1-yl)methyl)-2,2'-dimethyl-[1,1':3',1"-terphenyl]-3-yl)benzo[d]oxazol-5-yl)methyl)proline;
243) ((6-(difluoromethoxy)-2-(3"-fluoro-2,2'-dimethyl-4"-(pyrrolidin-1-ylmethyl)-[1,1':3',1"-terphenyl]-3-yl)benzo[d]oxazol-5-yl)methyl)proline;
244) ((6-(difluoromethoxy)-2-(3"-(difluoromethoxy)-2,2'-dimethyl-4"-(pyrrolidin-1-ylmethyl)-[1,1':3',1"-terphenyl]-3-yl)benzo[d]oxazol-5-yl)methyl)-L-proline.

245) ((2-(3"-cyano-2,2'-dimethyl-4"-(pyrrolidin-1-ylmethyl)-[1,1':3',1"-terphenyl]-3-yl)-6-(difluoromethoxy)benzo[d]oxazol-5-yl)methyl)-L-proline;
246) ((6-(difluoromethoxy)-2-(3'-(6-methoxy-5-(((S)-3-methylpyrrolidin-1-yl)methyl)pyridin-2-yl)-2,2'-dimethyl-[1,1'-biphenyl]-3-yl)benzo[d]oxazol-5-yl)methyl)-L-proline;
247) ((6-(difluoromethoxy)-2-(2,2'-dimethyl-3'-(2-((S)-pyrrolidin-2-yl)-1H-imidazol-4-yl)-[1,1'-biphenyl]-3-yl)benzo[d]oxazol-5-yl)methyl)-L-proline;
248) ((6-(difluoromethoxy)-2-(3"-fluoro-2,2'-dimethyl-4"-(((S)-3-phenylpyrrolidin-1-yl)methyl)-[1,1':3',1"-terphenyl]-3-yl)benzo[d]oxazol-5-yl)methyl)proline;
249) ((6-(difluoromethoxy)-2-(3"-(4-fluorophenethoxy)-2,2'-dimethyl-4"-(pyrrolidin-1-ylmethyl)-[1,1':3',1"-terphenyl]-3-yl)benzo[d]oxazol-5-yl)methyl)proline;
250) ((2-(3"-(cyclopropylmethoxy)-2,2'-dimethyl-4"-(pyrrolidin-1-ylmethyl)-[1,1':3',1"-terphenyl]-3-yl)-6-(difluoromethoxy)benzo[d]oxazol-5-yl)methyl)proline;
251) ((2-(4"-(((R)-3-(1H-tetrazol-5-yl)pyrrolidin-1-yl)methyl)-3"-fluoro-2,2'-dimethyl-[1,1':3',1"-terphenyl]-3-yl)-6-(difluoromethoxy)benzo[d]oxazol-5-yl)methyl)proline;
252) ((2-(4"-(((S)-3-((benzyloxy)methyl)pyrrolidin-1-yl)methyl)-3"-fluoro-2,2'-dimethyl-[1,1':3',1"-terphenyl]-3-yl)-6-(difluoromethoxy)benzo[d]oxazol-5-yl)methyl)proline;
253) ((6-(difluoromethoxy)-2-(2"-fluoro-2,2'-dimethyl-4"-(pyrrolidin-1-ylmethyl)-[1,1':3',1"-terphenyl]-3-yl)benzo[d]oxazol-5-yl)methyl)-L-proline;
254) ((6-(difluoromethoxy)-2-(3",5"-dimethoxy-2,2'-dimethyl-4"-(pyrrolidin-1-ylmethyl)-[1,1':3',1"-terphenyl]-3-yl)benzo[d]oxazol-5-yl)methyl)-L-proline hydrochloride;
255) ((6-(difluoromethoxy)-2-(2,2'-dimethyl-4"-(pyrrolidin-2-yl)-[1,1':3',1"-terphenyl]-3-yl)benzo[d]oxazol-5-yl)methyl)-L-proline;
256) ((2-(4"-((S)-amino(carboxy)methyl)-2,2'-dimethyl-[1,1':3',1"-terphenyl]-3-yl)-6-(difluoromethoxy)benzo[d]oxazol-5-yl)methyl)-L-proline;
257) ((6-(difluoromethoxy)-2-(4"-(((S)-3-((S)-2-((methoxycarbonyl)amino)-3-methylbutanamido)pyrrolidin-1-yl)methyl)-2,2'-dimethyl-[1,1':3',1"-terphenyl]-3-yl)benzo[d]oxazol-5-yl)methyl)-L-proline;
258) ((6-(difluoromethoxy)-2-(3"-fluoro-2,2'-dimethyl-4"-((5-ureidoisoindolin-2-yl)methyl)-[1,1':3',1"-terphenyl]-3-yl)benzo[d]oxazol-5-yl)methyl)-L-proline;
259) (S)-1-((2-(3'-(7-cyano-5-(((S)-3-methylpyrrolidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)pyrrolidine-3-carboxylic acid;
260) ((6-(difluoromethoxy)-2-(3"-fluoro-2,2'-dimethyl-4"-((3-ureidopyrrolidin-1-yl)methyl)-[1,1':3',1"-terphenyl]-3-yl)benzo[d]oxazol-5-yl)methyl)-L-proline;
261) ((2-(3'-(5-(((S)-3-chloropyrrolidin-1-yl)methyl)-7-cyanobenzo[d]oxazol-2-yl)-2,2'-dimethyl-[1,1'-biphenyl]-3-yl)-6-(difluoromethoxy)benzo[d]oxazol-5-yl)methyl)-L-proline;
262) ((6-(difluoromethoxy)-2-(3'-(4-fluoro-6-(pyrrolidin-1-ylmethyl)pyridin-3-yl)-2,2'-dimethyl-[1,1'-biphenyl]-3-yl)benzo[d]oxazol-5-yl)methyl)-L-proline;
263) ((6-(difluoromethoxy)-2-(2,2'-dimethyl-3'-(6-(pyrrolidin-1-ylmethyl)pyridin-3-yl)-[1,1'-biphenyl]-3-yl)benzo[d]oxazol-5-yl)methyl)-L-proline;
264) ((6-(difluoromethoxy)-2-(2,2'-dimethyl-3'-(5-(pyrrolidin-1-ylmethyl)pyridin-2-yl)-[1,1'-biphenyl]-3-yl)benzo[d]oxazol-5-yl)methyl)-L-proline;
265) ((6-(difluoromethoxy)-2-(3'-(5-fluoro-6-(pyrrolidin-1-ylmethyl)pyridin-3-yl)-2,2'-dimethyl-[1,1'-biphenyl]-3-yl)benzo[d]oxazol-5-yl)methyl)-L-proline;
266) ((6-(difluoromethoxy)-2-(3'-(6-methoxy-5-(pyrrolidin-1-ylmethyl)pyridin-2-yl)-2,2'-dimethyl-[1,1'-biphenyl]-3-yl)benzo[d]oxazol-5-yl)methyl)-L-proline;
267) ((6-(difluoromethoxy)-2-(2,2'-dimethyl-3'-(6-oxo-5-(pyrrolidin-1-ylmethyl)-1,6-dihydropyridin-2-yl)-[1,1'-biphenyl]-3-yl)benzo[d]oxazol-5-yl)methyl)-L-proline;
268) ((6-(difluoromethoxy)-2-(2'-(difluoromethyl)-3'-(5-fluoro-6-(pyrrolidin-1-ylmethyl)pyridin-3-yl)-2-methyl-[1,1'-biphenyl]-3-yl)benzo[d]oxazol-5-yl)methyl)-L-proline;
269) ((6-(difluoromethoxy)-2-(3'-(5-fluoro-6-(pyrrolidin-1-ylmethyl)pyridin-3-yl)-2'-(fluoromethyl)-2-methyl-[1,1'-biphenyl]-3-yl)benzo[d]oxazol-5-yl)methyl)-L-proline;
270) ((6-(difluoromethoxy)-2-(3'-(2-fluoro-6-(pyrrolidin-1-ylmethyl)pyridin-3-yl)-2,2'-dimethyl-[1,1'-biphenyl]-3-yl)benzo[d]oxazol-5-yl)methyl)-L-proline;
271) ((6-(difluoromethoxy)-2-(3'-(5-((3,3-dimethylazetidin-1-yl)methyl)-6-methoxypyridin-2-yl)-2,2'-dimethyl-[1,1'-biphenyl]-3-yl)benzo[d]oxazol-5-yl)methyl)-L-proline;
272) ((6-(difluoromethoxy)-2-(3'-(6-methoxy-5-(((R)-3-methylpyrrolidin-1-yl)methyl)pyridin-2-yl)-2,2'-dimethyl-[1,1'-biphenyl]-3-yl)benzo[d]oxazol-5-yl)methyl)-L-proline;
273) ((6-(difluoromethoxy)-2-(3'-(6-methoxy-5-(((S)-3-methylpyrrolidin-1-yl)methyl)pyridin-2-yl)-2,2'-dimethyl-[1,1'-biphenyl]-3-yl)benzo[d]oxazol-5-yl)methyl)-D-proline;
274) ((6-(difluoromethoxy)-2-(2,2'-dimethyl-3'-(5-(pyrrolidin-1-ylmethyl)-4-vinylpyridin-2-yl)-[1,1'-biphenyl]-3-yl)benzo[d]oxazol-5-yl)methyl)-L-proline;
275) ((6-(difluoromethoxy)-2-(3'-(5-((3-(difluoromethyl)pyrrolidin-1-yl)methyl)-6-methoxypyridin-2-yl)-2,2'-dimethyl-[1,1'-biphenyl]-3-yl)benzo[d]oxazol-5-yl)methyl)-L-proline;
276) ((6-(difluoromethoxy)-2-(3'-(6-methoxy-5-((((5-oxopyrrolidin-2-yl)methyl)amino)methyl)pyridin-2-yl)-2,2'-dimethyl-[1,1'-biphenyl]-3-yl)benzo[d]oxazol-5-yl)methyl)-L-proline;
277) ((6-(difluoromethoxy)-2-(3'-(6-methoxy-5-(((S)-2-methylpyrrolidin-1-yl)methyl)pyridin-2-yl)-2,2'-dimethyl-[1,1'-biphenyl]-3-yl)benzo[d]oxazol-5-yl)methyl)-L-proline;
278) ((2-(3'-(5-(((1s,4s)-7-azabicyclo[2.2.1]heptan-7-yl)methyl)-6-methoxypyridin-2-yl)-2,2'-dimethyl-[1,1'-biphenyl]-3-yl)-6-(difluoromethoxy)benzo[d]oxazol-5-yl)methyl)-L-proline;
279) ((6-(difluoromethoxy)-2-(3'-(6-methoxy-5-(((R)-2-methylpyrrolidin-1-yl)methyl)pyridin-2-yl)-2,2'-dimethyl-[1,1'-biphenyl]-3-yl)benzo[d]oxazol-5-yl)methyl)-L-proline;
280) ((6-(difluoromethoxy)-2-(2,2'-dimethyl-3'-(5-(pyrrolidin-1-ylmethyl)thiophen-2-yl)-[1,1'-biphenyl]-3-yl)benzo[d]oxazol-5-yl)methyl)-L-proline;
281) ((6-(difluoromethoxy)-2-(2,2'-dimethyl-3'-(2-(pyrrolidin-1-ylmethyl)pyrimidin-5-yl)-[1,1'-biphenyl]-3-yl)benzo[d]oxazol-5-yl)methyl)-L-proline
282) ((6-(difluoromethoxy)-2-(2,2'-dimethyl-3'-(2-(4-methylpiperazin-1-yl)pyrimidin-5-yl)-[1,1'-biphenyl]-3-yl)benzo[d]oxazol-5-yl)methyl)-L-proline;
283) ((6-(difluoromethoxy)-2-(2,2'-dimethyl-3'-(2-(pyrrolidin-1-ylmethyl)pyrimidin-5-yl)-[1,1'-biphenyl]-3-yl)benzo[d]oxazol-5-yl)methyl)-L-proline;

284) ((6-(difluoromethoxy)-2-(2,2'-dimethyl-3'-(5-(pyrrolidin-1-ylmethyl)pyrazin-2-yl)-[1,1'-biphenyl]-3-yl)benzo[d]oxazol-5-yl)methyl)-L-proline;

285) ((6-(difluoromethoxy)-2-(3'-(6-methoxy-5-(pyrrolidin-1-ylmethyl)pyrazin-2-yl)-2,2'-dimethyl-[1,1'-biphenyl]-3-yl)benzo[d]oxazol-5-yl)methyl)-L-proline;

286) ((6-(difluoromethoxy)-2-(3'-(6-methoxy-5-(((R)-3-methylpyrrolidin-1-yl)methyl)pyrazin-2-yl)-2,2'-dimethyl-[1,1'-biphenyl]-3-yl)benzo[d]oxazol-5-yl)methyl)-L-proline;

287) ((2-(2'-chloro-3'-(6-methoxy-5-((((5-oxopyrrolidin-2-yl)methyl)amino)methyl)pyrazin-2-yl)-2-methyl-[1,1'-biphenyl]-3-yl)-6-(difluoromethoxy)benzo[d]oxazol-5-yl)methyl)-L-proline;

288) ((6-(difluoromethoxy)-2-(2,2'-dimethyl-3'-(1,2,3,4-tetrahydroisoquinolin-6-yl)-[1,1'-biphenyl]-3-yl)benzo[d]oxazol-5-yl)methyl)-L-proline;

289) ((6-(difluoromethoxy)-2-(3'-(isoindolin-5-yl)-2,2'-dimethyl-[1,1'-biphenyl]-3-yl)benzo[d]oxazol-5-yl)methyl)-L-proline;

290) ((2-(3'-(2-(2-carboxyethyl)isoindolin-5-yl)-2,2'-dimethyl-[1,1'-biphenyl]-3-yl)-6-(difluoromethoxy)benzo[d]oxazol-5-yl)methyl)-L-proline;

291) ((2-(3'-(2-(carboxymethyl)isoindolin-5-yl)-2,2'-dimethyl-[1,1'-biphenyl]-3-yl)-6-(difluoromethoxy)benzo[d]oxazol-5-yl)methyl)-L-proline;

292) ((2-(3'-(2-(1-carboxyethyl)isoindolin-5-yl)-2,2'-dimethyl-[1,1'-biphenyl]-3-yl)-6-(difluoromethoxy)benzo[d]oxazol-5-yl)methyl)-L-proline;

293) ((2-(3'-(2-amino-1H-benzo[d]imidazol-5-yl)-2,2'-dimethyl-[1,1'-biphenyl]-3-yl)-6-(difluoromethoxy)benzo[d]oxazol-5-yl)methyl)-L-proline;

294) ((6-(difluoromethoxy)-2-(3'-(5-((3,3-dimethylpyrrolidin-1-yl)methyl)-6-methoxypyridin-2-yl)-2,2'-dimethyl-[1,1'-biphenyl]-3-yl)benzo[d]oxazol-5-yl)methyl)-L-proline;

295) ((2-(3'-(7-cyano-5-(pyrrolidin-1-ylmethyl)-1H-benzo[d]imidazol-2-yl)-2,2'-dimethyl-[1,1'-biphenyl]-3-yl)-6-(difluoromethoxy)benzo[d]oxazol-5-yl)methyl)-L-proline;

296) ((2-(3'-(6,7-difluoro-5-(pyrrolidin-1-ylmethyl)-1H-benzo[d]imidazol-2-yl)-2,2'-dimethyl-[1,1'-biphenyl]-3-yl)-6-(difluoromethoxy)benzo[d]oxazol-5-yl)methyl)-L-proline;

297) ((6-(difluoromethoxy)-2-(3'-(6-fluoro-5-(pyrrolidin-1-ylmethyl)-1H-benzo[d]imidazol-2-yl)-2,2'-dimethyl-[1,1'-biphenyl]-3-yl)benzo[d]oxazol-5-yl)methyl)-L-proline;

298) ((2-(3'-(6,7-difluoro-1-methyl-5-(pyrrolidin-1-ylmethyl)-1H-benzo[d]imidazol-2-yl)-2,2'-dimethyl-[1,1'-biphenyl]-3-yl)-6-(difluoromethoxy)benzo[d]oxazol-5-yl)methyl)-L-proline;

299) ((2-(3'-(6,7-difluoro-5-(pyrrolidin-1-ylmethyl)-1-(2,2,2-trifluoroethyl)-1H-benzo[d]imidazol-2-yl)-2,2'-dimethyl-[1,1'-biphenyl]-3-yl)-6-(difluoromethoxy)benzo[d]oxazol-5-yl)methyl)-L-proline;

300) ((2-(3'-(4,5-difluoro-6-(pyrrolidin-1-ylmethyl)-1-(2,2,2-trifluoroethyl)-1H-benzo[d]imidazol-2-yl)-2,2'-dimethyl-[1,1'-biphenyl]-3-yl)-6-(difluoromethoxy)benzo[d]oxazol-5-yl)methyl)-L-proline;

301) ((6-(difluoromethoxy)-2-(2,2'-dimethyl-3'-(5-(pyrrolidin-1-ylmethyl)-7-(trifluoromethyl)-1H-benzo[d]imidazol-2-yl)-[1,1'-biphenyl]-3-yl)benzo[d]oxazol-5-yl)methyl)-L-proline;

302) ((2-(2'-chloro-3'-(5-(((2-hydroxyethyl)amino)methyl)picolinamido)-2-methyl-[1,1'-biphenyl]-3-yl)-6-(difluoromethoxy)benzo[d]oxazol-5-yl)methyl)-L-proline;

303) ((6-(difluoromethoxy)-2-(2,2'-dimethyl-3'-(5,6,7,8-tetrahydroimidazo[1,2-a]pyrazine-2-carboxamido)-[1,1'-biphenyl]-3-yl)benzo[d]oxazol-5-yl)methyl)-L-proline;

304) ((6-(difluoromethoxy)-2-(2,2'-dimethyl-3'-(4-methyl-5-(pyrrolidin-1-ylmethyl)oxazol-2-yl)-[1,1'-biphenyl]-3-yl)benzo[d]oxazol-5-yl)methyl)-L-proline;

305) ((6-(difluoromethoxy)-2-(2,2'-dimethyl-3'-(6-(pyrrolidin-1-ylmethyl)-[1,2,4]triazolo[1,5-a]pyridin-2-yl)-[1,1'-biphenyl]-3-yl)benzo[d]oxazol-5-yl)methyl)-L-proline;

306) ((6-(difluoromethoxy)-2-(2,2'-dimethyl-3'-(4-(pyrrolidin-1-yl)piperidin-1-yl)-[1,1'-biphenyl]-3-yl)benzo[d]oxazol-5-yl)methyl)-L-proline;

307) ((6-(difluoromethoxy)-2-(3'-(4-(((1-(hydroxymethyl)cyclopropyl)methyl)amino)piperidin-1-yl)-2,2'-dimethyl-[1,1'-biphenyl]-3-yl)benzo[d]oxazol-5-yl)methyl)-L-proline;

308) ((6-(difluoromethoxy)-2-(3'-(4-((3,3-dimethylazetidin-1-yl)methyl)piperidin-1-yl)-2,2'-dimethyl-[1,1'-biphenyl]-3-yl)benzo[d]oxazol-5-yl)methyl)-L-proline;

309) ((6-(difluoromethoxy)-2-(2,2'-dimethyl-3'-(4-(pyrrolidin-1-ylmethyl)piperidin-1-yl)-[1,1'-biphenyl]-3-yl)benzo[d]oxazol-5-yl)methyl)-L-proline;

310) ((6-(difluoromethoxy)-2-(3'-(5-((((1R,2S)-2-hydroxycyclopentyl)amino)methyl)benzo[d]oxazol-2-yl)-2,2'-dimethyl-[1,1'-biphenyl]-3-yl)benzo[d]oxazol-5-yl)methyl)-D-proline;

311) ((6-(difluoromethoxy)-2-(3'-(5-((2,2-dimethylpyrrolidin-1-yl)methyl)benzo[d]oxazol-2-yl)-2,2'-dimethyl-[1,1'-biphenyl]-3-yl)benzo[d]oxazol-5-yl)methyl)-L-proline;

312) ((6-(difluoromethoxy)-2-(3'-(5-((3,3-dimethylazetidin-1-yl)methyl)benzo[d]oxazol-2-yl)-2,2'-dimethyl-[1,1'-biphenyl]-3-yl)benzo[d]oxazol-5-yl)methyl)-L-proline;

313) ((6-(difluoromethoxy)-2-(2,2'-dimethyl-3'-(5-((2-methylazetidin-1-yl)methyl)benzo[d]oxazol-2-yl)-[1,1'-biphenyl]-3-yl)benzo[d]oxazol-5-yl)methyl)-L-proline;

314) ((6-(difluoromethoxy)-2-(2,2'-dimethyl-3'-(5-methyl-4,5,6,7-tetrahydrooxazolo[4,5-c]pyridin-2-yl)-[1,1'-biphenyl]-3-yl)benzo[d]oxazol-5-yl)methyl)-L-proline;

315) ((2-(3'-(5-((3-carbamoylpyrrolidin-1-yl)methyl)-7-cyanobenzo[d]oxazol-2-yl)-2,2'-dimethyl-[1,1'-biphenyl]-3-yl)-6-(difluoromethoxy)benzo[d]oxazol-5-yl)methyl)-L-proline; or 316) ((2-(3'-(7-cyano-5-((3-cyano-3-methylpyrrolidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline.

The present invention also provides a pharmaceutical composition comprising a compound of any of the present invention and a pharmaceutically acceptable excipient, such as hydroxypropyl methyl cellulose. In the composition, the said compound in a weight ratio to the said excipient within the range from about 0.0001 to about 10.

The present invention additionally provided a use of a pharmaceutical composition of Formula I for the preparation of a medicament for treating a disease in a subject.

The present invention further provides some preferred technical solutions with regard to above-mentioned uses.

In some embodiments, a medicament thus prepared can be used for the treatment or prevention of, or for delaying or preventing onset or progression in, cancer, cancer metastasis, an immunological disorder. The cancer is colon cancer, gastric cancer, thyroid cancer, lung cancer, leukemia, pancreatic cancer, melanoma, multiple melanoma, brain cancer, renal cancer, prostate cancer, ovarian cancer or breast cancer.

The present invention provided a method of inhibiting PD-1/PD-L1 interaction, said method comprising administering to a patient a compound, or a pharmaceutically acceptable salt or a stereoisomer thereof.

The present invention provided a method of treating a disease associated with inhibition of PD-1/PD-L1 interaction, said method comprising administering to a patient in need thereof a therapeutically effective amount of a compound of the present invention, or a pharmaceutically acceptable salt or a stereoisomer thereof. Wherein the disease is colon cancer, gastric cancer, thyroid cancer, lung cancer, leukemia, pancreatic cancer, melanoma, multiple melanoma, brain cancer, renal cancer, prostate cancer, ovarian cancer, or breast cancer.

The present invention provided a method of enhancing, stimulating and/or increasing the immune response in a patient, said method comprising administering to the patient in need thereof a therapeutically effective amount of a compound of the present invention, or a pharmaceutically acceptable salt or a stereoisomer thereof.

The present invention also provides a use of the present compound or its pharmaceutical composition for the preparation of a medicament.

In some embodiments, the medicament is used for the treatment or prevention of cancer.

In some embodiments, the cancer is colon cancer, gastric cancer, thyroid cancer, lung cancer, leukemia, pancreatic cancer, melanoma, multiple melanoma, brain cancer, renal cancer, prostate cancer, ovarian cancer or breast cancer.

In some embodiments, the medicament is used as an inhibitor of PD-1/PD-L1 interaction.

In some embodiments, the medicament is used for enhancing, stimulating and/or increasing the immune response in a patient.

The general chemical terms used in the formula above have their usual meanings. For example, the term "halogen", as used herein, unless otherwise indicated, means fluoro, chloro, bromo or iodo. The preferred halogen groups include F, Cl and Br.

As used herein, unless otherwise indicated, alkyl includes saturated monovalent hydrocarbon radicals having straight, branched or cyclic moieties. For example, alkyl radicals include methyl, ethyl, propyl, isopropyl, cyclcopropyl, n-butyl, isobutyl, sec-butyl, t-butyl, cyclcobutyl, n-pentyl, 3-(2-methyl) butyl, 2-pentyl, 2-methylbutyl, neopentyl, cyclcopentyl, n-hexyl, 2-hexyl, 2-methylpentyl and cyclohexyl. Similarly, $C_1$-4, as in $C_{1-4}$alkyl is defined to identify the group as having 1, 2, 3, or 4 carbon atoms in a linear or branched arrangement.

Alkenyl and alkynyl groups include straight, branched chain or cyclic alkenes and alkynes. Likewise, "$C_{2-8}$ alkenyl" and "$C_{2-8}$ alkynyl" means an alkenyl or alkynyl radicals having 2, 3, 4, 5, 6, 7 or 8 carbon atoms in a linear or branched arrangement.

Alkoxy radicals are oxygen ethers formed from the previously described straight, branched chain or cyclic alkyl groups.

The term "aryl", as used herein, unless otherwise indicated, refers to an unsubstituted or substituted mono- or polycyclic ring system containing carbon ring atoms. The preferred aryls are mono cyclic or bicyclic 6-10 membered aromatic ring systems. Phenyl and naphthyl are preferred aryls. The most preferred aryl is phenyl.

The term "heterocyclyl", as used herein, unless otherwise indicated, represents an unsubstituted or substituted stable three to ten membered saturated or partially unsaturated monocyclic, spirocyclic, bridged bicyclic or fused bicyclic ring system which consists of carbon atoms and one to three heteroatoms selected from N, O or S, and wherein the nitrogen or sulfur heteroatoms may optionally be oxidized, and the nitrogen heteroatom may optionally be quaternized. The heterocyclyl group may be attached at any heteroatom or carbon atom which results in the creation of a stable structure. Examples of such heterocyclyl groups include, but are not limited to azetidinyl, pyrrolidinyl, piperidinyl, piperazinyl, oxopiperazinyl, oxopiperidinyl, oxoazepinyl, azepinyl, tetrahydrofuranyl, dioxolanyl, tetrahydroimidazolyl, tetrahydrothiazolyl, tetrahydrooxazolyl, tetrahydropyranyl, morpholinyl, thiomorpholinyl, thiamorpholinyl sulfoxide, thiamorpholinyl sulfone and oxadiazolyl.

The term "heteroaryl", as used herein, unless otherwise indicated, represents an unsubstituted or substituted stable five or six membered monocyclic aromatic ring system or an unsubstituted or substituted nine or ten membered benzofused heteroaromatic ring system or bicyclic heteroaromatic ring system which consists of carbon atoms and from one to four heteroatoms selected from N, O or S, and wherein the nitrogen or sulfur heteroatoms may optionally be oxidized, and the nitrogen heteroatom may optionally be quaternized. The heteroaryl group may be attached at any heteroatom or carbon atom which results in the creation of a stable structure. Examples of heteroaryl groups include, but are not limited to thienyl, furanyl, imidazolyl, isoxazolyl, oxazolyl, pyrazolyl, pyrrolyl, thiazolyl, thiadiazolyl, triazolyl, pyridyl, pyridazinyl, indolyl, azaindolyl, indazolyl, benzimidazolyl, benzofuranyl, benzothienyl, benzisoxazolyl, benzoxazolyl, benzopyrazolyl, benzothiazolyl, benzothiadiazolyl, benzotriazolyl adeninyl, quinolinyl or isoquinolinyl.

The term "alkenyloxy" refers to the group —O-alkenyl, where alkenyl is defined as above.

The term "alknyloxy" refers to the group —O-alknyl, where alknyl is defined as above.

The term "cycloalkyl" to a cyclic saturated alkyl chain having from 3 to 12 carbon atoms, for example, cyclopropyl, cyclobutyl, cyclobutyl, cyclobutyl.

The term "substituted" refers to a group in which one or more hydrogen atoms are each independently replaced with the same or different substituent(s). Typical substituents include, but are not limited to, halogen (F, Cl, Br or I), $C_{1-8}$ alkyl, $C_{3-12}$ cycloalkyl, —$OR^1$, $SR^1$, =O, =S, —$C(O)R^1$, —$C(S)R^1$, =$NR^1$, —$C(O)OR^1$, —$C(S)OR^1$, —$NR^1R^2$, —$C(O)NR^1R^2$, cyano, nitro, —$S(O)_2R^1$, —$OS(O_2)OR^1$, —$OS(O)_2R^1$, —$OP(O)(OR^1)(OR^2)$; wherein $R^1$ and $R^2$ is independently selected from —H, lower alkyl, lower haloalkyl. In some embodiments, the substituent(s) is independently selected from the group consisting of —F, —Cl, —Br, —I, —OH, trifluromethoxy, ethoxy, propyloxy, isopropyloxy, n-butyloxy, isobutyloxy, t-butyloxy, —$SCH_3$, —$SC_2H_5$, formaldehyde group, —$C(OCH_3)$, cyano, nitro, $CF_3$, —$OCF_3$, amino, dimethylamino, methyl thio, sulfonyl and acetyl.

The term "composition", as used herein, is intended to encompass a product comprising the specified ingredients in the specified amounts, as well as any product which results, directly or indirectly, from combinations of the specified ingredients in the specified amounts. Accordingly, pharmaceutical compositions containing the compounds of the present invention as the active ingredient as well as methods of preparing the instant compounds are also part of the present invention. Furthermore, some of the crystalline forms for the compounds may exist as polymorphs and as such are intended to be included in the present invention. In addition, some of the compounds may form solvates with water (i.e., hydrates) or common organic solvents and such solvates are also intended to be encompassed within the scope of this invention.

Examples of substituted alkyl group include, but not limited to, 2-aminoethyl, 2-hydroxyethyl, pentachloroethyl, trifluoromethyl, methoxymethyl, pentafluoroethyl and piperazinylmethyl.

Examples of substituted alkoxy groups include, but not limited to, aminomethoxy, thrifluoromethoxy, 2-diethylaminoethoxy, 2-ethoxycarbonylethoxy, 3-hydroxypropoxy.

The compounds of the present invention may also be present in the form of pharmaceutically acceptable salts. For use in medicine, the salts of the compounds of this invention refer to non-toxic "pharmaceutically acceptable salts". The pharmaceutically acceptable salt forms include pharmaceutically acceptable acidic/anionic or basic/cationic salts. The pharmaceutically acceptable acidic/anionic salt generally takes a form in which the basic nitrogen is protonated with an inorganic or organic acid. Representative organic or inorganic acids include hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic. Pharmaceutically acceptable basic/cationic salts include, and are not limited to aluminum, calcium, chloroprocaine, choline, diethanolamine, ethylenediamine, lithium, magnesium, potassium, sodium and zinc.

The present invention includes within its scope the prodrugs of the compounds of this invention. In general, such prodrugs will be functional derivatives of the compounds that are readily converted in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "Design of Prodrugs", ed. H. Bundgaard, Elsevier, 1985.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques know in the art as well as those methods set forth herein.

The present invention includes compounds described herein can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof.

The above Formula I are shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

When a tautomer of the compound of Formula I exists, the present invention includes any possible tautomers and pharmaceutically acceptable salts thereof, and mixtures thereof, except where specifically stated otherwise.

When the compound of Formula I and pharmaceutically acceptable salts thereof exist in the form of solvates or polymorphic forms, the present invention includes any possible solvates and polymorphic forms. A type of a solvent that forms the solvate is not particularly limited so long as the solvent is pharmacologically acceptable. For example, water, ethanol, propanol, acetone or the like can be used.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, formic, hydrochloric, maleic, phosphoric, sulfuric and tartaric acids, particularly preferred are formic and hydrochloric acid. Since the compounds of Formula I are intended for pharmaceutical use they are preferably provided in substantially pure form, for example at least 60% pure, more suitably at least 75% pure, especially at least 98% pure (% are on a weight for weight basis).

The pharmaceutical compositions of the present invention comprise a compound represented by Formula I (or a pharmaceutically acceptable salt thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula I, or a prodrug, or a metabolite, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as oil-in-water emulsion, or as a water-in-oil liquid emulsion. In addition to the common dosage forms set out above, the compound represented by Formula I, or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound, or a pharmaceutically acceptable salt, of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include such as lactose, terra alba, sucrose, talc, gelatin, agar, pectin, acacia, magnesium stearate, and stearic acid. Examples of liquid carriers include such as sugar syrup, peanut oil, olive oil, and water. Examples of gaseous carriers include such as carbon dioxide and nitrogen. In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient. For example, a formulation intended for the oral administration to humans may contain from about 0.5 mg to about 5 g of active agent, compounded with an appropriate and convenient amount of carrier material which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or a pharmaceutically acceptable salt thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including antioxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

Generally, dosage levels on the order of from about 0.01 mg/kg to about 150 mg/kg of body weight per day are useful in the treatment of the above-indicated conditions, or alternatively about 0.5 mg to about 7 g per patient per day. For example, colon cancer, rectal cancer, mantle cell lymphoma, multiple myeloma, breast cancer, prostate cancer, glioblastoma, squamous cell esophageal cancer, liposarcoma, T-cell lymphoma melanoma, pancreatic cancer, glioblastoma or lung cancer, may be effectively treated by the administration of from about 0.01 to 50 mg of the compound per kilogram of body weight per day, or alternatively about 0.5 mg to about 3.5 g per patient per day.

It is understood, however, that lower or higher doses than those recited above may be required. Specific dose level and treatment regimens for any particular subject will depend upon a variety of factors, including the activity of the specific compound employed, the age, body weight, general health, sex, diet, time of administration, route of administration, rate of excretion, drug combination, the severity and course of the particular disease undergoing therapy, the subject disposition to the disease, and the judgment of the treating physician.

These and other aspects will become apparent from the following written description of the invention.

The following Examples are provided to better illustrate the present invention. All parts and percentages are by weight and all temperatures are degrees Celsius, unless explicitly stated otherwise.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to inhibit the activity of PD-1/PD-L1 protein/protein interaction according to at least one assay described herein.

EXAMPLES

Experimental procedures for compounds of the invention are provided below. Open Access Preparative LCMS Purification of some of the compounds prepared was performed on Waters mass directed fractionation systems. The basic equipment setup, protocols and control software for the operation of these systems have been described in detail in literature. See, e.g., Blom, "Two-Pump At Column Dilution Configuration for Preparative LC-MS", K. Blom, J. Combi. Chem., 2002, 4, 295-301; Blom et al, "Optimizing Preparative LC-MS Configurations and Methods for Parallel Synthesis Purification", J. Combi. Chem., 2003, 5, 670-83; and Blom et al., "Preparative LC-MS Purification: Improved Compound Specific Method Optimization", J. Combi. Chem., 2004, 6, 874-883.

The compounds described herein can be obtained from commercial sources or synthesized by conventional methods as shown below using commercially available starting materials and reagents. The following abbreviations have been used in the examples:

EA: Ethyl Acetate;
STAB: Sodium triacetoxyborohydride;
TBAI: Tetrabutylammonium Iodide;
DMF: Dimethylformamide;
THF: Tetrahydrofuran;
TEA: Triethylamine;
TLC: Preparative thin layer chromatography;
AcOH or HOAC: Ethanoic acid;
BSA: Bovine serum album;
DCM: Dichloromethane;
DDQ: 2,3-Dichloro-5,6-dicyano-p-benzoquinone;
DMSO: Dimethyl sulfoxide;
EtOAc: Ethyl acetate;
h or hrs: hour or hours;
HTRF: Homogeneous Time Resolved Fluorescence;
MeOH: Methanol;
min: minute;
PE: petroleum ether;
Pd (dppf)Cl$_2$: [1,1'-Bis(diphenylphosphino)ferrocene]dichloropalladium;
rt or RT: room temperature;
TBAI: Tetrabutylammonium Iodide;
THF: Tetrahydrofuran;
Pd$_2$(dba)$_3$: Tris(dibenzylideneacetone)dipalladium;
NBS: N-Bromosuccinimide
BPO: Benzoyl peroxide
TLC: Preparative thin layer chromatography.

Syntheses of Intermediates

Example A Synthesis of Intermediate A methyl ((6-(difluoromethoxy)-2-(2-methyl-3-(4,4,5,5-tetramethyl-1,3,2-dioxaborolan-2-yl)phenyl)benzo[d]oxazol-5-yl)methyl)-L-prolinate

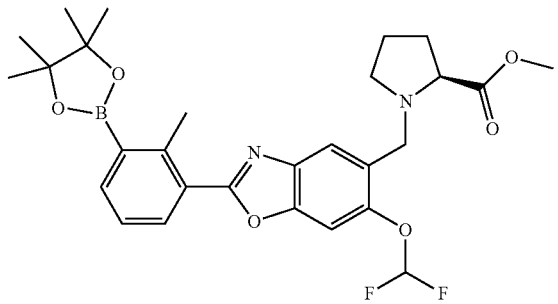

intermediate A

Step 1: Preparation of methyl 2,4-dihydroxy-5-nitrobenzoate

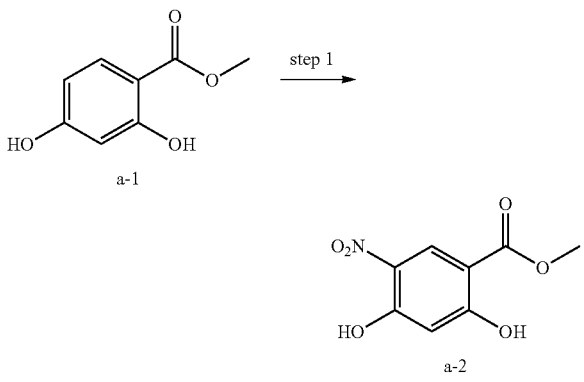

Methyl 2,4-dihydroxybenzoate (850 g) was dissolved in a mixture of glacial AcOH (3.6 L) and Ac₂O (900 mL). After cooling the clear solution to 10° C. (ice bath), a mixture of concentrated HNO₃ (65%) (455 ml) in glacial AcOH (500 mL) was added over 1 h. The light brown solution was allowed to rise to 15-20° C. and stirring was continued for a further 1 h. The reaction solution was poured into H₂O (3 L). The precipitate was filtered and rinsed with small amounts of H₂O. Then pour the crude product into MeOH (2 L) with stirring. The precipitate was filtered, rinsed with small amounts of MeOH, dried under vacuum to get the title product 480 g.

Step 2: Preparation of methyl 5-amino-2,4-dihydroxybenzoate

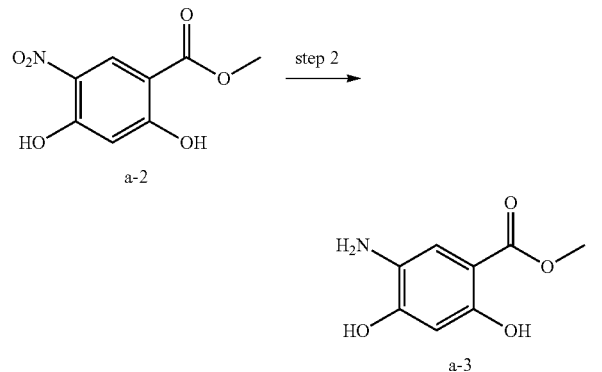

A mixture of compound a-2 (77.1 g) and 10% Pd(OH)/C (11.5 g) in methanol (2 L) was stirred under 1.1 atm of hydrogen pressure at room temperature for 3 hrs. The catalyst was then removed by filtration, the solid residue was washed with methanol (300 mL) and the solvent was removed in vacuo. This resulted in 72 g methyl 5-amino-2, 4-dihydroxybenzoate.

Step 3: Preparation of methyl 2-(3-bromo-2-methylphenyl)-6-hydroxybenzo[d]oxazole-5-carboxylate

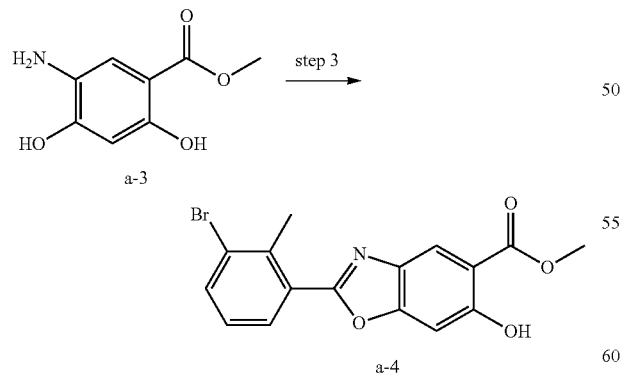

A mixture of methyl 5-amino-2,4-dihydroxybenzoate (32.9 g) and 3-bromo-2-methylbenzaldehyde (32.5 g) in MeOH (1 L) was stirred for 2.5 hrs at 80° C., Then the resulting mixture was concentered under reduced pressure. The mixture was added DCM (500 ml), and DDQ (55.6 g) was added. The mixture was stirred at room temperature for 1 h. The reaction was diluted with DCM and washed with aqueous Na₂S₂O₃ solution and NaHCO₃ solution. The organic phases were dried over MgSO₄, filtered and the filtrate was concentrated. The crude product was purified by column chromatography (PE:DCM=1/1) to afford 45 g methyl 2-(3-bromo-2-methylphenyl)-6-hydroxybenzo[d]oxazole-5-carboxylate as a brown solid.

Step 4: Preparation of methyl 2-(3-bromo-2-methylphenyl)-6-(difluoromethoxy)benzo[d]oxazole-5-carboxylate

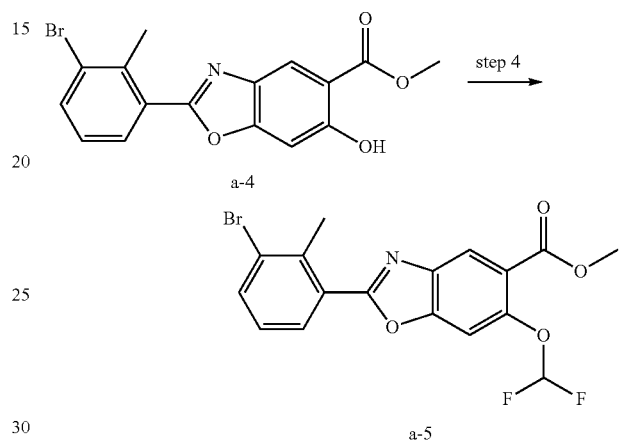

Methyl 2-(3-bromo-2-methylphenyl)-6-hydroxybenzo[d]oxazole-5-carboxylate (10.0 g), sodium 2-bromo-2,2-difluoroacetate (5.46 g), Cs₂CO₃ (27.09 g), KI (4.59 g), TBAI (10.22 g) was added into DMF (200 mL), The mixture was stirred at 100° C. for 3 hrs. The reaction was diluted with DCM and washed with saturated NaCl solution. The crude product was purified by column chromatography (PE: DCM=1/1) to afford 5 g methyl 2-(3-bromo-2-methylphenyl)-6-(difluoromethoxy)benzo[d]oxazole-5-carboxylate.

Step 5: Preparation of (2-(3-bromo-2-methylphenyl)-6-(difluoromethoxy)benzo[d]oxazol-5-yl)methanol

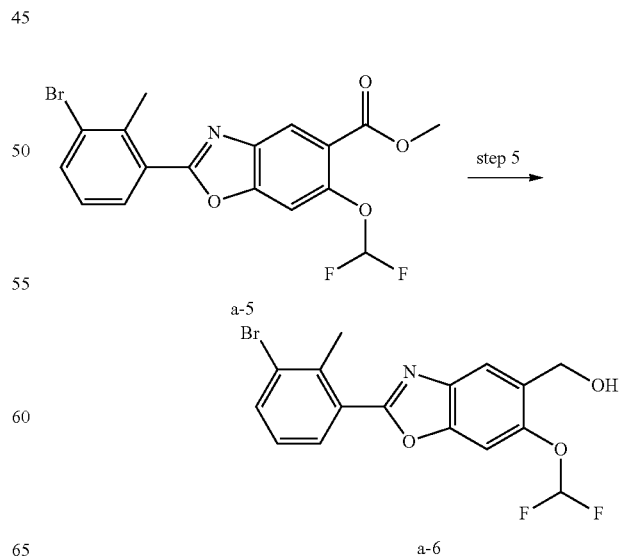

To a solution of methyl 2-(3-bromo-2-methylphenyl)-6-(difluoromethoxy) benzo[d]oxazole-5-carboxylate (1.30 g) in THF (50 mL) was added LiAlH₄ in THF (2.5 M) dropwise at −10° C. The mixture was warmed up to room temperature. After 1 h, the mixture was quenched with 1 mL H₂O and 1 mL 10% NaOH solution, washed with 1 M HCl, water and brine. The organic layers were dried over Na₂SO₄, filtered and the filtrate was concentrated. This resulted (2-(3-bromo-2-methylphenyl)-6-(difluoromethoxy)benzo[d]oxazol-5-yl) methanol as a yellow solid (1.2 g).

Step 6: Preparation of 2-(3-bromo-2-methylphenyl)-6-(difluoromethoxy) benzo[d]oxazole-5-carbaldehyde

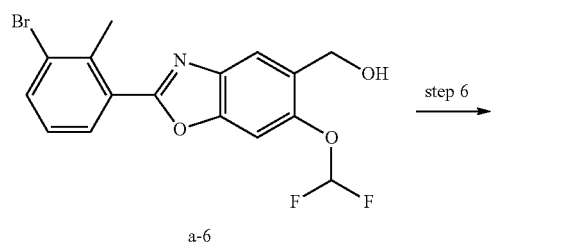

To a solution of (2-(3-bromo-2-methylphenyl)-6-(difluoromethoxy) benzo [d]oxazol-5-yl) methanol (1.40 g) in dry THF (15 mL) was added Dess-Martin (2.39 g) in portions at 10° C. The resulting solution was stirred for 1 h at room temperature. The mixture was filtered through celite. The solids were washed with DCM, and the combined filtrates were washed with sodium bicarbonate aqueous solution, water and brine, dried and concentrated. The residue was purified by column chromatography (eluting with hexane-EtOAc using a gradient from 20:1 to 5:1) to afford 2-(3-bromo-2-methylphenyl)-6-(difluoromethoxy) benzo[d]oxazole-5-carbaldehyde (1.27 g).

Step 7: Preparation of methyl ((2-(3-bromo-2-methylphenyl)-6-(difluoromethoxy) benzo[d]oxazol-5-yl) methyl)-L-prolinate

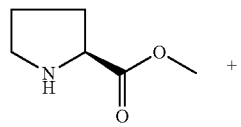

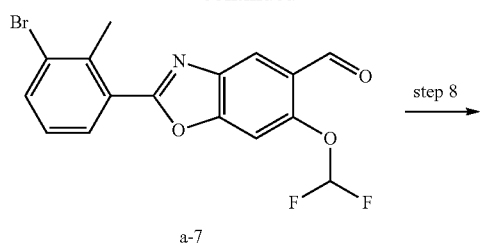

A solution of 2-(3-bromo-2-methylphenyl)-6-(difluoromethoxy) benzo[d]oxazole-5-carbaldehyde (1.0 g), methyl L-proline (1.7 g), HOAC (316 mg) in MeOH was stirred at room temperature for 30 mins. The mixture was added NaBH₃CN (498 mg), then was heated at 60° C. for 2 hrs. The mixture was cooled, diluted with DCM and washed with H₂O and NaCl solution. The organic phases were dried over MgSO₄, filtered and the filtrate was concentrated. The residue was purified by column chromatography (DCM:MeOH=10:1), to afford 671 mg methyl ((2-(3-bromo-2-methylphenyl)-6-(difluoromethoxy) benzo[d]oxazol-5-yl) methyl)-L-prolinate as a white solid.

Step 8: Preparation of methyl ((6-(difluoromethoxy)-2-(2-methyl-3-(4,4,5,5-tetramethyl-1,3,2-dioxaborolan-2-yl)phenyl)benzo[d]oxazol-5-yl) methyl)-L-prolinate

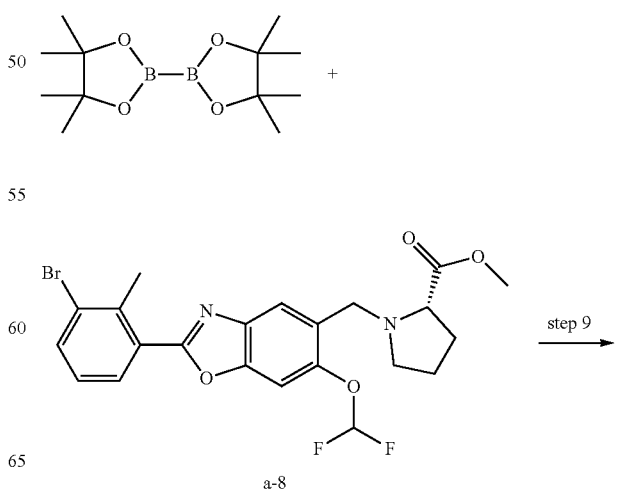

-continued

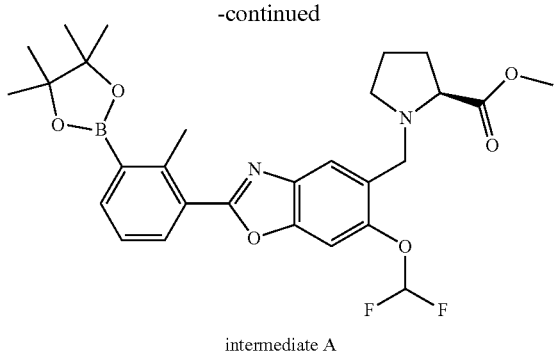

intermediate A

To a solution of methyl ((2-(3-bromo-2-methylphenyl)-6-(difluoromethoxy) benzo[d]oxazol-5-yl)methyl)-L-prolinate (680 mg) in 1,4-dioxane (16.0 ml) was added Bis(pinacolato)diboron (1.20 g), Pd(dppf)Cl$_2$·DCM (100 mg), and KOAc (102 mg) under N$_2$ protection. The reaction mixture was heated at 100° C. for 10 hrs. It was diluted with 30 mL of water and then extracted with DCM (90 ml×2). The combined organic extracts were washed with brine, dried over MgSO$_4$ and concentrated in vacuo. The residue was purified by silicagel (eluting with hexane-EtOAc using a gradient from 4:1 to 2:1) to afford methyl ((6-(difluoromethoxy)-2-(2-methyl-3-(4,4,5,5-tetramethyl-1,3,2-dioxaborolan-2-yl)phenyl)benzo[d]oxazol-5-yl)methyl)-L-prolinate (500 mg). LC-MS (m/z): 543.2 (M+H)$^+$.

Example B Synthesis of Intermediate B methyl ((6-(difluoromethoxy)-2-(2,2'-dimethyl-3'-(4,4,5,5-tetramethyl-1,3,2-dioxaborolan-2-yl)-[1,1'-biphenyl]-3-yl)benzo[d]oxazol-5-yl)methyl)-L-prolinate intermediate B

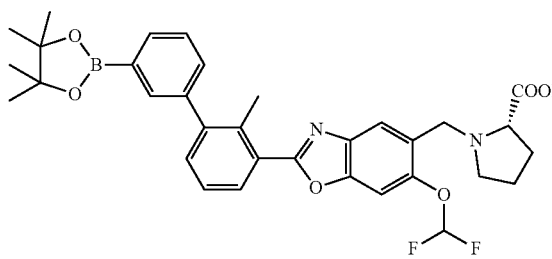

Step 1: Preparation of methyl ((2-(3'-bromo-2,2'-dimethyl-[1,1'-biphenyl]-3-yl)-6-(difluoromethoxy)benzo[d]oxazol-5-yl)methyl)-L-prolinate

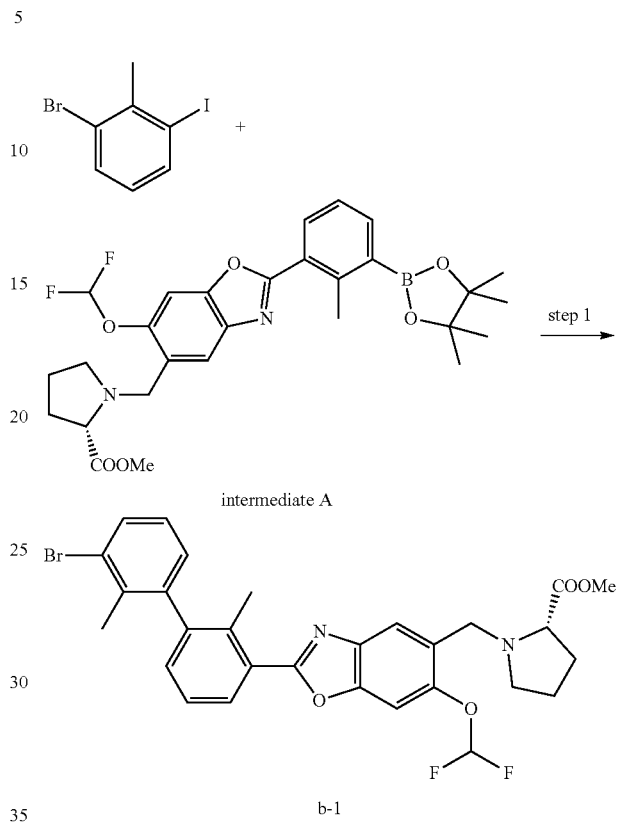

To a solution of intermediate A (21.7 g), 1-bromo-3-iodo-2-methylbenzene (9.0 g) in toluene (150 mL), EtOH (30 mL), 10% Na$_2$CO$_3$ aq. (30 mL), Pd(dppf)Cl$_2$·DCM (1.0 g) was added under N$_2$ protection. The mixture was allowed to stir at 90° C. overnight. The reaction was quenched with H$_2$O (100 mL) and extracted with EtOAc (100 mL) for 3 times. The organic layers were combined and washed with brine. The resulting solution was concentrated and purified by silicagel (eluting with Hexane-EtOAc using a gradient from 10:1 to 4:1) to afford methyl ((2-(3'-bromo-2,2'-dimethyl-[1,1'-biphenyl]-3-yl)-6-(difluoromethoxy)benzo[d]oxazol-5-yl)methyl)-L-prolinate (18.2 g) as a brown oil.

Step 2: Preparation of methyl ((6-(difluoromethoxy)-2-(2,2'-dimethyl-3'-(4,4,5,5-tetramethyl-1,3,2-dioxaborolan-2-yl)-[1,1'-biphenyl]-3-yl)benzo[d]oxazol-5-yl)methyl)-L-prolinate

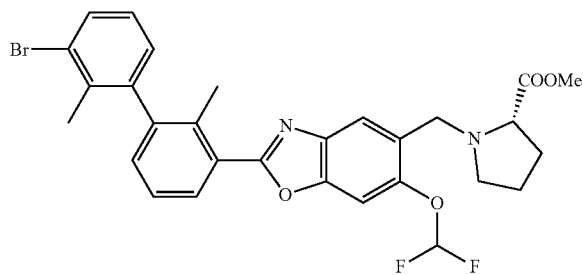 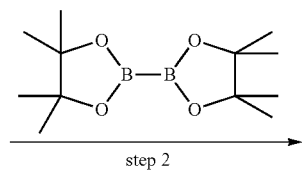

b-1

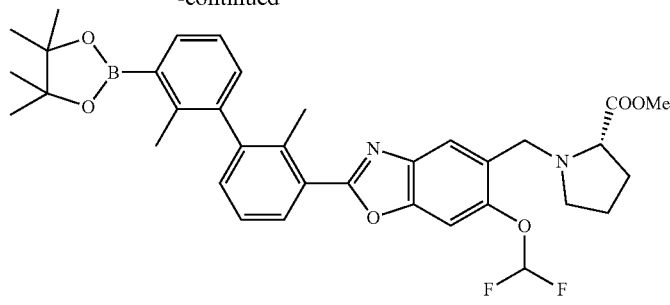

intermediate B

To a solution of compound b-1 (18.2 g) in 1,4-dioxane (120 mL) was added Bis(pinacolato)diboron (12.4 g), Pd(dppf)Cl$_2$·DCM (1.0 g) and KOAc (9.9 g) under N$_2$ protection. The reaction mixture was heated at 100° C. for 6 hrs. It was diluted with 300 mL of water and then extracted with EtOAc (150 ml) for three times. The combined organic extracts were washed with brine, dried over MgSO$_4$ and concentrated in vacuo. The residue was purified by silicagel (eluting with hexane-EtOAc using a gradient from 20:1 to 10:1) to afford methyl ((6-(difluoromethoxy)-2-(2,2'-dimethyl-3'-(4,4,5,5-tetramethyl-1,3,2-dioxaborolan-2-yl)-[1,1'-biphenyl]-3-yl)benzo[d]oxazol-5-yl)methyl)-L-prolinate (15.1 g) as a brown oil. LC-MS (m/z): 633.9 (M+H)$^+$.

Example 1 Synthesis of Compound 1

((6-(difluoromethoxy)-2-(3'-(6-(difluoromethoxy)-5-((((1R,2S)-2-hydroxycyclopentyl)(methyl)amino)methyl)benzo[d]oxazol-2-yl)-2,2'-dimethyl-[1,1'-biphenyl]-3-yl)benzo[d]oxazol-5-yl)methyl)-L-proline Compound 1

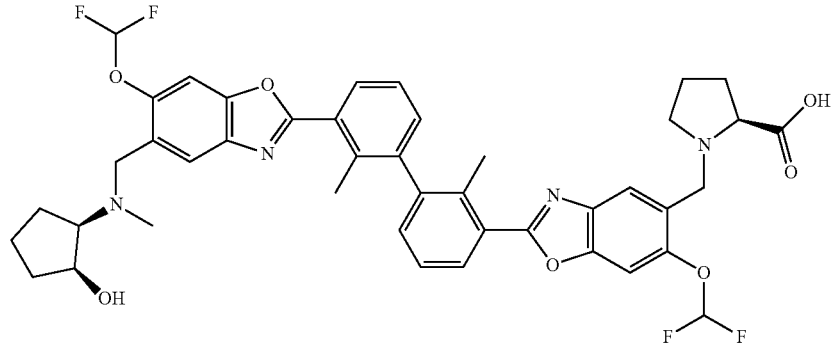

Step 1: Preparation of methyl ((6-(difluoromethoxy)-2-(3'-(6-(difluoromethoxy)-5-(hydroxymethyl)benzo[d]oxazol-2-yl)-2,2'-dimethyl-[1,1'-biphenyl]-3-yl)benzo[d]oxazol-5-yl)methyl)-L-prolinate

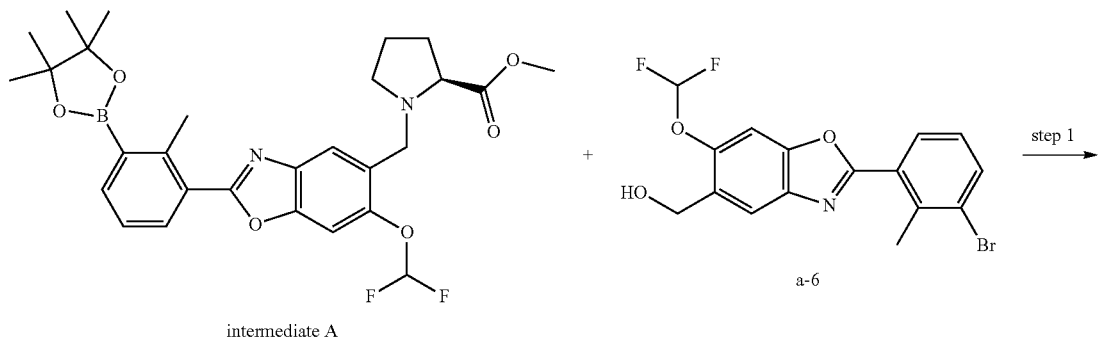

intermediate A a-6 step 1

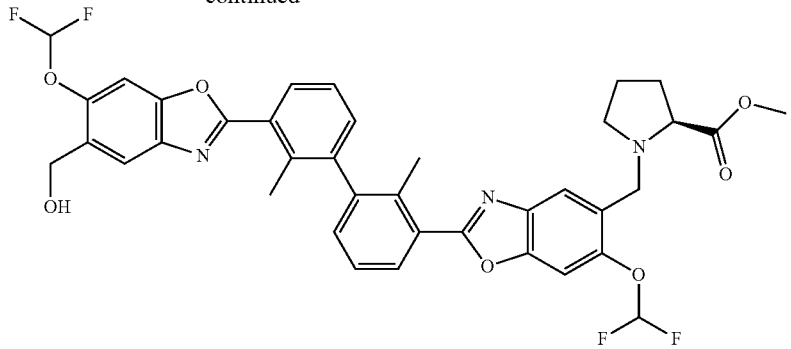

1-1

To a mixture of intermediate A (5 g) in 1,4-dioxane (80 mL)/H₂O (16 mL) was added compound a-6 (3.9 g), K₂CO₃ (3.8 g) and Pd(dppf)Cl₂CH₂Cl₂ (732 mg). The mixture was stirred at 80° C. for 12 hrs under N₂ atmosphere. Until the raw material is almost finished and the reaction stopped, the mixture was poured into H₂O (300 mL) and extracted with DCM (100 mL) for 3 times. The organic layers were washed with brine, dried over anhydrous Na₂SO₄, filtered, concentrated to get a residue. The residue was further purified by Silica gel column to get the compound 1-1 (3.7 g).

Step 2: Preparation of methyl ((2-(3'-(5-(chloromethyl)-6-(difluoromethoxy)benzo[d]oxazol-2-yl)-2, 2'-dimethyl-[1,1'-biphenyl]-3-yl)-6-(difluoromethoxy) benzo[d] oxazol-5-yl) methyl)-L-prolinate

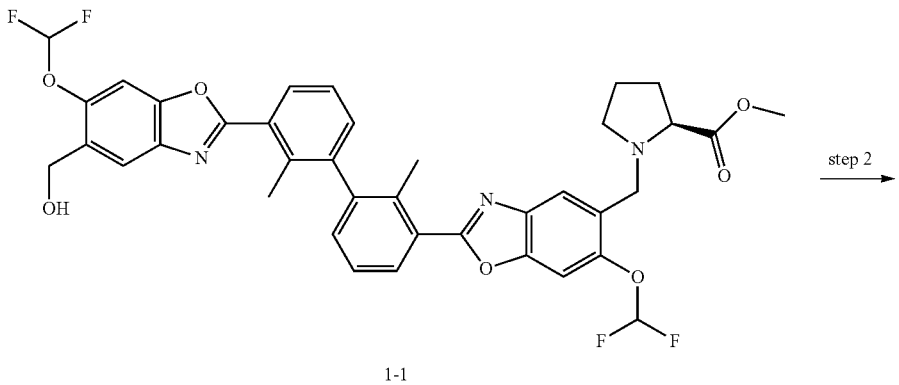

1-1

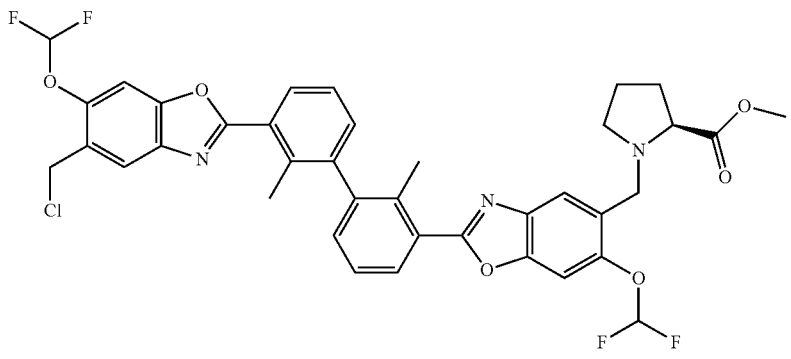

1-2

Compound 1-1 (1.5 g) was dissolved in DCM (20 mL). SOCl₂ (495 mg) was added dropwises and stirred at room temperature for 1 h. Until the raw material was vanished and the reaction stops, the resulting mixture was concentered under reduced pressure. This resulted in 1.56 g compound 1-2 (crude).

Step 3: Preparation of methyl ((6-(difluoromethoxy)-2-(3'-(6-(difluoromethoxy)-5-((((1R,2S)-2-hydroxycyclopentyl)amino)methyl)benzo[d]oxazol-2-yl)-2,2'-dimethyl-[1,1'-biphenyl]-3-yl)benzo[d]oxazol-5-yl)methyl)-L-prolinate

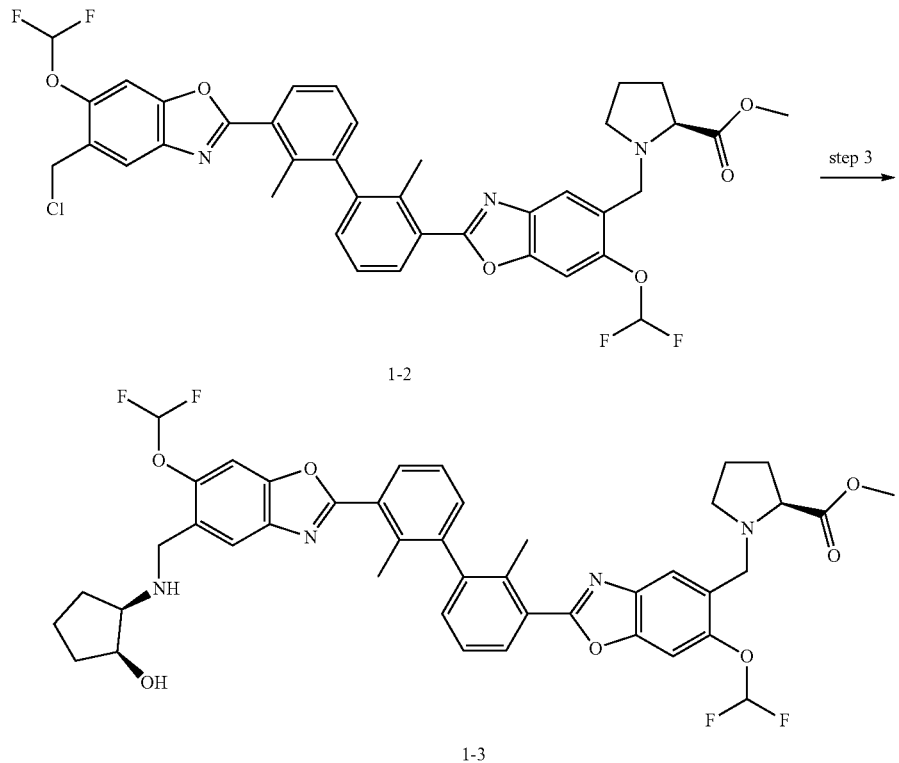

A mixture of compound 1-2 (300 mg), (1S, 2R)-2-aminocyclopentan-1-ol (168 mg), K₂CO₃ (283 mg), KI (68 mg) in CH₃CN (10 mL) was stirred at 50° C. for 1.5 hrs. Until the raw material was almost finished and the reaction stops, the reaction solution was poured into H₂O (30 mL) and extracted with DCM (15 mL) for 3 times. The organic layers were washed with brined, dried over anhydrous Na₂SO₄, filtered and concentrated under reduced pressure to get the crude product. The crude product was further purified by Silica gel column (DCM/MeOH) to get compound 1-3 (240 mg).

Step 4: Preparation of methyl ((6-(difluoromethoxy)-2-(3'-(6-(difluoromethoxy)-5-((((1R,2S)-2-hydroxycyclopentyl)(methyl) amino)methyl)benzo[d]oxazol-2-yl)-2,2'-dimethyl-[1,1'-biphenyl]-3-yl)benzo[d]oxazol-5-yl)methyl)-L-prolinate

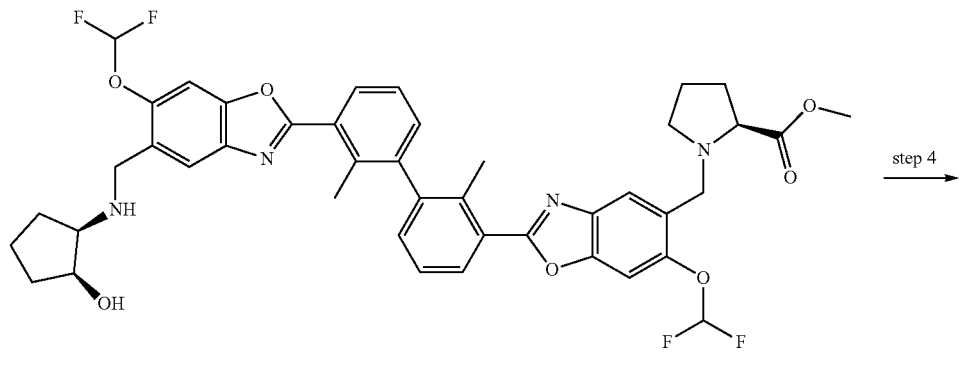

-continued

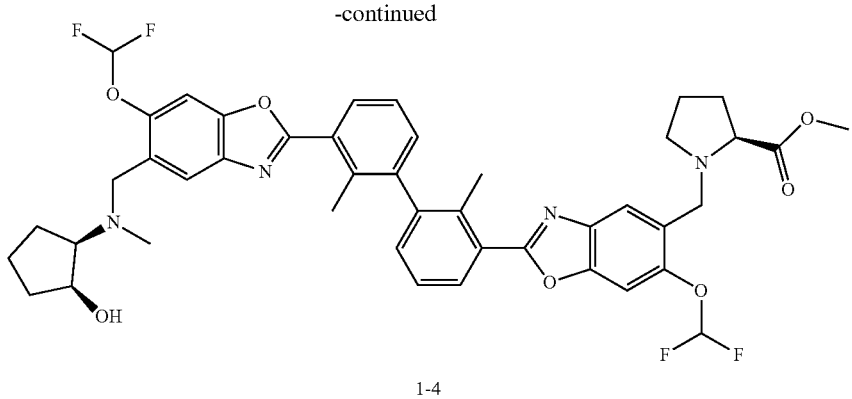

1-4

A mixture of compound 1-3 (240 mg), HCHO (45 mg), CH₃COOH (36 mg) in MeOH (5 mL)/DCM (5 mL) was stirred at 30° C. for 30 mins, then NaBH₃CN (57 mg) was added and continue stirred, until the raw material was almost finished and the reaction stops. The reaction solution was poured into H₂O (30 mL) and extracted with DCM (15 mL) for 3 times. The organic layers were washed with brine, dried over anhydrous Na₂SO₄, filtered and concentrated under reduced pressure to get the crude product. The crude product was further purified by Silica gel column (DCM/MeOH) to get compound 1-4 (200 mg).

Step 5: Preparation of (((6-(difluoromethoxy)-2-(3'-(6-(difluoromethoxy)-5-((((1R,2S)-2-hydroxycyclopentyl)(methyl)amino)methyl)benzo[d]oxazol-2-yl)-2,2'-dimethyl-[1,1'-biphenyl]-3-yl)benzo[d]oxazol-5-yl)methyl)-L-proline (compound 1)

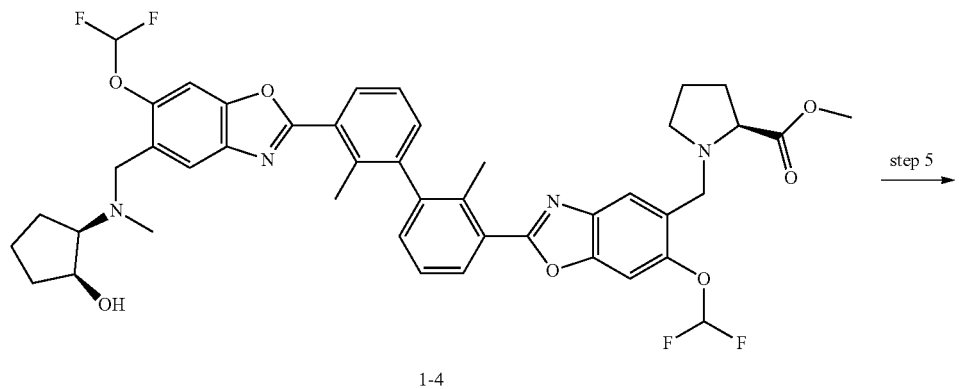

1-4 step 5

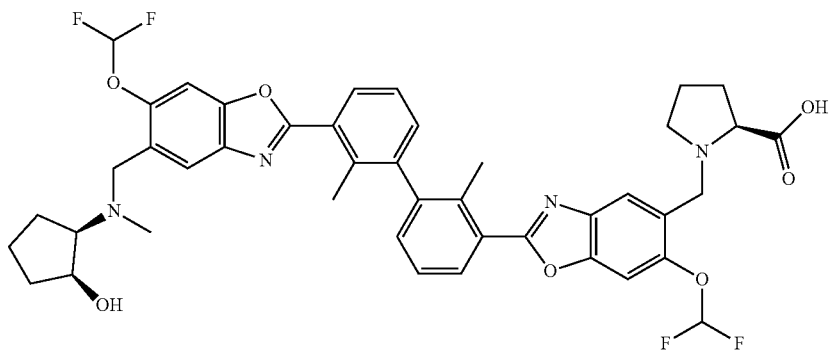

Compound 1

Compound 1-4 (200 mg) and LiOH (51 mg) was dissolved in a mixture of THF (8 mL)/H₂O (2 mL) and stirred at 35° C. for 12 hrs. The reaction solution was poured into H₂O (30 mL) and extracted with DCM (10 mL)/MeOH (5 mL) for 3 times. The organic layers were combined, dried over anhydrous MgSO₄, filtered and concentrated under reduced pressure. This resulted in 160 mg ((6-(difluoromethoxy)-2-(3'-(6-(difluoromethoxy)-5-(((((1R,2S)-2-hydroxycyclopentyl)(methyl)amino)methyl)benzo[d]oxazol-2-yl)-2,2'-dimethyl-[1,1'-biphenyl]-3-yl)benzo[d]oxazol-5-yl)methyl)-L-proline (compound 1). LC-MS (m/z): 803.3 (M+H)⁺.

Example 2 Synthesis of Compound 2

(2'S)-(((2,2'-dimethyl-[1,1'-biphenyl]-3,3'-diyl)bis(6-(difluoromethoxy)benzo[d]oxazole-2,5-diyl))bis(methylene))di-L-proline

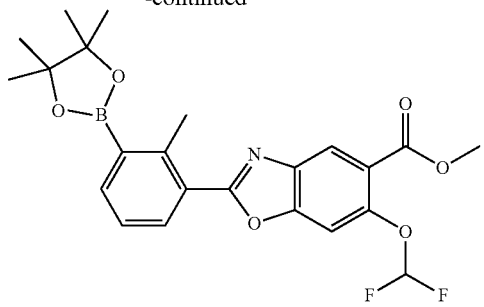

2-1

To a solution of compound a-5 (880 mg) in 1, 4-dioxane (16.0 mL) was added Bis (pinacolato) diboron (1.80 g), Pd(dppf)Cl₂·DCM (150 mg), and KOAc (130 mg). The reaction mixture was heated at 100° C. for 10 hrs. It was diluted with 30 mL water and then extracted with DCM (90 mL×2). The combined organic extracts were washed with

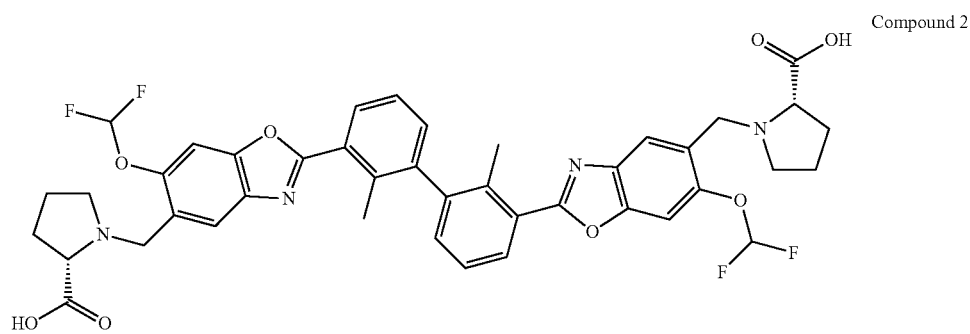 [SMILES: Cc1c(-c2nc3cc(CN4CCC[C@H]4C(=O)O)c(OC(F)F)cc3o2)cccc1-c1cccc(-c2nc3cc(CN4CCC[C@H]4C(=O)O)c(OC(F)F)cc3o2)c1C]

Compound 2

Step 1: Preparation of methyl 6-(difluoromethoxy)-2-(2-methyl-3-(4,4,5,5-tetramethyl-1,3,2-dioxaborolan-2-yl)phenyl)benzo[d]oxazole-5-carboxylate brine, dried over MgSO₄ and concentrated in vacuo to get the residue. The residue was purified by silicagel (eluting with hexane-EtOAc using a gradient from 4:1 to 2:1) to afford compound 2-1 (600 mg).

Step 2: Preparation of dimethyl2, 2'-(2, 2'-dimethyl-[1, 1'-biphenyl]-3, 3'-diyl) bis (6-(difluoromethoxy) benzo[d]oxazole-5-carboxylate)

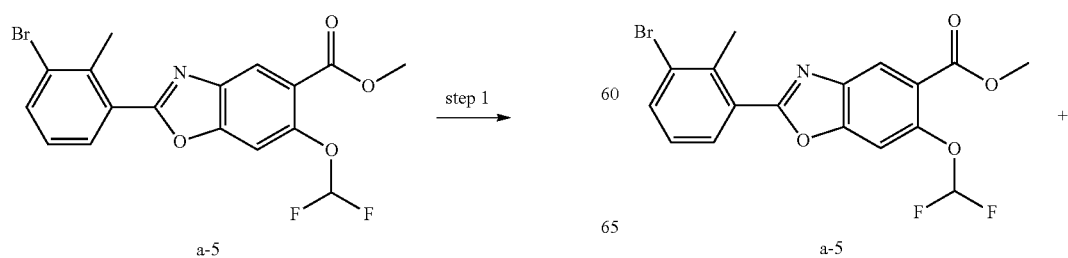

a-5          step 1          a-5          +

-continued

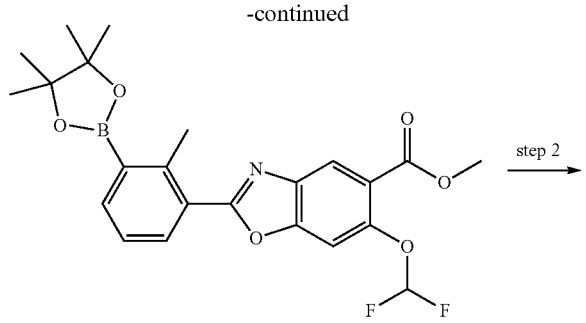

2-1

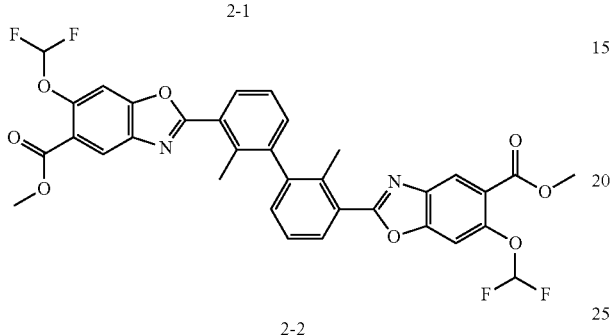

2-2

A mixture of compound 2-1 (8 g), compound a-5 (8.95 g), K₂CO₃ (5.25 g) and Pd(dppf)cl₂·DCM (1.65 g) in 1,4-Dioxane (160 mL)/H₂O (16 mL) was evacuated and refilled three times using nitrogen. The mixture was heated at reflux for 2 hrs. The reaction was added 200 mL H₂O and extracted with EtOAc (2×200 mL). The combined organic layers were washed with brine (100 mL), and then dried over Na₂SO₄. The resulting solution was filtered and concentrated to get a residue. The residue was purified by Column chromatography (EA) to get the compound 2-2 (6.3 g).

Step 3: Preparation of ((2,2'-dimethyl-[1,1'-biphenyl]-3,3'-diyl)bis(6-(difluoromethoxy) benzo[d] oxazole-2,5-diyl))dimethanol

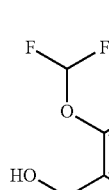

2-2

2-3

The LiAlH₄ (2.5M) was added dropwise to the solution of compound 2-2 (6.3 g) in THF (150 mL) at 0° C. The mixture was stirred at 0° C. for 30 mins. The reaction mixture was quenched with H₂O at 0° C. The mixture was dried over Na₂SO₄, filtered and concentrated to get the compound 2-3 (5.7 g).

Step 4: Preparation of 2,2'-(2,2'-dimethyl-[1,1'-biphenyl]-3,3'-diyl)bis(6-(difluoromethoxy) benzo[d]oxazole-5-carbaldehyde)

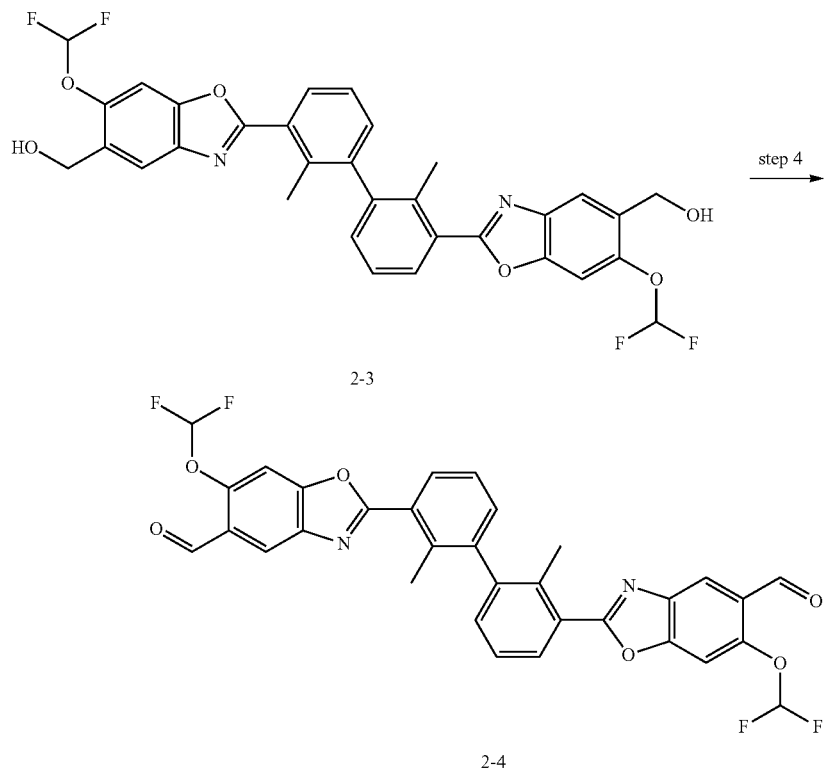

The Dess-Martin (11.95 g) was added to the solution of compound 2-3 (5.70 g) in THF (100 mL). The mixture was stirred at RT for 2 hrs. The reaction was quenched with NaHCO₃ and Na₂SO₃ and extracted with EtOAc (2×100 mL). The combined organic layers were washed with brine (100 mL), dried over Na₂SO₄, filtered and concentrated to get the compound 2-4 (5.5 g).

Step 5: Preparation of (2'S)-(((2,2'-dimethyl-[1,1'-biphenyl]-3,3'-diyl)bis(6-(difluoromethoxy)benzo[d]oxazole-2,5-diyl))bis(methylene))di-L-proline (compound 2)

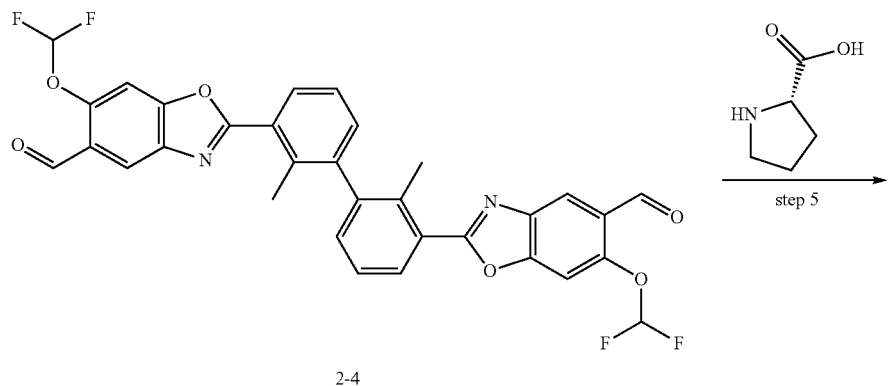

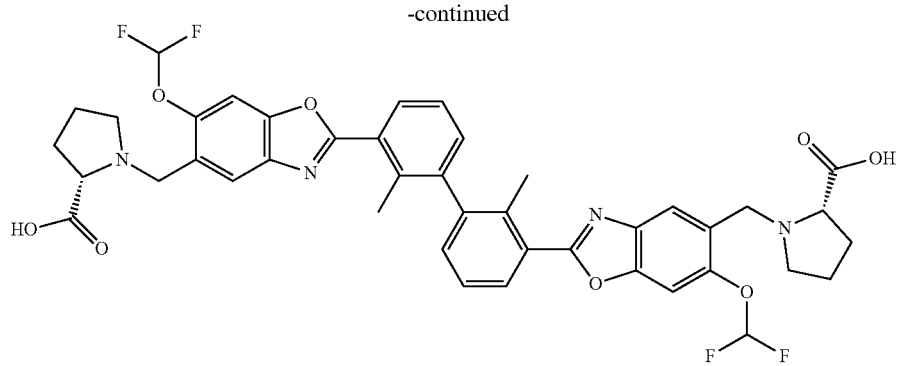

Compound 2

A mixture of compound 2-4 (4 g), L-proline (4.58 g) and AcOH (0.82 g) in MeOH (100 mL) was stirred for 30 mins. NaBH₃CN was added to the mixture and the mixture was stirred for 12 hrs. The reaction was added 200 mL H₂O and extracted with DCM (2×200 mL). The combined organic layers were dried over Na₂SO₄. The resulting solution was filtered and concentrated to get the crude product. The crude product was purified by Column chromatography (DCM/MeOH=10:1) to get 2.56 g (2'S)-(((2,2'-dimethyl-[1,1'-biphenyl]-3,3'-diyl)bis(6-(difluoromethoxy)benzo[d]oxazole-2,5-diyl))bis(methylene))di-L-proline (compound 2). LC-MS (m/z): 803.3 (M+H)⁺.

Example 3 Synthesis of Compound 3

((6-(difluoromethoxy)-2-(3'-(6-(difluoromethoxy)-5-(((S)-2-(methoxycarbonyl)pyrrolidin-1-yl)methyl) benzo[d]oxazol-2-yl)-2,2'-dimethyl-[1,1'-biphenyl]-3-yl)benzo[d]oxazol-5-yl)methyl)-L-proline

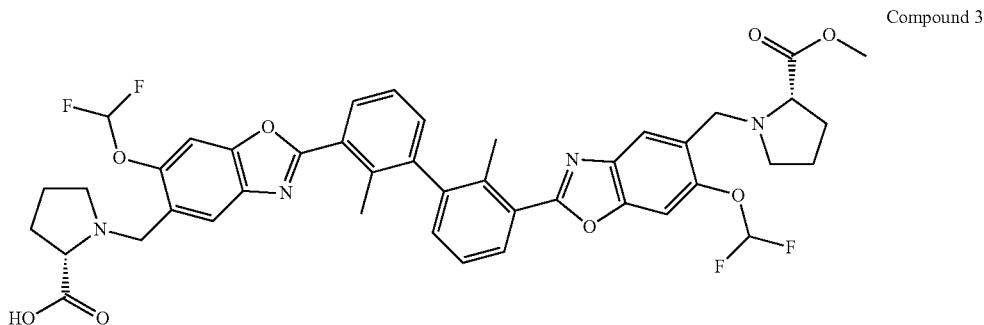 [SMILES: COC(=O)[C@@H]1CCCN1Cc1cc2nc(-c3cccc(-c4cccc(-c5nc6cc(CN7CCC[C@H]7C(=O)O)c(OC(F)F)cc6o5)c4C)c3C)oc2cc1OC(F)F]

Compound 3

Step 1 Preparation of methyl ((6-(difluoromethoxy)-2-(3'-(6-(difluoromethoxy)-5-formyl-benzo[d]oxazol-2-yl)-2,2'-dimethyl-[1,1'-biphenyl]-3-yl)benzo[d]oxazol-5-yl)methyl)-L-prolinate

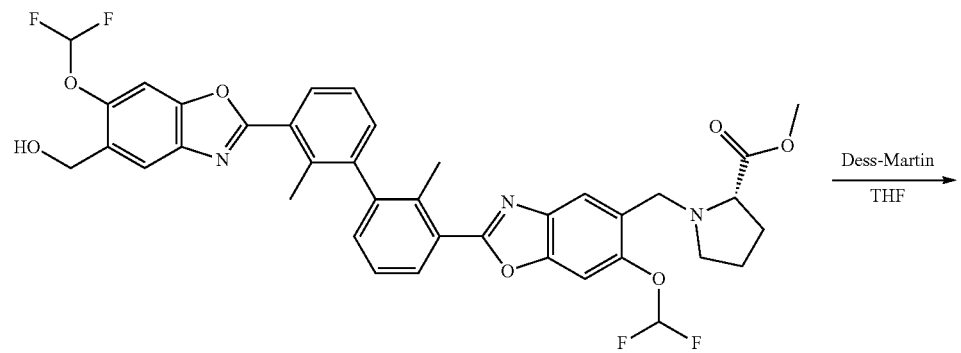

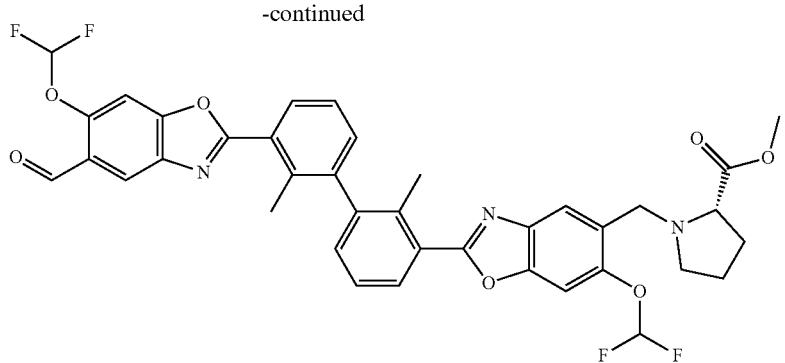

3-1

The Dess-Martin (11.79 g) was added to the solution of compound 1-1 (10.00 g) in THF (200 ml) in portions. The mixture was stirred for 2 h at RT. The reaction was quenched with $Na_2SO_3$ and sodium bicarbonate aqueous solution. The Reaction was extracted with EtOAc (2×150 ml). The combined organic phase was washed with brine (100 ml), dried over $Na_2SO_4$, filtered and concentrated to get the compound 3-1 (9.50 g).

Step 2: Preparation of ((6-(difluoromethoxy)-2-(3'-(6-(difluoromethoxy)-5-(((S)-2-(methoxycarbonyl)pyrrolidin-1-yl)methyl)benzo[d]oxazol-2-yl)-2,2'-dimethyl-[1,1'-biphenyl]-3-yl)benzo[d]oxazol-5-yl)methyl)-L-proline

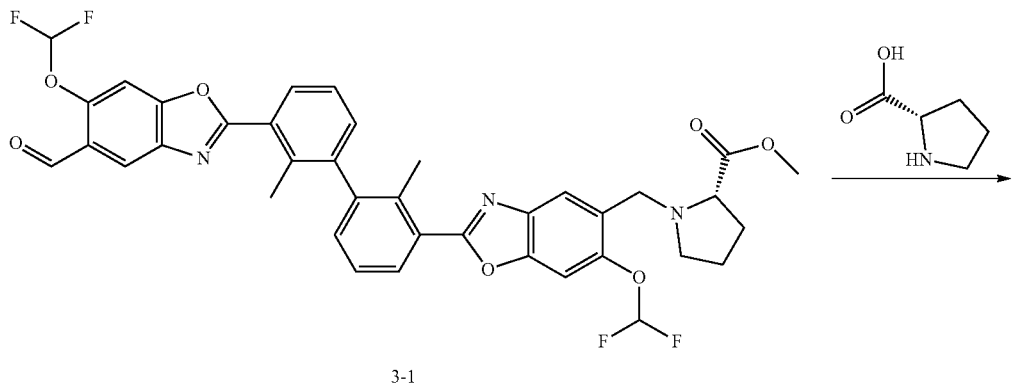

3-1

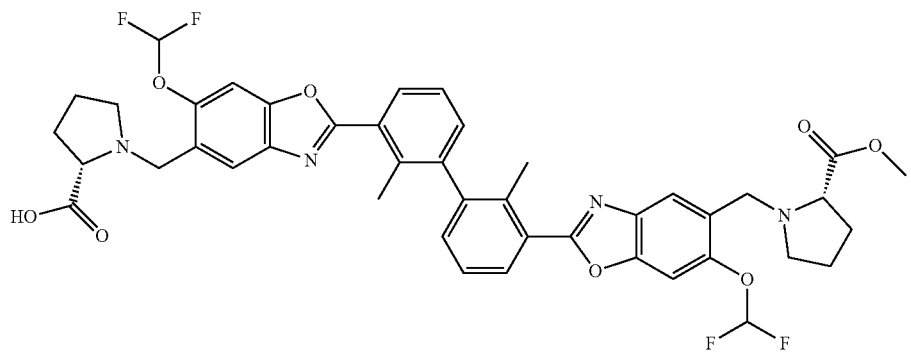

Compound 3

A mixture of compound 3-1 (5.90 g), L-proline (2.85 g) and AcOH (0.51 g) in MeOH (60 mL) was stirred for 30 mins. Then NaBH$_3$CN (1.55 g) was added to the mixture. The reaction was stirred for 3 hrs. The reaction was added 100 mL H$_2$O and extracted with DCM (2×100 mL). The combined organic layers were dried over Na$_2$SO$_4$, filtered and concentrated to get the residue. The residue was purified by Column chromatography (DCM/MeOH=10:1) to get ((6-(difluoromethoxy)-2-(3'-(6-(difluoromethoxy)-5-(((S)-2-(methoxycarbonyl)pyrrolidin-1-yl)methyl)benzo[d]oxazol-2-yl)-2,2'-dimethyl-[1,1'-biphenyl]-3-yl)benzo[d]oxazol-5-yl)methyl)-L-proline (3.6 g). LC-MS (m/z): 817.3 (M+H)$^+$.

Example 4 Synthesis of Compound 4

((2-(2'-cyano-3'-(6-(difluoromethoxy)-5-((3,3-dimethylazetidin-1-yl)methyl)benzo[d]oxazol-2-yl)-2-methyl-[1,1'-biphenyl]-3-yl)-6-(difluoromethoxy)benzo[d]oxazol-5-yl)methyl)-L-proline Compound 4

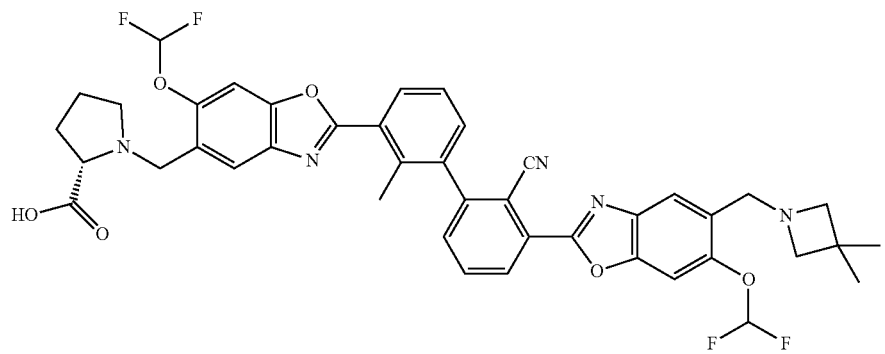

Step 1: Preparation of 2-bromo-6-vinylbenzonitrile

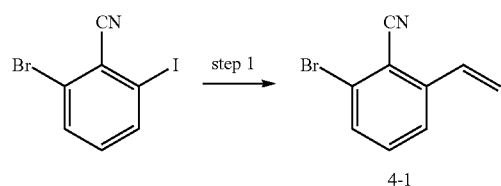

A mixture of 2-bromo-6-iodobenzonitrile (10 g), 4,4,5,5-tetramethyl-2-vinyl-1,3,2-dioxaborolane (5 g), [1,1'-Bis(diphenylphosphino)ferrocene]dichloropalladium(II) (2.5 g), and Potassium carbonate (13.4 g) in 1,4-dioxane (100 mL)/H$_2$O (20 mL) was stirred at 80° C. for 12 hrs under N$_2$ atmosphere. The reaction solution was poured into H$_2$O (30 mL) and extracted with DCM (15 mL×3). The organic layers were washed with brine, dried overanhydrous Na$_2$SO$_4$, filtered and concentrated under reduced pressure to get the crude product. The crude product was further purified by Silica gel column to get the compound 4-1 (5 g).

Step 2: Preparation of 2-bromo-6-formylbenzonitrile

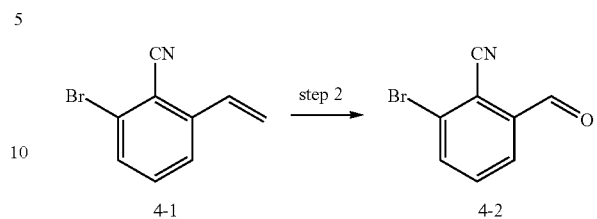

A mixture of compound 4-1 (1 g) and sodium periodate (3.67 g) in THF (20 mL)/H$_2$O (6 mL) was stirred under ice bath, then potassium osmate (20 mg) was added and the mixture was stirred at room temperature for 4 hrs. The reaction mixture was poured into H$_2$O (150 mL) and extracted with EA (100 mL) for 2 times, the organic layers were washed with brine, dried over anhydrous Na$_2$SO$_4$, filtered and concentrated to get the title compound 4-2 (800 mg).

Step 3: Preparation of methyl 2-(3-bromo-2-cyanophenyl)-6-hydroxybenzo[d]oxazole-5-carboxylate

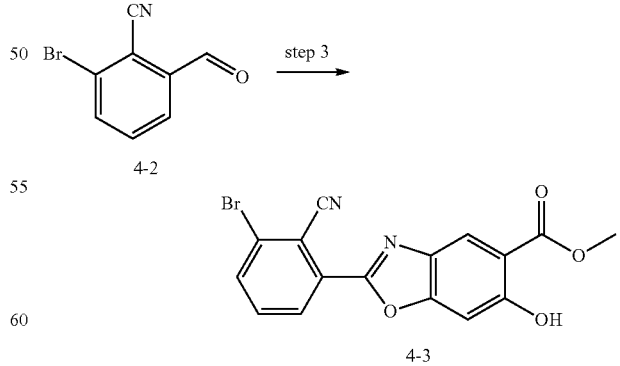

A mixture of compound 4-2 (1 g) and methyl 5-amino-2,4-dihydroxybenzoate (870 mg) in MeOH (150 mL) was stirred at 80° C. for 2.5 hrs, then the reaction mixture was concentrated under reduced pressure and dissolved in dichloromethane. 2,3-Dichloro-5,6-dicyano-1,4-benzoquinone (1.3 g) was added into the solution and continue stirred at room temperature. After 1 h, the mixture was filtered, the filter cake was washed with dichloromethane and the filtrate was concentrate under reduced pressure to get the crude product. The crude product was suspended in methanol, the solution was filtered, and the filter cake was dried in a vacuum oven to get the title compound (1.4 g).

Step 4: Preparation of methyl 2-(3-bromo-2-cyanophenyl)-6-(difluoromethoxy)benzo[d]oxazole-5-carboxylate

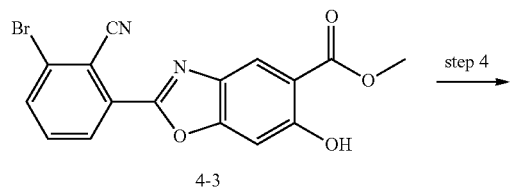

4-3 step 4

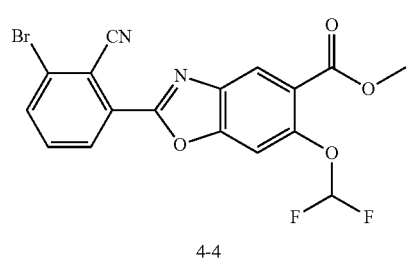

4-4

Sodium chlorodifluoroacetate (850 mg), Cesium carbonate (2.62 g) was added into a stirred solution of Methyl 2-(3-bromo-2-cyanophenyl)-6-hydroxybenzo[d]oxazole-5-carboxylate (1 g) in DMF (20 mL)/H₂O (0.6 mL), the reaction mixture was heated to 80° C. and stirred for 4 hrs. Then the mixture was poured into H₂O (100 mL) and extracted with EA (80 mL) for 2 times. The combined organic layers were washed with brine, dried over anhydrous Na₂SO₄, filtered and concentrated to get the crude product. The crude product was further purified by Silica gel column to get the title compound 4-4 (800 mg).

Step 5: Preparation of 2-bromo-6-(6-(difluoromethoxy)-5-(hydroxymethyl)benzo[d]oxazol-2-yl)benzonitrile

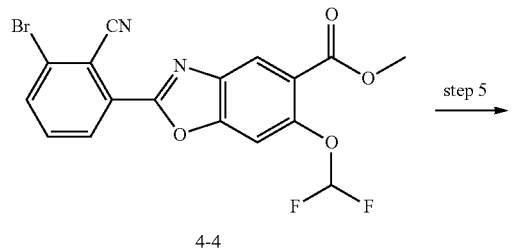

4-4 step 5

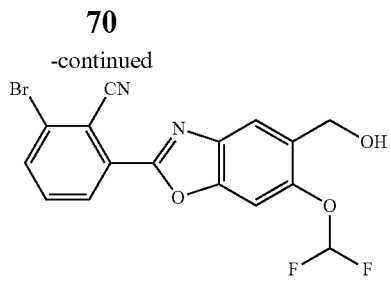

4-5

This compound was prepared using similar procedures as described as step 5 in example A, with compound 4-4 replacing compound a-4. The mixture was concentrated under reduced pressure to get the title compound 4-5.

Step 6: Preparation of 2-bromo-6-(5-(chloromethyl)-6-(difluoromethoxy)benzo[d]oxazol-2-yl)benzonitrile

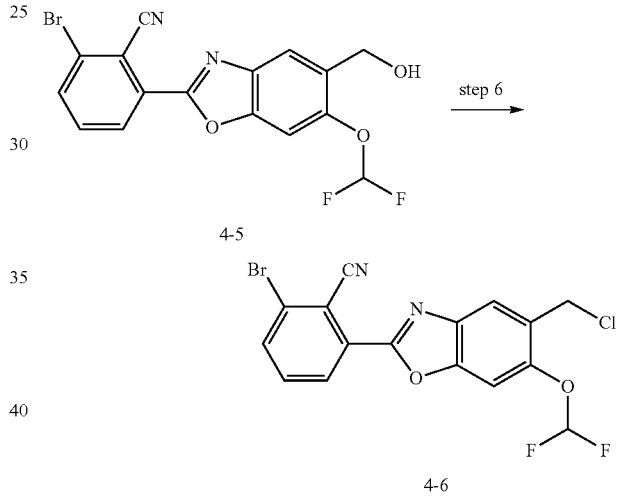

4-5 step 6

4-6

This compound was prepared using similar procedures as described as step 2 in example 1, with compound 4-5 replacing compound 1-1. The crude product was used directly in the next step.

Step 7: Preparation of 2-bromo-6-(6-(difluoromethoxy)-5-((3,3-dimethylazetidin-1-yl)methyl)benzo[d]oxazol-2-yl)benzonitrile

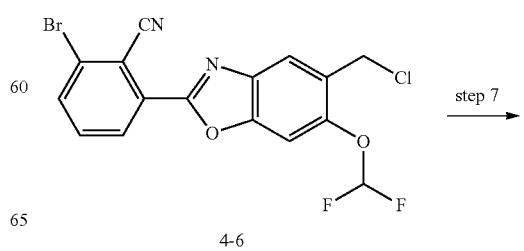

4-6 step 7

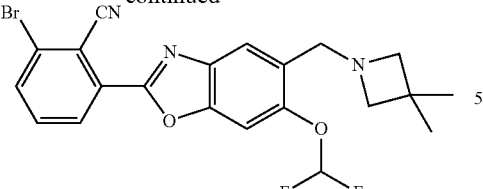

4-7

This compound was prepared using similar procedures as described as step 3 in example 1, with compound 4-6 replacing compound 1-2, and with 3,3-dimethylazetidine replacing (1S, 2R)-2-aminocyclopentan-1-ol. The crude product was further purified by Silica gel column (PE/EA) to get the title compound (290 mg).

Step 8: Preparation of methyl ((2-(2'-cyano-3'-(6-(difluoromethoxy)-5-((3,3-dimethylazetidin-1-yl) methyl)benzo[d]oxazol-2-yl)-2-methyl-[1,1'-biphenyl]-3-yl)-6-(difluoromethoxy)benzo[d]oxazol-5-yl) methyl)-L-prolinate

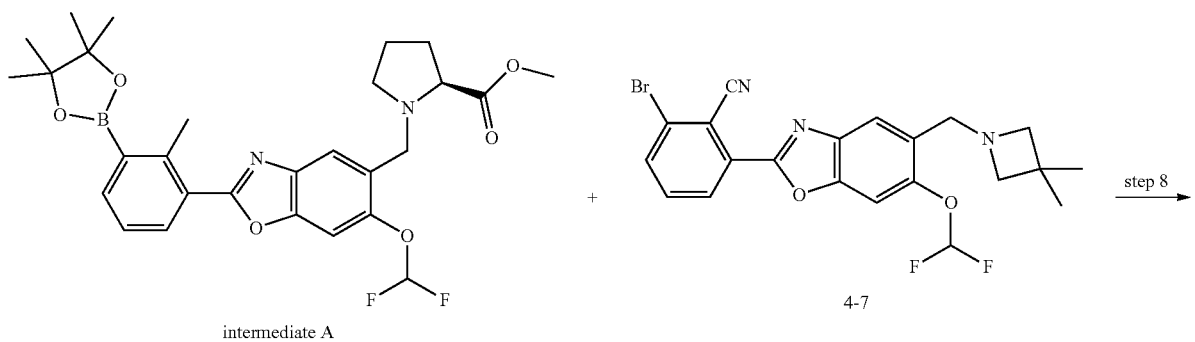

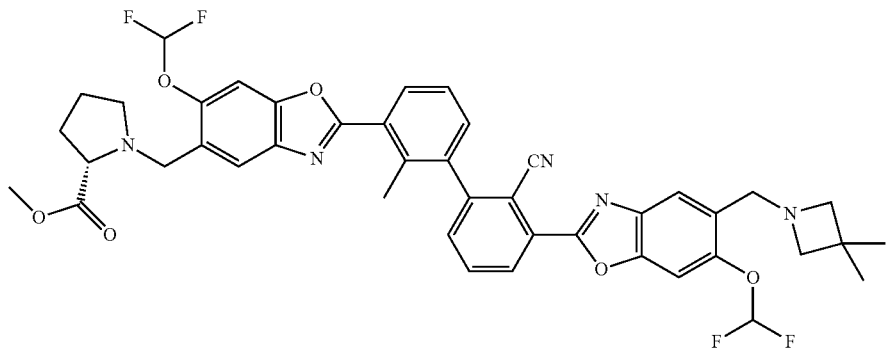

4-8

This compound was prepared using similar procedures as described as step 1 in example 1 with compound 4-7 replacing compound a-6. The crude product was further purified by Silica gel column to get the title compound.

Step 9: Preparation of ((2-(2'-cyano-3'-(6-(difluoromethoxy)-5-((3,3-dimethylazetidin-1-yl)methyl)benzo[d]oxazol-2-yl)-2-methyl-[1,1'-biphenyl]-3-yl)-6-(difluoromethoxy)benzo[d]oxazol-5-yl)methyl)-L-proline

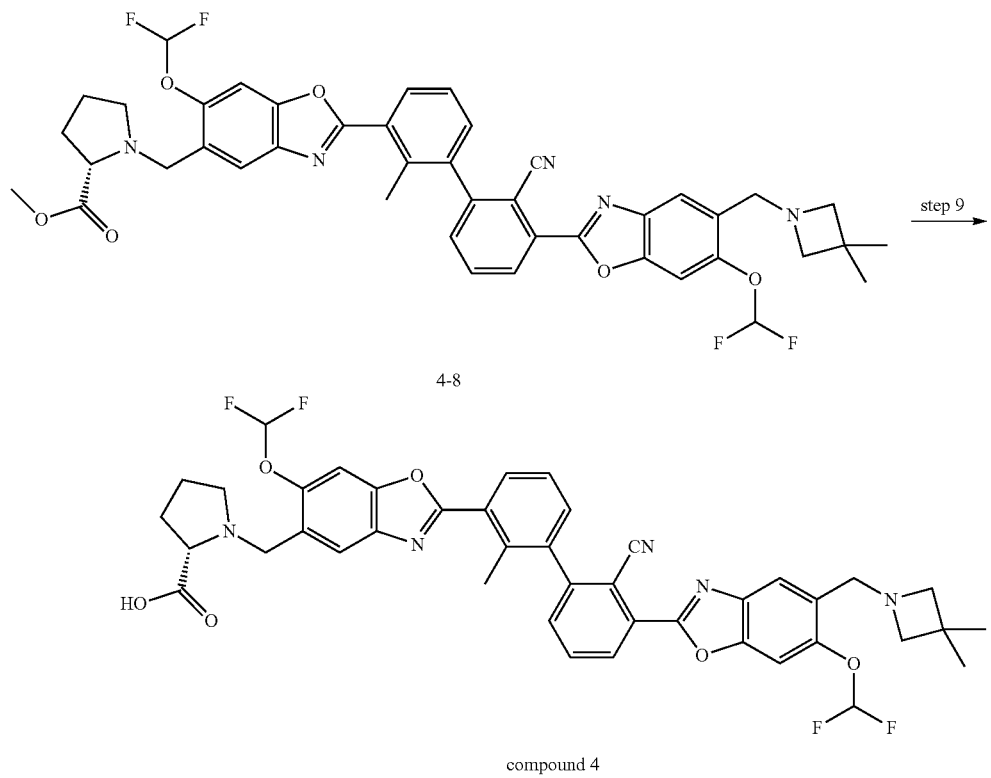

This compound was prepared using similar procedures as described as step 5 in example 1, with compound 4-8 replacing compound 1-4. The mixture was concentrated under reduced pressure to get the title compound. LC-MS (m/z): 784.3 (M+H)$^+$.

The compounds of table 1 were prepared in a similar manner to Examples 1-4 via different reaction starting materials and suitable reagents.

TABLE 1

| EX No. | Chemical Name | Structure | Physical Data (MS) (M + H)$^+$ |
|---|---|---|---|
| 5 | ((6-(difluoromethoxy)-2-(3'-(6-(difluoromethoxy)-5-(pyrrolidin-1-ylmethyl)benzo[d]oxazol-2-yl)-2,2'-dimethyl-[1,1'-biphenyl]-3-yl)benzo[d]oxazol-5-yl)methyl)-L-proline | 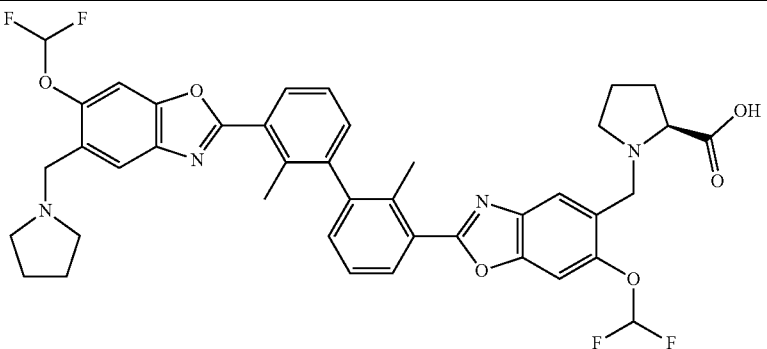 | 759.3 |

TABLE 1-continued

| EX No. | Chemical Name | Structure | Physical Data (MS) (M + H)+ |
|---|---|---|---|
| 6 | ((6-(difluoromethoxy)-2-(3'-(6-(difluoromethoxy)-5-(pyrrolidin-1-ylmethyl)benzo[d]oxazol-2-yl)-2'-fluoro-2-methyl-[1,1'-biphenyl]-3-yl)benzo[d]oxazol-5-yl)methyl)-L-proline | 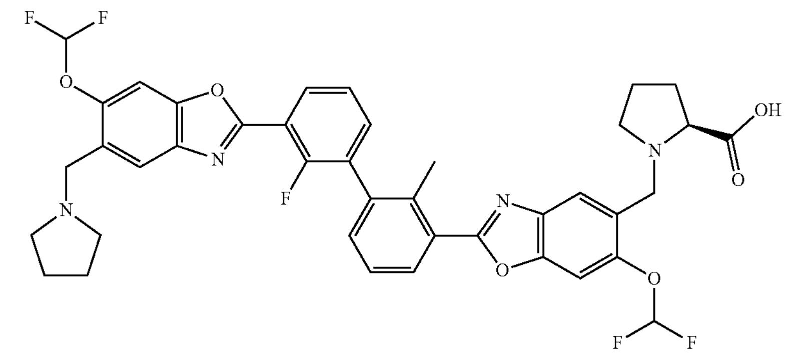 [SMILES: Cc1c(-c2nc3cc(CN4CCCC4)c(OC(F)F)cc3o2)cccc1-c1cccc(-c2nc3cc(CN4CCC[C@H]4C(=O)O)c(OC(F)F)cc3o2)c1C] | 763.3 |
| 7 | ((6-(difluoromethoxy)-2-(3'-(6-(difluoromethoxy)-5-(((2-hydroxyethyl)amino)methyl)benzo[d]oxazol-2-yl)-2,2'-dimethyl-[1,1'-biphenyl]-3-yl)benzo[d]oxazol-5-yl)methyl)-L-proline | 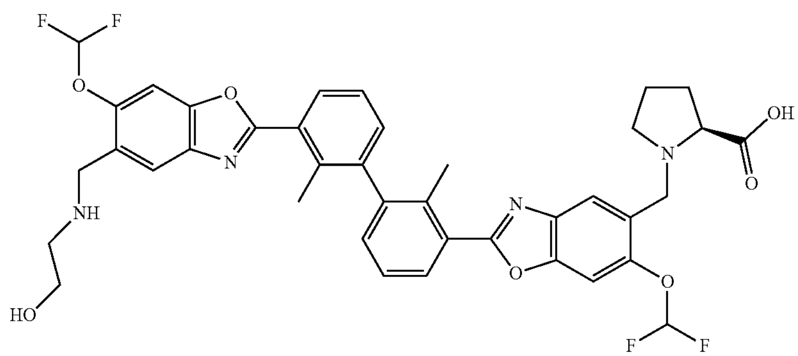 [SMILES: Cc1c(-c2nc3cc(CNCCO)c(OC(F)F)cc3o2)cccc1-c1cccc(-c2nc3cc(CN4CCC[C@H]4C(=O)O)c(OC(F)F)cc3o2)c1C] | 749.3 |
| 8 | ((2-(3'-(5-(azetidin-1-ylmethyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline | 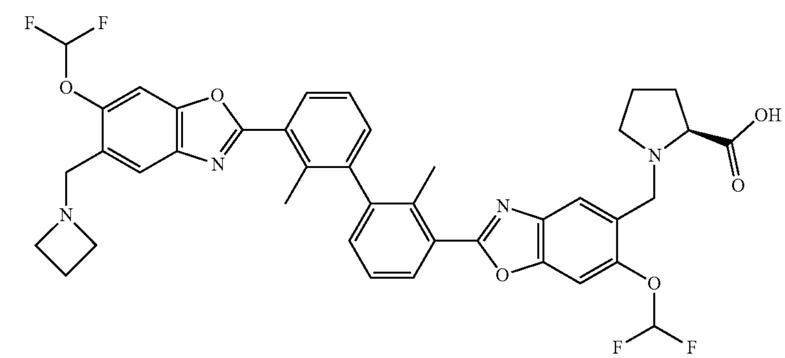 [SMILES: Cc1c(-c2nc3cc(CN4CCC4)c(OC(F)F)cc3o2)cccc1-c1cccc(-c2nc3cc(CN4CCC[C@H]4C(=O)O)c(OC(F)F)cc3o2)c1C] | 744.3 |
| 9 | ((6-(difluoromethoxy)-2-(3'-(6-(difluoromethoxy)-5-((3-fluoroazetidin-1-yl)methyl)benzo[d]oxazol-2-yl)-2,2'-dimethyl-[1,1'-biphenyl]-3-yl)benzo[d]oxazol-5-yl)methyl)-L-proline | 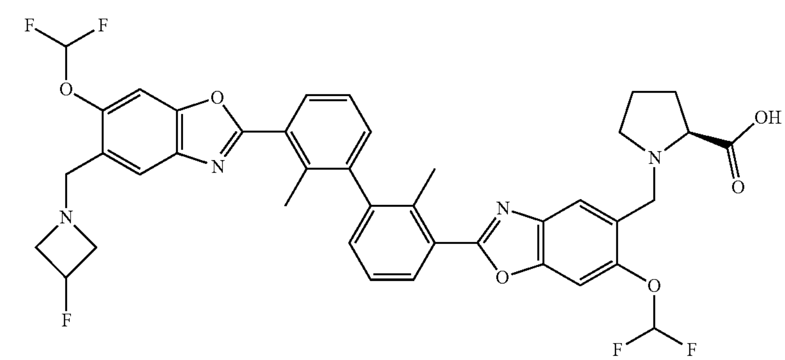 [SMILES: Cc1c(-c2nc3cc(CN4CC(F)C4)c(OC(F)F)cc3o2)cccc1-c1cccc(-c2nc3cc(CN4CCC[C@H]4C(=O)O)c(OC(F)F)cc3o2)c1C] | 763.3 |

TABLE 1-continued

| EX No. | Chemical Name | Structure | Physical Data (MS) (M + H)+ |
|---|---|---|---|
| 10 | ((6-(difluoromethoxy)-2-(3'-(6-(difluoromethoxy)-5-((3-fluoropyrrolidin-1-yl)methyl)benzo[d]oxazol-2-yl)-2,2'-dimethyl-[1,1'-biphenyl]-3-yl)benzo[d]oxazol-5-yl)methyl)-L-proline | 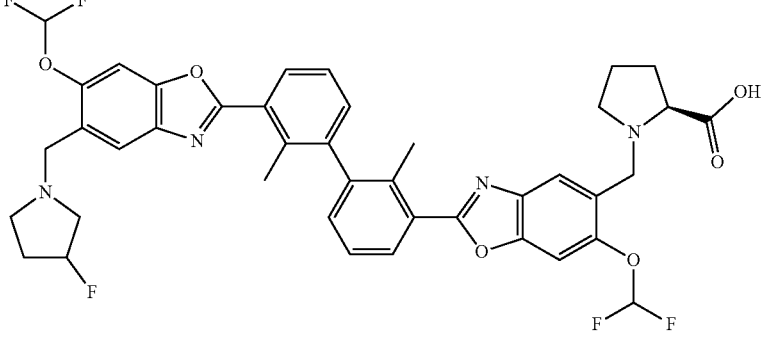 | 777.3 |
| 11 | ((2-(3'-(5-(((S)-2-carbamoylpyrrolidin-1-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline | 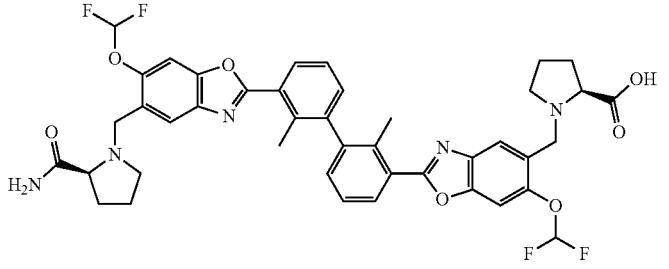 [SMILES: Cc1c(-c2nc3cc(CN4CCC[C@H]4C(N)=O)c(OC(F)F)cc3o2)cccc1-c1cccc(-c2nc3cc(CN4CCC[C@H]4C(=O)O)c(OC(F)F)cc3o2)c1C] | 802.3 |
| 12 | ((6-(difluoromethoxy)-2-(3'-(6-(difluoromethoxy)-5-(((S)-2-(hydroxymethyl)pyrrolidin-1-yl)methyl)benzo[d]oxazol-2-yl)-2,2'-dimethyl-[1,1'-biphenyl]-3-yl)benzo[d]oxazol-5-yl)methyl)-L-proline | 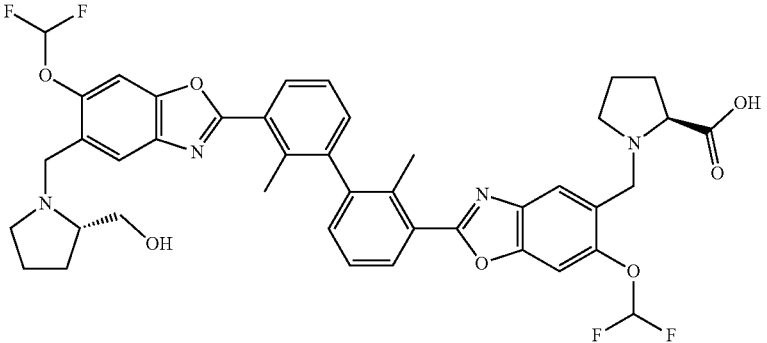 [SMILES: Cc1c(-c2nc3cc(CN4CCC[C@H]4CO)c(OC(F)F)cc3o2)cccc1-c1cccc(-c2nc3cc(CN4CCC[C@H]4C(=O)O)c(OC(F)F)cc3o2)c1C] | 789.3 |
| 13 | ((6-(difluoromethoxy)-2-(3'-(6-(difluoromethoxy)-5-(morpholinomethyl)benzo[d]oxazol-2-yl)-2,2'-dimethyl-[1,1'-biphenyl]-3-yl)benzo[d]oxazol-5-yl)methyl)-L-proline | 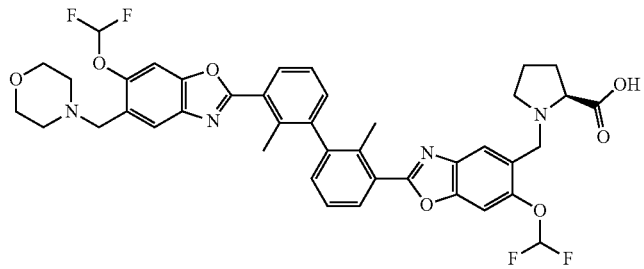 [SMILES: Cc1c(-c2nc3cc(CN4CCOCC4)c(OC(F)F)cc3o2)cccc1-c1cccc(-c2nc3cc(CN4CCC[C@H]4C(=O)O)c(OC(F)F)cc3o2)c1C] | 775.3 |

TABLE 1-continued

| EX No. | Chemical Name | Structure | Physical Data (MS) (M + H)+ |
|---|---|---|---|
| 14 | ((6-(difluoromethoxy)-2-(3'-(6-(difluoromethoxy)-5-((3-hydroxypyrrolidin-1-yl)methyl)benzo[d]oxazol-2-yl)-2,2'-dimethyl-[1,1'-biphenyl]-3-yl)benzo[d]oxazol-5-yl)methyl)-L-proline | 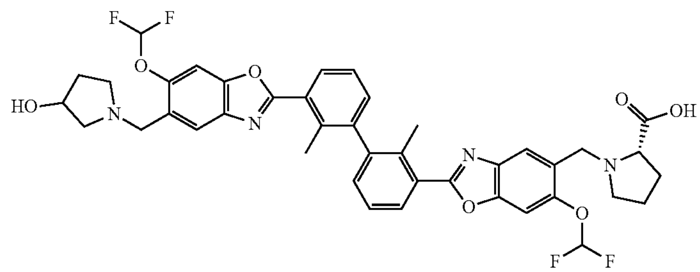 [SMILES: Cc1c(-c2nc3cc(CN4CCC(O)C4)c(OC(F)F)cc3o2)cccc1-c1cccc(-c2nc3cc(CN4CCC[C@H]4C(=O)O)c(OC(F)F)cc3o2)c1C] | 775.3 |
| 15 | ((6-(difluoromethoxy)-2-(3'-(6-(difluoromethoxy)-5-((methylamino)methyl)benzo[d]oxazol-2-yl)-2,2'-dimethyl-[1,1'-biphenyl]-3-yl)benzo[d]oxazol-5-yl)methyl)-L-proline | 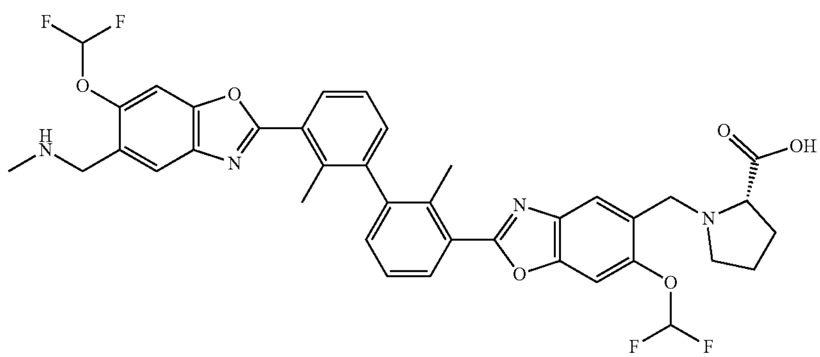 | 719.2 |
| 16 | ((6-(difluoromethoxy)-2-(3'-(6-(difluoromethoxy)-5-((dimethylamino)methyl)benzo[d]oxazol-2-yl)-2,2'-dimethyl-[1,1'-biphenyl]-3-yl)benzo[d]oxazol-5-yl)methyl)-L-proline | 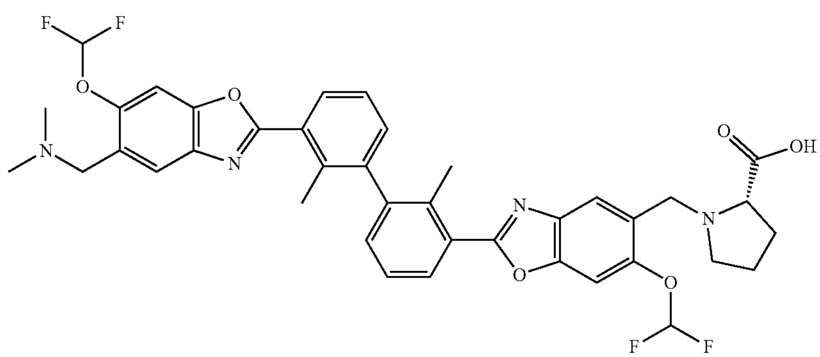 [SMILES: Cc1c(-c2nc3cc(CN(C)C)c(OC(F)F)cc3o2)cccc1-c1cccc(-c2nc3cc(CN4CCC[C@H]4C(=O)O)c(OC(F)F)cc3o2)c1C] | 733.3 |
| 17 | ((6-(difluoromethoxy)-2-(3'-(6-(difluoromethoxy)-5-(((2-hydroxyethyl)(methyl)amino)methyl)benzo[d]oxazol-2-yl)-2,2'-dimethyl-[1,1'-biphenyl]-3-yl)benzo[d]oxazol-5-yl)methyl)-L-proline | 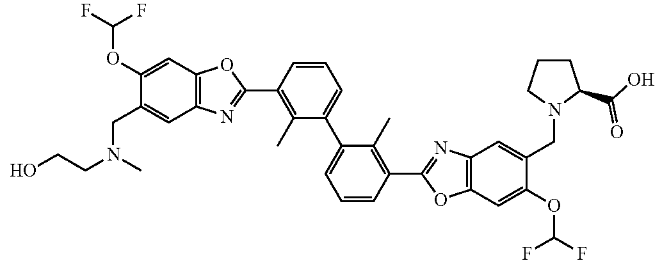 [SMILES: Cc1c(-c2nc3cc(CN(C)CCO)c(OC(F)F)cc3o2)cccc1-c1cccc(-c2nc3cc(CN4CCC[C@H]4C(=O)O)c(OC(F)F)cc3o2)c1C] | 763.3 |

TABLE 1-continued

| EX No. | Chemical Name | Structure | Physical Data (MS) (M + H)+ |
|---|---|---|---|
| 18 | ((6-(difluoromethoxy)-2-(3'-(6-(difluoromethoxy)-5-(((3R,4R)-3,4-difluoropyrrolidin-1-yl)methyl)benzo[d]oxazol-2-yl)-2,2'-dimethyl-[1,1'-biphenyl]-3-yl)benzo[d]oxazol-5-yl)methyl)-L-proline | 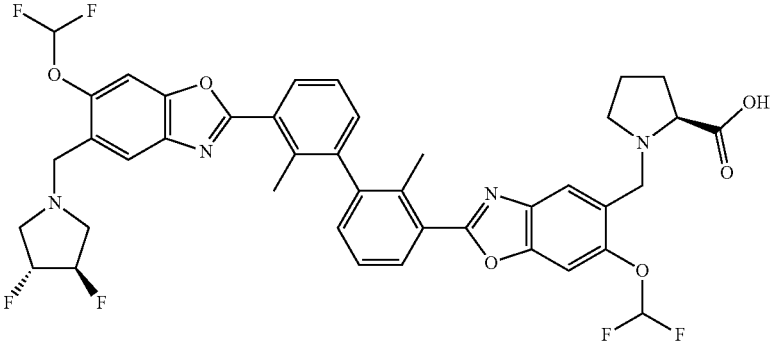 [SMILES: Cc1c(-c2nc3cc(CN4C[C@@H](F)[C@H](F)C4)c(OC(F)F)cc3o2)cccc1-c1cccc(-c2nc3cc(CN4CCC[C@H]4C(=O)O)c(OC(F)F)cc3o2)c1C] | 795.3 |
| 19 | ((6-(difluoromethoxy)-2-(3'-(6-(difluoromethoxy)-5-(((((S)-5-oxopyrrolidin-2-yl)methyl)amino)methyl)benzo[d]oxazol-2-yl)-2,2'-dimethyl-[1,1'-biphenyl]-3-yl)benzo[d]oxazol-5-yl)methyl)-L-proline | 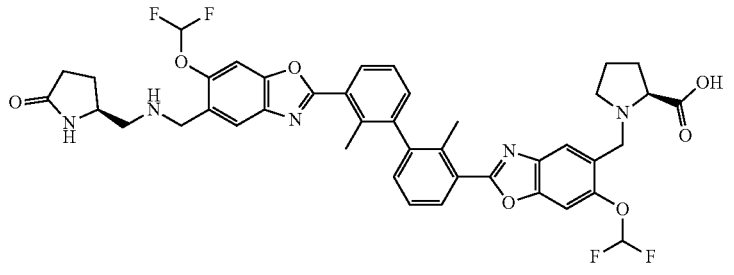 [SMILES: Cc1c(-c2nc3cc(CNC[C@@H]4CCC(=O)N4)c(OC(F)F)cc3o2)cccc1-c1cccc(-c2nc3cc(CN4CCC[C@H]4C(=O)O)c(OC(F)F)cc3o2)c1C] | 802.3 |
| 20 | ((6-(difluoromethoxy)-2-(3'-(6-(difluoromethoxy)-5-((3-hydroxyazetidin-1-yl)methyl)benzo[d]oxazol-2-yl)-2,2'-dimethyl-[1,1'-biphenyl]-3-yl)benzo[d]oxazol-5-yl)methyl)-L-proline | 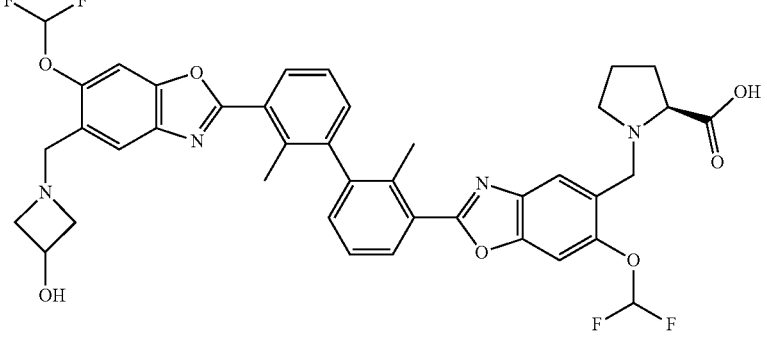 | 761.3 |
| 21 | ((6-(difluoromethoxy)-2-(3'-(6-(difluoromethoxy)-5-((ethylamino)methyl)benzo[d]oxazol-2-yl)-2,2'-dimethyl-[1,1'-biphenyl]-3-yl)benzo[d]oxazol-5-yl)methyl)-L-proline | 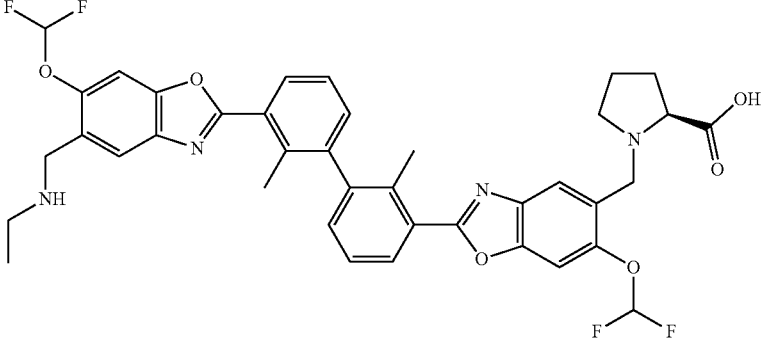 [SMILES: CCNCc1cc2nc(-c3cccc(-c4cccc(-c5nc6cc(CN7CCC[C@H]7C(=O)O)c(OC(F)F)cc6o5)c4C)c3C)oc2cc1OC(F)F] | 733.3 |

TABLE 1-continued

| EX No. | Chemical Name | Structure | Physical Data (MS) (M + H)+ |
|---|---|---|---|
| 22 | ((6-(difluoromethoxy)-2-(3'-(6-(difluoromethoxy)-5-(((3,3,3-trifluoro-2-hydroxypropyl)amino)methyl)benzo[d]oxazol-2-yl)-2,2'-dimethyl-[1,1'-biphenyl]-3-yl)benzo[d]oxazol-5-yl)methyl)-L-proline | 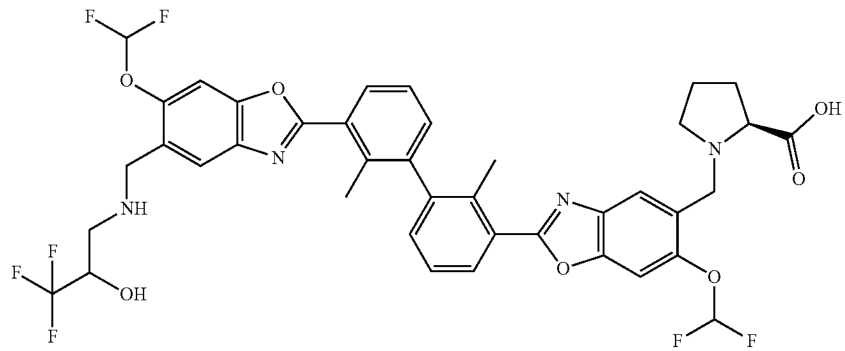 [SMILES: Cc1c(-c2nc3cc(CNCC(O)C(F)(F)F)c(OC(F)F)cc3o2)cccc1-c1cccc(-c2nc3cc(CN4CCC[C@H]4C(=O)O)c(OC(F)F)cc3o2)c1C] | 817.2 |
| 23 | ((6-(difluoromethoxy)-2-(3'-(6-(difluoromethoxy)-5-((3,4-dimethylpiperazin-1-yl)methyl)benzo[d]oxazol-2-yl)-2,2'-dimethyl-[1,1'-biphenyl]-3-yl)benzo[d]oxazol-5-yl)methyl)-L-proline | 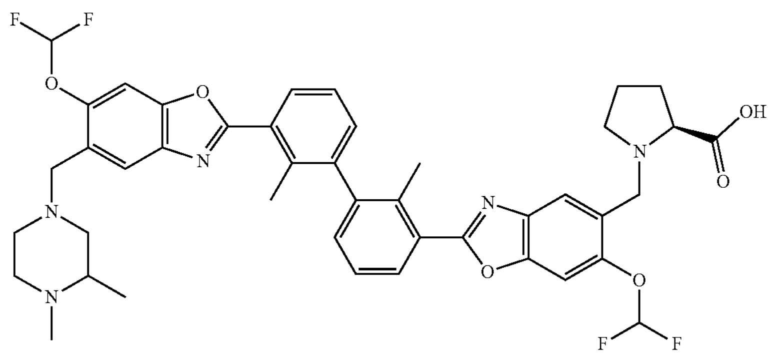 [SMILES: Cc1c(-c2nc3cc(CN4CCN(C)C(C)C4)c(OC(F)F)cc3o2)cccc1-c1cccc(-c2nc3cc(CN4CCC[C@H]4C(=O)O)c(OC(F)F)cc3o2)c1C] | 802.3 |
| 24 | ((2-(3'-(5-(aminomethyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline | 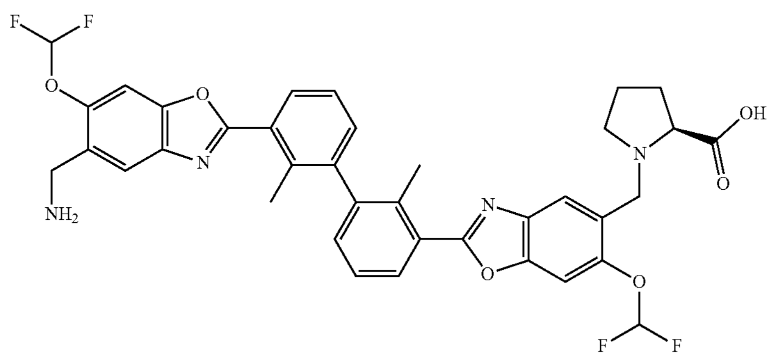 [SMILES: Cc1c(-c2nc3cc(CN)c(OC(F)F)cc3o2)cccc1-c1cccc(-c2nc3cc(CN4CCC[C@H]4C(=O)O)c(OC(F)F)cc3o2)c1C] | 705.2 |
| 25 | ((6-(difluoromethoxy)-2-(3'-(6-(difluoromethoxy)-5-(((((1R,2S)-2-hydroxycyclopentyl)amino)methyl)benzo[d]oxazol-2-yl)-2,2'-dimethyl-[1,1'-biphenyl]-3-yl)benzo[d]oxazol-5-yl)methyl)-L-proline | 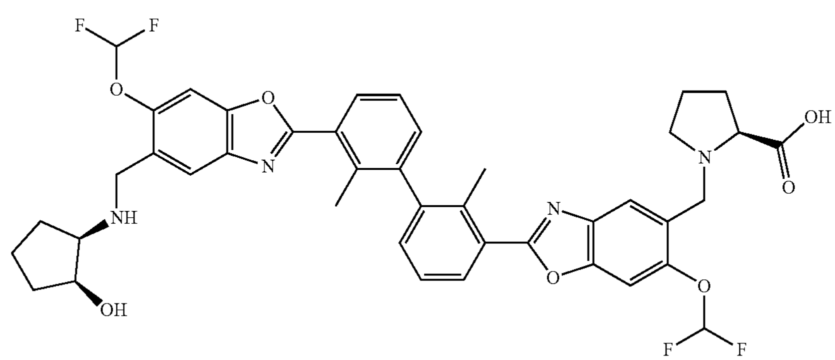 [SMILES: Cc1c(-c2nc3cc(CN[C@@H]4CCC[C@@H]4O)c(OC(F)F)cc3o2)cccc1-c1cccc(-c2nc3cc(CN4CCC[C@H]4C(=O)O)c(OC(F)F)cc3o2)c1C] | 789.3 |

TABLE 1-continued

| EX No. | Chemical Name | Structure | Physical Data (MS) (M + H)+ |
|---|---|---|---|
| 26 | ((6-(difluoromethoxy)-2-(3'-(6-(difluoromethoxy)-5-(((((1R,2S)-2-hydroxycyclopentyl)(methyl)amino)methyl)benzo[d]oxazol-2-yl)-2,2'-dimethyl-[1,1'-biphenyl]-3-yl)benzo[d]oxazol-5-yl)methyl)-D-proline | 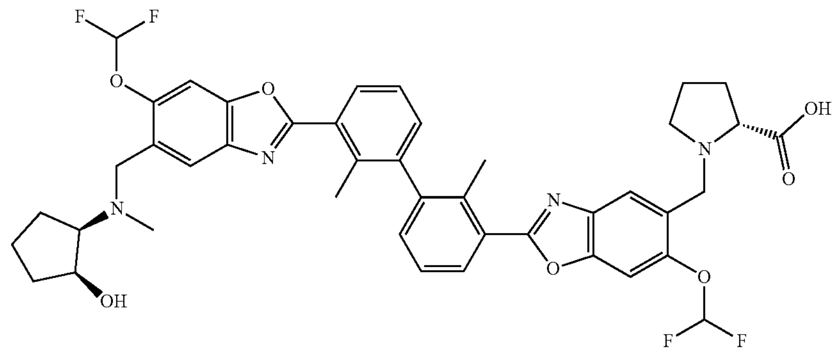 [SMILES: Cc1c(-c2nc3cc(CN(C)[C@@H]4CCC[C@@H]4O)c(OC(F)F)cc3o2)cccc1-c1cccc(-c2nc3cc(CN4CCC[C@@H]4C(=O)O)c(OC(F)F)cc3o2)c1C] | 803.3 |
| 27 | ((6-(difluoromethoxy)-2-(3'-(6-(difluoromethoxy)-5-(((((1S,2R)-2-hydroxycyclopentyl)amino)methyl)benzo[d]oxazol-2-yl)-2,2'-dimethyl-[1,1'-biphenyl]-3-yl)benzo[d]oxazol-5-yl)methyl)-L-proline | 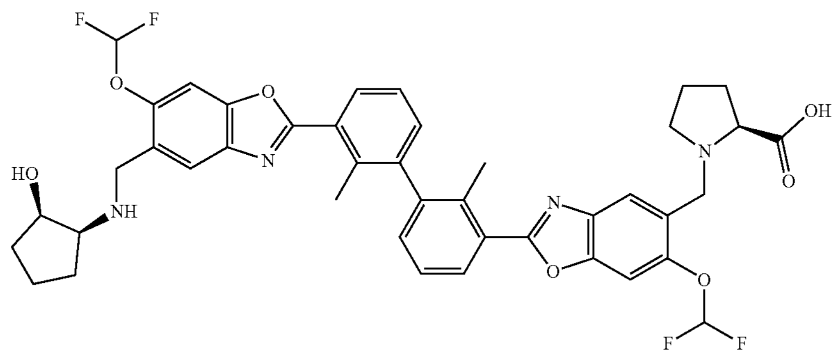 [SMILES: Cc1c(-c2nc3cc(CN[C@H]4CCC[C@H]4O)c(OC(F)F)cc3o2)cccc1-c1cccc(-c2nc3cc(CN4CCC[C@H]4C(=O)O)c(OC(F)F)cc3o2)c1C] | 789.3 |
| 28 | ((6-(difluoromethoxy)-2-(3'-(6-(difluoromethoxy)-5-((oxetan-3-ylamino)methyl)benzo[d]oxazol-2-yl)-2,2'-dimethyl-[1,1'-biphenyl]-3-yl)benzo[d]oxazol-5-yl)methyl)-L-proline | 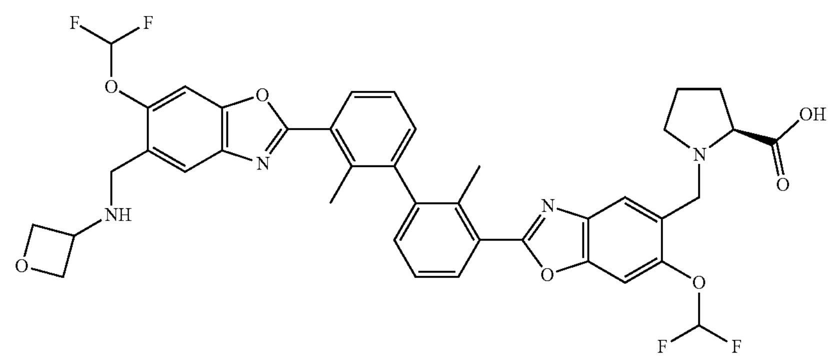 [SMILES: Cc1c(-c2nc3cc(CNC4COC4)c(OC(F)F)cc3o2)cccc1-c1cccc(-c2nc3cc(CN4CCC[C@H]4C(=O)O)c(OC(F)F)cc3o2)c1C] | 761.3 |
| 29 | ((6-(difluoromethoxy)-2-(3'-(6-(difluoromethoxy)-5-(((((R)-tetrahydrofuran-2-yl)methyl)amino)methyl)benzo[d]oxazol-2-yl)-2,2'-dimethyl-[1,1'-biphenyl]-3-yl)benzo[d]oxazol-5-yl)methyl)-L-proline | 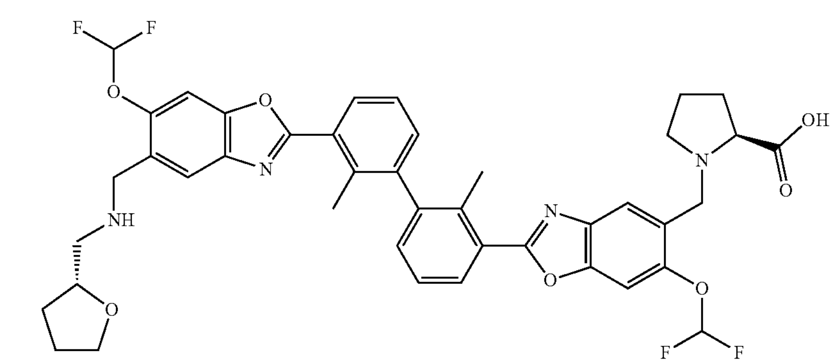 [SMILES: Cc1c(-c2nc3cc(CNC[C@H]4CCCO4)c(OC(F)F)cc3o2)cccc1-c1cccc(-c2nc3cc(CN4CCC[C@H]4C(=O)O)c(OC(F)F)cc3o2)c1C] | 789.3 |

TABLE 1-continued

| EX No. | Chemical Name | Structure | Physical Data (MS) (M + H)+ |
|---|---|---|---|
| 30 | ((6-(difluoromethoxy)-2-(3'-(6-(difluoromethoxy)-5-((methyl(((R)-tetrahydrofuran-2-yl)methyl)amino)methyl)benzo[d]oxazol-2-yl)-2,2'-dimethyl-[1,1'-biphenyl]-3-yl)benzo[d]oxazol-5-yl)methyl)-L-proline | 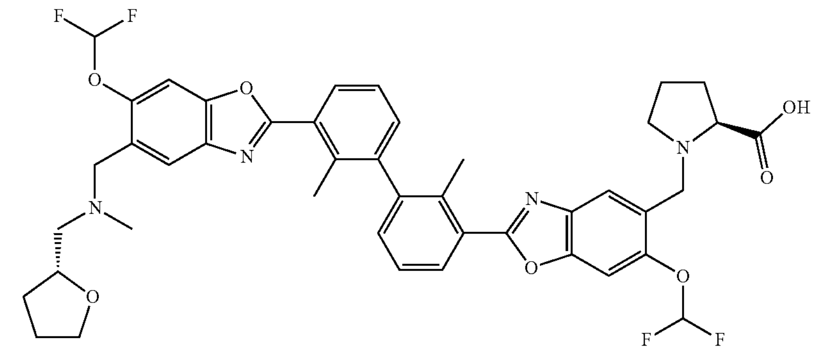 [SMILES: Cc1c(-c2nc3cc(CN(C)C[C@H]4CCCO4)c(OC(F)F)cc3o2)cccc1-c1cccc(-c2nc3cc(CN4CCC[C@H]4C(=O)O)c(OC(F)F)cc3o2)c1C] | 803.3 |
| 31 | ((6-(difluoromethoxy)-2-(3'-(6-(difluoromethoxy)-5-(((S)-2-(hydroxymethyl)azetidin-1-yl)methyl)benzo[d]oxazol-2-yl)-2,2'-dimethyl-[1,1'-biphenyl]-3-yl)benzo[d]oxazol-5-yl)methyl)-L-proline | 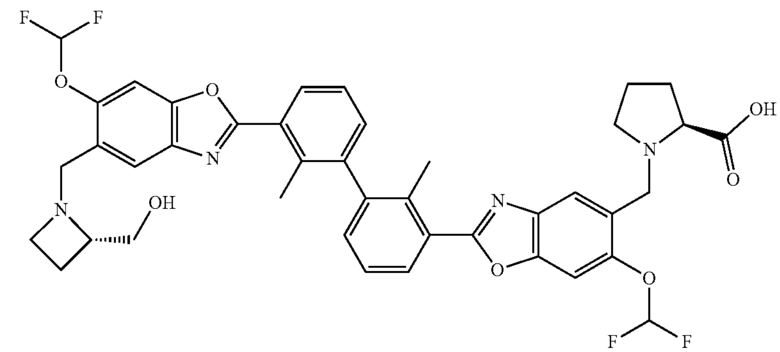 [SMILES: Cc1c(-c2nc3cc(CN4CC[C@H]4CO)c(OC(F)F)cc3o2)cccc1-c1cccc(-c2nc3cc(CN4CCC[C@H]4C(=O)O)c(OC(F)F)cc3o2)c1C] | 775.3 |
| 32 | ((6-(difluoromethoxy)-2-(3'-(6-(difluoromethoxy)-5-(((2-(methylsulfonyl)ethyl)amino)methyl)benzo[d]oxazol-2-yl)-2,2'-dimethyl-[1,1'-biphenyl]-3-yl)benzo[d]oxazol-5-yl)methyl)-L-proline | 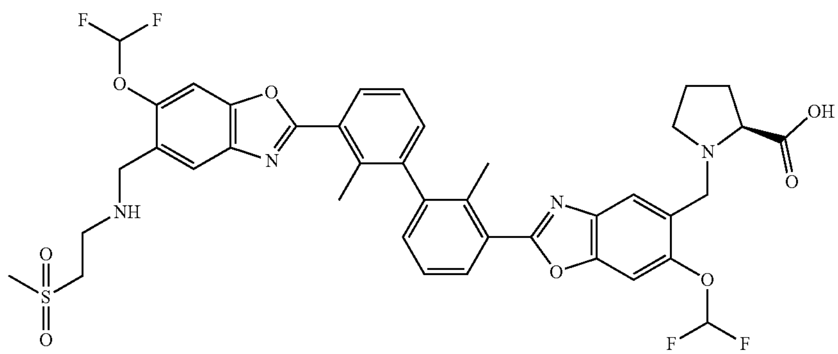 [SMILES: Cc1c(-c2nc3cc(CNCCS(C)(=O)=O)c(OC(F)F)cc3o2)cccc1-c1cccc(-c2nc3cc(CN4CCC[C@H]4C(=O)O)c(OC(F)F)cc3o2)c1C] | 811.2 |
| 33 | ((6-(difluoromethoxy)-2-(3'-(6-(difluoromethoxy)-5-((3-(dimethylamino)azetidin-1-yl)methyl)benzo[d]oxazol-2-yl)-2,2'-dimethyl-[1,1'-biphenyl]-3-yl)benzo[d]oxazol-5-yl)methyl)-L-proline | 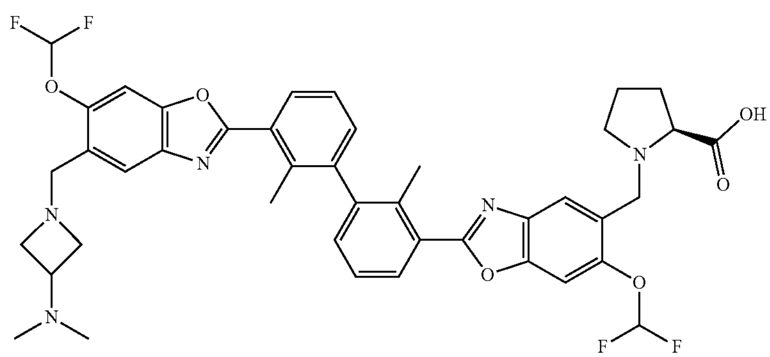 [SMILES: Cc1c(-c2nc3cc(CN4CC(N(C)C)C4)c(OC(F)F)cc3o2)cccc1-c1cccc(-c2nc3cc(CN4CCC[C@H]4C(=O)O)c(OC(F)F)cc3o2)c1C] | 788.3 |

TABLE 1-continued

| EX No. | Chemical Name | Structure | Physical Data (MS) (M + H)+ |
|---|---|---|---|
| 34 | ((6-(difluoromethoxy)-2-(3'-(6-(difluoromethoxy)-5-((3,3-dimethylazetidin-1-yl)methyl)benzo[d]oxazol-2-yl)-2,2'-dimethyl-[1,1'-biphenyl]-3-yl)benzo[d]oxazol-5-yl)methyl)-L-proline | 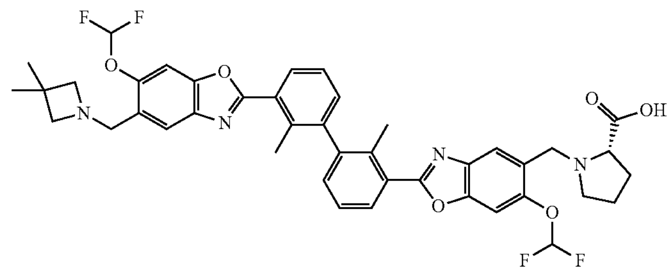 [SMILES: Cc1c(-c2nc3cc(CN4CC(C)(C)C4)c(OC(F)F)cc3o2)cccc1-c1cccc(-c2nc3cc(CN4CCC[C@H]4C(=O)O)c(OC(F)F)cc3o2)c1C] | 773.3 |
| 35 | ((6-(difluoromethoxy)-2-(3'-(6-(difluoromethoxy)-5-(((R)-2-(hydroxymethyl)azetidin-1-yl)methyl)benzo[d]oxazol-2-yl)-2,2'-dimethyl-[1,1'-biphenyl]-3-yl)benzo[d]oxazol-5-yl)methyl)-L-proline | 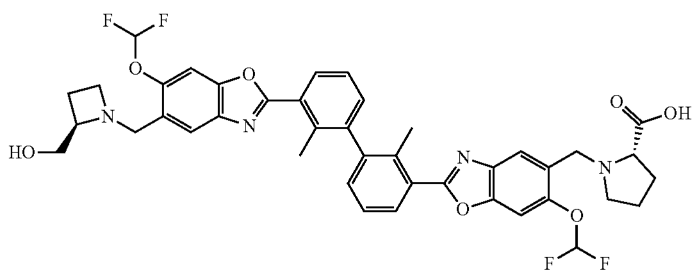 [SMILES: Cc1c(-c2nc3cc(CN4CC[C@@H]4CO)c(OC(F)F)cc3o2)cccc1-c1cccc(-c2nc3cc(CN4CCC[C@H]4C(=O)O)c(OC(F)F)cc3o2)c1C] | 775.3 |
| 36 | ((6-(difluoromethoxy)-2-(3'-(6-(difluoromethoxy)-5-((2-methylazetidin-1-yl)methyl)benzo[d]oxazol-2-yl)-2,2'-dimethyl-[1,1'-biphenyl]-3-yl)benzo[d]oxazol-5-yl)methyl)-L-proline | 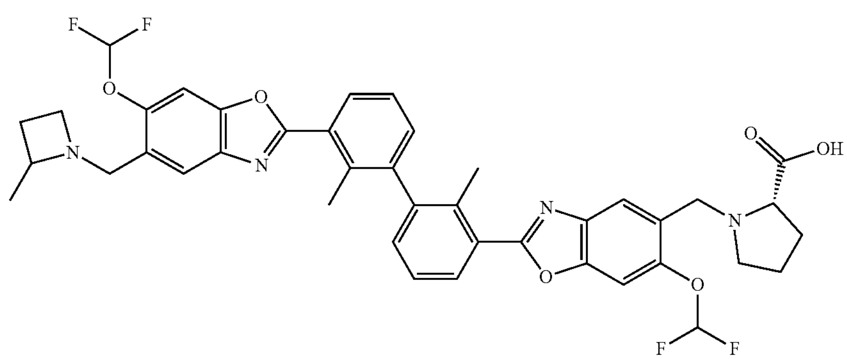 [SMILES: Cc1c(-c2nc3cc(CN4CCC4C)c(OC(F)F)cc3o2)cccc1-c1cccc(-c2nc3cc(CN4CCC[C@H]4C(=O)O)c(OC(F)F)cc3o2)c1C] | 759.3 |
| 37 | ((6-(difluoromethoxy)-2-(3'-(6-(difluoromethoxy)-5-((2-hydroxy-2-methylazetidin-1-yl)methyl)benzo[d]oxazol-2-yl)-2,2'-dimethyl-[1,1'-biphenyl]-3-yl)benzo[d]oxazol-5-yl)methyl)-L-proline | 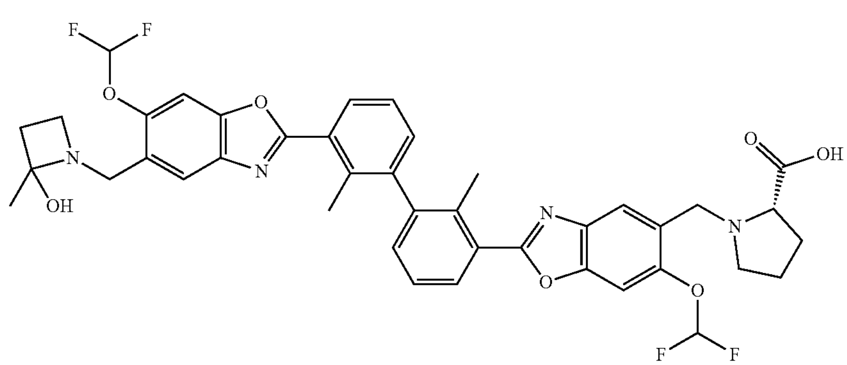 [SMILES: Cc1c(-c2nc3cc(CN4CCC[C@H]4C(=O)O)c(OC(F)F)cc3o2)cccc1-c1cccc(-c2nc3cc(CN4CCC4(C)O)c(OC(F)F)cc3o2)c1C] | 775.3 |

TABLE 1-continued

| EX No. | Chemical Name | Structure | Physical Data (MS) (M + H)+ |
|---|---|---|---|
| 38 | ((6-(difluoromethoxy)-2-(3'-(6-(difluoromethoxy)-5-((2-methylpyrrolidin-1-yl)methyl)benzo[d]oxazol-2-yl)-2,2'-dimethyl-[1,1'-biphenyl]-3-yl)benzo[d]oxazol-5-yl)methyl)-L-proline | 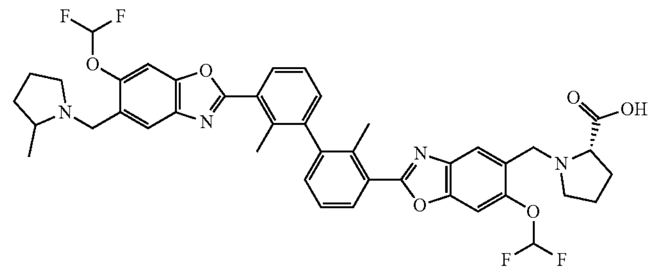 [SMILES: Cc1c(-c2nc3cc(CN4CCCC4C)c(OC(F)F)cc3o2)cccc1-c1cccc(-c2nc3cc(CN4CCC[C@H]4C(=O)O)c(OC(F)F)cc3o2)c1C] | 773.3 |
| 39 | ((2-(3'-(5-((6-oxa-1-azaspiro[3.3]heptan-1-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline | 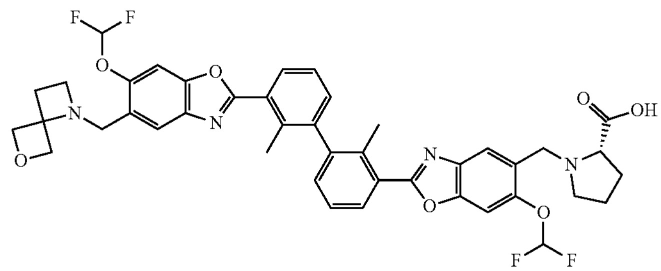 [SMILES: Cc1c(-c2nc3cc(CN4CCC[C@H]4C(=O)O)c(OC(F)F)cc3o2)cccc1-c1cccc(-c2nc3cc(CN4CCC45COC5)c(OC(F)F)cc3o2)c1C] | 787.3 |
| 40 | ((2-(3'-(5-((2-amino-2-methylazetidin-1-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline | 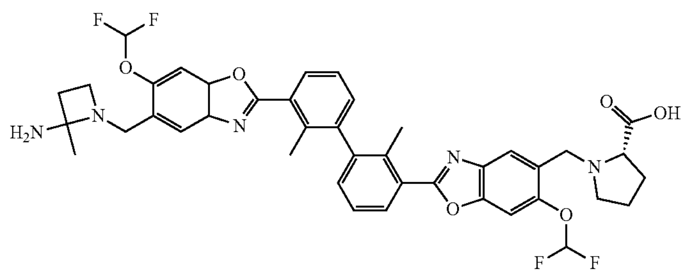 [SMILES: Cc1c(C2=NC3C=C(CN4CCC4(C)N)C(OC(F)F)=CC3O2)cccc1-c1cccc(-c2nc3cc(CN4CCC[C@H]4C(=O)O)c(OC(F)F)cc3o2)c1C] | 774.3 |
| 41 | ((6-(difluoromethoxy)-2-(3'-(6-(difluoromethoxy)-5-((3-(methylsulfonyl)azetidin-1-yl)methyl)benzo[d]oxazol-2-yl)-2,2'-dimethyl-[1,1'-biphenyl]-3-yl)benzo[d]oxazol-5-yl)methyl)-L-proline | 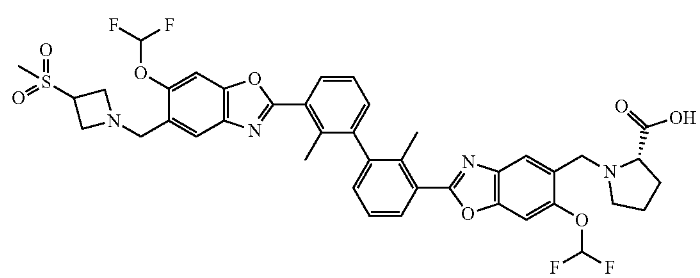 [SMILES: Cc1c(-c2nc3cc(CN4CC(S(C)(=O)=O)C4)c(OC(F)F)cc3o2)cccc1-c1cccc(-c2nc3cc(CN4CCC[C@H]4C(=O)O)c(OC(F)F)cc3o2)c1C] | 823.2 |
| 42 | ((6-(difluoromethoxy)-2-(3'-(6-(difluoromethoxy)-5-(((R)-2-ethylazetidin-1-yl)methyl)benzo[d]oxazol-2-yl)-2,2'-dimethyl-[1,1'-biphenyl]-3-yl)benzo[d]oxazol-5-yl)methyl)-L-proline | 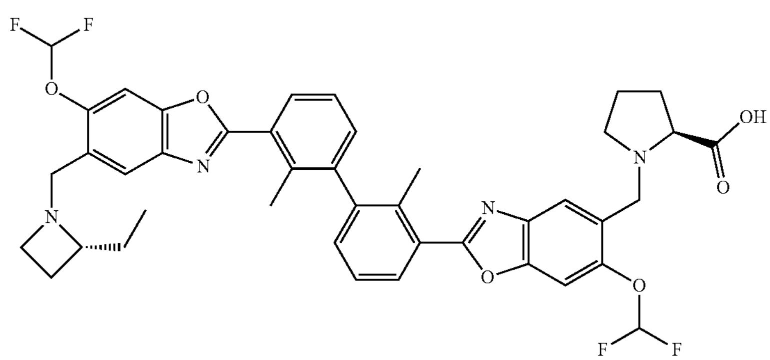 [SMILES: CC[C@@H]1CCN1Cc1cc2nc(-c3cccc(-c4cccc(-c5nc6cc(CN7CCC[C@H]7C(=O)O)c(OC(F)F)cc6o5)c4C)c3C)oc2cc1OC(F)F] | 773.3 |

TABLE 1-continued

| EX No. | Chemical Name | Structure | Physical Data (MS) (M + H)+ |
|---|---|---|---|
| 43 | ((6-(difluoromethoxy)-2-(3'-(6-(difluoromethoxy)-5-((3-methoxyazetidin-1-yl)methyl)benzo[d]oxazol-2-yl)-2,2'-dimethyl-[1,1'-biphenyl]-3-yl)benzo[d]oxazol-5-yl)methyl)-L-proline | 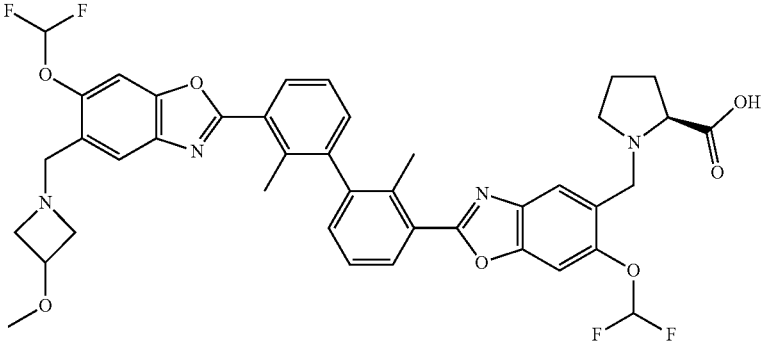 [SMILES: COC1CN(Cc2cc3nc(-c4cccc(-c5cccc(-c6nc7cc(CN8CCC[C@H]8C(=O)O)c(OC(F)F)cc7o6)c5C)c4C)oc3cc2OC(F)F)C1] | 775.3 |
| 44 | ((6-(difluoromethoxy)-2-(3'-(6-(difluoromethoxy)-5-((3-hydroxy-3-methylazetidin-1-yl)methyl)benzo[d]oxazol-2-yl)-2,2'-dimethyl-[1,1'-biphenyl]-3-yl)benzo[d]oxazol-5-yl)methyl)-L-proline | 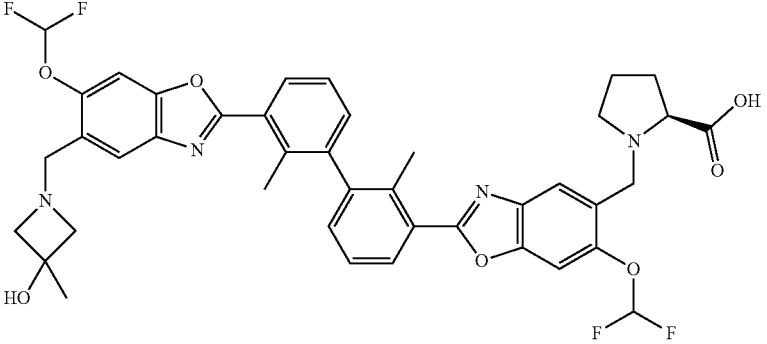 [SMILES: Cc1c(-c2nc3cc(CN4CC(C)(O)C4)c(OC(F)F)cc3o2)cccc1-c1cccc(-c2nc3cc(CN4CCC[C@H]4C(=O)O)c(OC(F)F)cc3o2)c1C] | 775.3 |
| 45 | ((6-(difluoromethoxy)-2-(3'-(6-(difluoromethoxy)-5-((3-((methylamino)methyl)azetidin-1-yl)methyl)benzo[d]oxazol-2-yl)-2,2'-dimethyl-[1,1'-biphenyl]-3-yl)benzo[d]oxazol-5-yl)methyl)-L-proline | 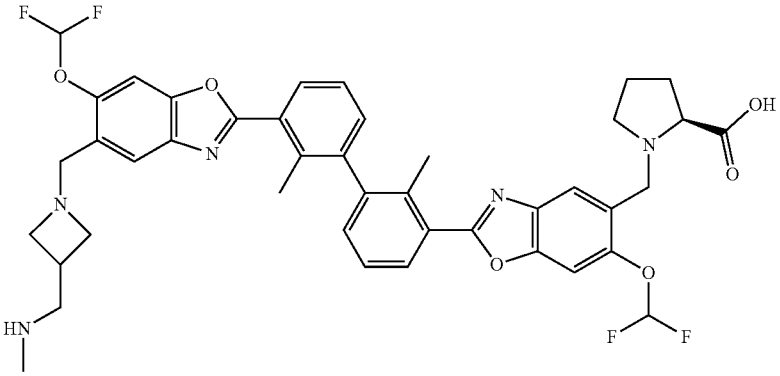 [SMILES: CNCC1CN(Cc2cc3nc(-c4cccc(-c5cccc(-c6nc7cc(CN8CCC[C@H]8C(=O)O)c(OC(F)F)cc7o6)c5C)c4C)oc3cc2OC(F)F)C1] | 788.3 |
| 46 | ((6-(difluoromethoxy)-2-(3'-(6-(difluoromethoxy)-5-((3-oxoazetidin-1-yl)methyl)benzo[d]oxazol-2-yl)-2,2'-dimethyl-[1,1'-biphenyl]-3-yl)benzo[d]oxazol-5-yl)methyl)-L-proline | 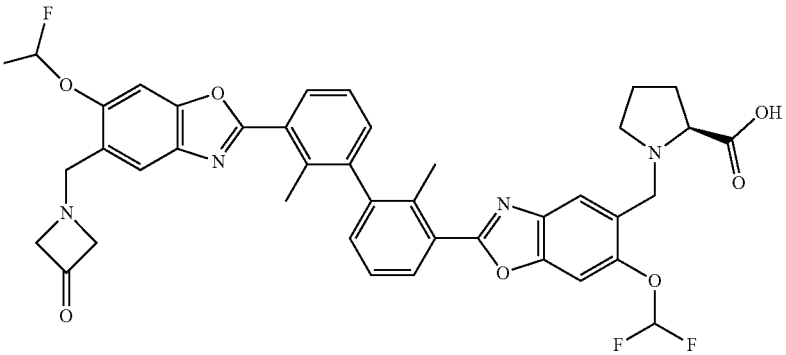 | 759.2 |

TABLE 1-continued

| EX No. | Chemical Name | Structure | Physical Data (MS) (M + H)+ |
|---|---|---|---|
| 47 | ((2-(3'-(5-((2-oxa-6-azaspiro[3.3]heptan-6-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline | 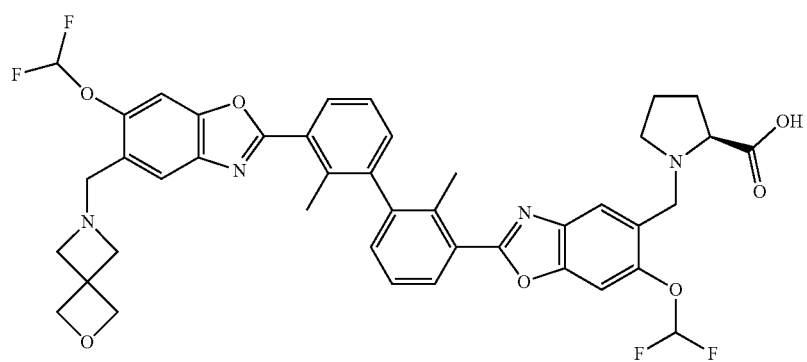 [SMILES: Cc1c(-c2nc3cc(CN4CC5(COC5)C4)c(OC(F)F)cc3o2)cccc1-c1cccc(-c2nc3cc(CN4CCC[C@H]4C(=O)O)c(OC(F)F)cc3o2)c1C] | 787.3 |
| 48 | ((2-(3'-(5-((2-azaspiro[3.3]heptan-2-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline | 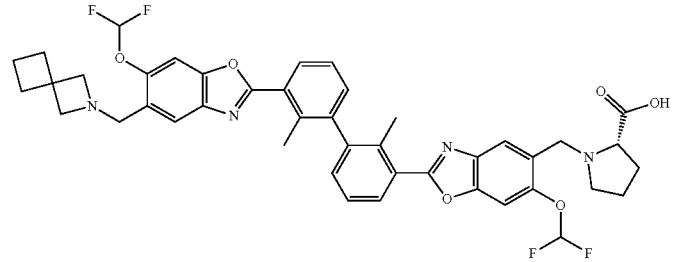 [SMILES: Cc1c(-c2nc3cc(CN4CC5(CCC5)C4)c(OC(F)F)cc3o2)cccc1-c1cccc(-c2nc3cc(CN4CCC[C@H]4C(=O)O)c(OC(F)F)cc3o2)c1C] | 785.3 |
| 49 | ((6-(difluoromethoxy)-2-(3'-(6-(difluoromethoxy)-5-((hexahydrocyclopenta[c]pyrrol-2(1H)-yl)methyl)benzo[d]oxazol-2-yl)-2,2'-dimethyl-[1,1'-biphenyl]-3-yl)benzo[d]oxazol-5-yl)methyl)-L-proline | 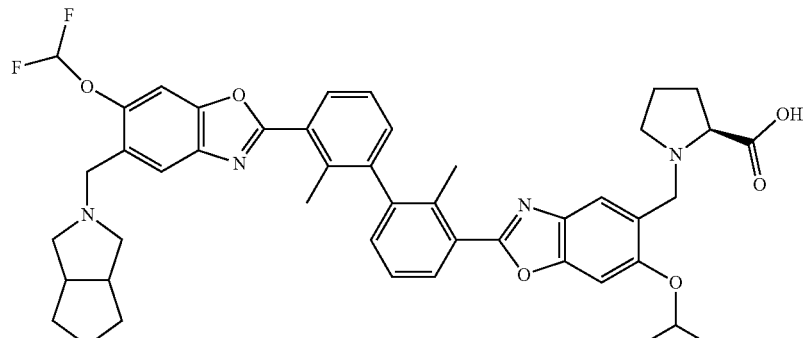 | 799.3 |
| 50 | ((6-(difluoromethoxy)-2-(3'-(6-(difluoromethoxy)-5-((hexahydropyrrolo[3,4-c]pyrrol-2(1H)-yl)methyl)benzo[d]oxazol-2-yl)-2,2'-dimethyl-[1,1'-biphenyl]-3-yl)benzo[d]oxazol-5-yl)methyl)-L-proline | 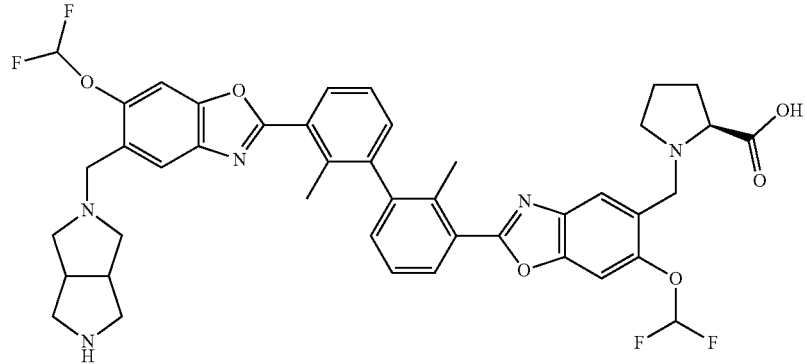 [SMILES: Cc1c(-c2nc3cc(CN4CC5CNCC5C4)c(OC(F)F)cc3o2)cccc1-c1cccc(-c2nc3cc(CN4CCC[C@H]4C(=O)O)c(OC(F)F)cc3o2)c1C] | 800.3 |

TABLE 1-continued

| EX No. | Chemical Name | Structure | Physical Data (MS) (M + H)+ |
|---|---|---|---|
| 51 | ((2-(3'-(5-((2,7-diazaspiro[3.5]nonan-2-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline | 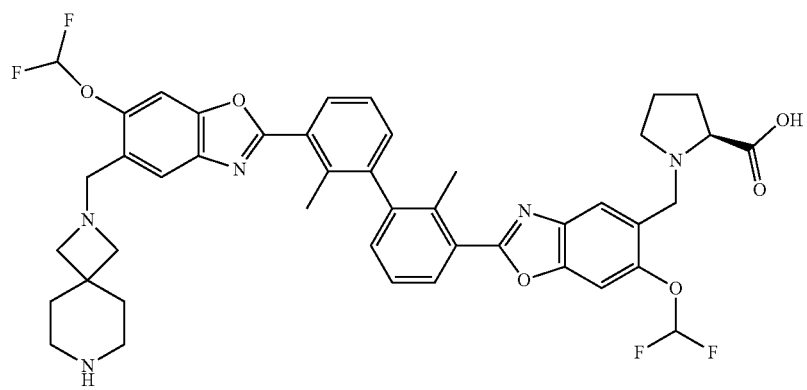 [SMILES: Cc1c(-c2nc3cc(CN4CC5(CCNCC5)C4)c(OC(F)F)cc3o2)cccc1-c1cccc(-c2nc3cc(CN4CCC[C@H]4C(=O)O)c(OC(F)F)cc3o2)c1C] | 814.3 |
| 52 | ((6-(difluoromethoxy)-2-(3'-(6-(difluoromethoxy)-5-(((3-(propylamino)propyl)amino)methyl)benzo[d]oxazol-2-yl)-2,2'-dimethyl-[1,1'-biphenyl]-3-yl)benzo[d]oxazol-5-yl)methyl)-L-proline | 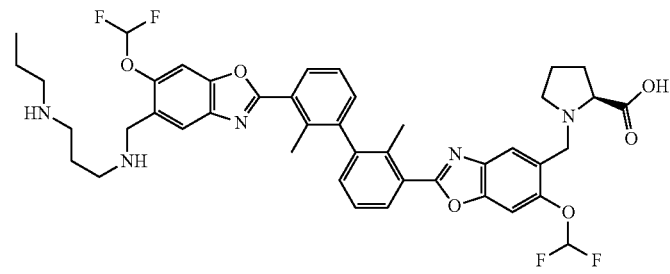 [SMILES: CCCNCCCNCc1cc2nc(-c3cccc(-c4cccc(-c5nc6cc(CN7CCC[C@H]7C(=O)O)c(OC(F)F)cc6o5)c4C)c3C)oc2cc1OC(F)F] | 804.3 |
| 53 | ((6-(difluoromethoxy)-2-(3'-(6-(difluoromethoxy)-5-((methyl(3-(propylamino)propyl)amino)methyl)benzo[d]oxazol-2-yl)-2,2'-dimethyl-[1,1'-biphenyl]-3-yl)benzo[d]oxazol-5-yl)methyl)-L-proline | 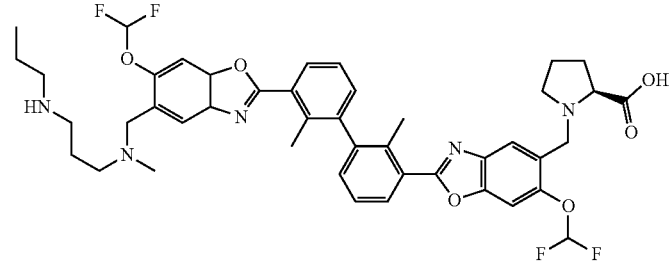 [SMILES: CCCNCCCN(C)CC1=CC2N=C(c3cccc(-c4cccc(-c5nc6cc(CN7CCC[C@H]7C(=O)O)c(OC(F)F)cc6o5)c4C)c3C)OC2C=C1OC(F)F] | 818.4 |
| 54 | ((6-(difluoromethoxy)-2-(3'-(6-(difluoromethoxy)-5-((2,2-dioxido-2-thia-6-azaspiro[3.3]heptan-6-yl)methyl)benzo[d]oxazol-2-yl)-2,2'-dimethyl-[1,1'-biphenyl]-3-yl)benzo[d]oxazol-5-yl)methyl)-L-proline | 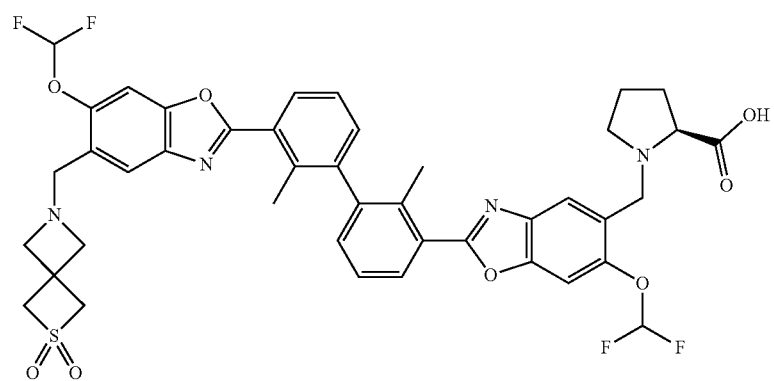 [SMILES: Cc1c(-c2nc3cc(CN4CC5(C4)CS(=O)(=O)C5)c(OC(F)F)cc3o2)cccc1-c1cccc(-c2nc3cc(CN4CCC[C@H]4C(=O)O)c(OC(F)F)cc3o2)c1C] | 835.2 |

TABLE 1-continued

| EX No. | Chemical Name | Structure | Physical Data (MS) (M + H)+ |
|---|---|---|---|
| 55 | ((6-(difluoromethoxy)-2-(3'-(6-(difluoromethoxy)-5-((tetrahydro-1H-furo[3,4-c]pyrrol-5(3H)-yl)methyl)benzo[d]oxazol-2-yl)-2,2'-dimethyl-[1,1'-biphenyl]-3-yl)benzo[d]oxazol-5-yl)methyl)-L-proline | 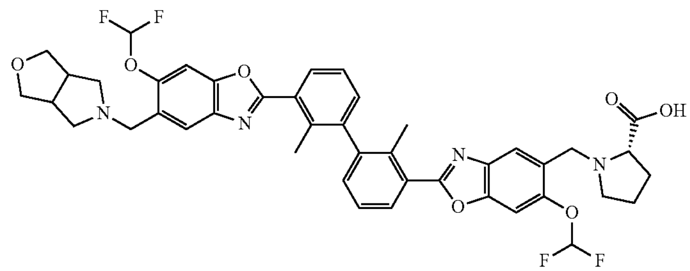 [SMILES: Cc1c(-c2nc3cc(CN4CC5COCC5C4)c(OC(F)F)cc3o2)cccc1-c1cccc(-c2nc3cc(CN4CCC[C@H]4C(=O)O)c(OC(F)F)cc3o2)c1C] | 801.3 |
| 56 | ((6-(difluoromethoxy)-2-(3'-(6-(difluoromethoxy)-5-((3-methylazetidin-1-yl)methyl)benzo[d]oxazol-2-yl)-2,2'-dimethyl-[1,1'-biphenyl]-3-yl)benzo[d]oxazol-5-yl)methyl)-L-proline | 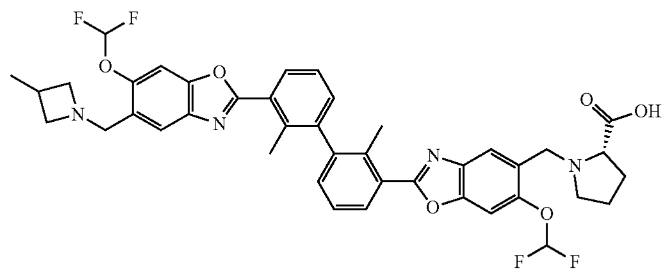 [SMILES: Cc1c(-c2nc3cc(CN4CC(C)C4)c(OC(F)F)cc3o2)cccc1-c1cccc(-c2nc3cc(CN4CCC[C@H]4C(=O)O)c(OC(F)F)cc3o2)c1C] | 759.3 |
| 57 | ((6-(difluoromethoxy)-2-(3'-(6-(difluoromethoxy)-5-((((1R,2R)-2-hydroxycyclopentyl)(methyl)amino)methyl)benzo[d]oxazol-2-yl)-2,2'-dimethyl-[1,1'-biphenyl]-3-yl)benzo[d]oxazol-5-yl)methyl)-L-proline | 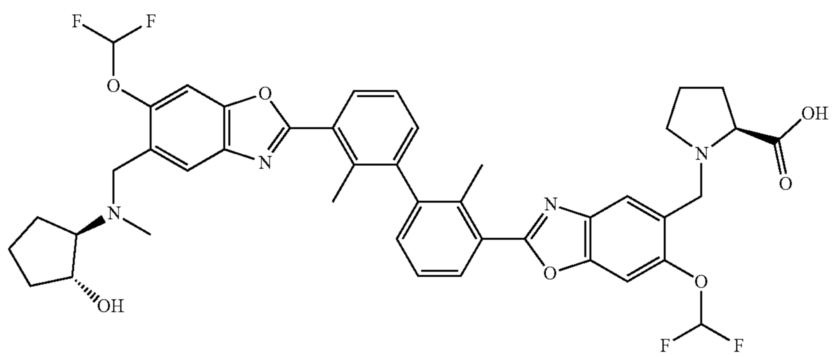 [SMILES: Cc1c(-c2nc3cc(CN(C)[C@@H]4CCC[C@H]4O)c(OC(F)F)cc3o2)cccc1-c1cccc(-c2nc3cc(CN4CCC[C@H]4C(=O)O)c(OC(F)F)cc3o2)c1C] | 803.3 |
| 58 | ((6-(difluoromethoxy)-2-(3'-(6-(difluoromethoxy)-5-(((3-((2-hydroxyethyl)amino)propyl)amino)methyl)benzo[d]oxazol-2-yl)-2,2'-dimethyl-[1,1'-biphenyl]-3-yl)benzo[d]oxazol-5-yl)methyl)-L-proline | 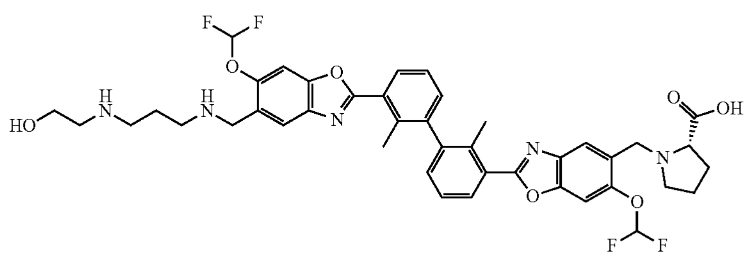 [SMILES: Cc1c(-c2nc3cc(CNCCCNCCO)c(OC(F)F)cc3o2)cccc1-c1cccc(-c2nc3cc(CN4CCC[C@H]4C(=O)O)c(OC(F)F)cc3o2)c1C] | 806.3 |
| 59 | ((6-(difluoromethoxy)-2-(3'-(6-(difluoromethoxy)-5-(((2-(dimethylamino)ethyl)(methyl)amino)methyl)benzo[d]oxazol-2-yl)-2,2'-dimethyl-[1,1'-biphenyl]-3-yl)benzo[d]oxazol-5-yl)methyl)-L-proline | 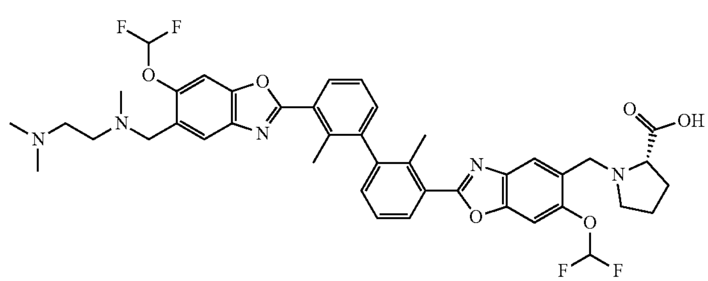 [SMILES: Cc1c(-c2nc3cc(CN(C)CCN(C)C)c(OC(F)F)cc3o2)cccc1-c1cccc(-c2nc3cc(CN4CCC[C@H]4C(=O)O)c(OC(F)F)cc3o2)c1C] | 790.3 |

TABLE 1-continued

| EX No. | Chemical Name | Structure | Physical Data (MS) (M + H)+ |
|---|---|---|---|
| 60 | ((6-(difluoromethoxy)-2-(3'-(6-(difluoromethoxy)-5-((2-methylazetidin-1-yl)methyl)benzo[d]oxazol-2-yl)-2,2'-dimethyl-[1,1'-biphenyl]-3-yl)benzo[d]oxazol-5-yl)methyl)-L-proline | 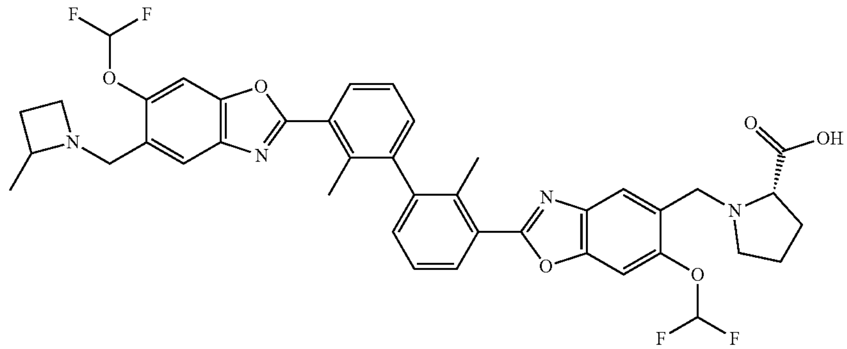 [SMILES: Cc1c(-c2nc3cc(CN4CCC4C)c(OC(F)F)cc3o2)cccc1-c1cccc(-c2nc3cc(CN4CCC[C@H]4C(=O)O)c(OC(F)F)cc3o2)c1C] | 759.3 |
| 61 | ((6-(difluoromethoxy)-2-(3'-(6-(difluoromethoxy)-5-((3-methylpyrrolidin-1-yl)methyl)benzo[d]oxazol-2-yl)-2,2'-dimethyl-[1,1'-biphenyl]-3-yl)benzo[d]oxazol-5-yl)methyl)-L-proline | 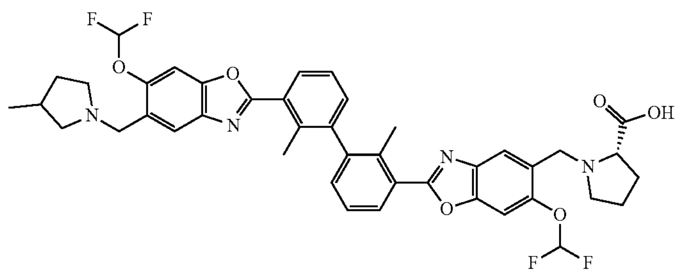 [SMILES: Cc1c(-c2nc3cc(CN4CCC(C)C4)c(OC(F)F)cc3o2)cccc1-c1cccc(-c2nc3cc(CN4CCC[C@H]4C(=O)O)c(OC(F)F)cc3o2)c1C] | 773.3 |
| 62 | ((6-(difluoromethoxy)-2-(3'-(6-(difluoromethoxy)-5-((2,2-dimethylpyrrolidin-1-yl)methyl)benzo[d]oxazol-2-yl)-2,2'-dimethyl-[1,1'-biphenyl]-3-yl)benzo[d]oxazol-5-yl)methyl)-L-proline | 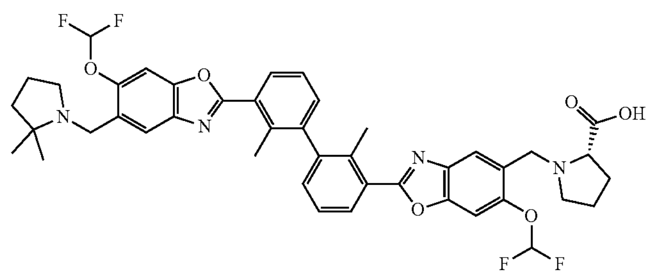 [SMILES: Cc1c(-c2nc3cc(CN4CCC[C@H]4C(=O)O)c(OC(F)F)cc3o2)cccc1-c1cccc(-c2nc3cc(CN4CCCC4(C)C)c(OC(F)F)cc3o2)c1C] | 787.3 |
| 63 | ((6-(difluoromethoxy)-2-(3'-(6-(difluoromethoxy)-5-(((S)-2-(methoxymethyl)pyrrolidin-1-yl)methyl)benzo[d]oxazol-2-yl)-2,2'-dimethyl-[1,1'-biphenyl]-3-yl)benzo[d]oxazol-5-yl)methyl)-L-proline | 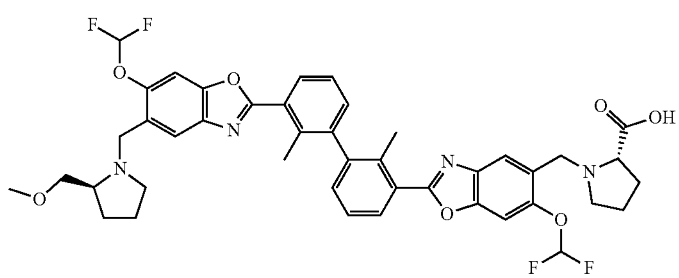 [SMILES: COC[C@@H]1CCCN1Cc1cc2nc(-c3cccc(-c4cccc(-c5nc6cc(CN7CCC[C@H]7C(=O)O)c(OC(F)F)cc6o5)c4C)c3C)oc2cc1OC(F)F] | 803.3 |
| 64 | ((6-(difluoromethoxy)-2-(3'-(6-(difluoromethoxy)-5-(((((S)-tetrahydrofuran-2-yl)methyl)amino)methyl)benzo[d]oxazol-2-yl)-2,2'-dimethyl-[1,1'-biphenyl]-3-yl)benzo[d]oxazol-5-yl)methyl)-L-proline | 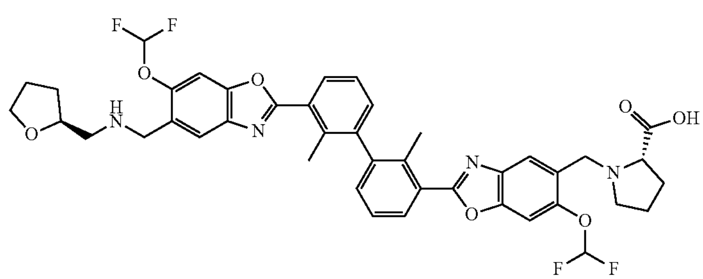 [SMILES: Cc1c(-c2nc3cc(CNC[C@@H]4CCCO4)c(OC(F)F)cc3o2)cccc1-c1cccc(-c2nc3cc(CN4CCC[C@H]4C(=O)O)c(OC(F)F)cc3o2)c1C] | 789.3 |

TABLE 1-continued

| EX No. | Chemical Name | Structure | Physical Data (MS) (M + H)+ |
|---|---|---|---|
| 65 | ((2-(2'-cyano-3'-(6-(difluoromethoxy)-5-(pyrrolidin-1-ylmethyl)benzo[d]oxazol-2-yl)-2-methyl-[1,1'-biphenyl]-3-yl)-6-(difluoromethoxy)benzo[d]oxazol-5-yl)methyl)proline | 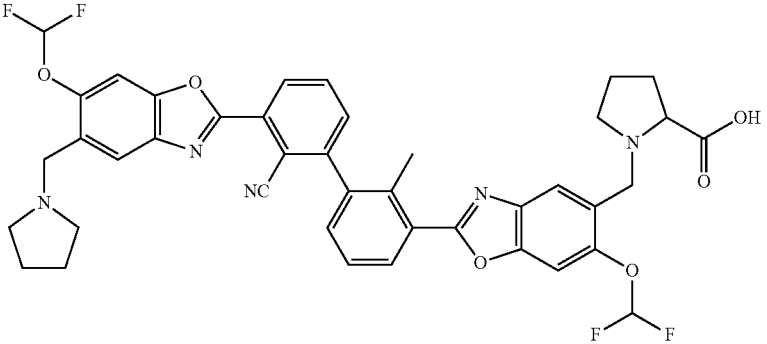 [SMILES: Cc1c(-c2nc3cc(CN4CCCC4C(=O)O)c(OC(F)F)cc3o2)cccc1-c1cccc(-c2nc3cc(CN4CCCC4)c(OC(F)F)cc3o2)c1C#N] | 770.3 |
| 66 | ((6-(difluoromethoxy)-2-(3'-(6-(difluoromethoxy)-5-(pyrrolidin-1-ylmethyl)benzo[d]oxazol-2-yl)-2,2'-dimethyl-[1,1'-biphenyl]-3-yl)benzo[d]oxazol-5-yl)methyl)-D-proline | 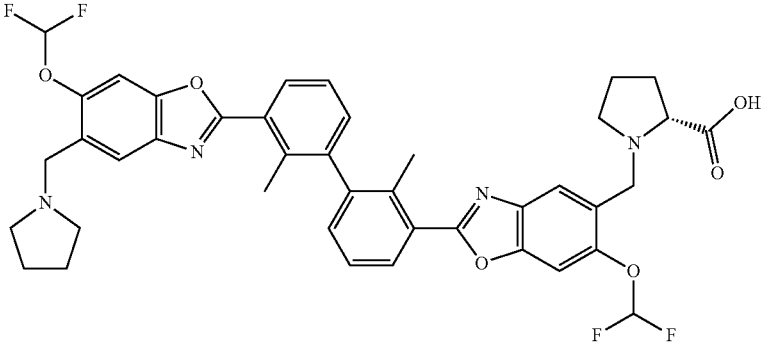 [SMILES: Cc1c(-c2nc3cc(CN4CCCC4)c(OC(F)F)cc3o2)cccc1-c1cccc(-c2nc3cc(CN4CCC[C@@H]4C(=O)O)c(OC(F)F)cc3o2)c1C] | 759.3 |
| 67 | ((6-(difluoromethoxy)-2-(3'-(6-(difluoromethoxy)-5-((3,3-dimethylpyrrolidin-1-yl)methyl)benzo[d]oxazol-2-yl)-2,2'-dimethyl-[1,1'-biphenyl]-3-yl)benzo[d]oxazol-5-yl)methyl)-L-proline | 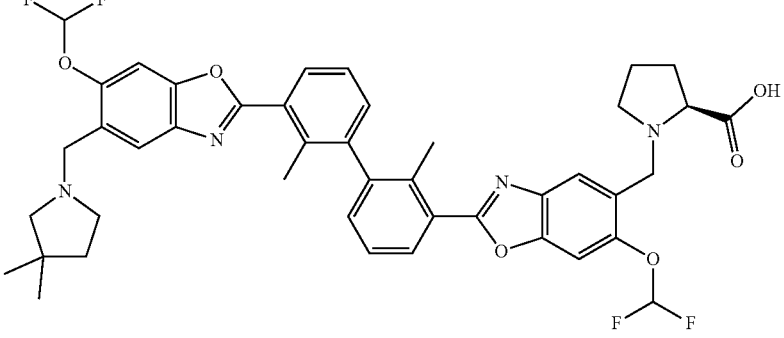 | 787.3 |
| 68 | ((2-(3'-(5-((3-(diethylamino)azetidin-1-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline | 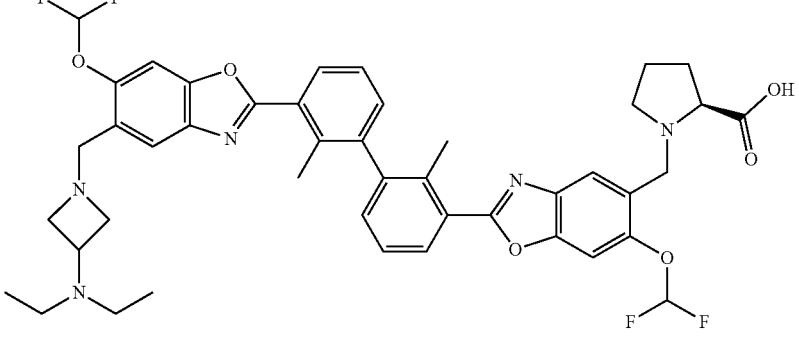 | 816.3 |

TABLE 1-continued

| EX No. | Chemical Name | Structure | Physical Data (MS) (M + H)+ |
|---|---|---|---|
| 69 | ((6-(difluoromethoxy)-2-(3'-(6-(difluoromethoxy)-5-((3-(2-hydroxypropan-2-yl)azetidin-1-yl)methyl)benzo[d]oxazol-2-yl)-2,2'-dimethyl-[1,1'-biphenyl]-3-yl)benzo[d]oxazol-5-yl)methyl)-L-proline | 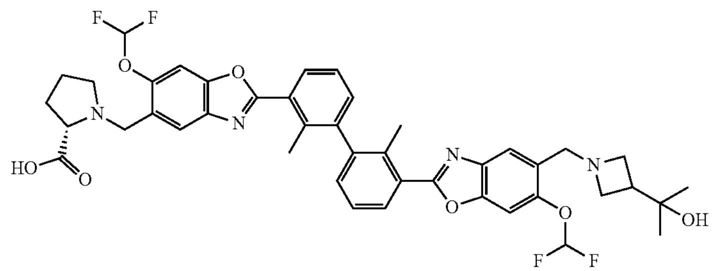 [SMILES: Cc1c(-c2nc3cc(CN4CC(C(C)(C)O)C4)c(OC(F)F)cc3o2)cccc1-c1cccc(-c2nc3cc(CN4CCC[C@H]4C(=O)O)c(OC(F)F)cc3o2)c1C] | 803.3 |
| 70 | ((6-(difluoromethoxy)-2-(3'-(6-(difluoromethoxy)-5-((2,5-dihydro-1H-pyrrol-1-yl)methyl)benzo[d]oxazol-2-yl)-2,2'-dimethyl-[1,1'-biphenyl]-3-yl)benzo[d]oxazol-5-yl)methyl)-L-proline | 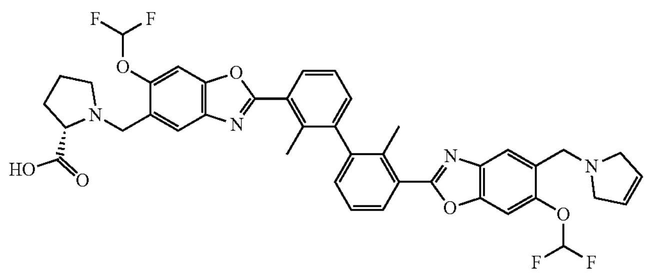 [SMILES: Cc1c(-c2nc3cc(CN4CC=CC4)c(OC(F)F)cc3o2)cccc1-c1cccc(-c2nc3cc(CN4CCC[C@H]4C(=O)O)c(OC(F)F)cc3o2)c1C] | 757.3 |
| 71 | ((2-(3'-(5-((2-azabicyclo[2.1.1]hexan-2-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline | 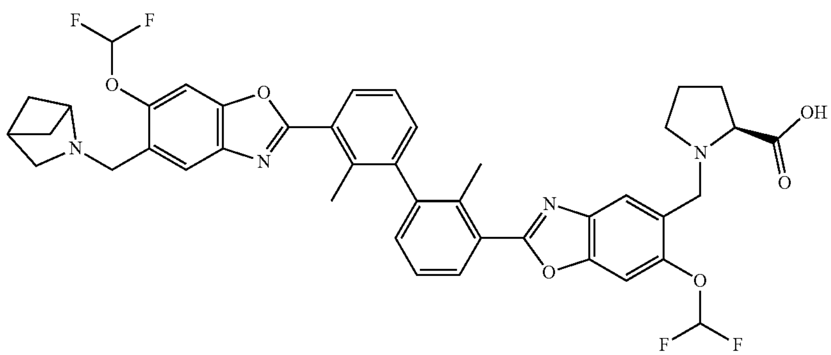 [SMILES: Cc1c(-c2nc3cc(CN4CC5CC4C5)c(OC(F)F)cc3o2)cccc1-c1cccc(-c2nc3cc(CN4CCC[C@H]4C(=O)O)c(OC(F)F)cc3o2)c1C] | 771.3 |
| 72 | ((2-(3'-(5-(((1s,4s)-7-azabicyclo[2.2.1]heptan-7-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline | 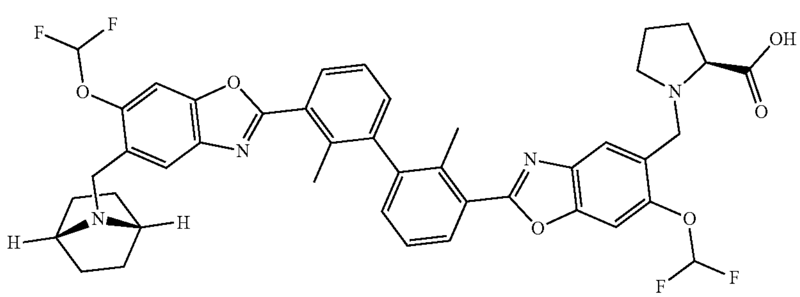 [SMILES: Cc1c(-c2nc3cc(CN4CCC[C@H]4C(=O)O)c(OC(F)F)cc3o2)cccc1-c1cccc(-c2nc3cc(CN4[C@H]5CC[C@@H]4CC5)c(OC(F)F)cc3o2)c1C] | 785.3 |
| 73 | ((2-(3'-(5-((((3,3-difluoro-1-(hydroxymethyl)cyclobutyl)methyl)amino)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline | 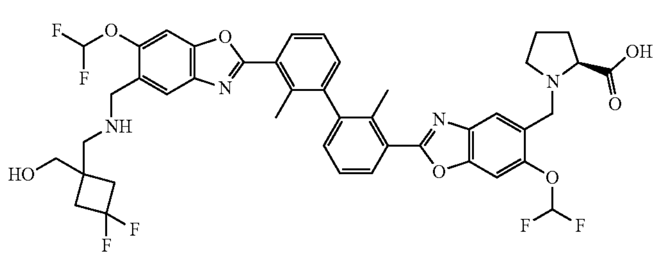 [SMILES: Cc1c(-c2nc3cc(CNCC4(CO)CC(F)(F)C4)c(OC(F)F)cc3o2)cccc1-c1cccc(-c2nc3cc(CN4CCC[C@H]4C(=O)O)c(OC(F)F)cc3o2)c1C] | 839.3 |

TABLE 1-continued

| EX No. | Chemical Name | Structure | Physical Data (MS) (M + H)+ |
|---|---|---|---|
| 74 | ((2-(3'-(5-((5-azaspiro[2.3]hexan-5-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline | 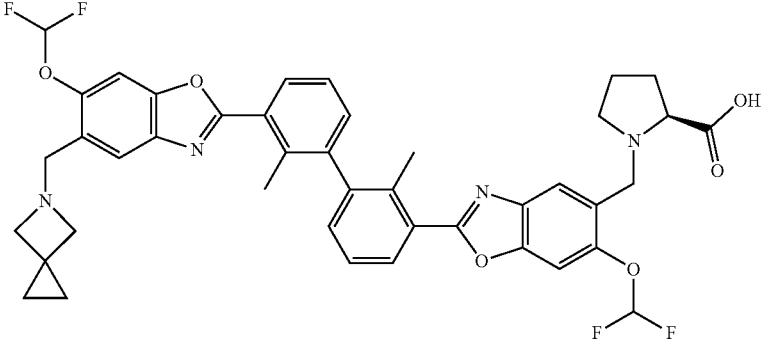 [SMILES: Cc1c(-c2nc3cc(CN4CC5(CC5)C4)c(OC(F)F)cc3o2)cccc1-c1cccc(-c2nc3cc(CN4CCC[C@H]4C(=O)O)c(OC(F)F)cc3o2)c1C] | 771.3 |
| 75 | ((6-(difluoromethoxy)-2-(3'-(6-(difluoromethoxy)-5-((3-oxo-6-azabicyclo[3.2.1]octan-6-yl)methyl)benzo[d]oxazol-2-yl)-2,2'-dimethyl-[1,1'-biphenyl]-3-yl)benzo[d]oxazol-5-yl)methyl)-L-proline | 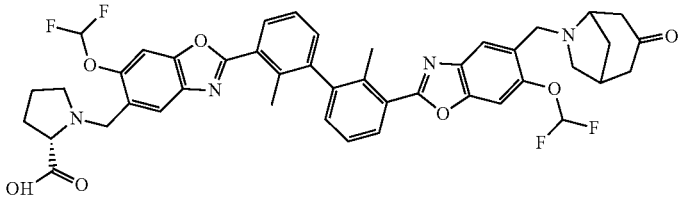 [SMILES: Cc1c(-c2nc3cc(CN4CC5CC(=O)CC4C5)c(OC(F)F)cc3o2)cccc1-c1cccc(-c2nc3cc(CN4CCC[C@H]4C(=O)O)c(OC(F)F)cc3o2)c1C] | 813.3 |
| 76 | ((2-(3'-(5-((1,1-difluoro-5-azaspiro[2.3]hexan-5-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline | 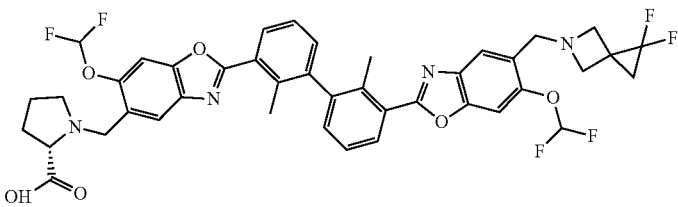 [SMILES: Cc1c(-c2nc3cc(CN4CC5(C4)CC5(F)F)c(OC(F)F)cc3o2)cccc1-c1cccc(-c2nc3cc(CN4CCC[C@H]4C(=O)O)c(OC(F)F)cc3o2)c1C] | 807.3 |
| 77 | ((6-(difluoromethoxy)-2-(3'-(6-(difluoromethoxy)-5-((3-(hydroxymethyl)-3-methylpyrrolidin-1-yl)methyl)benzo[d]oxazol-2-yl)-2,2'-dimethyl-[1,1'-biphenyl]-3-yl)benzo[d]oxazol-5-yl)methyl)-L-proline | 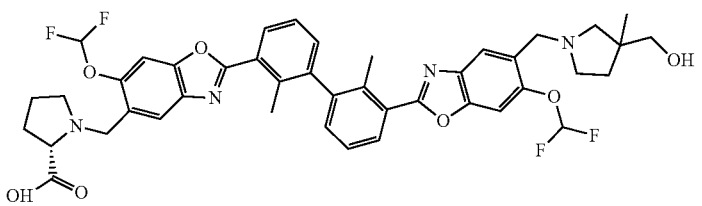 [SMILES: Cc1c(-c2nc3cc(CN4CCC(C)(CO)C4)c(OC(F)F)cc3o2)cccc1-c1cccc(-c2nc3cc(CN4CCC[C@H]4C(=O)O)c(OC(F)F)cc3o2)c1C] | 803.3 |
| 78 | ((6-(difluoromethoxy)-2-(3'-(6-(difluoromethoxy)-5-((3-(hydroxymethyl)-3-methylazetidin-1-yl)methyl)benzo[d]oxazol-2-yl)-2,2'-dimethyl-[1,1'-biphenyl]-3-yl)benzo[d]oxazol-5-yl)methyl)-L-proline | 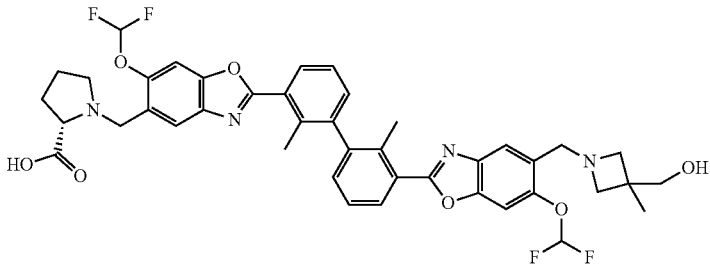 [SMILES: Cc1c(-c2nc3cc(CN4CC(C)(CO)C4)c(OC(F)F)cc3o2)cccc1-c1cccc(-c2nc3cc(CN4CCC[C@H]4C(=O)O)c(OC(F)F)cc3o2)c1C] | 789.3 |

TABLE 1-continued

| EX No. | Chemical Name | Structure | Physical Data (MS) (M + H)+ |
|---|---|---|---|
| 79 | ((2-(3'-(5-((3-cyano-3-methylazetidin-1-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline | 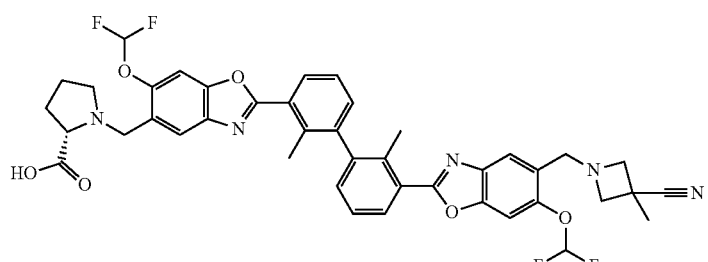 | 784.3 |
| 80 | ((2-(3'-(5-((3-cyanoazetidin-1-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline | 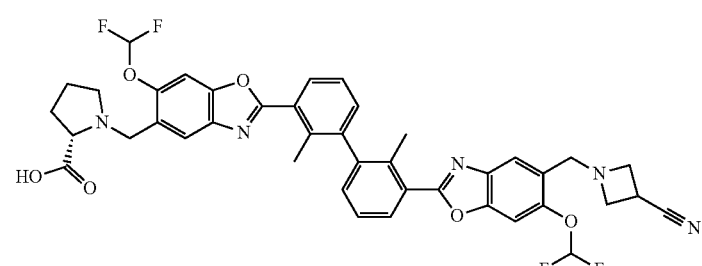 | 770.3 |
| 81 | ((6-(difluoromethoxy)-2-(3'-(6-(difluoromethoxy)-5-((3-methyleneazetidin-1-yl)methyl)benzo[d]oxazol-2-yl)-2,2'-dimethyl-[1,1'-biphenyl]-3-yl)benzo[d]oxazol-5-yl)methyl)-L-proline | 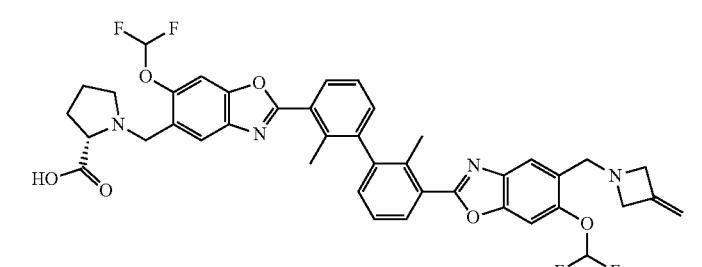 | 757.3 |
| 82 | ((2-(3'-(5-((3-(cyanomethylene)azetidin-1-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline | 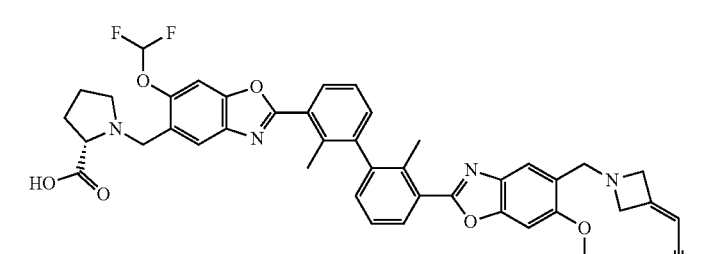 | 782.3 |
| 83 | ((2-(2,2'-dicyano-3'-(6-(difluoromethoxy)-5-((3,3-dimethylazetidin-1-yl)methyl)benzo[d]oxazol-2-yl)-[1,1'-biphenyl]-3-yl)-6-(difluoromethoxy)benzo[d]oxazol-5-yl)methyl)-L-proline | 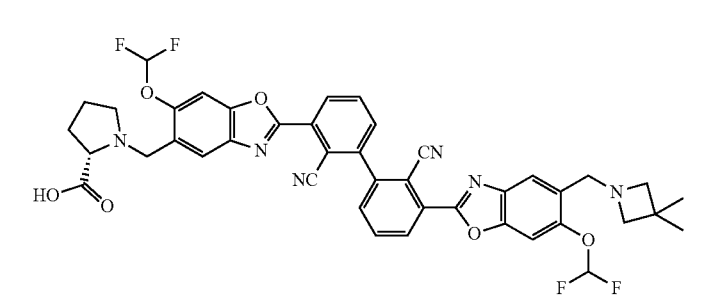 [SMILES: CC1(C)CN(Cc2cc3nc(-c4cccc(-c5cccc(-c6nc7cc(CN8CCC[C@H]8C(=O)O)c(OC(F)F)cc7o6)c5C#N)c4C#N)oc3cc2OC(F)F)C1] | 795.3 |

TABLE 1-continued

| EX No. | Chemical Name | Structure | Physical Data (MS) (M + H)+ |
|---|---|---|---|
| 85 | (R)-1-((6-(difluoromethoxy)-2-(3'-(6-(difluoromethoxy)-5-((3,3-dimethylazetidin-1-yl)methyl)benzo[d]oxazol-2-yl)-2,2'-dimethyl-[1,1'-biphenyl]-3-yl)benzo[d]oxazol-5-yl)methyl)pyrrolidine-3-carboxylic acid | 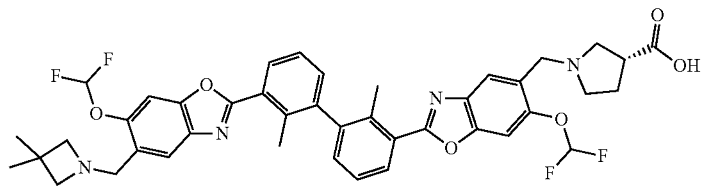 [SMILES: Cc1c(-c2nc3cc(CN4CC[C@@H](C(=O)O)C4)c(OC(F)F)cc3o2)cccc1-c1cccc(-c2nc3cc(CN4CC(C)(C)C4)c(OC(F)F)cc3o2)c1C] | 773.3 |
| 86 | (S)-1-((6-(difluoromethoxy)-2-(3'-(6-(difluoromethoxy)-5-((3,3-dimethylazetidin-1-yl)methyl)benzo[d]oxazol-2-yl)-2,2'-dimethyl-[1,1'-biphenyl]-3-yl)benzo[d]oxazol-5-yl)methyl)pyrrolidine-3-carboxylic acid | 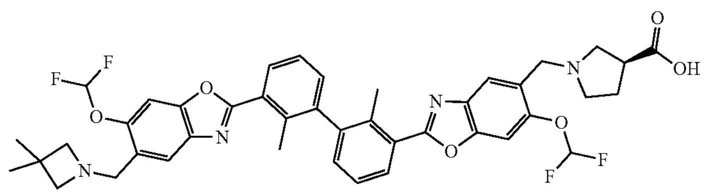 [SMILES: Cc1c(-c2nc3cc(CN4CC[C@H](C(=O)O)C4)c(OC(F)F)cc3o2)cccc1-c1cccc(-c2nc3cc(CN4CC(C)(C)C4)c(OC(F)F)cc3o2)c1C] | 773.3 |
| 87 | ((2-(2'-cyano-3'-(6-(difluoromethoxy)-5-((3,3-dimethylazetidin-1-yl)methyl)benzo[d]oxazol-2-yl)-2-methyl-[1,1'-biphenyl]-3-yl)-6-(difluoromethoxy)benzo[d]oxazol-5-yl)methyl)-D-proline | 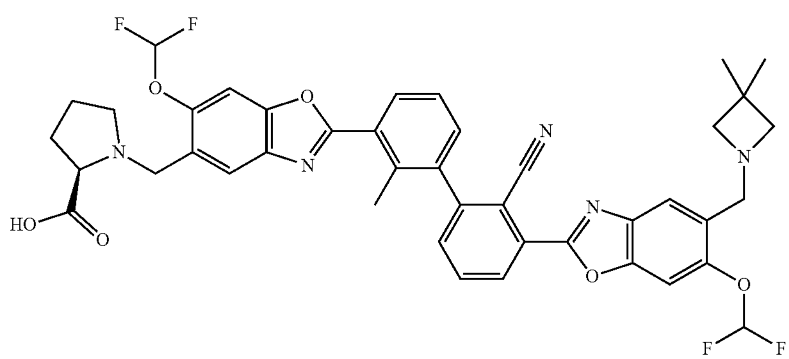 [SMILES: Cc1c(-c2nc3cc(CN4CCC[C@@H]4C(=O)O)c(OC(F)F)cc3o2)cccc1-c1cccc(-c2nc3cc(CN4CC(C)(C)C4)c(OC(F)F)cc3o2)c1C#N] | 784.3 |
| 317 | ((2-(3'-(6-(difluoromethoxy)-5-(pyrrolidin-1-ylmethyl)benzo[d]oxazol-2-yl)-2,2'-dimethyl-[1,1'-biphenyl]-3-yl)benzo[d]oxazol-5-yl)methyl)-L-proline | 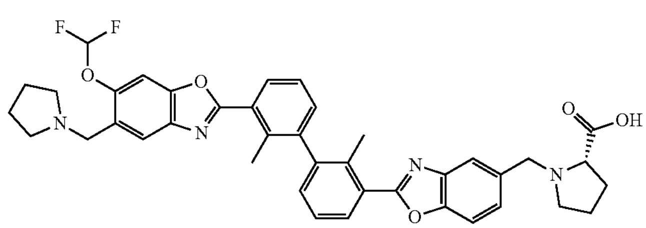 [SMILES: Cc1c(-c2nc3cc(CN4CCC[C@H]4C(=O)O)ccc3o2)cccc1-c1cccc(-c2nc3cc(CN4CCCC4)c(OC(F)F)cc3o2)c1C] | 693.3 |

Example 100 Synthesis of Compound 100

((6-(difluoromethoxy)-2-(2,2'-dimethyl-3'-(5-(pyrrolidin-1-ylmethyl)-7-(trifluoromethyl)benzo[d]oxazol-2-yl)-[1,1'-biphenyl]-3-yl)benzo[d]oxazol-5-yl)methyl)-L-proline Compound 100

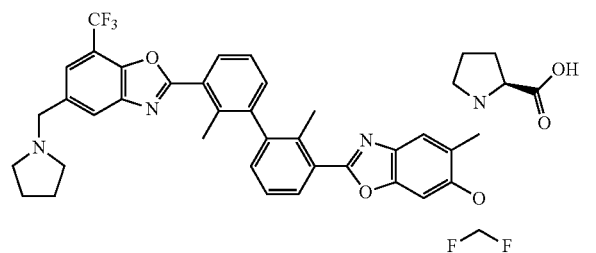

Step 1: Preparation of 4-hydroxy-3-nitro-5-(trifluoromethyl)benzaldehyde

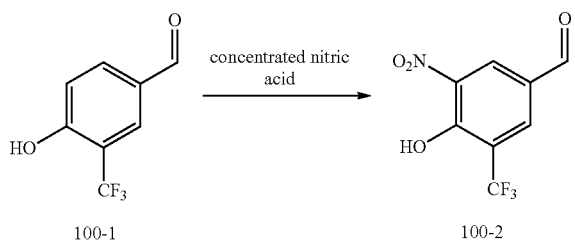 [SMILES: O=Cc1ccc(O)c(C(F)(F)F)c1 ; O=Cc1cc([N+](=O)[O-])c(O)c(C(F)(F)F)c1]

4-hydroxy-3-(trifluoromethyl)benzaldehyde (1 g) was dissolved in concentrated $H_2SO_4$ (10 mL). After the mixture was cooled to 5° C. (ice bath), concentrated $HNO_3$ (65%) (612 mg) was added dropwise and the mixture was stirred for another 30 mins. Until the raw material was almost finished and the reaction stopped, the mixture was poured into ice water (30 mL), isolated by filtration. This resulted in compound 100-2 (1 g).

Step 2: Preparation of 2-nitro-4-(pyrrolidin-1-ylmethyl)-6-(trifluoromethyl)phenol

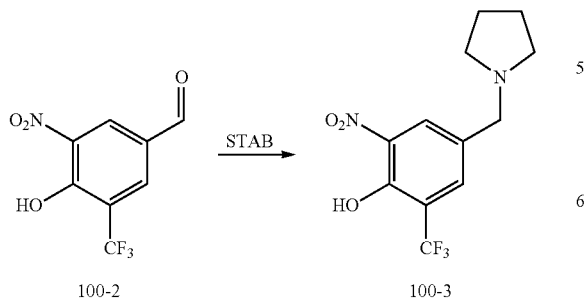

A mixture of compound 100-2 (500 mg), pyrrolidine (454 mg), $CH_3COOH$ (255 mg) in 1,4-dioxane (10 mL) was stirred for 30 mins at 30° C., Then sodium triacetoxyborohydride (1.35 g) was added and continue stirred. Until the raw material was almost finished and the reaction stopped, the reaction solution was poured into $H_2O$ (30 mL), extracted with DCM (15 mL) for 3 times, brine and dry using anhydrous $Na_2SO_4$, The precipitate was filtered and dried under vacuum, The crude product was further purified by Silica gel column (DCM/MeOH=20:1) to get compound 100-3 (420 mg).

Step 3: Preparation of 2-amino-4-(pyrrolidin-1-ylmethyl)-6-(trifluoromethyl)phenol

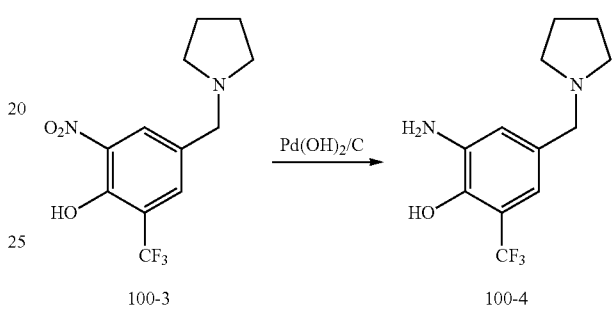

A mixture of compound 100-3 (420 mg) and 10% Pd(OH)/C (150 mg) in methanol (10 mL) was stirred under 1.1 atm of hydrogen pressure at room temperature for 3 hrs. The catalyst was then removed by filtration, the solid residue was washed with methanol (300 mL) and the solvent was removed in vacuo. This resulted in 300 mg compound 100-4.

Step 4: Preparation of 2-(3-bromo-2-methyl-phenyl)-5-(pyrrolidin-1-ylmethyl)-7-(trifluoromethyl)-1,3-benzoxazole

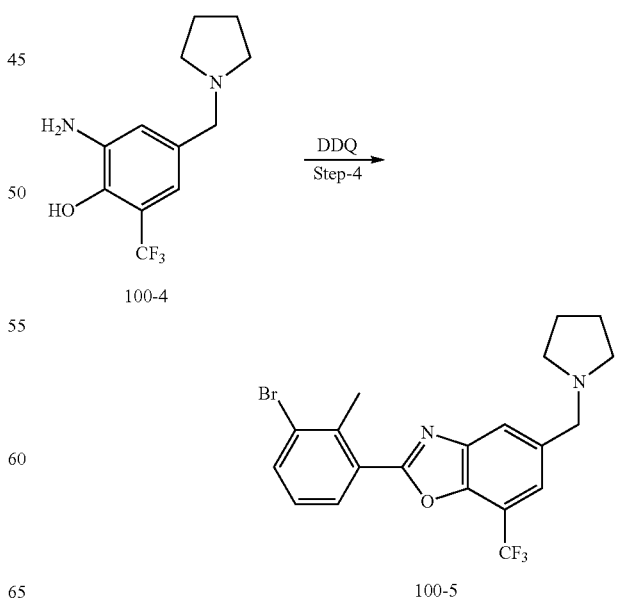

This compound was prepared using similar procedures as described as step 3 in example A, with compound 100-4 replacing compound a-3. The crude product was used directly in the next step.

Step 5: Preparation of methyl (2S)-1-[[6-(difluoromethoxy)-2-[2-methyl-3-[2-methyl-3-[5-(pyrrolidin-1-ylmethyl)-7-(trifluoromethyl)-1,3-benzoxazol-2-yl]phenyl]phenyl]-1,3-benzoxazol-5-yl]methyl]pyrrolidine-2-carboxylate

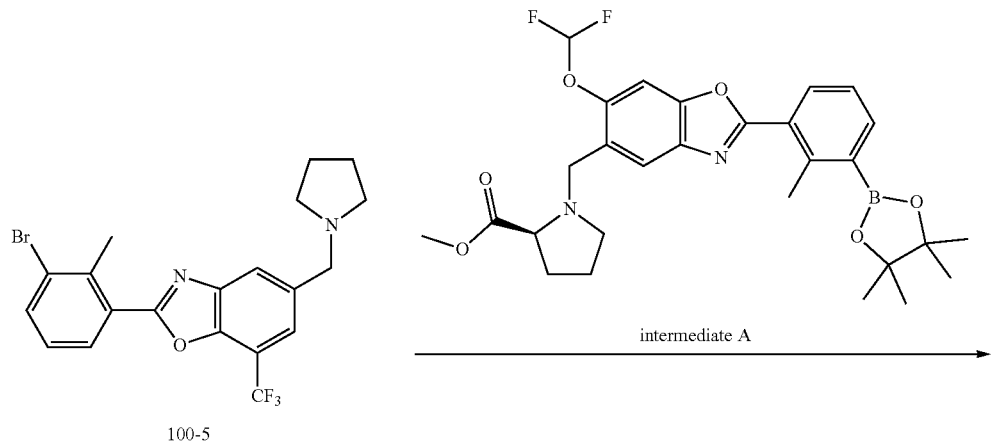

100-5

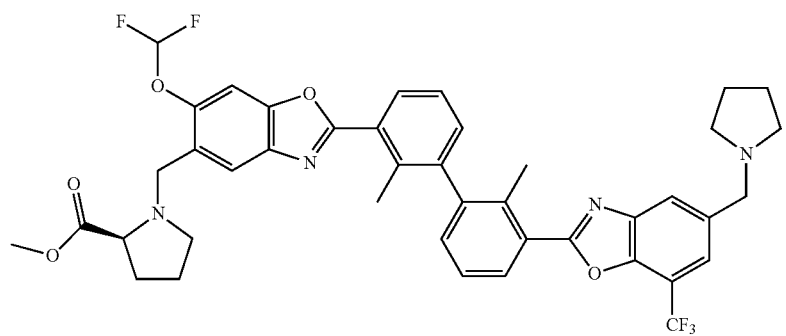

100-6

Intermediate A (345.72 mg), compound 100-5 (280 mg), 1,1'-Bis(diphenylphosphino) ferrocene palladium(II)dichloride (53 mg), and potassium carbonate (88.10 mg) dissolved in 1,4-dioxane (8 mL) and H₂O (2 mL), stirred for 12 hrs at 80° C. under N₂. The reaction solution was poured into H₂O (30 mL) and extracted by DCM (15 mL) for 3 times. The organic layers were washed with brine, dried over anhydrous Na₂SO₄, filtered and concentrated under vacuum to get the crude product. The crude product was further purified by Silica gel column to get the compound 100-6 (300 mg).

Step 6: Preparation of (2S)-1-[[6-(difluoromethoxy)-2-[2-methyl-3-[2-methyl-3-[5-(pyrrolidin-1-ylmethyl)-7-(trifluoromethyl)-1,3-benzoxazol-2-yl]phenyl]phenyl]-1,3-benzoxazol-5-yl]methyl]pyrrolidine-2-carboxylic acid (compound 100)

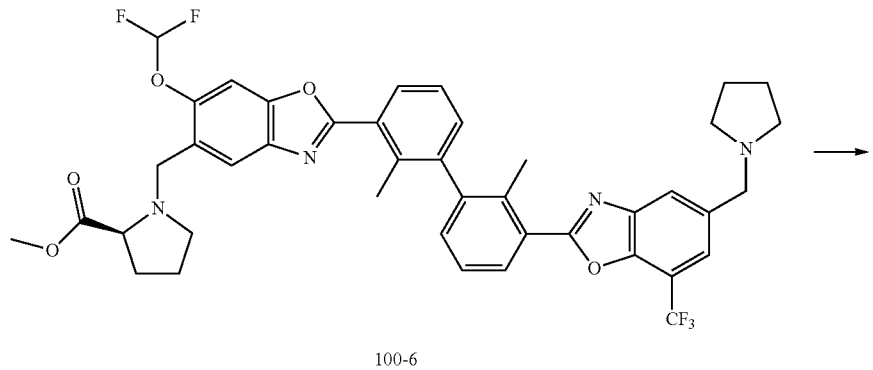

100-6

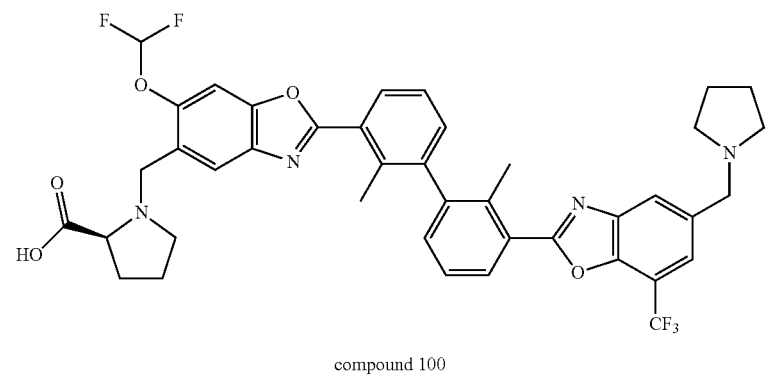

compound 100

This compound was prepared using similar procedures as described as step 5 in example 1, with compound 100-6 replacing compound 1-4. The precipitate was filtered and dried under vacuum. This resulted in (2S)-1-[[6-(difluoromethoxy)-2-[2-methyl-3-[2-methyl-3-[5-(pyrrolidin-1-ylmethyl)-7-(trifluoromethyl)-1,3-benzoxazol-2-yl]phenyl]phenyl]-1,3-benzoxazol-5-yl]methyl]pyrrolidine-2-carboxylic acid (compound 100). LC-MS (m/z): 761.3 (M+H)⁺.

Example 101 Synthesis of Compound 101

((6-(difluoromethoxy)-2-(2,2'-dimethyl-3'-(5-(pyrrolidin-1-ylmethyl)-6-(trifluoromethyl)benzo[d]oxazol-2-yl)-[1,1'-biphenyl]-3-yl)benzo[d]oxazol-5-yl)methyl)-L-proline Compound 101

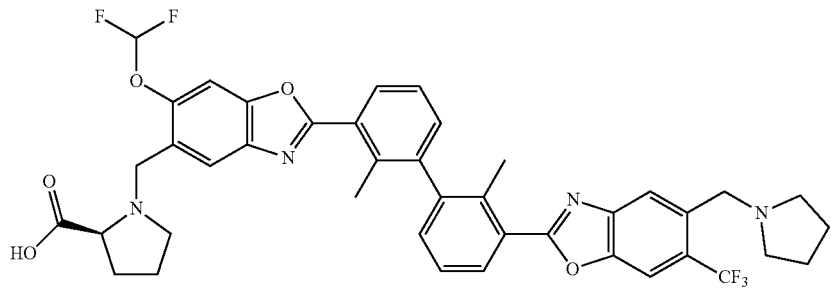

Step 1: Preparation of methyl 4-hydroxy-2-(trifluoromethyl)benzoate

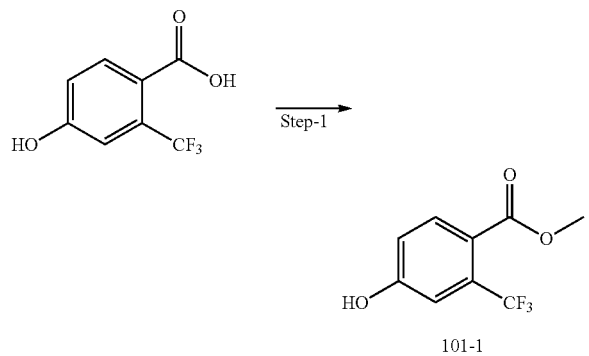

101-1

To the solution of Methyl 4-hydroxy-2-(trifluoromethyl) benzoate 4-Hydroxy-2-(trifluoromethyl) benzoic acid (18.0 g) in methanol (300 ml) was added concentrated sulfuric acid (10 ml) dropwise, the mixture was stirred under reflux for 12 hrs. After cooling to room temperature, water (200 ml) was added to the reaction mixture, methanol was distilled off under reduced pressure and the mixture was extracted twice with ethyl acetate (200 ml). The organic layer was washed with water, saturated sodium bicarbonate water and saturated aqueous sodium chloride solution, dried over sodium sulfate, filtration and concentration under reduced pressure.

Title compound (18 g) was obtained.

Step 2: Preparation of methyl 4-hydroxy-5-nitro-2-(trifluoromethyl)benzoate

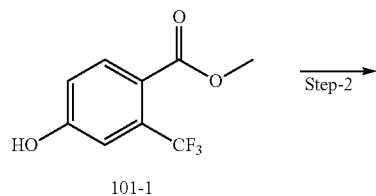

101-1

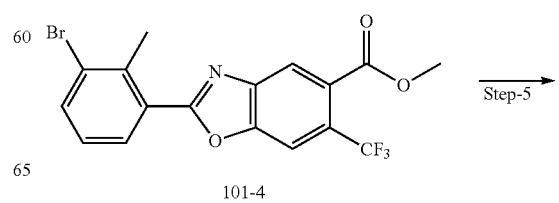

101-2

This compound was prepared using similar procedures as described as step 1 in example 100, with compound 101-1 replacing compound 100-1. The crude product was purified by silica gel column chromatography (hexane/ethyl acetate) to get the title compound.

Step 3: Preparation of methyl 5-amino-4-hydroxy-2-(trifluoromethyl)benzoate

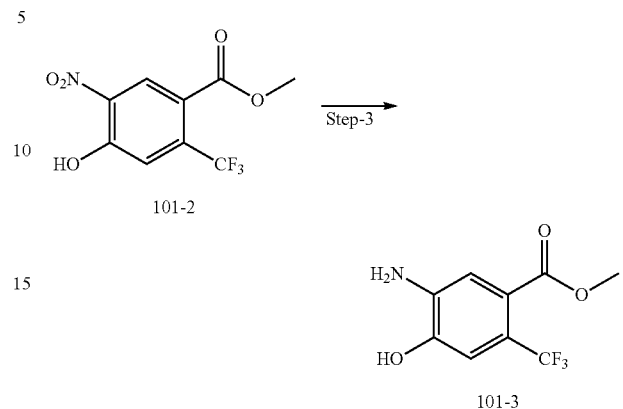

This compound was prepared using similar procedures as described as step 3 in example 100, with compound 101-2 replacing compound 100-3. The filtrate was concentrate under reduced pressure to get the title compound.

Step 4: Preparation of methyl 2-(3-bromo-2-methylphenyl)-6-(trifluoromethyl)benzo[d]oxazole-5-carboxylate

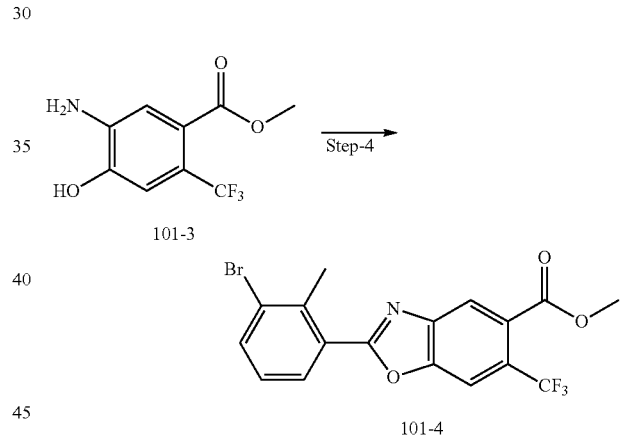

This compound was prepared using similar procedures as described as step 3 in example A, with compound 101-3 replacing compound a-3. The crude product was suspended in methanol, filtered and dried in a vacuum oven. The title compound was obtained.

Step 5: Preparation of (2-(3-bromo-2-methylphenyl)-6-(trifluoromethyl)benzo[d]oxazol-5-yl)methanol

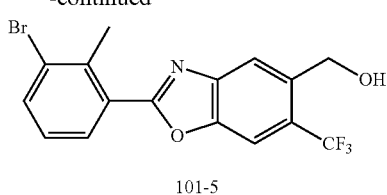

101-5

This compound was prepared using a similar procedure as described as step 5 in example A with compound 101-4 replacing compound a-5. The filtrate was concentrate under reduced pressure and the title compound was obtained.

Step 6: Preparation of 2-(3-bromo-2-methylphenyl)-5-(chloromethyl)-6-(trifluoromethyl)benzo[d]oxazole

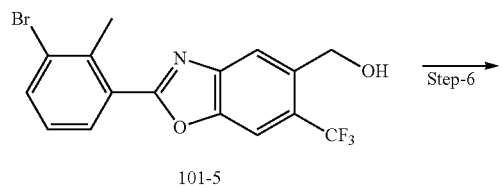

101-5 → Step-6 → 101-6

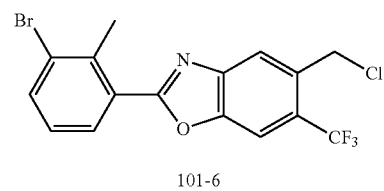

101-6

This compound was prepared using a similar procedure as described as step 2 in example 1, with compound 101-5 replacing compound 1-1. The crude product was used directly in the next step.

Step 7: Preparation of 2-(3-bromo-2-methylphenyl)-5-(pyrrolidin-1-ylmethyl)-6-(trifluoromethyl)benzo[d]oxazole

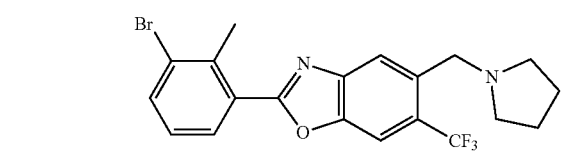

101-6 → Step-7

101-7

This compound was prepared using a similar procedure as described as step 3 in example 1, with compound 101-6 replacing compound 1-2, and with pyrrolidine replacing (1S, 2R)-2-aminocyclopentan-1-ol. The crude product was further purified by Silica gel column (PE/EA) to get the title compound.

Step 8: Preparation of methyl ((6-(difluoromethoxy)-2-(2,2'-dimethyl-3'-(5-(pyrrolidin-1-ylmethyl)-6-(trifluoromethyl)benzo[d]oxazol-2-yl)-[1,1'-biphenyl]-3-yl)benzo[d]oxazol-5-yl)methyl)-L-prolinate

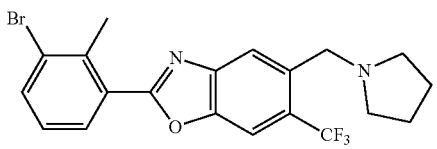

101-7

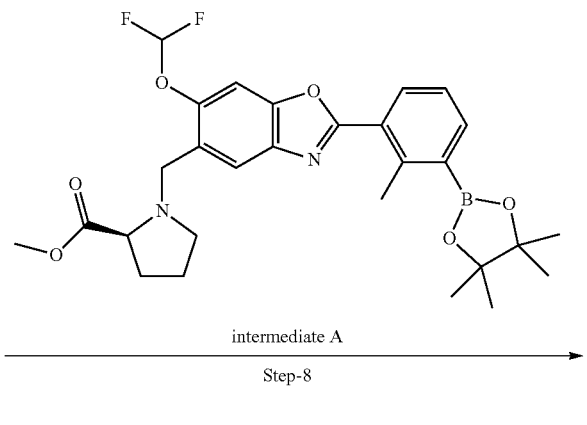

intermediate A

Step-8

-continued

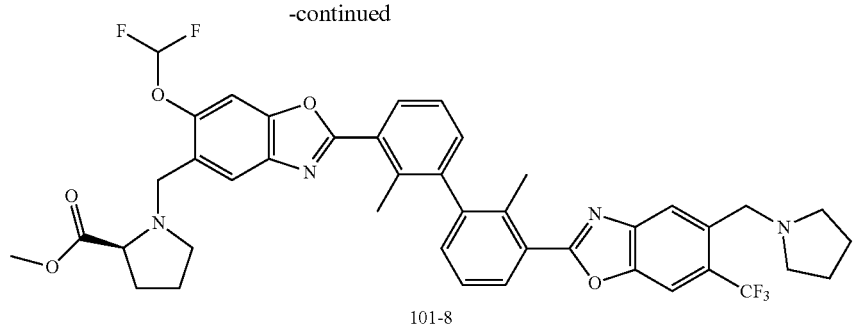
101-8

This compound was prepared using a similar procedure as described as step 1 in example 1, with compound 101-7 replacing compound a-6. The crude product was further purified by Silica gel column to get the title compound.

Step 9: Preparation of (((6-(difluoromethoxy)-2-(2,2'-dimethyl-3'-(5-(pyrrolidin-1-ylmethyl)-6-(trifluoromethyl)benzo[d]oxazol-2-yl)-[1,1'-biphenyl]-3-yl)benzo[d]oxazol-5-yl)methyl)-L-proline

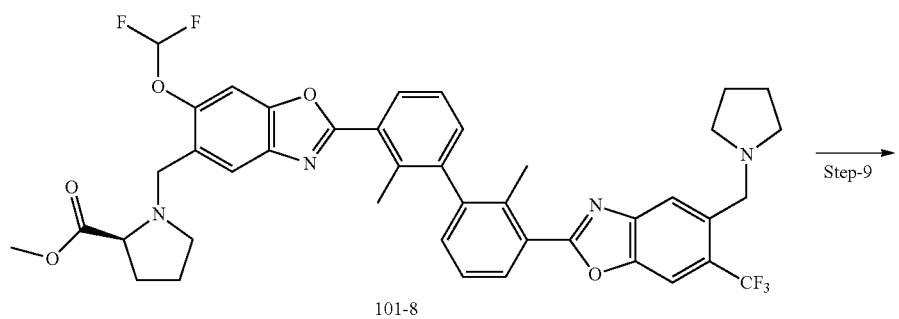
101-8

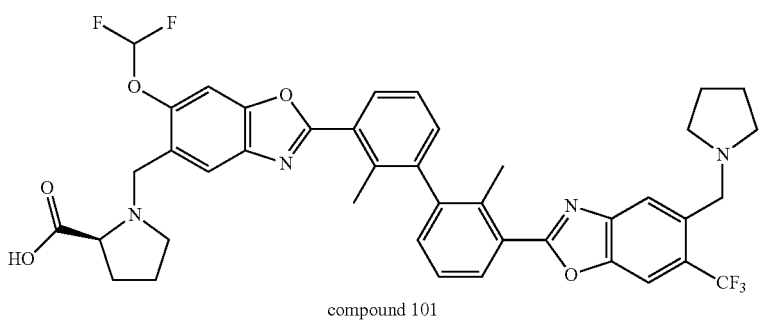
compound 101

This compound was prepared using similar procedures as described as step 5 in example 1, with compound 101-8 replacing compound 1-4. The mixture was concentrated under reduced pressure to get the title compound. LC-MS (m/z): 761.3 (M+H)⁺.

Example 102 Synthesis of Compound 102

((2-(3'-(6,7-difluoro-5-(pyrrolidin-1-ylmethyl)benzo[d]oxazol-2-yl)-2,2'-dimethyl-[1,1'-biphenyl]-3-yl)-6-(difluoromethoxy)benzo[d]oxazol-5-yl)methyl)-L-proline

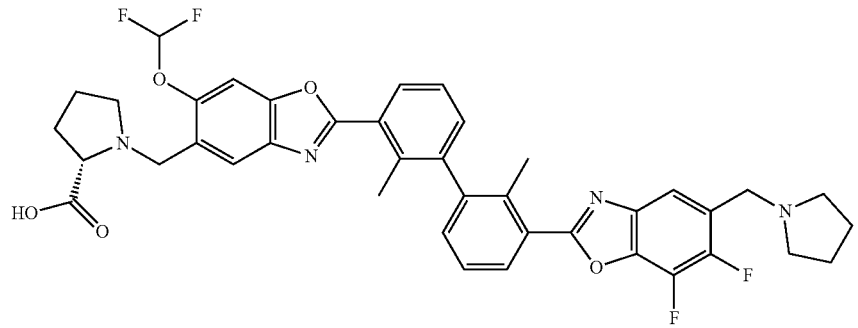

Compound 102

Step 1: Preparation of methyl 2,3-difluoro-4-hydroxy-5-nitrobenzoate

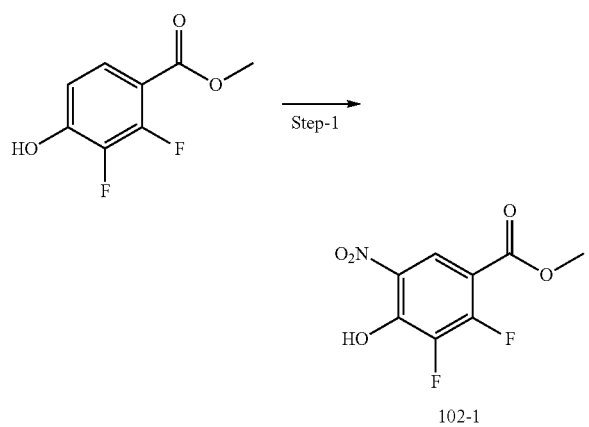

102-1

This compound was prepared using similar procedures as described as step 1 in example A, with methyl 2,3-difluoro-4-hydroxybenzoate replacing compound a-1. The crude product was purified by silica gel column chromatography (hexane/ethyl acetate) to get the title compound.

Step 2: Preparation of methyl 5-amino-2,3-difluoro-4-hydroxybenzoate

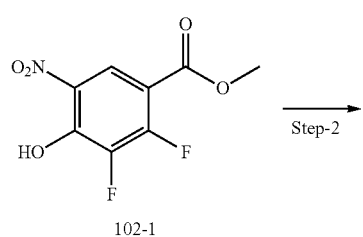

102-1

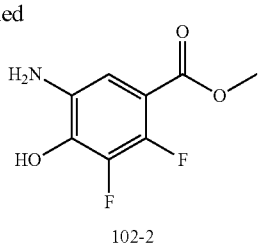

102-2

This compound was prepared using similar procedures as described as step 2 in example A, with compound 102-1 replacing compound a-2. The filtrate was concentrate under reduced pressure and the title compound was obtained.

Step 3: Preparation of methyl 2-(3-bromo-2-methylphenyl)-6,7-difluorobenzo[d]oxazole-5-carboxylate

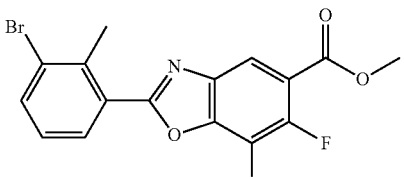

102-2

102-3

This compound was prepared using similar procedures as described as step 3 in example A, with compound 102-2 replacing compound a-3. The crude product was dissolved in methanol, filtered and dried in a vacuum oven. The title compound was obtained.

Step 4: Preparation of (2-(3-bromo-2-methylphenyl)-6,7-difluorobenzo[d]oxazol-5-yl)methanol

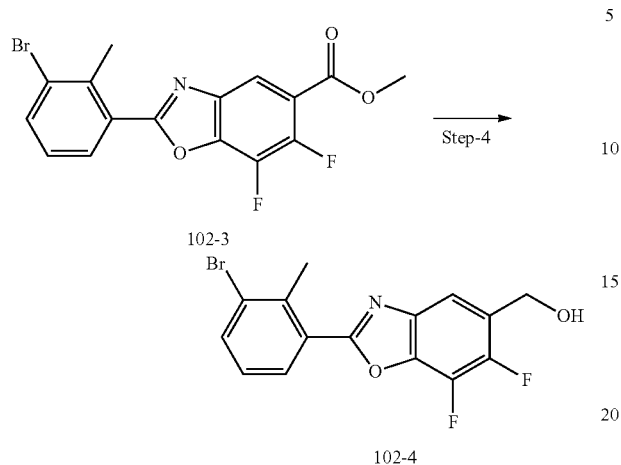

This compound was prepared using a similar procedure as described as step 5 in example A, with compound 102-3 replacing compound a-5. The filtrate was concentrate under reduced pressure and the title compound was obtained.

Step 5: Preparation of methyl ((2-(3'-(6,7-difluoro-5-(hydroxymethyl)benzo[d]oxazol-2-yl)-2,2'-dimethyl-[1,1'-biphenyl]-3-yl)-6-(difluoromethoxy)benzo[d]oxazol-5-yl)methyl)-L-prolinate

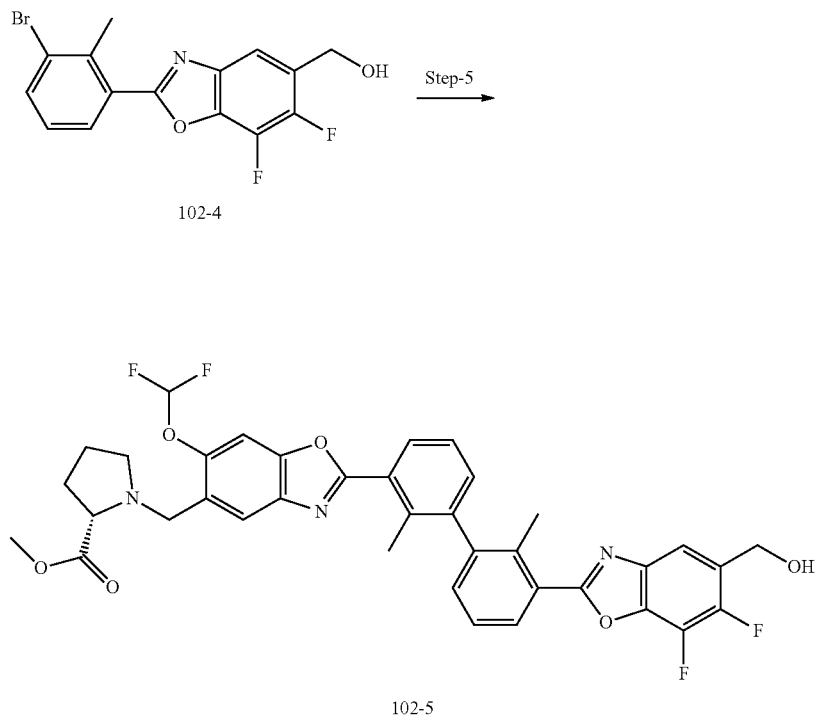

This compound was prepared using a similar procedure as described as step 1 in example 1, with compound 102-4 replacing compound a-6. The crude product was further purified by Silica gel column to get title compound.

Step 6: Preparation of methyl ((2-(3'-(5-(chloromethyl)-6,7-difluorobenzo[d]oxazol-2-yl)-2,2'-dimethyl-[1,1'-biphenyl]-3-yl)-6-(difluoromethoxy)benzo[d]oxazol-5-yl)methyl)-L-prolinate

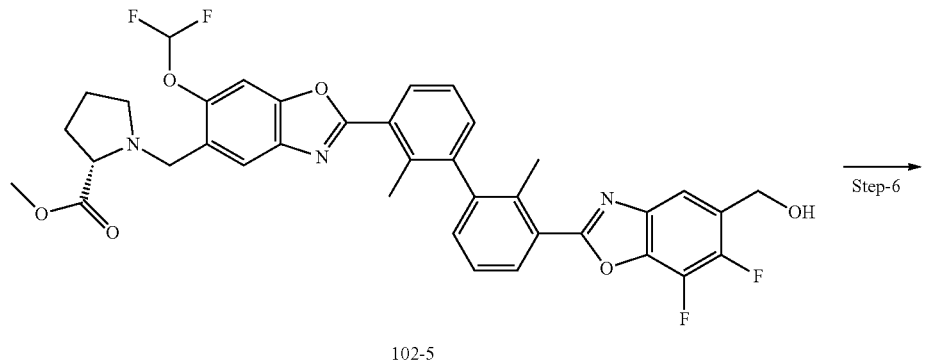

102-5

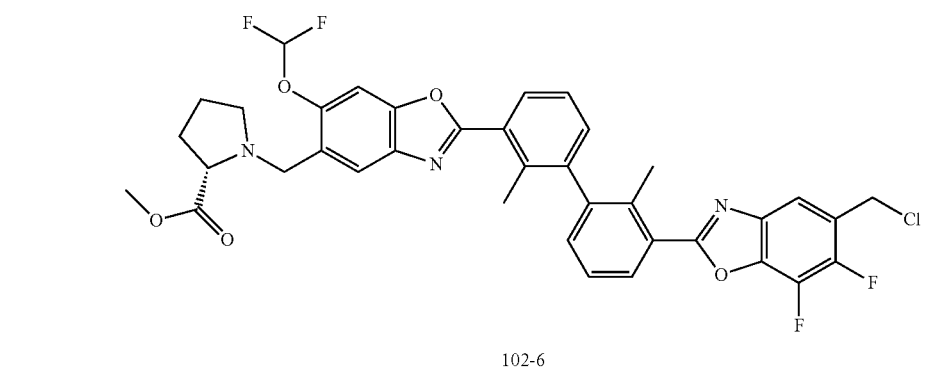

102-6

This compound was prepared using a similar procedure as described as step 2 in example 1, with compound 102-5 replacing compound 1-1. The crude product was used directly in the next step.

Step 7: Preparation of methyl ((2-(3'-(6,7-difluoro-5-(pyrrolidin-1-ylmethyl)benzo[d]oxazol-2-yl)-2,2'-dimethyl-[1,1'-biphenyl]-3-yl)-6-(difluoromethoxy)benzo[d]oxazol-5-yl)methyl)-L-prolinate

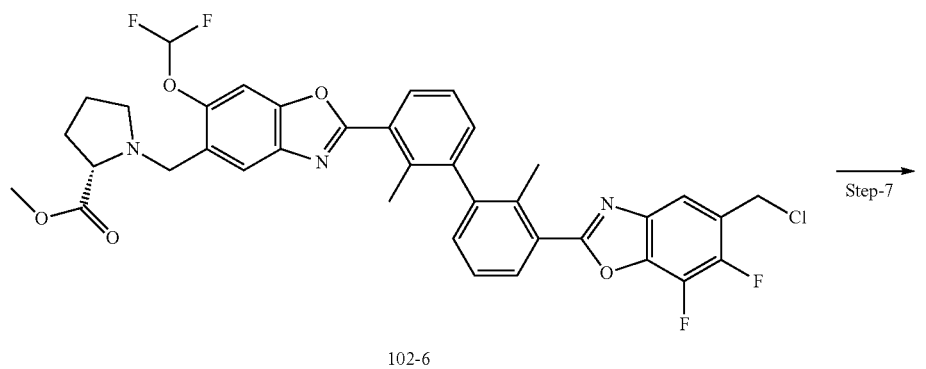

102-6

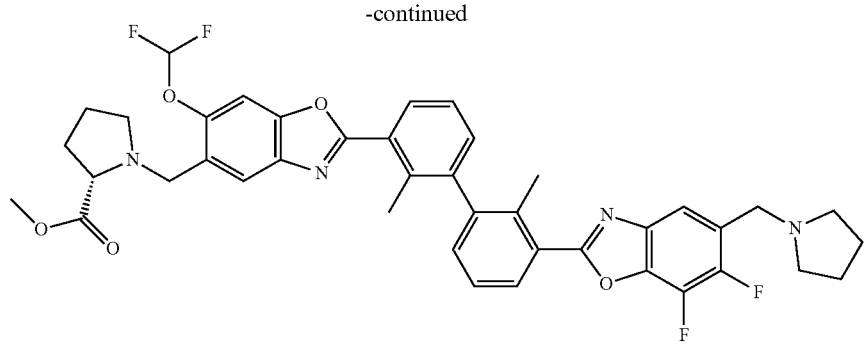

102-7

This compound was prepared using a similar procedure as described as step 3 in example 1, with compound 102-6 replacing compound 1-2, and with pyrrolidine replacing (1S,2R)-2-aminocyclopentan-1-ol. The crude product was further purified by Silica gel column (PE/EA) to get title compound.

Step 8: Preparation of ((2-(3'-(6,7-difluoro-5-(pyrrolidin-1-ylmethyl)benzo[d]oxazol-2-yl)-2,2'-dimethyl-[1,1'-biphenyl]-3-yl)-6-(difluoromethoxy)benzo[d]oxazol-5-yl)methyl)-L-proline

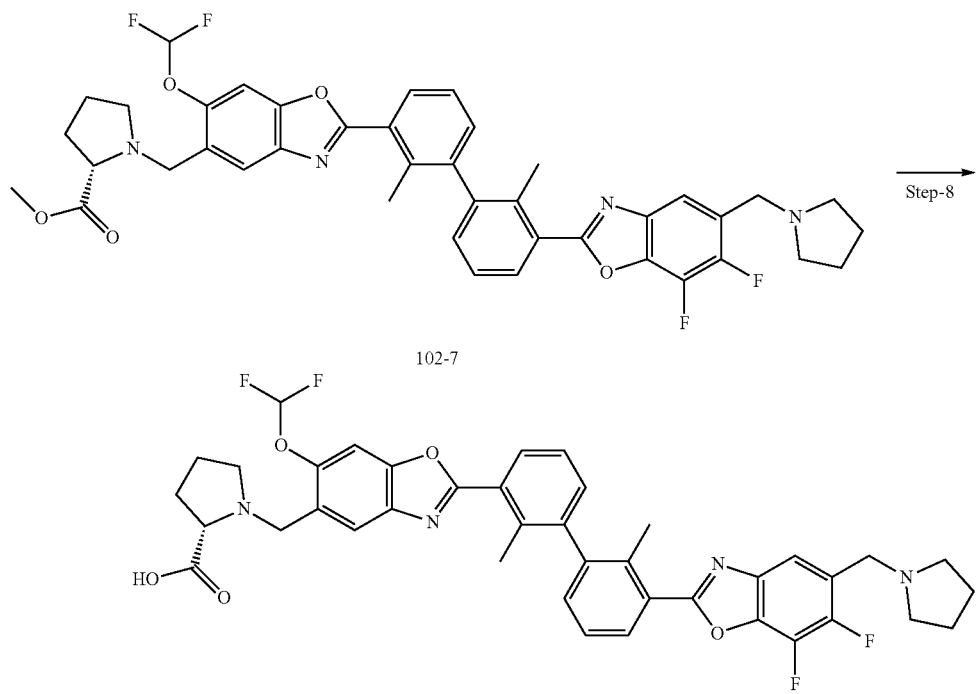

This compound was prepared using a similar procedure as described as step 5 in example 1 with compound 102-7 replacing compound 1-4. The crude product was further purified by Silica gel column to get title compound. LC-MS (m/z): 729.3 (M+H)+. 1H NMR (500 MHz, DMSO-d6) δ8.21 (dd, J=7.9, 1.4 Hz, 1H), 8.19-8.14 (m, 2H), 8.08 (s, 1H), 7.82 (s, 1H), 7.62-7.54 (m, 2H), 7.51-7.44 (m, 2H), 7.40 (t, J=71.9 Hz, 1H), 4.58 (s, 2H), 4.36-4.20 (m, 2H), 3.91 (s, 1H), 3.46 (s, 3H), 3.20-3.07 (m, 2H), 2.96 (s, 1H), 2.45 (d, J=4.0 Hz, 6H), 2.35-2.25 (m, 1H), 2.08-1.76 (m, 8H).

Example 103 Synthesis of Compound 103

((2-(3'-(7-cyano-5-((3,3-dimethylazetidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline

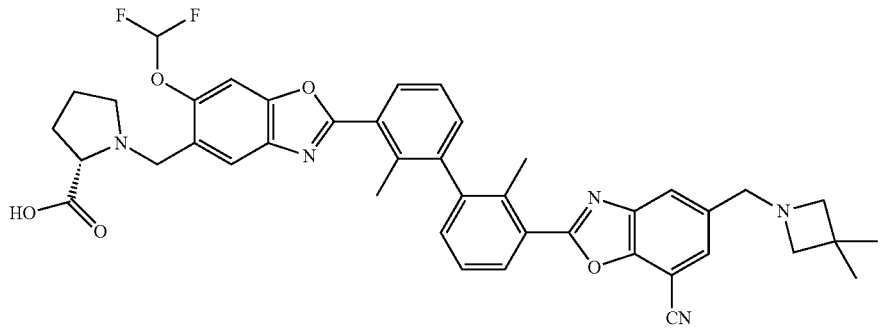

Compound 103

Step 1: Preparation of methyl 3-cyano-4-hydroxy-5-nitrobenzoate

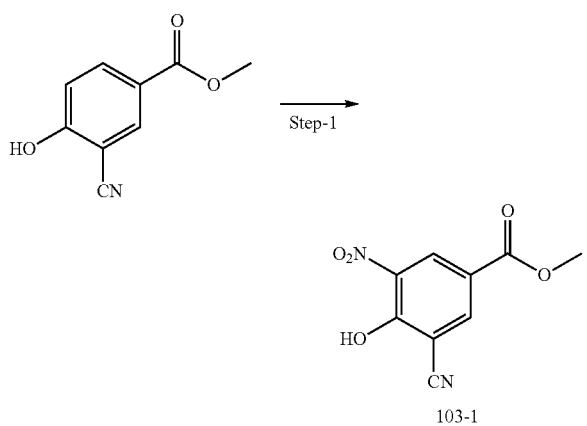

103-1

This compound was prepared using similar procedures as described as step 1 in example A, with Methyl 3-cyano-4-hydroxybenzoate replacing compound a-1. The crude product was purified by silica gel column chromatography (hexane/ethyl acetate) and the title compound was obtained.

Step 2: Preparation of methyl 3-amino-5-cyano-4-hydroxybenzoate

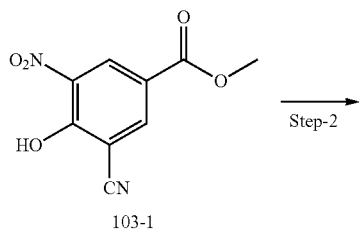

103-1

103-2

This compound was prepared using similar procedures as described as step 2 in example A, with compound 103-1 replacing compound a-2. The filtrate was concentrate under reduced pressure and the title compound was obtained.

Step 3: Preparation of methyl 2-(3-bromo-2-methylphenyl)-7-cyanobenzo[d]oxazole-5-carboxylate

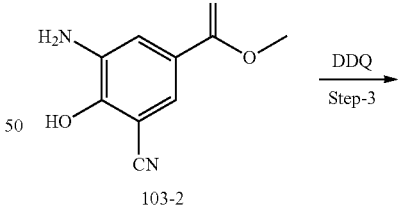

103-2

103-3

This compound was prepared using similar procedures as described as step 3 in example A, with compound 103-2 replacing compound a-3. The crude product was further purified by Silica gel column to get the title compound.

Step 4: Preparation of 2-(3-bromo-2-methylphenyl)-
5-(hydroxymethyl)benzo[d]oxazole-7-carbonitrile

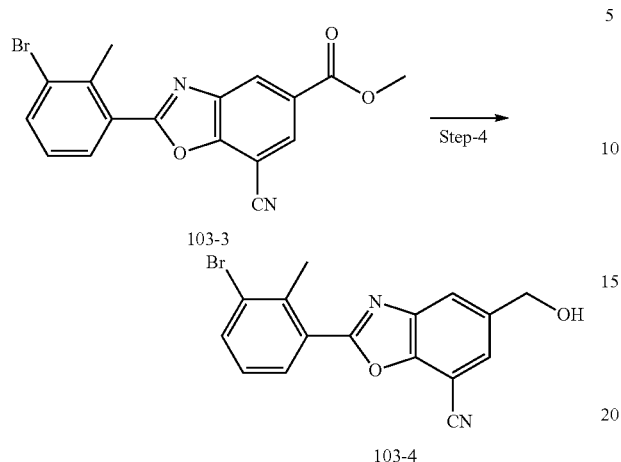

This compound was prepared using similar procedures as described as step 5 in example A, with compound 103-3 replacing compound a-5. The filtrate was concentrate under reduced pressure to get the title compound.

Step 5: Preparation of methyl ((2-(3'-(7-cyano-5-
(hydroxymethyl)benzo[d]oxazol-2-yl)-2,2'-dimethyl-
[1,1'-biphenyl]-3-yl)-6-(difluoromethoxy)benzo[d]
oxazol-5-yl)methyl)-L-prolinate

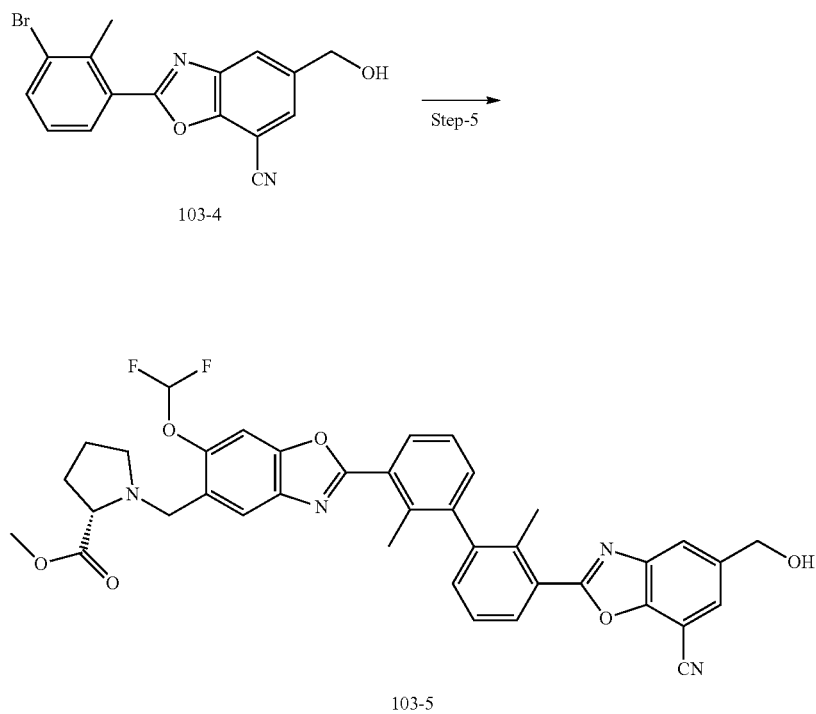

This compound was prepared using similar procedures as described as step 1 in example 1 with compound 103-4 replacing compound a-6. The crude product was further purified by Silica gel column to get the title compound.

Step 6: Preparation of methyl ((2-(3'-(5-(chloromethyl)-7-cyanobenzo[d]oxazol-2-yl)-2,2'-dimethyl-[1,1'-biphenyl]-3-yl)-6-(difluoromethoxy)benzo[d]oxazol-5-yl)methyl)-L-prolinate

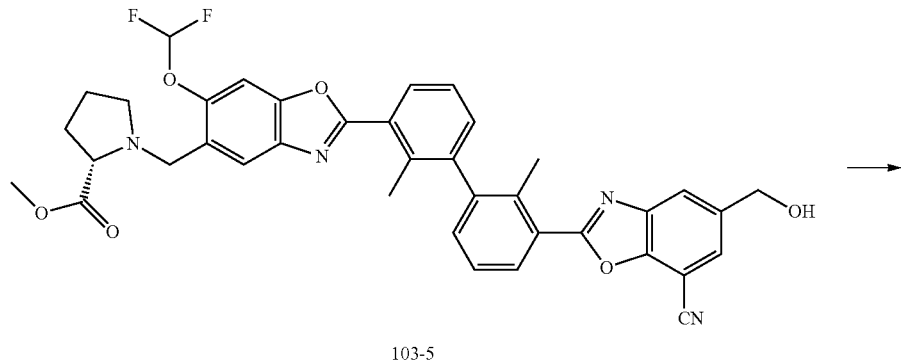

103-5

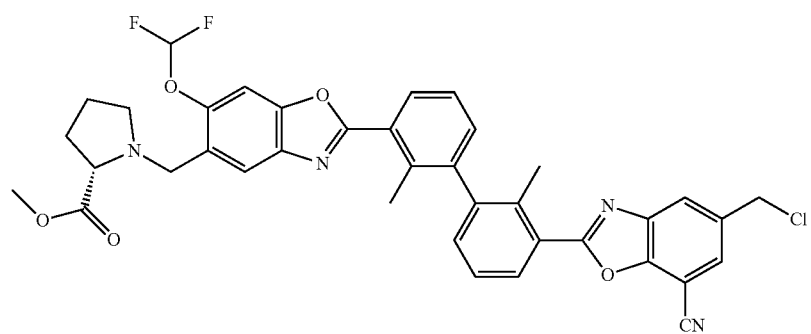

103-6

This compound was prepared using a similar procedure as described as step 2 in example 1, with compound 103-5 replacing compound 1-1. The crude product was used directly in the next step.

Step 7: Preparation of methyl ((2-(3'-(7-cyano-5-((3,3-dimethylazetidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-prolinate

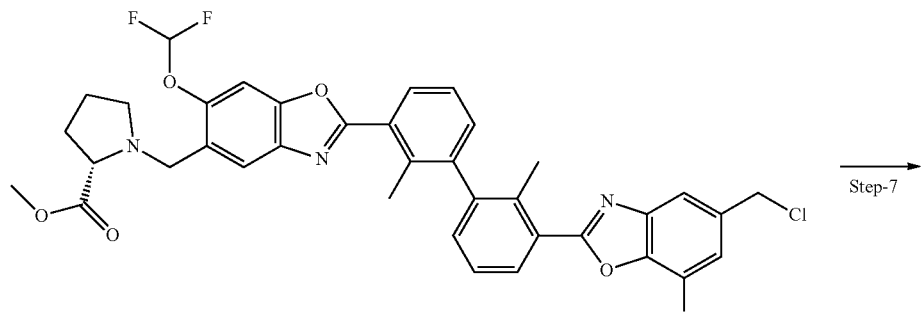

103-6

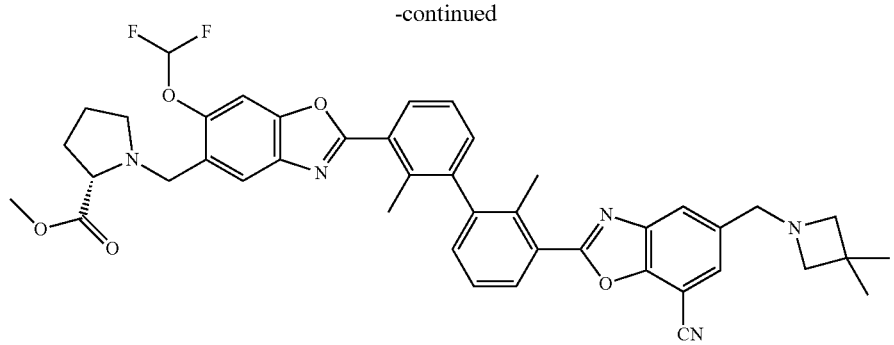

103-7

This compound was prepared using a similar procedure as described as step 3 in example 1, with compound 103-6 replacing compound 1-2, and with 3,3-dimethylazetidine replacing (1S, 2R)-2-aminocyclopentan-1-ol. The crude product was further purified by Silica gel column (PE/EA) to get the title compound.

Step 8: Preparation of ((2-(3'-(7-cyano-5-((3,3-dimethylazetidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline

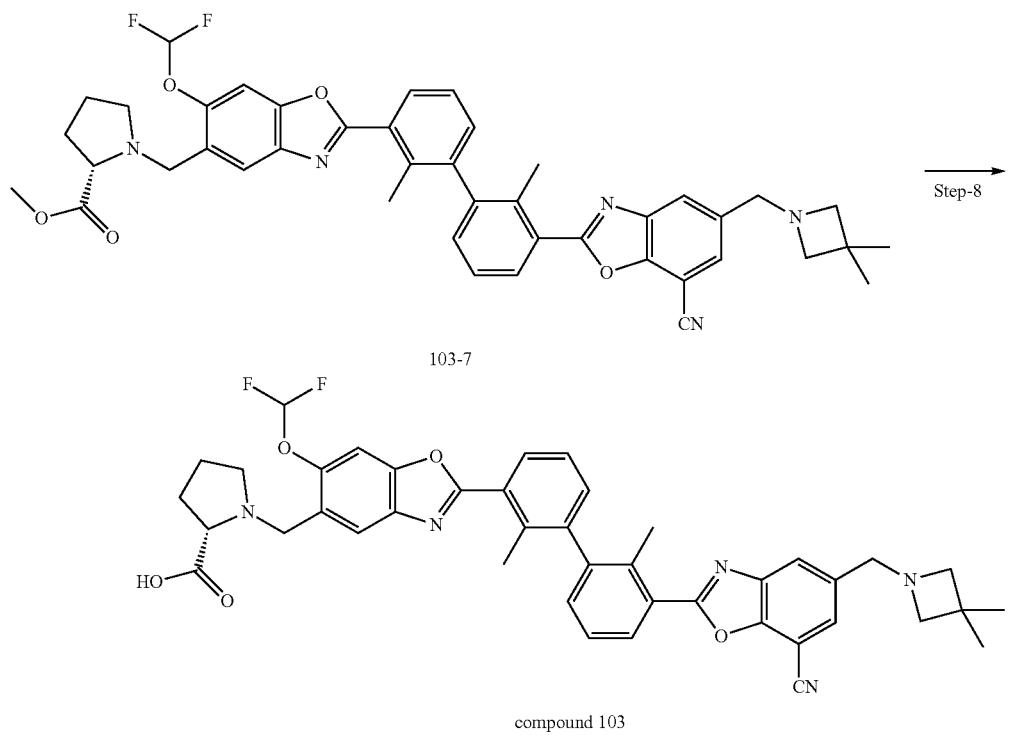

This compound was prepared using similar procedures as described as step 5 in example 1 with compound 103-7 replacing compound 1-4. The crude product was further purified by Silica gel column to get the title compound. LC-MS (m/z): 732.3 (M+H)⁺. 1H NMR (500 MHz, DMSO-d6) 8.20 (dd, J=7.9, 1.4 Hz, 1H), 8.16 (dd, J=7.9, 1.5 Hz, 1H), 8.09 (s, 1H), 7.97 (s, 1H), 7.85 (s, 1H), 7.73 (s, 1H), 7.62-7.51 (m, 2H), 7.50-7.41 (m, 2H), 7.38 (t, J=71.9 Hz, 1H), 3.96 (s, 2H), 3.75 (s, 2H), 3.36 (dd, J=9.1, 5.4 Hz, 1H), 3.07 (td, J=9.4, 8.4, 3.3 Hz, 1H), 2.99 (s, 3H), 2.56 (q, J=8.5 Hz, 1H), 2.44 (d, 6H, J=2.5 Hz), 2.17-2.08 (m, 1H), 1.90-1.68 (m, 4H), 1.20 (s, 6H).

The compounds of table 2 were prepared in a similar manner to Examples 100-103 via different reaction starting materials and suitable reagents.

TABLE 2

| EX No. | Chemical Name | Structure | Physical Data (MS) (M + H)+ |
|---|---|---|---|
| 88 | ((6-(difluoromethoxy)-2-(2,2'-dimethyl-3'-(5-((3-methylpyrrolidin-1-yl)methyl)-7-(trifluoromethyl)benzo[d]oxazol-2-yl)-[1,1'-biphenyl]-3-yl)benzo[d]oxazol-5-yl)methyl)-L-proline | 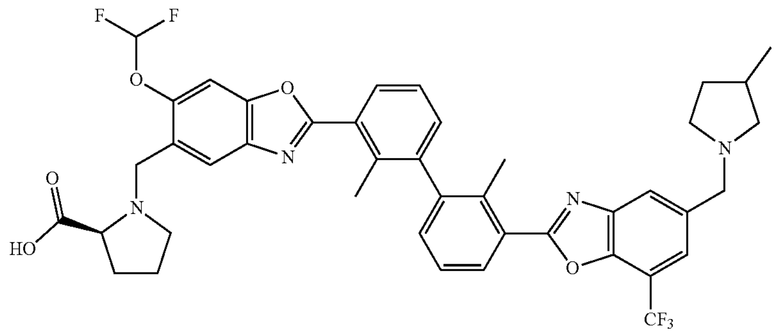 | 775.3 |
| 89 | ((2-(3'-(5-((2-azabicyclo[2.1.1]hexan-2-yl)methyl)-7-(trifluoromethyl)benzo[d]oxazol-2-yl)-2,2'-dimethyl-[1,1'-biphenyl]-3-yl)-6-(difluoromethoxy)benzo[d]oxazol-5-yl)methyl)-L-proline | 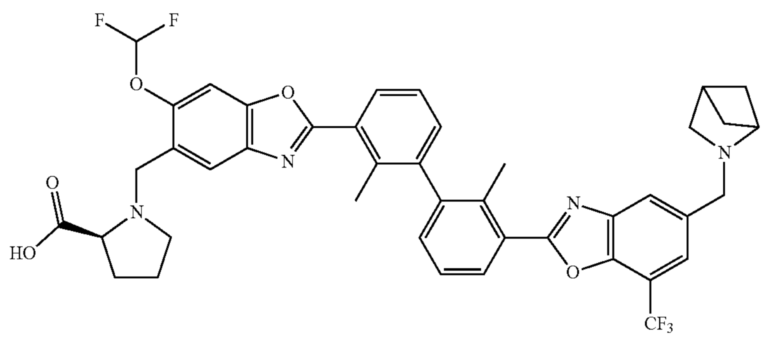 [SMILES: Cc1c(-c2nc3cc(CN4CCC[C@H]4C(=O)O)c(OC(F)F)cc3o2)cccc1-c1cccc(-c2nc3cc(CN4CC5CC4C5)cc(C(F)(F)F)c3o2)c1C] | 773.3 |
| 90 | ((6-(difluoromethoxy)-2-(2,2'-dimethyl-3'-(5-((3-methylpyrrolidin-1-yl)methyl)-7-(trifluoromethyl)benzo[d]oxazol-2-yl)-[1,1'-biphenyl]-3-yl)benzo[d]oxazol-5-yl)methyl)-D-proline | 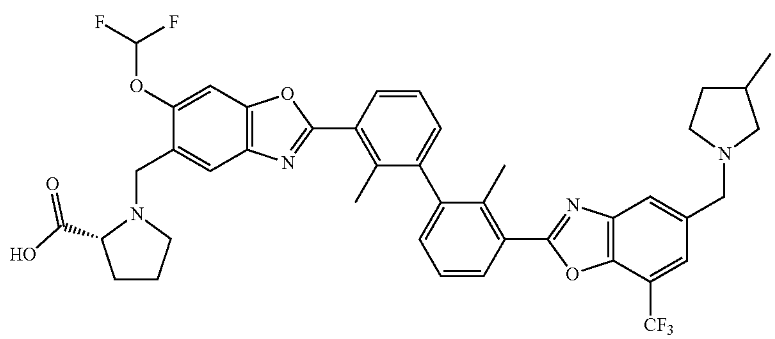 [SMILES: Cc1c(-c2nc3cc(CN4CCC[C@@H]4C(=O)O)c(OC(F)F)cc3o2)cccc1-c1cccc(-c2nc3cc(CN4CCC(C)C4)cc(C(F)(F)F)c3o2)c1C] | 775.3 |
| 91 | (3R)-1-((6-(difluoromethoxy)-2-(2,2'-dimethyl-3'-(5-((3-methylpyrrolidin-1-yl)methyl)-7-(trifluoromethyl)benzo[d]oxazol-2-yl)-[1,1'-biphenyl]-3-yl)benzo[d]oxazol-5-yl)methyl)pyrrolidine-3-carboxylic acid | 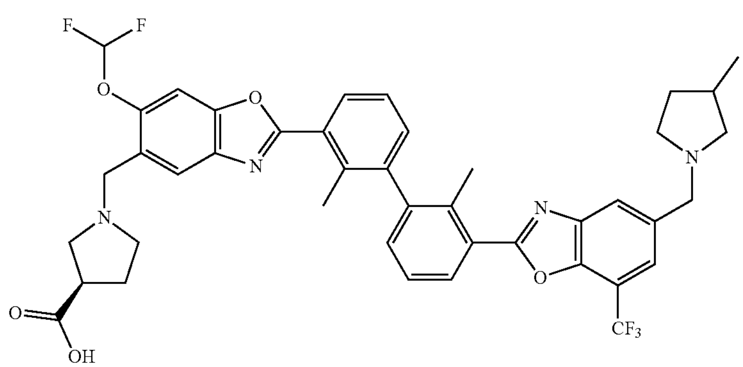 [SMILES: Cc1c(-c2nc3cc(CN4CC[C@@H](C(=O)O)C4)c(OC(F)F)cc3o2)cccc1-c1cccc(-c2nc3cc(CN4CCC(C)C4)cc(C(F)(F)F)c3o2)c1C] | 775.3 |

TABLE 2-continued

| EX No. | Chemical Name | Structure | Physical Data (MS) (M + H)+ |
|---|---|---|---|
| 92 | (3S)-1-(((6-(difluoromethoxy)-2-(2,2'-dimethyl-3'-(5-((3-methylpyrrolidin-1-yl)methyl)-7-(trifluoromethyl)benzo[d]oxazol-2-yl)-[1,1'-biphenyl]-3-yl)benzo[d]oxazol-5-yl)methyl)pyrrolidine-3-carboxylic acid | 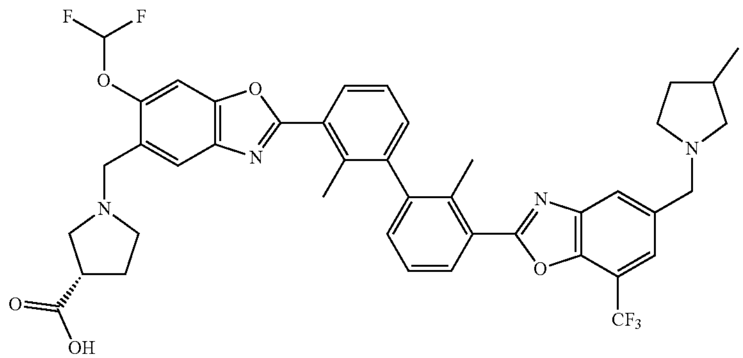 [SMILES: Cc1c(-c2nc3cc(CN4CC[C@H](C(=O)O)C4)c(OC(F)F)cc3o2)cccc1-c1cccc(-c2nc3cc(CN4CCC(C)C4)cc(C(F)(F)F)c3o2)c1C] | 775.3 |
| 93 | ((6-(difluoromethoxy)-2-(3'-(5-((3,3-dimethylazetidin-1-yl)methyl)-7-(trifluoromethyl)benzo[d]oxazol-2-yl)-2,2'-dimethyl-[1,1'-biphenyl]-3-yl)benzo[d]oxazol-5-yl)methyl)-L-proline | 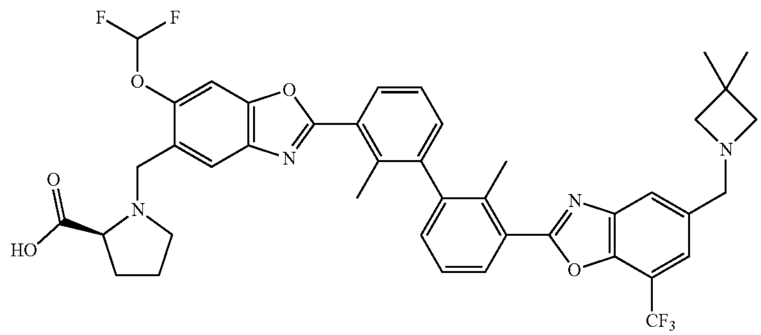 [SMILES: Cc1c(-c2nc3cc(CN4CCC[C@H]4C(=O)O)c(OC(F)F)cc3o2)cccc1-c1cccc(-c2nc3cc(CN4CC(C)(C)C4)cc(C(F)(F)F)c3o2)c1C] | 775.3 |
| 94 | ((2-(3'-(5-(azetidin-1-ylmethyl)-7-methylbenzo[d]oxazol-2-yl)-2,2'-dimethyl-[1,1'-biphenyl]-3-yl)-6-(difluoromethoxy)benzo[d]oxazol-5-yl)methyl)-L-proline | 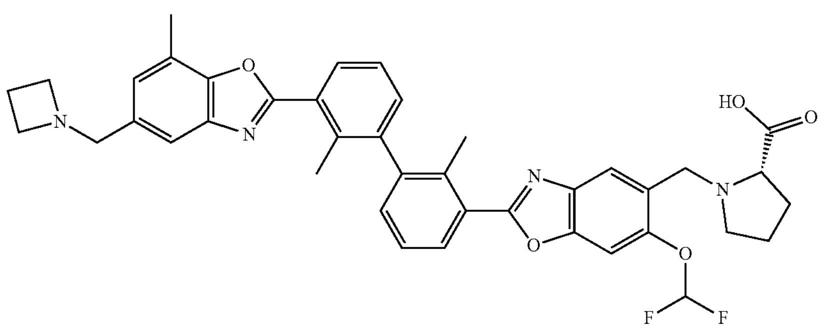 [SMILES: Cc1c(-c2nc3cc(CN4CCC[C@H]4C(=O)O)c(OC(F)F)cc3o2)cccc1-c1cccc(-c2nc3cc(CN4CCC4)cc(C)c3o2)c1C] | 693.3 |
| 95 | ((6-(difluoromethoxy)-2-(3'-(7-fluoro-5-(pyrrolidin-1-ylmethyl)benzo[d]oxazol-2-yl)-2,2'-dimethyl-[1,1'-biphenyl]-3-yl)benzo[d]oxazol-5-yl)methyl)-L-proline | 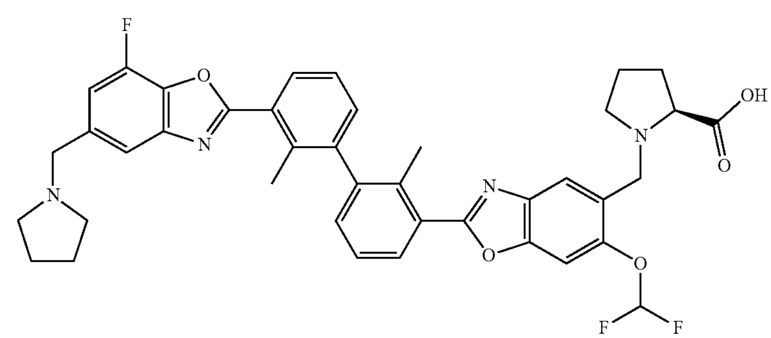 [SMILES: Cc1c(-c2nc3cc(CN4CCC[C@H]4C(=O)O)c(OC(F)F)cc3o2)cccc1-c1cccc(-c2nc3cc(CN4CCCC4)cc(F)c3o2)c1C] | 711.3 |

TABLE 2-continued

| EX No. | Chemical Name | Structure | Physical Data (MS) (M + H)+ |
|---|---|---|---|
| 96 | ((6-(difluoromethoxy)-2-(3'-(5-((ethylamino)methyl)-6-fluorobenzo[d]oxazol-2-yl)-2,2'-dimethyl-[1,1'-biphenyl]-3-yl)benzo[d]oxazol-5-yl)methyl)-L-proline | 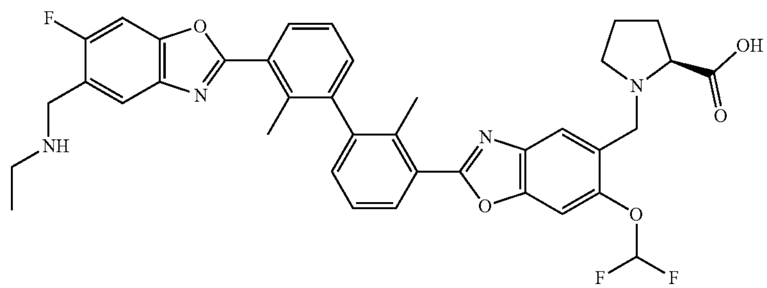 | 685.3 |
| 97 | ((2-(3'-(6-chloro-5-((ethylamino)methyl)benzo[d]oxazol-2-yl)-2,2'-dimethyl-[1,1'-biphenyl]-3-yl)-6-(difluoromethoxy)benzo[d]oxazol-5-yl)methyl)-L-proline | 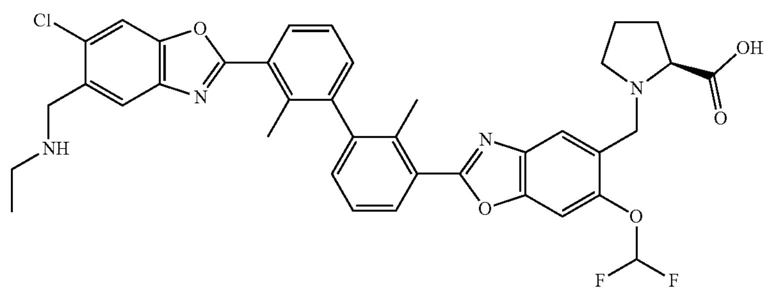 [SMILES: CCNCc1cc2nc(-c3cccc(-c4cccc(-c5nc6cc(CN7CCC[C@H]7C(=O)O)c(OC(F)F)cc6o5)c4C)c3C)oc2cc1Cl] | 701.2 |
| 312 | ((6-(difluoromethoxy)-2-(3'-(5-((3,3-dimethylazetidin-1-yl)methyl)benzo[d]oxazol-2-yl)-2,2'-dimethyl-[1,1'-biphenyl]-3-yl)benzo[d]oxazol-5-yl)methyl)-L-proline | 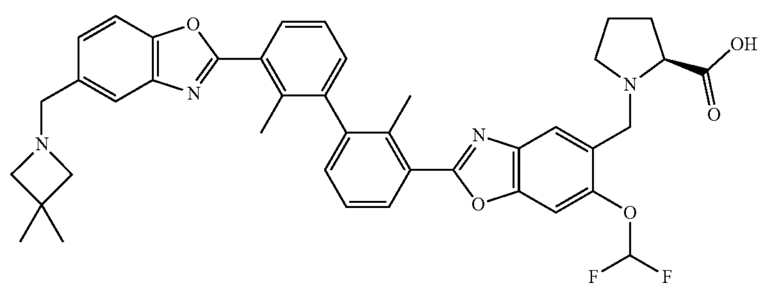 [SMILES: Cc1c(-c2nc3cc(CN4CC(C)(C)C4)ccc3o2)cccc1-c1cccc(-c2nc3cc(CN4CCC[C@H]4C(=O)O)c(OC(F)F)cc3o2)c1C] | 707.3 |
| 313 | ((6-(difluoromethoxy)-2-(2,2'-dimethyl-3'-(5-((2-methylazetidin-1-yl)methyl)benzo[d]oxazol-2-yl)-[1,1'-biphenyl]-3-yl)benzo[d]oxazol-5-yl)methyl)-L-proline | 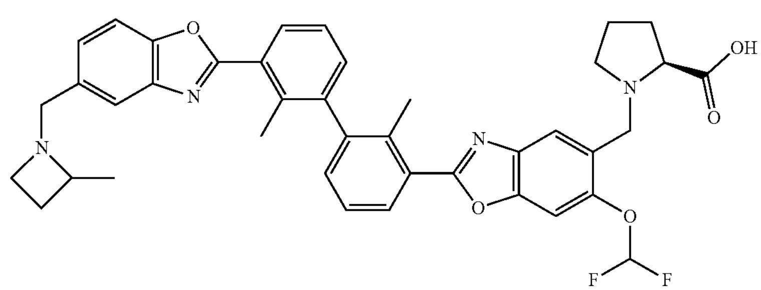 [SMILES: Cc1c(-c2nc3cc(CN4CCC4C)ccc3o2)cccc1-c1cccc(-c2nc3cc(CN4CCC[C@H]4C(=O)O)c(OC(F)F)cc3o2)c1C] | 693.3 |
| 104 | ((6-(difluoromethoxy)-2-(3'-(5-((2-hydroxy-2-methylazetidin-1-yl)methyl)benzo[d]oxazol-2-yl)-2,2'-dimethyl-[1,1'-biphenyl]-3-yl)benzo[d]oxazol-5-yl)methyl)-L-proline | 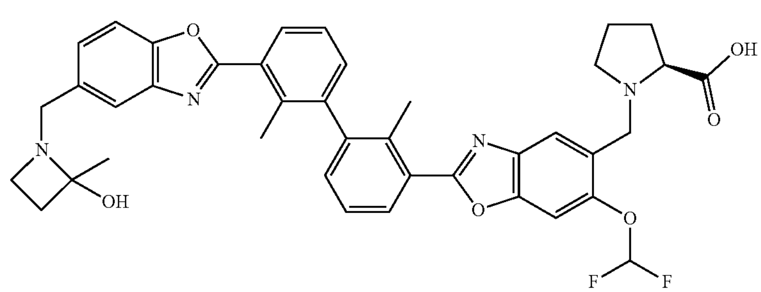 [SMILES: Cc1c(-c2nc3cc(CN4CCC4(C)O)ccc3o2)cccc1-c1cccc(-c2nc3cc(CN4CCC[C@H]4C(=O)O)c(OC(F)F)cc3o2)c1C] | 709.3 |

TABLE 2-continued

| EX No. | Chemical Name | Structure | Physical Data (MS) (M + H)+ |
|---|---|---|---|
| 105 | ((6-(difluoromethoxy)-2-(3'-(5-((2-(hydroxymethyl)azetidin-1-yl)methyl)benzo[d]oxazol-2-yl)-2,2'-dimethyl-[1,1'-biphenyl]-3-yl)benzo[d]oxazol-5-yl)methyl)-L-proline | 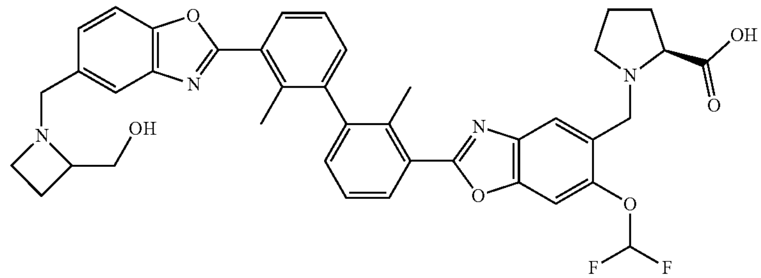 [SMILES: Cc1c(-c2nc3cc(CN4CCC4CO)ccc3o2)cccc1-c1cccc(-c2nc3cc(CN4CCC[C@H]4C(=O)O)c(OC(F)F)cc3o2)c1C] | 709.3 |
| 106 | ((2-(3'-(5-((6-oxa-1-azaspiro[3.3]heptan-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline | 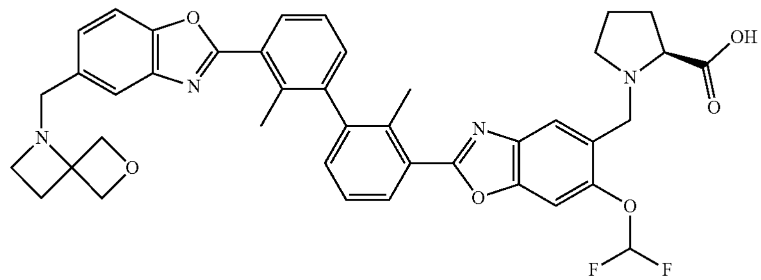 [SMILES: Cc1c(-c2nc3cc(CN4CCC45COC5)ccc3o2)cccc1-c1cccc(-c2nc3cc(CN4CCC[C@H]4C(=O)O)c(OC(F)F)cc3o2)c1C] | 721.3 |
| 107 | ((2-(3'-(5-((1-azaspiro[3.3]heptan-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline | 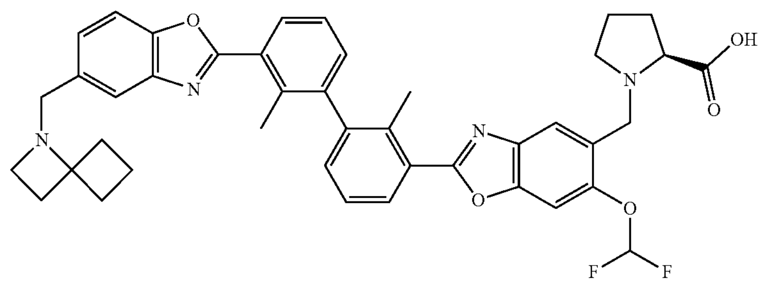 [SMILES: Cc1c(-c2nc3cc(CN4CCC45CCC5)ccc3o2)cccc1-c1cccc(-c2nc3cc(CN4CCC[C@H]4C(=O)O)c(OC(F)F)cc3o2)c1C] | 719.3 |
| 108 | ((6-(difluoromethoxy)-2-(2,2'-dimethyl-3'-(6-(pyrrolidin-1-ylmethyl)benzo[d]oxazol-2-yl)-[1,1'-biphenyl]-3-yl)benzo[d]oxazol-5-yl)methyl)-L-proline | 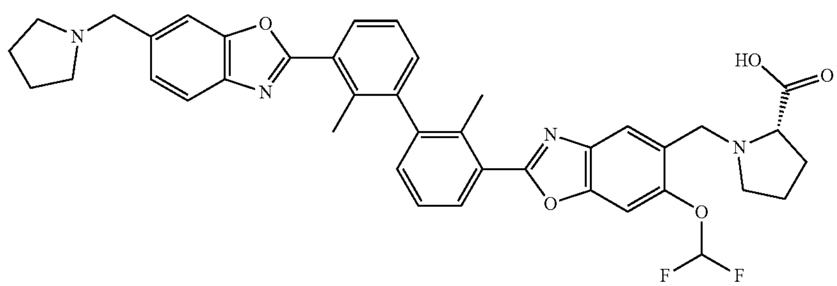 [SMILES: Cc1c(-c2nc3ccc(CN4CCCC4)cc3o2)cccc1-c1cccc(-c2nc3cc(CN4CCC[C@H]4C(=O)O)c(OC(F)F)cc3o2)c1C] | 693.3 |
| 109 | ((6-(difluoromethoxy)-2-(3'-(6-((3,3-dimethylazetidin-1-yl)methyl)benzo[d]oxazol-2-yl)-2,2'-dimethyl-[1,1'-biphenyl]-3-yl)benzo[d]oxazol-5-yl)methyl)-L-proline | 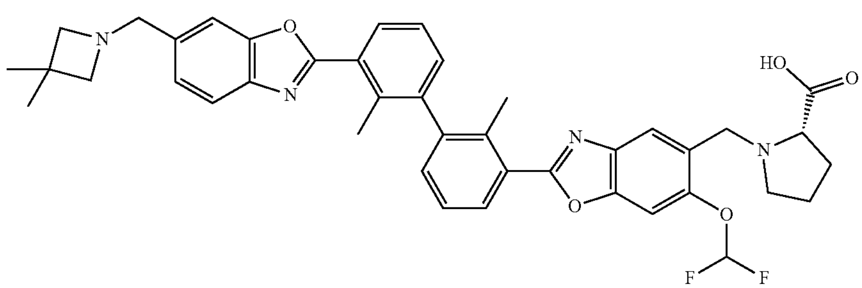 [SMILES: Cc1c(-c2nc3ccc(CN4CC(C)(C)C4)cc3o2)cccc1-c1cccc(-c2nc3cc(CN4CCC[C@H]4C(=O)O)c(OC(F)F)cc3o2)c1C] | 707.3 |

TABLE 2-continued

| EX No. | Chemical Name | Structure | Physical Data (MS) (M + H)+ |
|---|---|---|---|
| 110 | ((2-(2'-chloro-3'-(6-((3,3-dimethylazetidin-1-yl)methyl)benzo[d]oxazol-2-yl)-2-methyl-[1,1'-biphenyl]-3-yl)-6-(difluoromethoxy)benzo[d]oxazol-5-yl)methyl)-L-proline | 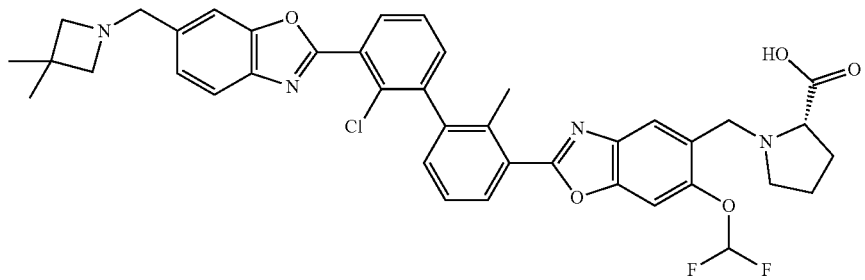 [SMILES: Cc1c(-c2nc3cc(CN4CCC[C@H]4C(=O)O)c(OC(F)F)cc3o2)cccc1-c1cccc(-c2nc3ccc(CN4CC(C)(C)C4)cc3o2)c1Cl] | 727.3 |
| 111 | ((2-(2'-chloro-3'-(6-((3,3-dimethylazetidin-1-yl)methyl)benzo[d]oxazol-2-yl)-2-methyl-[1,1'-biphenyl]-3-yl)-6-(difluoromethoxy)benzo[d]oxazol-5-yl)methyl)-D-proline | 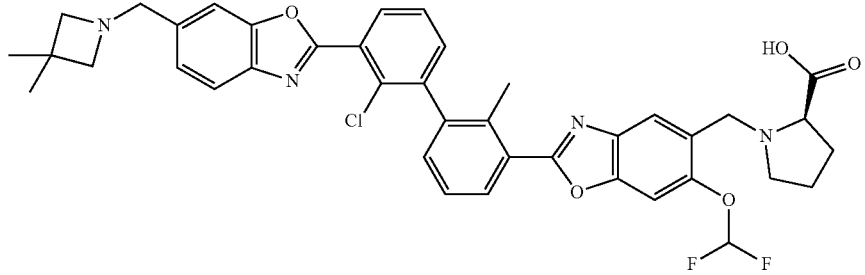 [SMILES: Cc1c(-c2nc3cc(CN4CCC[C@@H]4C(=O)O)c(OC(F)F)cc3o2)cccc1-c1cccc(-c2nc3ccc(CN4CC(C)(C)C4)cc3o2)c1Cl] | 727.3 |
| 112 | ((6-(difluoromethoxy)-2-(2,2'-dimethyl-3'-(6-(pyrrolidin-1-ylmethyl)oxazolo[5,4-b]pyridin-2-yl)-[1,1'-biphenyl]-3-yl)benzo[d]oxazol-5-yl)methyl)-L-proline | 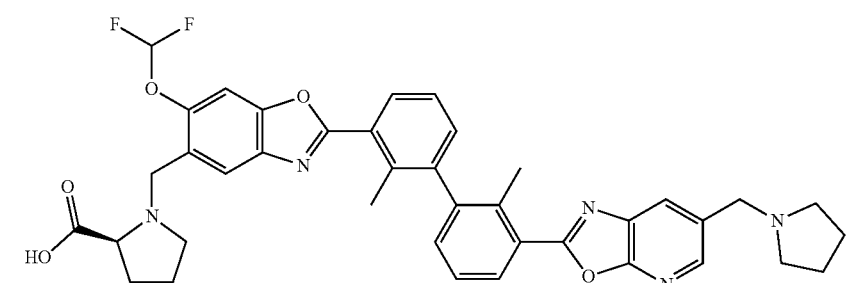 | 694.3 |
| 113 | ((6-(difluoromethoxy)-2-(3'-(6-((3,3-dimethylazetidin-1-yl)methyl)oxazolo[5,4-b]pyridin-2-yl)-2,2'-dimethyl-[1,1'-biphenyl]-3-yl)benzo[d]oxazol-5-yl)methyl)-L-proline | 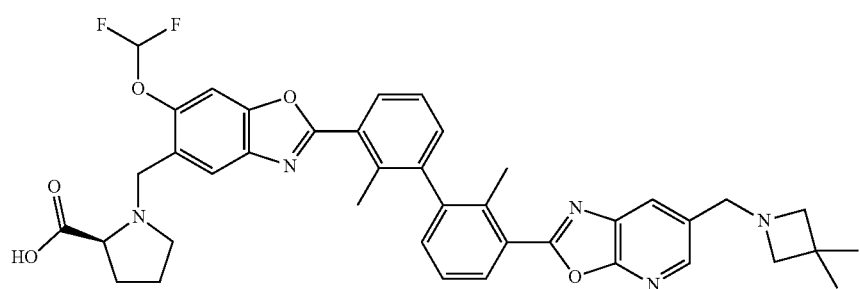 | 708.3 |
| 114 | ((6-(difluoromethoxy)-2-(2,2'-dimethyl-3'-(6-(((R)-3-methylpyrrolidin-1-yl)methyl)oxazolo[5,4-b]pyridin-2-yl)-[1,1'-biphenyl]-3-yl)benzo[d]oxazol-5-yl)methyl)-L-proline | 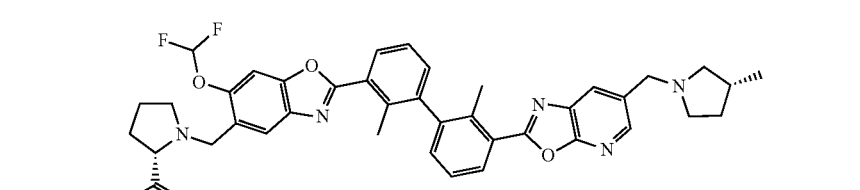 | 708.3 |

TABLE 2-continued

| EX No. | Chemical Name | Structure | Physical Data (MS) (M + H)+ |
|---|---|---|---|
| 115 | ((6-(difluoromethoxy)-2-(2,2'-dimethyl-3'-(6-((((5-oxopyrrolidin-2-yl)methyl)amino)methyl)oxazolo[5,4-b]pyridin-2-yl)-[1,1'-biphenyl]-3-yl)benzo[d]oxazol-5-yl)methyl)-L-proline | 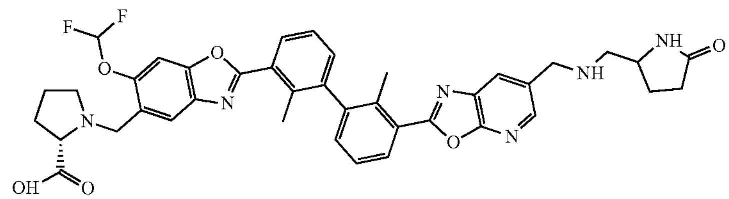 [SMILES: Cc1c(-c2nc3cc(CN4CCC[C@H]4C(=O)O)c(OC(F)F)cc3o2)cccc1-c1cccc(-c2nc3cc(CNCC4CCC(=O)N4)cnc3o2)c1C] | 737.3 |
| 116 | ((6-(difluoromethoxy)-2-(3'-(6-((3-(dimethylamino)azetidin-1-yl)methyl)oxazolo[5,4-b]pyridin-2-yl)-2,2'-dimethyl-[1,1'-biphenyl]-3-yl)benzo[d]oxazol-5-yl)methyl)-L-proline | 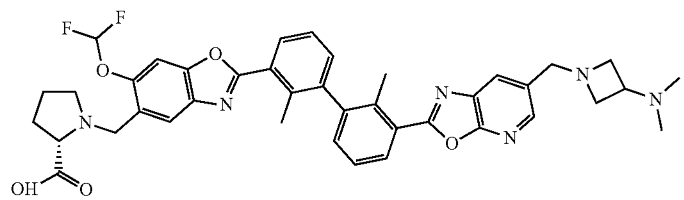 [SMILES: Cc1c(-c2nc3cc(CN4CCC[C@H]4C(=O)O)c(OC(F)F)cc3o2)cccc1-c1cccc(-c2nc3cc(CN4CC(N(C)C)C4)cnc3o2)c1C] | 723.3 |
| 117 | ((2-(3'-(6,7-difluoro-5-(pyrrolidin-1-ylmethyl)benzo[d]oxazol-2-yl)-2'-methoxy-2-methyl-[1,1'-biphenyl]-3-yl)-6-(difluoromethoxy)benzo[d]oxazol-5-yl)methyl)-L-proline | 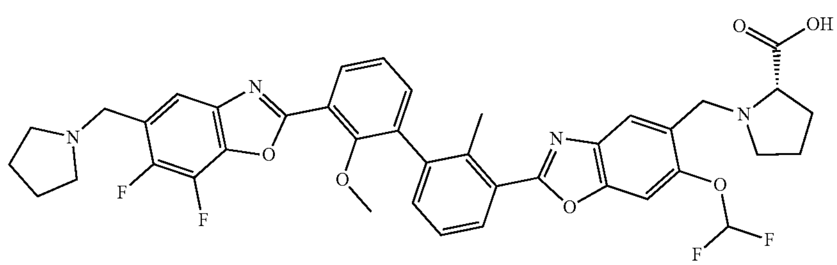 [SMILES: COc1c(-c2nc3cc(CN4CCCC4)c(F)c(F)c3o2)cccc1-c1cccc(-c2nc3cc(CN4CCC[C@H]4C(=O)O)c(OC(F)F)cc3o2)c1C] | 745.3 |
| 118 | ((2-(2'-cyano-3'-(6,7-difluoro-5-(pyrrolidin-1-ylmethyl)benzo[d]oxazol-2-yl)-2-methyl-[1,1'-biphenyl]-3-yl)-6-(difluoromethoxy)benzo[d]oxazol-5-yl)methyl)-L-proline | 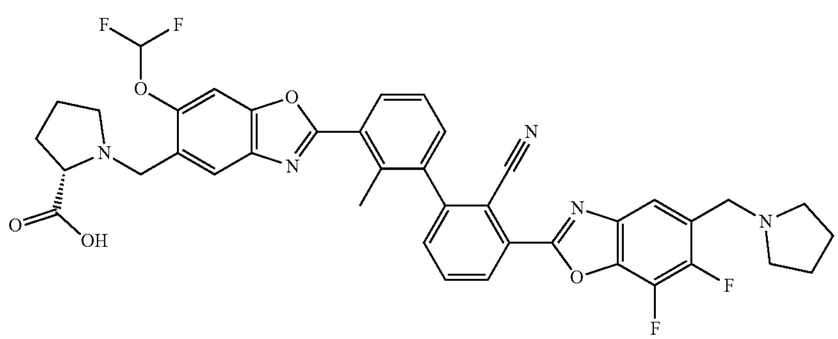 [SMILES: Cc1c(-c2nc3cc(CN4CCC[C@H]4C(=O)O)c(OC(F)F)cc3o2)cccc1-c1cccc(-c2nc3cc(CN4CCCC4)c(F)c(F)c3o2)c1C#N] | 740.2 |
| 119 | ((2-(3'-(6-((6-cyanopyridin-3-yl)methoxy)-5-(((2-hydroxyethyl)amino)methyl)benzo[d]oxazol-2-yl)-2,2'-dimethyl-[1,1'-biphenyl]-3-yl)-6-(difluoromethoxy)benzo[d]oxazol-5-yl)methyl)-L-proline | 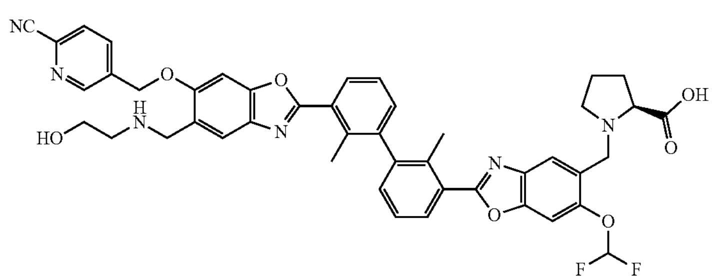 [SMILES: Cc1c(-c2nc3cc(CNCCO)c(OCc4ccc(C#N)nc4)cc3o2)cccc1-c1cccc(-c2nc3cc(CN4CCC[C@H]4C(=O)O)c(OC(F)F)cc3o2)c1C] | 815.3 |

TABLE 2-continued

| EX No. | Chemical Name | Structure | Physical Data (MS) (M + H)+ |
|---|---|---|---|
| 120 | ((2-(3'-(6-((5-cyanopyridin-3-yl)methoxy)-5-(((2-hydroxyethyl)amino)methyl)benzo[d]oxazol-2-yl)-2,2'-dimethyl-[1,1'-biphenyl]-3-yl)-6-(difluoromethoxy)benzo[d]oxazol-5-yl)methyl)-L-proline | 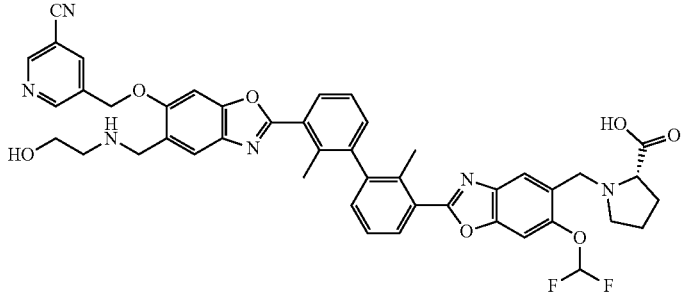 [SMILES: Cc1c(-c2nc3cc(CNCCO)c(OCc4cncc(C#N)c4)cc3o2)cccc1-c1cccc(-c2nc3cc(CN4CCC[C@H]4C(=O)O)c(OC(F)F)cc3o2)c1C] | 815.3 |
| 121 | ((6-(difluoromethoxy)-2-(3'-(5-(((2-hydroxyethyl)amino)methyl)-6-((5-(methylsulfonyl)pyridin-3-yl)methoxy)benzo[d]oxazol-2-yl)-2,2'-dimethyl-[1,1'-biphenyl]-3-yl)benzo[d]oxazol-5-yl)methyl)-L-proline | 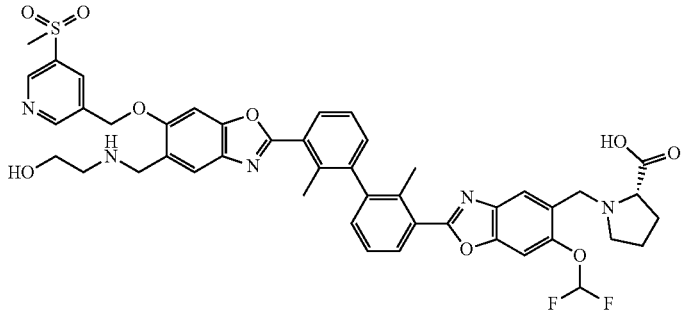 [SMILES: Cc1c(-c2nc3cc(CNCCO)c(OCc4cncc(S(C)(=O)=O)c4)cc3o2)cccc1-c1cccc(-c2nc3cc(CN4CCC[C@H]4C(=O)O)c(OC(F)F)cc3o2)c1C] | 868.3 |
| 122 | ((6-(difluoromethoxy)-2-(3'-(5-((ethylamino)methyl)-6-((5-(methylsulfonyl)pyridin-3-yl)methoxy)benzo[d]oxazol-2-yl)-2,2'-dimethyl-[1,1'-biphenyl]-3-yl)benzo[d]oxazol-5-yl)methyl)-L-proline | 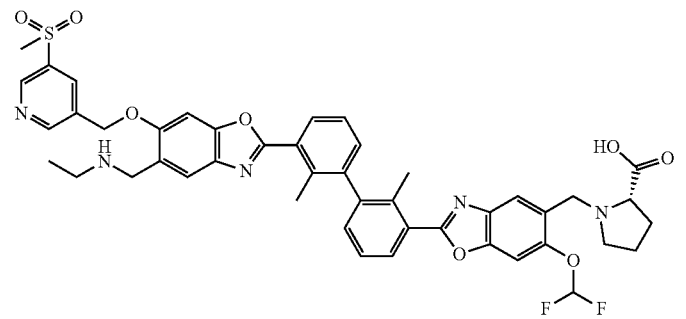 [SMILES: CCNCc1cc2nc(-c3cccc(-c4cccc(-c5nc6cc(CN7CCC[C@H]7C(=O)O)c(OC(F)F)cc6o5)c4C)c3C)oc2cc1OCc1cncc(S(C)(=O)=O)c1] | 852.3 |
| 123 | ((6-(difluoromethoxy)-2-(3'-(5-((dimethylamino)methyl)-6-((5-(methylsulfonyl)pyridin-3-yl)methoxy)benzo[d]oxazol-2-yl)-2,2'-dimethyl-[1,1'-biphenyl]-3-yl)benzo[d]oxazol-5-yl)methyl)-L-proline | 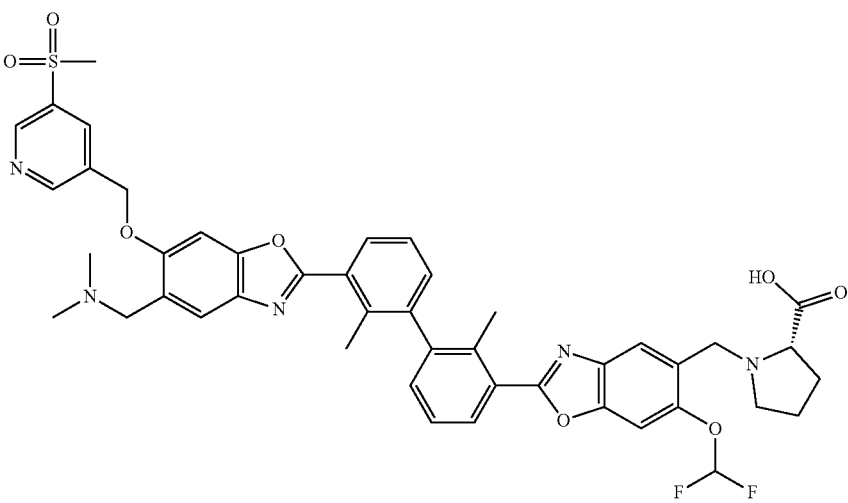 [SMILES: CNCc1cc2nc(-c3cccc(-c4cccc(-c5nc6cc(CN7CCC[C@H]7C(=O)O)c(OC(F)F)cc6o5)c4C)c3C)oc2cc1OCc1cccc(S(C)(=O)=O)c1] | 852.3 |

TABLE 2-continued

| EX No. | Chemical Name | Structure | Physical Data (MS) (M + H)+ |
|---|---|---|---|
| 124 | ((6-(difluoromethoxy)-2-(2,2'-dimethyl-3'-(5-((methylamino)methyl)-6-((3-(methylsulfonyl)benzyl)oxy)benzo[d]oxazol-2-yl)-[1,1'-biphenyl]-3-yl)benzo[d]oxazol-5-yl)methyl)-L-proline | 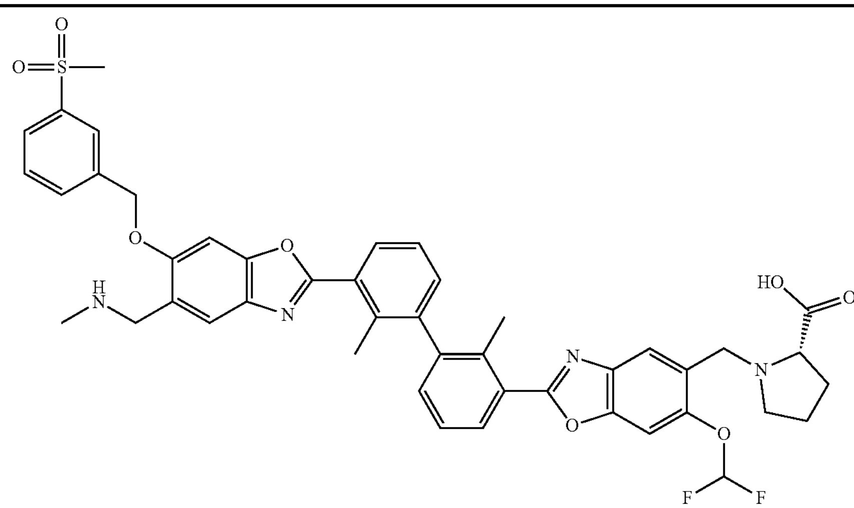 | 837.3 |
| 125 | ((6-(difluoromethoxy)-2-(2,2'-dimethyl-3'-(5-((methylamino)methyl)-6-((4-(methylsulfonyl)benzyl)oxy)benzo[d]oxazol-2-yl)-[1,1'-biphenyl]-3-yl)benzo[d]oxazol-5-yl)methyl)-L-proline | 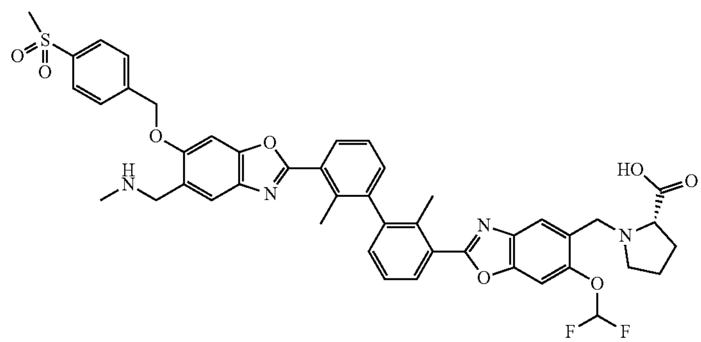 [SMILES: CNCc1cc2nc(-c3cccc(-c4cccc(-c5nc6cc(CN7CCC[C@H]7C(=O)O)c(OC(F)F)cc6o5)c4C)c3C)oc2cc1OCc1ccc(S(C)(=O)=O)cc1] | 837.3 |
| 126 | ((6-(difluoromethoxy)-2-(3'-(5-((dimethylamino)methyl)-6-((4-(methylsulfonyl)benzyl)oxy)benzo[d]oxazol-2-yl)-2,2'-dimethyl-[1,1'-biphenyl]-3-yl)benzo[d]oxazol-5-yl)methyl)-L-proline | 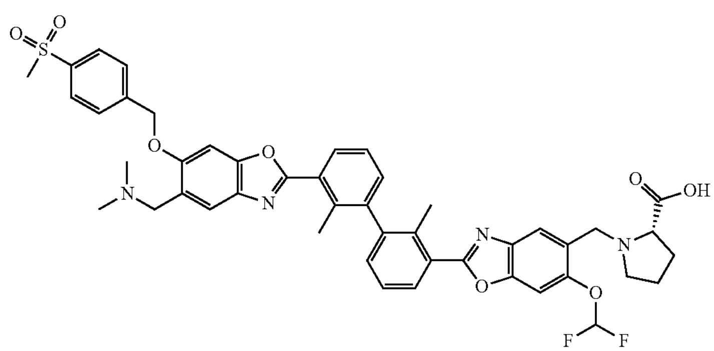 [SMILES: Cc1c(-c2nc3cc(CN(C)C)c(OCc4ccc(S(C)(=O)=O)cc4)cc3o2)cccc1-c1cccc(-c2nc3cc(CN4CCC[C@H]4C(=O)O)c(OC(F)F)cc3o2)c1C] | 851.3 |
| 127 | ((2-(3'-(7-cyano-5-(pyrrolidin-1-ylmethyl)benzo[d]oxazol-2-yl)-2,2'-dimethyl-[1,1'-biphenyl]-3-yl)-6-(difluoromethoxy)benzo[d]oxazol-5-yl)methyl)-L-proline | 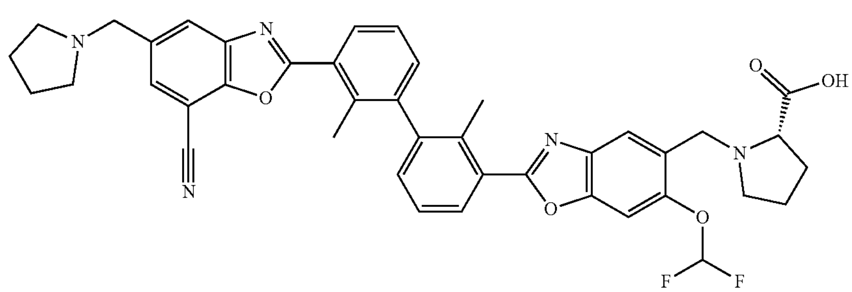 [SMILES: Cc1c(-c2nc3cc(CN4CCC[C@H]4C(=O)O)c(OC(F)F)cc3o2)cccc1-c1cccc(-c2nc3cc(CN4CCCC4)cc(C#N)c3o2)c1C] | 718.3 |

TABLE 2-continued

| EX No. | Chemical Name | Structure | Physical Data (MS) (M + H)+ |
|---|---|---|---|
| 128 | ((2-(2-cyano-3'-(6-(difluoromethoxy)-5-((3,3-dimethylazetidin-1-yl)methyl)benzo[d]oxazol-2-yl)-2'-methyl-[1,1'-biphenyl]-3-yl)-6-(difluoromethoxy)benzo[d]oxazol-5-yl)methyl)-L-proline | 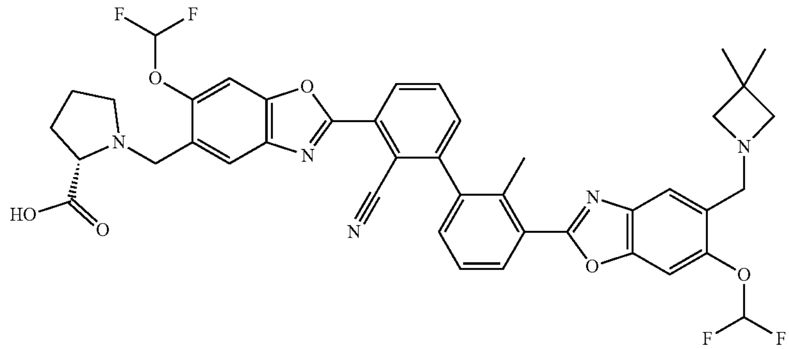 [SMILES: Cc1c(-c2nc3cc(CN4CC(C)(C)C4)c(OC(F)F)cc3o2)cccc1-c1cccc(-c2nc3cc(CN4CCC[C@H]4C(=O)O)c(OC(F)F)cc3o2)c1C#N] | 784.3 |
| 129 | ((2-(3'-(7-cyano-5-((3-(hydroxymethyl)-3-methylazetidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline | 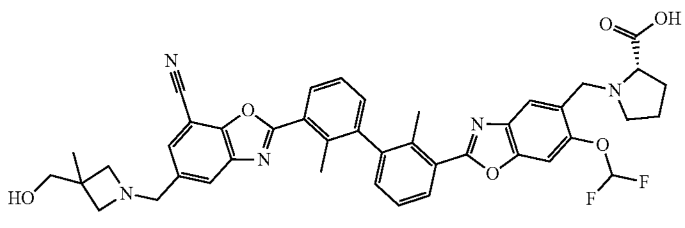 [SMILES: Cc1c(-c2nc3cc(CN4CCC[C@H]4C(=O)O)c(OC(F)F)cc3o2)cccc1-c1cccc(-c2nc3cc(CN4CC(C)(CO)C4)cc(C#N)c3o2)c1C] | 748.3 |
| 130 | ((2-(3'-(7-cyano-5-(((S)-3-methylpyrrolidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline | 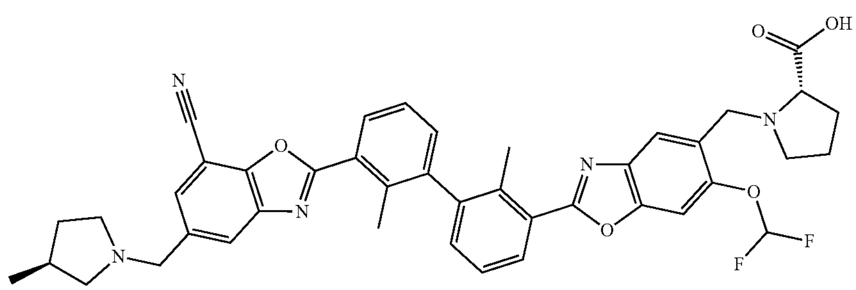 [SMILES: Cc1c(-c2nc3cc(CN4CCC[C@H]4C(=O)O)c(OC(F)F)cc3o2)cccc1-c1cccc(-c2nc3cc(CN4CC[C@H](C)C4)cc(C#N)c3o2)c1C] | 732.3 |
| 131 | ((2-(3'-(7-cyano-5-(((R)-3-methylpyrrolidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline | 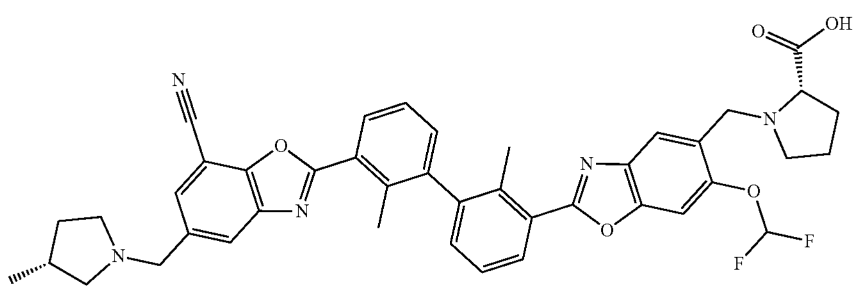 [SMILES: Cc1c(-c2nc3cc(CN4CCC[C@H]4C(=O)O)c(OC(F)F)cc3o2)cccc1-c1cccc(-c2nc3cc(CN4CC[C@@H](C)C4)cc(C#N)c3o2)c1C] | 732.3 |
| 132 | ((2-(3'-(7-cyano-5-(((R)-3-methylpyrrolidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-D-proline | 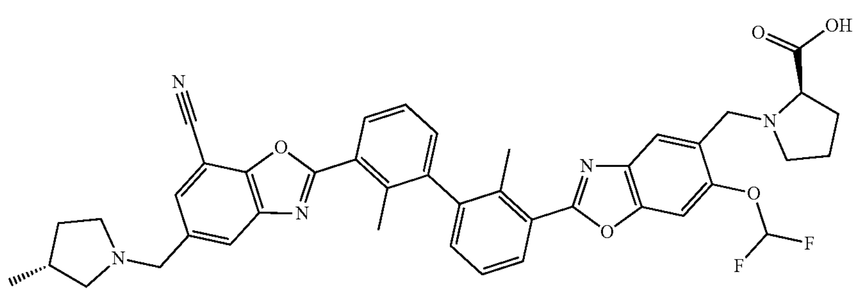 [SMILES: Cc1c(-c2nc3cc(CN4CCC[C@@H]4C(=O)O)c(OC(F)F)cc3o2)cccc1-c1cccc(-c2nc3cc(CN4CC[C@@H](C)C4)cc(C#N)c3o2)c1C] | 732.3 |

TABLE 2-continued

| EX No. | Chemical Name | Structure | Physical Data (MS) (M + H)+ |
|---|---|---|---|
| 133 | ((2-(3'-(7-cyano-5-(((3-methyloxetan-3-yl)amino)methyl)benzo[d]oxazol-2-yl)-2,2'-dimethyl-[1,1'-biphenyl]-3-yl)-6-(difluoromethoxy)benzo[d]oxazol-5-yl)methyl)-L-proline | 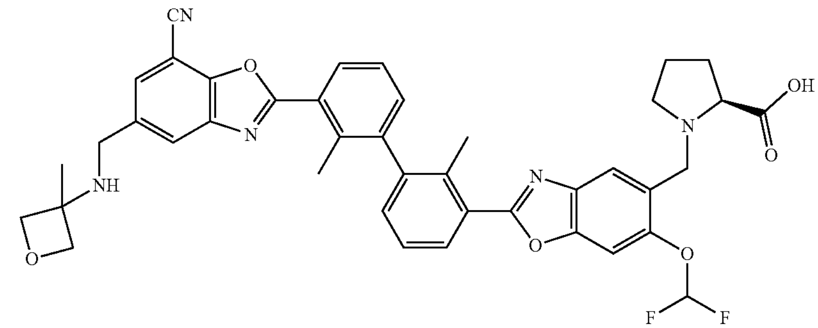 [SMILES: Cc1c(-c2nc3cc(CN4CCC[C@H]4C(=O)O)c(OC(F)F)cc3o2)cccc1-c1cccc(-c2nc3cc(CNC4(C)COC4)cc(C#N)c3o2)c1C] | 734.3 |
| 134 | ((2-(3'-(7-cyano-5-((3-(dimethylamino)azetidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline | 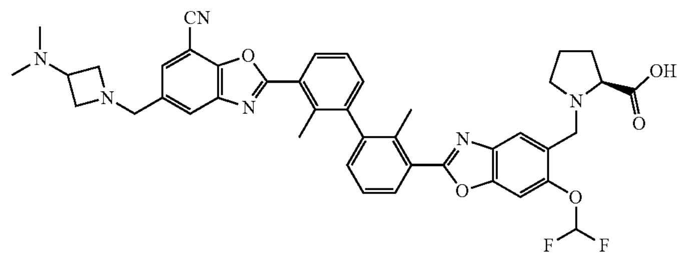 [SMILES: Cc1c(-c2nc3cc(CN4CCC[C@H]4C(=O)O)c(OC(F)F)cc3o2)cccc1-c1cccc(-c2nc3cc(CN4CC(N(C)C)C4)cc(C#N)c3o2)c1C] | 747.3 |
| 135 | ((2-(3'-(7-cyano-5-((2-(2-hydroxyethyl)piperidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline | 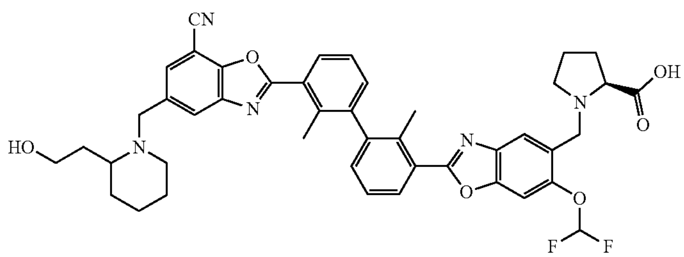 [SMILES: Cc1c(-c2nc3cc(CN4CCC[C@H]4C(=O)O)c(OC(F)F)cc3o2)cccc1-c1cccc(-c2nc3cc(CN4CCCCC4CCO)cc(C#N)c3o2)c1C] | 776.3 |
| 136 | ((2-(3'-(7-cyano-5-(((cyanomethyl)(methyl)amino)methyl)benzo[d]oxazol-2-yl)-2,2'-dimethyl-[1,1'-biphenyl]-3-yl)-6-(difluoromethoxy)benzo[d]oxazol-5-yl)methyl)-L-proline | 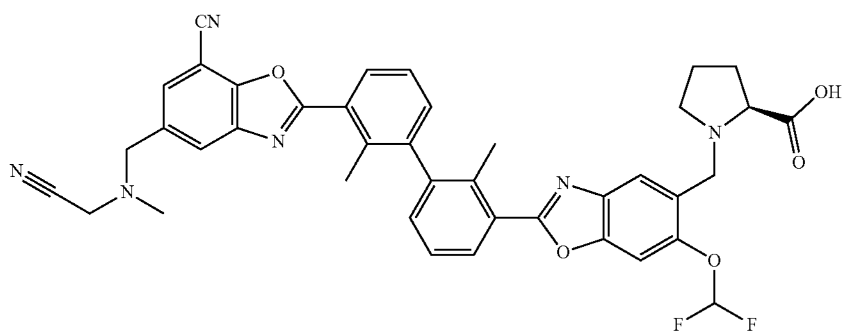 [SMILES: Cc1c(-c2nc3cc(CN4CCC[C@H]4C(=O)O)c(OC(F)F)cc3o2)cccc1-c1cccc(-c2nc3cc(CN(C)CC#N)cc(C#N)c3o2)c1C] | 717.3 |
| 137 | ((2-(3'-(7-cyano-5-((3-(hydroxymethyl)azetidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline | 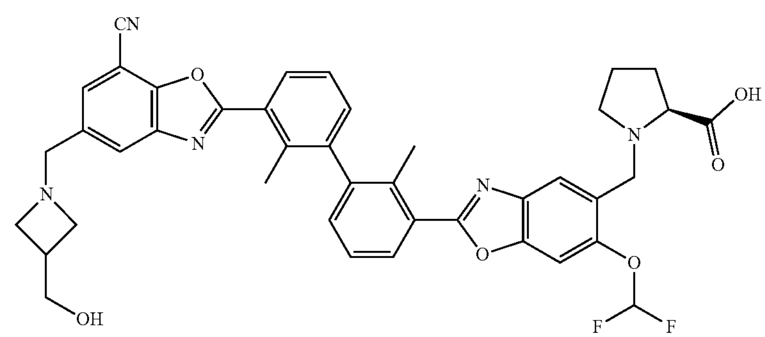 [SMILES: Cc1c(-c2nc3cc(CN4CCC[C@H]4C(=O)O)c(OC(F)F)cc3o2)cccc1-c1cccc(-c2nc3cc(CN4CC(CO)C4)cc(C#N)c3o2)c1C] | 734.3 |

TABLE 2-continued

| EX No. | Chemical Name | Structure | Physical Data (MS) (M + H)+ |
|---|---|---|---|
| 138 | ((2-(3'-(7-cyano-5-(((2-hydroxy-2-methylpropyl)amino)methyl)benzo[d]oxazol-2-yl)-2,2'-dimethyl-[1,1'-biphenyl]-3-yl)-6-(difluoromethoxy)benzo[d]oxazol-5-yl)methyl)-L-proline | 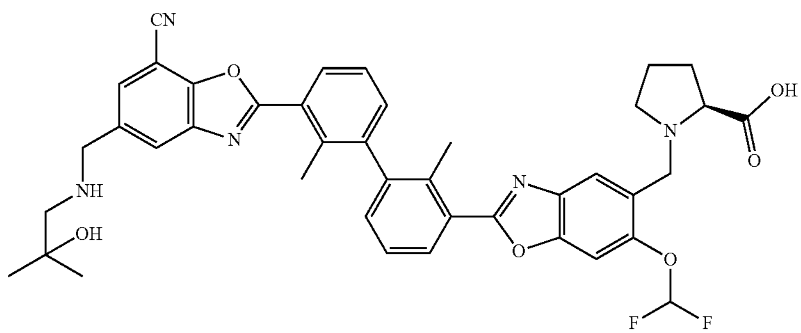 [SMILES: Cc1c(-c2nc3cc(CN4CCC[C@H]4C(=O)O)c(OC(F)F)cc3o2)cccc1-c1cccc(-c2nc3cc(CNCC(C)(C)O)cc(C#N)c3o2)c1C] | 736.3 |
| 139 | ((2-(3'-(7-cyano-5-(((((5-oxopyrrolidin-2-yl)methyl)amino)methyl)benzo[d]oxazol-2-yl)-2,2'-dimethyl-[1,1'-biphenyl]-3-yl)-6-(difluoromethoxy)benzo[d]oxazol-5-yl)methyl)-L-proline | 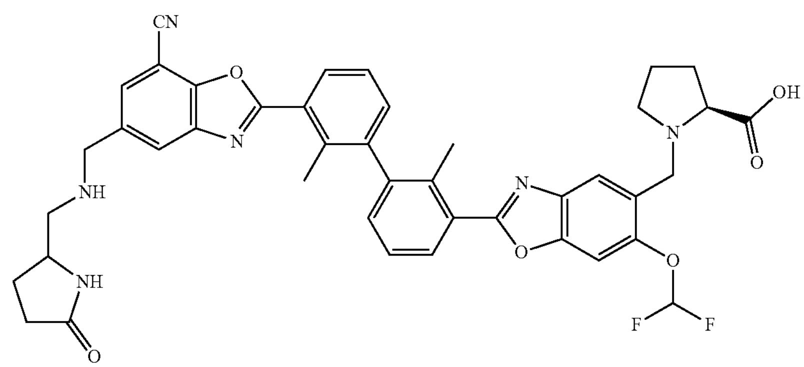 [SMILES: Cc1c(-c2nc3cc(CN4CCC[C@H]4C(=O)O)c(OC(F)F)cc3o2)cccc1-c1cccc(-c2nc3cc(CNCC4CCC(=O)N4)cc(C#N)c3o2)c1C] | 761.3 |
| 140 | ((2-(3'-(7-cyano-5-((3,3-dimethylazetidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-D-proline | 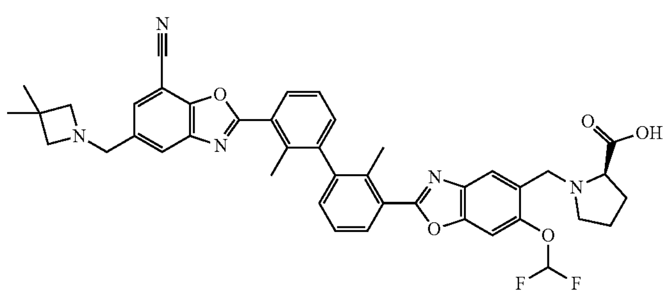 [SMILES: Cc1c(-c2nc3cc(CN4CCC[C@@H]4C(=O)O)c(OC(F)F)cc3o2)cccc1-c1cccc(-c2nc3cc(CN4CC(C)(C)C4)cc(C#N)c3o2)c1C] | 732.3 |
| 141 | ((2-(3'-(7-cyano-5-((ethyl(2-hydroxyethyl)amino)methyl)benzo[d]oxazol-2-yl)-2,2'-dimethyl-[1,1'-biphenyl]-3-yl)-6-(difluoromethoxy)benzo[d]oxazol-5-yl)methyl)-L-proline | 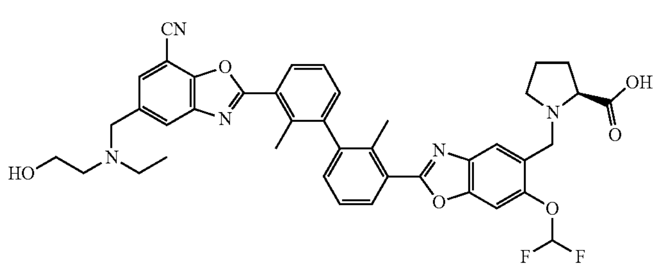 [SMILES: CCN(CCO)Cc1cc(C#N)c2oc(-c3cccc(-c4cccc(-c5nc6cc(CN7CCC[C@H]7C(=O)O)c(OC(F)F)cc6o5)c4C)c3C)nc2c1] | 736.3 |

TABLE 2-continued

| EX No. | Chemical Name | Structure | Physical Data (MS) (M + H)+ |
|---|---|---|---|
| 142 | ((2-(3'-(7-cyano-5-((3-cyanopyrrolidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline | 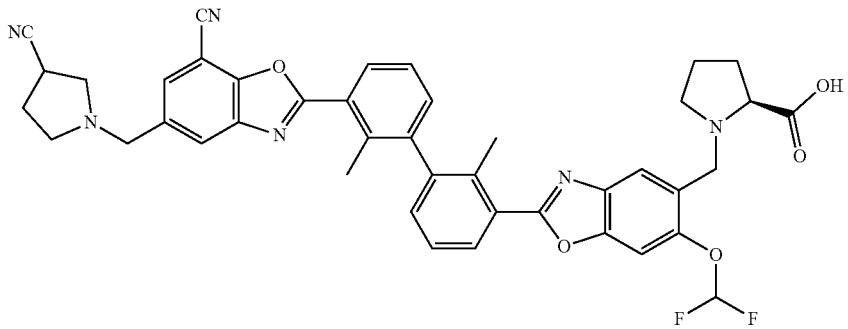 [SMILES: Cc1c(-c2nc3cc(CN4CCC[C@H]4C(=O)O)c(OC(F)F)cc3o2)cccc1-c1cccc(-c2nc3cc(CN4CCC(C#N)C4)cc(C#N)c3o2)c1C] | 743.3 |
| 143 | ((2-(3'-(7-cyano-5-((3-cyanopyrrolidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-D-proline | 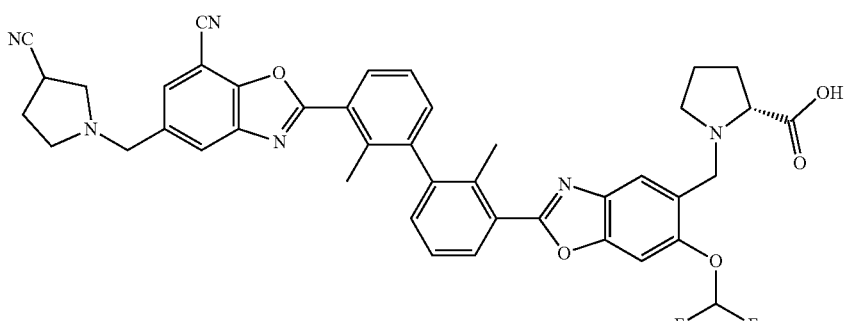 | 743.3 |
| 144 | ((2-(3'-(7-cyano-5-((3-ethynyl-3-hydroxyazetidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline | 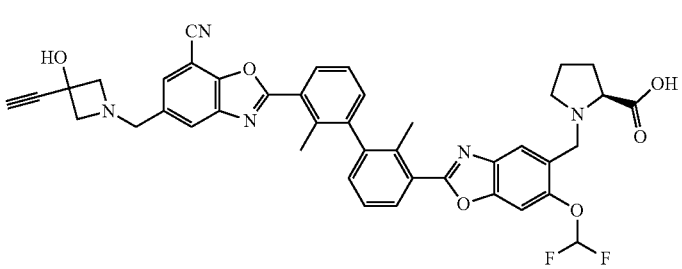 [SMILES: C#CC1(O)CN(Cc2cc(C#N)c3oc(-c4cccc(-c5cccc(-c6nc7cc(CN8CCC[C@H]8C(=O)O)c(OC(F)F)cc7o6)c5C)c4C)nc3c2)C1] | 744.3 |
| 145 | ((2-(3'-(7-cyano-5-(pyrrolidin-1-ylmethyl)benzo[d]oxazol-2-yl)-2,2'-dimethyl-[1,1'-biphenyl]-3-yl)-6-(difluoromethoxy)benzo[d]oxazol-5-yl)methyl)-D-proline | 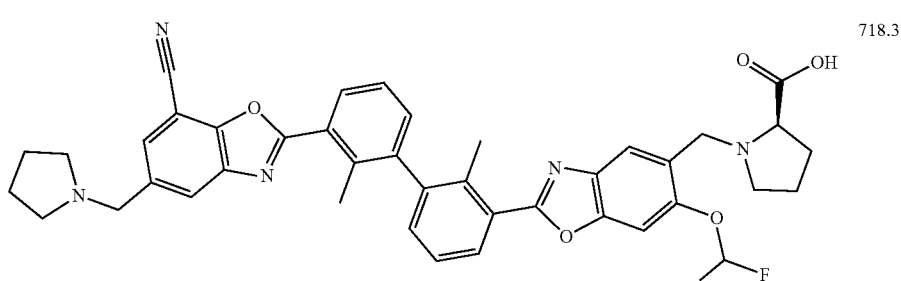 | 718.3 |
| 146 | ((2-(3'-(7-cyano-5-((7-oxo-2,6-diazaspiro[3.4]octan-2-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline | 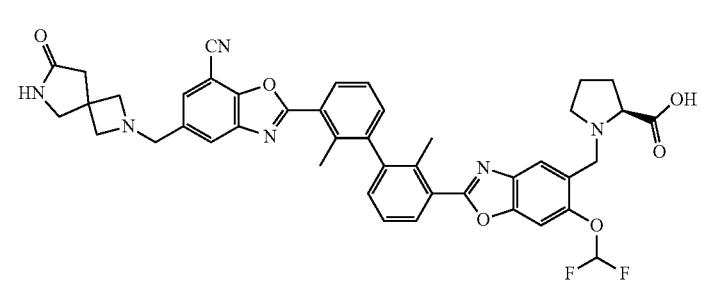 [SMILES: Cc1c(-c2nc3cc(CN4CCC[C@H]4C(=O)O)c(OC(F)F)cc3o2)cccc1-c1cccc(-c2nc3cc(CN4CC5(CNC(=O)C5)C4)cc(C#N)c3o2)c1C] | 773.3 |

TABLE 2-continued

| EX No. | Chemical Name | Structure | Physical Data (MS) (M + H)+ |
|---|---|---|---|
| 147 | ((2-(3'-(5-((bis(1-hydroxypropan-2-yl)amino)methyl)-7-cyanobenzo[d]oxazol-2-yl)-2,2'-dimethyl-[1,1'-biphenyl]-3-yl)-6-(difluoromethoxy)benzo[d]oxazol-5-yl)methyl)-L-proline | 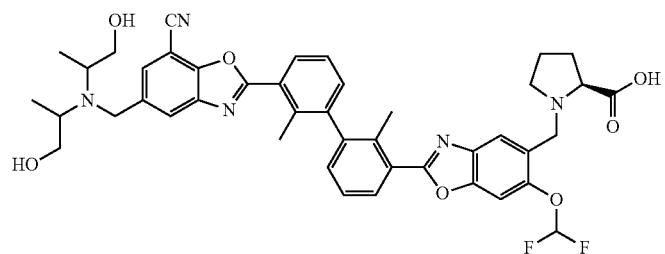 [SMILES: Cc1c(-c2nc3cc(CN4CCC[C@H]4C(=O)O)c(OC(F)F)cc3o2)cccc1-c1cccc(-c2nc3cc(CN(C(C)CO)C(C)CO)cc(C#N)c3o2)c1C] | 780.3 |
| 148 | ((2-(3'-(7-cyano-5-((3-morpholinoazetidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline | 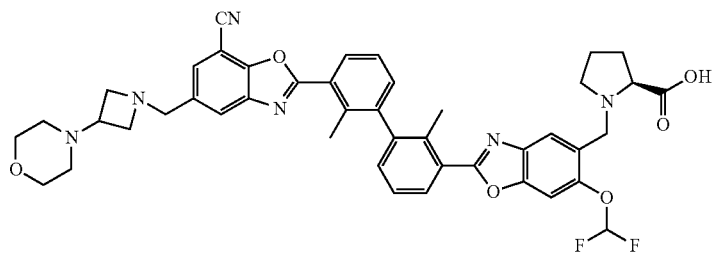 [SMILES: Cc1c(-c2nc3cc(CN4CCC[C@H]4C(=O)O)c(OC(F)F)cc3o2)cccc1-c1cccc(-c2nc3cc(CN4CC(N5CCOCC5)C4)cc(C#N)c3o2)c1C] | 789.3 |
| 149 | ((2-(3'-(7-cyano-5-((3-(methyl(oxetan-3-yl)amino)azetidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline | 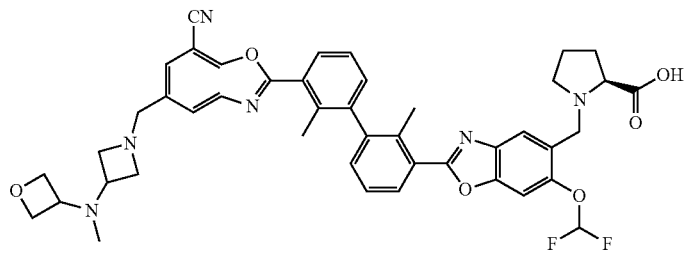 [SMILES: Cc1c(/C2=N/C=C/C(CN3CC(N(C)C4COC4)C3)=C\C(C#N)=C\O2)cccc1-c1cccc(-c2nc3cc(CN4CCC[C@H]4C(=O)O)c(OC(F)F)cc3o2)c1C] | 789.3 |
| 150 | ((2-(3'-(7-cyano-5-((3-hydroxy-3-methyl-[1,3'-biazetidin]-1'-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline | 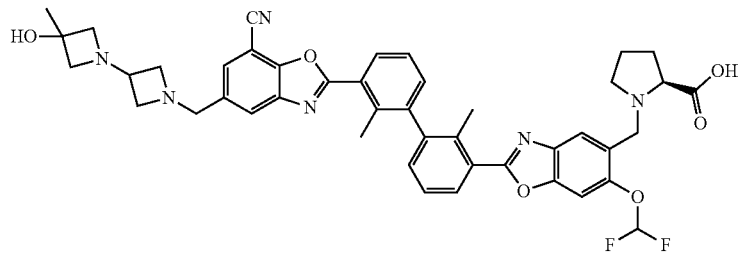 [SMILES: Cc1c(-c2nc3cc(CN4CCC[C@H]4C(=O)O)c(OC(F)F)cc3o2)cccc1-c1cccc(-c2nc3cc(CN4CC(N5CC(C)(O)C5)C4)cc(C#N)c3o2)c1C] | 789.3 |
| 151 | ((2-(3'-(7-cyano-5-((6-oxo-2,5-diazaspiro[3.4]octan-2-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline | 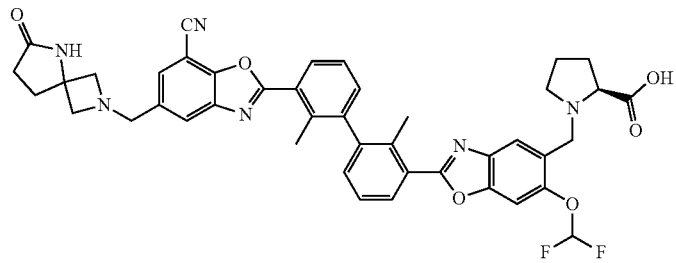 [SMILES: Cc1c(-c2nc3cc(CN4CCC[C@H]4C(=O)O)c(OC(F)F)cc3o2)cccc1-c1cccc(-c2nc3cc(CN4CC5(CCC(=O)N5)C4)cc(C#N)c3o2)c1C] | 773.3 |

TABLE 2-continued

| EX No. | Chemical Name | Structure | Physical Data (MS) (M + H)+ |
|---|---|---|---|
| 152 | ((2-(3'-(7-cyano-5-(((3-((dimethylamino)methyl)pyrrolidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline | 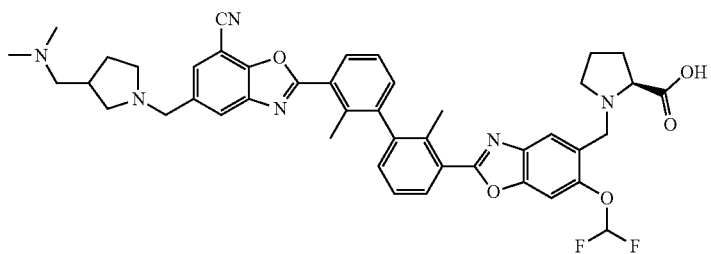 [SMILES: Cc1c(-c2nc3cc(CN4CCC[C@H]4C(=O)O)c(OC(F)F)cc3o2)cccc1-c1cccc(-c2nc3cc(CN4CCC(CN(C)C)C4)cc(C#N)c3o2)c1C] | 775.3 |
| 153 | ((2-(3'-(7-cyano-5-((1,1-difluoro-5-azaspiro[2.4]heptan-5-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline | 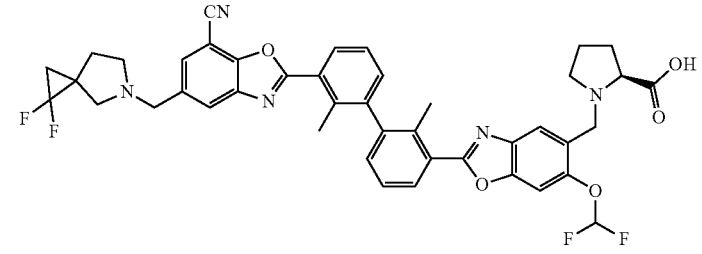 [SMILES: Cc1c(-c2nc3cc(CN4CCC[C@H]4C(=O)O)c(OC(F)F)cc3o2)cccc1-c1cccc(-c2nc3cc(CN4CCC5(C4)CC5(F)F)cc(C#N)c3o2)c1C] | 780.3 |
| 154 | ((2-(3'-(7-cyano-5-(((R)-3-(hydroxymethyl)pyrrolidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline | 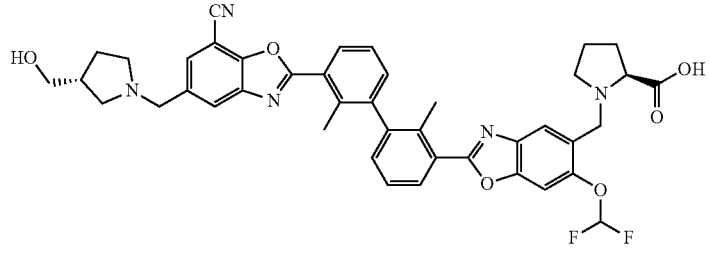 [SMILES: Cc1c(-c2nc3cc(CN4CCC[C@H]4C(=O)O)c(OC(F)F)cc3o2)cccc1-c1cccc(-c2nc3cc(CN4CC[C@@H](CO)C4)cc(C#N)c3o2)c1C] | 748.3 |
| 155 | ((2-(3'-(7-cyano-5-(((3-hydroxycyclobutyl)amino)methyl)benzo[d]oxazol-2-yl)-2,2'-dimethyl-[1,1'-biphenyl]-3-yl)-6-(difluoromethoxy)benzo[d]oxazol-5-yl)methyl)-L-proline | 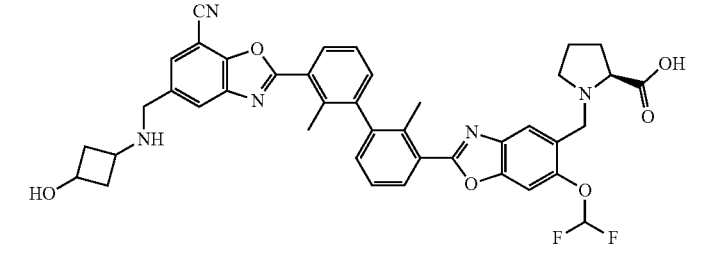 [SMILES: Cc1c(-c2nc3cc(CN4CCC[C@H]4C(=O)O)c(OC(F)F)cc3o2)cccc1-c1cccc(-c2nc3cc(CNC4CC(O)C4)cc(C#N)c3o2)c1C] | 734.3 |
| 156 | ((2-(3'-(5-((3-amino-4-methylpyrrolidin-1-yl)methyl)-7-cyanobenzo[d]oxazol-2-yl)-2,2'-dimethyl-[1,1'-biphenyl]-3-yl)-6-(difluoromethoxy)benzo[d]oxazol-5-yl)methyl)-L-proline | 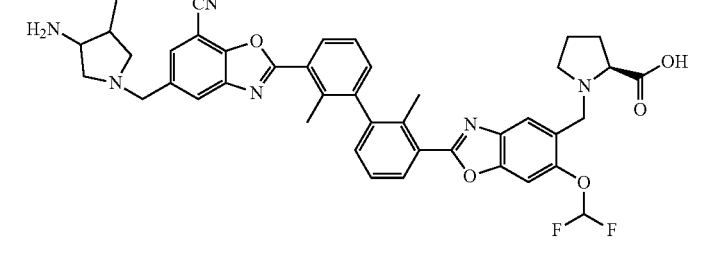 | 747.3 |

TABLE 2-continued

| EX No. | Chemical Name | Structure | Physical Data (MS) (M + H)+ |
|---|---|---|---|
| 157 | ((2-(3'-(5-(((azetidin-3-ylmethyl)amino)methyl)-7-cyanobenzo[d]oxazol-2-yl)-2,2'-dimethyl-[1,1'-biphenyl-3-yl)-6-(difluoromethoxy)benzo[d]oxazol-5-yl)methyl)-L-proline | 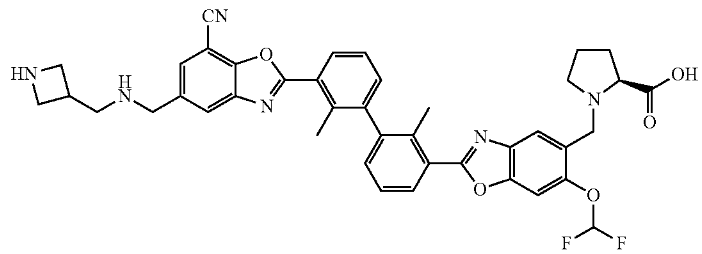 [SMILES: Cc1c(-c2nc3cc(CN4CCC[C@H]4C(=O)O)c(OC(F)F)cc3o2)cccc1-c1cccc(-c2nc3cc(CNCC4CNC4)cc(C#N)c3o2)c1C] | 733.3 |
| 158 | ((2-(3'-(7-cyano-5-((3-(dimethylamino)-4-methylpyrrolidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline | 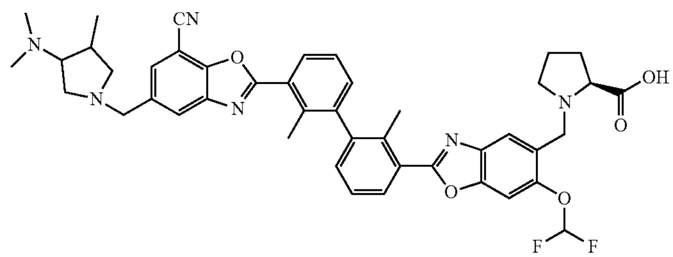 [SMILES: Cc1c(-c2nc3cc(CN4CCC[C@H]4C(=O)O)c(OC(F)F)cc3o2)cccc1-c1cccc(-c2nc3cc(CN4CC(C)C(N(C)C)C4)cc(C#N)c3o2)c1C] | 775.3 |
| 159 | ((2-(3'-(7-cyano-5-((3-((dimethylamino)methyl)-3-methylazetidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline | 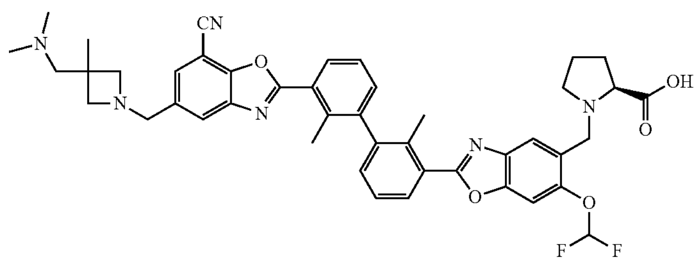 [SMILES: Cc1c(-c2nc3cc(CN4CCC[C@H]4C(=O)O)c(OC(F)F)cc3o2)cccc1-c1cccc(-c2nc3cc(CN4CC(C)(CN(C)C)C4)cc(C#N)c3o2)c1C] | 775.3 |
| 160 | ((2-(3'-(7-cyano-5-(((((1-methyl-1H-imidazol-4-yl)methyl)amino)methyl)benzo[d]oxazol-2-yl)-2,2'-dimethyl-[1,1'-biphenyl]-3-yl)-6-(difluoromethoxy)benzo[d]oxazol-5-yl)methyl)-L-proline | 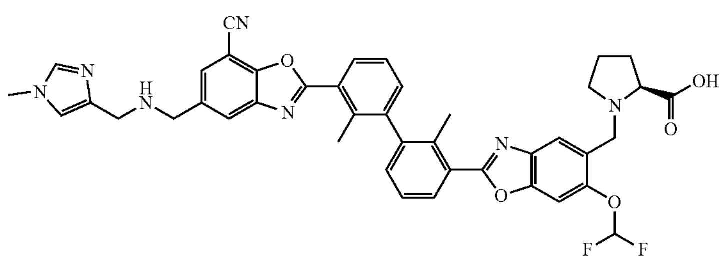 [SMILES: Cc1c(-c2nc3cc(CN4CCC[C@H]4C(=O)O)c(OC(F)F)cc3o2)cccc1-c1cccc(-c2nc3cc(CNCc4cn(C)cn4)cc(C#N)c3o2)c1C] | 758.3 |
| 161 | ((2-(3'-(5-((3-(aminomethyl)-3-methylazetidin-1-yl)methyl)-7-cyanobenzo[d]oxazol-2-yl)-2,2'-dimethyl-[1,1'-biphenyl]-3-yl)-6-(difluoromethoxy)benzo[d]oxazol-5-yl)methyl)-L-proline | 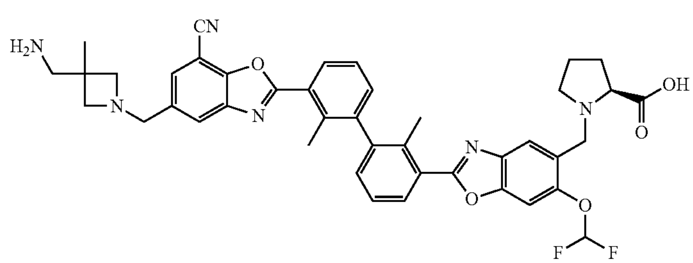 [SMILES: Cc1c(-c2nc3cc(CN4CCC[C@H]4C(=O)O)c(OC(F)F)cc3o2)cccc1-c1cccc(-c2nc3cc(CN4CC(C)(CN)C4)cc(C#N)c3o2)c1C] | 747.3 |

TABLE 2-continued

| EX No. | Chemical Name | Structure | Physical Data (MS) (M + H)+ |
|---|---|---|---|
| 162 | ((2-(3'-(7-cyano-5-((3-fluoropyrrolidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline | 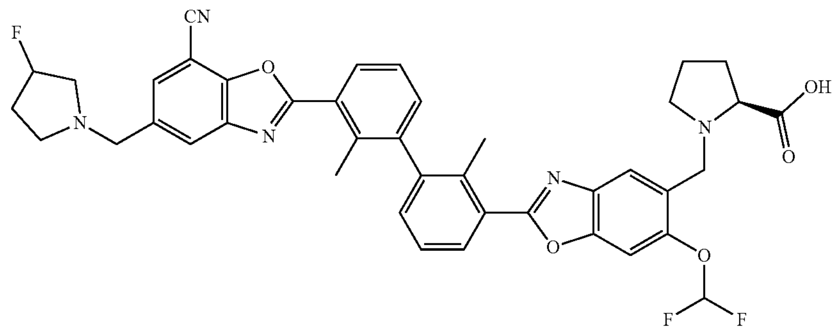 [SMILES: Cc1c(-c2nc3cc(CN4CCC[C@H]4C(=O)O)c(OC(F)F)cc3o2)cccc1-c1cccc(-c2nc3cc(CN4CCC(F)C4)cc(C#N)c3o2)c1C] | 736.3 |
| 163 | ((2-(3'-(7-cyano-5-((3-fluoropyrrolidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-D-proline | 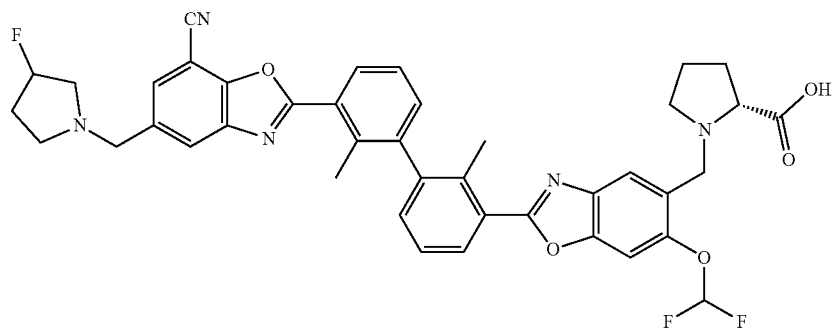 [SMILES: Cc1c(-c2nc3cc(CN4CCC[C@@H]4C(=O)O)c(OC(F)F)cc3o2)cccc1-c1cccc(-c2nc3cc(CN4CCC(F)C4)cc(C#N)c3o2)c1C] | 736.3 |
| 164 | ((2-(3'-(7-cyano-5-((3,4-difluoropyrrolidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline | 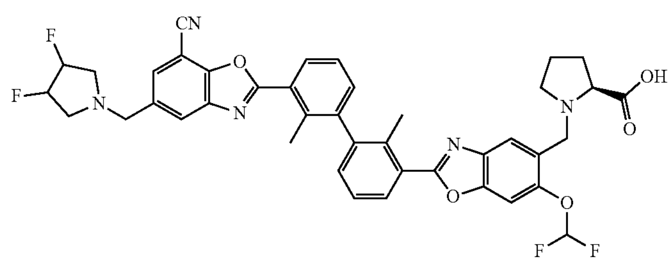 [SMILES: Cc1c(-c2nc3cc(CN4CCC[C@H]4C(=O)O)c(OC(F)F)cc3o2)cccc1-c1cccc(-c2nc3cc(CN4CC(F)C(F)C4)cc(C#N)c3o2)c1C] | 754.3 |
| 165 | ((2-(3'-(7-cyano-5-(((R)-3-cyanopyrrolidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline | 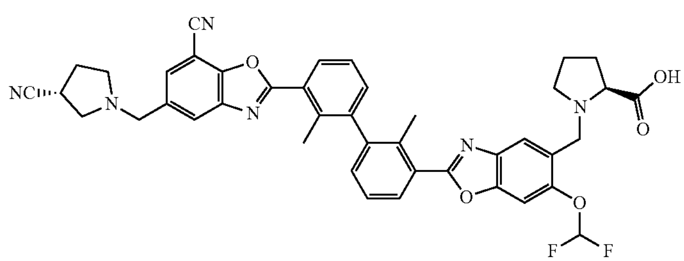 [SMILES: Cc1c(-c2nc3cc(CN4CCC[C@H]4C(=O)O)c(OC(F)F)cc3o2)cccc1-c1cccc(-c2nc3cc(CN4CC[C@@H](C#N)C4)cc(C#N)c3o2)c1C] | 743.3 |
| 166 | ((6-(difluoromethoxy)-2-3'-(5-((3-fluoropyrrolidin-1-yl)methyl)-7-(trifluoromethyl)benzo[d]oxazol-2-yl)-2,2'-dimethyl-[1,1'-biphenyl]-3-yl)benzo[d]oxazol-5-yl)methyl)-L-proline | 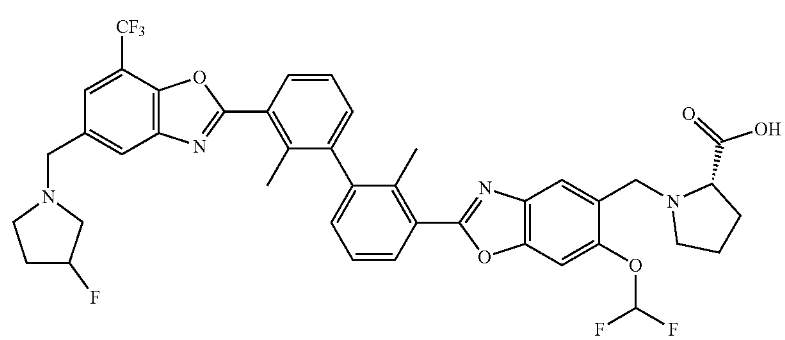 [SMILES: Cc1c(-c2nc3cc(CN4CCC[C@H]4C(=O)O)c(OC(F)F)cc3o2)cccc1-c1cccc(-c2nc3cc(CN4CCC(F)C4)cc(C(F)(F)F)c3o2)c1C] | 779.3 |

TABLE 2-continued

| EX No. | Chemical Name | Structure | Physical Data (MS) (M + H)+ |
|---|---|---|---|
| 167 | ((2-(3'-(7-cyano-5-((3-fluoro-3-methylpyrrolidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline | 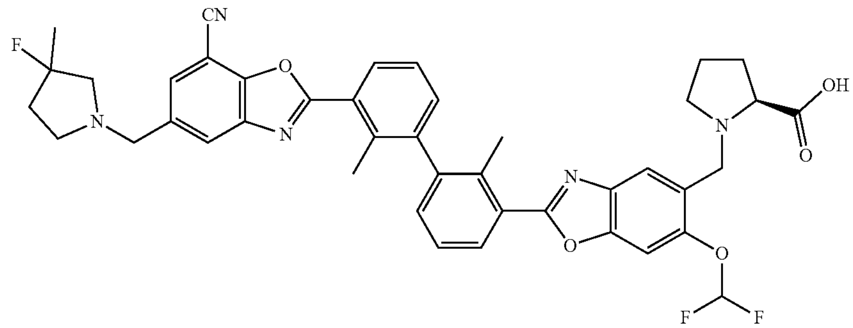 [SMILES: Cc1c(-c2nc3cc(CN4CCC[C@H]4C(=O)O)c(OC(F)F)cc3o2)cccc1-c1cccc(-c2nc3cc(CN4CCC(C)(F)C4)cc(C#N)c3o2)c1C] | 750.3 |
| 168 | ((2-(3'-(7-cyano-5-(((R)-3-(fluoromethyl)pyrrolidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline | 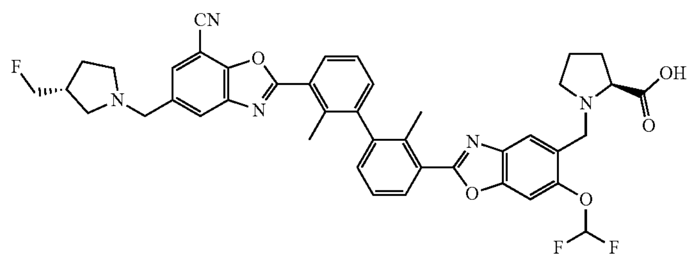 [SMILES: Cc1c(-c2nc3cc(CN4CCC[C@H]4C(=O)O)c(OC(F)F)cc3o2)cccc1-c1cccc(-c2nc3cc(CN4CC[C@@H](CF)C4)cc(C#N)c3o2)c1C] | 750.3 |
| 169 | (R)-1-((2-(3'-(7-cyano-5-(pyrrolidin-1-ylmethyl)benzo[d]oxazol-2-yl)-2,2'-dimethyl-[1,1'-biphenyl]-3-yl)-6-(difluoromethoxy)benzo[d]oxazol-5-yl)methyl)pyrrolidine-3-carboxylic acid | 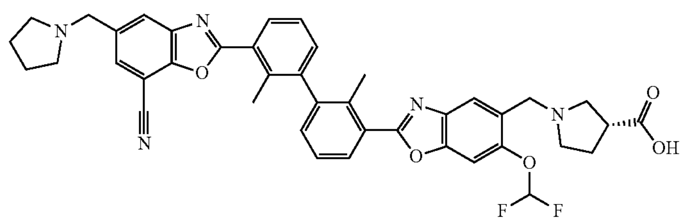 [SMILES: Cc1c(-c2nc3cc(CN4CC[C@@H](C(=O)O)C4)c(OC(F)F)cc3o2)cccc1-c1cccc(-c2nc3cc(CN4CCCC4)cc(C#N)c3o2)c1C] | 718.3 |
| 170 | ((6-(difluoromethoxy)-2-(3'-(6-((3,3-dimethylazetidin-1-yl)methyl)oxazolo[5,4-b]pyridin-2-yl)-2,2'-dimethyl-[1,1'-biphenyl]-3-yl)benzo[d]oxazol-5-yl)methyl)-D-proline | 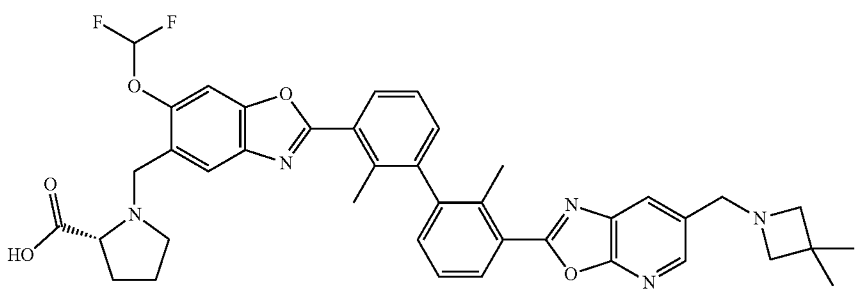 [SMILES: Cc1c(-c2nc3cc(CN4CCC[C@@H]4C(=O)O)c(OC(F)F)cc3o2)cccc1-c1cccc(-c2nc3cc(CN4CC(C)(C)C4)cnc3o2)c1C] | 708.3 |
| 318 | ((2-(3'-(7-cyano-5-((3,3-dimethylazetidin-1-yl)methyl)benzo[d]oxazol-2-yl)-2,2'-dimethyl-[1,1'-biphenyl]-3-yl)benzo[d]oxazol-5-yl)methyl)-L-proline | 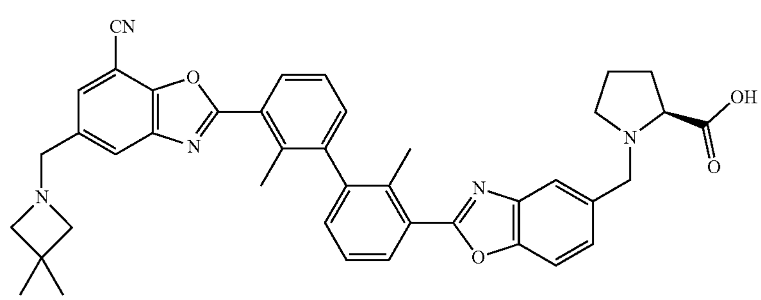 [SMILES: Cc1c(-c2nc3cc(CN4CCC[C@H]4C(=O)O)ccc3o2)cccc1-c1cccc(-c2nc3cc(CN4CC(C)(C)C4)cc(C#N)c3o2)c1C] | 666.3 |

TABLE 2-continued

| EX No. | Chemical Name | Structure | Physical Data (MS) (M + H)+ |
|---|---|---|---|
| 84 | ((6-(difluoromethoxy)-2-(3'-(5-((3,4-dimethylpyrrolidin-1-yl)methyl)-7-(trifluoromethyl)benzo[d]oxazol-2-yl)-2,2'-dimethyl-[1,1'-biphenyl]-3-yl)benzo[d]oxazol-5-yl)methyl)-L-proline | 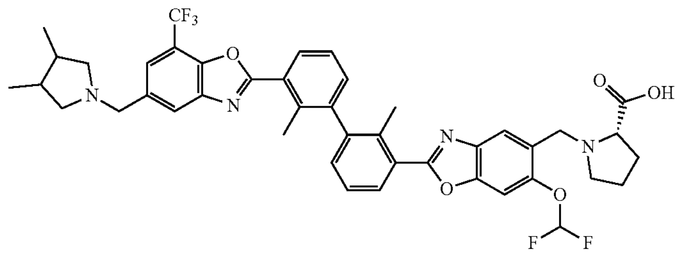 [SMILES: Cc1c(-c2nc3cc(CN4CCC[C@H]4C(=O)O)c(OC(F)F)cc3o2)cccc1-c1cccc(-c2nc3cc(CN4CC(C)C(C)C4)cc(C(F)(F)F)c3o2)c1C] | 789.3 |
| 259 | (S)-1-((2-(3'-(7-cyano-5-(((S)-3-methylpyrrolidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)pyrrolidine-3-carboxylic acid | 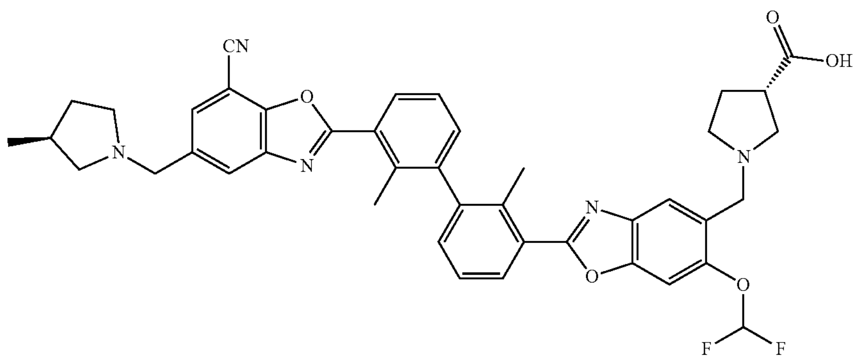 [SMILES: Cc1c(-c2nc3cc(CN4CC[C@H](C(=O)O)C4)c(OC(F)F)cc3o2)cccc1-c1cccc(-c2nc3cc(CN4CC[C@H](C)C4)cc(C#N)c3o2)c1C] | 732.3 |
| 261 | ((2-(3'-(5-(((S)-3-chloropyrrolidin-1-yl)methyl)-7-cyanobenzo[d]oxazol-2-yl)-2,2'-dimethyl-[1,1'-biphenyl]-3-yl)-6-(difluoromethoxy)benzo[d]oxazol-5-yl)methyl)-L-proline | 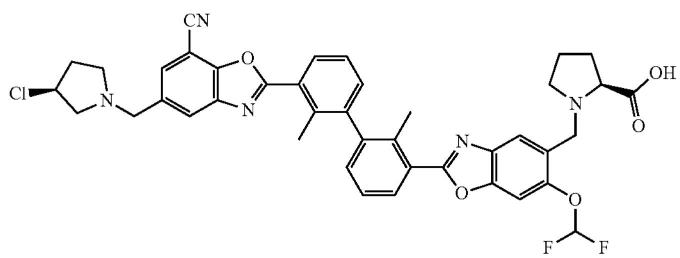 [SMILES: Cc1c(-c2nc3cc(CN4CCC[C@H]4C(=O)O)c(OC(F)F)cc3o2)cccc1-c1cccc(-c2nc3cc(CN4CC[C@H](Cl)C4)cc(C#N)c3o2)c1C] | 752.2 |
| 315 | ((2-(3'-(5-((3-carbamoylpyrrolidin-1-yl)methyl)-7-cyanobenzo[d]oxazol-2-yl)-2,2'-dimethyl-[1,1'-biphenyl]-3-yl)-6-(difluoromethoxy)benzo[d]oxazol-5-yl)methyl)-L-proline | 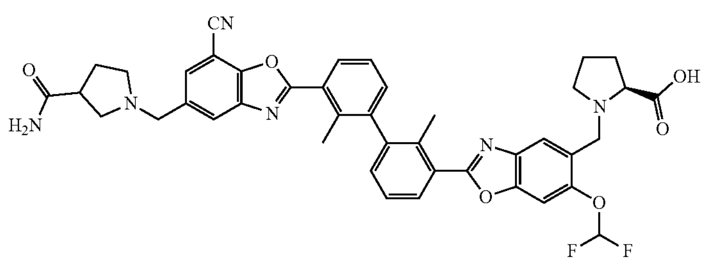 [SMILES: Cc1c(-c2nc3cc(CN4CCC[C@H]4C(=O)O)c(OC(F)F)cc3o2)cccc1-c1cccc(-c2nc3cc(CN4CCC(C(N)=O)C4)cc(C#N)c3o2)c1C] | 761.3 |
| 316 | ((2-(3'-(7-cyano-5-((3-cyano-3-methylpyrrolidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline | 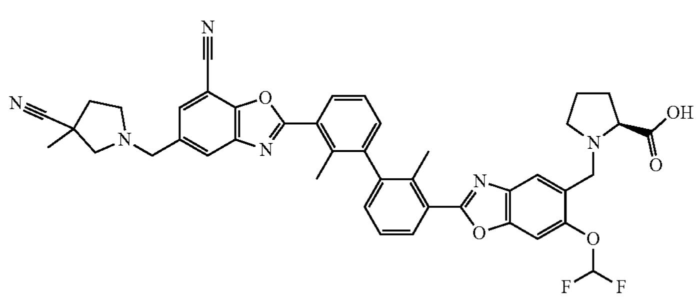 [SMILES: Cc1c(-c2nc3cc(CN4CCC[C@H]4C(=O)O)c(OC(F)F)cc3o2)cccc1-c1cccc(-c2nc3cc(CN4CCC(C)(C#N)C4)cc(C#N)c3o2)c1C] | 757.3 |

Example 171 Synthesis of Compound 171

(S)-1-((8-((3'-(5-(((S)-2-carboxypyrrolidin-1-yl)methyl)-6-(difluoromethoxy)benzo[d]oxazol-2-yl)-2,2'-dimethyl-[1,1'-biphenyl]-3-yl)amino)-1,7-naphthyridin-3-yl)methyl)-2-methylpyrrolidine-2-carboxylic acid

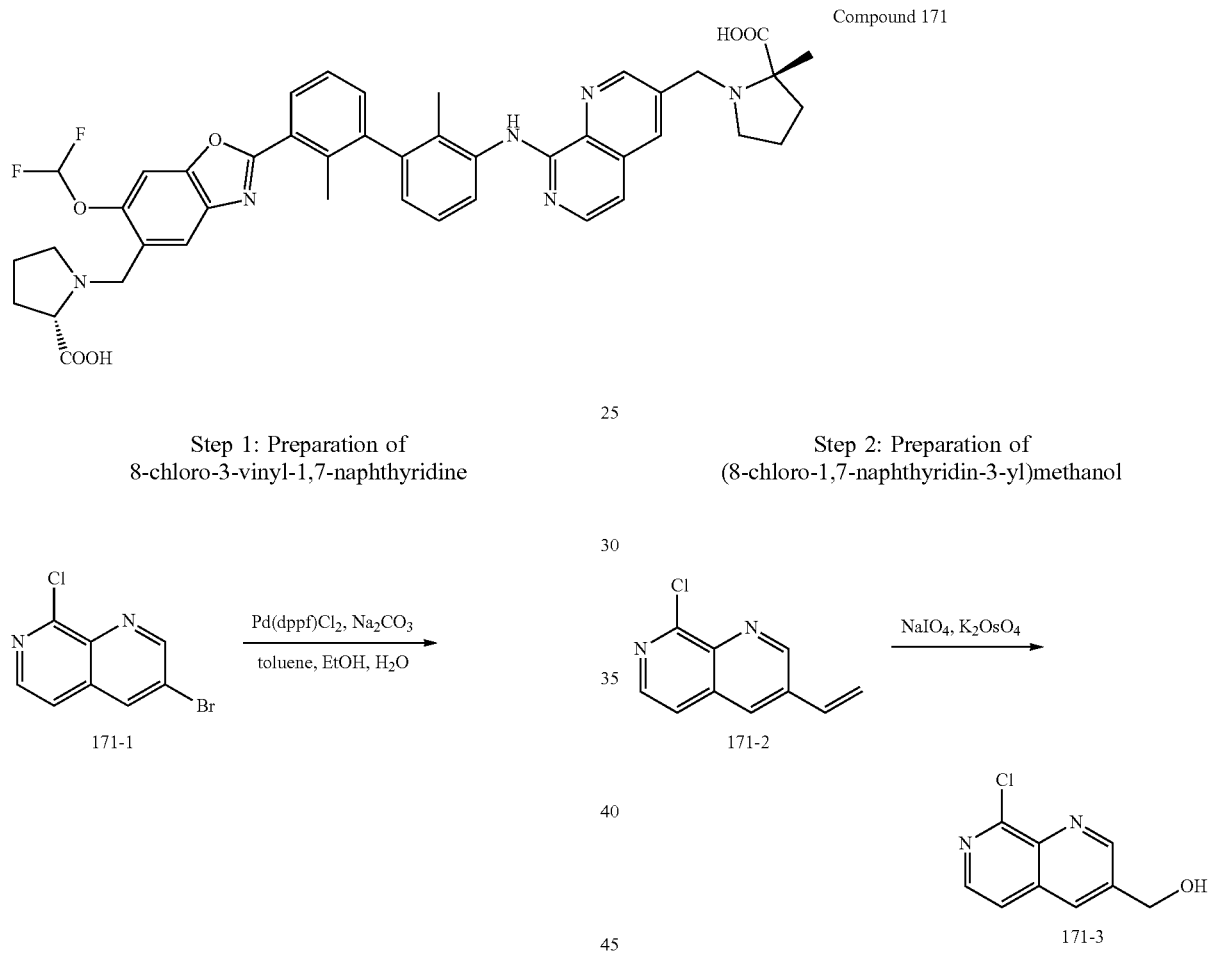

Compound 171

Step 1: Preparation of 8-chloro-3-vinyl-1,7-naphthyridine

To a solution of compound 171-1 (2.43 g) in toluene (30 mL), EtOH (10 mL), 10% $Na_2CO_3$ aq. (10 mL) and Pd(dppf)$Cl_2 \cdot DCM$ (420 mg) was added. And then 4,4,5,5-tetramethyl-2-vinyl-1,3,2-dioxaborolane (3.1 g) was added dropwise under $N_2$ protection. The mixture was allowed to stir at 100° C. for 16 h. The reaction was quenched with $H_2O$ (50 mL) and extracted by EtOAc for 3 times. The organic layers were combined and washed with brine. The resulting solution was concentrated and purified by silicagel (eluting with hexane-EtOAc using a gradient from 8:1 to 5:1) to afford 8-chloro-3-vinyl-1,7-naphthyridine (1.1 g) as a brown solid.

Step 2: Preparation of (8-chloro-1,7-naphthyridin-3-yl)methanol

To a solution of compound 171-2 (380 mg) in 1,4-dioxane (20 mL)/water (20 mL), $K_2OsO_4$ (4.0 mg) was added and stirred for 30 min at room temperature. $NaIO_4$ (1.0 g) was added in small portions at the same temperature. After stirring for 3 h, the reaction mixture was quenched with saturated $Na_2S_2O_3$ solution and extracted with DCM (40 mL) for 3 times. The organic layers were combined and dried over $Na_2SO_4$. The resulting solution was concentrated to afford 8-chloro-1,7-naphthyridine-3-carbaldehyde.

The above 8-chloro-1,7-naphthyridine-3-carbaldehyde (320 mg) was dissolved in 20 mL MeOH, and $NaBH_4$ (200 mg) was added in one portion. The resulting mixture was stirred for 2 h at room temperature then quenched with water (30 mL). The mixture was extracted with DCM (20 mL) for 3 times and the organic phases were dried over $Na_2SO_4$. The resulting solution was concentrated and purified by silicagel (eluting with DCM-EtOAc using a gradient from 1:1 to 1:2) to afford (8-chloro-1,7-naphthyridin-3-yl)methanol (240 mg) as a white solid.

Step 3: Preparation of (8-((3-bromo-2-methylphenyl)amino)-1,7-naphthyridin-3-yl)methanol

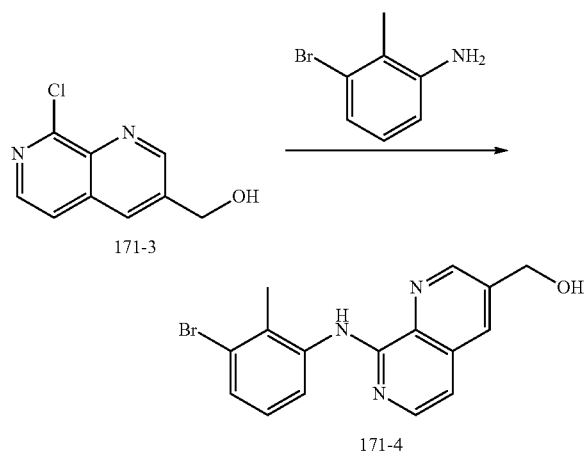

To a microwave reaction vial were added 3-bromo-2-methylaniline (2.50 g), compound 171-3 (1.86 g), t-BuOH (15 mL) and HCl (4.0 M in 1,4-dioxane, 3 mL). The vial was capped and the reaction mixture was heated at 100° C. for 4 h in microwave oven. It was diluted with 20 mL of water and then extracted with DCM (50 ml×2). The combined organic extracts were washed with brine, dried over $MgSO_4$ and concentrated in vacuo. The residue was concentrated and recrystallized by DCM:Hexane (1:1) to afford (8-((3-bromo-2-methylphenyl)amino)-1,7-naphthyridin-3-yl)methanol (2.0 g) as an off-white solid.

Step 4: Preparation of methyl ((5-(difluoromethoxy)-2-(3'-((3-(hydroxymethyl)-1,7-naphthyridin-8-yl)amino)-2,2'-dimethyl-[1,1'-biphenyl]-3-yl)benzo[d]oxazol-6-yl)methyl)-L-prolinate

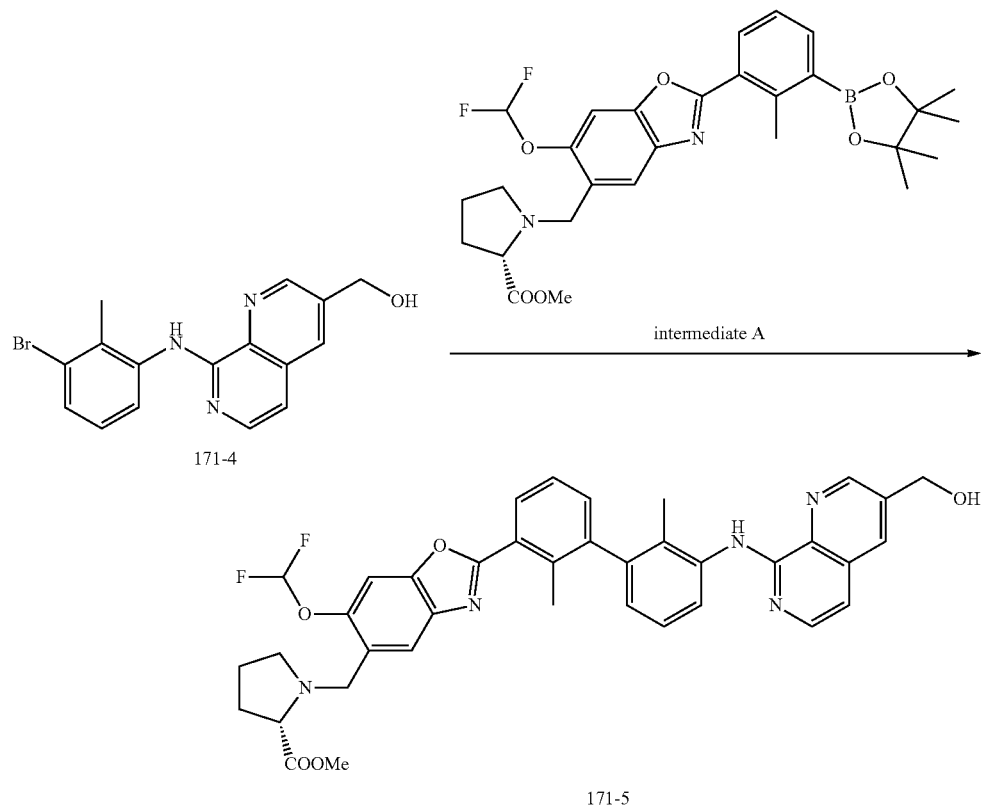

To a solution of compound 171-4 (0.69 g), intermediate A (1.5 g) in toluene (15 mL), EtOH (5 mL), 10% $Na_2CO_3$ aq. (5 mL), Pd(dppf)$Cl_2$·DCM (78 mg) was added under $N_2$ protection. The mixture was allowed to stir at 110° C. overnight. The reaction was quenched with $H_2O$ (20 mL) and extracted by EtOAc (50 mL) for 3 times. The organic layers were combined and washed with brine. The resulting solution was concentrated and purified by silicagel (eluting with Hexane-EtOAc using a gradient from 3:1 to 1:1) to afford compound 171-5 (0.88 g) as a brown oil.

Step 5: Preparation of methyl (S)-1-((8-((3'-(6-(difluoromethoxy)-5-(((S)-2-(methoxycarbonyl)pyrrolidin-1-yl)methyl)benzo[d]oxazol-2-yl)-2,2'-dimethyl-[1,1'-biphenyl]-3-yl)amino)-1,7-naphthyridin-3-yl)methyl)-2-methylpyrrolidine-2-carboxylate

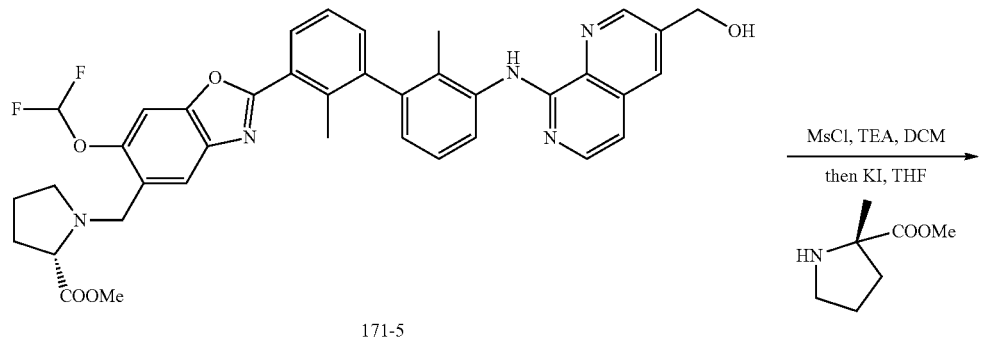

To a solution of compound 171-5 (250 mg) and TEA (100 mg) in DCM (5.0 mL), MsCl (89 mg) was added dropwise at 0° C. The reaction was allowed to stir at room temperature for 4 hrs. The resulting mixture was concentrated under vacuo and redissolved by THF (5 mL). Methyl (S)-2-methylpyrrolidine-2-carboxylate (143 mg) and KI (1 mg) was added to the solution and then the reaction was continued to stir at room temperature overnight unstill above methanesulfonate was consumed. The residue was concentrated and purified directly by RP-column (mobile phase: MeCN:water=10:90 with 0.1% HCl) to afford compound 171-6 (105 mg) as an off-white solid.

Step 6: Preparation of (S)-1-((8-((3'-(5-(((S)-2-carboxypyrrolidin-1-yl)methyl)-6-(difluoromethoxy)benzo[d]oxazol-2-yl)-2,2'-dimethyl-[1,1'-biphenyl]-3-yl)amino)-1,7-naphthyridin-3-yl)methyl)-2-methylpyrrolidine-2-carboxylic acid

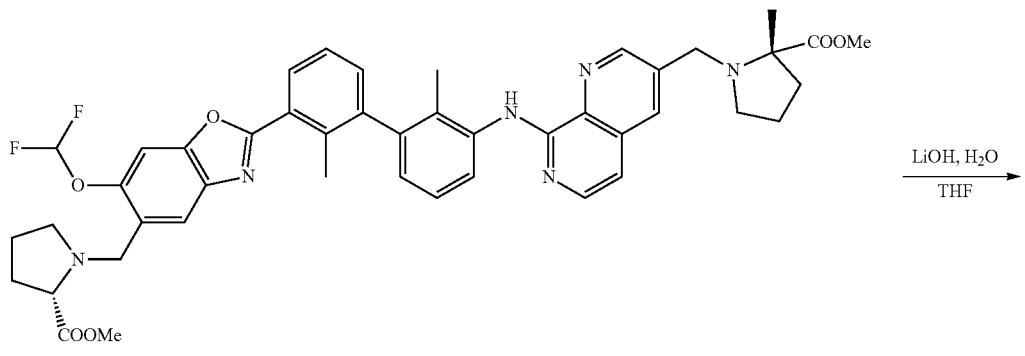

-continued

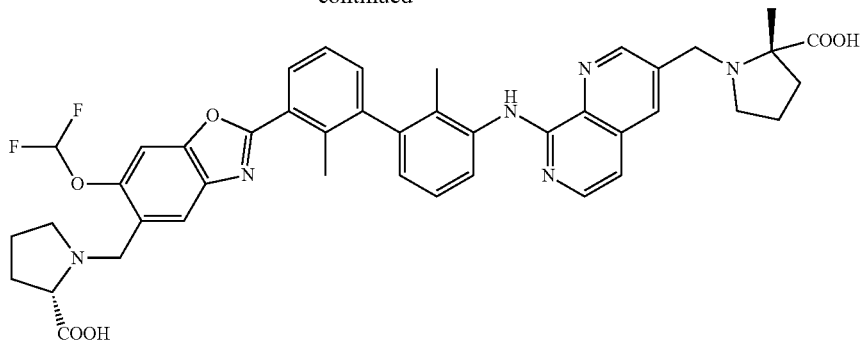

compound 171

To a solution of compound 171-6 (105 mg) in THF/water=1:1 (4 mL) was added LiOH (40 mg). The resulting mixture was stirred for 24 h at room temperature. THF layer was separated and purified by RP-column (mobile phase: MeCN:water (0.1% HCl) using a gradient from 10:90 to 30:70) to afford 78 mg (S)-1-((8-((3'-(5-(((S)-2-carboxypyrrolidin-1-yl)methyl)-6-(difluoromethoxy)benzo[d]oxazol-2-yl)-2,2'-dimethyl-[1,1'-biphenyl]-3-yl)amino)-1,7-naphthyridin-3-yl)methyl)-2-methylpyrrolidine-2-carboxylic acid (compound 171). LC-MS (m/z): 777.3 (M+H)+. 1H NMR (500 MHz, Methanol-d4) δ 9.23 (d, 1H, J=2.1 Hz), 8.60 (d, 1H, J=2.0 Hz), 8.20 (dd, 1H, J=7.9, 1.5 Hz), 8.07 (s, 1H), 7.76 (s, 1H), 7.69-7.63 (m, 2H), 7.57 (t, 1H, J=7.8 Hz), 7.53 (t, 1H, J=7.7 Hz), 7.46 (dd, 1H, J=7.6, 1.5 Hz), 7.38 (dd, 1H, J=7.6, 1.4 Hz), 7.35 (d, 1H, J=6.9 Hz), 7.12 (t, 1H, $J_{F-H}$=72.6 Hz), 4.83 (d, 1H, J=13.2 Hz), 4.74 (d, 1H, J=13.3 Hz), 4.62 (d, 1H, J=13.2 Hz), 4.49 (d, 1H, J=13.2 Hz), 4.33 (dd, 1H, J=9.6, 7.2 Hz), 3.66-3.62 (m, 1H), 3.52-3.37 (m, 3H), 2.63-2.56 (m, 1H), 2.55 (s, 3H), 2.41-2.32 (m, 1H), 2.29-2.14 (m, 4H), 2.09 (s, 3H), 2.06-1.98 (m, 2H), 1.75 (s, 3H).

The compounds of table 3 were prepared in a similar manner to Example 171 via different reaction starting materials and suitable reagents.

TABLE 3

| EX No. | Chemical Name | Structure | Physical Data (MS) (M + H)+ |
|---|---|---|---|
| 172 | ((2-(3'-((3-(((carboxymethyl)amino)methyl)-1,7-naphthyridin-8-yl)amino)-2,2'-dimethyl-[1,1'-biphenyl]-3-yl)-6-(difluoromethoxy)benzo[d]oxazol-5-yl)methyl)-L-proline | 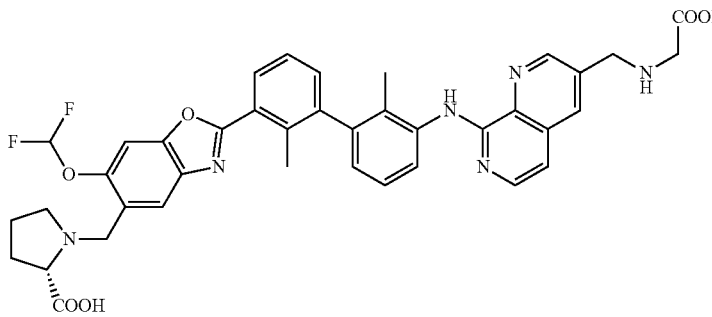 | 723.3 |
| 173 | (S)-1-((8-((3'-(5-(((S)-2-carboxypyrrolidin-1-yl)methyl)-6-(difluoromethoxy)benzo[d]oxazol-2-yl)-2,2'-dimethyl-[1,1'-biphenyl]-3-yl)amino)-1,7-naphthyridin-3-yl)methyl)piperidine-2-carboxylic acid | 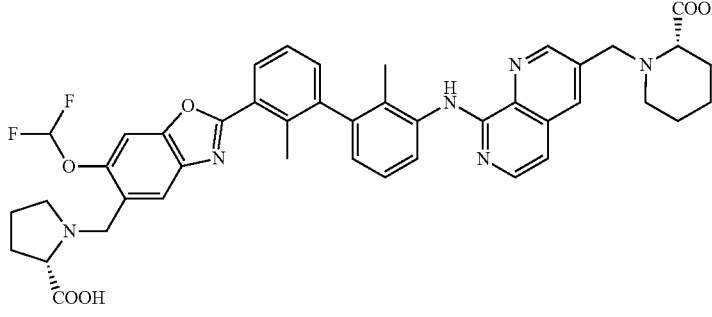 | 777.3 |

TABLE 3-continued

| EX No. | Chemical Name | Structure | Physical Data (MS) (M + H)+ |
|---|---|---|---|
| 174 | ((6-(difluoromethoxy)-2-(3'-((3-((3-fluoropyrrolidin-1-yl)methyl)-1,7-naphthyridin-8-yl)amino)-2,2'-dimethyl-[1,1'-biphenyl]-3-yl)benzo[d]oxazol-5-yl)methyl)-L-proline | 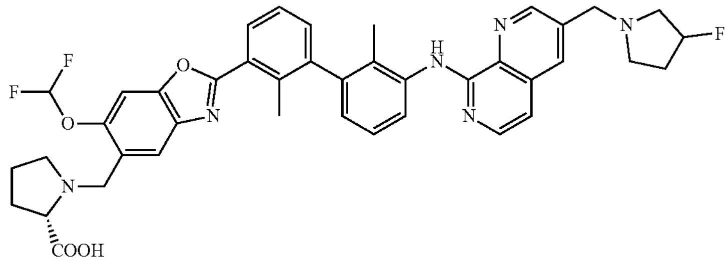 [SMILES: Cc1c(Nc2nccc3cc(CN4CCC(F)C4)cnc23)cccc1-c1cccc(-c2nc3cc(CN4CCC[C@H]4C(=O)O)c(OC(F)F)cc3o2)c1C] | 737.3 |
| 175 | ((6-(difluoromethoxy)-2-(3'-((3-((3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)-L-proline | 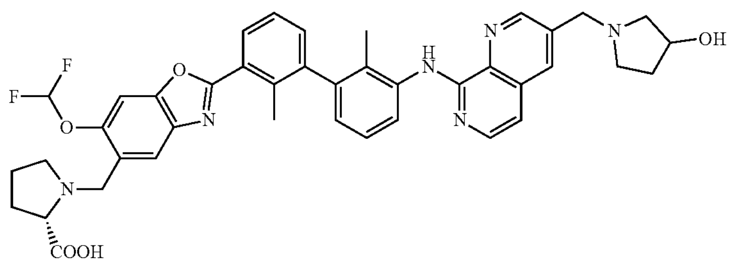 [SMILES: Cc1c(Nc2nccc3cc(CN4CCC(O)C4)cnc23)cccc1-c1cccc(-c2nc3cc(CN4CCC[C@H]4C(=O)O)c(OC(F)F)cc3o2)c1C] | 735.3 |
| 176 | ((6-(difluoromethoxy)-2-(2,2'-dimethyl-3'-((3-(morpholinomethyl)-1,7-naphthyridin-8-yl)amino)-[1,1'-biphenyl]-3-yl)benzo[d]oxazol-5-yl)methyl)-L-proline | 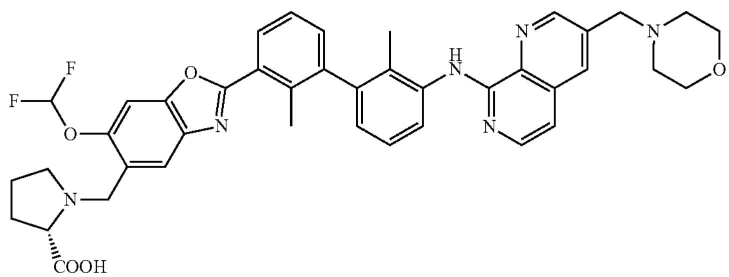 [SMILES: Cc1c(Nc2nccc3cc(CN4CCOCC4)cnc23)cccc1-c1cccc(-c2nc3cc(CN4CCC[C@H]4C(=O)O)c(OC(F)F)cc3o2)c1C] | 735.3 |
| 177 | ((2-(3'-((3-(azetidin-1-ylmethyl)-1,7-naphthyridin-8-yl)amino)-2,2'-dimethyl-[1,1'-biphenyl]-3-yl)-6-(difluoromethoxy)benzo[d]oxazol-5-yl)methyl)proline | 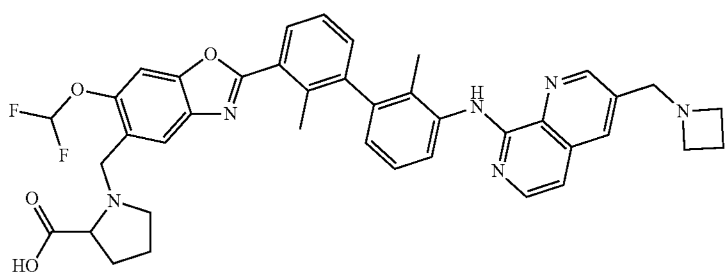 [SMILES: Cc1c(Nc2nccc3cc(CN4CCC4)cnc23)cccc1-c1cccc(-c2nc3cc(CN4CCCC4C(=O)O)c(OC(F)F)cc3o2)c1C] | 705.3 |
| 178 | ((6-(difluoromethoxy)-2-(3'-((3-((3-hydroxyazetidin-1-yl)methyl)-1,7-naphthyridin-8-yl)amino)-2,2'-dimethyl-[1,1'-biphenyl]-3-yl)benzo[d]oxazol-5-yl)methyl)proline | 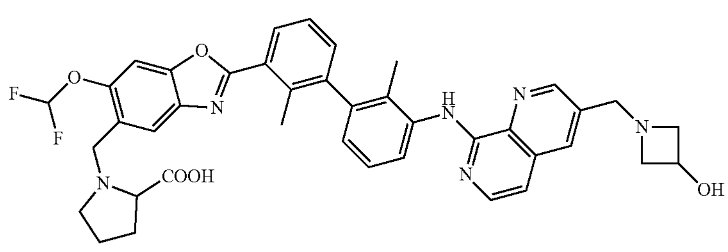 [SMILES: Cc1c(Nc2nccc3cc(CN4CC(O)C4)cnc23)cccc1-c1cccc(-c2nc3cc(CN4CCCC4C(=O)O)c(OC(F)F)cc3o2)c1C] | 721.3 |
| 179 | ((6-(difluoromethoxy)-2-(2,2'-dimethyl-3'-((3-((((5-oxopyrrolidin-2-yl)methyl)amino)methyl)-1,7-naphthyridin-8-yl)amino)-[1,1'-biphenyl]-3-yl)benzo[d]oxazol-5-yl)methyl)proline | 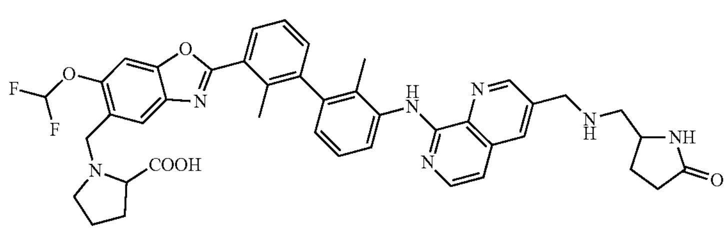 [SMILES: Cc1c(Nc2nccc3cc(CNCC4CCC(=O)N4)cnc23)cccc1-c1cccc(-c2nc3cc(CN4CCCC4C(=O)O)c(OC(F)F)cc3o2)c1C] | 762.3 |

TABLE 3-continued

| EX No. | Chemical Name | Structure | Physical Data (MS) (M + H)+ |
|---|---|---|---|
| 180 | (3S)-1-((6-(difluoromethoxy)-2-(3'-((3-((3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid | 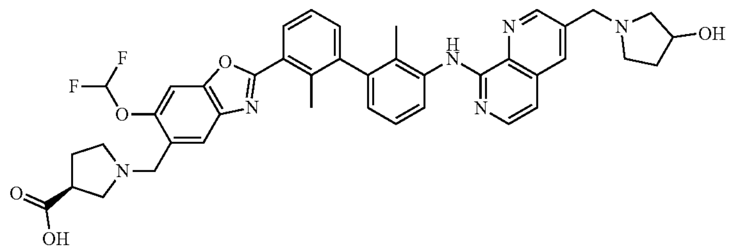 [SMILES: Cc1c(Nc2nccc3cc(CN4CCC(O)C4)cnc23)cccc1-c1cccc(-c2nc3cc(CN4CC[C@H](C(=O)O)C4)c(OC(F)F)cc3o2)c1C] | 735.3 |
| 181 | (3R)-1-((6-(difluoromethoxy)-2-(3'-((3-((3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid | 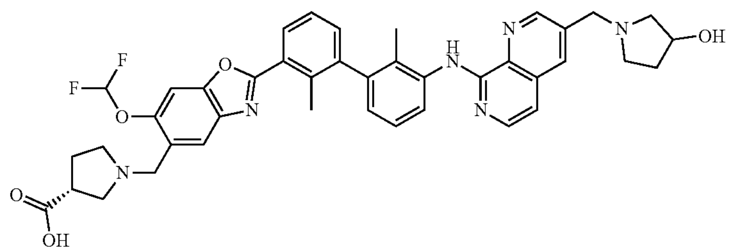 [SMILES: Cc1c(Nc2nccc3cc(CN4CCC(O)C4)cnc23)cccc1-c1cccc(-c2nc3cc(CN4CC[C@@H](C(=O)O)C4)c(OC(F)F)cc3o2)c1C] | 735.3 |
| 182 | ((6-(difluoromethoxy)-2-(3'-((3-((3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)-D-proline | 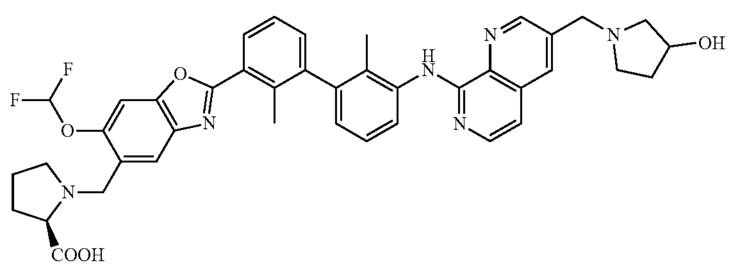 [SMILES: Cc1c(Nc2nccc3cc(CN4CCC(O)C4)cnc23)cccc1-c1cccc(-c2nc3cc(CN4CCC[C@@H]4C(=O)O)c(OC(F)F)cc3o2)c1C] | 735.3 |
| 183 | ((5-(difluoromethoxy)-2-(2,2'-dimethyl-3'-((4-(pyrrolidin-1-ylmethyl)pyridin-2-yl)amino)-[1,1'-biphenyl]-3-yl)benzo[d]oxazol-6-yl)methyl)-L-proline | 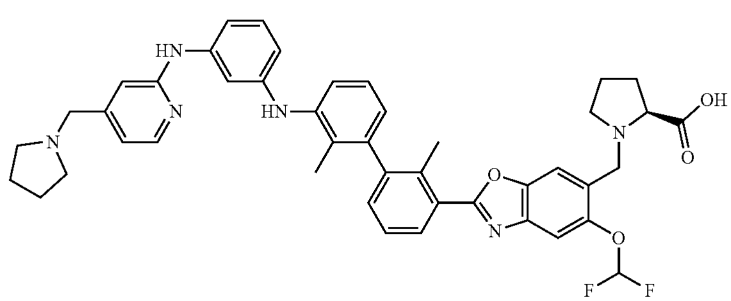 [SMILES: Cc1c(Nc2cccc(Nc3cc(CN4CCCC4)ccn3)c2)cccc1-c1cccc(-c2nc3cc(OC(F)F)c(CN4CCC[C@H]4C(=O)O)cc3o2)c1C] | 668.3 |

Example 314 Synthesis of Compound 314

((6-(difluoromethoxy)-2-(2,2'-dimethyl-3'-(5-methyl-4,5,6,7-tetrahydrooxazolo[4,5-c]pyridin-2-yl)-[1,1'-biphenyl]-3-yl)benzo[d]oxazol-5-yl)methyl)-L-proline

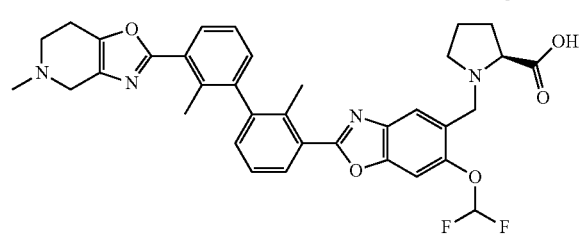

Compound 314

Step 1: Preparation of benzyl (3S,4S)-3-(3-bromo-2-methylbenzamido)-4-hydroxypiperidine-1-carboxylate

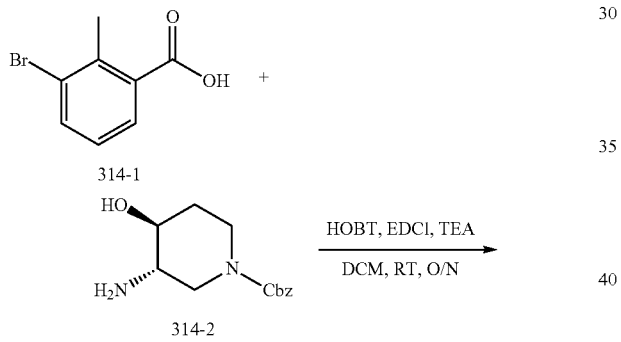

3-bromo-2-methylbenzoic acid (800 mg), benzyl (3S,4S)-3-amino-4-hydroxypiperidine-1-carboxylate (931.13 mg), EDCI (1.43 g), HOBT (1.01 g) and TEA (1.13 g) were added sequentially in DCM (50 mL), the mixture was stirred at room temperature overnight. The reaction solution was diluted with methylene chloride and washed sequentially with saturated aqueous sodium hydrogen carbonate and aqueous sodium chloride. The organic phase was dried with $Na_2SO_4$ and concentrated to white-like solid benzyl (3S,4S)-3-(3-bromo-2-methylbenzamido)-4-hydroxypiperidine-1-carboxylate (1.4 g, crude).

Step 2: Preparation of benzyl (S)-3-(3-bromo-2-methylbenzamido)-4-oxopiperidine-1-carboxylate

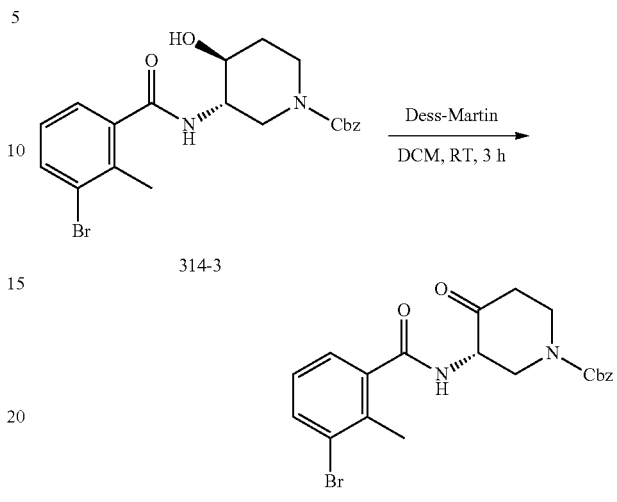

At room temperature, Dess-Martin (2.65 g) was batched into compound 314-3 (1.4 g) in DCM (30 mL) solution and stirred for 3 hrs. LC-MS determined that the reaction was completed; the reaction mixture was quenched with $Na_2S_2O_3$ solution and extracted with EA three times. The organic layers were washed with $NaHCO_3$ solution, dried over $Na_2SO_4$ and concentrated to get the benzyl (S)-3-(3-bromo-2-methylbenzamido)-4-oxopiperidine-1-carboxylate (1.1 g, crude) as light yellow solid.

Step 3: Preparation of benzyl 2-(3-bromo-2-methylphenyl)-6,7-dihydrooxazolo[4,5-c]pyridine-5(4H)-carboxylate

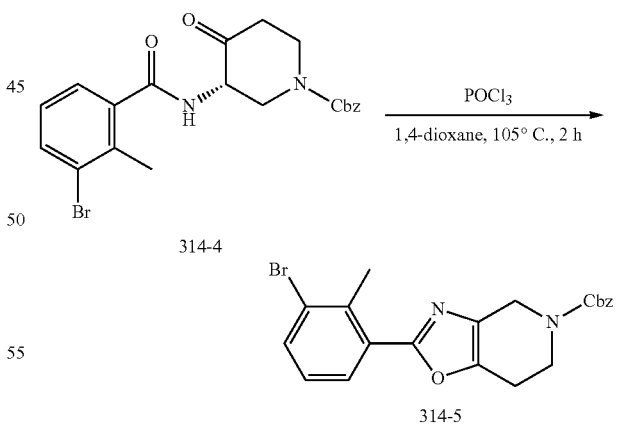

A solution of $POCl_3$ (757.52 mg) in 1,4-dioxane (5 mL) was added dropwise to a solution of compound 314-4 (891 mg) in 1,4-dioxane (15 mL). The temperature was then raised to 105° C. and stirring was continued for 2 hrs. The reaction mixture was slowly added dropwise to ice water and extracted with ethyl acetate. The organic phase was washed with saturated aqueous $NaHCO_3$ and saturated NaCl, dried over $Na_2SO_4$, and concentrated to get a residue, the residue was purified by chromatographic chromatography (DCM:MeOH=20:1) to obtain white-like solid compound 314-5 (800 mg).

Step 4: Preparation of benzyl (S)-2-(3'-(6-(difluoromethoxy)-5-((2-(methoxycarbonyl)pyrrolidin-1-yl)methyl)benzo[d]oxazol-2-yl)-2,2'-dimethyl-[1,1'-biphenyl]-3-yl)-6,7-dihydrooxazolo[4,5-c]pyridine-5(4H)-carboxylate

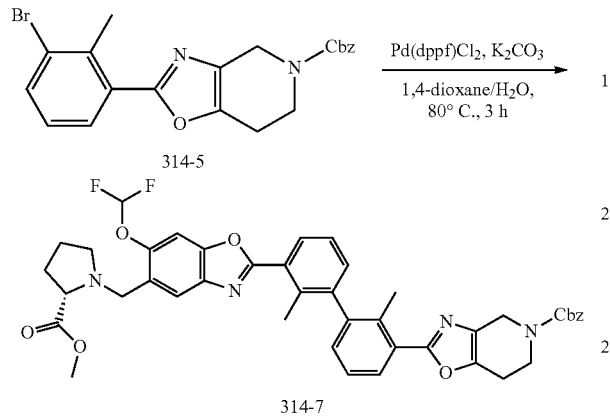

Compound 314-5 (800 mg), intermediate A (1015 mg), Pd(dppf)Cl$_2$ (343 mg) and K$_2$CO$_3$ (129.38 mg) were added to a mixture of 1,4-dixane (20 mL) and H$_2$O (5 mL). The reaction mixture was evacuated and refilled three times using N$_2$, heated to 80° C. and stirred for 3 hrs.

LC-MS monitored the reaction completely. The reaction mixture was concentrated and purified by TLC (PE:EA=1:3) to obtain benzyl (S)-2-(3'-(6-(difluoromethoxy)-5-((2-(methoxycarbonyl)pyrrolidin-1-yl)methyl)benzo[d]oxazol-2-yl)-2,2'-dimethyl-[1,1'-biphenyl]-3-yl)-6,7-dihydrooxazolo[4,5-c]pyridine-5(4H)-carboxylate (800 mg) as white-like solid.

Step 5: Preparation of methyl ((6-(difluoromethoxy)-2-(2,2'-dimethyl-3'-(4,5,6,7-tetrahydrooxazolo[4,5-c]pyridin-2-yl)-[1,1'-biphenyl]-3-yl)benzo[d]oxazol-5-yl)methyl)-L-prolinate

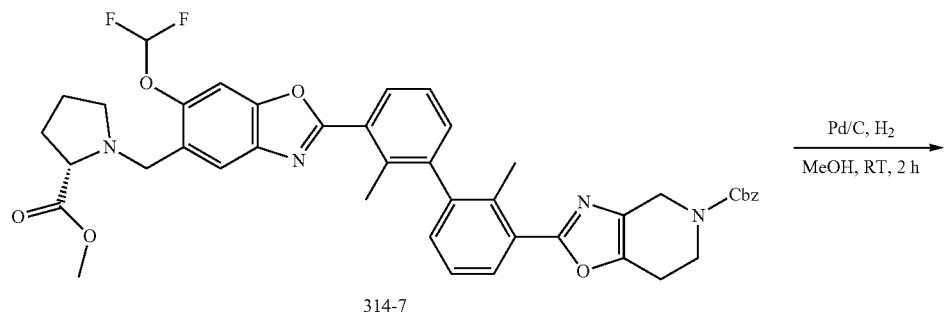

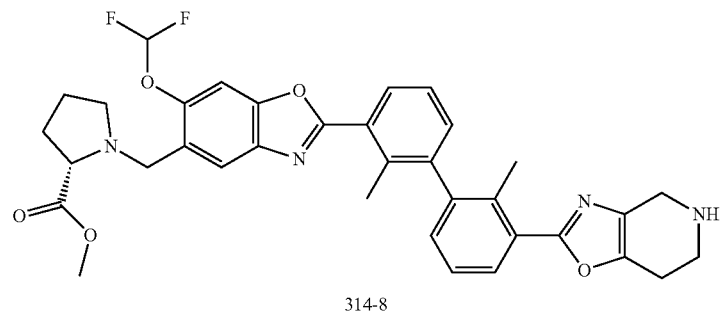

Pd/C (200 mg) was added to a solution of compound 314-7 (800 mg) in MeOH (50 mL). The mixture was stirred at room temperature for 5 hrs under H$_2$ atmosphere. The reaction mixture was filtered and concentrated to obtain methyl ((6-(difluoromethoxy)-2-(2,2'-dimethyl-3'-(4,5,6,7-tetrahydrooxazolo[4,5-c]pyridin-2-yl)-[1,1'-biphenyl]-3-yl)benzo[d]oxazol-5-yl)methyl)-L-prolinate (500 mg, crude) as white-like solid.

Step 6: Preparation of methyl ((6-(difluoromethoxy)-2-(2,2'-dimethyl-3'-(5-methyl-4,5,6,7-tetrahydrooxazolo[4,5-c]pyridin-2-yl)-[1,1'-biphenyl]-3-yl)benzo[d]oxazol-5-yl)methyl)-L-prolinate

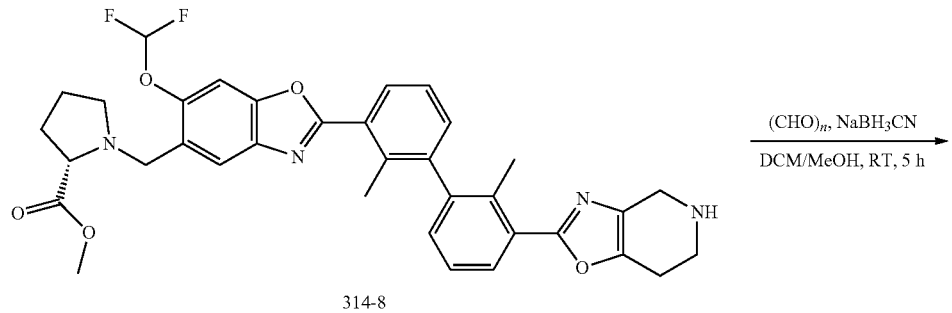

314-8

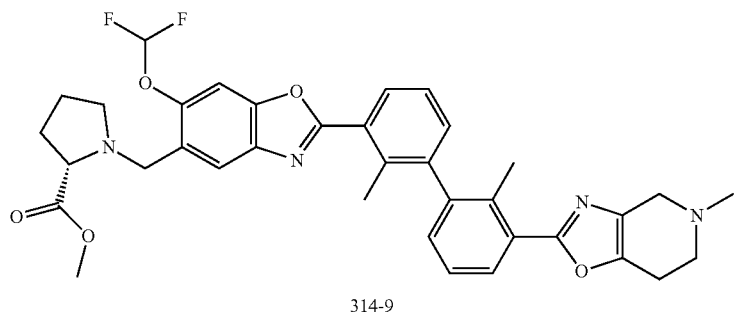

314-9

(CHO)$_n$ (72 mg) was added to a solution of compound 314-8 (500 mg) in DCM (30 mL) and MeOH (10 mL). After the mixture was stirred for 30 min, NaBH$_3$CN (150 mg) was added to the reaction solution in batches and stirred at room temperature overnight. The reaction was concentrated and purified by TLC (DCM:MeOH=20:1) to obtain methyl ((6-(difluoromethoxy)-2-(2,2'-dimethyl-3'-(5-methyl-4,5,6,7-tetrahydrooxazolo[4,5-c]pyridin-2-yl)-[1,1'-biphenyl]-3-yl)benzo[d]oxazol-5-yl)methyl)-L-prolinate (400 mg) as white-like solid.

Step 7: Preparation of ((6-(difluoromethoxy)-2-(2,2'-dimethyl-3'-(5-methyl-4,5,6,7-tetrahydrooxazolo[4,5-c]pyridin-2-yl)-[1,1'-biphenyl]-3-yl)benzo[d]oxazol-5-yl)methyl)-L-proline

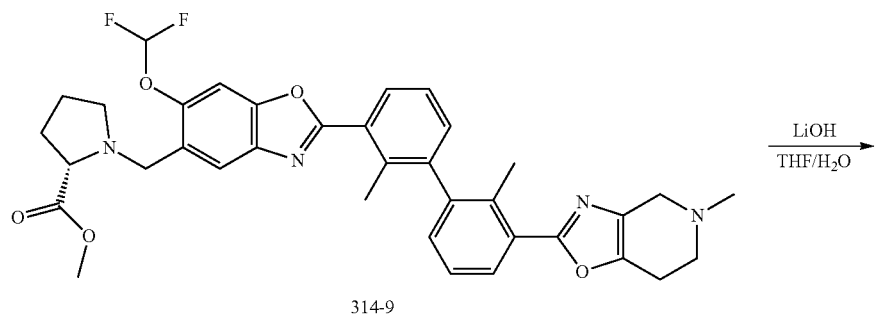

314-9

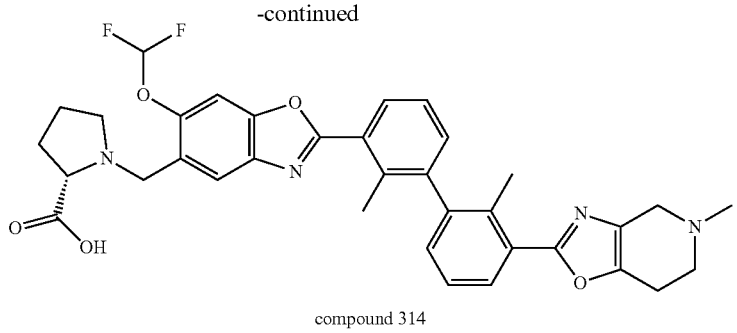

compound 314

This compound was prepared using similar procedures as described as step 5 in example 1, with compound 314-9 replacing compound 1-4. The crude product was purified by TLC purification (DCM:MeOH=4:1) to give 210 mg ((6-(difluoromethoxy)-2-(2,2'-dimethyl-3'-(5-methyl-4,5,6,7-tetrahydrooxazolo[4,5-c]pyridin-2-yl)-[1,1'-biphenyl]-3-yl) benzo[d]oxazol-5-yl)methyl)-L-proline (compound 314) as off-white solid. LC-MS (m/z): 629.3 (M+HF.

The compounds of table 4 were prepared in a similar manner to Examples 314 via different reaction starting materials and suitable reagents.

TABLE 4

| EX No. | Chemical Name | Structure | Physical Data (MS) (M + H)+ |
|---|---|---|---|
| 184 | ((2-(3'-(5-(carboxymethyl)-4,5,6,7-tetrahydrooxazolo[4,5-c]pyridin-2-yl)-2,2'-dimethyl-[1,1'-biphenyl]-3-yl)-6-(difluoromethoxy)benzo[d]oxazol-5-yl)methyl)-L-proline | 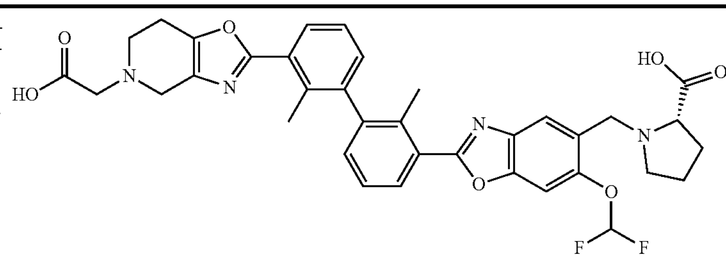 | 673.2 |
| 185 | ((6-(difluoromethoxy)-2-(2,2'-dimethyl-3'-(5-(2-(methylsulfonyl)ethyl)-4,5,6,7-tetrahydrooxazolo[4,5-c]pyridin-2-yl)-[1,1'-biphenyl]-3-yl)benzo[d]oxazol-5-yl)methyl)-L-proline | 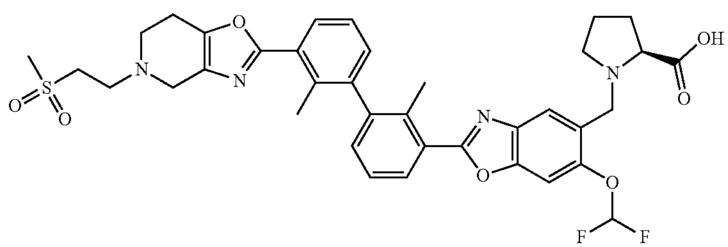 [SMILES: Cc1c(-c2nc3c(o2)CCN(CCS(C)(=O)=O)C3)cccc1-c1cccc(-c2nc3cc(CN4CCC[C@H]4C(=O)O)c(OC(F)F)cc3o2)c1C] | 721.3 |
| 186 | ((2-(3'-(5-(1-carboxyethyl)-4,5,6,7-tetrahydrooxazolo[4,5-c]pyridin-2-yl)-2,2'-dimethyl-[1,1'-biphenyl]-3-yl)-6-(difluoromethoxy)benzo[d]oxazol-5-yl)methyl)-L-proline | 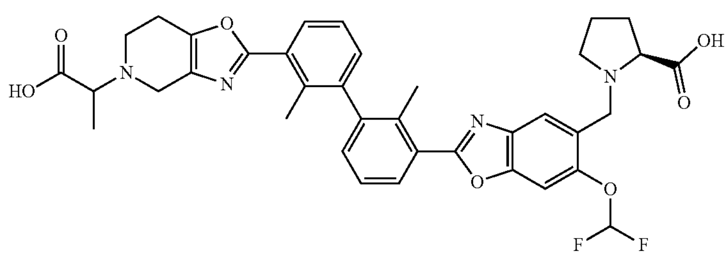 [SMILES: Cc1c(-c2nc3c(o2)CCN(C(C)C(=O)O)C3)cccc1-c1cccc(-c2nc3cc(CN4CCC[C@H]4C(=O)O)c(OC(F)F)cc3o2)c1C] | 687.3 |
| 187 | ((2-(3'-(5-(2-carboxyethyl)-4,5,6,7-tetrahydrooxazolo[4,5-c]pyridin-2-yl)-2,2'-dimethyl-[1,1'-biphenyl]-3-yl)-6-(difluoromethoxy)benzo[d]oxazol-5-yl)methyl)-L-proline | 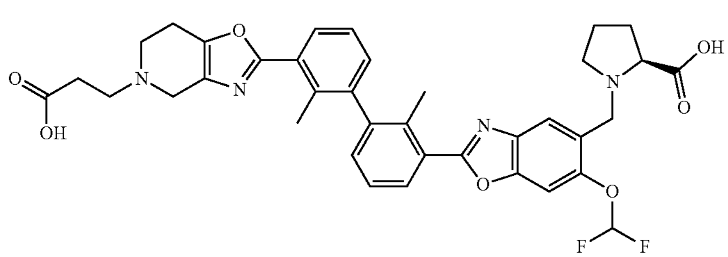 [SMILES: Cc1c(-c2nc3c(o2)CCN(CCC(=O)O)C3)cccc1-c1cccc(-c2nc3cc(CN4CCC[C@H]4C(=O)O)c(OC(F)F)cc3o2)c1C] | 687.3 |

TABLE 4-continued

| EX No. | Chemical Name | Structure | Physical Data (MS) (M + H)+ |
|---|---|---|---|
| 188 | ((6-(difluoromethoxy)-2-(2,2'-dimethyl-3'-(5-methyl-4,5,6,7-tetrahydrooxazolo[5,4-c]pyridin-2-yl)-[1,1'-biphenyl]-3-yl)benzo[d]oxazol-5-yl)methyl)-L-proline | 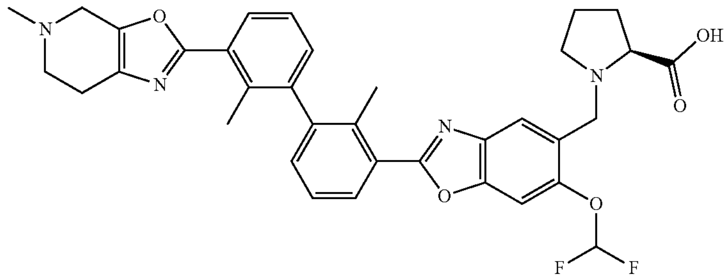 [SMILES: Cc1c(-c2nc3c(o2)CN(C)CC3)cccc1-c1cccc(-c2nc3cc(CN4CCC[C@H]4C(=O)O)c(OC(F)F)cc3o2)c1C] | 629.3 |
| 189 | ((6-(difluoromethoxy)-2-(3'-(5-(2-hydroxyethyl)-4,5,6,7-tetrahydrooxazolo[5,4-c]pyridin-2-yl)-2,2'-dimethyl-[1,1'-biphenyl]-3-yl)benzo[d]oxazol-5-yl)methyl)-L-proline | 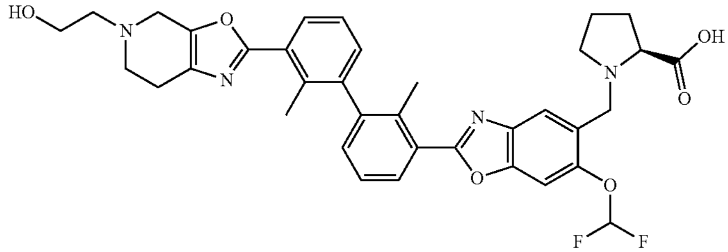 [SMILES: Cc1c(-c2nc3c(o2)CN(CCO)CC3)cccc1-c1cccc(-c2nc3cc(CN4CCC[C@H]4C(=O)O)c(OC(F)F)cc3o2)c1C] | 659.3 |
| 190 | ((6-(difluoromethoxy)-2-(2,2'-dimethyl-3'-(4,5,6,7-tetrahydrooxazolo[4,5-c]pyridin-2-yl)-[1,1'-biphenyl]-3-yl)benzo[d]oxazol-5-yl)methyl)-L-proline | 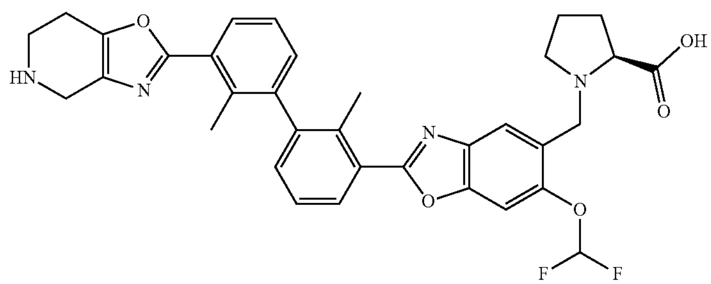 [SMILES: Cc1c(-c2nc3c(o2)CCNC3)cccc1-c1cccc(-c2nc3cc(CN4CCC[C@H]4C(=O)O)c(OC(F)F)cc3o2)c1C] | 615.2 |
| 191 | ((6-(difluoromethoxy)-2-(2,2'-dimethyl-3'-(5-(4,4,4-trifluorobutyl)-4,5,6,7-tetrahydrooxazolo[4,5-c]pyridin-2-yl)-[1,1'-biphenyl]-3-yl)benzo[d]oxazol-5-yl)methyl)proline | 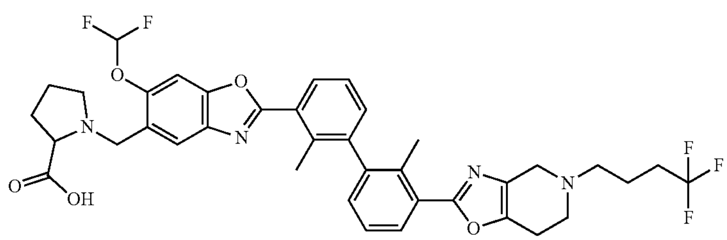 [SMILES: Cc1c(-c2nc3c(o2)CCN(CCCC(F)(F)F)C3)cccc1-c1cccc(-c2nc3cc(CN4CCCC4C(=O)O)c(OC(F)F)cc3o2)c1C] | 725.3 |
| 192 | ((6-(difluoromethoxy)-2-(2,2'-dimethyl-3'-(5-(oxetan-2-ylmethyl)-4,5,6,7-tetrahydrooxazolo[4,5-c]pyridin-2-yl)-[1,1'-biphenyl]-3-yl)benzo[d]oxazol-5-yl)methyl)proline | 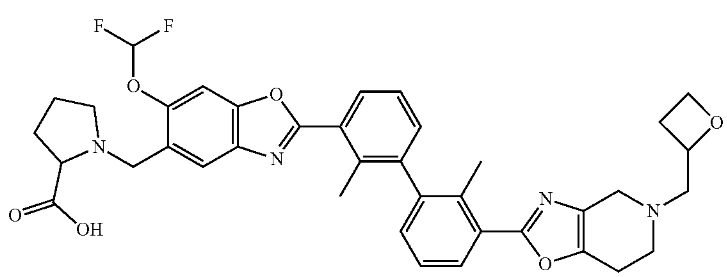 [SMILES: Cc1c(-c2nc3c(o2)CCN(CC2CCO2)C3)cccc1-c1cccc(-c2nc3cc(CN4CCCC4C(=O)O)c(OC(F)F)cc3o2)c1C] | 685.3 |

TABLE 4-continued

| EX No. | Chemical Name | Structure | Physical Data (MS) (M + H)+ |
|---|---|---|---|
| 193 | ((6-(difluoromethoxy)-2-(2,2'-dimethyl-3'-(5-((5-oxopyrrolidin-2-yl)methyl)-4,5,6,7-tetrahydrooxazolo[4,5-c]pyridin-2-yl)-[1,1'-biphenyl]-3-yl)benzo[d]oxazol-5-yl)methyl)proline | 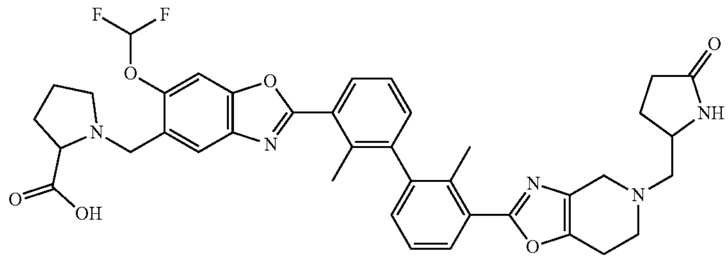 [SMILES: Cc1c(-c2nc3c(o2)CCN(CC2CCC(=O)N2)C3)cccc1-c1cccc(-c2nc3cc(CN4CCCC4C(=O)O)c(OC(F)F)cc3o2)c1C] | 712.3 |
| 194 | ((6-(difluoromethoxy)-2-(2,2'-dimethyl-3'-(5-(pyridin-3-ylmethyl)-4,5,6,7-tetrahydrooxazolo[4,5-c]pyridin-2-yl)-[1,1'-biphenyl]-3-yl)benzo[d]oxazol-5-yl)methyl)proline | 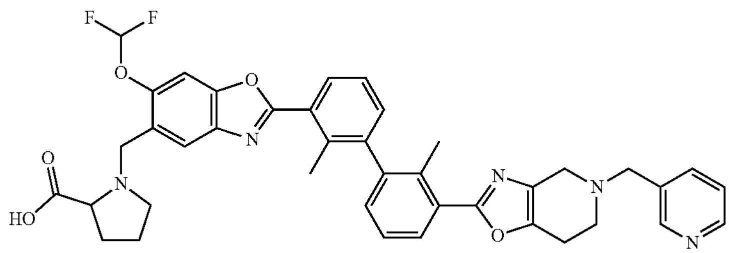 [SMILES: Cc1c(-c2nc3c(o2)CCN(Cc2cccnc2)C3)cccc1-c1cccc(-c2nc3cc(CN4CCCC4C(=O)O)c(OC(F)F)cc3o2)c1C] | 706.3 |
| 195 | ((2-(3'-(5-(cyanomethyl)-4,5,6,7-tetrahydrooxazolo[4,5-c]pyridin-2-yl)-2,2'-dimethyl-[1,1'-biphenyl]-3-yl)-6-(difluoromethoxy)benzo[d]oxazol-5-yl)methyl)proline | 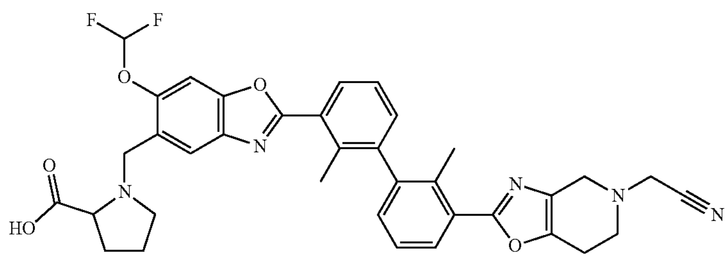 [SMILES: Cc1c(-c2nc3c(o2)CCN(CC#N)C3)cccc1-c1cccc(-c2nc3cc(CN4CCCC4C(=O)O)c(OC(F)F)cc3o2)c1C] | 654.2 |
| 196 | ((2-(3'-(5-(2-amino-2-oxoethyl)-4,5,6,7-tetrahydrooxazolo[4,5-c]pyridin-2-yl)-2,2'-dimethyl-[1,1'-biphenyl]-3-yl)-6-(difluoromethoxy)benzo[d]oxazol-5-yl)methyl)proline | 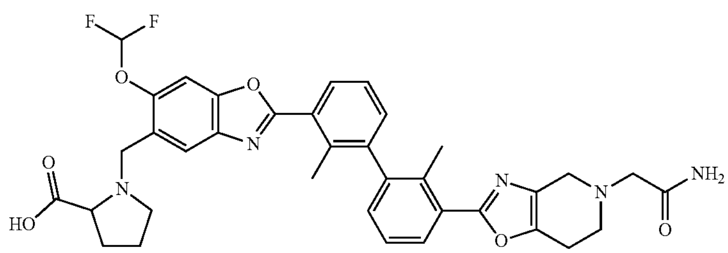 [SMILES: Cc1c(-c2nc3c(o2)CCN(CC(N)=O)C3)cccc1-c1cccc(-c2nc3cc(CN4CCCC4C(=O)O)c(OC(F)F)cc3o2)c1C] | 672.3 |
| 197 | ((6-(difluoromethoxy)-2-(3'-(5-(ethylsulfonyl)-4,5,6,7-tetrahydrooxazolo[4,5-c]pyridin-2-yl)-2,2'-dimethyl-[1,1'-biphenyl]-3-yl)benzo[d]oxazol-5-yl)methyl)proline | 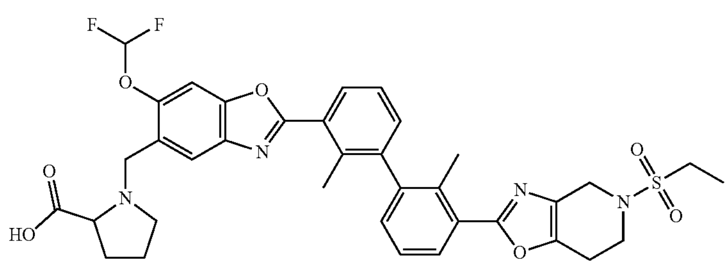 [SMILES: CCS(=O)(=O)N1CCc2oc(-c3cccc(-c4cccc(-c5nc6cc(CN7CCCC7C(=O)O)c(OC(F)F)cc6o5)c4C)c3C)nc2C1] | 707.2 |
| 198 | ((6-(difluoromethoxy)-2-(2,2'-dimethyl-3'-(5-(3,3,3-trifluoropropyl)-4,5,6,7-tetrahydrooxazolo[4,5-c]pyridin-2-yl)-[1,1'-biphenyl]-3-yl)benzo[d]oxazol-5-yl)methyl)proline | 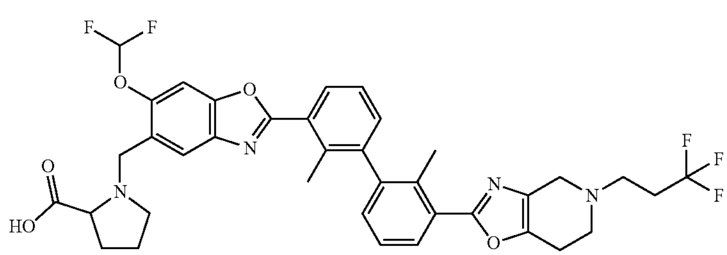 [SMILES: Cc1c(-c2nc3c(o2)CCN(CCC(F)(F)F)C3)cccc1-c1cccc(-c2nc3cc(CN4CCCC4C(=O)O)c(OC(F)F)cc3o2)c1C] | 711.2 |

TABLE 4-continued

| EX No. | Chemical Name | Structure | Physical Data (MS) (M + H)+ |
|---|---|---|---|
| 199 | ((6-(difluoromethoxy)-2-(3'-(5-(3-hydroxypropyl)-4,5,6,7-tetrahydrooxazolo[4,5-c]pyridin-2-yl)-2,2'-dimethyl-[1,1'-biphenyl]-3-yl)benzo[d]oxazol-5-yl)methyl)proline | 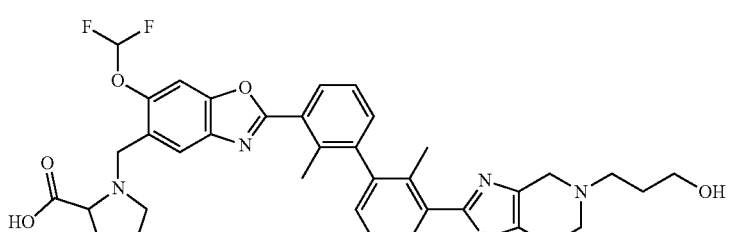 | 673.3 |
| 200 | ((6-(difluoromethoxy)-2-(3'-(5-(3-fluoropropyl)-4,5,6,7-tetrahydrooxazolo[4,5-c]pyridin-2-yl)-2,2'-dimethyl-[1,1'-biphenyl]-3-yl)benzo[d]oxazol-5-yl)methyl)proline | 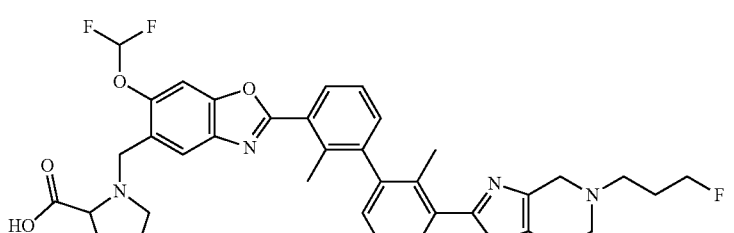 | 675.3 |
| 201 | ((2-(3'-(5-(2,2-difluoroethyl)-4,5,6,7-tetrahydrooxazolo[4,5-c]pyridin-2-yl)-2,2'-dimethyl-[1,1'-biphenyl]-3-yl)-6-(difluoromethoxy)benzo[d]oxazol-5-yl)methyl)proline | 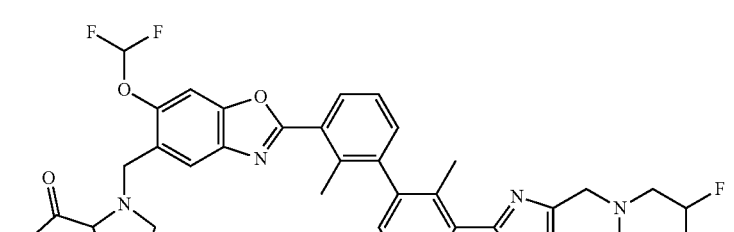 | 679.3 |
| 202 | ((6-(difluoromethoxy)-2-(3'-(5,6-dihydro-4H-pyrrolo[3,4-d]oxazol-2-yl)-2,2'-dimethyl-[1,1'-biphenyl]-3-yl)benzo[d]oxazol-5-yl)methyl)proline | 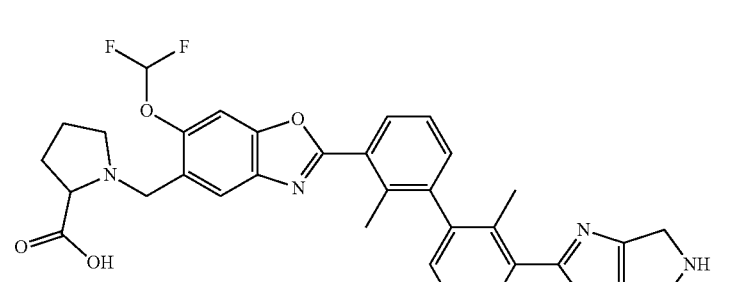 | 601.2 |
| 203 | ((6-(difluoromethoxy)-2-(3'-(6,7-dihydro-4H-pyrano[3,4-d]oxazol-2-yl)-2,2'-dimethyl-[1,1'-biphenyl]-3-yl)benzo[d]oxazol-5-yl)methyl)proline | 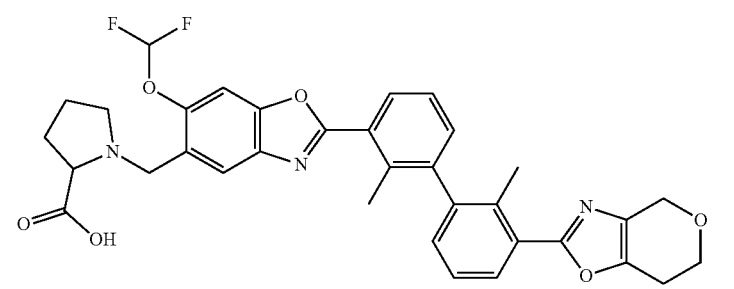 [SMILES: Cc1c(-c2nc3c(o2)CCOC3)cccc1-c1cccc(-c2nc3cc(CN4CCCC4C(=O)O)c(OC(F)F)cc3o2)c1C] | 616.2 |

TABLE 4-continued

| EX No. | Chemical Name | Structure | Physical Data (MS) (M + H)+ |
|---|---|---|---|
| 204 | ((6-(difluoromethoxy)-2-(3'-(5,6-dihydro-4H-cyclopenta[d]oxazol-2-yl)-2,2'-dimethyl-[1,1'-biphenyl]-3-yl)benzo[d]oxazol-5-yl)methyl)proline | 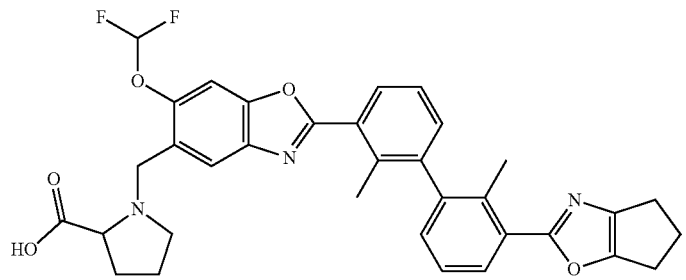 [SMILES: Cc1c(-c2nc3c(o2)CCC3)cccc1-c1cccc(-c2nc3cc(CN4CCCC4C(=O)O)c(OC(F)F)cc3o2)c1C] | 600.2 |
| 205 | ((6-(difluoromethoxy)-2-(2,2'-dimethyl-3'-(4,5,6,7-tetrahydrobenzo[d]oxazol-2-yl)-[1,1'-biphenyl]-3-yl)benzo[d]oxazol-5-yl)methyl)proline | 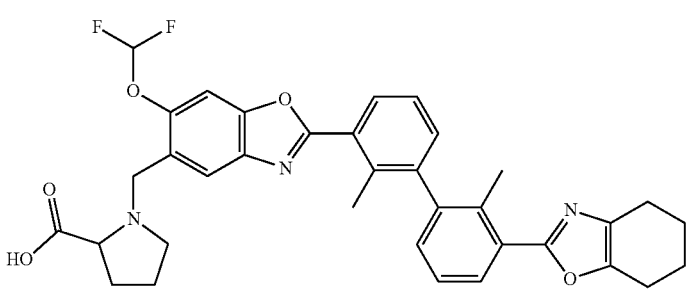 [SMILES: Cc1c(-c2nc3c(o2)CCCC3)cccc1-c1cccc(-c2nc3cc(CN4CCCC4C(=O)O)c(OC(F)F)cc3o2)c1C] | 614.2 |
| 206 | ((6-(difluoromethoxy)-2-(3'-(5-(2-hydroxyethyl)-4,5,6,7-tetrahydrooxazolo[4,5-c]pyridin-2-yl)-2,2'-dimethyl-[1,1'-biphenyl]-3-yl)benzo[d]oxazol-5-yl)methyl)-L-proline | 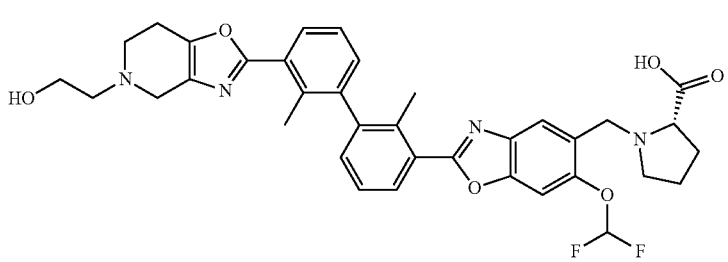 [SMILES: Cc1c(-c2nc3c(o2)CCN(CCO)C3)cccc1-c1cccc(-c2nc3cc(CN4CCC[C@H]4C(=O)O)c(OC(F)F)cc3o2)c1C] | 659.3 |
| 207 | 2-((2-(2'-cyano-2-methyl-3'-(4,5,6,7-tetrahydrooxazolo[4,5-c]pyridin-2-yl)-[1,1'-biphenyl]-3-yl)-6-(difluoromethoxy)benzo[d]oxazol-5-yl)methyl)pyrrolidine-1-carboxylic acid | 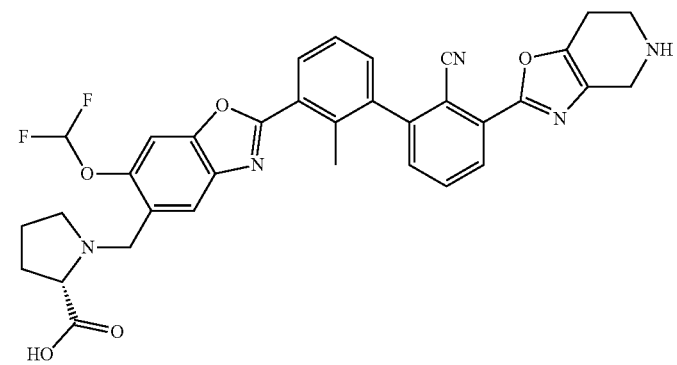 [SMILES: Cc1c(-c2nc3cc(CN4CCC[C@H]4C(=O)O)c(OC(F)F)cc3o2)cccc1-c1cccc(-c2nc3c(o2)CCNC3)c1C#N] | 626.2 |

Example 208 Synthesis of Compound 208

((2-(3'-((2-chloro-5-((5-(difluoromethoxy)pyridin-3-yl)methoxy)-4-(((R)-3-hydroxypyrrolidin-1-yl)methyl)phenoxy)methyl)-2,2'-dimethyl-[1,1'-biphenyl]-3-yl)-6-(difluoromethoxy)benzo[d]oxazol-5-yl)methyl)-L-proline

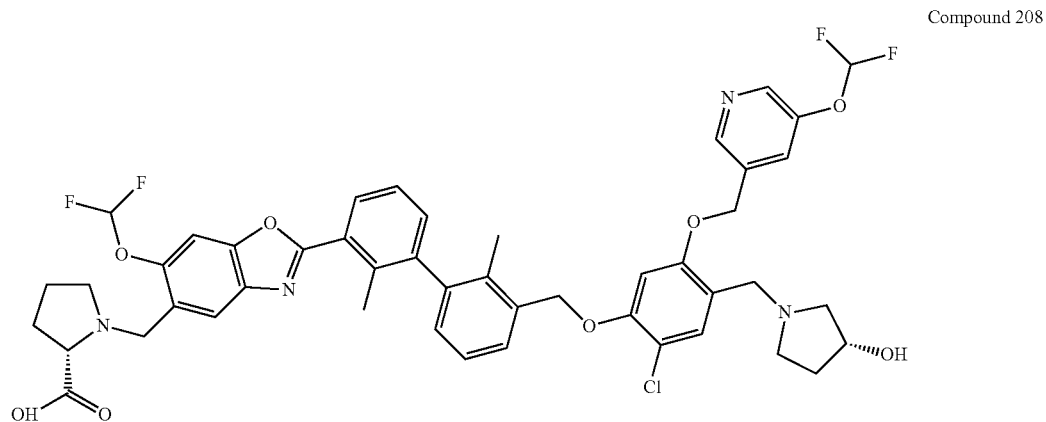 [SMILES: Cc1c(COc2cc(OCc3cncc(OC(F)F)c3)c(CN3CC[C@@H](O)C3)cc2Cl)cccc1-c1cccc(-c2nc3cc(CN4CCC[C@H]4C(=O)O)c(OC(F)F)cc3o2)c1C]

Compound 208

Step 1: Preparation of 1-bromo-3-(chloromethyl)-2-methylbenzene

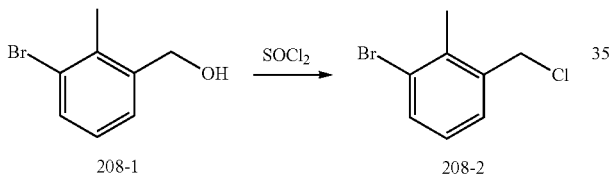

(3-bromo-2-methylphenyl)methanol (20 g) was dissolved in DCM (200 ml), stirred at room temperature, and slowly added 20 ml SOCl$_2$. The mixture was stirred for 2 hrs and then concentrated to give 1-bromo-3-(chloromethyl)-2-methylbenzene (23.1 g).

Step 2: Preparation of 4-((3-bromo-2-methylbenzyl)oxy)-5-chloro-2-hydroxybenzaldehyde

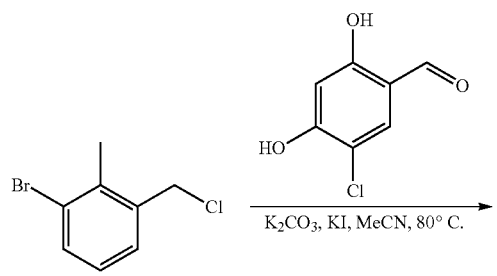

-continued 208-3

A mixture of 1-bromo-3-(chloromethyl)-2-methylbenzene (2.0 g), 5-chloro-2,4-dihydroxybenzaldehyde (2.34 g), potassium carbonate (3.78 g), KI (1.51 g) in acetonitrile (20 mL) was stirred at 80° C. overnight. The reaction was completed and added 20 mL water to concentrate, filtered and dried to give 4-((3-bromo-2-methylbenzyl)oxy)-5-chloro-2-hydroxybenzaldehyde (2.8 g).

Step 3: Preparation of 4-((3-bromo-2-methylbenzyl)oxy)-5-chloro-2-((5-(difluoromethoxy)pyridin-3-yl)methoxy)benzaldehyde

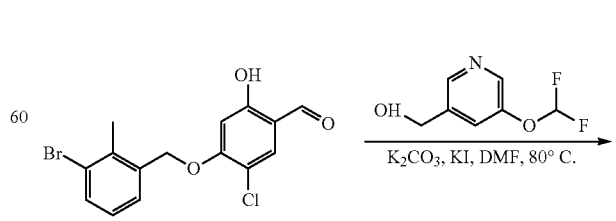

-continued

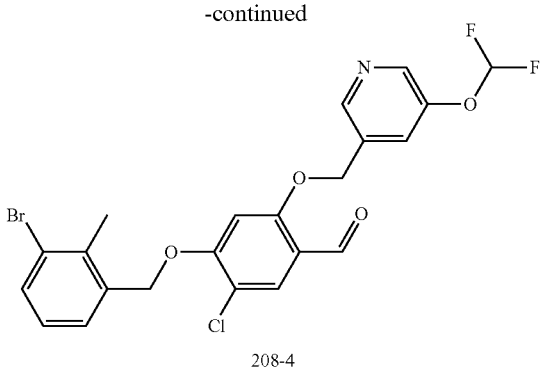

208-4

Compound 208-3 (500 mg), (5-(difluoromethoxy)pyridin-3-yl)methanol (408 mg), potassium carbonate (585 mg), KI (195 mg) was added to acetonitrile (10 mL), the reaction mixture was stirred at 80° C. overnight. 10 mL water was added, the mixture was concentrated, filtered and dried to give 4-((3-bromo-2-methylbenzyl) oxy)-5-chloro-2-((5-(difluoromethoxy) pyridin-3-yl) methoxy) benzaldehyde (478 mg).

Step 4: Preparation of methyl ((2-(3'-((2-chloro-5-((5-(difluoromethoxy)pyridin-3-yl)methoxy)-4-formylphenoxy)methyl)-2,2'-dimethyl-[1,1'-biphenyl]-3-yl)-6-(difluoromethoxy)benzo[d]oxazol-5-yl)methyl)-L-prolinat

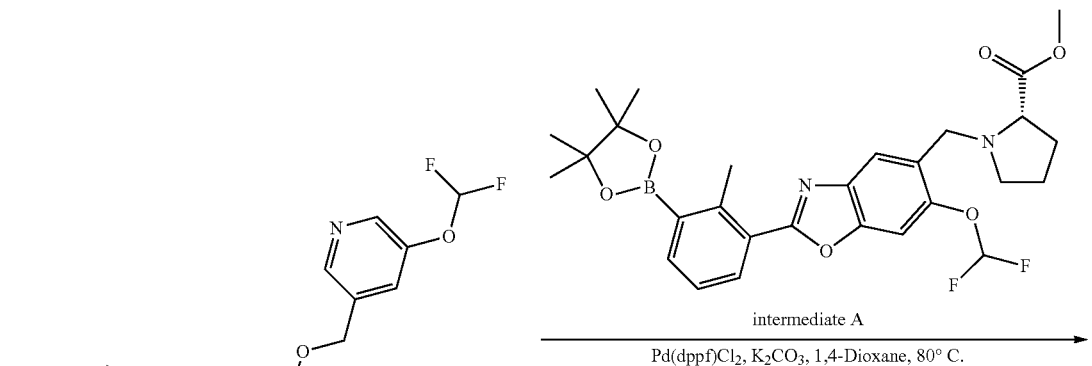

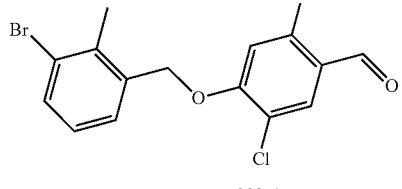

208-4

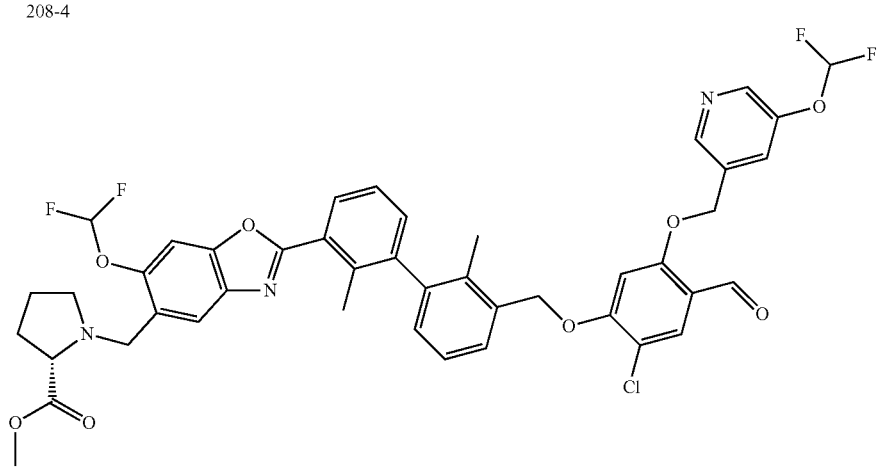

208-5

Compound 208-4 (470 mg), intermediate A (597 mg) and potassium carbonate (236 mg) were added to 1,4-dioxane (12 mL) and water (3 mL) with stirring, and then Pd(dppf)Cl$_2$ was added to the mixture under N$_2$ atmosphere. The reaction mixture was heated to 80° C. and stirred overnight. The mixture was quenched with water (30 mL) and extract with DCM (30 mL×3). The organic layers were dried over anhydrous sodium sulfate, filter, concentrate and purified by column (DCM/MeOH: 15/1) to obtain compound 208-5 (550 mg).

Step 5: Preparation of methyl ((2-(3'-((2-chloro-5-((5-(difluoromethoxy)pyridin-3-yl)methoxy)-4-(((R)-3-hydroxypyrrolidin-1-yl)methyl)phenoxy)methyl)-2,2'-dimethyl-[1,1'-biphenyl]-3-yl)-6-(difluoromethoxy)benzo[d]oxazol-5-yl)methyl)-L-prolinate

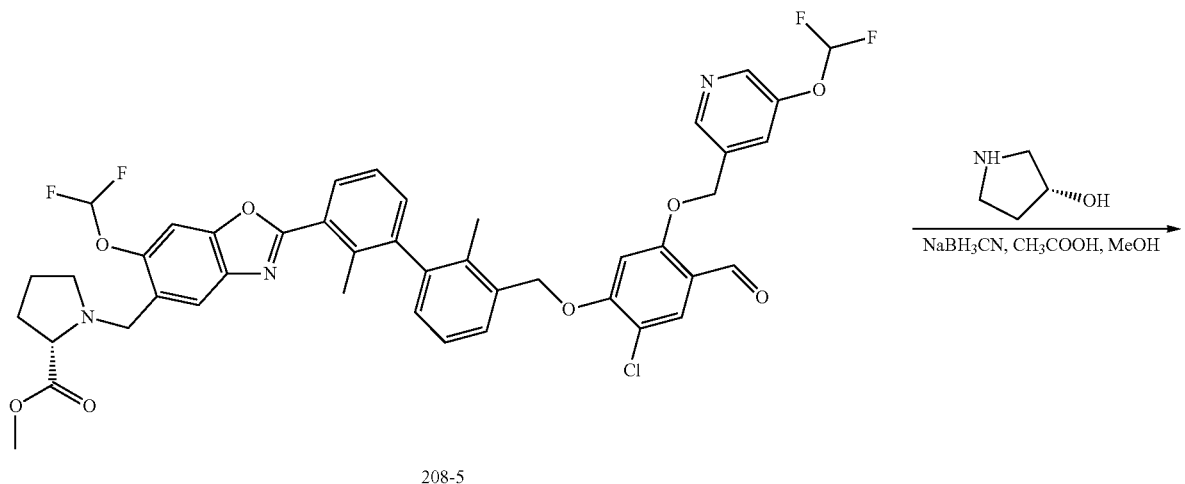

208-5

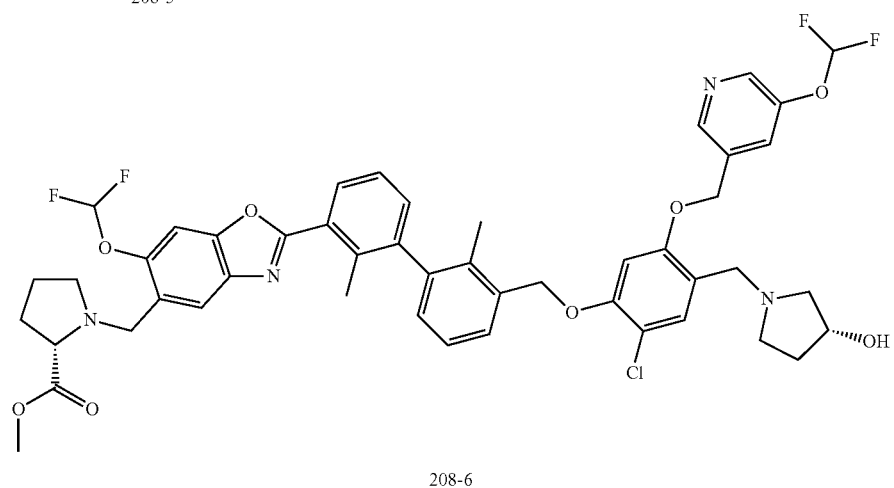

208-6

Compound 208-5 (270 mg), (R)-pyrrolidin-3-ol (80 mg), glacial acetic acid (40 mg) were added to 10 mL methanol with stirring, the mixture was heated to 50° C. and stirred for 1 h. After the mixture was cooled to room temperature, sodium cyanoborohydride was added and the mixture was stirred at room temperature for 2 hrs. Then the mixture was diluted with water (10 mL) and extract with DCM (15 mL×3), the organic layers were dried over anhydrous sodium sulfate, filtered, concentrated and purified by column (DCM/MeOH=15/1) to obtain compound 208-6 (110 mg).

Step 6: Preparation of ((2-(3'-((2-chloro-5-((5-(difluoromethoxy)pyridin-3-yl)methoxy)-4-(((R)-3-hydroxypyrrolidin-1-yl)methyl)phenoxy)methyl)-2,2'-dimethyl-[1,1'-biphenyl]-3-yl)-6-(difluoromethoxy)benzo[d]oxazol-5-yl)methyl)-L-proline (compound 208)

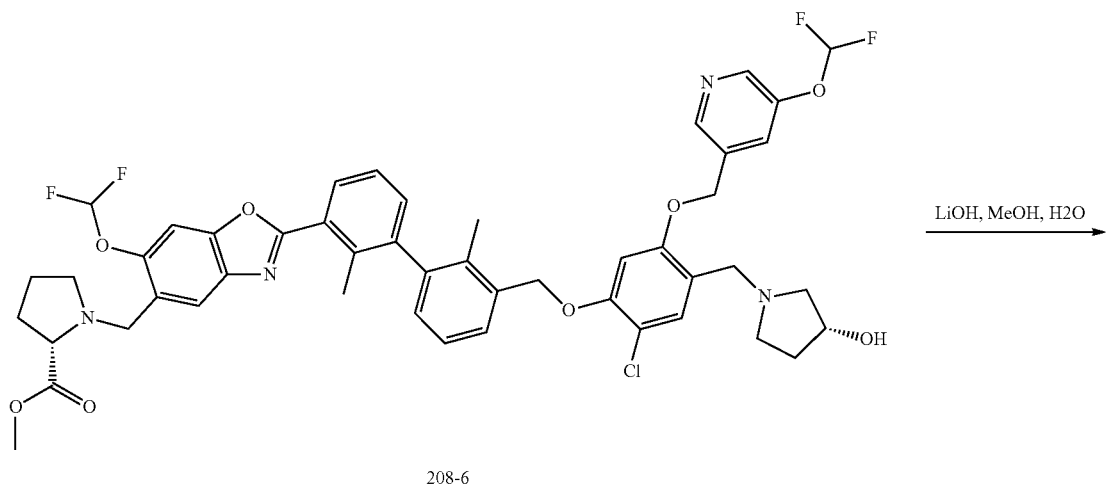

208-6

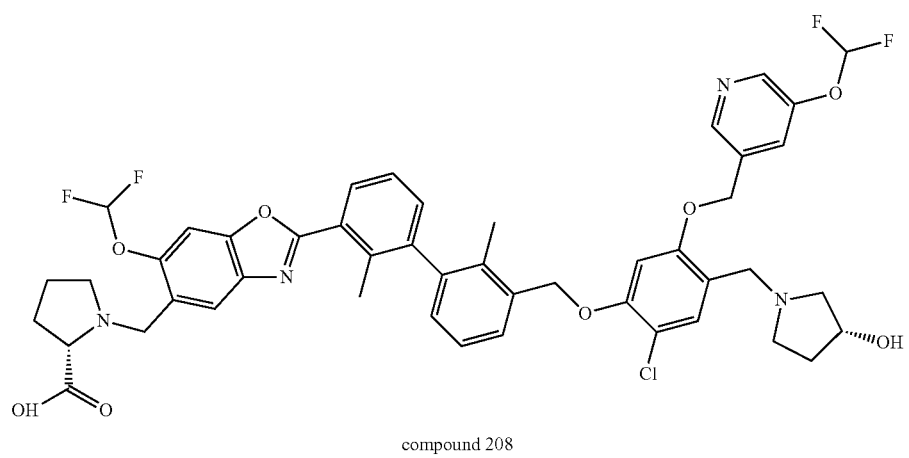

compound 208

Compound 208-6 (110 mg) was added to 5 mL methanol under stirring, and 8 mg LiOH was weighed and dissolved in 1 mL water, and then added to the mixture, the reaction mixture was heated to 35° C. overnight. The mixture was added with 10 mL water and extracted with DCM (15 mL×3). The organic layers were dried over anhydrous sodium sulfate, filtered and concentrated to give 105 mg ((2-(3'-((2-chloro-5-((5-(difluoromethoxy)pyridin-3-yl)methoxy)-4-(((R)-3-hydroxypyrrolidin-1-yl)methyl)phenoxy)methyl)-2,2'-dimethyl-[1,1'-biphenyl]-3-yl)-6-(difluoromethoxy)benzo[d]oxazol-5-yl)methyl)-L-proline (compound 208). LC-MS (m/z): 905.3 (M+H)$^+$.

The compounds of table 5 were prepared in a similar manner to Example 208 via different reaction starting materials and suitable reagents.

TABLE 5

| EX No. | Chemical Name | Structure | Physical Data (MS) (M + H)+ |
|---|---|---|---|
| 209 | ((2-(3'-((2-chloro-5-((5-(difluoromethoxy)pyridin-3-yl)methoxy)-4-((3-fluoropyrrolidin-1-yl)methyl)phenoxy)methyl)-2,2'-dimethyl-[1,1'-biphenyl]-3-yl)-6-(difluoromethoxy)benzo[d]oxazol-5-yl)methyl)-L-proline | 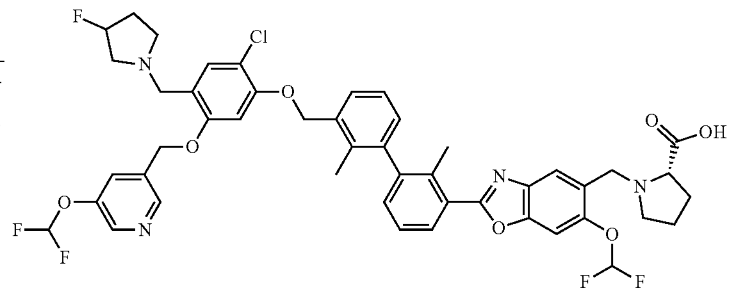 | 907.3 |
| 210 | ((2-(3'-(4-(((2-acetamidoethyl)amino)methyl)-2-chloro-5-((3-cyanobenzyl)oxy)phenoxy)methyl)-2,2'-dimethyl-[1,1'-biphenyl]-3-yl)-6-(difluoromethoxy)benzo[d]oxazol-5-yl)methyl)-L-proline | 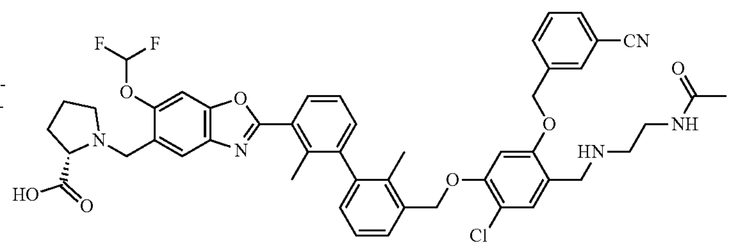 | 878.3 |
| 211 | ((2-(3'-(4-(((S)-2-carboxypyrrolidin-1-yl)methyl)-2-chloro-5-((3-cyanobenzyl)oxy)phenoxy)methyl)-2,2'-dimethyl-[1,1'-biphenyl]-3-yl)-6-(difluoromethoxy)benzo[d]oxazol-5-yl)methyl)-L-proline | 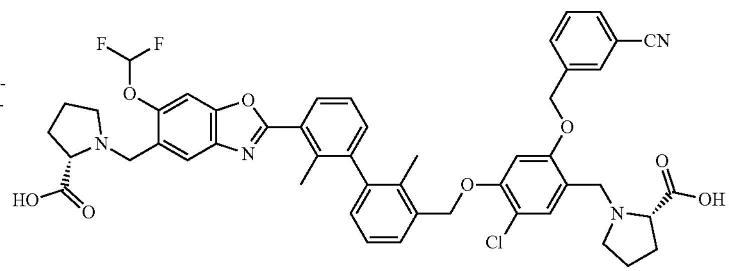 | 891.3 |
| 212 | ((6-(difluoromethoxy)-2-(3'-(((4,6-dimethoxy-5-(pyrrolidin-1-ylmethyl)pyrimidin-2-yl)oxy)methyl)-2,2'-dimethyl-[1,1'-biphenyl]-3-yl)benzo[d]oxazol-5-yl)methyl)-L-proline | 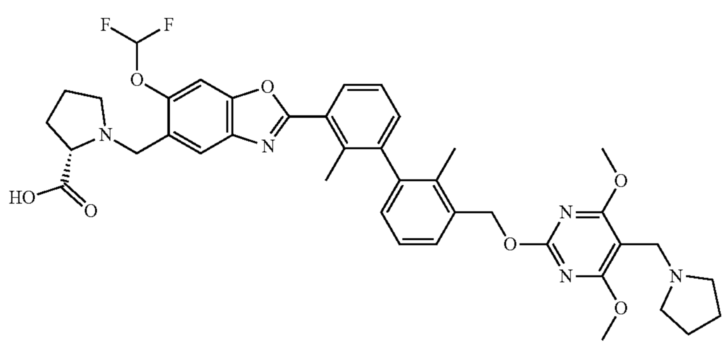 [SMILES: COc1nc(OCc2cccc(-c3cccc(-c4nc5cc(CN6CCC[C@H]6C(=O)O)c(OC(F)F)cc5o4)c3C)c2C)nc(OC)c1CN1CCCC1] | 744.3 |
| 213 | ((6-(difluoromethoxy)-2-(3'-(((5-((3,3-dimethylazetidin-1-yl)methyl)-4,6-dimethoxypyrimidin-2-yl)oxy)methyl)-2,2'-dimethyl-[1,1'-biphenyl]-3-yl)benzo[d]oxazol-5-yl)methyl)-L-proline | 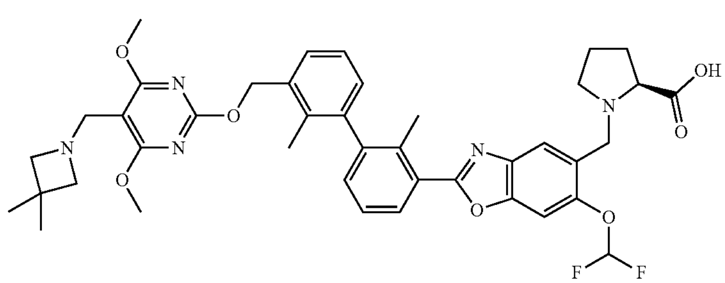 [SMILES: COc1nc(OCc2cccc(-c3cccc(-c4nc5cc(CN6CCC[C@H]6C(=O)O)c(OC(F)F)cc5o4)c3C)c2C)nc(OC)c1CN1CC(C)(C)C1] | 758.3 |

TABLE 5-continued

| EX No. | Chemical Name | Structure | Physical Data (MS) (M + H)+ |
|---|---|---|---|
| 214 | ((6-(difluoromethoxy)-2-(2,2'-dimethyl-3'-((5-(((((S)-5-oxopyrrolidin-2-yl)methyl)amino)methyl)pyridin-2-yl)oxy)-[1,1'-biphenyl]-3-yl)benzo[d]oxazol-5-yl)methyl)-L-proline | 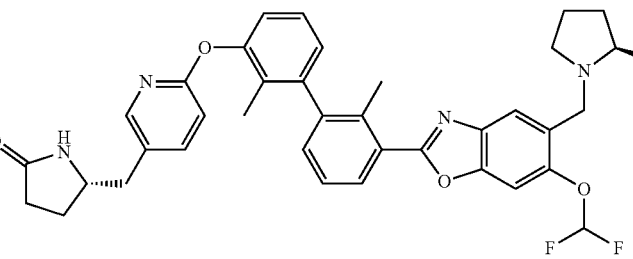 | 712.3 |

Example 242 Synthesis of Compound 242

((6-(difluoromethoxy)-2-(4''-((3-fluoropyrrolidin-1-yl)methyl)-2,2'-dimethyl-[1,1':3',1''-terphenyl]-3-yl)benzo[d]oxazol-S-yl)methyl)proline Compound 242

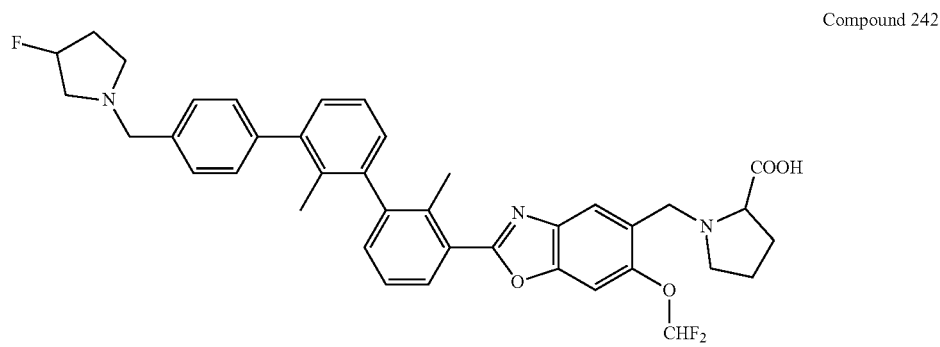 [SMILES: Cc1c(-c2ccc(CN3CCC(F)C3)cc2)cccc1-c1cccc(-c2nc3cc(CN4CCCC4C(=O)O)c(OC(F)F)cc3o2)c1C]

Step 1: Preparation of 4-(4,4,5,5-tetramethyl-1,3,2-dioxaborolan-2-yl)benzaldehyde

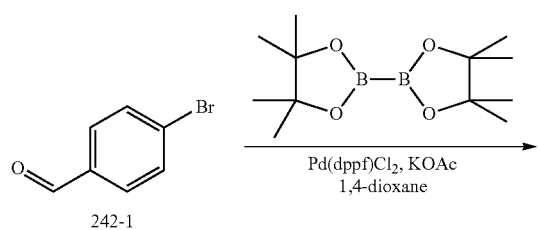

To a solution of 4-bromobenzaldehyde (9.25 g) in 1,4-dioxane (120 mL) was added Bis(pinacolato)diboron (15.8 g), Pd(dppf)Cl₂·DCM (0.48 g) and KOAc (20.0 g). The reaction mixture was heated at 100° C. for 4 hrs. The mixture was diluted with 150 mL of water and then extracted with EtOAc (150 mL×2). The combined organic extracts were washed with brine, dried over MgSO₄ and concentrated in vacuo. The residue was purified by silicagel (eluting with hexane-EtOAc using a gradient from 20:1 to 10:1) to afford 4-(4,4,5,5-tetramethyl-1,3,2-dioxaborolan-2-yl)benzaldehyde (11.2 g) as white solid.

Step 2: Preparation of 3'-bromo-2'-methyl-[1,1'-biphenyl]-4-carbaldehyde

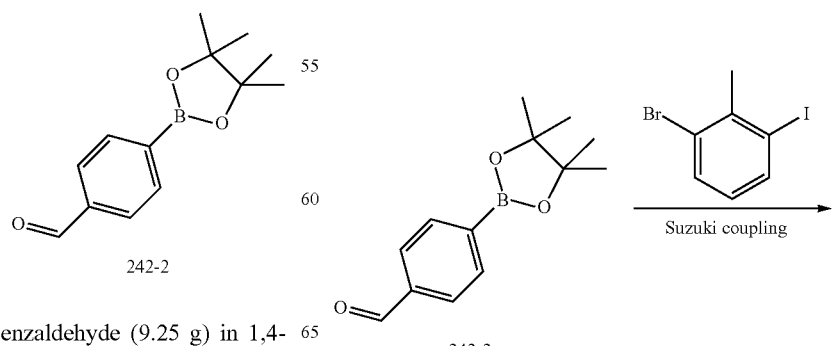

217

-continued

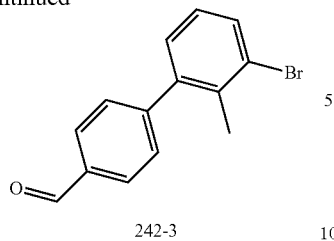

242-3

To a solution of compound 242-2 (60 mL) in EtOH (20 mL), was added 10% Na₂CO₃ aq. (20 mL) and Pd(dppf)Cl₂·DCM (420 mg), and then 1-bromo-3-iodo-2-methylbenzene (9.0 g) was added dropwise under N₂ protection. The mixture was stirred at 100° C. for 16 hrs. The reaction was quenched with H₂O (50 mL) and extracted with EtOAc (100 mL) for 3 times. The organic layers were combined and washed with brine. The resulting solution was concentrated and purified by silicagel (eluting with hexane-EtOAc using a gradient from 20:1 to 10:1) to afford 3'-bromo-2'-methyl-[1,1'-biphenyl]-4-carbaldehyde (3.2 g) as a light yellow solid.

Step 3: Preparation of 1-((3'-bromo-2'-methyl-[1,1'-biphenyl]-4-yl)methyl)-3-fluoropyrrolidine

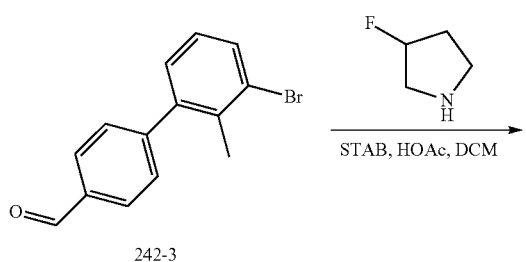

218

-continued

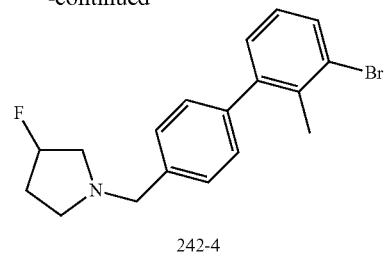

242-4

3'-bromo-2'-methyl-[1,1'-biphenyl]-4-carbaldehyde (275 mg) was dissolved in 5 mL DCM. 3-fluoropyrrolidine (120 mg) and HOAC was added in one portion. The resulting mixture was stirred for 1 h at room temperature then STAB (420 mg) was added in one portion at the same temperature. The reaction was allowed to stir at room temperature for 3 h. The resulting mixture was quenched with saturated Na₂CO₃ and extracted with EtOAc (20 mL) for 3 times and the organic phase was dried over Na₂SO₄. The resulting solution was concentrated to afford 1-((3'-bromo-2'-methyl-[1,1'-biphenyl]-4-yl)methyl)-3-fluoropyrrolidine (320 mg) as a colorless oil.

Step 4: Preparation of methyl ((6-(difluoromethoxy)-2-(4"-((3-fluoropyrrolidin-1-yl)methyl)-2,2'-dimethyl-[1,1':3',1"-terphenyl]-3-yl)benzo[d]oxazol-5-yl)methyl)prolinate

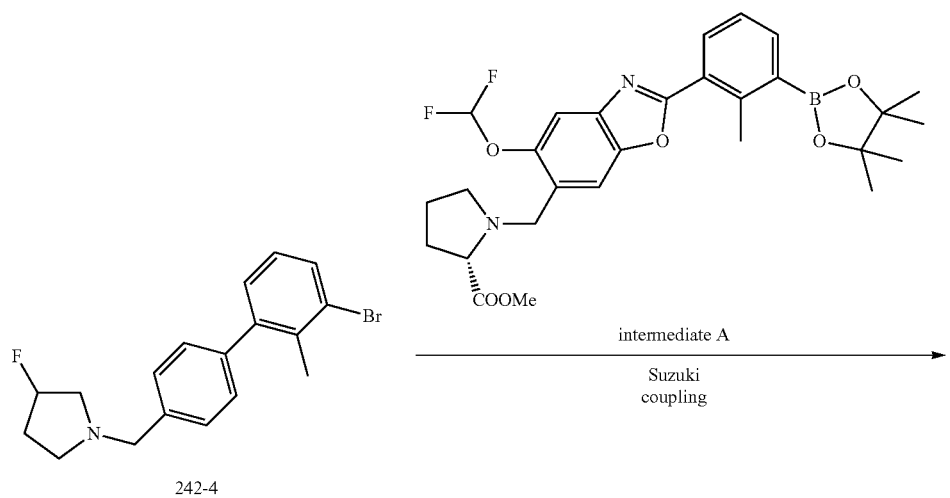

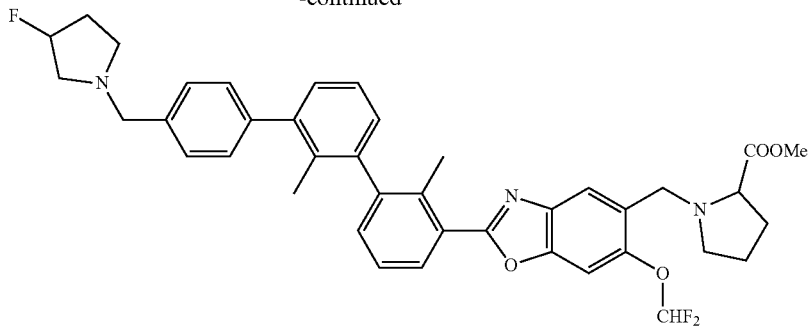

242-5

This compound was prepared using similar procedures as described as step 4 in example 171, with compound 242-4 replacing compound 171-4. The resulting mixture was purified by RP-column (mobile phase: MeCN:water (0.1% HCl) using a gradient from 40:60 to 50:50) to afford compound 242-5 (288 mg).

Step 5: Preparation of ((6-(difluoromethoxy)-2-(4"-((3-fluoropyrrolidin-1-yl)methyl)-2,2'-dimethyl-[1,1':3',1"-terphenyl]-3-yl)benzo[d]oxazol-5-yl)methyl)proline

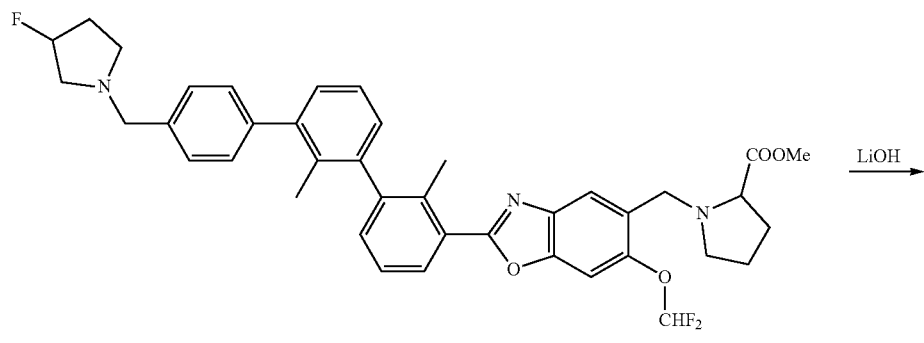

242-5

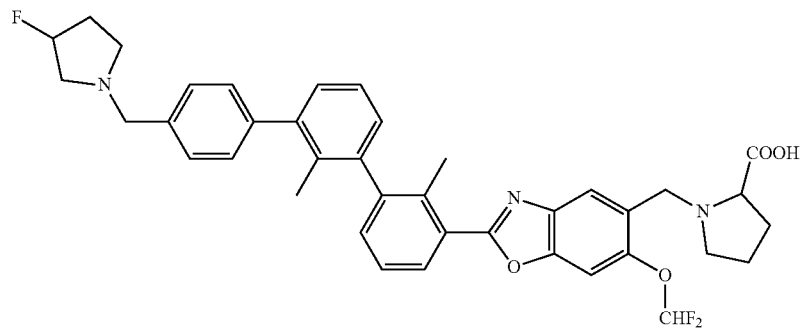

compound 242

This compound was prepared using similar procedures as described as step 6 in example 171, with compound 242-5 replacing compound 171-6. The crude product was purified by RP-column (mobile phase: MeCN:water (0.1% HCl) using a gradient from 40:60 to 50:50) to afford methyl ((6-(difluoromethoxy)-2-(4"-((3-fluoropyrrolidin-1-yl)methyl)-2,2'-dimethyl-[1,1':3',1"-terphenyl]-3-yl)benzo[d]oxazol-5-yl)methyl)prolinate as a white solid (168 mg) (compound 242). LC-MS (m/z): 670.3 (M+H)$^+$.

Example 243 Synthesis of Compound 243

((6-(difluoromethoxy)-2-(4"-((3-fluoropyrrolidin-1-yl)methyl)-2,2'-dimethyl-[1,1':3',1"-terphenyl]-3-yl)benzo[d]oxazol-5-yl)methyl)proline This compound was prepared using similar procedures as described as step 1 in example 1, with 4-bromo-2-fluorobenzaldehyde replacing compound a-6, and with intermediate B replacing intermediate A. The resulting solution was concentrated and purified by silicagel (eluting with Hexane-EtOAc using a gradient from 5:1) to afford the title compound as a yellow oil.

Compound 243

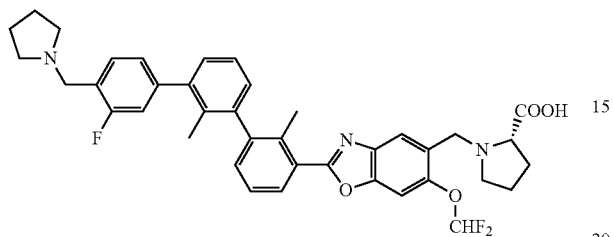

Step 1: Preparation of methyl ((6-(difluoromethoxy)-2-(3"-fluoro-4"-formyl-2,2'-dimethyl-[1,1':3',1"-terphenyl]-3-yl)benzo[d]oxazol-5-yl)methyl)-L-prolinate Step 2: Preparation of methyl ((6-(difluoromethoxy)-2-(4"-((3-fluoropyrrolidin-1-yl)methyl)-2,2'-dimethyl-[1,1':3',1"-terphenyl]-3-yl)benzo[d]oxazol-5-yl)methyl)prolinate

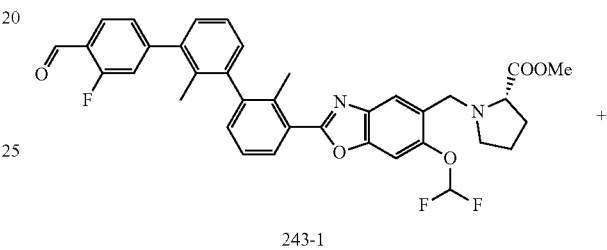

243-1

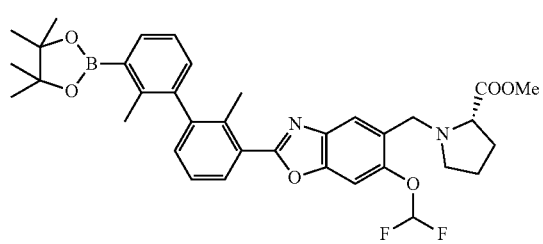

intermediate B

STAB, HOAc

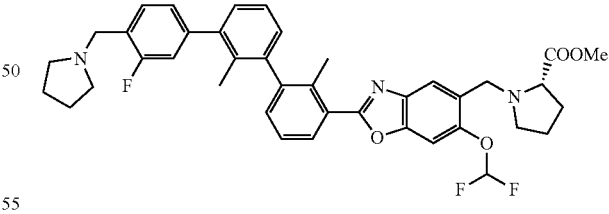

243-2

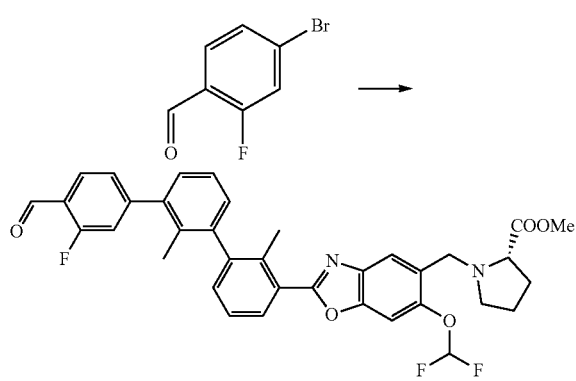

243-1

This compound was prepared using similar procedures as described as step 5 in example 2, with compound 243-1 replacing compound 2-4, and with pyrrolidine replacing L-proline. The resulting solution was concentrated to afford the title compound as a colorless oil.

Step 5: Preparation of ((6-(difluoromethoxy)-2-(3"-fluoro-2,2'-dimethyl-4"-(pyrrolidin-1-ylmethyl)-[1,1':3',1"-terphenyl]-3-yl)benzo[d]oxazol-5-yl)methyl)-L-proline

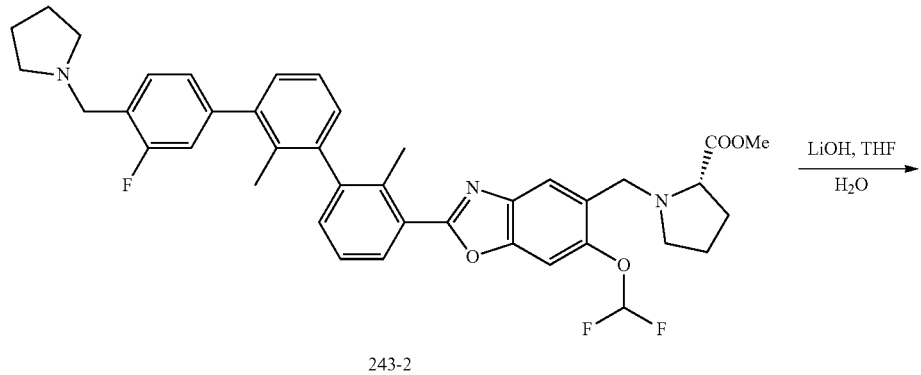

243-2

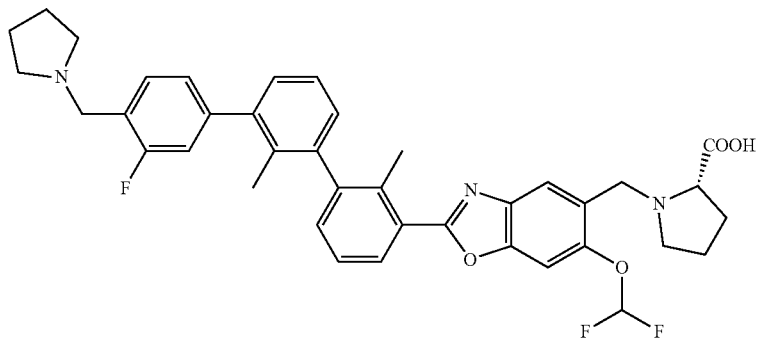

compound 243

This compound was prepared using similar procedures as described as step 5 in example 1, with compound 243-2 replacing compound 1-4. The crude product was purified by RP-column (mobile phase: MeCN:water (0.1% HCl) using a gradient from 10:90 to 30:70) to afford the title compound. LC-MS (m/z): 670.3 (M+H)$^+$. $^1$H NMR (500 MHz, Methanol-d4) δ: 8.16 (dd, 1H, J=7.9, 1.5 Hz), 8.07 (s, 1H), 7.76 (s, 1H), 7.70 (t, 1H, J=7.7 Hz), 7.50 (t, 1H, J=7.7 Hz), 7.43-7.27 (m, 5H), 7.20 (dd, 1H, J=7.5, 1.4 Hz), 7.12 (t, 1H, J$_{F-H}$=72.6 Hz), 4.75 (d, 1H, J=13.1 Hz), 4.54 (d, 1H, J=13.1 Hz), 4.54 (s, 2H), 4.37 (dd, 1H, J=9.5, 7.4 Hz), 3.66-3.60 (m, 3H), 3.45-3.40 (m, 1H), 3.29-3.23 (m, 2H), 2.65-2.57 (m, 1H), 2.49 (s, 3H), 2.28-2.14 (m, 4H), 2.10-2.00 (m, 3H), 1.96 (s, 3H).

Example 244 Synthesis of Compound 244

((6-(difluoromethoxy)-2-(3"-(difluoromethoxy)-2,2'-dimethyl-4"-(pyrrolidin-1-ylmethyl)-[1,1':3',1"-terphenyl]-3-yl)benzo[d]oxazol-5-yl)methyl)-L-proline Compound 244

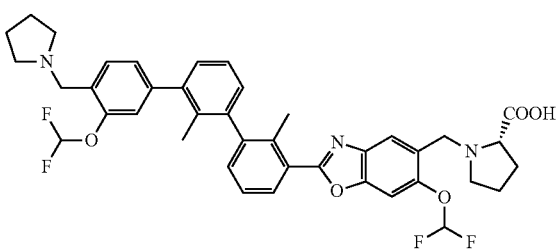

Step 1: Preparation of 4-bromo-2-(difluoromethoxy)benzaldehyde

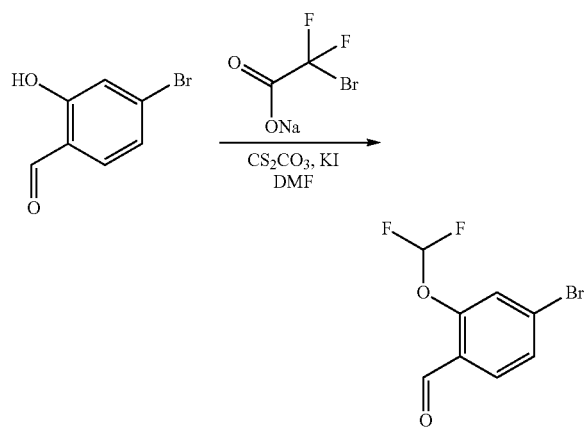

244-1

To a solution of 4-bromo-2-hydroxybenzaldehyde (4.0 g) in DMF (50 mL), Cs$_2$CO$_3$ (9.8 g), KI (400 mg) was added. The mixture was stirred at room temperature for 30 mins, and then sodium 2-bromo-2,2-difluoroacetate (6.0 g) was added in small portions. The mixture was stirred at 75° C. overnight. The mixture was diluted with 100 mL of water and then extracted with EtOAc (100 ml) for three times. The combined organic extracts were washed with brine, dried over MgSO$_4$ and concentrated in vacuo. The residue was purified by silicagel (eluting with hexane-EtOAc using a gradient from 8:1 to 5:1) to afford 4-bromo-2-(difluoromethoxy)benzaldehyde (2.8 g) as a brown oil.

Step 2: Preparation of 5-bromo-2-(pyrrolidin-1-ylmethyl)benzonitrile

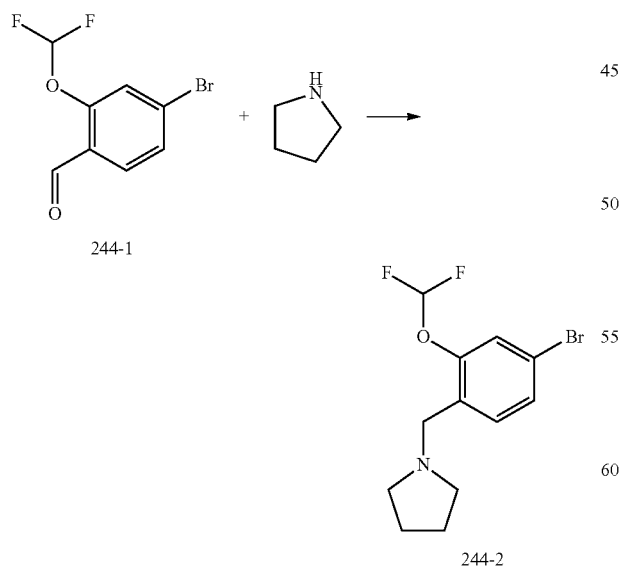

This compound was prepared using similar procedures as described as step 5 in example 2, with compound 244-1 replacing compound 2-4, and with pyrrolidine replacing L-proline. The crude product was purified by silicagel (eluting with DCM-MeOH using a gradient from 20:1 to 10:1) to afford the title compound.

Step 3: Preparation of methyl ((6-(difluoromethoxy)-2-(3''-(difluoromethoxy)-2,2'-dimethyl-4''-(pyrrolidin-1-ylmethyl)-[1,1':3',1''-terphenyl]-3-yl)benzo[d]oxazol-5-yl)methyl)-L-prolinate

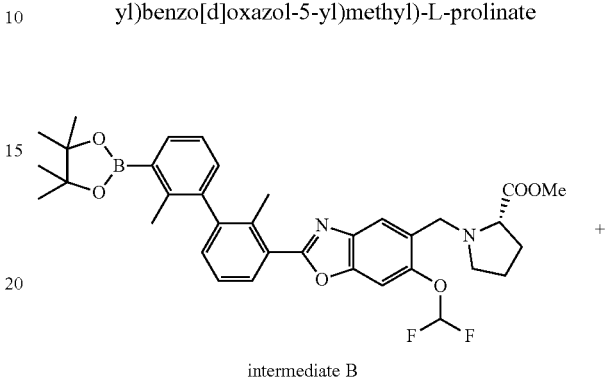

intermediate B

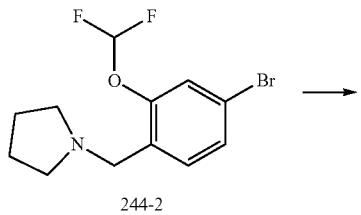

244-3

This compound was prepared using similar procedures as described as step 1 in example 1, with compound 244-2 replacing compound a-6, and with intermediate B replacing intermediate A. The resulting solution was concentrated and purified by silicagel (eluting with Hexane-EtOAc using a gradient from 5:1 to 1:1) to get the title compound.

Step 4: Preparation of ((6-(difluoromethoxy)-2-(3"-(difluoromethoxy)-2,2'-dimethyl-4"-(pyrrolidin-1-ylmethyl)-[1,1':3',1"-terphenyl]-3-yl)benzo[d]oxazol-5-yl)methyl)-L-proline

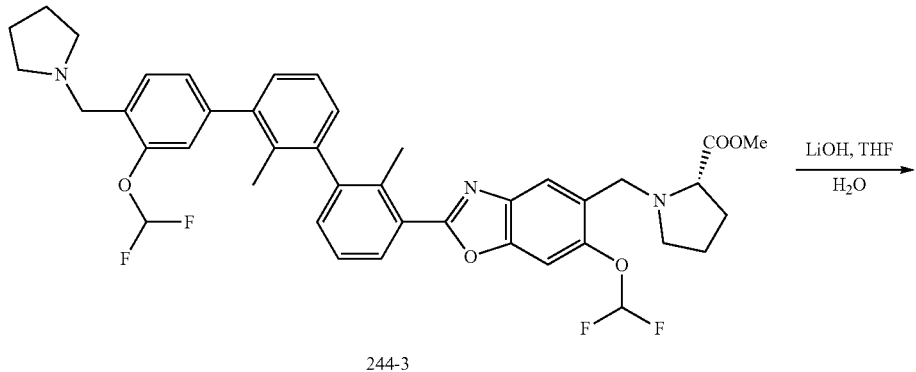

244-3

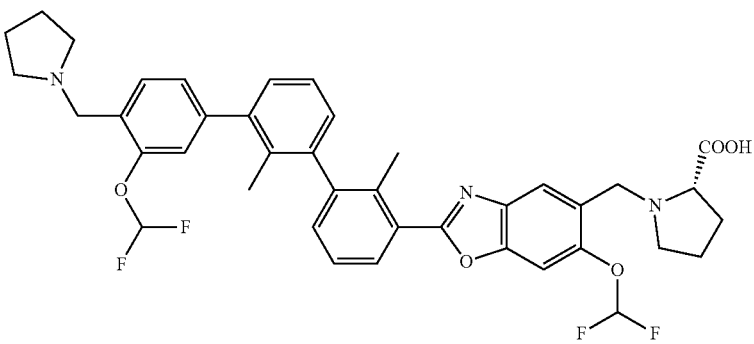

compound 244

This compound was prepared using similar procedures as described as step 5 in example 1, with compound 244-3 replacing compound 1-4. The crude product was purified by RP-column (mobile phase: MeCN:water (0.1% HCl) using a gradient from 10:90 to 35:65) to afford the title compound. LC-MS (m/z): 718.3 (M+H)+. $^1$H NMR (500 MHz, Methanol-d4), δ: 8.16 (dd, 1H, J=7.9, 1.5 Hz), 8.07 (s, 1H), 7.76 (s, 1H), 7.73 (d, 1H, J=7.9 Hz), 7.50 (t, 1H, J=7.7 Hz), 7.42-7.36 (m, 3H), 7.34 (d, 1H, J=1.4 Hz), 7.30 (dd, 1H, J=7.7, 1.4 Hz), 7.21 (dd, 1H, J=7.4, 1.4 Hz), 7.13 (td, 2H, J=72.8, 2.4 Hz), 4.73 (d, 1H, J=13.2 Hz), 4.61 (d, 1H, J=13.2 Hz), 4.53 (s, 2H), 4.30 (dd, 1H, J=9.7, 7.1 Hz), 3.69-3.56 (m, 3H), 3.44-3.38 (m, 1H), 3.31-3.28 (m, 2H), 2.62-2.55 (m, 1H), 2.50 (s, 3H), 2.23-2.15 (m, 4H), 2.12-2.00 (m, 3H), 1.96 (s, 3H)

Example 245 Synthesis of Compound 245

((2-(3"-cyano-2,2'-dimethyl-4"-(pyrrolidin-1-ylmethyl)-[1,1':3',1"-terphenyl]-3-yl)-6-(difluoromethoxy)benzo[d]oxazol-5-yl)methyl)-L-proline Compound 245

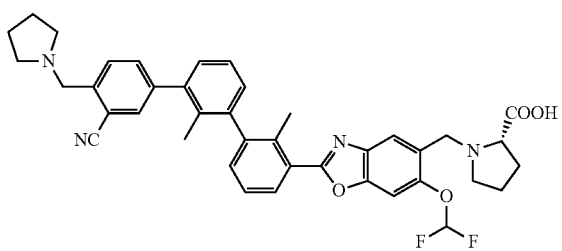

Step 1: Preparation of 5-bromo-2-(bromomethyl)benzonitrile

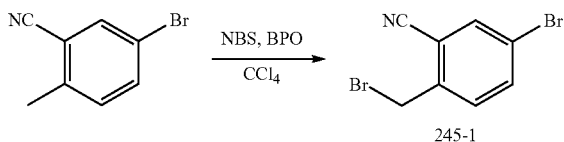

245-1

To a solution of 5-bromo-2-methylbenzonitrile (20.0 g), NBS (19.6 g) in CCl$_4$ (300 mL) was added BPO (2.4 g) under N$_2$ protection. The mixture was allowed to stir at 70° C. overnight. The reaction was quenched with saturated NaHCO$_3$ solution (200 mL). The organic layers were combined and washed with brine. The resulting solution was concentrated and purified by silicagel (eluting with Hexane-EtOAc using a gradient from 20:1 to 1:1) to afford 5-bromo-2-(bromomethyl)benzonitrile (15.2 g) as a yellow solid crude product.

Step 2: Preparation of 5-bromo-2-(pyrrolidin-1-ylmethyl)benzonitrile

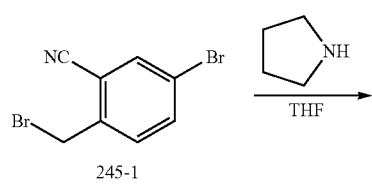

245-1

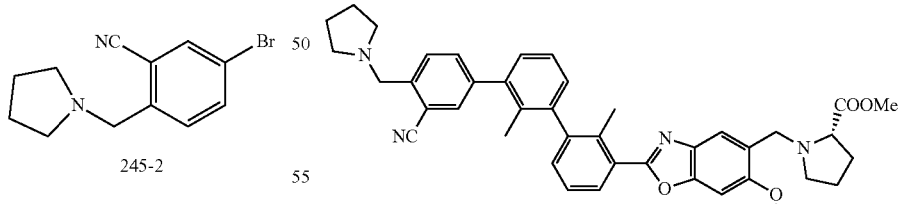

245-2

To a solution of compound 245-1 (5.4 g) in THF (60 mL) was added Pyrrolidine (2.85 g) added dropwise under 0° C. The reaction mixture was heated to 40° C. for 5 hrs. The reaction mixture was diluted with 200 mL of water and then extracted with EtOAc (150 ml) for three times. The combined organic extracts were washed with brine, dried over MgSO$_4$ and concentrated in vacuo. The residue was purified by silicagel (eluting with hexane-EtOAc using a gradient from 2:1 to 1:2) to afford 5-bromo-2-(pyrrolidin-1-ylmethyl)benzonitrile (3.8 g) as a brown oil.

Step 3: Preparation of methyl ((2-(3"-cyano-2,2'-dimethyl-4"-(pyrrolidin-1-ylmethyl)-[1,1':3',1"-terphenyl]-3-yl)-6-(difluoromethoxy)benzo[d]oxazol-5-yl)methyl)-L-prolinate

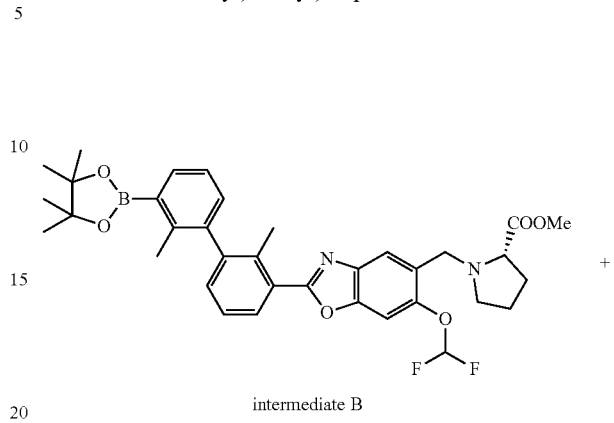

intermediate B

+

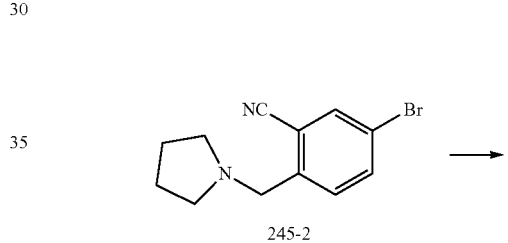

245-3

This compound was prepared using similar procedures as described as step 1 in example 1, with compound 245-2 replacing compound a-6, and with intermediate B replacing intermediate A. The crude product purified by silicagel (eluting with Hexane-EtOAc using a gradient from 5:1 to 1:1) to get the title compound.

Step 4: Preparation of ((2-(3"-cyano-2,2'-dimethyl-4"-(pyrrolidin-1-ylmethyl)-[1,1':3',1"-terphenyl]-3-yl)-6-(difluoromethoxy)benzo[d]oxazol-5-yl)methyl)-L-proline

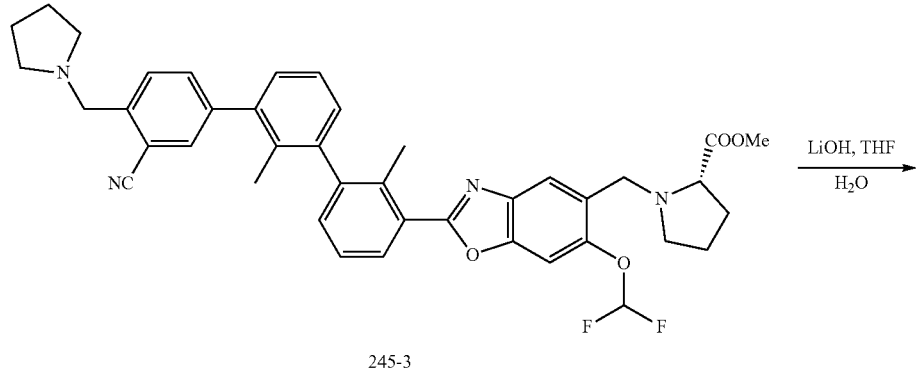

245-3

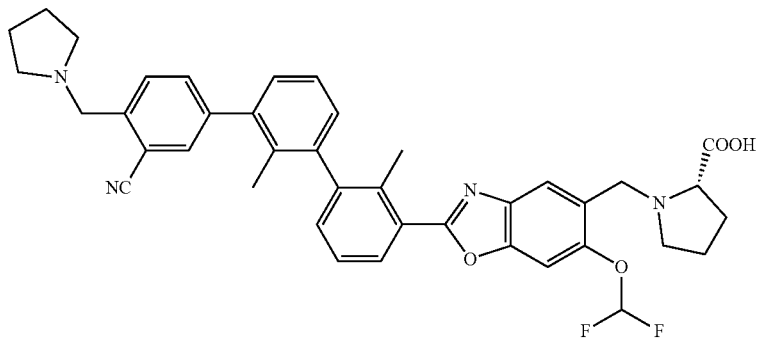

compound 245

This compound was prepared using similar procedures as described as step 5 in example 1, with compound 245-3 replacing compound 1-4. The crude product was purified by RP-column (mobile phase: MeCN:water (0.1% HCl) using a gradient from 10:90 to 35:65) to get the title compound. LC-MS (m/z): 677.3 (M+H)$^+$. $^1$H NMR (500 MHz, Methanol-d4) δ: 8.21 (dd, 1H, J=7.9, 1.5 Hz), 8.10 (s, 1H), 7.76 (s, 1H), 7.70 (t, 1H, J=7.7 Hz), 7.50 (t, 1H, J=7.7 Hz), 7.49-7.28 (m, 5H), 7.20 (dd, 1H, J=7.5, 1.4 Hz), 7.12 (t, 1H, $J_{F-H}$=72.6 Hz), 4.73 (d, 1H, J=13.1 Hz), 4.51 (d, 1H, J=13.1 Hz), 4.51 (s, 2H), 4.37 (dd, 1H, J=9.5, 7.4 Hz), 3.69-3.51 (m, 3H), 3.47-3.42 (m, 1H), 3.25-3.20 (m, 2H), 2.65-2.57 (m, 1H), 2.49 (s, 3H), 2.28-2.12 (m, 4H), 2.10-2.00 (m, 3H), 1.96 (s, 3H).

Example 246 Synthesis of Compound 246

((6-(difluoromethoxy)-2-(3'-(6-methoxy-5-(((S)-3-methylpyrrolidin-1-yl)methyl)pyridin-2-yl)-2,2'-dimethyl-[1,1'-biphenyl]-3-yl)benzo[d]oxazol-5-yl)methyl)-L-proline Compound 246

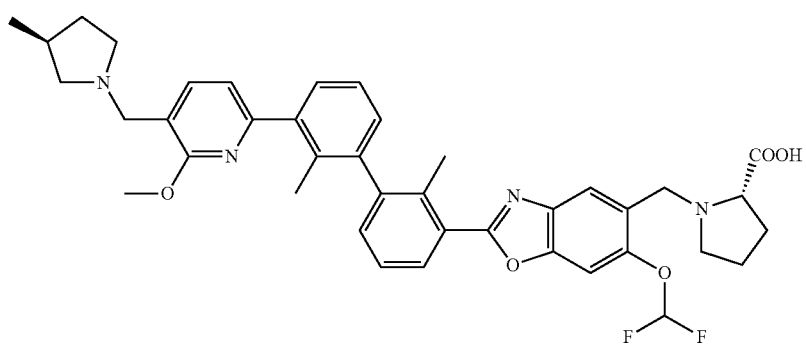

Step 1: Preparation of methyl ((6-(difluoromethoxy)-2-(3'-(5-formyl-6-methoxypyridin-2-yl)-2,2'-dimethyl-[1,1'-biphenyl]-3-yl)benzo[d]oxazol-5-yl)methyl)-L-prolinate

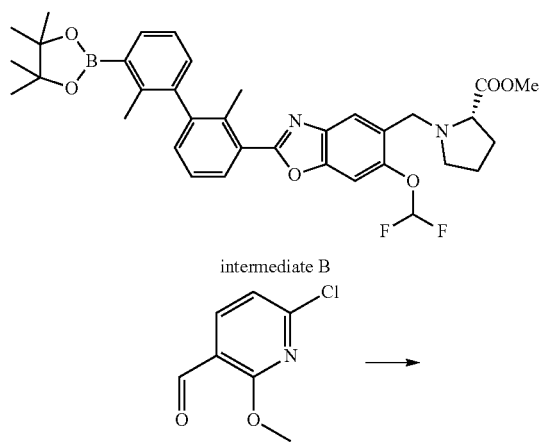

intermediate B

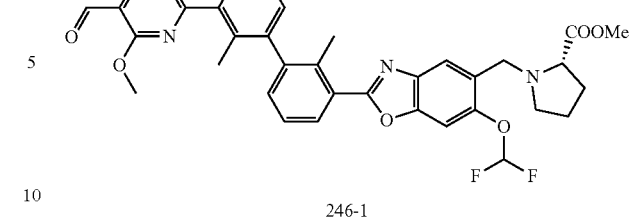

246-1

This compound was prepared using similar procedures as described as step 1 in example 1, with 6-chloro-2-methoxynicotinaldehyde replacing compound a-6, and with intermediate B replacing intermediate A. The crude product was purified by silicagel (Hexane-EtOAc=3:1) to get the titled compound.

Step 2: Methyl ((6-(difluoromethoxy)-2-(3'-(6-methoxy-5-(((S)-3-methylpyrrolidin-1-yl)methyl)pyridin-2-yl)-2,2'-dimethyl-[1,1'-biphenyl]-3-yl)benzo[d]oxazol-5-yl)methyl)-L-prolinate

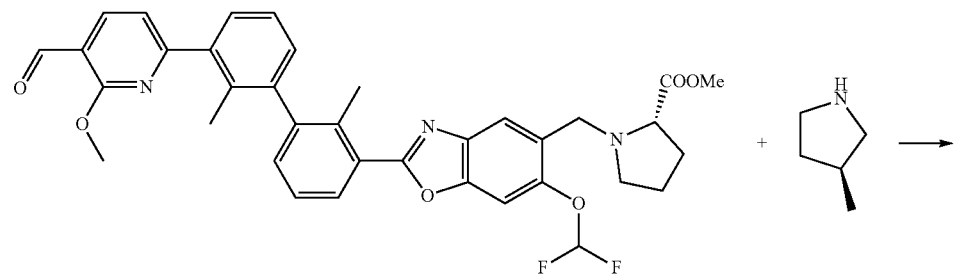

246-1

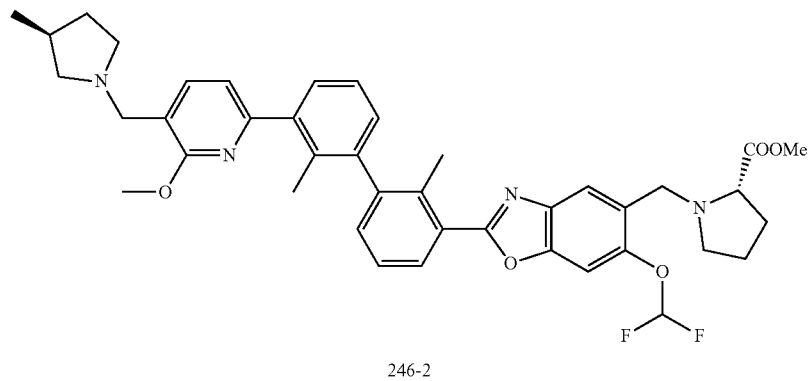

246-2

This compound was prepared using similar procedures as described as step 5 in example 2, with compound 246-1 replacing compound 2-4, and with (S)-3-methylpyrrolidine replacing L-proline. The resulting solution was concentrated to afford the title compound.

Step 3: ((6-(difluoromethoxy)-2-(3'-(6-methoxy-5-(((S)-3-methylpyrrolidin-1-yl)methyl)pyridin-2-yl)-2,2'-dimethyl-[1,1'-biphenyl]-3-yl)benzo[d]oxazol-5-yl)methyl)-L-proline

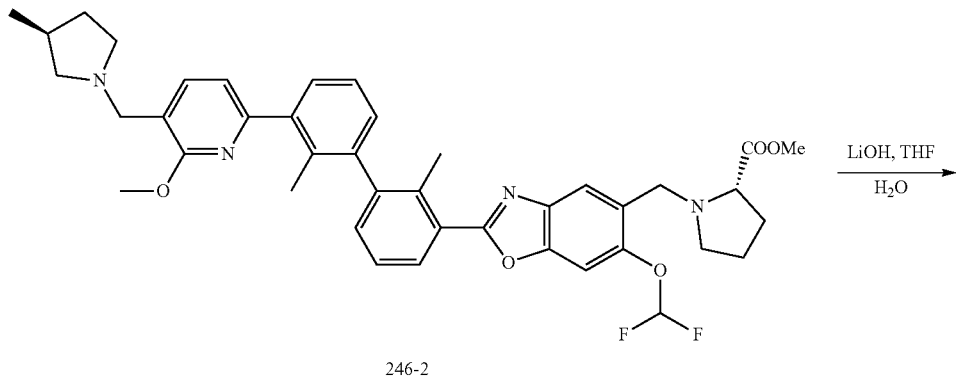

246-2

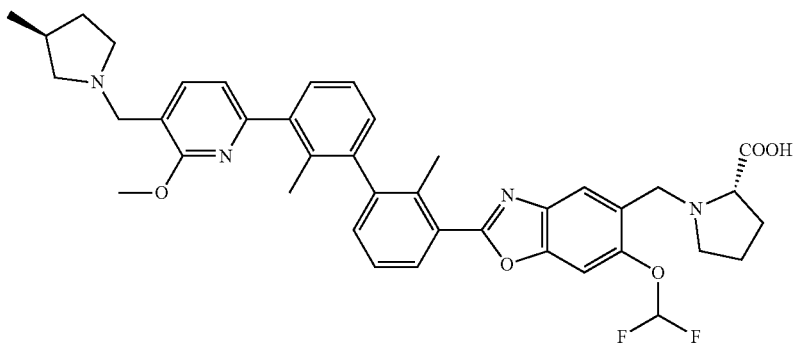

compound 246

This compound was prepared using similar procedures as described as step 5 in example 1, with compound 246-2 replacing compound 1-4. The organic layer was separated and purified by RP-column (mobile phase: MeCN:water (0.1% HCl) using a gradient from 15:85 to 30:70) to afford ((6-(difluoromethoxy)-2-(3''-(difluoromethoxy)-2,2'-dimethyl-4''-(pyrrolidin-1-ylmethyl)-[1,1':3',1''-terphenyl]-3-yl)benzo[d]oxazol-5-yl)methyl)-L-proline (30.8 mg) as a white solid. LC-MS (m/z): 697.3 (M+H)+. $^1$H NMR (500 MHz, DMSO-$d_6$) δ 8.11 (dd, 1H, J=7.9, 1.5 Hz), 7.96 (s, 1H), 7.77 (d, 1H, J=7.5 Hz), 7.72 (s, 1H), 7.54-7.37 (m, 5H), 7.24-7.19 (m, 1H), 7.16 (d, 1H, J=7.5 Hz), 3.95 (s, 2H), 3.89 (s, 3H), 3.58 (s, 2H), 3.11-3.03 (m, 1H), 2.78 (t, 1H, J=2.8 Hz), 2.68-2.60 (m, 1H), 2.60-2.52 (m, 3H), 2.45 (s, 3H), 2.22-2.16 (m, 1H), 2.15-2.07 (m, 2H), 2.05 (s, 3H), 2.02-1.93 (m, 1H), 1.88-1.70 (m, 3H), 1.34-1.27 (m, 1H), 1.00 (d, J=6.7 Hz, 3H).

Example 247 Synthesis of Compound 247

((6-(difluoromethoxy)-2-(2,2'-dimethyl-3'-(2-((S)-pyrrolidin-2-yl)-1H-imidazol-4-yl)-[1,1'-biphenyl]-3-yl)benzo[d]oxazol-5-yl)methyl)-L-proline Compound 247

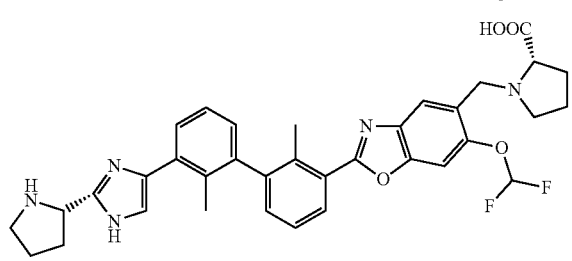

Step 1: Preparation of tert-butyl (S)-2-(4-(3'-(6-(difluoromethoxy)-5-(((S)-2-(methoxycarbonyl)pyrrolidin-1-yl)methyl)benzo[d]oxazol-2-yl)-2,2'-dimethyl-[1,1'-biphenyl]-3-yl)-1H-imidazol-2-yl)pyrrolidine-1-carboxylate

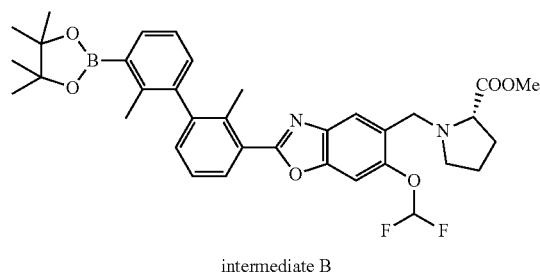

intermediate B

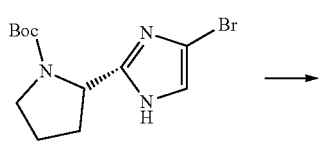

-continued

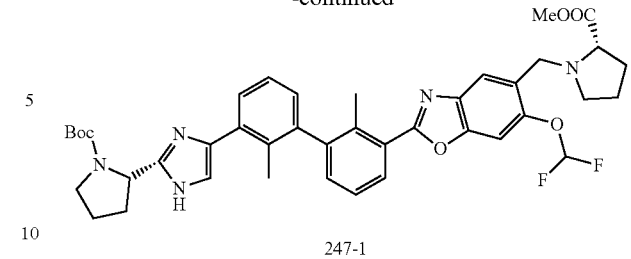

247-1

This compound was prepared using similar procedures as described as step 1 in example 1, with tert-butyl (S)-2-(4-bromo-1H-imidazol-2-yl)pyrrolidine-1-carboxylate replacing compound a-6, and with intermediate B replacing intermediate A. The resulting solution was concentrated and purified by silicagel (eluting with Hexane-EtOAc using a gradient from 5:1 to 1:1) to afford tert-butyl (S)-2-(4-(3'-(6-(difluoromethoxy)-5-(((S)-2-(methoxycarbonyl)pyrrolidin-1-yl)methyl)benzo[d]oxazol-2-yl)-2,2'-dimethyl-[1,1'-biphenyl]-3-yl)-1H-imidazol-2-yl)pyrrolidine-1-carboxylate (98 mg) as a yellow oil.

Step 2: Preparation of methyl ((6-(difluoromethoxy)-2-(2,2'-dimethyl-3'-(2-((S)-pyrrolidin-2-yl)-1H-imidazol-4-yl)-[1,1'-biphenyl]-3-yl)benzo[d]oxazol-5-yl)methyl)-L-prolinate

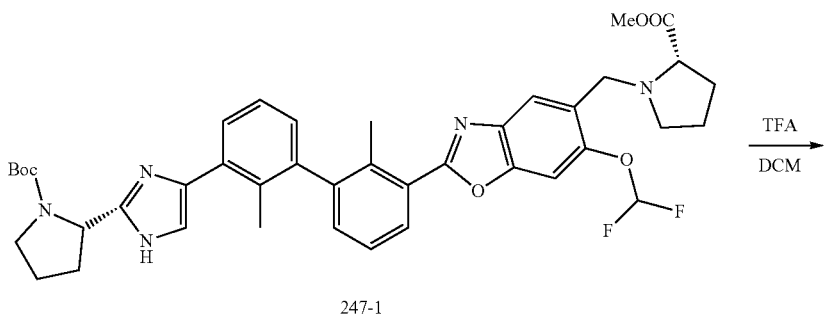

247-1

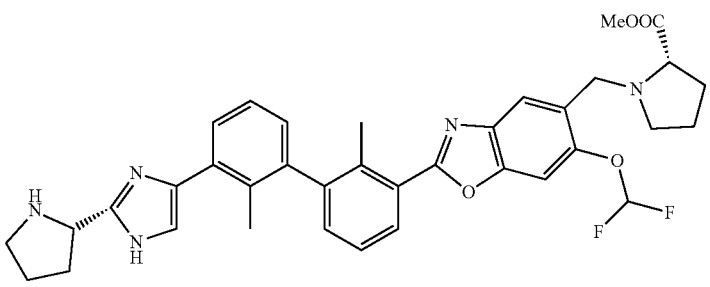

247-2

A mixture of compound 247-1 (76.0 mg) in DCM/TFA=7:1 (4 mL) was stirred for 4 hrs at room temperature. The resulting solution was concentrated under high vacuum to afford compound 247-2 (60 mg) as a yellow semi-solid.

Step 3: Preparation of ((6-(difluoromethoxy)-2-(2,2'-dimethyl-3'-(2-((S)-pyrrolidin-2-yl)-1H-imidazol-4-yl)-[1,1'-biphenyl]-3-yl)benzo[d]oxazol-5-yl)methyl)-L-proline

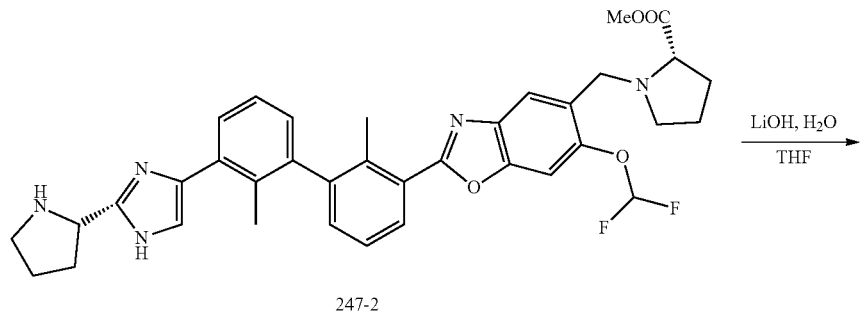

247-2

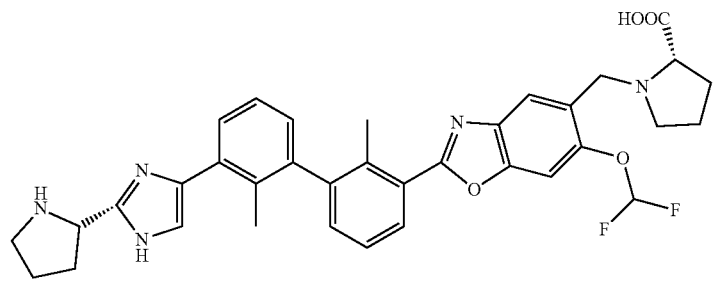

compound 247

This compound was prepared using similar procedures as described as step 5 in example 1, with compound 247-2 replacing compound 1-4. The crude product was purified by RP-column (mobile phase: MeCN:water (0.1% HCl) using a gradient from 10:90 to 35:65) to afford ((6-(difluoromethoxy)-2-(2,2'-dimethyl-3'-(2-((S)-pyrrolidin-2-yl)-1H-imidazol-4-yl)-[1,1'-biphenyl]-3-yl)benzo[d]oxazol-5-yl)methyl)-L-proline (70.6 mg) as a white solid. LC-MS (m/z): 628.3 (M+H)+. 1H NMR (500 MHz, Methanol-d4), δ: 8.19 (dd, 1H, J=8.0, 1.5 Hz), 8.07 (s, 1H), 7.76 (d, 1H, J=10.8 Hz), 7.61 (dd, 1H, J=7.8, 1.3 Hz), 7.52 (t, 1H, J=7.8 Hz), 7.46 (t, 1H, J=7.6 Hz), 7.38 (dd, 1H, J=7.6, 1.4 Hz), 7.32 (dd, 1H, J=7.6, 1.4 Hz), 7.13 (t, 1H, $J_{F-H}$=72.6 Hz), 5.16 (t, 1H, J=9.3, 7.7 Hz), 4.79 (d, 1H, J=13.2), 4.62 (d, 1H, J=13.3), 4.48 (t, 1H, J=9.3 Hz), 3.67-3.55 (m, 3H), 3.50-3.42 (m, 1H), 2.75-2.60 (m, 2H), 2.58-2.50 (m, 1H), 2.49 (s, 3H), 2.43-2.34 (m, 1H), 2.29-2.17 (m, 3H), 2.15 (s, 3H), 2.11-1.99 (m, 1H).

The compounds of table 6 were prepared in a similar manner to Examples 242-247 via different reaction starting materials and suitable reagents.

TABLE 6

| EX No. | Chemical Name | Structure | Physical Data (MS) (M + H)+ |
|---|---|---|---|
| 215 | ((6-(difluoromethoxy)-2-(2'-fluoro-2-methyl-4''-(((((S)-5-oxopyrrolidin-2-yl)methyl)amino)methyl)-[1,1':3',1''-terphenyl]-3-yl)benzo[d]oxazol-5-yl)methyl)-L-proline | 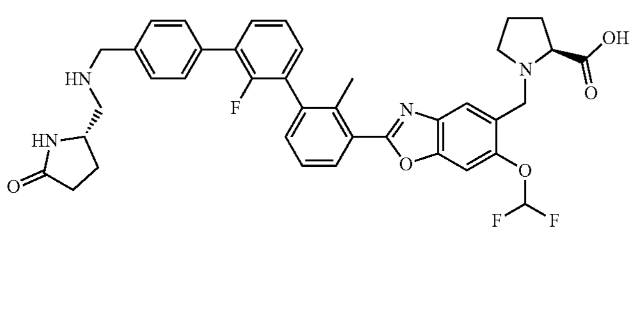 [SMILES: Cc1c(-c2nc3cc(CN4CCC[C@H]4C(=O)O)c(OC(F)F)cc3o2)cccc1-c1cccc(-c2ccc(CNC[C@@H]3CCC(=O)N3)cc2)c1F] | 699.3 |

TABLE 6-continued

| EX No. | Chemical Name | Structure | Physical Data (MS) (M + H)+ |
|---|---|---|---|
| 216 | ((6-(difluoromethoxy)-2-(3''-(difluoromethoxy)-2'-fluoro-2-methyl-4''-(((((S)-5-oxopyrrolidin-2-yl)methyl)amino)methyl)-[1,1':3',1''-terphenyl]-3-yl)benzo[d]oxazol-5-yl)methyl)-L-proline | 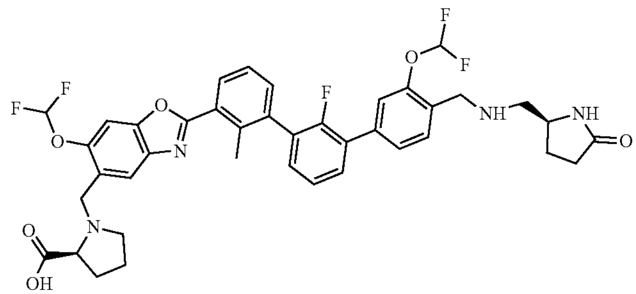 [SMILES: Cc1c(-c2nc3cc(CN4CCC[C@H]4C(=O)O)c(OC(F)F)cc3o2)cccc1-c1cccc(-c2ccc(CNC[C@@H]3CCC(=O)N3)c(OC(F)F)c2)c1F] | 765.3 |
| 217 | ((6-(difluoromethoxy)-2-(4''-(((2-hydroxyethyl)amino)methyl)-2,2'-dimethyl-[1,1':3',1''-terphenyl]-3-yl)benzo[d]oxazol-5-yl)methyl)-L-proline | 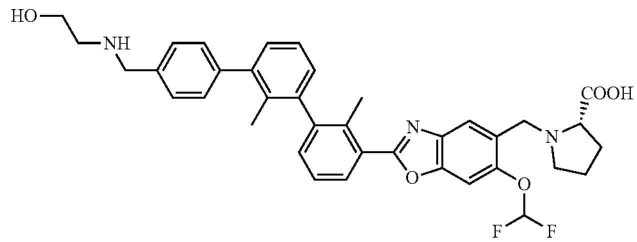 [SMILES: Cc1c(-c2ccc(CNCCO)cc2)cccc1-c1cccc(-c2nc3cc(CN4CCC[C@H]4C(=O)O)c(OC(F)F)cc3o2)c1C] | 642.3 |
| 218 | ((6-(difluoromethoxy)-2-(2,2',3''-trimethyl-4''-(pyrrolidin-1-ylmethyl)-[1,1':3',1''-terphenyl]-3-yl)benzo[d]oxazol-5-yl)methyl)proline | 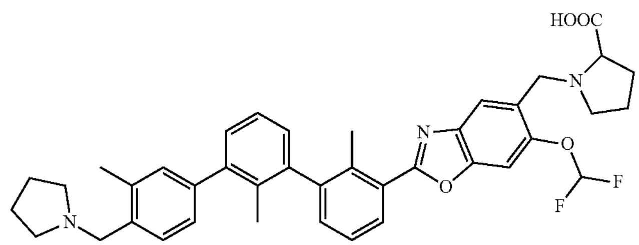 [SMILES: Cc1cc(-c2cccc(-c3cccc(-c4nc5cc(CN6CCCC6C(=O)O)c(OC(F)F)cc5o4)c3C)c2C)ccc1CN1CCCC1] | 666.3 |
| 219 | ((2-(3''-chloro-2,2'-dimethyl-4''-(pyrrolidin-1-ylmethyl)-[1,1':3',1''-terphenyl]-3-yl)-6-(difluoromethoxy)benzo[d]oxazol-5-yl)methyl)proline | 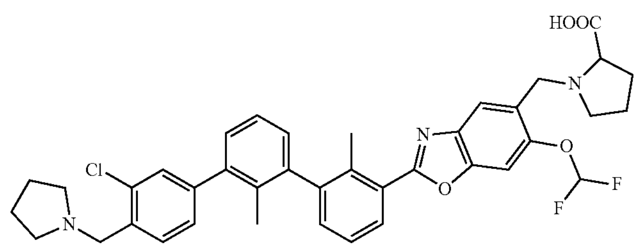 [SMILES: Cc1c(-c2ccc(CN3CCCC3)c(Cl)c2)cccc1-c1cccc(-c2nc3cc(CN4CCCC4C(=O)O)c(OC(F)F)cc3o2)c1C] | 686.3 |
| 220 | ((6-(difluoromethoxy)-2-(2''-fluoro-2,2'-dimethyl-4''-(pyrrolidin-1-ylmethyl)-[1,1':3',1''-terphenyl]-3-yl)benzo[d]oxazol-5-yl)methyl)proline | 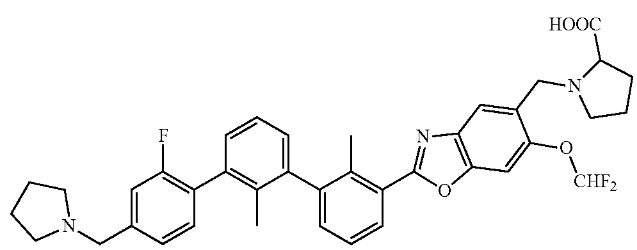 [SMILES: Cc1c(-c2nc3cc(CN4CCCC4C(=O)O)c(OC(F)F)cc3o2)cccc1-c1cccc(-c2ccc(CN3CCCC3)cc2F)c1C] | 670.3 |
| 221 | ((2-(2'-bromo-2''-fluoro-2-methyl-4''-(pyrrolidin-1-ylmethyl)-[1,1':3',1''-terphenyl]-3-yl)-6-(difluoromethoxy)benzo[d]oxazol-5-yl)methyl)proline | 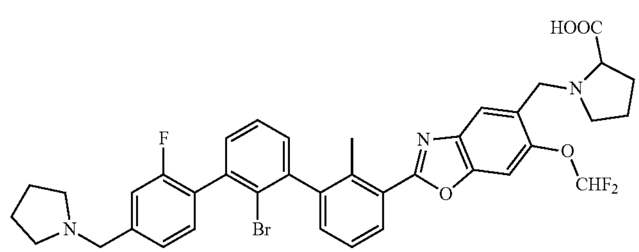 [SMILES: Cc1c(-c2nc3cc(CN4CCCC4C(=O)O)c(OC(F)F)cc3o2)cccc1-c1cccc(-c2ccc(CN3CCCC3)cc2F)c1Cl] | 733.2 |

TABLE 6-continued

| EX No. | Chemical Name | Structure | Physical Data (MS) (M + H)+ |
|---|---|---|---|
| 222 | ((2-(2'-chloro-2''-fluoro-2-methyl-4''-(pyrrolidin-1-ylmethyl)-[1,1':3',1''-terphenyl]-3-yl)-6-(difluoromethoxy)benzo[d]oxazol-5-yl)methyl)proline | 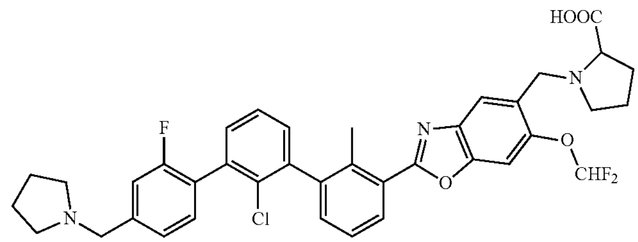 | 690.2 |
| 223 | ((2-(2'-chloro-2''-fluoro-2-methyl-4''-(pyrrolidin-1-ylmethyl)-[1,1':3',1''-terphenyl]-3-yl)-6-(difluoromethoxy)benzo[d]oxazol-5-yl)methyl)-L-proline | 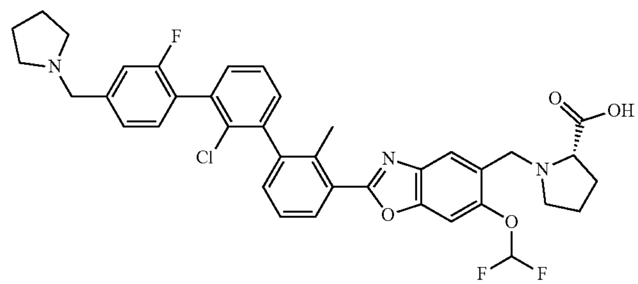 [SMILES: Cc1c(-c2nc3cc(CN4CCC[C@H]4C(=O)O)c(OC(F)F)cc3o2)cccc1-c1cccc(-c2ccc(CN3CCCC3)cc2F)c1Cl] | 690.2 |
| 224 | ((2-(2'-chloro-2''-fluoro-2-methyl-4''-(pyrrolidin-1-ylmethyl)-[1,1':3',1''-terphenyl]-3-yl)-6-(difluoromethoxy)benzo[d]oxazol-5-yl)methyl)-D-proline | 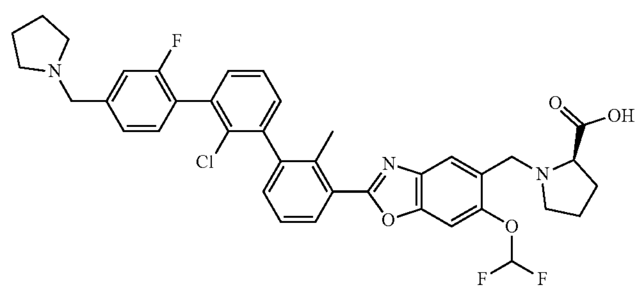 [SMILES: Cc1c(-c2nc3cc(CN4CCC[C@@H]4C(=O)O)c(OC(F)F)cc3o2)cccc1-c1cccc(-c2ccc(CN3CCCC3)cc2F)c1Cl] | 690.2 |
| 225 | ((6-(difluoromethoxy)-2-(4''-guanidino-2,2'-dimethyl-[1,1':3,1''-terphenyl]-3-yl)benzo[d]oxazol-5-yl)methyl)-L-proline | 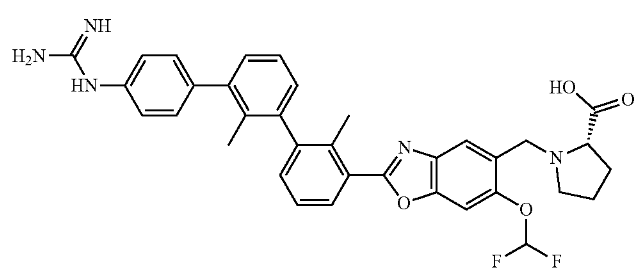 [SMILES: Cc1c(-c2ccc(NC(=N)N)cc2)cccc1-c1cccc(-c2nc3cc(CN4CCC[C@H]4C(=O)O)c(OC(F)F)cc3o2)c1C] | 626.3 |
| 226 | ((6-(difluoromethoxy)-2-(4''-(((3-(dimethylamino)propyl)(methyl)amino)methyl)-2,2'-dimethyl-[1,1':3',1''-terphenyl]-3-yl)benzo[d]oxazol-5-yl)methyl)-L-proline | 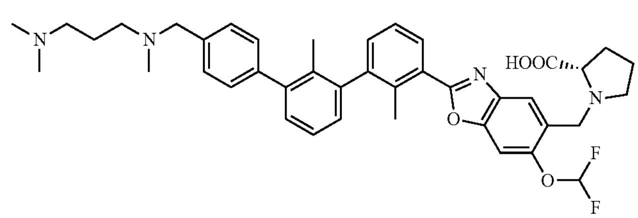 [SMILES: Cc1c(-c2ccc(CN(C)CCCN(C)C)cc2)cccc1-c1cccc(-c2nc3cc(CN4CCC[C@H]4C(=O)O)c(OC(F)F)cc3o2)c1C] | 697.4 |

TABLE 6-continued

| EX No. | Chemical Name | Structure | Physical Data (MS) (M + H)+ |
|---|---|---|---|
| 227 | ((6-(difluoromethoxy)-2-(4"-((3-methoxypyrrolidin-1-yl)methyl)-2,2'-dimethyl-[1,1':3',1"-terphenyl]-3-yl)benzo[d]oxazol-5-yl)methyl)-L-proline | 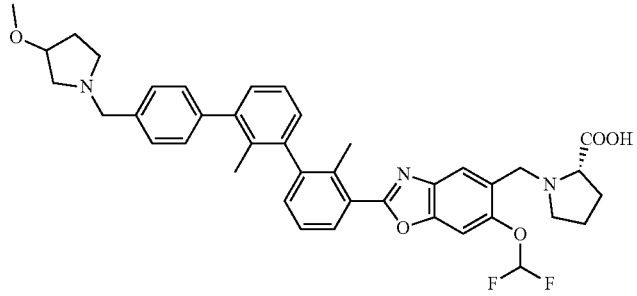 [SMILES: COC1CCN(Cc2ccc(-c3cccc(-c4cccc(-c5nc6cc(CN7CCC[C@H]7C(=O)O)c(OC(F)F)cc6o5)c4C)c3C)cc2)C1] | 682.3 |
| 228 | ((6-(difluoromethoxy)-2-(4"-((3-(dimethylamino)pyrrolidin-1-yl)methyl)-2,2'-dimethyl-[1,1':3',1"-terphenyl]-3-yl)benzo[d]oxazol-5-yl)methyl)-L-proline | 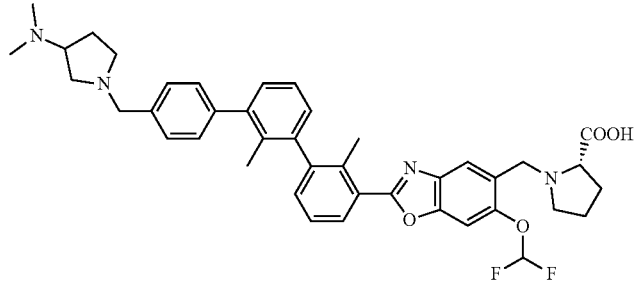 [SMILES: Cc1c(-c2ccc(CN3CCC(N(C)C)C3)cc2)cccc1-c1cccc(-c2nc3cc(CN4CCC[C@H]4C(=O)O)c(OC(F)F)cc3o2)c1C] | 695.3 |
| 229 | ((2-(3"-chloro-2,2'-dimethyl-4"-(pyrrolidin-1-ylmethyl)-[1,1':3',1"-terphenyl]-3-yl)-6-(difluoromethoxy)benzo[d]oxazol-5-yl)methyl)-L-proline | 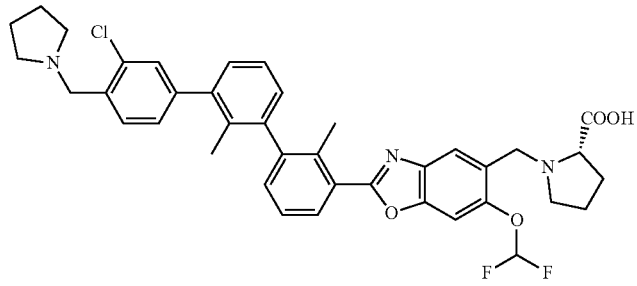 [SMILES: Cc1c(-c2ccc(CN3CCCC3)c(Cl)c2)cccc1-c1cccc(-c2nc3cc(CN4CCC[C@H]4C(=O)O)c(OC(F)F)cc3o2)c1C] | 686.3 |
| 230 | ((6-(difluoromethoxy)-2-(2,2',3"-trimethyl-4"-(pyrrolidin-1-ylmethyl)-[1,1':3',1"-terphenyl]-3-yl)benzo[d]oxazol-5-yl)methyl)-L-proline | 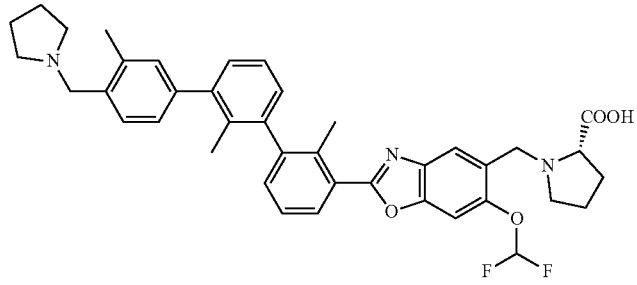 [SMILES: Cc1cc(-c2cccc(-c3cccc(-c4nc5cc(CN6CCC[C@H]6C(=O)O)c(OC(F)F)cc5o4)c3C)c2C)ccc1CN1CCCC1] | 666.3 |
| 231 | ((2-(2"-chloro-2,2'-dimethyl-4"-(pyrrolidin-1-ylmethyl)-[1,1':3',1"-terphenyl]-3-yl)-6-(difluoromethoxy)benzo[d]oxazol-5-yl)methyl)-L-proline | 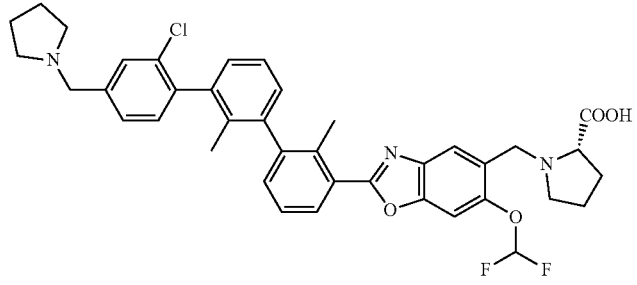 [SMILES: Cc1c(-c2nc3cc(CN4CCC[C@H]4C(=O)O)c(OC(F)F)cc3o2)cccc1-c1cccc(-c2ccc(CN3CCCC3)cc2Cl)c1C] | 686.3 |

TABLE 6-continued

| EX No. | Chemical Name | Structure | Physical Data (MS) (M + H)+ |
|---|---|---|---|
| 232 | ((6-(difluoromethoxy)-2-(2,2'-dimethyl-4''-(pyrrolidin-1-ylmethyl)-3''-(trifluoromethoxy)-[1,1':3',1''-terphenyl]-3-yl)benzo[d]oxazol-5-yl)methyl)-L-proline | 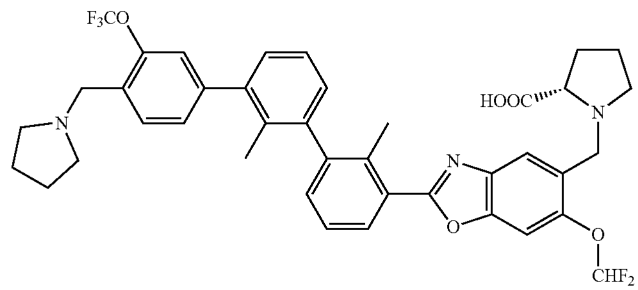 [SMILES: Cc1c(-c2ccc(CN3CCCC3)c(OC(F)(F)F)c2)cccc1-c1cccc(-c2nc3cc(CN4CCC[C@H]4C(=O)O)c(OC(F)F)cc3o2)c1C] | 736.3 |
| 233 | ((6-(difluoromethoxy)-2-(2,2'-dimethyl-4''-(pyrrolidin-1-ylmethyl)-3''-(trifluoromethyl)-[1,1':3',1''-terphenyl]-3-yl)benzo[d]oxazol-5-yl)methyl)-L-proline | 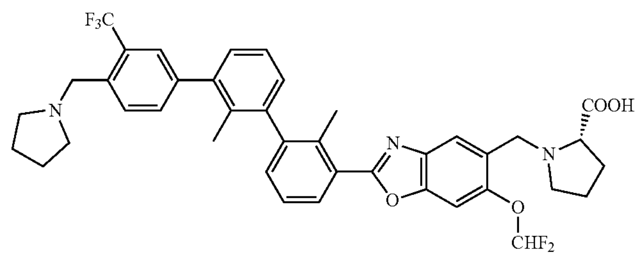 [SMILES: Cc1c(-c2ccc(CN3CCCC3)c(C(F)(F)F)c2)cccc1-c1cccc(-c2nc3cc(CN4CCC[C@H]4C(=O)O)c(OC(F)F)cc3o2)c1C] | 720.3 |
| 234 | ((6-(difluoromethoxy)-2-(2,2',3'',5''-tetramethyl-4''-(pyrrolidin-1-ylmethyl)-[1,1':3',1''-terphenyl]-3-yl)benzo[d]oxazol-5-yl)methyl)-L-proline | 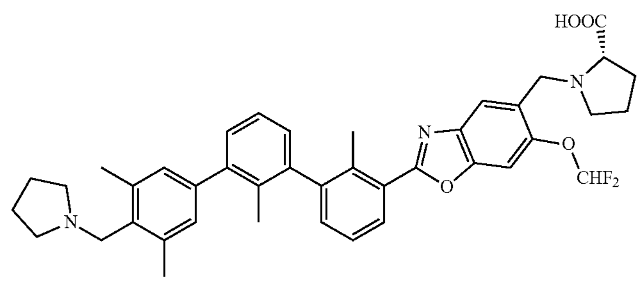 [SMILES: Cc1cc(-c2cccc(-c3cccc(-c4nc5cc(CN6CCC[C@H]6C(=O)O)c(OC(F)F)cc5o4)c3C)c2C)cc(C)c1CN1CCCC1] | 680.3 |
| 235 | ((6-(difluoromethoxy)-2-(3''-fluoro-5''-methoxy-2,2'-dimethyl-4''-(pyrrolidin-1-ylmethyl)-[1,1':3',1''-terphenyl]-3-yl)benzo[d]oxazol-5-yl)methyl)-L-proline | 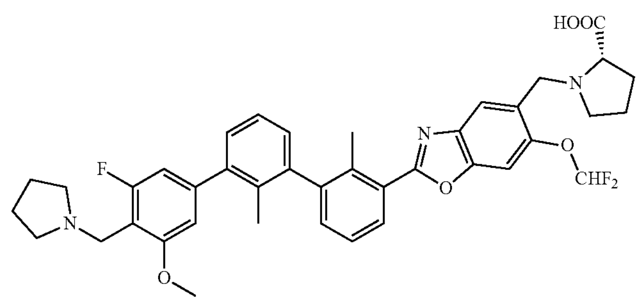 [SMILES: COc1cc(-c2cccc(-c3cccc(-c4nc5cc(CN6CCC[C@H]6C(=O)O)c(OC(F)F)cc5o4)c3C)c2C)cc(F)c1CN1CCCC1] | 700.3 |
| 236 | ((2-(3''-carboxy-2,2'-dimethyl-4''-(pyrrolidin-1-ylmethyl)-[1,1':3',1''-terphenyl]-3-yl)-6-(difluoromethoxy)benzo[d]oxazol-5-yl)methyl)-L-proline | 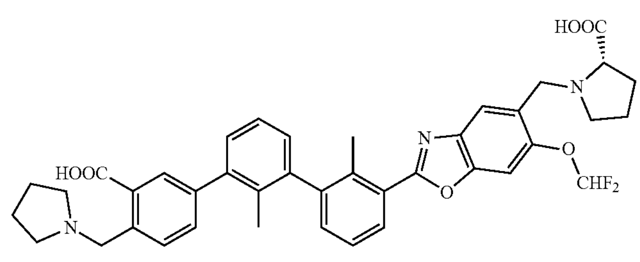 [SMILES: Cc1c(-c2ccc(CN3CCCC3)c(C(=O)O)c2)cccc1-c1cccc(-c2nc3cc(CN4CCC[C@H]4C(=O)O)c(OC(F)F)cc3o2)c1C] | 696.3 |

TABLE 6-continued

| EX No. | Chemical Name | Structure | Physical Data (MS) (M + H)+ |
|---|---|---|---|
| 237 | ((6-(difluoromethoxy)-2-(4"-((3,3-dimethylazetidin-1-yl)methyl)-3"-fluoro-2,2'-dimethyl-[1,1':3',1"-terphenyl]-3-yl)benzo[d]oxazol-5-yl)methyl)-L-proline | 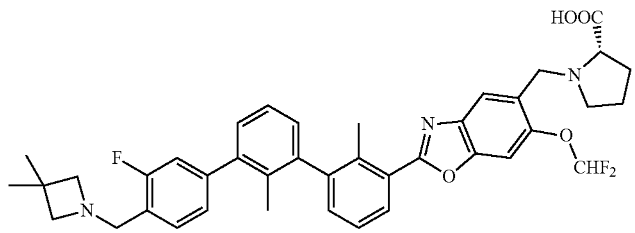 [SMILES: Cc1c(-c2ccc(CN3CC(C)(C)C3)c(F)c2)cccc1-c1cccc(-c2nc3cc(CN4CCC[C@H]4C(=O)O)c(OC(F)F)cc3o2)c1C] | 684.3 |
| 238 | ((6-(difluoromethoxy)-2-(3"-fluoro-2,2'-dimethyl-4"-((3-methylpyrrolidin-1-yl)methyl)-[1,1':3',1"-terphenyl]-3-yl)benzo[d]oxazol-5-yl)methyl)-L-proline | 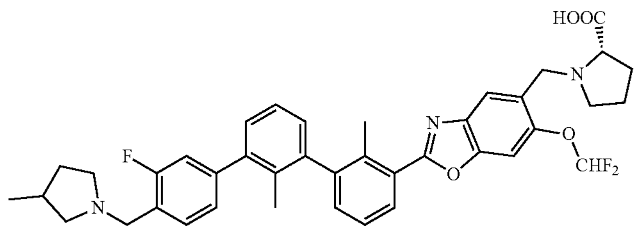 [SMILES: Cc1c(-c2ccc(CN3CCC(C)C3)c(F)c2)cccc1-c1cccc(-c2nc3cc(CN4CCC[C@H]4C(=O)O)c(OC(F)F)cc3o2)c1C] | 684.3 |
| 239 | ((6-(difluoromethoxy)-2-(3"-fluoro-4"-(((2-hydroxyethyl)amino)methyl)-2,2'-dimethyl-[1,1':3',1"-terphenyl]-3-yl)benzo[d]oxazol-5-yl)methyl)-L-proline | 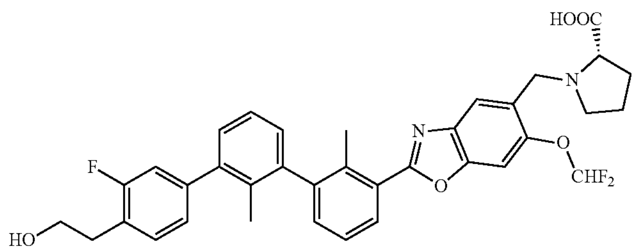 [SMILES: Cc1c(-c2ccc(CCO)c(F)c2)cccc1-c1cccc(-c2nc3cc(CN4CCC[C@H]4C(=O)O)c(OC(F)F)cc3o2)c1C] | 660.3 |
| 240 | ((2-(3"-cyano-4"-(((S)-3-(hydroxymethyl)pyrrolidin-1-yl)methyl)-2,2'-dimethyl-[1,1':3',1"-terphenyl]-3-yl)-6-(difluoromethoxy)benzo[d]oxazol-5-yl)methyl)-L-proline | 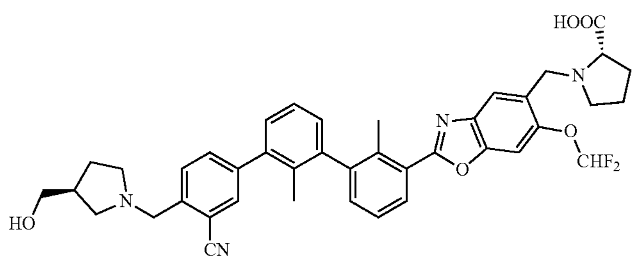 [SMILES: Cc1c(-c2ccc(CN3CC[C@H](CO)C3)c(C#N)c2)cccc1-c1cccc(-c2nc3cc(CN4CCC[C@H]4C(=O)O)c(OC(F)F)cc3o2)c1C] | 707.3 |
| 241 | ((6-(difluoromethoxy)-2-(3"-fluoro-4"-(isoindolin-2-ylmethyl)-2,2'-dimethyl-[1,1':3',1"-terphenyl]-3-yl)benzo[d]oxazol-5-yl)methyl)proline | 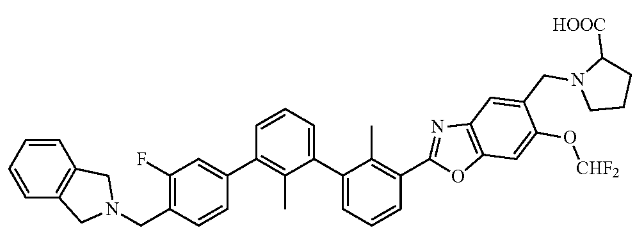 [SMILES: Cc1c(-c2ccc(CN3Cc4ccccc4C3)c(F)c2)cccc1-c1cccc(-c2nc3cc(CN4CCCC4C(=O)O)c(OC(F)F)cc3o2)c1C] | 718.3 |
| 248 | ((6-(difluoromethoxy)-2-(3"-fluoro-2,2'-dimethyl-4"-(((S)-3-phenylpyrrolidin-1-yl)methyl)-[1,1':3',1"-terphenyl]-3-yl)benzo[d]oxazol-5-yl)methyl)proline | 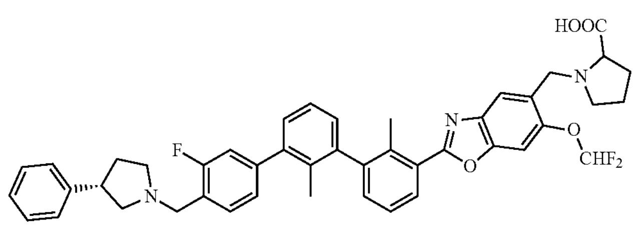 [SMILES: Cc1c(-c2ccc(CN3CC[C@@H](c4ccccc4)C3)c(F)c2)cccc1-c1cccc(-c2nc3cc(CN4CCCC4C(=O)O)c(OC(F)F)cc3o2)c1C] | 746.3 |

TABLE 6-continued

| EX No. | Chemical Name | Structure | Physical Data (MS) (M + H)+ |
|---|---|---|---|
| 249 | ((6-(difluoromethoxy)-2-(3''-(4-fluorophenethoxy)-2,2'-dimethyl-4''-(pyrrolidin-1-ylmethyl)-[1,1':3',1''-terphenyl]-3-yl)benzo[d]oxazol-5-yl)methyl)proline | 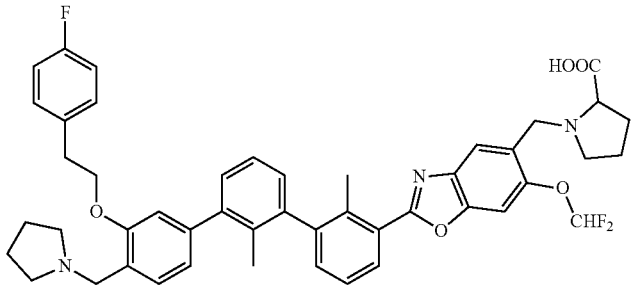 [SMILES: Cc1c(-c2ccc(CN3CCCC3)c(OCCc3ccc(F)cc3)c2)cccc1-c1cccc(-c2nc3cc(CN4CCCC4C(=O)O)c(OC(F)F)cc3o2)c1C] | 790.3 |
| 250 | ((2-(3''-(cyclopropylmethoxy)-2,2'-dimethyl-4''-(pyrrolidin-1-ylmethyl)-[1,1':3',1''-terphenyl]-3-yl)-6-(difluoromethoxy)benzo[d]oxazol-5-yl)methyl)proline | 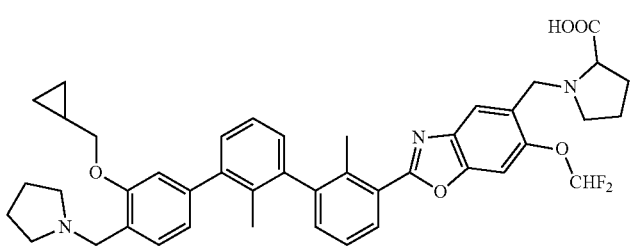 [SMILES: Cc1c(-c2ccc(CN3CCCC3)c(OCC3CC3)c2)cccc1-c1cccc(-c2nc3cc(CN4CCCC4C(=O)O)c(OC(F)F)cc3o2)c1C] | 722.3 |
| 251 | ((2-(4''-(((R)-3-(1H-tetrazol-5-yl)pyrrolidin-1-yl)methyl)-3''-fluoro-2,2'-dimethyl-[1,1':3',1''-terphenyl]-3-yl)-6-(difluoromethoxy)benzo[d]oxazol-5-yl)methyl)proline | 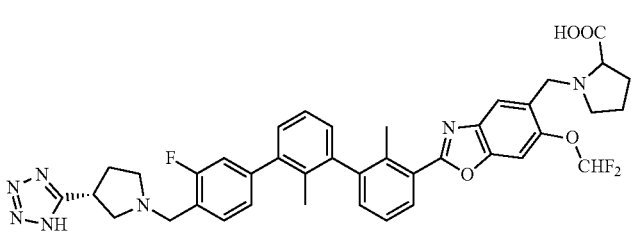 [SMILES: Cc1c(-c2ccc(CN3CC[C@@H](c4nnn[nH]4)C3)c(F)c2)cccc1-c1cccc(-c2nc3cc(CN4CCCC4C(=O)O)c(OC(F)F)cc3o2)c1C] | 738.3 |
| 252 | ((2-(4''-(((S)-3-((benzyloxy)methyl)pyrrolidin-1-yl)methyl)-3''-fluoro-2,2'-dimethyl-[1,1':3',1''-terphenyl]-3-yl)-6-(difluoromethoxy)benzo[d]oxazol-5-yl)methyl)proline | 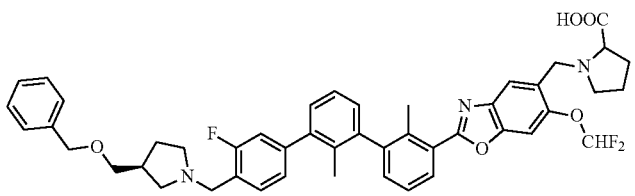 [SMILES: Cc1c(-c2ccc(CN3CC[C@H](COCc4ccccc4)C3)c(F)c2)cccc1-c1cccc(-c2nc3cc(CN4CCCC4C(=O)O)c(OC(F)F)cc3o2)c1C] | 790.3 |
| 253 | ((6-(difluoromethoxy)-2-(2''-fluoro-2,2'-dimethyl-4''-(pyrrolidin-1-ylmethyl)-[1,1':3',1''-terphenyl]-3-yl)benzo[d]oxazol-5-yl)methyl)-L-proline | 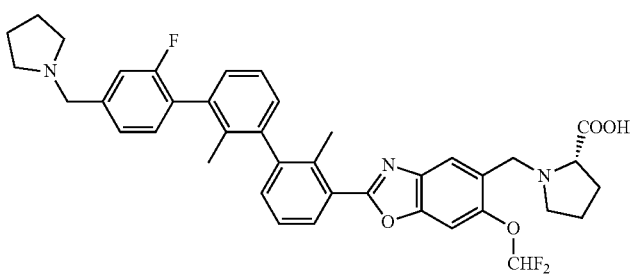 [SMILES: Cc1c(-c2nc3cc(CN4CCC[C@H]4C(=O)O)c(OC(F)F)cc3o2)cccc1-c1cccc(-c2ccc(CN3CCCC3)cc2F)c1C] | 670.3 |
| 254 | ((6-(difluoromethoxy)-2-(3'',5''-dimethoxy-2,2'-dimethyl-4''-(pyrrolidin-1-ylmethyl)-[1,1':3',1''-terphenyl]-3-yl)benzo[d]oxazol-5-yl)methyl)-L-proline hydrochloride | 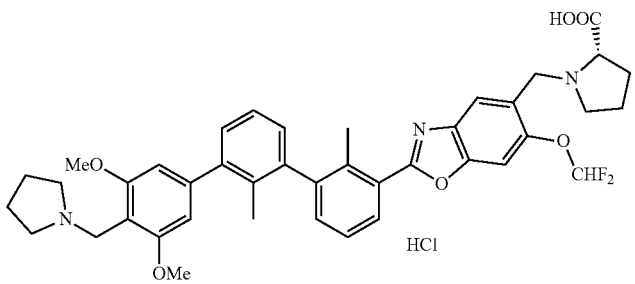 [SMILES: COc1cc(-c2cccc(-c3cccc(-c4nc5cc(CN6CCC[C@H]6C(=O)O)c(OC(F)F)cc5o4)c3C)c2C)cc(OC)c1CN1CCCC1 ; Cl] | 748.3 |

TABLE 6-continued

| EX No. | Chemical Name | Structure | Physical Data (MS) (M + H)+ |
|---|---|---|---|
| 255 | ((6-(difluoromethoxy)-2-(2,2'-dimethyl-4''-(pyrrolidin-2-yl)-[1,1':3',1''-terphenyl]-3-yl)benzo[d]oxazol-5-yl)methyl)-L-proline | 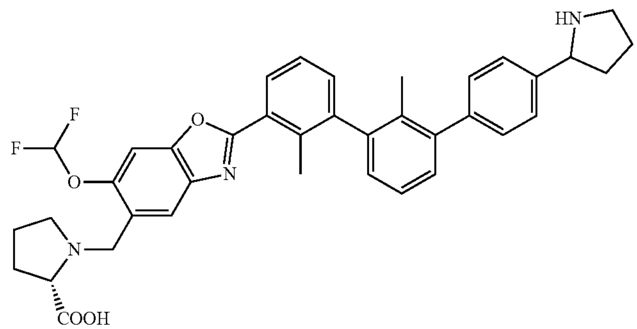 [SMILES: Cc1c(-c2ccc(C3CCCN3)cc2)cccc1-c1cccc(-c2nc3cc(CN4CCC[C@H]4C(=O)O)c(OC(F)F)cc3o2)c1C] | 638.3 |
| 256 | ((2-(4''-((S)-amino(carboxy)methyl)-2,2'-dimethyl-[1,1':3',1''-terphenyl]-3-yl)-6-(difluoromethoxy)benzo[d]oxazol-5-yl)methyl)-L-proline | 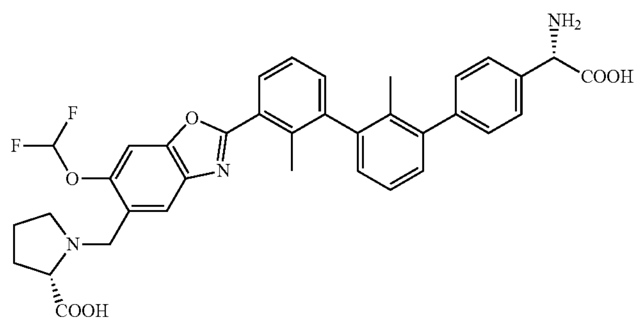 [SMILES: Cc1c(-c2ccc([C@H](N)C(=O)O)cc2)cccc1-c1cccc(-c2nc3cc(CN4CCC[C@H]4C(=O)O)c(OC(F)F)cc3o2)c1C] | 642.2 |
| 257 | ((6-(difluoromethoxy)-2-(4''-(((S)-3-((S)-2-((methoxycarbonyl)amino)-3-methylbutanamido)pyrrolidin-1-yl)methyl)-2,2'-dimethyl-[1,1':3',1''-terphenyl]-3-yl)benzo[d]oxazol-5-yl)methyl)-L-proline | 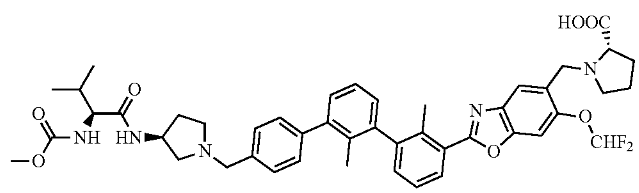 [SMILES: COC(=O)N[C@H](C(=O)N[C@H]1CCN(Cc2ccc(-c3cccc(-c4cccc(-c5nc6cc(CN7CCC[C@H]7C(=O)O)c(OC(F)F)cc6o5)c4C)c3C)cc2)C1)C(C)C] | 824.4 |
| 258 | ((6-(difluoromethoxy)-2-(3''-fluoro-2,2'-dimethyl-4''-((5-ureidoisoindolin-2-yl)methyl)-[1,1':3',1''-terphenyl]-3-yl)benzo[d]oxazol-5-yl)methyl)-L-proline | 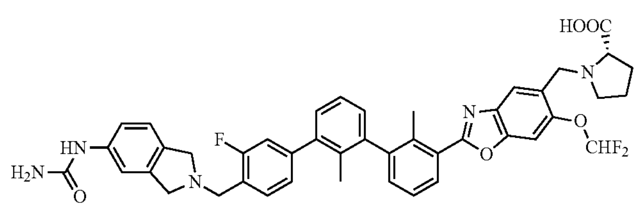 [SMILES: Cc1c(-c2ccc(CN3Cc4ccc(NC(N)=O)cc4C3)c(F)c2)cccc1-c1cccc(-c2nc3cc(CN4CCC[C@H]4C(=O)O)c(OC(F)F)cc3o2)c1C] | 776.3 |
| 260 | ((6-(difluoromethoxy)-2-(3''-fluoro-2,2'-dimethyl-4''-((3-ureidopyrrolidin-1-yl)methyl)-[1,1':3',1''-terphenyl]-3-yl)benzo[d]oxazol-5-yl)methyl)-L-proline | 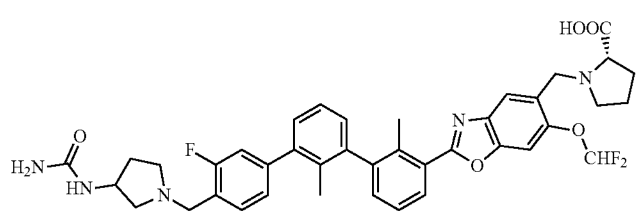 [SMILES: Cc1c(-c2ccc(CN3CCC(NC(N)=O)C3)c(F)c2)cccc1-c1cccc(-c2nc3cc(CN4CCC[C@H]4C(=O)O)c(OC(F)F)cc3o2)c1C] | 728.3 |
| 262 | ((6-(difluoromethoxy)-2-(3'-(4-fluoro-6-(pyrrolidin-1-ylmethyl)pyridin-3-yl)-2,2'-dimethyl-[1,1'-biphenyl]-3-yl)benzo[d]oxazol-5-yl)methyl)-L-proline | 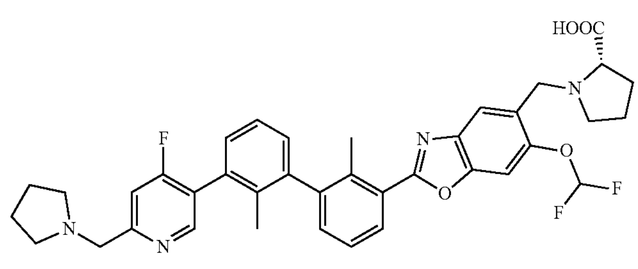 [SMILES: Cc1c(-c2nc3cc(CN4CCC[C@H]4C(=O)O)c(OC(F)F)cc3o2)cccc1-c1cccc(-c2cnc(CN3CCCC3)cc2F)c1C] | 671.3 |

TABLE 6-continued

| EX No. | Chemical Name | Structure | Physical Data (MS) (M + H)+ |
|---|---|---|---|
| 263 | ((6-(difluoromethoxy)-2-(2,2'-dimethyl-3'-(6-(pyrrolidin-1-ylmethyl)pyridin-3-yl)-[1,1'-biphenyl]-3-yl)benzo[d]oxazol-5-yl)methyl)-L-proline | 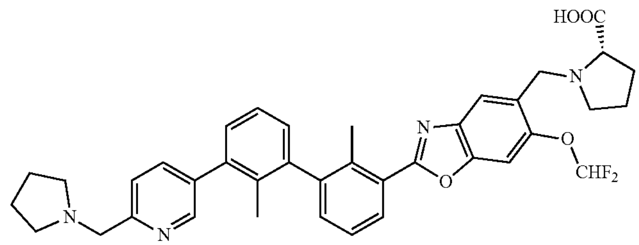 | 653.3 |
| 264 | ((6-(difluoromethoxy)-2-(2,2'-dimethyl-3'-(5-(pyrrolidin-1-ylmethyl)pyridin-2-yl)-[1,1'-biphenyl]-3-yl)benzo[d]oxazol-5-yl)methyl)-L-proline | 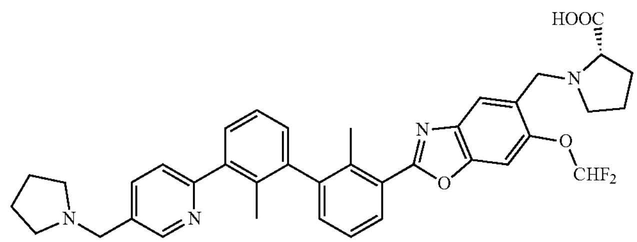 [SMILES: Cc1c(-c2ccc(CN3CCCC3)cn2)cccc1-c1cccc(-c2nc3cc(CN4CCC[C@H]4C(=O)O)c(OC(F)F)cc3o2)c1C] | 653.3 |
| 265 | ((6-(difluoromethoxy)-2-(3'-(5-fluoro-6-(pyrrolidin-1-ylmethyl)pyridin-3-yl)-2,2'-dimethyl-[1,1'-biphenyl]-3-yl)benzo[d]oxazol-5-yl)methyl)-L-proline | 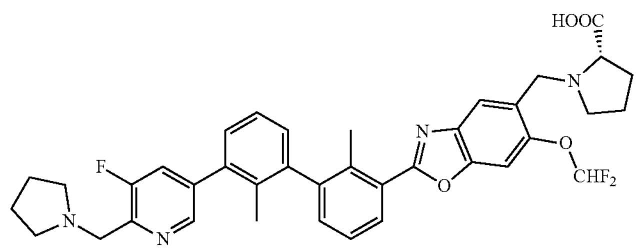 [SMILES: Cc1c(-c2cnc(CN3CCCC3)c(F)c2)cccc1-c1cccc(-c2nc3cc(CN4CCC[C@H]4C(=O)O)c(OC(F)F)cc3o2)c1C] | 671.3 |
| 266 | ((6-(difluoromethoxy)-2-(3'-(6-methoxy-5-(pyrrolidin-1-ylmethyl)pyridin-2-yl)-2,2'-dimethyl-[1,1'-biphenyl]-3-yl)benzo[d]oxazol-5-yl)methyl)-L-proline | 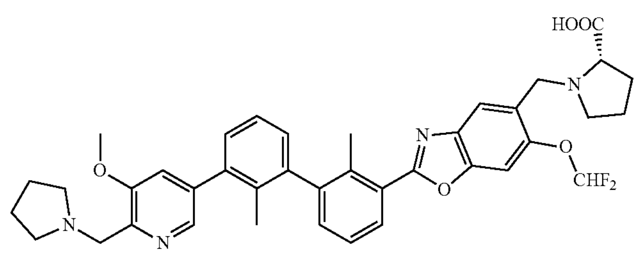 [SMILES: COc1cc(-c2cccc(-c3cccc(-c4nc5cc(CN6CCC[C@H]6C(=O)O)c(OC(F)F)cc5o4)c3C)c2C)cnc1CN1CCCC1] | 683.3 |
| 267 | ((6-(difluoromethoxy)-2-(2,2'-dimethyl-3'-(6-oxo-5-(pyrrolidin-1-ylmethyl)-1,6-dihydropyridin-2-yl)-[1,1'-biphenyl]-3-yl)benzo[d]oxazol-5-yl)methyl)-L-proline | 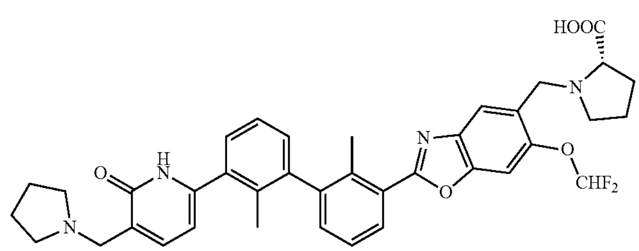 [SMILES: Cc1c(-c2ccc(CN3CCCC3)c(=O)[nH]2)cccc1-c1cccc(-c2nc3cc(CN4CCC[C@H]4C(=O)O)c(OC(F)F)cc3o2)c1C] | 669.3 |
| 268 | ((6-(difluoromethoxy)-2-(2'-(difluoromethyl)-3'-(5-fluoro-6-(pyrrolidin-1-ylmethyl)pyridin-3-yl)-2-methyl-[1,1'-biphenyl]-3-yl)benzo[d]oxazol-5-yl)methyl)-L-proline | 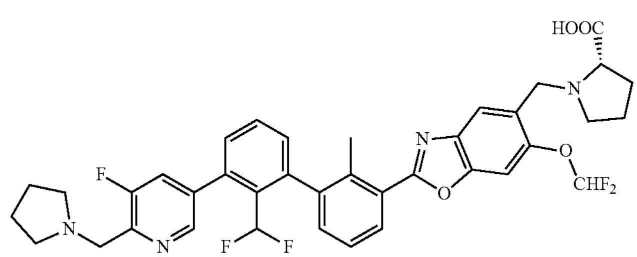 [SMILES: Cc1c(-c2nc3cc(CN4CCC[C@H]4C(=O)O)c(OC(F)F)cc3o2)cccc1-c1cccc(-c2cnc(CN3CCCC3)c(F)c2)c1C(F)F] | 707.3 |

TABLE 6-continued

| EX No. | Chemical Name | Structure | Physical Data (MS) (M + H)+ |
|---|---|---|---|
| 269 | ((6-(difluoromethoxy)-2-(3'-(5-fluoro-6-(pyrrolidin-1-ylmethyl)pyridin-3-yl)-2'-(fluoromethyl)-2-methyl-[1,1'-biphenyl]-3-yl)benzo[d]oxazol-5-yl)methyl)-L-proline | 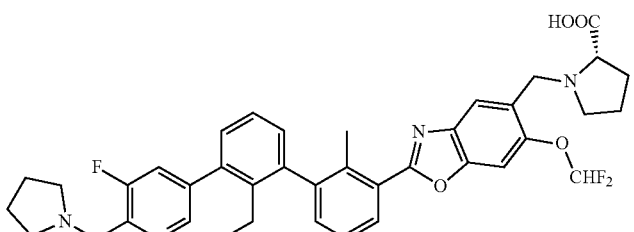 | 689.3 |
| 270 | ((6-(difluoromethoxy)-2-(3'-(2-fluoro-6-(pyrrolidin-1-ylmethyl)pyridin-3-yl)-2,2'-dimethyl-[1,1'-biphenyl]-3-yl)benzo[d]oxazol-5-yl)methyl)-L-proline | 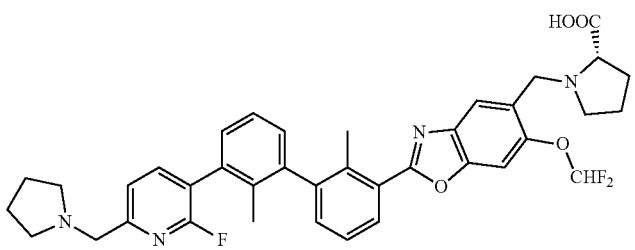 [SMILES: Cc1c(-c2nc3cc(CN4CCC[C@H]4C(=O)O)c(OC(F)F)cc3o2)cccc1-c1cccc(-c2ccc(CN3CCCC3)nc2F)c1C] | 671.3 |
| 271 | ((6-(difluoromethoxy)-2-(3'-(5-((3,3-dimethylazetidin-1-yl)methyl)-6-methoxypyridin-2-yl)-2,2'-dimethyl-[1,1'-biphenyl]-3-yl)benzo[d]oxazol-5-yl)methyl)-L-proline | 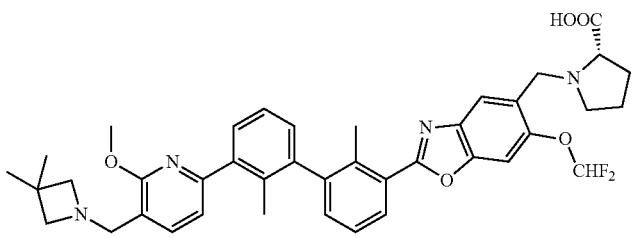 [SMILES: COc1nc(-c2cccc(-c3cccc(-c4nc5cc(CN6CCC[C@H]6C(=O)O)c(OC(F)F)cc5o4)c3C)c2C)ccc1CN1CC(C)(C)C1] | 697.3 |
| 272 | ((6-(difluoromethoxy)-2-(3'-(6-methoxy-5-(((R)-3-methylpyrrolidin-1-yl)methyl)pyridin-2-yl)-2,2'-dimethyl-[1,1'-biphenyl]-3-yl)benzo[d]oxazol-5-yl)methyl)-L-proline | 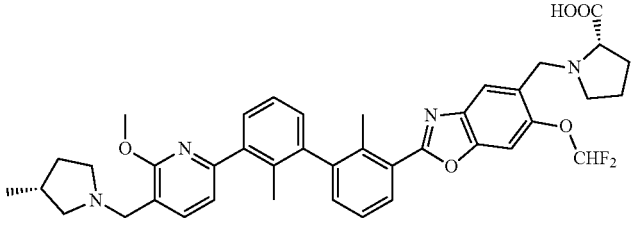 [SMILES: COc1nc(-c2cccc(-c3cccc(-c4nc5cc(CN6CCC[C@H]6C(=O)O)c(OC(F)F)cc5o4)c3C)c2C)ccc1CN1CC[C@@H](C)C1] | 697.3 |
| 273 | ((6-(difluoromethoxy)-2-(3'-(6-methoxy-5-(((S)-3-methylpyrrolidin-1-yl)methyl)pyridin-2-yl)-2,2'-dimethyl-[1,1'-biphenyl]-3-yl)benzo[d]oxazol-5-yl)methyl)-D-proline | 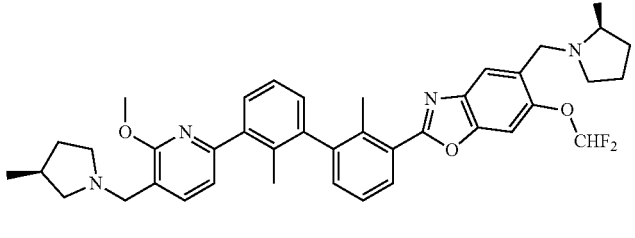 | 697.3 |
| 274 | ((6-(difluoromethoxy)-2-(2,2'-dimethyl-3'-(5-(pyrrolidin-1-ylmethyl)-4-vinylpyridin-2-yl)-[1,1'-biphenyl]-3-yl)benzo[d]oxazol-5-yl)methyl)-L-proline | 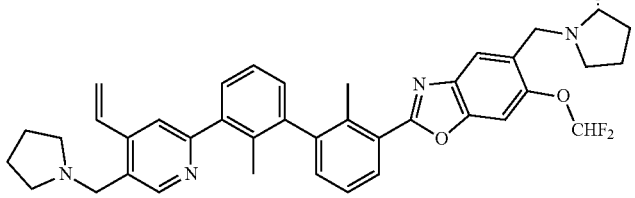 | 679.3 |

TABLE 6-continued

| EX No. | Chemical Name | Structure | Physical Data (MS) (M + H)+ |
|---|---|---|---|
| 275 | ((6-(difluoromethoxy)-2-(3'-(5-((3-(difluoromethyl)pyrrolidin-1-yl)methyl)-6-methoxypyridin-2-yl)-2,2'-dimethyl-[1,1'-biphenyl]-3-yl)benzo[d]oxazol-5-yl)methyl)-L-proline | 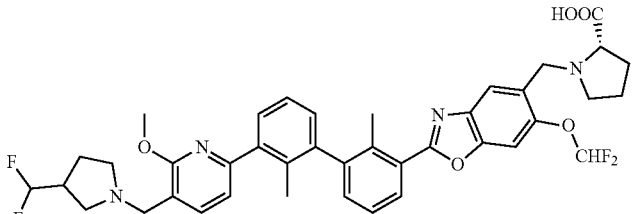 | 733.3 |
| 276 | ((6-(difluoromethoxy)-2-(3'-(6-methoxy-5-((((5-oxopyrrolidin-2-yl)methyl)amino)methyl)pyridin-2-yl)-2,2'-dimethyl-[1,1'-biphenyl]-3-yl)benzo[d]oxazol-5-yl)methyl)-L-proline | 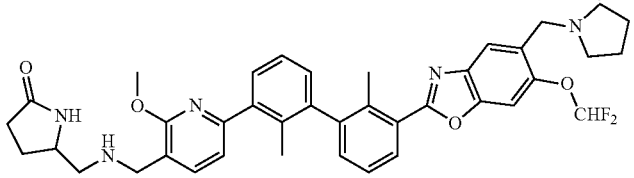 | 726.3 |
| 277 | ((6-(difluoromethoxy)-2-(3'-(6-methoxy-5-(((S)-2-methylpyrrolidin-1-yl)methyl)pyridin-2-yl)-2,2'-dimethyl-[1,1'-biphenyl]-3-yl)benzo[d]oxazol-5-yl)methyl)-L-proline | 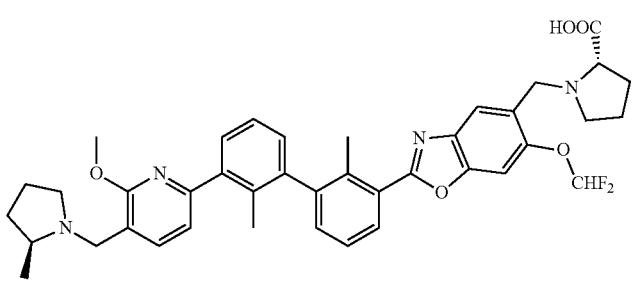 [SMILES: COc1nc(-c2cccc(-c3cccc(-c4nc5cc(CN6CCC[C@H]6C(=O)O)c(OC(F)F)cc5o4)c3C)c2C)ccc1CN1CCC[C@@H]1C] | 697.3 |
| 278 | ((2-(3'-(5-(((1s,4s)-7-azabicyclo[2.2.1]heptan-7-yl)methyl)-6-methoxypyridin-2-yl)-2,2'-dimethyl-[1,1'-biphenyl]-3-yl)-6-(difluoromethoxy)benzo[d]oxazol-5-yl)methyl)-L-proline | 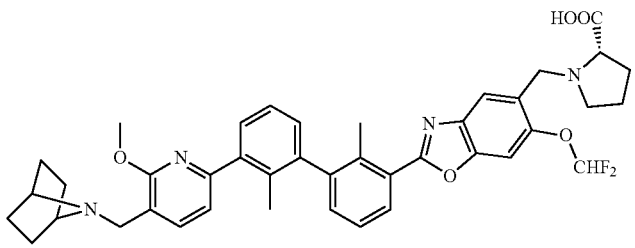 [SMILES: COc1nc(-c2cccc(-c3cccc(-c4nc5cc(CN6CCC[C@H]6C(=O)O)c(OC(F)F)cc5o4)c3C)c2C)ccc1CN1C2CCC1CC2] | 709.3 |
| 279 | ((6-(difluoromethoxy)-2-(3'-(6-methoxy-5-(((R)-2-methylpyrrolidin-1-yl)methyl)pyridin-2-yl)-2,2'-dimethyl-[1,1'-biphenyl]-3-yl)benzo[d]oxazol-5-yl)methyl)-L-proline | 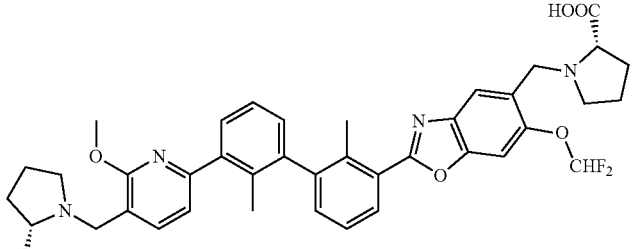 | 697.3 |

TABLE 6-continued

| EX No. | Chemical Name | Structure | Physical Data (MS) (M + H)+ |
|---|---|---|---|
| 280 | ((6-(difluoromethoxy)-2-(2,2'-dimethyl-3'-(5-(pyrrolidin-1-ylmethyl)thiophen-2-yl)-[1,1'-biphenyl]-3-yl)benzo[d]oxazol-5-yl)methyl)-L-proline | 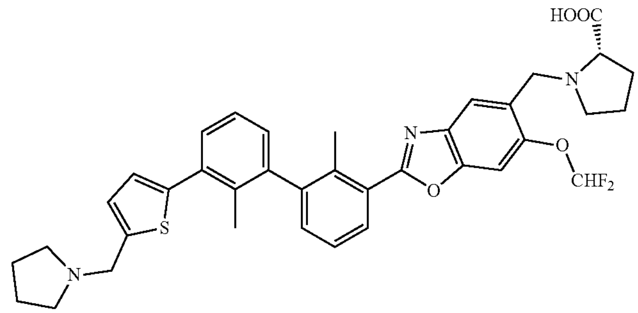 [SMILES: Cc1c(-c2nc3cc(CN4CCC[C@H]4C(=O)O)c(OC(F)F)cc3o2)cccc1-c1cccc(-c2ccc(CN3CCCC3)s2)c1C] | 658.3 |
| 281 | ((6-(difluoromethoxy)-2-(2,2'-dimethyl-3'-(2-(pyrrolidin-1-ylmethyl)pyrimidin-5-yl)-[1,1'-biphenyl]-3-yl)benzo[d]oxazol-5-yl)methyl)-L-proline | 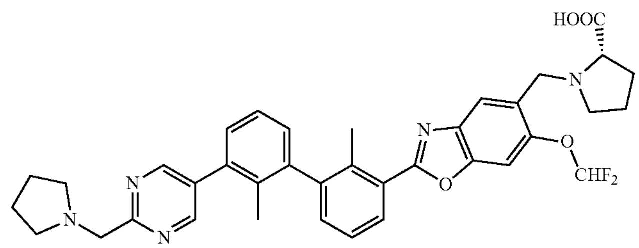 [SMILES: Cc1c(-c2cnc(CN3CCCC3)nc2)cccc1-c1cccc(-c2nc3cc(CN4CCC[C@H]4C(=O)O)c(OC(F)F)cc3o2)c1C] | 654.3 |
| 282 | ((6-(difluoromethoxy)-2-(2,2'-dimethyl-3'-(2-(4-methylpiperazin-1-yl)pyrimidin-5-yl)-[1,1'-biphenyl]-3-yl)benzo[d]oxazol-5-yl)methyl)-L-proline | 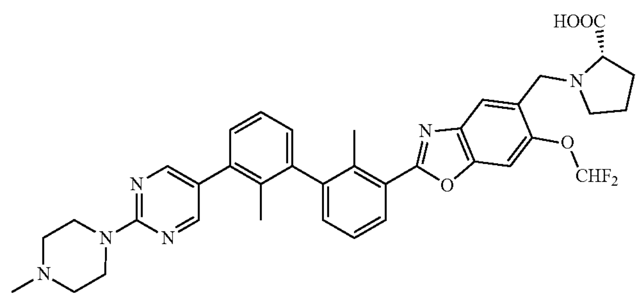 [SMILES: Cc1c(-c2cnc(N3CCN(C)CC3)nc2)cccc1-c1cccc(-c2nc3cc(CN4CCC[C@H]4C(=O)O)c(OC(F)F)cc3o2)c1C] | 669.3 |
| 283 | ((6-(difluoromethoxy)-2-(2,2'-dimethyl-3'-(2-(pyrrolidin-1-yl)pyrimidin-5-yl)-[1,1'-biphenyl]-3-yl)benzo[d]oxazol-5-yl)methyl)-L-proline | 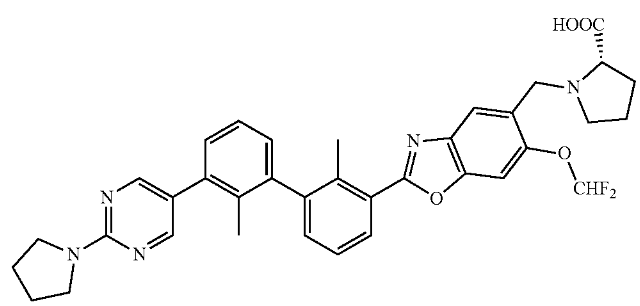 [SMILES: Cc1c(-c2cnc(N3CCCC3)nc2)cccc1-c1cccc(-c2nc3cc(CN4CCC[C@H]4C(=O)O)c(OC(F)F)cc3o2)c1C] | 640.3 |
| 284 | ((6-(difluoromethoxy)-2-(2,2'-dimethyl-3'-(5-(pyrrolidin-1-ylmethyl)pyrazin-2-yl)-[1,1'-biphenyl]-3-yl)benzo[d]oxazol-5-yl)methyl)-L-proline | 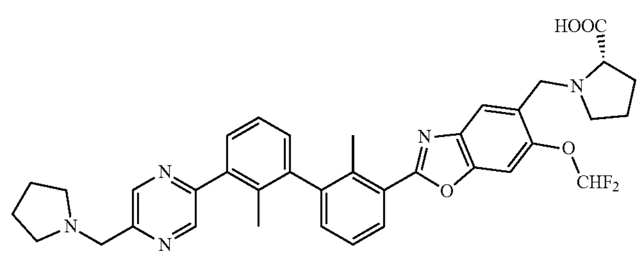 [SMILES: Cc1c(-c2cnc(CN3CCCC3)cn2)cccc1-c1cccc(-c2nc3cc(CN4CCC[C@H]4C(=O)O)c(OC(F)F)cc3o2)c1C] | 654.3 |

TABLE 6-continued

| EX No. | Chemical Name | Structure | Physical Data (MS) (M + H)+ |
|---|---|---|---|
| 285 | ((6-(difluoromethoxy)-2-(3'-(6-methoxy-5-(pyrrolidin-1-ylmethyl)pyrazin-2-yl)-2,2'-dimethyl-[1,1'-biphenyl]-3-yl)benzo[d]oxazol-5-yl)methyl)-L-proline | 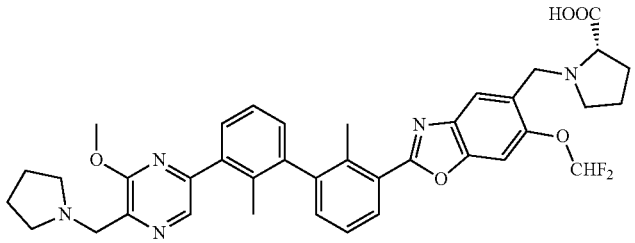 [SMILES: COc1nc(-c2cccc(-c3cccc(-c4nc5cc(CN6CCC[C@H]6C(=O)O)c(OC(F)F)cc5o4)c3C)c2C)cnc1CN1CCCC1] | 684.3 |
| 286 | ((6-(difluoromethoxy)-2-(3'-(6-methoxy-5-(((R)-3-methylpyrrolidin-1-yl)methyl)pyrazin-2-yl)-2,2'-dimethyl-[1,1'-biphenyl]-3-yl)benzo[d]oxazol-5-yl)methyl)-L-proline | 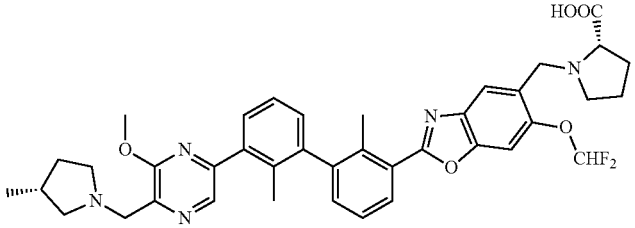 [SMILES: COc1nc(-c2cccc(-c3cccc(-c4nc5cc(CN6CCC[C@H]6C(=O)O)c(OC(F)F)cc5o4)c3C)c2C)cnc1CN1CC[C@@H](C)C1] | 698.3 |
| 287 | ((2-(2'-chloro-3'-(6-methoxy-5-((((5-oxopyrrolidin-2-yl)methyl)amino)methyl)pyrazin-2-yl)-2-methyl-[1,1'-biphenyl]-3-yl)-6-(difluoromethoxy)benzo[d]oxazol-5-yl)methyl)-L-proline | 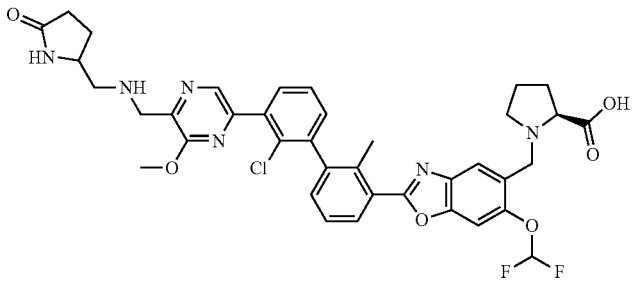 [SMILES: COc1nc(-c2cccc(-c3cccc(-c4nc5cc(CN6CCC[C@H]6C(=O)O)c(OC(F)F)cc5o4)c3C)c2Cl)cnc1CNCC1CCC(=O)N1] | 747.2 |
| 288 | ((6-(difluoromethoxy)-2-(2,2'-dimethyl-3'-(1,2,3,4-tetrahydroisoquinolin-6-yl)-[1,1'-biphenyl]-3-yl)benzo[d]oxazol-5-yl)methyl)-L-proline | 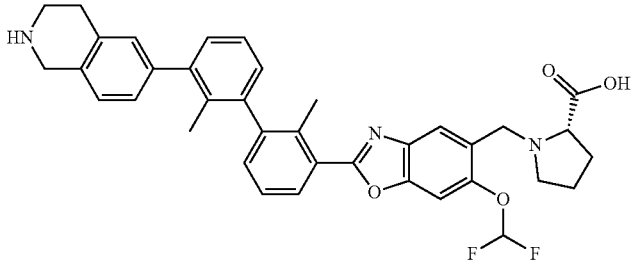 [SMILES: Cc1c(-c2ccc3c(c2)CCNC3)cccc1-c1cccc(-c2nc3cc(CN4CCC[C@H]4C(=O)O)c(OC(F)F)cc3o2)c1C] | 624.3 |
| 289 | ((6-(difluoromethoxy)-2-(3'-(isoindolin-5-yl)-2,2'-dimethyl-[1,1'-biphenyl]-3-yl)benzo[d]oxazol-5-yl)methyl)-L-proline | 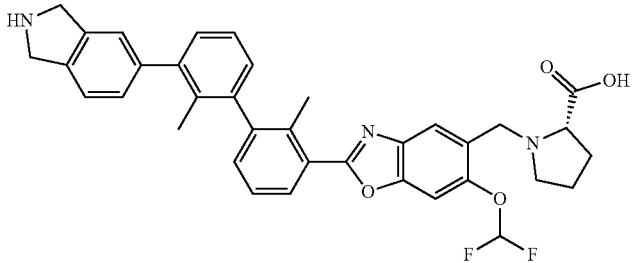 [SMILES: Cc1c(-c2ccc3c(c2)CNC3)cccc1-c1cccc(-c2nc3cc(CN4CCC[C@H]4C(=O)O)c(OC(F)F)cc3o2)c1C] | 610.2 |

TABLE 6-continued

| EX No. | Chemical Name | Structure | Physical Data (MS) (M + H)+ |
|---|---|---|---|
| 290 | ((2-(3'-(2-(2-carboxyethyl)isoindolin-5-yl)-2,2'-dimethyl-[1,1'-biphenyl]-3-yl)-6-(difluoromethoxy)benzo[d]oxazol-5-yl)methyl)-L-proline | 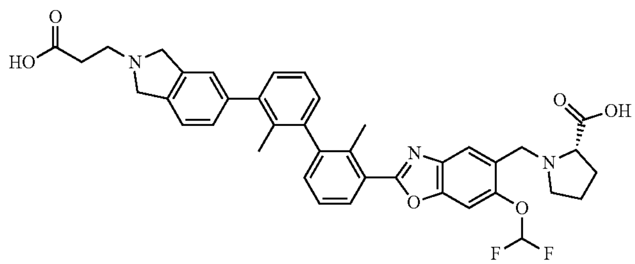 [SMILES: Cc1c(-c2ccc3c(c2)CN(CCC(=O)O)C3)cccc1-c1cccc(-c2nc3cc(CN4CCC[C@H]4C(=O)O)c(OC(F)F)cc3o2)c1C] | 682.3 |
| 291 | ((2-(3'-(2-(carboxymethyl)isoindolin-5-yl)-2,2'-dimethyl-[1,1'-biphenyl]-3-yl)-6-(difluoromethoxy)benzo[d]oxazol-5-yl)methyl)-L-proline | 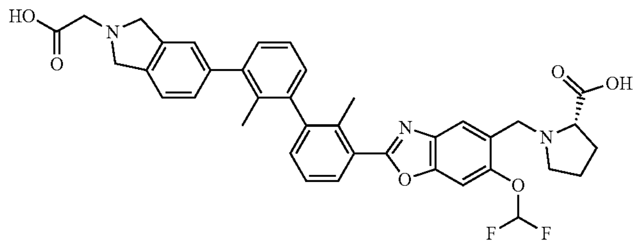 [SMILES: Cc1c(-c2ccc3c(c2)CN(CC(=O)O)C3)cccc1-c1cccc(-c2nc3cc(CN4CCC[C@H]4C(=O)O)c(OC(F)F)cc3o2)c1C] | 668.3 |
| 292 | ((2-(3'-(2-(1-carboxyethyl)isoindolin-5-yl)-2,2'-dimethyl-[1,1'-biphenyl]-3-yl)-6-(difluoromethoxy)benzo[d]oxazol-5-yl)methyl)-L-proline | 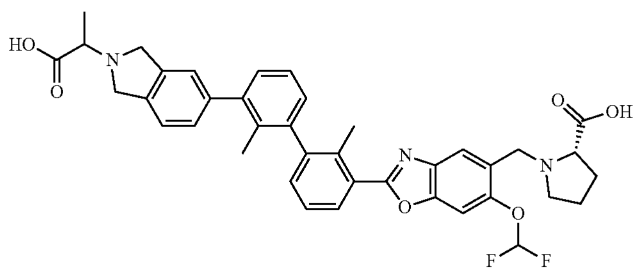 [SMILES: Cc1c(-c2ccc3c(c2)CN(C(C)C(=O)O)C3)cccc1-c1cccc(-c2nc3cc(CN4CCC[C@H]4C(=O)O)c(OC(F)F)cc3o2)c1C] | 682.3 |
| 293 | ((2-(3'-(2-amino-1H-benzo[d]imidazol-5-yl)-2,2'-dimethyl-[1,1'-biphenyl]-3-yl)-6-(difluoromethoxy)benzo[d]oxazol-5-yl)methyl)-L-proline | 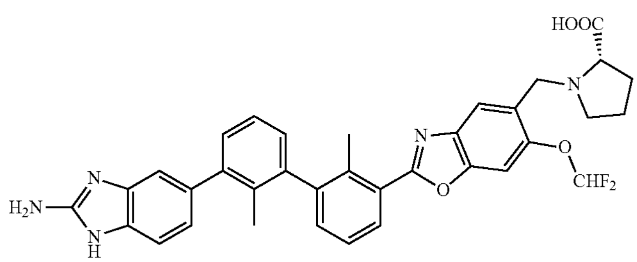 [SMILES: Cc1c(-c2ccc3[nH]c(N)nc3c2)cccc1-c1cccc(-c2nc3cc(CN4CCC[C@H]4C(=O)O)c(OC(F)F)cc3o2)c1C] | 624.2 |
| 294 | ((6-(difluoromethoxy)-2-(3'-(5-((3,3-dimethylpyrrolidin-1-yl)methyl)-6-methoxypyridin-2-yl)-2,2'-dimethyl-[1,1'-biphenyl]-3-yl)benzo[d]oxazol-5-yl)methyl)-L-proline | 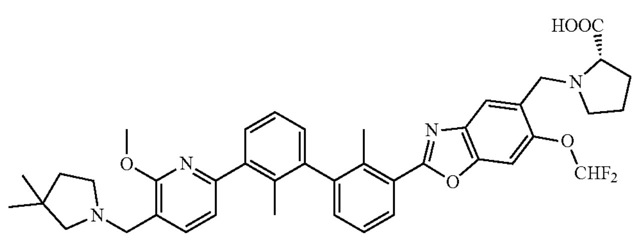 [SMILES: COc1nc(-c2cccc(-c3cccc(-c4nc5cc(CN6CCC[C@H]6C(=O)O)c(OC(F)F)cc5o4)c3C)c2C)ccc1CN1CCC(C)(C)C1] | 711.3 |

Example 295 Synthesis of Compound 295

((2-(3'-(7-cyano-5-(pyrrolidin-1-ylmethyl)-1H-benzo[d]imidazol-2-yl)-2,2'-dimethyl-[1,1'-biphenyl]-3-yl)-6-(difluoromethoxy)benzo[d]oxazol-5-yl)methyl)-L-proline

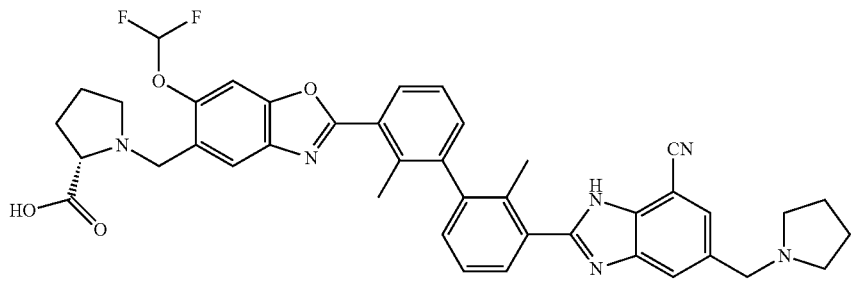

Compound 295

Step 1: Preparation of methyl 4-amino-3-iodo-5-nitrobenzoate

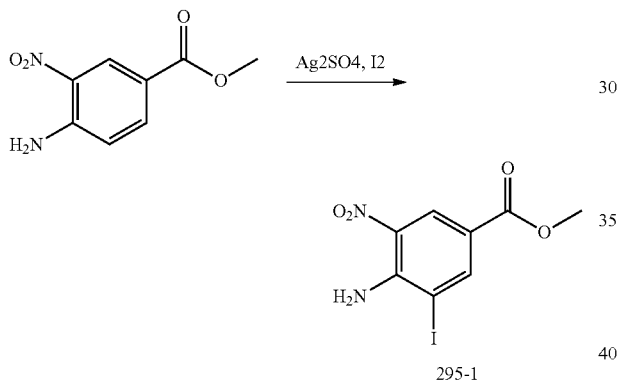

Methyl 4-amino-3-nitro-benzoate (5 g) was added to a mixture of Ag$_2$SO$_4$ (7.93 g) and I2 (6.47 g) in EtOH (20 mL) at room temperature. The mixture was stirred at room temperature overnight. The reaction mixture was diluted with water (20 mL) and extracted with ethyl acetate. The organic layers were washed with aqueous Na$_2$S$_2$O$_3$, dried over MgSO$_4$ and evaporated to dryness. The residue was purified by chromatography on silica gel to give the desired product methyl 4-amino-3-iodo-5-nitro-benzoate (7 g) as a yellow solid.

Step 2: Preparation of methyl 3,4-diamino-5-iodobenzoate

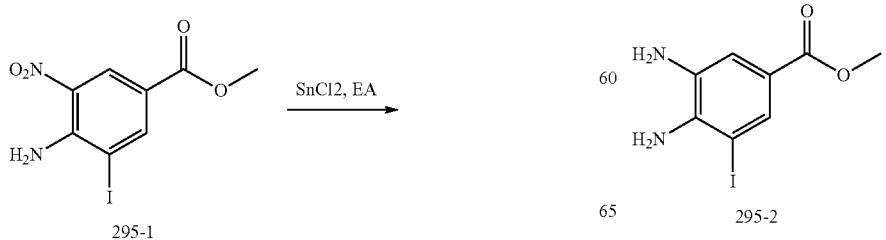

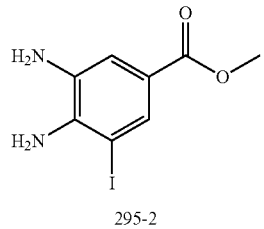

To a solution of compound 295-1 (3 g) in EA (30 mL) was added SnCl$_2$ (8.42 g). The reaction mixture was stirred at 70° C. for 16 hrs. EA (50 mL) was added to the reaction mixture and the organic layer was washed with aqueous NaHCO$_3$, dried over MgSO$_4$ and evaporated to dryness. The residue was purified by chromatography on silica gel to give the desired product methyl 3,4-diamino-5-iodo-benzoate (2.6 g) as a yellow solid.

Step 3: Preparation of methyl 2-(3-bromo-2-methylphenyl)-7-iodo-1H-benzo[d]imidazole-5-carboxylate

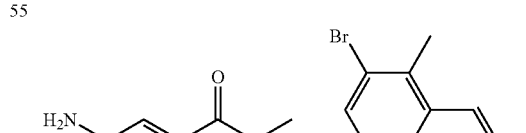

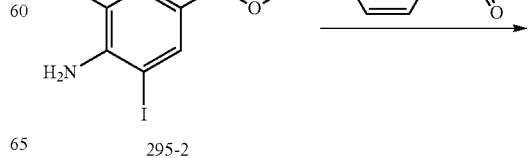

-continued

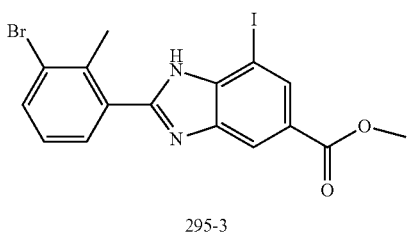

295-3

A mixture of compound 295-2 (2.6 g), 3-bromo-2-methylbenzaldehyde (1.77 g) and AcOH (30 mL) was stirred at 80° C. for 16 hrs. EA (50 mL) was added to the reaction mixture and the organic layer was washed with water, dried over MgSO₄ and evaporated to dryness. The residue was purified by chromatography on silica gel to give the desired product methyl 2-(3-bromo-2-methyl-phenyl)-7-iodo-1H-benzimidazole-5-carboxylate (3.2 g) as a yellow solid.

Step 4: Preparation of 2-(3-bromo-2-methylphenyl)-7-iodo-1H-benzo[d]imidazole-5-carboxylic acid

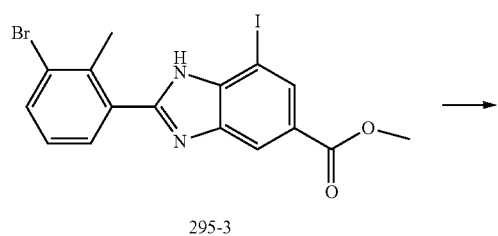

To a solution of compound 295-3 (2 g) in MeOH (20 mL) was added the solution of NaOH (849.10 mg) in H₂O (6 mL). The reaction mixture was stirred at 50° C. overnight. The mixture was concentrated. H₂O (10 mL) was added to the mixture and adjusted pH to 5 with 2N HCl, The precipitate was filtered and the filter cake was washed with H₂O. The product was dried in a vacuum oven (45° C., 3 hours) to yield 2-(3-bromo-2-methyl-phenyl)-7-iodo-1H-benzimidazole-5-carboxylic acid (1.8 g) of the title compound as an off-white solid.

Step 5: Preparation of (2-(3-bromo-2-methylphenyl)-7-iodo-1H-benzo[d]imidazol-5-yl)methanol

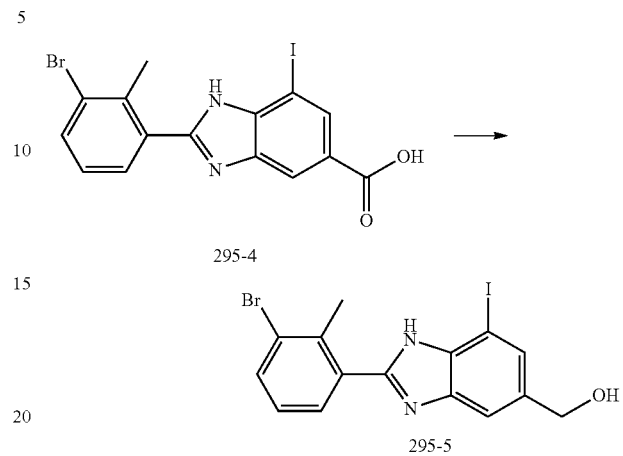

Borane-tetrahydrofuran complex (20 mL) was added to a solution of compound 295-4 (1.8 g) in THF (20 mL) at −30° C. The reaction mixture was then stirred at 60° C. for 16 hrs. The mixture was cooled to room temperature and 2N HCl (20 mL) was added. After 10 mins, the mixture was diluted with ethyl acetate and washed with water. The organic layer was dried over MgSO₄ and evaporated to dryness. The residue was purified by chromatography on silica gel to give the desired product [2-(3-bromo-2-methyl-phenyl)-7-iodo-1H-benzimidazol-5-yl] methanol (1 g) as a white solid.

Step 6: Preparation of 2-(3-bromo-2-methylphenyl)-5-(hydroxymethyl)-1H-benzo[d]imidazole-7-carbonitrile

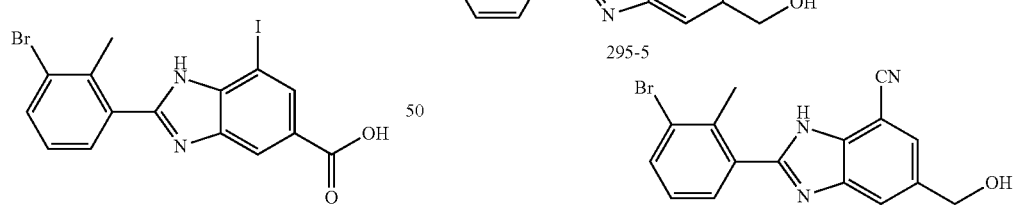

A mixture of compound 295-5 (500 mg), Zn(CN)₂ (66.02 mg) Pd(PPh₃)₄ (130.34 mg) in DMF (10 mL) was stirred at 90° C. for 3 hrs under nitrogen. The reaction mixture was diluted with water (10 mL) and extracted with ethyl acetate. Then, the organic layer was washed with aqueous NaCl, dried over MgSO₄ and evaporated to dryness. The residue was purified by chromatography on silica gel to give the desired product 2-(3-bromo-2-methyl-phenyl)-6-(hydroxymethyl)-3H-benzimidazole-4-carbonitrile (150 mg) as a yellow oil.

Step 7: Preparation of 2-(3-bromo-2-methylphenyl)-5-(chloromethyl)-1H-benzo[d]imidazole-7-carbonitrile

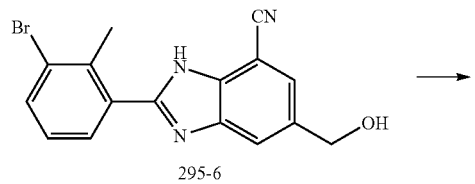

295-6

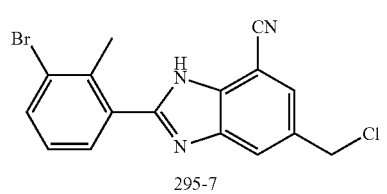

295-7

This compound was prepared using similar procedures as described as step 2 in example 1, with compound 295-6 replacing compound 1-1. The mixture was concentrated to give the title compound.

Step 8: Preparation of 2-(3-bromo-2-methylphenyl)-5-(pyrrolidin-1-ylmethyl)-1H-benzo[d]imidazole-7-carbonitrile

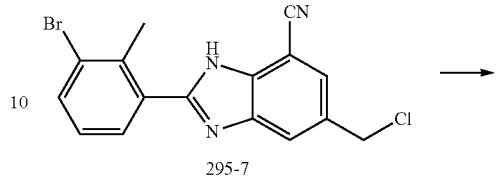

295-7

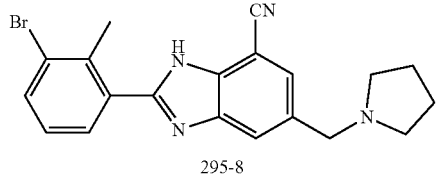

295-8

This compound was prepared using similar procedures as described as step 3 in example 1, with compound 295-7 replacing compound 1-2, and with pyrrolidine replacing (1S, 2R)-2-aminocyclopentan-1-ol. The crude product was purified by chromatography on silica gel to give the title compound.

Step 9: Preparation of methyl ((2-(3'-(7-cyano-5-(pyrrolidin-1-ylmethyl)-1H-benzo[d]imidazol-2-yl)-2,2'-dimethyl-[1,1'-biphenyl]-3-yl)-6-(difluoromethoxy)benzo[d]oxazol-5-yl)methyl)-L-prolinate

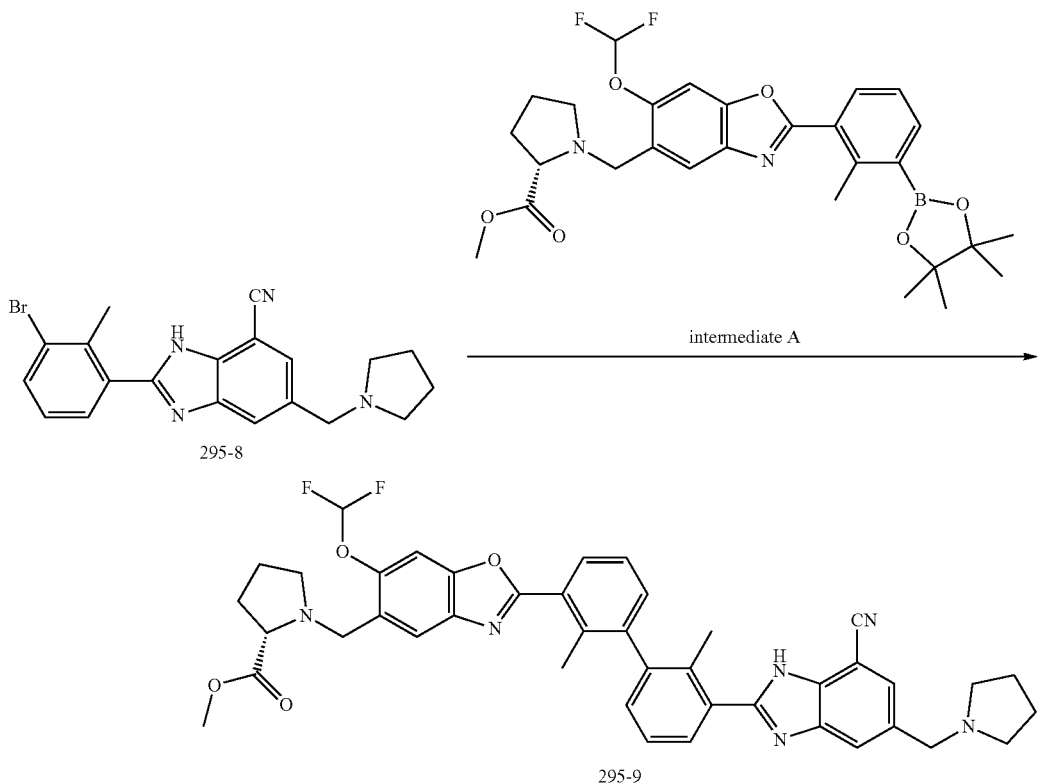

295-9

This compound was prepared using similar procedures as described as step 1 in example 1, with compound 295-8 replacing compound a-6. The crude product was purified by chromatography on silica gel to give the title compound.

Step 10: Preparation of ((2-(3'-(7-cyano-5-(pyrrolidin-1-ylmethyl)-1H-benzo[d]imidazol-2-yl)-2,2'-dimethyl-[1,1'-biphenyl]-3-yl)-6-(difluoromethoxy)benzo[d]oxazol-5-yl)methyl)-L-proline

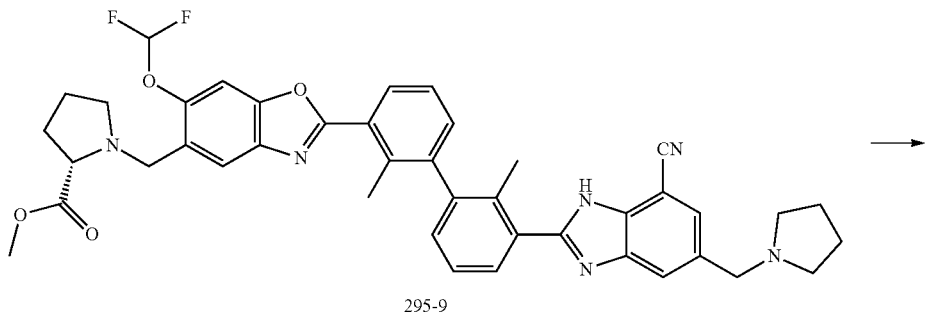

295-9

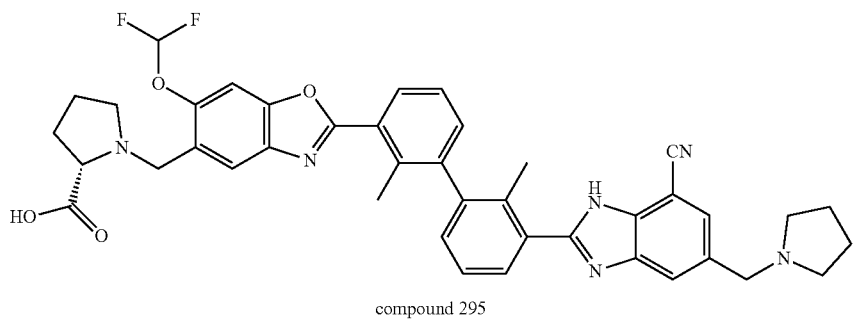

compound 295

This compound was prepared using similar procedures as described as step 5 in example 1, with compound 295-9 replacing compound 1-4. The crude product was purified by pre-HPLC to give the desired product (2S)-1-[[2-[3-[3-[7-cyano-5-(pyrrolidin-1-ylmethyl)-1H-benzimidazol-2-yl]-2-methyl-phenyl]-2-methyl-phenyl]-6-(difluoromethoxy)-1,3-benzoxazol-5-yl]methyl]pyrrolidine-2-carboxylic acid. LC-MS (m/z): 717.3 $(M+H)^+$.

The compounds of table 7 were prepared in a similar manner to Example 295 via different reaction starting materials and suitable reagents.

TABLE 7

| EX No. | Chemical Name | Structure | Physical Data (MS) $(M + H)^+$ |
|---|---|---|---|
| 296 | ((2-(3'-(6,7-difluoro-5-(pyrrolidin-1-ylmethyl)-1H-benzo[d]imidazol-2-yl)-2,2'-dimethyl-[1,1'-biphenyl]-3-yl)-6-(difluoromethoxy)benzo[d]oxazol-5-yl)methyl)-L-proline | 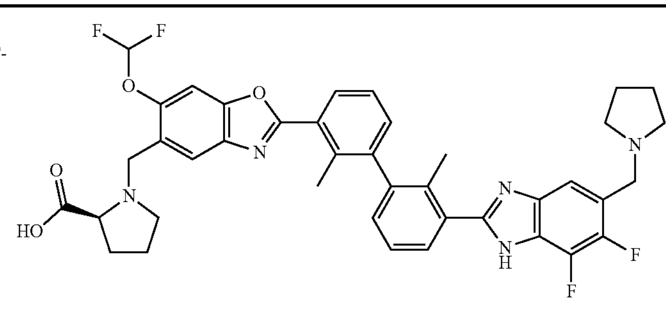 | 728.3 |

TABLE 7-continued

| EX No. | Chemical Name | Structure | Physical Data (MS) (M + H)+ |
|---|---|---|---|
| 297 | ((6-(difluoromethoxy)-2-(3'-(6-fluoro-5-(pyrrolidin-1-ylmethyl)-1H-benzo[d]imidazol-2-yl)-2,2'-dimethyl-[1,1'-biphenyl]-3-yl)benzo[d]oxazol-5-yl)methyl)-L-proline | 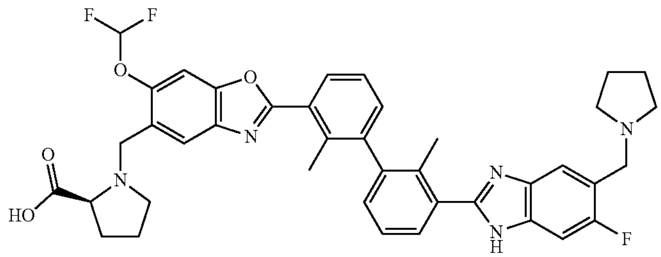 [SMILES: Cc1c(-c2nc3cc(CN4CCCC4)c(F)cc3[nH]2)cccc1-c1cccc(-c2nc3cc(CN4CCC[C@H]4C(=O)O)c(OC(F)F)cc3o2)c1C] | 710.3 |
| 298 | ((2-(3'-(6,7-difluoro-1-methyl-5-(pyrrolidin-1-ylmethyl)-1H-benzo[d]imidazol-2-yl)-2,2'-dimethyl-[1,1'-biphenyl]-3-yl)-6-(difluoromethoxy)benzo[d]oxazol-5-yl)methyl)-L-proline | 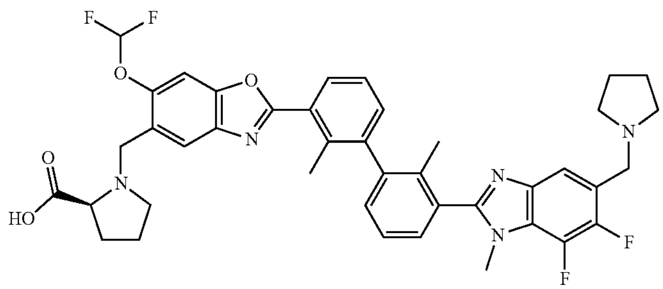 [SMILES: Cc1c(-c2nc3cc(CN4CCC[C@H]4C(=O)O)c(OC(F)F)cc3o2)cccc1-c1cccc(-c2nc3cc(CN4CCCC4)c(F)c(F)c3n2C)c1C] | 742.3 |
| 299 | ((2-(3'-(6,7-difluoro-5-(pyrrolidin-1-ylmethyl)-1-(2,2,2-trifluoroethyl)-1H-benzo[d]imidazol-2-yl)-2,2'-dimethyl-[1,1'-biphenyl]-3-yl)-6-(difluoromethoxy)benzo[d]oxazol-5-yl)methyl)-L-proline | 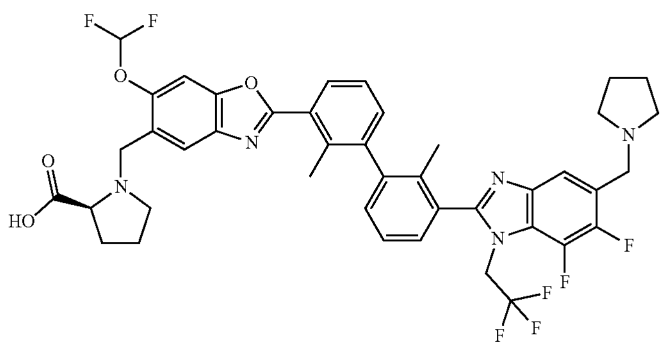 [SMILES: Cc1c(-c2nc3cc(CN4CCC[C@H]4C(=O)O)c(OC(F)F)cc3o2)cccc1-c1cccc(-c2nc3cc(CN4CCCC4)c(F)c(F)c3n2CC(F)(F)F)c1C] | 810.3 |
| 300 | ((2-(3'-(4,5-difluoro-6-(pyrrolidin-1-ylmethyl)-1-(2,2,2-trifluoroethyl)-1H-benzo[d]imidazol-2-yl)-2,2'-dimethyl-[1,1'-biphenyl]-3-yl)-6-(difluoromethoxy)benzo[d]oxazol-5-yl)methyl)-L-proline | 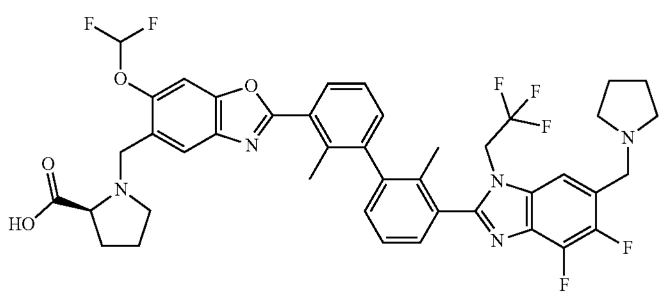 [SMILES: Cc1c(-c2nc3cc(CN4CCC[C@H]4C(=O)O)c(OC(F)F)cc3o2)cccc1-c1cccc(-c2nc3c(F)c(F)c(CN4CCCC4)cc3n2CC(F)(F)F)c1C] | 810.3 |
| 301 | ((6-(difluoromethoxy)-2-(2,2'-dimethyl-3'-(5-(pyrrolidin-1-ylmethyl)-7-(trifluoromethyl)-1H-benzo[d]imidazol-2-yl)-[1,1'-biphenyl]-3-yl)benzo[d]oxazol-5-yl)methyl)-L-proline | 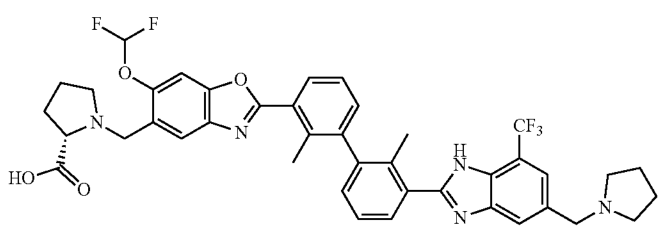 [SMILES: Cc1c(-c2nc3cc(CN4CCCC4)cc(C(F)(F)F)c3[nH]2)cccc1-c1cccc(-c2nc3cc(CN4CCC[C@H]4C(=O)O)c(OC(F)F)cc3o2)c1C] | 760.3 |

TABLE 7-continued

| EX No. | Chemical Name | Structure | Physical Data (MS) (M + H)+ |
|---|---|---|---|
| 302 | ((2-(2'-chloro-3'-(5-(((2-hydroxyethyl)amino)methyl)picolinamido)-2-methyl-[1,1'-biphenyl]-3-yl)-6-(difluoromethoxy)benzo[d]oxazol-5-yl)methyl)-L-proline | 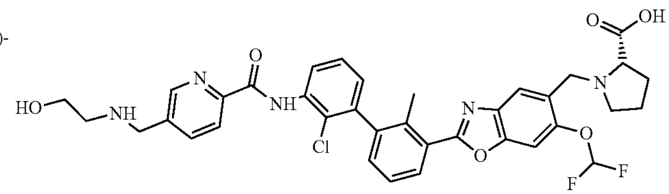 | 706.2 |
| 303 | ((6-(difluoromethoxy)-2-(2,2'-dimethyl-3'-(5,6,7,8-tetrahydroimidazo[1,2-a]pyrazine-2-carboxamido)-[1,1'-biphenyl]-3-yl)benzo[d]oxazol-5-yl)methyl)-L-proline | 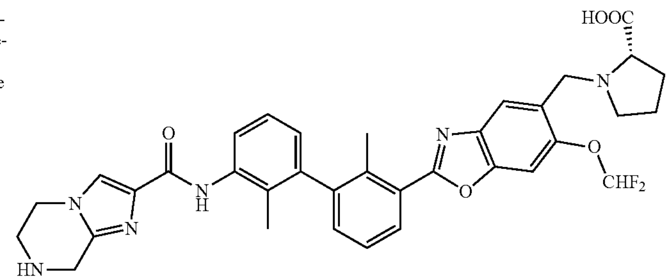 | 657.3 |

Example 304 Synthesis of Compound 304

((6-(difluoromethoxy)-2-(2,2'-dimethyl-3'-(4-methyl-5-(pyrrolidin-1-ylmethyl)oxazol-2-yl)-[1,1'-biphenyl]-3-yl)benzo[d]oxazol-S-yl)methyl)-L-proline

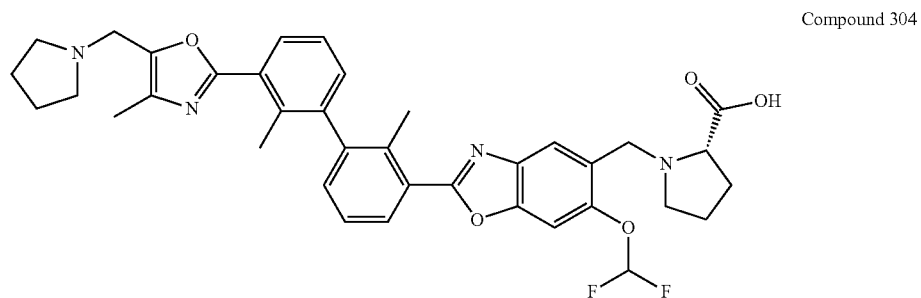 [SMILES: Cc1nc(-c2cccc(-c3cccc(-c4nc5cc(CN6CCC[C@H]6C(=O)O)c(OC(F)F)cc5o4)c3C)c2C)oc1CN1CCCC1]

Compound 304

Step-1: methyl 2-bromo-4-methyl-oxazole-S-carboxylate

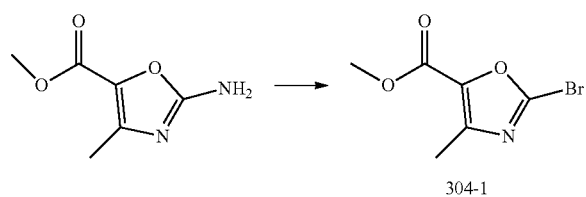

304-1 tert-Butyl nitrite (2.24 g) was added to a suspension of methyl 2-amino-4-methyl-oxazole-5-carboxylate (1.7 g) CuBr$_2$ (7.28 g) in acetonitrile (20 mL). The mixture was stirred at room temperature overnight. The reaction mixture was diluted with water (50 mL) and extracted with ethyl acetate. Then, the organic layer was washed with aqueous NaCl, dried over MgSO$_4$ and evaporated to dryness. The residue was purified by chromatography on silica gel to give the desired product methyl 2-bromo-4-methyl-oxazole-5-carboxylate (800 mg) as a white solid.

Step-2: Preparation of methyl 2-(3-bromo-2-methyl-phenyl)-4-methyl-oxazole-5-carboxylate

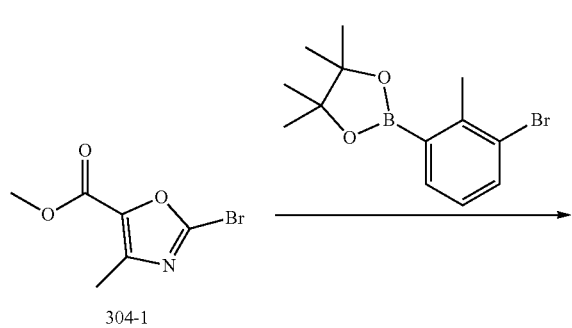

This compound was prepared using similar procedures as described as step 1 in example 1. The crude product was purified by chromatography on silica gel to give the title compound.

Step-3: Preparation of [2-(3-bromo-2-methyl-phenyl)-4-methyl-oxazol-5-yl]methanol

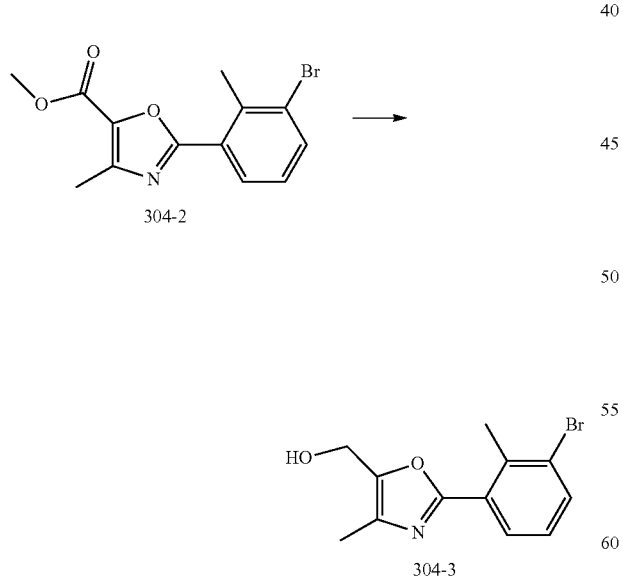

This compound was prepared using similar procedures as described as step 5 in example A, with compound 304-2 replacing compound a-4. The crude product was purified by chromatography on silica gel to get the title compound.

Step-4: Preparation of 2-(3-bromo-2-methyl-phenyl)-5-(chloromethyl)-4-methyl-oxazole

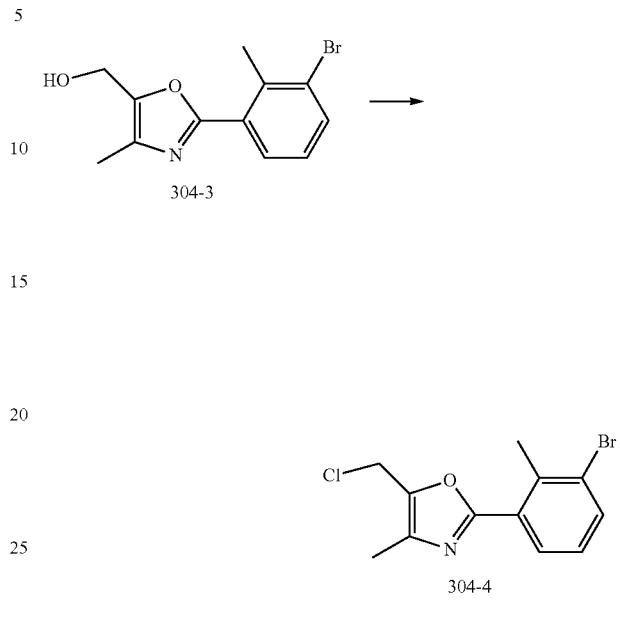

This compound was prepared using similar procedures as described as step 2 in example 1, with compound 304-3 replacing compound 1-1. The mixture was concentrated to give the title compound.

Step-5: Preparation of 2-(3-bromo-2-methyl-phenyl)-4-methyl-5-(pyrrolidin-1-ylmethyl)oxazole

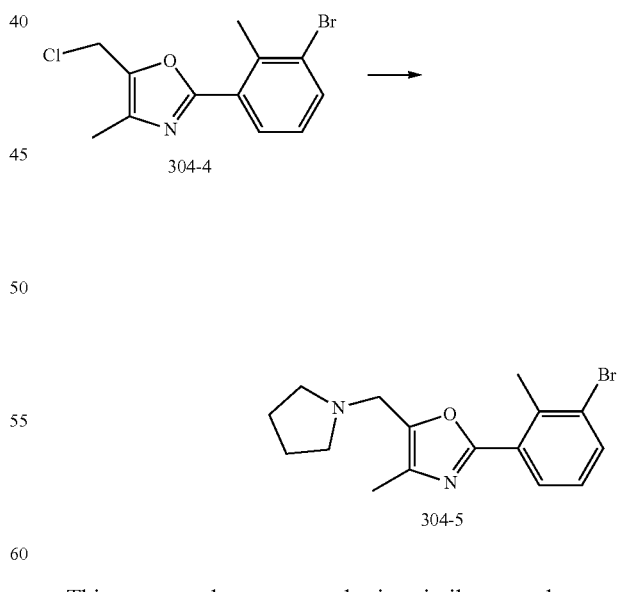

This compound was prepared using similar procedures as described as step 3 in example 1, with compound 304-4 replacing compound 1-2, and with pyrrolidine replacing (1S, 2R)-2-aminocyclopentan-1-ol. The crude product was purified by chromatography on silica gel to get the title compound.

Step-6: Preparation of methyl (2S)-1-[[6-(difluoromethoxy)-2-[2-methyl-3-[2-methyl-3-[4-methyl-5-(pyrrolidin-1-ylmethyl)oxazol-2-yl]phenyl]phenyl]-1,3-benzoxazol-5-yl]methyl]pyrrolidine-2-carboxylate

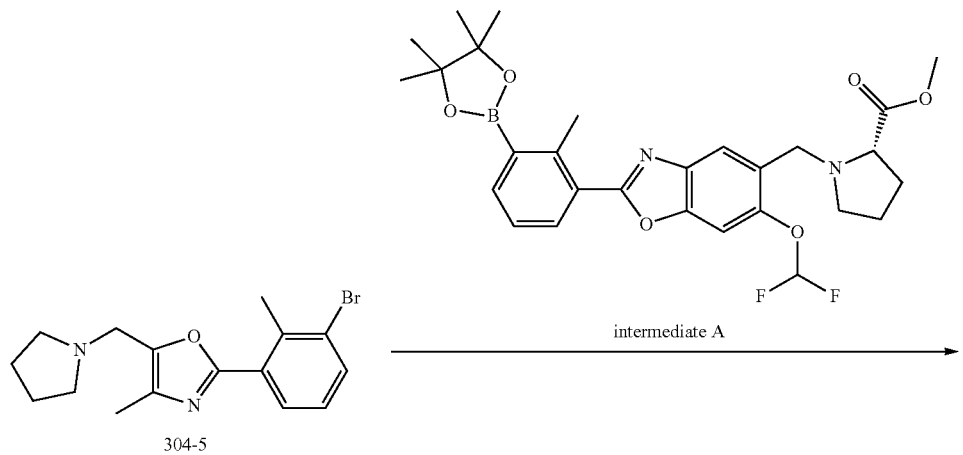

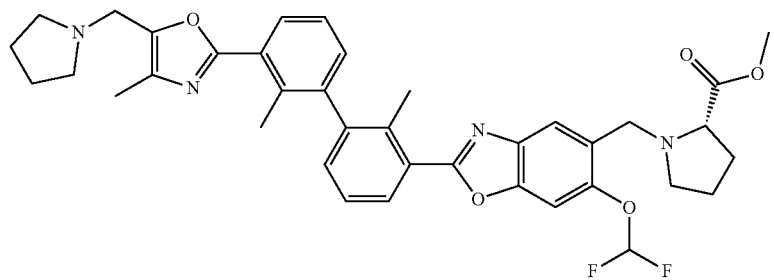

This compound was prepared using similar procedures as described as step 1 in example 1, with compound 304-5 replacing compound a-6. The crude product was purified by chromatography on silica gel to get the title compound.

Step-7: Preparation of ((6-(difluoromethoxy)-2-(2,2'-dimethyl-3'-(4-methyl-5-(pyrrolidin-1-ylmethyl)oxazol-2-yl)-[1,1'-biphenyl]-3-yl)benzo[d]oxazol-5-yl)methyl)-L-proline

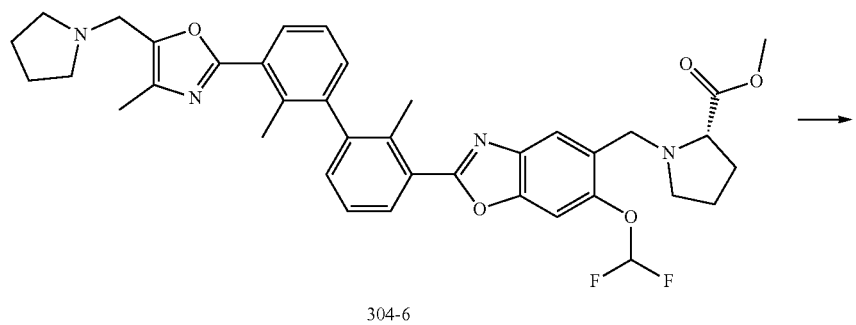

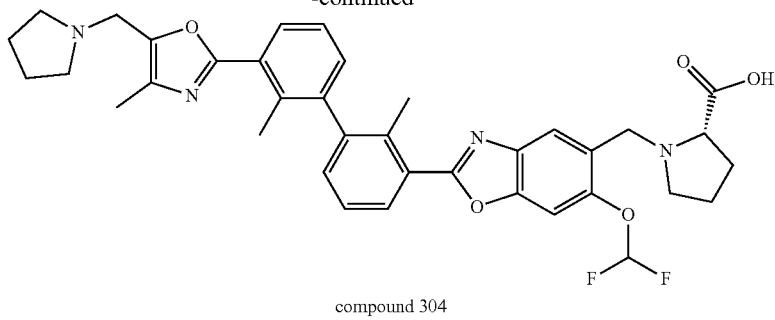

compound 304

This compound was prepared using similar procedures as described as step 5 in example 1, with compound 304-6 replacing compound 1-4. The crude product was purified by pre-HPLC to give the title compound. LC-MS (m/z): 657.3 (M+H)$^+$.

Example 305 Synthesis of Compound 305

((6-(difluoromethoxy)-2-(2,2'-dimethyl-3'-(6-(pyrrolidin-1-ylmethyl)-[1,2,4]triazolo[1,5-a]pyridin-2-yl)-[1,1'-biphenyl]-3-yl)benzo[d]oxazol-5-yl)methyl)-L-proline Compound 305

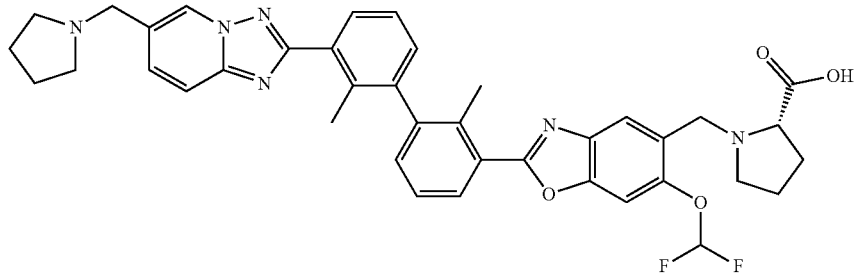

Step-1: Preparation of ethyl N-[[5-(hydroxymethyl)-2-pyridyl]carbamothioyl]carbamate Step-2: Preparation of (2-amino-[1,2,4]triazolo[1,5-a]pyridin-6-yl)methanol

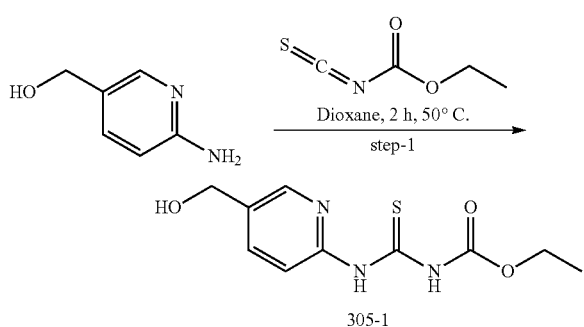

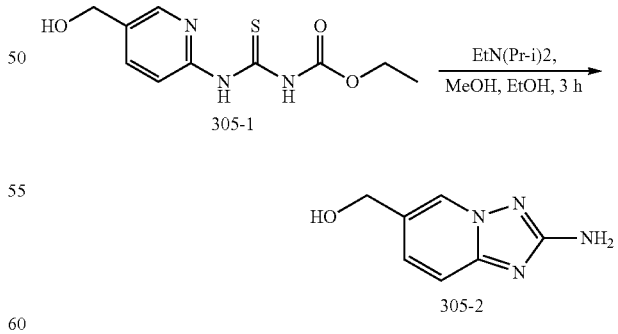

To a solution of (6-aminopyridin-3-yl)methanol (5 g) in 1,4-dioxane (25 mL) was added ethyl N-(thioxomethylene)carbamate (7.92 g). The reaction mixture was stirred at 50° C. for 3 hrs. The mixture was concentrated to get a residue. The residue was directly used for the next step.

Hydroxylamine hydrochloride (5.13 g) was added to a solution of compound 305-1 (9.5 g) in methanol (15 mL)/ethanol (15 mL), followed by N, N-diisopropylethylamine (9.62 g). The reaction mixture was then stirred at 50° C. for 3 hrs. The crude was cooled and the precipitate was filtered to give the desired product (5.0 g) as green oil.

Step-3: Preparation of (2-bromo-[1,2,4]triazolo[1,5-a]pyridin-6-yl)methanol

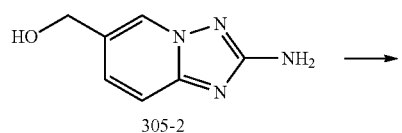
305-2

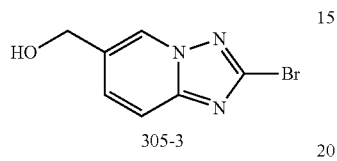
305-3 tert-Butyl nitrite (5.6 g) was added to a suspension of compound 305-2 (5 g) and copper(II) bromide (1.22 g) in acetonitrile (50 mL). The mixture was stirred at room temperature for 1 h.

The reaction mixture was diluted with DCM and washed with water. The organic phase was dried, filtered and concentrated to almost dry. The residue was purified by chromatography on silica gel to give the desired product (3.2 g) as a white solid.

Step-4: Preparation of [2-(3-bromo-2-methyl-phenyl)-[1,2,4]triazolo[1,5-a]pyridin-6-yl]methanol

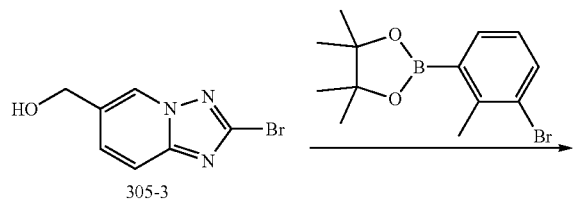

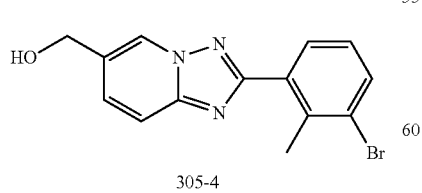
305-4

This compound was prepared using similar procedures as described as step 1 in example 1. The residue was purified by chromatography on silica gel to give the title compound.

Step-5: Preparation of 2-(3-bromo-2-methyl-phenyl)-6-(chloromethyl)-[1,2,4]triazolo[1,5-a]pyridine

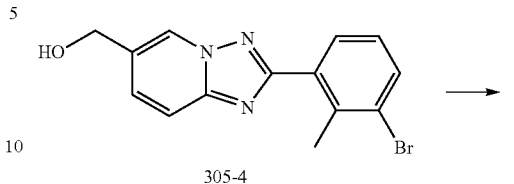
305-4

305-5

This compound was prepared using similar procedures as described as step 2 in example 1, with compound 305-4 replacing compound 1-1. The crude product was used directly in the next step.

Step-6: Preparation of 2-(3-bromo-2-methyl-phenyl)-6-(pyrrolidin-1-ylmethyl)-[1,2,4]triazolo[1,5-a]pyridine

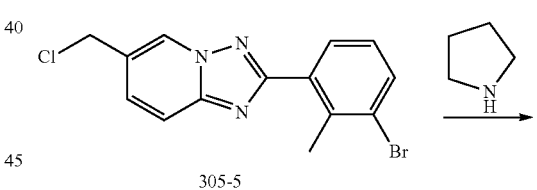
305-5

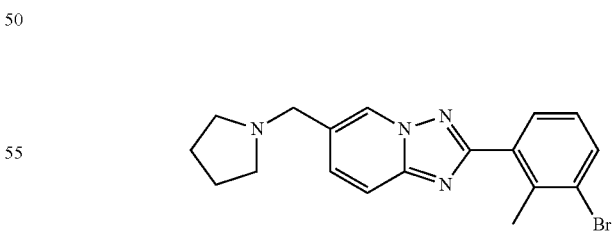
305-6

This compound was prepared using similar procedures as described as step 3 in example 1, with compound 305-5 replacing compound 1-2, and with pyrrolidine replacing (1S, 2R)-2-aminocyclopentan-1-ol. The crude product was purified by chromatography on silica gel to get the title compound.

Step-7: Preparation of methyl (2S)-1-[[6-(difluoromethoxy)-2-[2-methyl-3-[2-methyl-3-[6-(pyrrolidin-1-ylmethyl)-[1,2,4]triazolo[1,5-a]pyridin-2-yl]phenyl]phenyl]-1,3-benzoxazol-5-yl]methyl]pyrrolidine-2-carboxylate

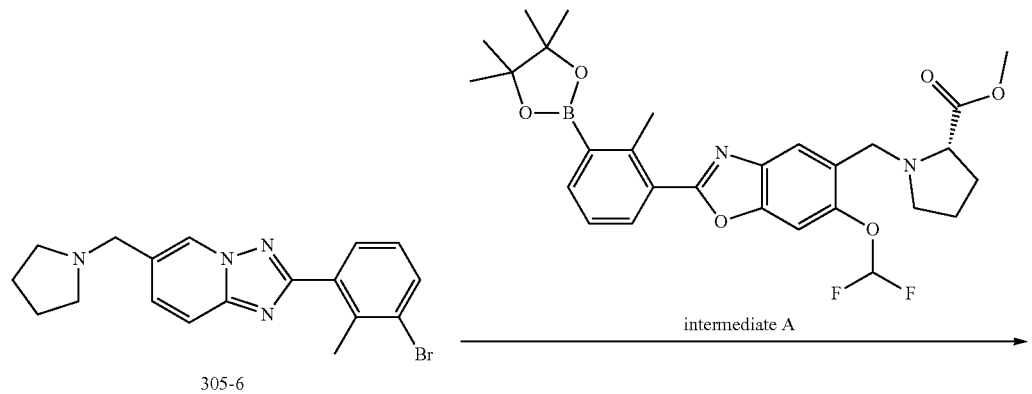

This compound was prepared using similar procedures as described as step 1 in example 1, with compound 305-6 replacing compound a-6. The crude product was purified by chromatography on silica gel to get the title compound.

Step-8: Preparation of ((6-(difluoromethoxy)-2-(2,2'-dimethyl-3'-(6-(pyrrolidin-1-ylmethyl)-[1,2,4]triazolo[1,5-a]pyridin-2-yl)-[1,1'-biphenyl]-3-yl)benzo[d]oxazol-5-yl)methyl)-L-proline

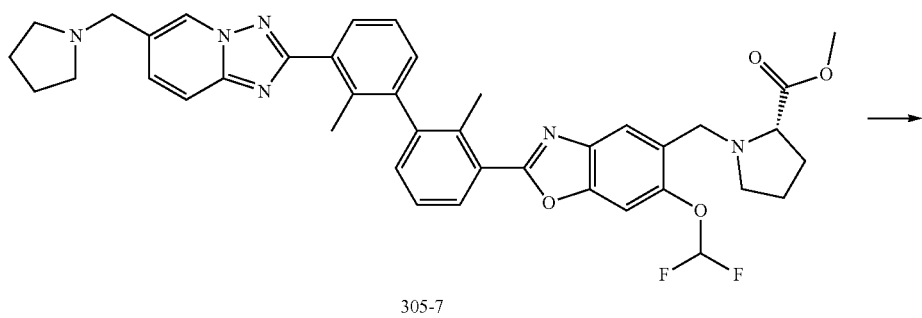

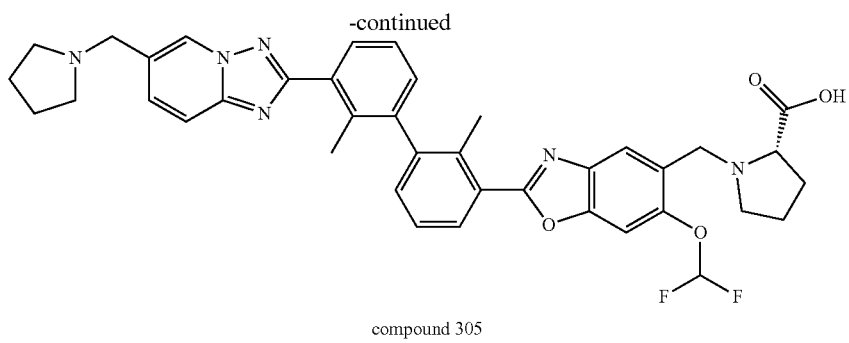

compound 305

This compound was prepared using similar procedures as described as step 5 in example 1, with compound 305-7 replacing compound 1-4. The crude product was purified by pre-HPLC to give the title compound. LC-MS (m/z): 693.3 (M+H)$^+$.

Example 306 Synthesis of Compound 306

((6-(difluoromethoxy)-2-(2,2'-dimethyl-3'-(4-(pyrrolidin-1-yl)piperidin-1-yl)-[1,1'-biphenyl]-3-yl)benzo[d]oxazol-5-yl)methyl)-L-proline

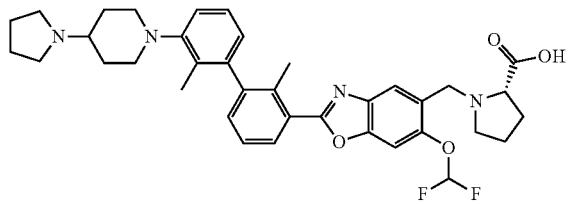

Compound 306

Step-1: Preparation of 1-(3-bromo-2-methyl-phenyl)-4-pyrrolidin-1-yl-piperidine

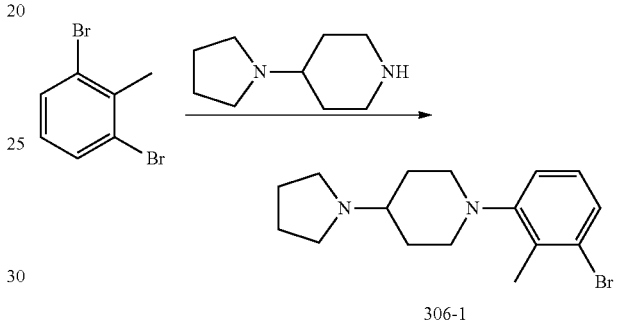

306-1

A mixture of 1,3-dibromo-2-methyl-benzene (1 g), 4-pyrrolidin-1-ylpiperidine (617.18 mg), Cs$_2$CO$_3$ (3.91 g), Pd$_2$(dba)$_3$ (366.10 mg), and xantphos (462.53 mg) in toluene (20 mL) was stirred at 100° C. overnight under nitrogen. The mixture was concentrated to get a residue. The residue was purified by chromatography on silica gel to give the desired product 1-(3-bromo-2-methyl-phenyl)-4-pyrrolidin-1-yl-piperidine (450 mg) as a red oil.

Step-2: Preparation of methyl (2S)-1-[[6-(difluoromethoxy)-2-[2-methyl-3-[2-methyl-3-(4-pyrrolidin-1-yl-1-piperidyl)phenyl]phenyl]-1,3-benzoxazol-5-yl]methyl]pyrrolidine-2-carboxylate

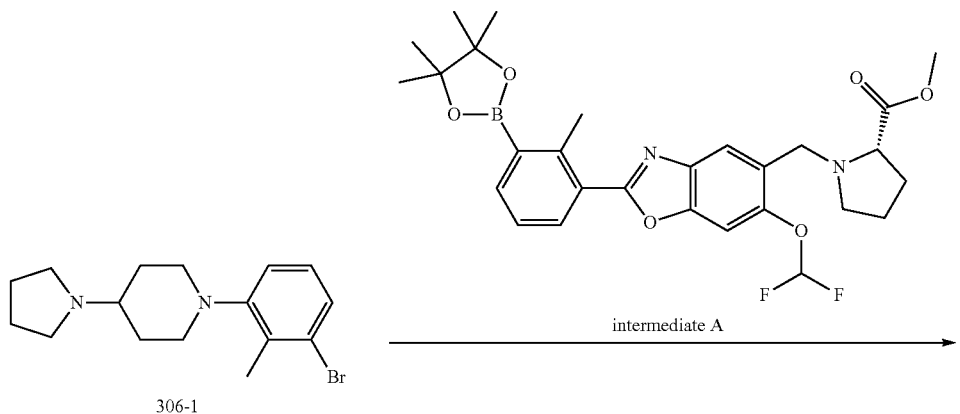

306-1                    intermediate A

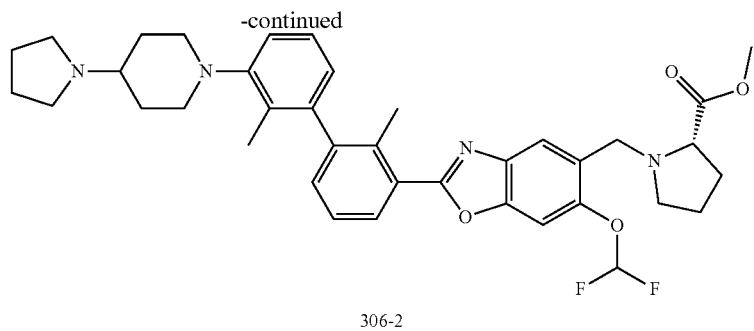

306-2

This compound was prepared using a similar procedure as described as step 1 in example 1, with compound 306-1 replacing compound a-6. The crude product was purified by chromatography on silica gel to get the title compound.

Step-3: Preparation of ((6-(difluoromethoxy)-2-(2, 2'-dimethyl-3'-(4-(pyrrolidin-1-yl)piperidin-1-yl)-[1, 1'-biphenyl]-3-yl)benzo[d]oxazol-5-yl)methyl)-L-proline

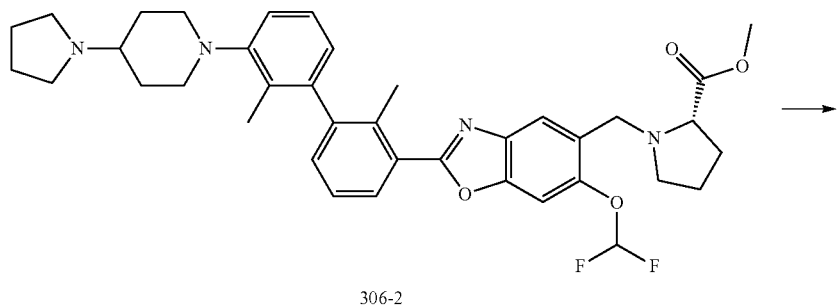

306-2

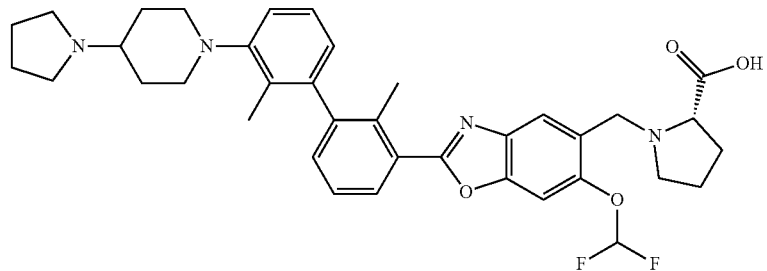

compound 306

This compound was prepared using a similar procedure as described as step 5 in example 1, with compound 306-2 replacing compound 1-4. The crude product was purified by pre-HPLC to give the title compound. LC-MS (m/z): 645.3 (M+H)$^+$.

The compounds of table 8 were prepared in a similar manner to Examples 304-306 via different reaction starting materials and suitable reagents.

TABLE 8

| EX No. | Chemical Name | Structure | Physical Data (MS) (M + H)+ |
|---|---|---|---|
| 307 | ((6-(difluoromethoxy)-2-(3'-(4-(((1-(hydroxymethyl)cyclopropyl)methyl)amino)piperidin-1-yl)-2,2'-dimethyl-[1,1'-biphenyl]-3-yl)benzo[d]oxazol-5-yl)methyl)-L-proline | 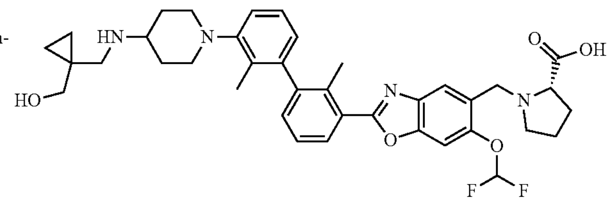 | 675.3 |
| 308 | ((6-(difluoromethoxy)-2-(3'-(4-((3,3-dimethylazetidin-1-yl)methyl)piperidin-1-yl)-2,2'-dimethyl-[1,1'-biphenyl]-3-yl)benzo[d]oxazol-5-yl)methyl)-L-proline | 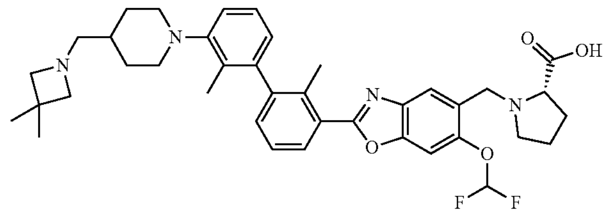 [SMILES: Cc1c(-c2nc3cc(CN4CCC[C@H]4C(=O)O)c(OC(F)F)cc3o2)cccc1-c1cccc(N2CCC(CN3CC(C)(C)C3)CC2)c1C] | 673.4 |
| 309 | ((6-(difluoromethoxy)-2-(2,2'-dimethyl-3'-(4-(pyrrolidin-1-ylmethyl)piperidin-1-yl)-[1,1'-biphenyl]-3-yl)benzo[d]oxazol-5-yl)methyl)-L-proline | 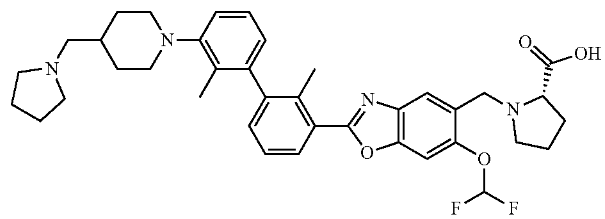 [SMILES: Cc1c(-c2nc3cc(CN4CCC[C@H]4C(=O)O)c(OC(F)F)cc3o2)cccc1-c1cccc(N2CCC(CN3CCCC3)CC2)c1C] | 659.3 |

The $^1$HNMR data of compounds 34, 61, 85, 88, 93, 113, 127, 130, 131, 135, 142 and 146 are as follows:

$^1$H NMR (500 MHz, DMSO-d$_6$) δ 8.24 (s, 1H), 8.17 (dd, J=8.0, 2.2 Hz, 2H), 8.08 (s, 1H), 7.88 (s, 1H), 7.81 (s, 1H), 7.64-7.51 (m, 2H), 7.49-7.20 (m, 4H), 4.52 (s, 2H), 4.38-4.12 (m, 2H), 3.94-3.84 (m, 4H), 3.26-2.86 (m, 3H), 2.45 (s, 6H), 2.37-1.71 (m, 4H), 1.31 (d, J=43.4 Hz, 6H). (Compound 34)

$^1$H NMR (500 MHz, Chloroform-d) δ 8.30-8.03 (m, 4H), 7.66-7.54 (m, 2H), 7.49-7.41 (m, 2H), 7.40-7.35 (m, 2H), 7.10-6.77 (m, 2H), 4.86-4.18 (m, 5H), 3.94-3.57 (m, 3H), 3.43-3.25 (m, 2H), 2.71-2.55 (m, 2H), 2.48 (d, J=3.7 Hz, 6H), 2.37-1.58 (m, 6H), 1.27-1.08 (m, 3H). (Compound 61)

$^1$H NMR (500 MHz, Chloroform-d) δ 8.13 (dd, J=7.8, 6.1 Hz, 2H), 7.99 (d, J=9.8 Hz, 2H), 7.52 (d, J=17.9 Hz, 2H), 7.48-7.42 (m, 2H), 7.37-7.34 (m, 2H), 6.83 (t, J=71.9 Hz, 1H), 6.80 (t, J=71.9 Hz, 1H), 4.29 (d, J=25.2 Hz, 4H), 3.70 (s, 4H), 3.42 (dd, J=10.6, 4.4 Hz, 1H), 3.21 (q, J=8.3 Hz, 2H), 3.09 (d, J=22.7 Hz, 2H), 2.46 (d, J=7.9 Hz, 6H), 2.34-2.22 (m, 2H), 1.35 (s, 6H). (Compound 85)

$^1$H NMR (500 MHz, Chloroform-d) δ 8.36 (s, 1H), 8.22 (dd, J=7.9, 1.5 Hz, 1H), 8.17-8.07 (m, 2H), 7.99 (s, 1H), 7.59 (s, 1H), 7.46 (dt, J=12.7, 7.7 Hz, 2H), 7.42-7.34 (m, 2H), 6.93 (t, J=72.1 Hz, 1H), 4.78-4.62 (m, 2H), 4.52 (t, J=12.8 Hz, 2H), 4.21 (t, J=8.0 Hz, 2H), 3.87-3.58 (m, 3H), 3.21-3.00 (m, 2H), 2.75-2.53 (m, 3H), 2.47 (d, J=15.4 Hz, 6H), 2.39-2.23 (m, 2H), 2.16 (t, J=7.9 Hz, 2H), 1.78 (d, J=62.1 Hz, 1H), 1.21-1.10 (m, 3H). (Compound 88)

$^1$H NMR (500 MHz, Chloroform-d) δ 8.18 (d, J=7.9 Hz, 1H), 8.06 (d, J=7.9 Hz, 1H), 7.93-7.76 (m, 2H), 7.55 (s, 1H), 7.49-7.26 (m, 5H), 6.76 (t, J=72.9 Hz, 1H), 4.29-3.39 (m, 6H), 3.23-2.91 (m, 6H), 2.38-2.47 (d, J=25.5 Hz, 6H), 2.09-1.60 (m, 3H), 1.23 (s, 6H). (Compound 93)

$^1$H NMR (500 MHz, DMSO-d$_6$) δ 8.38 (s, 1H), 8.26 (s, 1H), 8.20 (dd, J=7.9, 1.4 Hz, 1H), 8.13 (ddd, J=23.5, 7.9, 1.5 Hz, 1H), 7.96 (d, J=10.1 Hz, 1H), 7.72 (d, J=13.9 Hz, 1H), 7.61-7.49 (m, 2H), 7.45 (ddd, J=13.6, 7.6, 1.5 Hz, 2H), 7.38 (d, J=71.9 Hz, 1H), 3.96 (s, 2H), 3.44-3.22 (m, 5H), 3.11-2.99 (m, 2H), 2.57 (q, J=8.5 Hz, 1H), 2.45 (d, J=5.8 Hz, 6H), 2.19-2.06 (m, 1H), 1.93-1.64 (m, 4H), 1.22 (d, J=7.5 Hz, 6H). (Compound 113)

$^1$H NMR (500 MHz, Chloroform-d) δ 8.24 (dd, J=7.9, 1.4 Hz, 1H), 8.17-8.07 (m, 2H), 8.03 (s, 1H), 7.79 (s, 1H), 7.60 (s, 1H), 7.48 (dt, J=15.0, 7.7 Hz, 2H), 7.43-7.35 (m, 2H), 6.94 (t, J=71.9 Hz, 1H), 4.60 (d, J=13.1 Hz, 1H), 4.50 (d, J=13.2 Hz, 1H), 3.97 (s, 3H), 3.71-3.60 (m, 1H), 3.15 (q, J=9.9 Hz, 1H), 2.76 (s, 4H), 2.47 (s, 6H), 2.33-2.24 (m, 1H), 2.15-2.06 (m, 1H), 2.06-1.97 (m, 2H), 1.91 (q, J=3.5, 3.0 Hz, 4H). (Compound 127)

$^1$H NMR (500 MHz, DMSO-d$_6$) δ 8.20 (dd, J=7.9, 1.4 Hz, 1H), 8.16 (dd, J=7.9, 1.4 Hz, 1H), 8.11 (d, J=1.5 Hz, 1H), 7.97 (s, 1H), 7.88 (d, J=1.5 Hz, 1H), 7.73 (s, 1H), 7.63-7.51 (m, 2H), 7.48 (dd, J=7.6, 1.4 Hz, 1H), 7.44 (dd, J=7.6, 1.4 Hz, 1H), 7.38 (t, J=73.7 Hz, 1H), 3.96 (s, 2H), 3.79-3.68 (m, 2H), 3.38-3.31 (m, 1H), 3.09-3.03 (m, 1H), 2.74-2.48 (m, 5H), 2.44 (d, J=2.9 Hz, 6H), 2.26-1.68 (m, 6H), 1.36-1.20 (m, 1H), 0.99 (d, J=6.7 Hz, 3H). (Compound 130)

$^1$H NMR (500 MHz, DMSO-d$_6$) δ 8.21 (dd, J=7.9, 1.4 Hz, 1H), 8.19 (s, 1H), 8.15 (dd, J=7.9, 1.4 Hz, 1H), 7.97 (s, 1H), 7.95 (s, 1H), 7.73 (s, 1H), 7.63-7.51 (m, 2H), 7.48 (dd, J=7.6, 1.4 Hz, 1H), 7.44 (dd, J=7.5, 1.4 Hz, 1H), 7.38 (t, J=73.7 Hz, 1H), 3.97 (s, 2H), 3.92-3.86 (m, 2H), 3.38-3.31 (m, 1H), 3.11-3.05 (m, 1H), 2.83-2.51 (m, 5H), 2.44 (d, J=4.1 Hz, 6H), 2.31-1.70 (m, 6H), 1.46-1.14 (m, 1H), 1.00 (d, J=6.3 Hz, 3H). (Compound 131)

$^1$H NMR (500 MHz, Chloroform-d) δ 8.25 (d, J=7.8 Hz, 1H), 8.14 (dd, J=7.9, 1.3 Hz, 1H), 8.10 (s, 1H), 7.94 (s, 1H), 7.77 (s, 1H), 7.61 (s, 1H), 7.48 (dt, J=15.2, 7.7 Hz, 2H), 7.42-7.34 (m, 2H), 6.93 (t, J=71.9 Hz, 1H), 4.55 (d, J=13.0 Hz, 1H), 4.37 (d, J=13.1 Hz, 2H), 3.94-3.35 (m, 5H), 3.17-2.82 (m, 4H), 2.51 (s, 3H), 2.47 (s, 3H), 2.47-2.29 (m, 2H), 2.16-1.46 (m, 10H). (Compound 135) H NMR (500 MHz, DMSO-$d_6$) δ 8.35-8.30 (m, 1H), 8.23 (dd, J=8.0, 1.5 Hz, 1H), 8.18 (dt, J=7.9, 1.3 Hz, 1H), 8.12 (d, J=1.4 Hz, 1H), 8.08 (s, 1H), 7.89 (s, 1H), 7.61 (dt, J=13.6, 7.7 Hz, 2H), 7.57-7.45 (m, 2H), 7.40 (t, J=73.2 Hz, 1H), 4.62-4.25 (m, 4H), 3.58-3.07 (m, 5H), 2.52-2.50 (m, 1H), 2.49-2.48 (m, 4H), 2.45 (d, J=5.5 Hz, 6H), 2.26-1.80 (m, 4H). (Compound 142)

$^1$H NMR (500 MHz, DMSO-$d_6$) δ 8.35 (s, 1H), 8.23 (d, J=7.9 Hz, 1H), 8.18 (d, J=7.8 Hz, 1H), 8.13-8.07 (m, 2H), 7.87 (s, 1H), 7.70 (s, 1H), 7.60 (dt, J=14.9, 7.7 Hz, 2H), 7.56-7.44 (m, 2H), 7.32 (t, J=73.2 Hz, 1H), 4.56-4.01 (m, 7H), 3.50 (s, 2H), 3.45-3.12 (m, 2H), 2.56 (s, 2H), 2.50-2.48 (m, 2H), 2.45 (d, J=5.5 Hz, 6H), 2.43-2.33 (m, 1H) 2.08-1.79 (m, 3H). (Compound 146)

Examples for Comparison

Prepare the following comparison example (as shown in Table 9) essentially as described for Example 7 in WO2018119266.

TABLE 9

| Com. EX. No. | Chemical Name | Structure |
|---|---|---|
| 1 | (2S,2'S)-1,1'-(((2,2'-dimethyl-[1,1'-biphenyl]-3,3'-diyl)bis(6-(cyanomethoxy)benzo[d]oxazole-2,5-diyl))-bis(methylene))-bis(piperidine-2-carboxylic acid) | 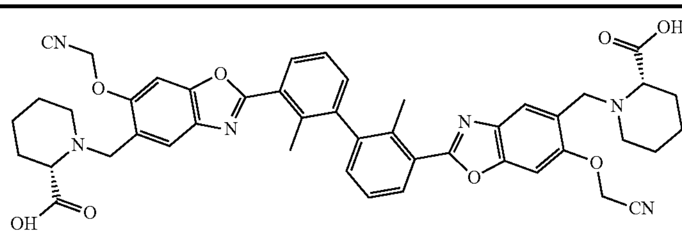 |

PD-1/PD-L1 Binding Assay (Alphascreen)

The assays were conducted in a standard black 384-well polystyrene plate with a final volume of 20 μL. Inhibitors were first serially diluted in DMSO and then added to the plate wells before the addition of other reaction components. The final concentration of DMSO in the assay was 1%. Add 100 nL/well of compound to the 384 reaction plate (6008280, PerkinElmer) with Echo and centrifuge at 1000 rpm for 1 minute. Add 5 μL/well 4×PD-L1 solutions to the 384 reaction plate, centrifuge at 1000 rpm for 1 minute, and add 5 μL/well 4×PD-1 solutions, centrifuge at 1000 rpm for 1 minute, and incubate at 25° C. for 15 minutes. The concentrations of the compounds were 300, 100, 33.33, 11.11, 3.70, 1.23, 0.41, 0.137, 0.046, 0.015, 0 nM, respectively. Add 10 μL/well 2× Anti-6×His AlphaLISA Acceptor beads and Streptavidin Donor beads solution (PerkinElmer-AL356F) to the above 384 reaction plate, centrifuge at 1000 rpm for 1 minute, and incubate at 25° C. in the dark for 120 minutes. Read the AlphaLISA signal value using the Envision Reader. IC50 determination was performed by fitting the curve of percent control activity versus the log of the inhibitor concentration using the GraphPad Prism 8.0 software.

Compounds of the present disclosure, as exemplified in the Examples, showed $IC_{50}$ values in the following ranges: "*" stands for "0.1 nM≤$IC_{50}$≤5 nM"; "" stands for "5 nM≤$IC_{50}$≤50 nM"; "*" stands for "$IC_{50}$>50 nM".

Data obtained for the Example compounds using the PD-1/PD-L1 binding assay (Alphascreen) described above is provided in Table 10.

TABLE 10

| EX No. | $IC_{50}$(nM) |
|---|---|
| 1 | 0.89 |
| 2 | 0.2 |
| 3 | 89 |
| 4 | 1.4 |
| 5 | 0.4 |
| 6 | 4.3 |
| 7 | 0.61 |
| 8 | 0.75 |
| 9 | 18 |
| 10 | 19 |
| 11 | 33 |
| 12 | 1.1 |
| 13 | 26 |
| 14 | 1.2 |
| 15 | 0.5 |
| 16 | 1.1 |
| 17 | 1.2 |
| 18 | 164 |
| 19 | 1.3 |
| 20 | 1.6 |
| 21 | 0.59 |

TABLE 10-continued

| EX No. | $IC_{50}$(nM) |
|---|---|
| 22 | 25 |
| 23 | 7.7 |
| 24 | 0.98 |
| 25 | 0.3 |
| 26 | * |
| 27 | 0.66 |
| 28 | 3.2 |
| 29 | 1.2 |
| 30 | * |
| 31 | 0.5 |
| 32 | 3.8 |
| 33 | 1.5 |
| 34 | 1.3 |
| 35 | 0.91 |
| 36 | 1.1 |
| 37 | * |
| 38 | * |
| 39 | 2.4 |
| 40 | * |
| 41 | ** |
| 42 | * |
| 43 | ** |
| 44 | 1.1 |
| 45 | * |
| 46 | ** |
| 47 | * |
| 48 | * |
| 49 | * |
| 50 | * |
| 51 | * |
| 52 | * |

TABLE 10-continued

| EX No. | IC$_{50}$(nM) |
|---|---|
| 53 | * |
| 54 | 6.3 |
| 55 | 0.57 |
| 56 | 0.83 |
| 57 | 1.2 |
| 58 | 0.79 |
| 59 | 2.5 |
| 60 | * |
| 61 | 1.6 |
| 62 | 2.6 |
| 63 | 5.7 |
| 64 | 1.8 |
| 65 | 1.3 |
| 66 | 1.8 |
| 67 | 6.7 |
| 68 | 2.4 |
| 69 | 0.49 |
| 70 | 3.3 |
| 71 | 0.37 |
| 72 | 0.98 |
| 73 | 0.42 |
| 74 | 1.1 |
| 75 | 10 |
| 76 | 32 |
| 77 | 1.2 |
| 78 | * |
| 79 | * |
| 80 | ** |
| 81 | ** |
| 82 | * |
| 83 | ** |
| 84 | * |
| 85 | * |
| 86 | 11 |
| 87 | * |
| 88 | * |
| 89 | * |
| 90 | 0.88 |
| 91 | * |
| 92 | * |
| 93 | * |
| 94 | 1.9 |
| 95 | 1.4 |
| 96 | 0.6 |
| 97 | * |
| 98 | * |
| 99 | 0.82 |
| 100 | * |
| 101 | 2.2 |
| 102 | 18 |
| 103 | 0.13 |
| 104 | 0.19 |
| 105 | * |
| 106 | * |
| 107 | * |
| 108 | * |
| 109 | 1.6 |
| 110 | * |
| 111 | * |
| 112 | * |
| 113 | 0.5 |
| 114 | 1 |
| 115 | * |
| 116 | * |
| 117 | * |
| 118 | 78 |
| 119 | 1.9 |
| 120 | 1.1 |
| 121 | 0.6 |
| 122 | * |
| 123 | * |
| 124 | * |
| 125 | * |
| 126 | * |
| 127 | 3.1 |
| 128 | 0.14 |
| 129 | 1.7 |
| 130 | * |

TABLE 10-continued

| EX No. | IC$_{50}$(nM) |
|---|---|
| 131 | 2.3 |
| 132 | 2 |
| 133 | * |
| 134 | * |
| 135 | * |
| 136 | * |
| 137 | * |
| 138 | * |
| 139 | * |
| 140 | * |
| 141 | * |
| 142 | * |
| 143 | * |
| 144 | * |
| 145 | * |
| 146 | * |
| 147 | * |
| 148 | ** |
| 149 | * |
| 150 | * |
| 151 | * |
| 152 | * |
| 153 | * |
| 154 | ** |
| 155 | * |
| 156 | * |
| 157 | * |
| 158 | * |
| 159 | * |
| 160 | * |
| 161 | * |
| 162 | ** |
| 163 | ** |
| 164 | ** |
| 165 | * |
| 166 | ** |
| 167 | ** |
| 168 | * |
| 169 | * |
| 170 | ** |
| 171 | * |
| 172 | 0.3 |
| 173 | 0.93 |
| 174 | 21 |
| 175 | 3.4 |
| 176 | 0.9 |
| 177 | 0.94 |
| 178 | 3.9 |
| 179 | * |
| 180 | * |
| 181 | * |
| 182 | * |
| 183 | ** |
| 184 | 2.3 |
| 185 | * |
| 186 | * |
| 187 | * |
| 188 | * |
| 189 | * |
| 190 | 0.2 |
| 191 | ** |
| 192 | ** |
| 193 | ** |
| 194 | ** |
| 195 | ** |
| 196 | ** |
| 197 | ** |
| 198 | *** |
| 199 | ** |
| 200 | ** |
| 201 | *** |
| 202 | 0.37 |
| 203 | 12 |
| 204 | * |
| 205 | * |
| 206 | 1.4 |
| 207 | ** |
| 208 | 114 |

TABLE 10-continued

| EX No. | IC$_{50}$(nM) |
|---|---|
| 209 | 1.4 |
| 210 | * |
| 211 | * |
| 212 | 8.4 |
| 213 | ** |
| 214 | *** |
| 215 | 2.8 |
| 216 | * |
| 217 | 0.67 |
| 218 | * |
| 219 | * |
| 220 | * |
| 221 | * |
| 222 | * |
| 223 | * |
| 224 | * |
| 225 | 2 |
| 226 | 4.7 |
| 227 | 4.1 |
| 228 | 4.3 |
| 229 | 6.9 |
| 230 | 1.5 |
| 231 | 78 |
| 232 | 7.8 |
| 233 | 41 |
| 234 | 0.52 |
| 235 | 1.8 |
| 236 | 290 |
| 237 | 2.7 |
| 238 | 2.3 |
| 239 | 0.99 |
| 240 | ** |
| 241 | ** |
| 242 | * |
| 243 | 2.5 |
| 244 | 2 |
| 245 | 3.8 |
| 246 | 1.8 |
| 247 | 5.2 |
| 248 | ** |
| 249 | ** |
| 250 | * |
| 251 | ** |
| 252 | * |
| 253 | 4.7 |
| 254 | 16 |
| 255 | 2.3 |
| 256 | *** |
| 257 | 4.4 |
| 258 | ** |
| 259 | * |
| 260 | ** |
| 261 | * |
| 262 | ** |
| 263 | 0.98 |
| 264 | * |
| 265 | 0.73 |
| 266 | ** |
| 267 | ** |
| 268 | * |
| 269 | ** |
| 270 | ** |
| 271 | * |
| 272 | 1.9 |
| 273 | ** |
| 274 | * |
| 275 | ** |
| 276 | * |
| 277 | * |
| 278 | * |
| 279 | * |
| 280 | 5.7 |
| 281 | 1.3 |
| 282 | ** |
| 283 | ** |
| 284 | ** |
| 285 | * |
| 286 | * |
| 287 | * |
| 288 | 1.5 |
| 289 | 0.66 |
| 290 | * |
| 291 | * |
| 292 | ** |
| 293 | 11 |
| 294 | * |
| 295 | ** |
| 296 | 12 |
| 297 | 26 |
| 298 | ** |
| 299 | *** |
| 300 | *** |
| 301 | ** |
| 302 | 0.29 |
| 303 | 1.6 |
| 304 | 27 |
| 305 | 0.87 |
| 306 | 1.5 |
| 307 | * |
| 308 | * |
| 309 | * |
| 310 | * |
| 311 | * |
| 312 | * |
| 313 | * |
| 314 | 8 |
| 315 | * |
| 316 | ** |

Pharmacokinetic Assay

Adult C57 female mice were received to single-dose of the test compounds with 1000 DMSO, 10% Kolliphor@HS 15 and 80% saline as excipients, the mice (n=9) were giving oral administration (intragastric administration) with the compounds at a dose of 100 mg/kg. Time of blood collection: 15 min, 30 min, 1 h, 2 h, 4 h, 7 h, 24 h. Approximately 0.1 mL of whole blood was collected from retro-orbital venous plexus of 3 mice at each time point, and placed into tubes that contained $K_2$-EDTA as an anticoagulant. The whole blood was centrifuged at 4° C. and 4000 rpm for 10 min. The plasma was transferred into centrifuge tubes, and stored at −20° C. until being analyzed. Concentrations of test compounds in the plasma samples were analyzed with liquid chromatography-tandem mass spectrometry (LC-MS/MS). Plasma concentration-time data of individual animals was analyzed using Microsoft Excel 2010. Non-compartmental model was introduced in concentration analysis. The pharmacokinetic parameters of the test compounds were calculated using WinNonlin (version 4.1; Pharsight) software. The data is shown in Table 11.

Adult C57 female mice were received to single-dose of the test compounds with 15% DMSO, 10% Kolliphor@HS 15 and 75% saline as excipients, the mice (n=3) were giving oral administration (intragastric administration) with the compounds at a dose of 5 mg/kg. Time of blood collection: 30 min, 2 h, 4 h. approximately 0.1 mL of whole blood was collected from retro-orbital venous plexus, and placed into tubes that contained $K_2$-EDTA as an anticoagulant. The whole blood were centrifuged at 4° C. and 4000 rpm for 10 min. The plasma was transferred into centrifuge tubes, and stored at −20° C. until being analyzed. Concentrations of test compounds in the plasma samples were analyzed with liquid chromatography-tandem mass spectrometry (LC-MS/MS). Plasma concentration-time data of individual animals was analyzed using Microsoft Excel 2010. The data is shown in Table 12.

TABLE 11

| EX No. | Dose (mg/kg) | $T_{1/2}$ (hr) | $T_{max}$ (hr) | $C_{max}$ (ng/mL) | AUC (hr*ng/mL) |
|---|---|---|---|---|---|
| Com. EX. No. 1 | 100 | 1.94 | 1 | 76 | 196 |
| 2 | 100 | 3.30 | 0.5 | 218 | 271 |
| 3 | 100 | 0.39 | 1 | 374 | 461 |
| 5 | 100 | 5.07 | 4 | 2597 | 25686 |
| 8 | 100 | 3.97 | 4 | 974 | 8243 |
| 12 | 100 | 7.97 | 2 | 1383 | 14536 |
| 14 | 100 | 6.20 | 1 | 589 | 3453 |
| 15 | 100 | 9.83 | 1 | 931 | 5711 |
| 16 | 100 | 4.80 | 4 | 1473 | 20947 |
| 95 | 100 | 6.48 | 4 | 2033 | 22866 |
| 98 | 100 | 4.47 | 1 | 1007 | 8699 |
| 28 | 100 | 2.79 | 1 | 1283 | 5805 |
| 29 | 100 | 4.67 | 1 | 3720 | 42711 |
| 108 | 100 | 21.7 | 1 | 713 | 10139 |
| 31 | 100 | 9.81 | 1 | 1003 | 6605 |
| 33 | 100 | 11.00 | 4 | 727 | 8915 |
| 34 | 100 | 6.99 | 4 | 4257 | 56146 |
| 36 | 100 | 8.26 | 1 | 1667 | 21381 |
| 61 | 100 | 5.37 | 4 | 8653 | 117700 |
| 62 | 100 | 9.69 | 4 | 4280 | 46470 |
| 63 | 100 | 5.80 | 1 | 2923 | 43669 |
| 64 | 100 | 7.20 | 7 | 4317 | 61468 |
| 65 |  | 10.74 | 4 | 2457 | 40371 |
| 100 | 100 | 10.5 | 4 | 18900 | 235468 |
| 171 | 100 | 3.66 | 1 | 965 | 3474 |
| 175 | 100 | 3.63 | 2 | 1627 | 19943 |
| 314 | 100 | 5.43 | 2 | 6353 | 28971 |
| 190 | 100 | 3.57 | 1 | 1280 | 8572 |
| 243 | 100 | 6.93 | 1 | 4887 | 67353 |
| 244 | 100 | 7.01 | 2 | 5737 | 78121 |
| 88 | 100 | NA | 24 | 117333 | 2024036 |
| 74 | 100 | 8.20 | 4 | 4463 | 59508 |
| 93 | 100 | NA | 4 | 9217 | 162649 |
| 103 | 100 | 23.40 | 4 | 5587 | 96382 |

TABLE 12

| EX No. | Dose (mg/kg) | Concentration (ng/mL) | | |
|---|---|---|---|---|
| | | 0.5 h | 2 h | 4 h |
| Com. EX. No. 1 | 5.0 | NA | NA | NA |
| 5 | 5.0 | 43.9 | 55.7 | 61.2 |
| 10 | 5.0 | 80.9 | 221 | 214 |
| 13 | 5.0 | 79.3 | 241 | 301 |
| 18 | 5.0 | 303 | 642 | 626 |
| 22 | 5.0 | 68.6 | 155 | 81.1 |
| 23 | 5.0 | 46.2 | 148 | 94.7 |
| 34 | 5.0 | 46.8 | 136 | 154 |
| 56 | 5.0 | 19.9 | 192 | 155 |
| 57 | 5.0 | 27.1 | 149 | 90.0 |
| 66 | 5.0 | NA | 137 | 111 |
| 67 | 5.0 | 143 | 418 | 462 |
| 70 | 5.0 | 36.4 | 151 | 158 |
| 72 | 5.0 | 42.6 | 140 | 132 |
| 80 | 5.0 | 247 | 299 | 167 |
| 81 | 5.0 | 115 | 468 | 383 |
| 85 | 5.0 | 75.9 | 146 | 135 |
| 89 | 5.0 | 21.3 | 124 | 109 |
| 101 | 5.0 | 178 | 640 | 579 |
| 102 | 5.0 | 85.9 | 282 | 292 |
| 103 | 5.0 | 48.9 | 185 | 135 |
| 114 | 5.0 | 65.6 | 237 | 152 |
| 117 | 5.0 | 121 | 319 | 243 |
| 127 | 5.0 | 61.3 | 253 | 216 |
| 131 | 5.0 | 108 | 301 | 470 |
| 136 | 5.0 | 673 | 736 | 545 |
| 142 | 5.0 | 211 | 243 | 171 |
| 144 | 5.0 | 243 | 386 | 222 |
| 162 | 5.0 | 277 | 670 | 441 |
| 164 | 5.0 | 294 | 877 | 853 |
| 165 | 5.0 | 376 | 404 | 219 |
| 191 | 5.0 | 520 | 1167 | 1333 |
| 192 | 5.0 | 469 | 440 | 268 |
| 195 | 5.0 | 256 | 255 | 125 |
| 197 | 5.0 | 527 | 741 | 369 |
| 198 | 5.0 | 674 | 1440 | 1097 |
| 201 | 5.0 | 428 | 792 | 527 |
| 203 | 5.0 | 819 | 1026 | 833 |
| 204 | 5.0 | 740 | 872 | 820 |
| 205 | 5.0 | 1002 | 1437 | 1420 |
| 209 | 5.0 | 21.4 | 54.9 | 19.2 |
| 227 | 5.0 | 36.9 | 149 | 114 |
| 231 | 5.0 | 36.9 | 160 | 156 |
| 233 | 5.0 | 143 | 322 | 296 |
| 237 | 5.0 | 58.5 | 178 | 186 |
| 241 | 5.0 | 102 | 234 | 294 |
| 242 | 5.0 | 90.4 | 223 | 202 |
| 245 | 5.0 | 101 | 237 | 191 |
| 246 | 5.0 | 87.2 | 261 | 285 |
| 248 | 5.0 | 89.0 | 271 | 369 |
| 252 | 5.0 | 694 | 2873 | 4153 |
| 253 | 5.0 | 42.3 | 199 | 181 |
| 272 | 5.0 | 66.1 | 198 | 141 |
| 276 | 5.0 | 131 | 291 | 238 |
| 280 | 5.0 | 33.6 | 171 | 113 |
| 283 | 5.0 | 522 | 1173 | 965 |
| 285 | 5.0 | 39.1 | 80.0 | 41.8 |
| 286 | 5.0 | 20.5 | 73.8 | 52.2 |
| 288 | 5.0 | 8.36 | 25.4 | 9.68 |
| 293 | 5.0 | 6.68 | 10.8 | 3.57 |
| 294 | 5.0 | 80.4 | 193 | 186 |
| 299 | 5.0 | 27.9 | 212 | 89.2 |
| 304 | 5.0 | 131 | 150 | 74.2 |
| 317 | 5.0 | 20.6 | 88.5 | 44.3 |

NA = not applicable

As shown in Table 11 and Table 12, we can see, the exemplified compounds of the present invention display unexpectedly better pharmacokinetic properties than the known compounds, Com. EX. No. 1.

NFAT Assay

PD-1/PD-L1 Blockade Bioassay contains two cells: PD-1 Effector Cells, which are the Jurkat T cells expressing hPD-1 and luciferase reporter genes; PD-L1 aAPC/CHO-$K_1$ Cells, which are the CHO-K1 cells expressing hPD-L1 and activate TCR's cell surface proteins. The antibody or small molecule compound is incubated with these two cells for a period of time, and the amount of the product is detected using Bio-Glo Luciferase reagent and chemiluminescence method to reflect the influence of antibody or small molecule compound on PD-1/PD-L1 interaction.

Assay buffer: 49.5 mL RPMI-1640; 0.5 mL FBS
Cell medium: 36 mL Ham's F-12; 4 mL FBS
Reaction Process:

1) Resuscitate PD-L1 aAPC/CHO-$K_1$ Cells on the first day and the cells were suspended and counted with cell recovery medium. The cells were diluted to 2.65*$10^5$/ml with cell medium. Seed cells at density of 6000 cells/well of 384-wells plates, incubator for 16-24 h;

2) Dilute the compound to 5 mM with DMSO. The 5 mM solution was used as the first concentration, and a 3-fold gradient dilution was performed, with a total of 9 concentration gradients, and the 10th concentration was used as the DMSO control;

3) Positive control antibody Atezolizumab was diluted to 4 μg/ml with assay buffer. 4 μg/ml was used as the first concentration, and a 2.5-fold gradient dilution was performed, with a total of 9 concentration gradients, and the 10th concentration was used as the assay buffer control;

4) Aspirate the medium from the 384-well plate. Add 10 μL/well of compound to the 384-well plate and incubate for 2 hours;

5) Resuscitate PD-1 effector cells and the cells were suspended and counted with cell recovery medium. The cells were diluted to 8.75*105/ml with cell medium. Seed cells at density of 8000 cells/well to 384-wells plates of step 4, incubator for 17 h;

6) Add 20 μL/well of Bio-Glo luciferase reagent to the 384 reaction plate of step 5, and incubate at 25° C. for 5-30 minutes.

7) Read the RLU (relative luminescence unit) value using the Envision multi-plate reader. The experimental data were plotted using compound concentration as X value and RLU as Y value.

The results are expressed as $EC_{50}$ value which is provided in Table 13.

TABLE 13

| EX No. | $EC_{50}$ (nM) |
|---|---|
| 5 | 317 |
| 103 | 254 |
| 317 | 4697 |
| 318 | 3225 |

The invention claimed is:

1. A compound of Formula (III), a stereoisomer, tautomer, pharmaceutically acceptable salt, or solvate thereof,

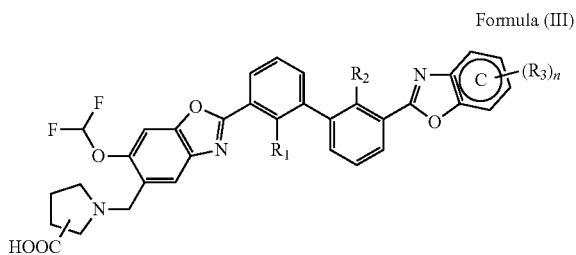

Formula (III)

wherein,
$R_1$ is selected from halogen, CN, $C_{1-6}$ alkyl, —$OCH_3$ or $C_{1-4}$ haloalkyl;
$R_2$ is selected from halogen, CN, $C_{1-6}$ alkyl, or $C_{1-4}$ haloalkyl;
ring C is phenyl or pyridyl;
$R_3$ is H, halogen, —$(CH_2)_s$—$NR_4R_5$, $C_{1-4}$ alkyl, $C_{1-4}$ alkoxyl, hydroxyl, oxo, CN, $(CH_2)_q$—$CONR_4R_5$, —$COR_4$, —$NR_4C(=O)NR_4R_5$, —$NR_4C(=NR_4)NR_4R_5$, —$S(O)_2R_4$, —$S(O)_2NR_4R_5$, —$S(O)R_4$, —$S(O)NR_4R_5$, $C_{2-6}$ alkenyl, $C_{2-6}$ alknyl, $C_{1-6}$ haloalkyl, $C_{5-6}$ aryl, $C_{5-6}$ heteroaryl, $C_{3-6}$ cycloalkyl or $C_{3-6}$ heterocycloalkyl, wherein the $C_{5-6}$ heteroaryl and $C_{3-6}$ heterocycloalkyl optionally comprising 1, 2 or 3 hetero atoms independently selected from N, S, or O; the $C_{1-4}$ alkyl, $C_{1-4}$ alkoxyl, $C_{2-6}$ alkenyl, $C_{2-6}$ alknyl, $C_{1-6}$ haloalkyl, $C_{5-6}$ aryl, $C_{5-6}$ heteroaryl, $C_{3-6}$ cycloalkyl and $C_{3-6}$ heterocycloalkyl are each optionally substituted with one or more substituents independently selected $R_6$ substituents;
$R_4$ and $R_5$ are each independently selected from H, $C_{1-4}$ alkyl, $C_{3-6}$ cycloalkyl, or $C_{3-6}$ heterocyclyl, wherein the $C_{1-4}$ alkyl, $C_{3-6}$ cycloalkyl, and $C_{3-6}$ heterocyclyl are each optionally substituted with one or more substitutents independently selected $R_6$ substituents; or
$R_4$ and $R_5$ together with the atoms to which they are attached form a 4-10-member heterocyclic ring optionally substituted with one or more substituents independently selected $R_6$ substituents;
$R_6$ is H, halogen, hydroxyl, oxo, CN, —$(CH_2)_k$—$NR_7R_8$, —$COR_7$, —$NR_7C(=O)NR_7R_8$, —$NR_7C(=NR_7)NR_7R_8$, —$S(O)_2R_7$, —$S(O)_2NR_7R_2$, —$S(O)R_7$, or —$S(O)NR_7R_8$, or $R_6$ is selected from substituted or unsubstituted $C_{1-4}$ alkyl, $C_{1-4}$ alkoxyl, $C_{2-6}$ alkenyl, $C_{2-6}$ alknyl, $C_{1-6}$ haloalkyl, $C_{5-6}$ aryl, $C_{5-6}$ heteroaryl, or $C_{3-10}$ heterocyclic ring, wherein the $C_{5-6}$ heteroaryl and $C_{3-10}$ heterocyclic ring optionally comprises 1, 2 or 3 hetero atoms independently selected from N, S, or O;
$R_7$ and $R_8$ are each independently selected from H, halogen, hydroxyl, oxo, CN, —$S(O)_2$—$C_{1-4}$ alkyl, —$NH_2$, —NH—$C_{1-4}$ alkyl, or —$(CH_2)$—$N(C_{1-4}$ alkyl$)_2$, or $R_7$ and $R_8$ are each independently selected from substituted or unsubstituted $C_{1-4}$ alkyl, $C_{1-4}$ alkoxyl, $C_{2-6}$ alkenyl, $C_{2-6}$ alknyl, $C_{1-6}$ haloalkyl, $C_{5-6}$ aryl, $C_{5-6}$ heteroaryl, $C_{3-6}$ cycloalkyl, or $C_{3-6}$ heterocycloalkyl; wherein the $C_{5-6}$ heteroaryl and $C_{3-6}$ heterocycloalkyl optionally comprises 1, 2 or 3 hetero atoms independently selected from N, S, or O;
n, q, k and s are each independently selected from 0, 1, 2, 3 or 4.

2. The compound of claim 1, a stereoisomer, tautomer, pharmaceutically acceptable salt, or solvate thereof, wherein,
$R_3$ is H, halogen, —$(CH_2)_s$—$NR_4R_5$, $C_{1-4}$ alkyl, $C_{1-4}$ alkoxyl, hydroxyl, oxo, CN, $(CH_2)_q$—$CONR_4R_5$, —$NR_4C(=NR_4)NR_4R_5$, —$S(O)_2R_4$, $C_{2-6}$ alkenyl, $C_{2-6}$ alknyl, $C_{1-6}$ haloalkyl or $C_{3-6}$ heterocycloalkyl, wherein the $C_{3-6}$ heterocycloalkyl optionally comprises 1, 2 or 3 hetero atoms independently selected from N, S, or O; the $C_{1-4}$ alkyl, $C_{1-4}$ alkoxyl, $C_{2-6}$ alkenyl, $C_{2-6}$ alknyl, $C_{1-6}$haloalkyl, and $C_{3-6}$ heterocycloalkyl are each optionally substituted with one or more substitutents independently selected $R_6$ substituents.

3. The compound of claim 1, a stereoisomer, tautomer, pharmaceutically acceptable salt, or solvate thereof, wherein,
$R_3$ is H, halogen, —$(CH_2)_s$—$NR_4R_5$, —CN, —$S(O)_2R_4$, $C_{1-4}$ alkyl, or $C_{1-4}$ alkoxyl, wherein the $C_{1-4}$ alkyl and the $C_{1-4}$ alkoxyl are each optionally substituted with one or more substitutents independently selected $R_6$ substituents.

4. The compound of claim 1, or a stereoisomer, tautomer, pharmaceutically acceptable salt, or solvate thereof, wherein,
$R_6$ is H, halogen, hydroxyl, oxo, CN, —$(CH_2)_k$—$NR_7R_8$, —$COR_7$, —$NR_7C(=O)NR_7R_8$, or —$S(O)_2R_7$, or $R_6$ is selected from substituted or unsubstituted $C_{1-4}$ alkyl, $C_{1-4}$ alkoxyl, $C_{2-6}$ alkenyl, $C_{2-6}$ alknyl, $C_{1-6}$ haloalkyl, $C_{5-6}$ aryl, $C_{5-6}$ heteroaryl, or $C_{3-10}$ heterocyclic ring, wherein the $C_{5-6}$ heteroaryl and $C_{3-10}$ heterocyclic ring are each optionally comprising 1, 2 or 3 hetero atoms independently selected from N, S, or O.

5. The compound of any claim 1, a stereoisomer, tautomer, pharmaceutically acceptable salt, or solvate thereof, wherein,
$R_6$ is H, halogen, hydroxyl, oxo, CN, —$(CH_2)$—N—$(C_{1-4}$ alkyl$)_2$, —$(CH_2)$—$NH_2$, —N—$(C_{1-4}$ alkyl$)_2$, —$NH_2$, —CO—$NH_2$, —$S(O)_2$—$C_{1-4}$ alkyl, $C_{1-4}$ alkyl-OH, $C_{1-4}$ alkyl, $C_{1-4}$ alkoxyl, $C_{2-6}$ alkenyl, $C_{2-6}$ alknyl, $C_{1-6}$ haloalkyl, $C_{5-6}$ aryl, $C_{5-6}$ heteroaryl, or $C_{3-10}$ heterocyclic ring, wherein the $C_{5-6}$ heteroaryl and $C_{3-10}$ heterocyclic ring are each optionally comprising 1, 2 or 3 hetero atoms independently selected from N, S, or O.

6. The compound of claim 1, a stereoisomer, tautomer, pharmaceutically acceptable salt, or solvate thereof, wherein, $R_6$ is halogen, oxo, —OH, —$NH_2$, —$N(CH_3)_2$, —$C_{1-4}$ alkyl-OH, —$C_{1-4}$ alkyl-NH—$CH_3$, —NH—$C_{1-4}$ alkyl, $C_{1-4}$ alkyl, $C_{1-4}$ haloalkyl, $C_{1-4}$ alkoxyl, $C_{5-6}$ aryl, $C_{5-6}$ heteroaryl, $C_{3-6}$ heterocyclyl, or $S(O)_2$—$C_{1-4}$ alky.

7. The compound of claim 1, a stereoisomer, tautomer, pharmaceutically acceptable salt, or solvate thereof, wherein, $R_1$ and $R_2$ are each independently selected from halogen, CN, —$C_{1-6}$ alkyl, or —$C_{1-4}$ haloalkyl;

ring C is phenyl or pyridyl;

$R_3$ is H, halogen, —$(CH_2)_s$—$NR_4R_5$, CN, —$C_{1-4}$ alkyl, or —$C_{1-4}$ alkoxyl, wherein the —$C_{1-4}$ alkyl and —$C_{1-4}$ alkoxyl are optionally substituted with one or more substitutents independently selected from halogen, —$C_{1-4}$ alkyl, —$C_{1-4}$ haloalkyl, —$C_{1-4}$ alkoxyl, $C_{5-6}$ heteroaryl, $C_{5-6}$ aryl, carboxyl, amino, hydroxyl, or $S(O)_2$—$C_{1-4}$ alkyl;

$R_4$ and $R_5$ are each independently selected from H, —$C_{1-4}$ alkyl, $C_{3-6}$ cycloalkyl, or $C_{3-6}$ heterocyclyl, wherein the —$C_{1-4}$ alkyl, $C_{3-6}$ cycloalkyl, and $C_{3-6}$ heterocyclyl are optionally substituted with halogen, —OH, $N(CH_3)_2$, —$C_{1-4}$ alkyl, —$C_{1-4}$haloalkyl, —$C_{3-6}$ heterocyclyl, —NH—$C_{1-4}$ alkyl, or $S(O)_2$—$C_{1-4}$ alkyl; or $R_4$ and $R_5$ together with the atoms to which they are attached form a 4- to 6-member heterocyclic ring optionally substituted with one or more substituents independently selected from —OH, —$N(CH_3)_2$, —$NH_2$, oxo, halogen, —$C_{1-4}$ alkyl, —$C_{1-4}$ alkoxyl, —$C_{1-4}$ alkyl-OH, —$C_{1-4}$ alkyl-NH—$CH_3$, or $S(O)_2$—$C_{1-4}$ alkyl;

n and s are each independently selected from 0, 1, 2, 3 or 4.

8. The compound of claim 1, a stereoisomer, tautomer, pharmaceutically acceptable salt, or solvate thereof, wherein $R_1$ is selected from F, Cl, —$CH_3$, —CN or —O—$CH_3$.

9. The compound of claim 8, a stereoisomer, tautomer, pharmaceutically acceptable salt, or solvate thereof, wherein $R_1$ is selected from —$CH_3$, F, or —O—$CH_3$.

10. The compound of claim 1, a stereoisomer, tautomer, pharmaceutically acceptable salt, or solvate thereof, wherein $R_2$ is selected from —$CH_3$, F, Cl, or Br.

11. The compound of claim 10, a stereoisomer, tautomer, pharmaceutically acceptable salt, or solvate thereof, wherein $R_2$ is —$CH_3$.

12. The compound of claim 1, a stereoisomer, tautomer, pharmaceutically acceptable salt, or solvate thereof wherein $R_3$ is selected from H, F, Cl, —$CH_3$, —$CF_3$, —O—$CF_3$, —O—$CHF_2$, —O—$CH_3$, —CN, —$NH_2$,

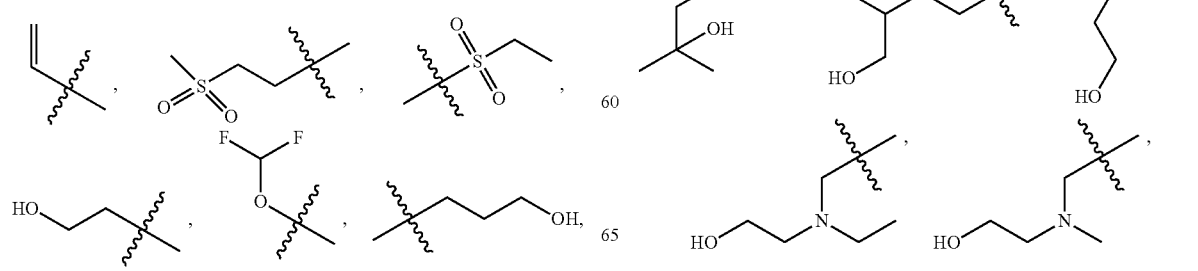

307
-continued
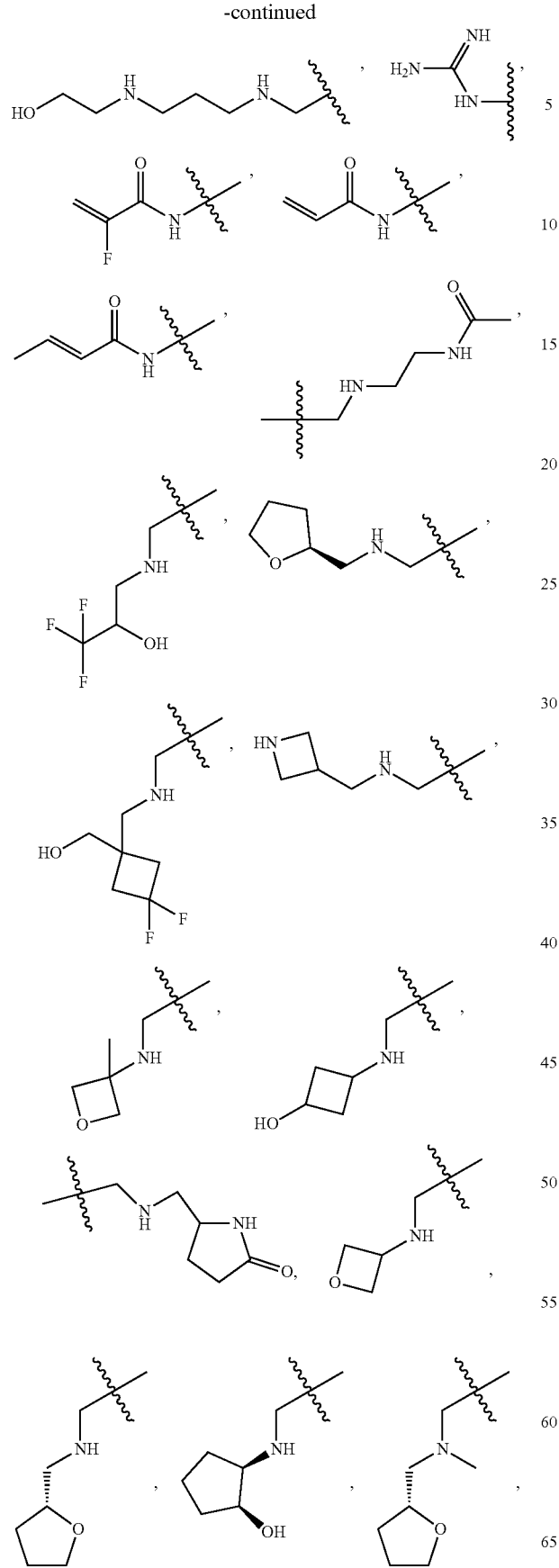
308
-continued
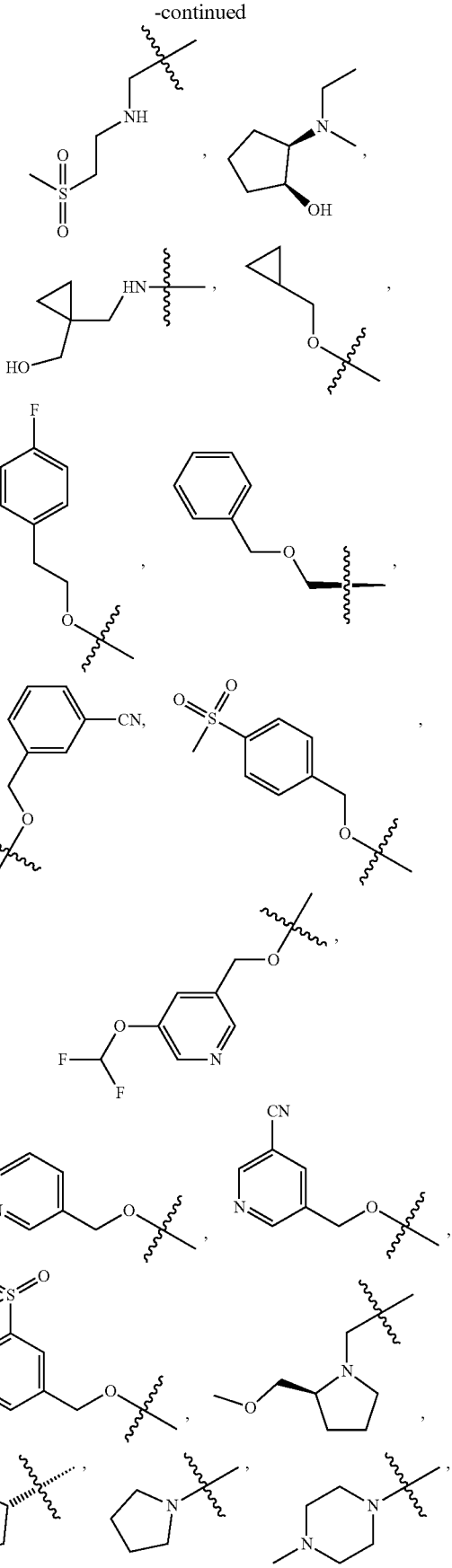

309
-continued
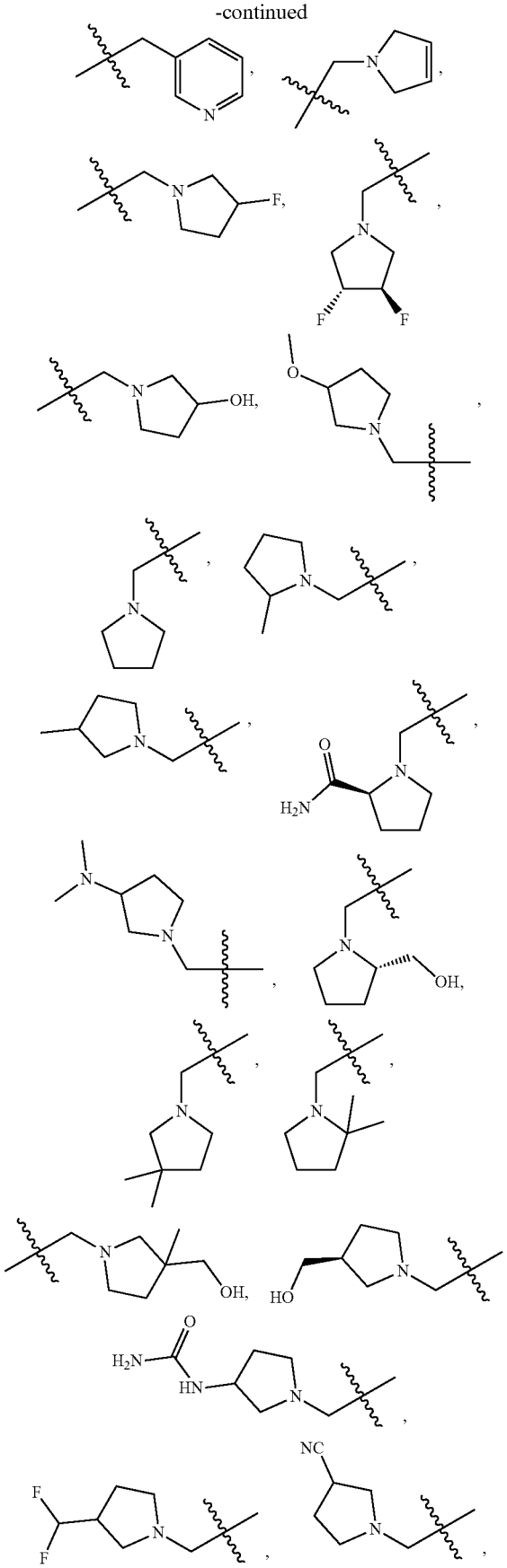
310
-continued
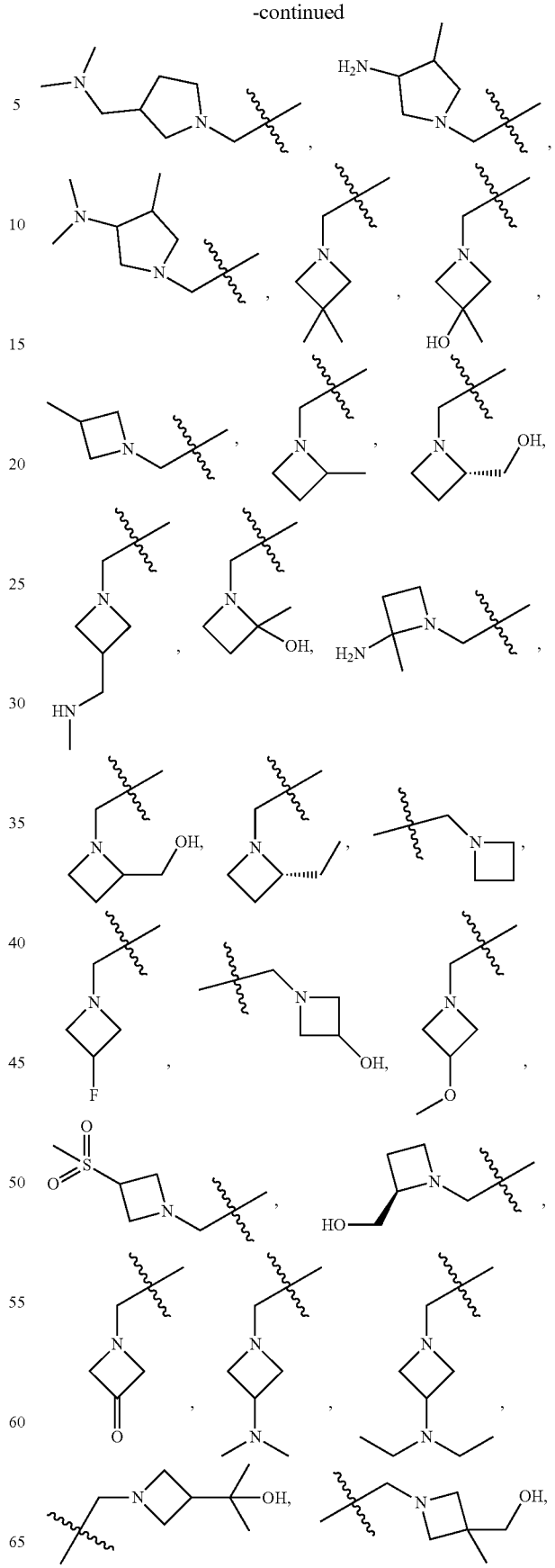

311
-continued

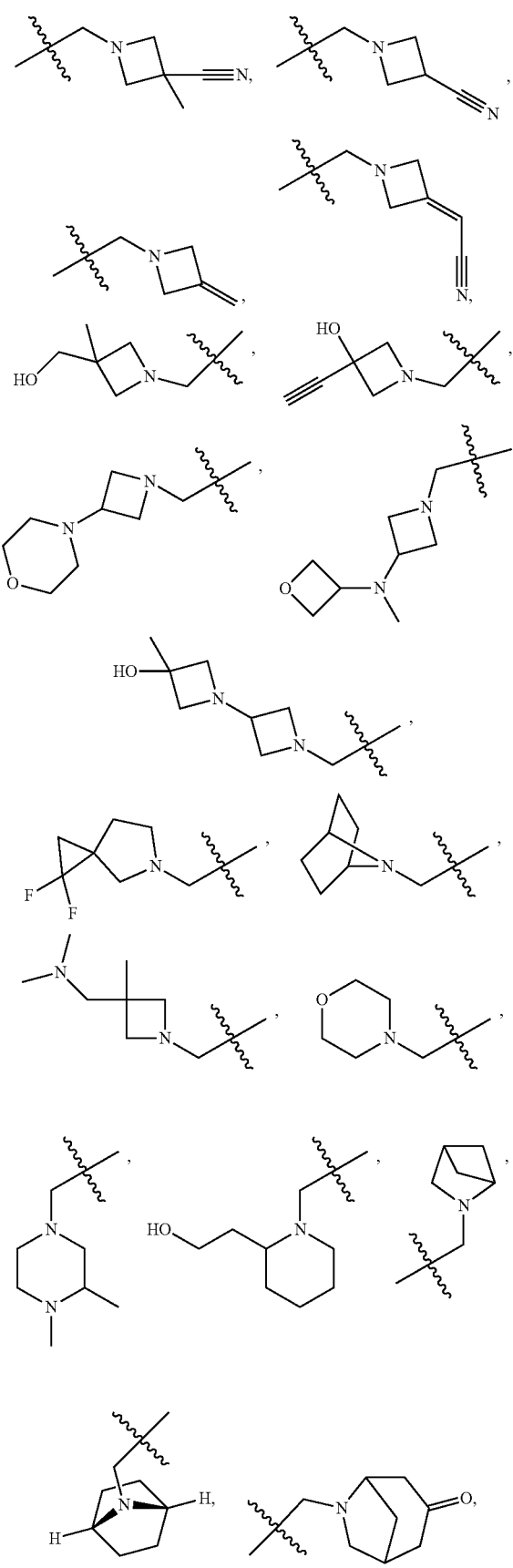

312
-continued

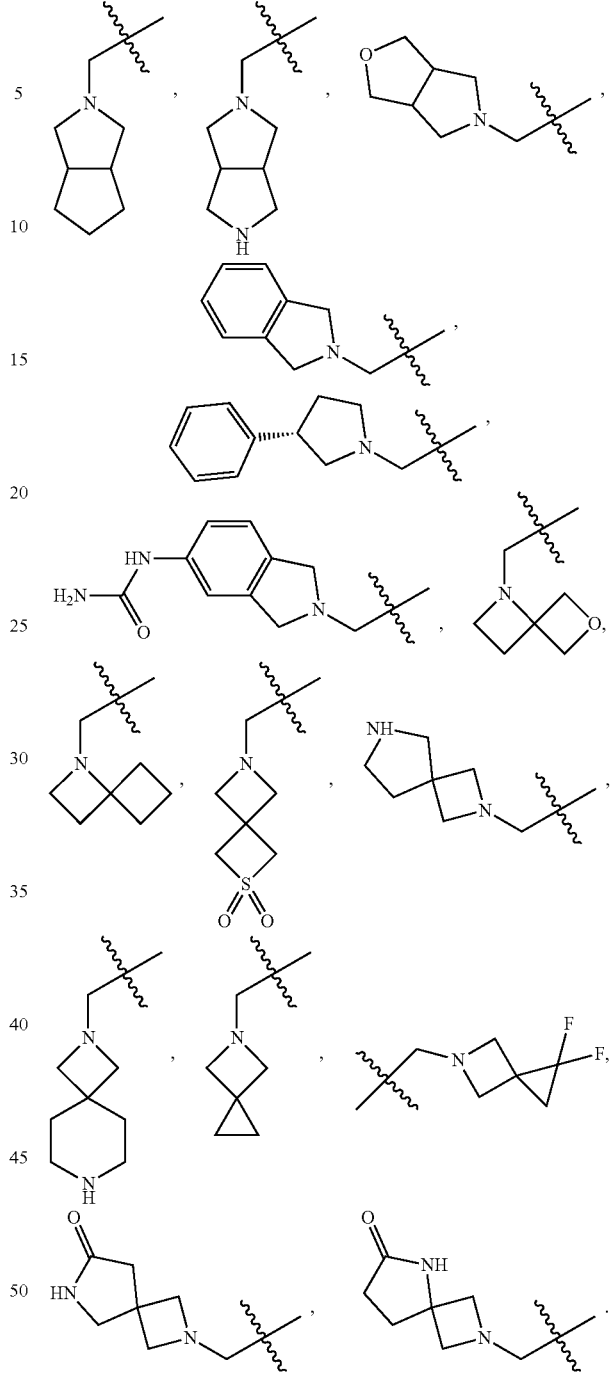

13. The compound of claim 1, a stereoisomer, tautomer, pharmaceutically acceptable salt or solvate thereof, wherein, $R_3$ is H, halogen, —$(CH_2)_s$—$NR_4R_5$, —CN, $C_{1-4}$ alkyl, or $C_{1-4}$ alkoxyl, wherein the $C_{1-4}$ alkyl and the $C_{1-4}$ alkoxyl are each optionally substituted with one or more halogen.

14. The compound of claim 1, a stereoisomer, tautomer, pharmaceutically acceptable salt or solvate thereof, wherein, $R_4$ and $R_5$ together with the atoms to which they are attached form a 4- to 6-member heterocyclic ring optionally substituted with one or more substituents independently selected from —OH, —$N(CH_3)_2$, halogen, —$C_{1-4}$ alkyl, —$C_{1-4}$ alkoxyl, —$C_{1-4}$ alkyl-OH, —CN, $C_{2-6}$ alkenyl, or $C_{2-6}$ alkynyl.

15. The compound of claim 1, a stereoisomer, tautomer, pharmaceutically acceptable salt or solvate thereof, wherein s is 1.

16. The compound of claim 8, a stereoisomer, tautomer, pharmaceutically acceptable salt or solvate thereof, wherein R₁ is —CH₃.

17. The compound of claim 1, a stereoisomer, tautomer, pharmaceutically acceptable salt, or solvate thereof, wherein the compound is:

1) ((6-(difluoromethoxy)-2-(3'-(6-(difluoromethoxy)-5-(((((1R,2S)-2-hydroxycyclopentyl)(methyl)amino)methyl)benzo[d]oxazol-2-yl)-2,2'-dimethyl-[1,1'-biphenyl]-3-yl)benzo[d]oxazol-5-yl)methyl)-L-proline;
2) (2'S)-(((2,2'-dimethyl-[1,1'-biphenyl]-3,3'-diyl)bis(6-(difluoromethoxy)benzo[d]oxazole-2,5-diyl))bis(methylene))di-L-proline;
3) ((6-(difluoromethoxy)-2-(3'-(6-(difluoromethoxy)-5-(((S)-2-(methoxycarbonyl)pyrrolidin-1-yl)methyl)benzo[d]oxazol-2-yl)-2,2'-dimethyl-[1,1'-biphenyl]-3-yl)benzo[d]oxazol-5-yl)methyl)-L-proline;
4) ((2-(2'-cyano-3'-(6-(difluoromethoxy)-5-((3,3-dimethylazetidin-1-yl)methyl)benzo[d]oxazol-2-yl)-2-methyl-[1,1'-biphenyl]-3-yl)-6-(difluoromethoxy)benzo[d]oxazol-5-yl)methyl)-L-proline;
5) ((6-(difluoromethoxy)-2-(3'-(6-(difluoromethoxy)-5-(pyrrolidin-1-ylmethyl)benzo[d]oxazol-2-yl)-2,2'-dimethyl-[1,1'-biphenyl]-3-yl)benzo[d]oxazol-5-yl)methyl)-L-proline;
6) ((6-(difluoromethoxy)-2-(3'-(6-(difluoromethoxy)-5-(pyrrolidin-1-ylmethyl)benzo[d]oxazol-2-yl)-2'-fluoro-2-methyl-[1,1'-biphenyl]-3-yl)benzo[d]oxazol-5-yl)methyl)-L-proline;
7) ((6-(difluoromethoxy)-2-(3'-(6-(difluoromethoxy)-5-(((2-hydroxyethyl)amino)methyl)benzo[d]oxazol-2-yl)-2,2'-dimethyl-[1,1'-biphenyl]-3-yl)benzo[d]oxazol-5-yl)methyl)-L-proline;
8) ((2-(3'-(5-(azetidin-1-ylmethyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline;
9) ((6-(difluoromethoxy)-2-(3'-(6-(difluoromethoxy)-5-((3-fluoroazetidin-1-yl)methyl)benzo[d]oxazol-2-yl)-2,2'-dimethyl-[1,1'-biphenyl]-3-yl)benzo[d]oxazol-5-yl)methyl)-L-proline;
10) ((6-(difluoromethoxy)-2-(3'-(6-(difluoromethoxy)-5-((3-fluoropyrrolidin-1-yl)methyl)benzo[d]oxazol-2-yl)-2,2'-dimethyl-[1,1'-biphenyl]-3-yl)benzo[d]oxazol-5-yl)methyl)-L-proline;
11) ((2-(3'-(5-(((S)-2-carbamoylpyrrolidin-1-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline;
12) ((6-(difluoromethoxy)-2-(3'-(6-(difluoromethoxy)-5-(((S)-2-(hydroxymethyl)pyrrolidin-1-yl)methyl)benzo[d]oxazol-2-yl)-2,2'-dimethyl-[1,1'-biphenyl]-3-yl)benzo[d]oxazol-5-yl)methyl)-L-proline;
13) ((6-(difluoromethoxy)-2-(3'-(6-(difluoromethoxy)-5-(morpholinomethyl)benzo[d]oxazol-2-yl)-2,2'-dimethyl-[1,1'-biphenyl]-3-yl)benzo[d]oxazol-5-yl)methyl)-L-proline;
14) ((6-(difluoromethoxy)-2-(3'-(6-(difluoromethoxy)-5-((3-hydroxypyrrolidin-1-yl)methyl)benzo[d]oxazol-2-yl)-2,2'-dimethyl-[1,1'-biphenyl]-3-yl)benzo[d]oxazol-5-yl)methyl)-L-proline;
15) ((6-(difluoromethoxy)-2-(3'-(6-(difluoromethoxy)-5-((methylamino)methyl)benzo[d]oxazol-2-yl)-2,2'-dimethyl-[1,1'-biphenyl]-3-yl)benzo[d]oxazol-5-yl)methyl)-L-proline;
16) ((6-(difluoromethoxy)-2-(3'-(6-(difluoromethoxy)-5-((dimethylamino)methyl)benzo[d]oxazol-2-yl)-2,2'-dimethyl-[1,1'-biphenyl]-3-yl)benzo[d]oxazol-5-yl)methyl)-L-proline;
17) ((6-(difluoromethoxy)-2-(3'-(6-(difluoromethoxy)-5-(((2-hydroxyethyl)(methyl)amino)methyl)benzo[d]oxazol-2-yl)-2,2'-dimethyl-[1,1'-biphenyl]-3-yl)benzo[d]oxazol-5-yl)methyl)-L-proline;
18) ((6-(difluoromethoxy)-2-(3'-(6-(difluoromethoxy)-5-(((3R,4R)-3,4-difluoropyrrolidin-1-yl)methyl)benzo[d]oxazol-2-yl)-2,2'-dimethyl-[1,1'-biphenyl]-3-yl)benzo[d]oxazol-5-yl)methyl)-L-proline;
19) ((6-(difluoromethoxy)-2-(3'-(6-(difluoromethoxy)-5-(((((S)-5-oxopyrrolidin-2-yl)methyl)amino)methyl)benzo[d]oxazol-2-yl)-2,2'-dimethyl-[1,1'-biphenyl]-3-yl)benzo[d]oxazol-5-yl)methyl)-L-proline;
20) ((6-(difluoromethoxy)-2-(3'-(6-(difluoromethoxy)-5-((3-hydroxyazetidin-1-yl)methyl)benzo[d]oxazol-2-yl)-2,2'-dimethyl-[1,1'-biphenyl]-3-yl)benzo[d]oxazol-5-yl)methyl)-L-proline;
21) ((6-(difluoromethoxy)-2-(3'-(6-(difluoromethoxy)-5-((ethylamino)methyl)benzo[d]oxazol-2-yl)-2,2'-dimethyl-[1,1'-biphenyl]-3-yl)benzo[d]oxazol-5-yl)methyl)-L-proline;
22) ((6-(difluoromethoxy)-2-(3'-(6-(difluoromethoxy)-5-(((3,3,3-trifluoro-2-hydroxypropyl)amino)methyl)benzo[d]oxazol-2-yl)-2,2'-dimethyl-[1,1'-biphenyl]-3-yl)benzo[d]oxazol-5-yl)methyl)-L-proline;
23) ((6-(difluoromethoxy)-2-(3'-(6-(difluoromethoxy)-5-((3,4-dimethylpiperazin-1-yl)methyl)benzo[d]oxazol-2-yl)-2,2'-dimethyl-[1,1'-biphenyl]-3-yl)benzo[d]oxazol-5-yl)methyl)-L-proline;
24) ((2-(3'-(5-(aminomethyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline;
25) ((6-(difluoromethoxy)-2-(3'-(6-(difluoromethoxy)-5-(((((1R,2S)-2-hydroxycyclopentyl)amino)methyl)benzo[d]oxazol-2-yl)-2,2'-dimethyl-[1,1'-biphenyl]-3-yl)benzo[d]oxazol-5-yl)methyl)-L-proline;
26) ((6-(difluoromethoxy)-2-(3'-(6-(difluoromethoxy)-5-(((((1R,2S)-2-hydroxycyclopentyl)(methyl)amino)methyl)benzo[d]oxazol-2-yl)-2,2'-dimethyl-[1,1'-biphenyl]-3-yl)benzo[d]oxazol-5-yl)methyl)-D-proline;
27) ((6-(difluoromethoxy)-2-(3'-(6-(difluoromethoxy)-5-(((((1S,2R)-2-hydroxycyclopentyl)amino)methyl)benzo[d]oxazol-2-yl)-2,2'-dimethyl-[1,1'-biphenyl]-3-yl)benzo[d]oxazol-5-yl)methyl)-L-proline;
28) ((6-(difluoromethoxy)-2-(3'-(6-(difluoromethoxy)-5-((oxetan-3-ylamino)methyl)benzo[d]oxazol-2-yl)-2,2'-dimethyl-[1,1'-biphenyl]-3-yl)benzo[d]oxazol-5-yl)methyl)-L-proline;
29) ((6-(difluoromethoxy)-2-(3'-(6-(difluoromethoxy)-5-(((((R)-tetrahydrofuran-2-yl)methyl)amino)methyl)benzo[d]oxazol-2-yl)-2,2'-dimethyl-[1,1'-biphenyl]-3-yl)benzo[d]oxazol-5-yl)methyl)-L-proline;
30) ((6-(difluoromethoxy)-2-(3'-(6-(difluoromethoxy)-5-((methyl(((R)-tetrahydrofuran-2-yl)methyl)amino)methyl)benzo[d]oxazol-2-yl)-2,2'-dimethyl-[1,1'-biphenyl]-3-yl)benzo[d]oxazol-5-yl)methyl)-L-proline;
31) ((6-(difluoromethoxy)-2-(3'-(6-(difluoromethoxy)-5-(((S)-2-(hydroxymethyl)azetidin-1-yl)methyl)benzo[d]

32) ((6-(difluoromethoxy)-2-(3'-(6-(difluoromethoxy)-5-(((2-(methylsulfonyl)ethyl)amino)methyl)benzo[d]oxazol-2-yl)-2,2'-dimethyl-[1,1'-biphenyl]-3-yl)benzo[d]oxazol-5-yl)methyl)-L-proline;
33) ((6-(difluoromethoxy)-2-(3'-(6-(difluoromethoxy)-5-((3-(dimethylamino)azetidin-1-yl)methyl)benzo[d]oxazol-2-yl)-2,2'-dimethyl-[1,1'-biphenyl]-3-yl)benzo[d]oxazol-5-yl)methyl)-L-proline;
34) ((6-(difluoromethoxy)-2-(3'-(6-(difluoromethoxy)-5-((3,3-dimethylazetidin-1-yl)methyl)benzo[d]oxazol-2-yl)-2,2'-dimethyl-[1,1'-biphenyl]-3-yl)benzo[d]oxazol-5-yl)methyl)-L-proline;
35) ((6-(difluoromethoxy)-2-(3'-(6-(difluoromethoxy)-5-(((R)-2-(hydroxymethyl)azetidin-1-yl)methyl)benzo[d]oxazol-2-yl)-2,2'-dimethyl-[1,1'-biphenyl]-3-yl)benzo[d]oxazol-5-yl)methyl)-L-proline;
36) ((6-(difluoromethoxy)-2-(3'-(6-(difluoromethoxy)-5-((2-methylazetidin-1-yl)methyl)benzo[d]oxazol-2-yl)-2,2'-dimethyl-[1,1'-biphenyl]-3-yl)benzo[d]oxazol-5-yl)methyl)-L-proline;
37) ((6-(difluoromethoxy)-2-(3'-(6-(difluoromethoxy)-5-((2-hydroxy-2-methylazetidin-1-yl)methyl)benzo[d]oxazol-2-yl)-2,2'-dimethyl-[1,1'-biphenyl]-3-yl)benzo[d]oxazol-5-yl)methyl)-L-proline;
38) ((6-(difluoromethoxy)-2-(3'-(6-(difluoromethoxy)-5-((2-methylpyrrolidin-1-yl)methyl)benzo[d]oxazol-2-yl)-2,2'-dimethyl-[1,1'-biphenyl]-3-yl)benzo[d]oxazol-5-yl)methyl)-L-proline;
39) ((2-(3'-(5-((6-oxa-1-azaspiro[3.3]heptan-1-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline;
40) ((2-(3'-(5-((2-amino-2-methylazetidin-1-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline;
41) ((6-(difluoromethoxy)-2-(3'-(6-(difluoromethoxy)-5-((3-(methylsulfonyl)azetidin-1-yl)methyl)benzo[d]oxazol-2-yl)-2,2'-dimethyl-[1,1'-biphenyl]-3-yl)benzo[d]oxazol-5-yl)methyl)-L-proline;
42) ((6-(difluoromethoxy)-2-(3'-(6-(difluoromethoxy)-5-(((R)-2-ethylazetidin-1-yl)methyl)benzo[d]oxazol-2-yl)-2,2'-dimethyl-[1,1'-biphenyl]-3-yl)benzo[d]oxazol-5-yl)methyl)-L-proline;
43) ((6-(difluoromethoxy)-2-(3'-(6-(difluoromethoxy)-5-((3-methoxyazetidin-1-yl)methyl)benzo[d]oxazol-2-yl)-2,2'-dimethyl-[1,1'-biphenyl]-3-yl)benzo[d]oxazol-5-yl)methyl)-L-proline;
44) ((6-(difluoromethoxy)-2-(3'-(6-(difluoromethoxy)-5-((3-hydroxy-3-methylazetidin-1-yl)methyl)benzo[d]oxazol-2-yl)-2,2'-dimethyl-[1,1'-biphenyl]-3-yl)benzo[d]oxazol-5-yl)methyl)-L-proline;
45) ((6-(difluoromethoxy)-2-(3'-(6-(difluoromethoxy)-5-((3-((methylamino)methyl)azetidin-1-yl)methyl)benzo[d]oxazol-2-yl)-2,2'-dimethyl-[1,1'-biphenyl]-3-yl)benzo[d]oxazol-5-yl)methyl)-L-proline;
46) ((6-(difluoromethoxy)-2-(3'-(6-(difluoromethoxy)-5-((3-oxoazetidin-1-yl)methyl)benzo[d]oxazol-2-yl)-2,2'-dimethyl-[1,1'-biphenyl]-3-yl)benzo[d]oxazol-5-yl)methyl)-L-proline;
47) ((2-(3'-(5-((2-oxa-6-azaspiro[3.3]heptan-6-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline;
48) ((2-(3'-(5-((2-azaspiro[3.3]heptan-2-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline;
49) ((6-(difluoromethoxy)-2-(3'-(6-(difluoromethoxy)-5-((hexahydrocyclopenta[c]pyrrol-2(1H)-yl)methyl)benzo[d]oxazol-2-yl)-2,2'-dimethyl-[1,1'-biphenyl]-3-yl)benzo[d]oxazol-5-yl)methyl)-L-proline;
50) ((6-(difluoromethoxy)-2-(3'-(6-(difluoromethoxy)-5-((hexahydropyrrolo[3,4-c]pyrrol-2(1H)-yl)methyl)benzo[d]oxazol-2-yl)-2,2'-dimethyl-[1,1'-biphenyl]-3-yl)benzo[d]oxazol-5-yl)methyl)-L-proline;
51) ((2-(3'-(5-((2,7-diazaspiro[3.5]nonan-2-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline;
52) ((6-(difluoromethoxy)-2-(3'-(6-(difluoromethoxy)-5-(((3-(propylamino)propyl)amino)methyl)benzo[d]oxazol-2-yl)-2,2'-dimethyl-[1,1'-biphenyl]-3-yl)benzo[d]oxazol-5-yl)methyl)-L-proline;
53) ((6-(difluoromethoxy)-2-(3'-(6-(difluoromethoxy)-5-((methyl(3-(propylamino)propyl)amino)methyl)benzo[d]oxazol-2-yl)-2,2'-dimethyl-[1,1'-biphenyl]-3-yl)benzo[d]oxazol-5-yl)methyl)-L-proline;
54) ((6-(difluoromethoxy)-2-(3'-(6-(difluoromethoxy)-5-((2,2-dioxido-2-thia-6-azaspiro[3.3]heptan-6-yl)methyl)benzo[d]oxazol-2-yl)-2,2'-dimethyl-[1,1'-biphenyl]-3-yl)benzo[d]oxazol-5-yl)methyl)-L-proline;
55) ((6-(difluoromethoxy)-2-(3'-(6-(difluoromethoxy)-5-((tetrahydro-1H-furo[3,4-c]pyrrol-5(3H)-yl)methyl)benzo[d]oxazol-2-yl)-2,2'-dimethyl-[1,1'-biphenyl]-3-yl)benzo[d]oxazol-5-yl)methyl)-L-proline;
56) ((6-(difluoromethoxy)-2-(3'-(6-(difluoromethoxy)-5-((3-methylazetidin-1-yl)methyl)benzo[d]oxazol-2-yl)-2,2'-dimethyl-[1,1'-biphenyl]-3-yl)benzo[d]oxazol-5-yl)methyl)-L-proline;
57) ((6-(difluoromethoxy)-2-(3'-(6-(difluoromethoxy)-5-(((1R,2R)-2-hydroxycyclopentyl)(methyl)amino)methyl)benzo[d]oxazol-2-yl)-2,2'-dimethyl-[1,1'-biphenyl]-3-yl)benzo[d]oxazol-5-yl)methyl)-L-proline;
58) ((6-(difluoromethoxy)-2-(3'-(6-(difluoromethoxy)-5-(((3-((2-hydroxyethyl)amino)propyl)amino)methyl)benzo[d]oxazol-2-yl)-2,2'-dimethyl-[1,1'-biphenyl]-3-yl)benzo[d]oxazol-5-yl)methyl)-L-proline;
59) ((6-(difluoromethoxy)-2-(3'-(6-(difluoromethoxy)-5-(((2-(dimethylamino)ethyl)(methyl)amino)methyl)benzo[d]oxazol-2-yl)-2,2'-dimethyl-[1,1'-biphenyl]-3-yl)benzo[d]oxazol-5-yl)methyl)-L-proline;
60) ((6-(difluoromethoxy)-2-(3'-(6-(difluoromethoxy)-5-((2-methylazetidin-1-yl)methyl)benzo[d]oxazol-2-yl)-2,2'-dimethyl-[1,1'-biphenyl]-3-yl)benzo[d]oxazol-5-yl)methyl)-L-proline;
61) ((6-(difluoromethoxy)-2-(3'-(6-(difluoromethoxy)-5-((3-methylpyrrolidin-1-yl)methyl)benzo[d]oxazol-2-yl)-2,2'-dimethyl-[1,1'-biphenyl]-3-yl)benzo[d]oxazol-5-yl)methyl)-L-proline;
62) ((6-(difluoromethoxy)-2-(3'-(6-(difluoromethoxy)-5-((2,2-dimethylpyrrolidin-1-yl)methyl)benzo[d]oxazol-2-yl)-2,2'-dimethyl-[1,1'-biphenyl]-3-yl)benzo[d]oxazol-5-yl)methyl)-L-proline;
63) ((6-(difluoromethoxy)-2-(3'-(6-(difluoromethoxy)-5-(((S)-2-(methoxymethyl)pyrrolidin-1-yl)methyl)benzo[d]oxazol-2-yl)-2,2'-dimethyl-[1,1'-biphenyl]-3-yl)benzo[d]oxazol-5-yl)methyl)-L-proline;
64) ((6-(difluoromethoxy)-2-(3'-(6-(difluoromethoxy)-5-(((((S)-tetrahydrofuran-2-yl)methyl)amino)methyl)

benzo[d]oxazol-2-yl)-2,2'-dimethyl-[1,1'-biphenyl]-3-yl)benzo[d]oxazol-5-yl)methyl)-L-proline;

65) ((2-(2'-cyano-3'-(6-(difluoromethoxy)-5-(pyrrolidin-1-ylmethyl)benzo[d]oxazol-2-yl)-2-methyl-[1,1'-biphenyl]-3-yl)-6-(difluoromethoxy)benzo[d]oxazol-5-yl)methyl)proline;

66) ((6-(difluoromethoxy)-2-(3'-(6-(difluoromethoxy)-5-(pyrrolidin-1-ylmethyl)benzo[d]oxazol-2-yl)-2,2'-dimethyl-[1,1'-biphenyl]-3-yl)benzo[d]oxazol-5-yl)methyl)-D-proline;

67) ((6-(difluoromethoxy)-2-(3'-(6-(difluoromethoxy)-5-((3,3-dimethylpyrrolidin-1-yl)methyl)benzo[d]oxazol-2-yl)-2,2'-dimethyl-[1,1'-biphenyl]-3-yl)benzo[d]oxazol-5-yl)methyl)-L-proline;

68) ((2-(3'-(5-((3-(diethylamino)azetidin-1-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline;

69) ((6-(difluoromethoxy)-2-(3'-(6-(difluoromethoxy)-5-((3-(2-hydroxypropan-2-yl)azetidin-1-yl)methyl)benzo[d]oxazol-2-yl)-2,2'-dimethyl-[1,1'-biphenyl]-3-yl)benzo[d]oxazol-5-yl)methyl)-L-proline;

70) ((6-(difluoromethoxy)-2-(3'-(6-(difluoromethoxy)-5-((2,5-dihydro-1H-pyrrol-1-yl)methyl)benzo[d]oxazol-2-yl)-2,2'-dimethyl-[1,1'-biphenyl]-3-yl)benzo[d]oxazol-5-yl)methyl)-L-proline;

71) ((2-(3'-(5-((2-azabicyclo[2.1.1]hexan-2-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline;

72) ((2-(3'-(5-(((1s,4s)-7-azabicyclo[2.2.1]heptan-7-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline;

73) ((2-(3'-(5-((((3,3-difluoro-1-(hydroxymethyl)cyclobutyl)methyl)amino)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline;

74) ((2-(3'-(5-((5-azaspiro[2.3]hexan-5-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline;

75) ((6-(difluoromethoxy)-2-(3'-(6-(difluoromethoxy)-5-((3-oxo-6-azabicyclo[3.2.1]octan-6-yl)methyl)benzo[d]oxazol-2-yl)-2,2'-dimethyl-[1,1'-biphenyl]-3-yl)benzo[d]oxazol-5-yl)methyl)-L-proline;

76) ((2-(3'-(5-((1,1-difluoro-5-azaspiro[2.3]hexan-5-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline;

77) ((6-(difluoromethoxy)-2-(3'-(6-(difluoromethoxy)-5-((3-(hydroxymethyl)-3-methylpyrrolidin-1-yl)methyl)benzo[d]oxazol-2-yl)-2,2'-dimethyl-[1,1'-biphenyl]-3-yl)benzo[d]oxazol-5-yl)methyl)-L-proline;

78) ((6-(difluoromethoxy)-2-(3'-(6-(difluoromethoxy)-5-((3-(hydroxymethyl)-3-methylazetidin-1-yl)methyl)benzo[d]oxazol-2-yl)-2,2'-dimethyl-[1,1'-biphenyl]-3-yl)benzo[d]oxazol-5-yl)methyl)-L-proline;

79) ((2-(3'-(5-((3-cyano-3-methylazetidin-1-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline;

80) ((2-(3'-(5-((3-cyanoazetidin-1-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline;

81) ((6-(difluoromethoxy)-2-(3'-(6-(difluoromethoxy)-5-((3-methyleneazetidin-1-yl)methyl)benzo[d]oxazol-2-yl)-2,2'-dimethyl-[1,1'-biphenyl]-3-yl)benzo[d]oxazol-5-yl)methyl)-L-proline;

82) ((2-(3'-(5-((3-(cyanomethylene)azetidin-1-yl)methyl)-6-(difluoromethoxy)benzo[d]oxazol-2-yl)-2,2'-dimethyl-[1,1'-biphenyl]-3-yl)-6-(difluoromethoxy)benzo[d]oxazol-5-yl)methyl)-L-proline;

83) ((2-(2,2'-dicyano-3'-(6-(difluoromethoxy)-5-((3,3-dimethylazetidin-1-yl)methyl)benzo[d]oxazol-2-yl)-[1,1'-biphenyl]-3-yl)-6-(difluoromethoxy)benzo[d]oxazol-5-yl)methyl)-L-proline;

84) ((6-(difluoromethoxy)-2-(3'-(5-((3,4-dimethylpyrrolidin-1-yl)methyl)-7-(trifluoromethyl)benzo[d]oxazol-2-yl)-2,2'-dimethyl-[1,1'-biphenyl]-3-yl)benzo[d]oxazol-5-yl)methyl)-L-proline;

85) (R)-1-((6-(difluoromethoxy)-2-(3'-(6-(difluoromethoxy)-5-((3,3-dimethylazetidin-1-yl)methyl)benzo[d]oxazol-2-yl)-2,2'-dimethyl-[1,1'-biphenyl]-3-yl)benzo[d]oxazol-5-yl)methyl)pyrrolidine-3-carboxylic acid;

86) (S)-1-((6-(difluoromethoxy)-2-(3'-(6-(difluoromethoxy)-5-((3,3-dimethylazetidin-1-yl)methyl)benzo[d]oxazol-2-yl)-2,2'-dimethyl-[1,1'-biphenyl]-3-yl)benzo[d]oxazol-5-yl)methyl)pyrrolidine-3-carboxylic acid;

87) ((2-(2'-cyano-3'-(6-(difluoromethoxy)-5-((3,3-dimethylazetidin-1-yl)methyl)benzo[d]oxazol-2-yl)-2-methyl-[1,1'-biphenyl]-3-yl)-6-(difluoromethoxy)benzo[d]oxazol-5-yl)methyl)-D-proline;

88) ((6-(difluoromethoxy)-2-(2,2'-dimethyl-3'-(5-((3-methylpyrrolidin-1-yl)methyl)-7-(trifluoromethyl)benzo[d]oxazol-2-yl)-[1,1'-biphenyl]-3-yl)benzo[d]oxazol-5-yl)methyl)-L-proline;

89) ((2-(3'-(5-((2-azabicyclo[2.1.1]hexan-2-yl)methyl)-7-(trifluoromethyl)benzo[d]oxazol-2-yl)-2,2'-dimethyl-[1,1'-biphenyl]-3-yl)-6-(difluoromethoxy)benzo[d]oxazol-5-yl)methyl)-L-proline;

90) ((6-(difluoromethoxy)-2-(2,2'-dimethyl-3'-(5-((3-methylpyrrolidin-1-yl)methyl)-7-(trifluoromethyl)benzo[d]oxazol-2-yl)-[1,1'-biphenyl]-3-yl)benzo[d]oxazol-5-yl)methyl)-D-proline;

91) (3R)-1-((6-(difluoromethoxy)-2-(2,2'-dimethyl-3'-(5-((3-methylpyrrolidin-1-yl)methyl)-7-(trifluoromethyl)benzo[d]oxazol-2-yl)-[1,1'-biphenyl]-3-yl)benzo[d]oxazol-5-yl)methyl)pyrrolidine-3-carboxylic acid;

92) (3S)-1-((6-(difluoromethoxy)-2-(2,2'-dimethyl-3'-(5-((3-methylpyrrolidin-1-yl)methyl)-7-(trifluoromethyl)benzo[d]oxazol-2-yl)-[1,1'-biphenyl]-3-yl)benzo[d]oxazol-5-yl)methyl)pyrrolidine-3-carboxylic acid;

93) ((6-(difluoromethoxy)-2-(3'-(5-((3,3-dimethylazetidin-1-yl)methyl)-7-(trifluoromethyl)benzo[d]oxazol-2-yl)-2,2'-dimethyl-[1,1'-biphenyl]-3-yl)benzo[d]oxazol-5-yl)methyl)-L-proline;

94) ((2-(3'-(5-(azetidin-1-ylmethyl)-7-methylbenzo[d]oxazol-2-yl)-2,2'-dimethyl-[1,1'-biphenyl]-3-yl)-6-(difluoromethoxy)benzo[d]oxazol-5-yl)methyl)-L-proline;

95) ((6-(difluoromethoxy)-2-(3'-(7-fluoro-5-(pyrrolidin-1-ylmethyl)benzo[d]oxazol-2-yl)-2,2'-dimethyl-[1,1'-biphenyl]-3-yl)benzo[d]oxazol-5-yl)methyl)-L-proline;

96) ((6-(difluoromethoxy)-2-(3'-(5-((ethylamino)methyl)-6-fluorobenzo[d]oxazol-2-yl)-2,2'-dimethyl-[1,1'-biphenyl]-3-yl)benzo[d]oxazol-5-yl)methyl)-L-proline;

97) ((2-(3'-(6-chloro-5-((ethylamino)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

98) ((6-(difluoromethoxy)-2-(2,2'-dimethyl-3'-(5-(pyrrolidin-1-ylmethyl)benzo[d]oxazol-2-yl)-[1,1'-biphenyl]-3-yl)benzo[d]oxazol-5-yl)methyl)-L-proline;

99) ((6-(difluoromethoxy)-2-(3'-(5-((((1R,2S)-2-hydroxycyclopentyl)amino)methyl)benzo[d]oxazol-2-yl)-2,2'-dimethyl-[1,1'-biphenyl]-3-yl)benzo[d]oxazol-5-yl)methyl)-L-proline;

100) ((6-(difluoromethoxy)-2-(2,2'-dimethyl-3'-(5-(pyrrolidin-1-ylmethyl)-7-(trifluoromethyl)benzo[d]oxazol-2-yl)-[1,1'-biphenyl]-3-yl)benzo[d]oxazol-5-yl)methyl)-L-proline;

101) ((6-(difluoromethoxy)-2-(2,2'-dimethyl-3'-(5-(pyrrolidin-1-ylmethyl)-6-(trifluoromethyl)benzo[d]oxazol-2-yl)-[1,1'-biphenyl]-3-yl)benzo[d]oxazol-5-yl)methyl)-L-proline;

102) ((2-(3'-(6,7-difluoro-5-(pyrrolidin-1-ylmethyl)benzo[d]oxazol-2-yl)-2,2'-dimethyl-[1,1'-biphenyl]-3-yl)-6-(difluoromethoxy)benzo[d]oxazol-5-yl)methyl)-L-proline;

103) ((2-(3'-(7-cyano-5-((3,3-dimethylazetidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

104) ((6-(difluoromethoxy)-2-(3'-(5-((2-hydroxy-2-methylazetidin-1-yl)methyl)benzo[d]oxazol-2-yl)-2,2'-dimethyl-[1,1'-biphenyl]-3-yl)benzo[d]oxazol-5-yl)methyl)-L-proline;

105) ((6-(difluoromethoxy)-2-(3'-(5-((2-(hydroxymethyl)azetidin-1-yl)methyl)benzo[d]oxazol-2-yl)-2,2'-dimethyl-[1,1'-biphenyl]-3-yl)benzo[d]oxazol-5-yl)methyl)-L-proline;

106) ((2-(3'-(5-((6-oxa-1-azaspiro[3.3]heptan-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

107) ((2-(3'-(5-((1-azaspiro[3.3]heptan-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

108) ((6-(difluoromethoxy)-2-(2,2'-dimethyl-3'-(6-(pyrrolidin-1-ylmethyl)benzo[d]oxazol-2-yl)-[1,1'-biphenyl]-3-yl)benzo[d]oxazol-5-yl)methyl)-L-proline;

109) ((6-(difluoromethoxy)-2-(3'-(6-((3,3-dimethylazetidin-1-yl)methyl)benzo[d]oxazol-2-yl)-2,2'-dimethyl-[1,1'-biphenyl]-3-yl)benzo[d]oxazol-5-yl)methyl)-L-proline;

110) ((2-(2'-chloro-3'-(6-((3,3-dimethylazetidin-1-yl)methyl)benzo[d]oxazol-2-yl)-2-methyl-[1,1'-biphenyl]-3-yl)-6-(difluoromethoxy)benzo[d]oxazol-5-yl)methyl)-L-proline;

111) ((2-(2'-chloro-3'-(6-((3,3-dimethylazetidin-1-yl)methyl)benzo[d]oxazol-2-yl)-2-methyl-[1,1'-biphenyl]-3-yl)-6-(difluoromethoxy)benzo[d]oxazol-5-yl)methyl)-D-proline;

112) ((6-(difluoromethoxy)-2-(2,2'-dimethyl-3'-(6-(pyrrolidin-1-ylmethyl)oxazolo[5,4-b]pyridin-2-yl)-[1,1'-biphenyl]-3-yl)benzo[d]oxazol-5-yl)methyl)-L-proline;

113) ((6-(difluoromethoxy)-2-(3'-(6-((3,3-dimethylazetidin-1-yl)methyl)oxazolo[5,4-b]pyridin-2-yl)-2,2'-dimethyl-[1,1'-biphenyl]-3-yl)benzo[d]oxazol-5-yl)methyl)-L-proline;

114) ((6-(difluoromethoxy)-2-(2,2'-dimethyl-3'-(6-(((R)-3-methylpyrrolidin-1-yl)methyl)oxazolo[5,4-b]pyridin-2-yl)-[1,1'-biphenyl]-3-yl)benzo[d]oxazol-5-yl)methyl)-L-proline;

115) ((6-(difluoromethoxy)-2-(2,2'-dimethyl-3'-(6-((((5-oxopyrrolidin-2-yl)methyl)amino)methyl)oxazolo[5,4-b]pyridin-2-yl)-[1,1'-biphenyl]-3-yl)benzo[d]oxazol-5-yl)methyl)-L-proline;

116) ((6-(difluoromethoxy)-2-(3'-(6-((3-(dimethylamino)azetidin-1-yl)methyl)oxazolo[5,4-b]pyridin-2-yl)-2,2'-dimethyl-[1,1'-biphenyl]-3-yl)benzo[d]oxazol-5-yl)methyl)-L-proline;

117) ((2-(3'-(6,7-difluoro-5-(pyrrolidin-1-ylmethyl)benzo[d]oxazol-2-yl)-2'-methoxy-2-methyl-[1,1'-biphenyl]-3-yl)-6-(difluoromethoxy)benzo[d]oxazol-5-yl)methyl)-L-proline;

118) ((2-(2'-cyano-3'-(6,7-difluoro-5-(pyrrolidin-1-ylmethyl)benzo[d]oxazol-2-yl)-2-methyl-[1,1'-biphenyl]-3-yl)-6-(difluoromethoxy)benzo[d]oxazol-5-yl)methyl)-L-proline;

119) ((2-(3'-(6-((6-cyanopyridin-3-yl)methoxy)-5-(((2-hydroxyethyl)amino)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

120) ((2-(3'-(6-((5-cyanopyridin-3-yl)methoxy)-5-(((2-hydroxyethyl)amino)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

121) ((6-(difluoromethoxy)-2-(3'-(5-(((2-hydroxyethyl)amino)methyl)-6-((5-(methylsulfonyl)pyridin-3-yl)methoxy)benzo[d]oxazol-2-yl)-2,2'-dimethyl-[1,1'-biphenyl]-3-yl)benzo[d]oxazol-5-yl)methyl)-L-proline;

122) ((6-(difluoromethoxy)-2-(3'-(5-((ethylamino)methyl)-6-((5-(methylsulfonyl)pyridin-3-yl)methoxy)benzo[d]oxazol-2-yl)-2,2'-dimethyl-[1,1'-biphenyl]-3-yl)benzo[d]oxazol-5-yl)methyl)-L-proline;

123) ((6-(difluoromethoxy)-2-(3'-(5-((dimethylamino)methyl)-6-((5-(methylsulfonyl)pyridin-3-yl)methoxy)benzo[d]oxazol-2-yl)-2,2'-dimethyl-[1,1'-biphenyl]-3-yl)benzo[d]oxazol-5-yl)methyl)-L-proline;

124) ((6-(difluoromethoxy)-2-(2,2'-dimethyl-3'-(5-((methylamino)methyl)-6-((3-(methylsulfonyl)benzyl)oxy)benzo[d]oxazol-2-yl)-[1,1'-biphenyl]-3-yl)benzo[d]oxazol-5-yl)methyl)-L-proline;

125) ((6-(difluoromethoxy)-2-(2,2'-dimethyl-3'-(5-((methylamino)methyl)-6-((4-(methylsulfonyl)benzyl)oxy)benzo[d]oxazol-2-yl)-[1,1'-biphenyl]-3-yl)benzo[d]oxazol-5-yl)methyl)-L-proline;

126) ((6-(difluoromethoxy)-2-(3'-(5-((dimethylamino)methyl)-6-((4-(methylsulfonyl)benzyl)oxy)benzo[d]oxazol-2-yl)-2,2'-dimethyl-[1,1'-biphenyl]-3-yl)benzo[d]oxazol-5-yl)methyl)-L-proline;

127) ((2-(3'-(7-cyano-5-(pyrrolidin-1-ylmethyl)benzo[d]oxazol-2-yl)-2,2'-dimethyl-[1,1'-biphenyl]-3-yl)-6-(difluoromethoxy)benzo[d]oxazol-5-yl)methyl)-L-proline;

128) ((2-(2-cyano-3'-(6-(difluoromethoxy)-5-((3,3-dimethylazetidin-1-yl)methyl)benzo[d]oxazol-2-yl)-2'-methyl-[1,1'-biphenyl]-3-yl)-6-(difluoromethoxy)benzo[d]oxazol-5-yl)methyl)-L-proline;

129) ((2-(3'-(7-cyano-5-((3-(hydroxymethyl)-3-methylazetidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

130) ((2-(3'-(7-cyano-5-(((S)-3-methylpyrrolidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

131) ((2-(3'-(7-cyano-5-(((R)-3-methylpyrrolidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

132) ((2-(3'-(7-cyano-5-(((R)-3-methylpyrrolidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-D-proline;

133) ((2-(3'-(7-cyano-5-(((3-methyloxetan-3-yl)amino)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

134) ((2-(3'-(7-cyano-5-((3-(dimethylamino)azetidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

135) ((2-(3'-(7-cyano-5-((2-(2-hydroxyethyl)piperidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

136) ((2-(3'-(7-cyano-5-(((cyanomethyl)(methyl)amino)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

137) ((2-(3'-(7-cyano-5-((3-(hydroxymethyl)azetidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

138) ((2-(3'-(7-cyano-5-(((2-hydroxy-2-methylpropyl)amino)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

139) ((2-(3'-(7-cyano-5-((((5-oxopyrrolidin-2-yl)methyl)amino)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

140) ((2-(3'-(7-cyano-5-((3,3-dimethylazetidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-D-proline;

141) ((2-(3'-(7-cyano-5-((ethyl(2-hydroxyethyl)amino)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

142) ((2-(3'-(7-cyano-5-((3-cyanopyrrolidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

143) ((2-(3'-(7-cyano-5-((3-cyanopyrrolidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-D-proline;

144) ((2-(3'-(7-cyano-5-((3-ethynyl-3-hydroxyazetidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

145) ((2-(3'-(7-cyano-5-(pyrrolidin-1-ylmethyl)benzo[d]oxazol-2-yl)-2,2'-dimethyl-[1,1'-biphenyl]-3-yl)-6-(difluoromethoxy)benzo[d]oxazol-5-yl)methyl)-D-proline;

146) ((2-(3'-(7-cyano-5-((7-oxo-2,6-diazaspiro[3.4]octan-2-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

147) ((2-(3'-(5-((bis(1-hydroxypropan-2-yl)amino)methyl)-7-cyanobenzo[d]oxazol-2-yl)-2,2'-dimethyl-[1,1'-biphenyl]-3-yl)-6-(difluoromethoxy)benzo[d]oxazol-5-yl)methyl)-L-proline;

148) ((2-(3'-(7-cyano-5-((3-morpholinoazetidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

149) ((2-(3'-(7-cyano-5-((3-(methyl(oxetan-3-yl)amino)azetidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

150) ((2-(3'-(7-cyano-5-((3-hydroxy-3-methyl-[1,3'-biazetidin]-1'-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

151) ((2-(3'-(7-cyano-5-((6-oxo-2,5-diazaspiro[3.4]octan-2-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

152) ((2-(3'-(7-cyano-5-((3-((dimethylamino)methyl)pyrrolidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

153) ((2-(3'-(7-cyano-5-((1,1-difluoro-5-azaspiro[2.4]heptan-5-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

154) ((2-(3'-(7-cyano-5-(((R)-3-(hydroxymethyl)pyrrolidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

155) ((2-(3'-(7-cyano-5-(((3-hydroxycyclobutyl)amino)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

156) ((2-(3'-(5-((3-amino-4-methylpyrrolidin-1-yl)methyl)-7-cyanobenzo[d]oxazol-2-yl)-2,2'-dimethyl-[1,1'-biphenyl]-3-yl)-6-(difluoromethoxy)benzo[d]oxazol-5-yl)methyl)-L-proline;

157) ((2-(3'-(5-(((azetidin-3-ylmethyl)amino)methyl)-7-cyanobenzo[d]oxazol-2-yl)-2,2'-dimethyl-[1,1'-biphenyl]-3-yl)-6-(difluoromethoxy)benzo[d]oxazol-5-yl)methyl)-L-proline;

158) ((2-(3'-(7-cyano-5-((3-(dimethylamino)-4-methylpyrrolidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

159) ((2-(3'-(7-cyano-5-((3-((dimethylamino)methyl)-3-methylazetidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

160) ((2-(3'-(7-cyano-5-((((1-methyl-1H-imidazol-4-yl)methyl)amino)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

161) ((2-(3'-(5-((3-(aminomethyl)-3-methylazetidin-1-yl)methyl)-7-cyanobenzo[d]oxazol-2-yl)-2,2'-dimethyl-[1,1'-biphenyl]-3-yl)-6-(difluoromethoxy)benzo[d]oxazol-5-yl)methyl)-L-proline;

162) ((2-(3'-(7-cyano-5-((3-fluoropyrrolidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

163) ((2-(3'-(7-cyano-5-((3-fluoropyrrolidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-D-proline;

164) ((2-(3'-(7-cyano-5-((3,4-difluoropyrrolidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

165) ((2-(3'-(7-cyano-5-(((R)-3-cyanopyrrolidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

166) ((6-(difluoromethoxy)-2-(3'-(5-((3-fluoropyrrolidin-1-yl)methyl)-7-(trifluoromethyl)benzo[d]oxazol-2-yl)-2,2'-dimethyl-[1,1'-biphenyl]-3-yl)benzo[d]oxazol-5-yl)methyl)-L-proline;

167) ((2-(3'-(7-cyano-5-((3-fluoro-3-methylpyrrolidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

168) ((2-(3'-(7-cyano-5-(((R)-3-(fluoromethyl)pyrrolidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline;

169) (R)-1-((2-(3'-(7-cyano-5-(pyrrolidin-1-ylmethyl)benzo[d]oxazol-2-yl)-2,2'-dimethyl-[1,1'-biphenyl]-3-yl)-6-(difluoromethoxy)benzo[d]loxazol-5-yl)methyl)pyrrolidine-3-carboxylic acid;

170) ((6-(difluoromethoxy)-2-(3'-(6-((3,3-dimethylazetidin-1-yl)methyl)oxazolo[5,4-b]pyridin-2-yl)-2,2'-dimethyl-[1,1'-biphenyl]-3-yl)benzo[d]oxazol-5-yl)methyl)-D-proline;

259) (S)-1-((2-(3'-(7-cyano-5-(((S)-3-methylpyrrolidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)pyrrolidine-3-carboxylic acid;

261) ((2-(3-(5-(((S)-3-chloropyrrolidin-1-yl)methyl)-7-cyanobenzo[d]oxazol-2-yl)-22-dimethyl-[1,1'-biphenyl]-3-yl)-6-(difluoromethoxy)benzo[d]oxazol-5-yl)methyl)-L-proline;

310) ((6-(difluoromethoxy)-2-(3'-(5-((((1R,2S)-2-hydroxycyclopentyl)amino)methyl)benzo[d]oxazol-2-yl)-2,2'-dimethyl-[1,1-biphenyl]-3-yl)benzo[d]oxazol-5-yl)methyl)-D-proline;

311) ((6-(difluoromethoxy)-2-(3'-(5-((2,2-dimethylpyrrolidin-1-yl)methyl)benzo[d]oxazol-2-yl)-2,2'-dimethyl-[1,1'-biphenyl]-3-yl)benzo[d]oxazol-5-yl)methyl)-L-proline;

312) ((6-(difluoromethoxy)-2-(3'-(5-((3,3-dimethylazetidin-1-yl)methyl)benzo[d]oxazol-2-yl)-2,2'-dimethyl-[1,1'-biphenyl]-3-yl)benzo[d]oxazol-5-yl)methyl)-L-proline;

313) ((6-(difluoromethoxy)-2-(2,2'-dimethyl-3'-(5-((2-methylazetidin-1-yl)methyl)benzo[d]oxazol-2-yl)-[1,1'-biphenyl]-3-yl)benzo[d]oxazol-5-yl)methyl)-L-proline;

315) ((2-(3'-(5-((3-carbamoylpyrrolidin-1-yl)methyl)-7-cyanobenzo[d]oxazol-2-yl)-2,2'-dimethyl-[1,1'-biphenyl]-3-yl)-6-(difluoromethoxy)benzo[d]oxazol-5-yl)methyl)-L-proline; or 316) ((2-(3'-(7-cyano-5-((3-cyano-3-methylpyrrolidin-1-yl)methyl)benzo[d]oxazol-2-yl)-2,2'-dimethyl-[1,1'-biphenyl]-3-yl)-6-(difluoromethoxy)benzo[d]oxazol-5-yl)methyl)-L-proline.

18. A pharmaceutical composition comprising a compound of claim 1, or a pharmaceutically acceptable salt or a stereoisomer thereof, and at least one pharmaceutically acceptable carrier or excipient.

19. A method of inhibiting interaction between programmed death 1 (PD-1 and programmed death-ligand 1 (PD-L1), said method comprising administering to a patient a compound of claim 1, or a pharmaceutically acceptable salt or a stereoisomer thereof.

20. The method of claim 19, wherein the patient has colon cancer, gastric cancer, thyroid cancer, lung cancer, leukemia, pancreatic cancer, melanoma, multiple melanoma, brain cancer, renal cancer, prostate cancer, ovarian cancer or breast cancer.

\* \* \* \* \*